US007785825B2

(12) United States Patent
van der Donk et al.

(10) Patent No.: US 7,785,825 B2
(45) Date of Patent: Aug. 31, 2010

(54) COMPOSITIONS AND METHODS FOR DEHYDRATION AND CYCLIZATION OF PEPTIDES, SYNTHETIC COMPOUNDS, AND LANTIBIOTICS

(75) Inventors: Willem A. van der Donk, Champaign, IL (US); Lili Xie, Brookline, MA (US); Champak Chatterjee, Urbana, IL (US); Moushumi Paul, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 389 days.

(21) Appl. No.: 11/034,275

(22) Filed: Jan. 12, 2005

(65) Prior Publication Data

US 2005/0164339 A1 Jul. 28, 2005

Related U.S. Application Data

(60) Provisional application No. 60/536,140, filed on Jan. 12, 2004.

(51) Int. Cl.
*C12P 21/06* (2006.01)
*C12N 9/00* (2006.01)
*C12N 9/14* (2006.01)

(52) U.S. Cl. ....................... 435/68.1; 435/183; 435/195

(58) Field of Classification Search ....................... None
See application file for complete search history.

(56) References Cited

FOREIGN PATENT DOCUMENTS

| | | | |
|---|---|---|---|
| BE | 0890259 | A | 3/1982 |
| WO | WO 01/90035 | | 11/2001 |

OTHER PUBLICATIONS

Guo et al., Protein tolerance to random amino acid change, (2004) Proc. Natl. Acad. Sci. USA 101: 9205-9210.*

Lazar et al., Trnasforming Growth Factor alpha: Mutation of aspartic Acid 47 and Leucine 48 Results in Different Biological Activities, (1988) Mol. Cell. Biol. 8:1247-1252.*

Hill et al., Functional Analysis of Conserved Histidines in ADP-Glucose Pyrophosphorylase from *Escherichia coli*, (1998) Biochem. Biophys. Res. Comm. 244:573-577.*

Lamla et al., The cell-free protein biosynthesis-applications and analysis of the system, Acta Biochimica Polonica, 2001, vol. 48, pp. 453-465.*

Aso et al., Characterization of a gene cluster of *Staphylococcus warneri* ISK-1 encoding the biosynthesis of and immunity to the lantibiotic, nukacin ISK-1, Biosci Biotechnol biochem, 2004, vol. 68, pp. 1663-1671.*

Bundgaard, H. (1985) "Formation of Prodrugs of Amines, Amides, Ureides, and Imides," *Methods in Enzymol.* 112:347-359.

Cane, D. E. (1995) "Isoprenoid Antibiotics" *Biotechnol.* 28:633-655.

Chatterjee, C. et al. (2005) "Biosynthesis and Mode of Action of Lantibiotics," *Chem. Rev.* 105:633-683.

Nielsen, N. M. et al. (1988) "Glycolamide Esters as Biolabile Prodrugs of Carboxylic Acid Agents: Synthesis, Stability, Bioconversion, and Physicochemical Properties," *J. Pharm. Sci.* 77(4):285-298.

Altena et al. (2000) "Biosynthesis of the Lantibiotic Mersacidin: Organization of Type B Lantibiotic Gene Cluster," *Appl. Environ. Microbiol.* 66(6):2565-2571.

Arnone et al. (1996) "New Versatile Fluorinated Chiral Building Blocks: Synthesis and Reactivity of Optically Pure a-(fluoroalkyl)-b-sulfinylenamines," *J. Org. Chem.* 61:3375-3387.

Aso et al. "Characterization of the Gene Cluster of *Staphylococcus warneri* ISK-1 Encoding Biosynthesis and Immunity of the Lantibiotic, Nukacin ISK-1," *Pubmed*, 2004.

Ayers et al. (1999) "Introduction of Unnatural Amino Acids into Proteins Using Expressed Protein Ligation," *Biopolymers* 51:343-354.

Ayi et al. (1995) "Enzymatic Hydrolysis of Methyl 3,3-difluoro-2-amino Esters. Synthesis of D- and L-3,3-difluoro-2-Amino Acids and their Derivatives," *J. Fluor. Chem.* 73:165-169.

Baldwin et al. (1987) "Penicillin Biosynthesis: Active Site Mapping with L-a-Aminoadipoyl-C-methyl-L-cysteinyl)-D-valine Variants" *J. Chem. Soc. Chem. Commun.* 1664-1667.

Banerjee et al. (1988) "Structure and Expression of a Gene Encoding the Precursor of Subtilin, a Small Protein Antibiotic" *J. Biol. Chem.* 262:9508-9514.

Barber et al. (1988). "Confirmation of the Structure of Nisin and its Major Degradation Product by FAB-MS and FAB-MS/MS" *Experientia* 44:266-70.

Baron et al. (1994). "Eukaryotic Selenocysteine Inserting tRNA Species Support Selenoprotein Synthesis in *Escherichia coli*," *Nucleic Acids Res.* 22:2228-2233.

Bauer et al. (2000) "Characterization of p40/GPR69A as a Peripheral Membrane Protein Related to the Lantibiotic Synthetase Component C," *Biochem. Biophys. Res. Commun.* 275:69-74.

Belokon et al. (1990) "General Method for the Asymmetric Synthesis of Anti-Diastereomers of b-substituted L-2-aminobutanoic Acids via Chiral Nickel(II) Schiff's Base Complexes of Dehydroaminobutanoic Acid. X-ray Crystal and Molecular Structure of the Nickel(II) Complex of the Schiff's Base from [(benzylprolyl)amino]benzophenone and dehydroaminobutanoic acid," *J. Chem. Soc. Perkin Trans.* 1:2301-2310.

(Continued)

*Primary Examiner*—David J Steadman
*Assistant Examiner*—Alexander D Kim
(74) *Attorney, Agent, or Firm*—Greenlee, Winner and Sullivan, P.C.

(57) ABSTRACT

Lantibiotics are synthesized on ribosomes as prepeptides and post-translationally modified to a mature form. These modifications include dehydrations and cyclizations. Compounds and related methods of generating compounds, modified by dehydration, cyclization, or dehydration and cyclization, are disclosed. The disclosure includes in vitro approaches to effecting dehydration and cyclization leading to production of biologically active compounds such as lantibiotics and variants thereof. Synthetic variants and methods including combinatorial approaches for generating diverse lantibiotics and other compounds are disclosed. The invention has broad potential for applications including food, agricultural, and medical industries.

18 Claims, 80 Drawing Sheets
(62 of 80 Drawing Sheet(s) Filed in Color)

OTHER PUBLICATIONS

Berry et al. (2002) "An Engineered Azurin Variant Containing a Selenocysteine Copper Ligand," *J. Am. Chem. Soc.* 124:2084-2085.
Besse et al. (1997) "The Redox Potential of Selenocystine in Unconstrained Cyclic Peptides" *Angew. Chem. Int. Ed. Engl.* 36:883-885.
Bertini et al. (1990) "pKa of Zinc-Bound Water and Nucleophilicity of Hydroxo-Containing Species. Ab initio Calculations on Models for Zinc Enzymes," *Inorg. Chem.* 29:1460-1463.
Bertini et al. (1984) "High Spin Cobalt(II) as a Probe for the Investigation of Metalloproteins," *Adv. Inorg. Biochem.* 6:71-111.
Bierbaum (1994) "Construction of an Expression System for Engineering of the Lantibiotic Pep5," *Appl. Environ. Microbiol.* 60:4332-4338.
Bierbaum et al. (1995) "Cloning, Sequencing and Production of the Lantibiotic Mersacidin," *FEMS Microbiol. Lett.* 127:121-126.
Böck et al. (1991). "Selenoprotein Synthesis: An Expansion of the Genetic Code," *Trends Biochem. Sci.* 16:463-467.
Breukink et al. (1999) "Use of Cell Wall Precursor Lipid II by a Pore-Forming Peptide Antibiotic," *Science* 286:2361-2364.
Breukink et al. (1999) "The Lantibiotic Nisin, a Special Case or Not," *Biochim. Biophys. Acta* 1462:223-234.
Brik et al. (2000) "Protein Synthesis by Solid-Phase Chemical Ligation Using a Safety Catch Linker," *J. Org. Chem.* 65:3829-3835.
Brötz et al. (1998) "Role of Lipid-Bound Peptidoglycan Precursors in the Formation of Pores by Nisin, Epidermin and other Lantibiotics," *Mol. Microbiol.* 30:317-327.
Bundgaard et al. (1988) "Glycoamide Esters as Biolabile Prodrugs of Carboxylic Acid Agents: Synthesis, Stability, Bioconversion, and Physiochemical Properites," *J. Pharm. Sci.* 77:285-298.
Bundgaard, H. (1992) "Means to Enhace Pentation: Prodrugs as a Means to Improve The Delivery of Peptide Drugs," *Adv. Drug Deliv. Rev.* 8:1-38.
Bundgaard, H. (1991) *A Textbook of Drug Design and Development*, Krosgaard-Larsen et al. eds., Ch. 5, "Design and Application of Prodrugs," pp. 113-191.
Burkoth et al. (2003) "Incorporation of Unprotected Heterocyclic Side Chains into Peptoid Oligomers via Solid-Phase Submonomer Synthesis," *J. Am. Chem. Soc.* 125:8841-8845.
Canne et al. (1999) "Chemical Protein Synthesis by Solid Phase Ligation of Unprotected Peptide Segments," *J. Am. Chem. Soc.* 121:8720-8727.
Caperelli et al. (1978) "Isotope-Tapping Experiments with Rabbit Liver Fructose Bisphosphatase," *Biochemistry* 17:1699-1704.
Carbon,C. (2000) "MRSA and MRSE: Is There an Answer," *Clin. Microbiol. Infect.* 6:supp2 17-22.
Casey et al. (1996) "Protein Prenyltransferases," *J. Biol. Chem.* 271:5289-5292.
Chan et al. (1996) "Structure-Activity Relationships in the Peptide Antibiotic Nisin: Role of Dehydroalanine 5," *Appl. Environ. Microbiol.* 62:2966-2969.
Chakicherla et al. (1995) "Role of the Leader and Structural Regions of Prelantibiotic Peptides as Assessed by Expressing Nisin-Subtilin Chimeras in *Bacillus subtilis* 168, and Characterization of their Physical, Chemical, and Antimicrobial Properties," *J. Biol. Chem.* 270:23533-23539.
Chatterjee et al. (1992) "Mersacidin, A New Antibiotic from Bacillus. In vitro and in vivo Antibacterial Activity," *J. Antibiot.* (Tokyo) 45:839-845.
Chen et al. (1999) "The Specific Genes for Lantibiotic Mutacin II Biosynthesis in *Streptococcus mutans* T8 are Clustered and Can be Transferred en bloc," *Appl. Environ. Microbiol.* 65:1356-60.
Chen et al. (1998) "Structure-Activity Study of the Lantibiotic Mutacin II from *Streptococcus mutans* T8 by a Gene Replacement Strategy," *Appl. Environ. Microbiol.* 64:2335-2340.
Chen et al. (2001) "Effect of Amino Acid Substitutions in Conserved Residues in the Leader Peptide on Biosynthesis of the Lantibiotic Mutacin II," *FEMS Microbiol Lett* 195:139-144.
Chikindas et al. (1995) "Mutacin II, a Bactericidal Antibiotic from *Streptococcus mutans*," *Antimicrob Agents Chemother.* 39:2656-2660.
Cleveland et al. (2001) "Bactriocins: Safe, Natural, Antimicrobials for Food Preservation," *Int. J. Food Microbiol.* 71:1-20.
Commans et al. (1999) "Selenocysteine Inserting tRNAs: an Overview," *FEMS Microbiol. Rev.* 23:335-351.
Cramer et al. (1985) "Arsenite-Inhibited Xanthine Oxidase—Determination of the Molybdenum-Sulfur-Arsenic Geometry by EXAFS," *J. Am. Chem. Soc.* 107:8164-8169.
Datta et al. (2002) "A Designed Phenylalanyl-tRNA Synthetase Variant Allows Efficient in vivo Incorporation of Aryl Ketone Functionality into Proteins," *J. Am. Chem. Soc.* 124:5652-5653.
Dawson et al. (1994) "Synthesis of Proteins by Native Chemical Ligation," *Science* 266:776-779.
Dawson et al. (2000) "Synthesis of Native Proteins by Chemical Ligation," *Annu. Rev. Biochem.* 69:923-960.
Delves-Broughton et al. (1996) "Applications of the Bacteriocin, Nisin," *Antonie van Leeuwenhoek* 69:193-202.
Demel et al. (1996) "Nisin Z, Mutant Nisin Z and Lacticin 481 Interactions with Anionic Lipids Correlate with Antimicrobial Activity. A Monolayer Study," *Eur. J. Biochem.* 235:267-274.
Dougherty et al. (1998) "Sequence and Analysis of the 60kb Conjugative, Bacteriocin-Producing Plasmid pMRC01 from *Lactococcus lactis* DPC3147," *Mol. Microbiol.* 29(4):1029-1038.
Driessen et al. (1995) "Mechanistic Studies of Lantibiotic-Induced Permeabilization of Phospholipid Vesicles," *Biochemistry* 34:1606-1614.
Dufour et al. (1991) "Plasmid-Encoded Determinants for Bacteriocin Production and Immunity in a *Lactococcus lactis* Strain and Purification of the Inhibitory Peptide," *J. Gen. Microbiol.* 137(10):2423-2429.
Duthaler, R.O. (1994) "Recent Developments in the Stereoselective Synthesis of a-Amino Acids," *Tetrahedron* 50:1539-1650.
Engelke et al. (1992) "Biosynthesis of the Lanbiotic Nisin: Genomic Organization and Membrane Localization of the NisB Protein," *Appl. Environ. Microbiol.* 58:3730-3743.
Ennahar et al. (2000) "Clazss IIa Bacteriocins: Biosynthesis, Structure and Activity," *FEMS Microbiol. Rev.* 224:85-106.
Enserink, M. (1999) "Promising Antibiotic Candidate Identified," *Science* 286:2245-2247.
Entian et al. (1996) "Genetics of Subtilin and Nisin Biosyntheses: Biosynthesis of Lantibiotics," *Antonie van Leeuwenhoek* 69:109-117.
Epand et al. (1999) "Diversity of Antimicrobial Peptides and Their Mechanisms of Action," *Biochim. Biophys. Acta.* 1462:11-28.
Evans et al. (1998) "Semisynthesis of Cytotoxic Proteins Using a Modified Protein Splicing Element," *Protein Sci.* 7:2256-2264.
Fiori et al. (2000) "Synthesis and Conformational Analysis of Apamin Analogues with Natural and Non-Natural Cystine/Selenosystine Connectivities," *Biopolymers* 53:550-564.
Fredenhagen et al. (1990) "Duramycins B and C, Two New Lanthionine Containing Antibiotics as Inhibitors of Phospholipase A2. Structural Revision of Duramycin and Cinnamycin," *J. Antibiot.* (Tokyo) 43:1403-1412.
Fu et al. (1996) "Identification of a Cysteine Residue Essential for Activity of Protein Farnesyltransferase. Cys299 is Exposed Only Upon Removal of Zinc from the Enzyme," *J. Biol. Chem.* 271:28541-28548.
Fu et al. (1998) "Kinetic Analysis of Zinc Ligand Mutants of Mammalian Protein Farnesyltransferase," *Biochemistry* 37:4465-72.
Galonic et al. (2003) "Oligosaccharide-Peptide Ligation of Glycosyl Thiolates with Dehydropeptides. Synthesis of S-Linked Mucin Glycopeptide Conjugates," *Chem. Eur. J.* 24:5997-6006.
Giedroc et al. (1986) "Gene 32 Protein, the Single-Stranded DNA Binding Protein from Bacteriophage T4, is a Zinc Metalloprotein," *Proc. Natl. Acad. Sci. U.S.A.* 83:8452-8456.
Gieselman et al. (2002) "Selenocysteine Drivatives for Chemoselective Ligations," *ChemBioChem.* 3:709-716.
Gieselman et al. (2001) "Synthesis of a Selenocystene-Containing Peptide by Native Chemical Ligation," *Org. Lett.* 3:1331-1334.
Gomez et al. (2002) "Trypsin Mediates Growth Phase-Dependent Transcriptional Regulation of Genes Involved in Biosynthesis of Ruminococcin A, A Lantibiotic Produced by a *Ruminococcus gnavis* Strain from a Human Intestinal Microbiota," *J. Bacteriol.* 184(1):18-28.

Gonzalez et al. (1996) "Cobalamin-Independent Methionine Synthase from *Escherichia coli*: A Zinc Metalloenzyme," *Biochemistry* 35:12228-12234.
Goulding et al. (1997) "Cobalamin-Dependent Methionine Synthase from *Escherichia coli*: Involvement of Zinc in Homocysteine Activation," *Biochemistry* 36:15749-15757.
Guder et al. (2000) "Posttranslationally Modified Bacteriocins—The Lantibiotics," *Biopolymers* 55:62-73.
Guo et al. (1997) "Zinc Site Redesign in T4 Gene 32 Protein: Structure and Stability of Co(II) Complexes Formed by Wild-Type and Metal Ligand Substitution Mutants," *Biochemistry* 36:730-742.
Gutowski-Eckel et al. (1994) "Growth Phase-Dependent Regulation and Membrane Localization of SpaB, A Protein Involved in Biosynthesis of the Lanbiotic Subtilin," *Appl. Environ. Microbiol.* 60:1-11.
Håvarstein et al. (1994) "The Leader Peptide of Colicin V Shares Consensus Sequences with Leader Peptides that are Common Among Peptide Bacteriocins Produced by Gram-Positive Bacteria," *Microbiology* 140(9):2383-2389.
Håvarstein et al. (1995) "A Family of Bacteriocin ABC Transporters Carry out Proteolytic Processing of their Substrates Concomitant with Export," *Mol. Microbiol.* 16:229-240.
Hechard et al. (2002) "Mode of Action of Modified and Unmodified Bacteriocins from Gram-Positive Bacteria," *Biochimie* 84:545-57.
Heider et al. (1993) "Selenium Metabolism in Micro-Organisms," *Adv. Microb. Physiol.* 35:71-109.
Herrera et al. (2000) "A Tyrosine-to-Threonine Mutation Converts Cycloartenol Synthase to an Oxidosqualene Cyclase that Forms Lanosterol as its Major Product," *J. Am. Chem. Soc.* 122:6765-6766.
Hightower et al. (1999) "Zinc-Catalyzed Sulfur Alkylation: Insights from Protein Farnesyltransferase," *Curr. Opin. Chem. Biol.* 3:176-181.
Hightower et al. (1998) "H-Ras Peptide and Protein Substrates Bind Protein Farnesyltransferase as an Ionized Thiolate," *Biochemistry* 37:15555-15562.
Hirsch, A. (1950) "The Assay of the Antibiotic Nisin," *J. Gen. Microbiol.* 4:70-83.
Horton et al. (1990) "Thio Sugars and Derivatives," In *Carbohydrates: Chemistry and Biochemistry* (W. W. Pigman and D. Horton, Ed.), pp. 799-842, Academic Press, New York.
Höss et al. (1993) "Peptide Modification by Incorporation of A-trifluoromethyl A-amino Acids Via Trifluoromethyl-Substituted Acylimines," *J. Fluor. Chem.* 61:163-170.
Houghten et al. (1991) "Generation and Use of Synthetic Peptide Combinatorial Libraries for Basic Research and Drug Discovery," *Nature* 354:84-86.
Huang et al. (1997) "Evidence for a Catalytic Role of Zinc in Protein Farnesyltransferase. Spectroscopy of Co2+-Farnesyltransferase Indicates Metal Coordination of the Substrate Thiolate," *J. Biol. Chem.* 272:20-23.
Hunt et al. (1984) "Mercurial-Promoted Zn2+ release from *Escherichia coli* aspartate transcarbamoylase," *J. Biol. Chem.* 259:14793-147803.
Hunt et al. (1985) "The Use of 4-(2-pyridylazo) Resorcinol in Studies of Zinc Release from *Escherichia coli* Aspartate Transcarbamoylase," *Anal. Biochem.* 146:150-157.
Hurst, A. (1981) "Nisin," *Adv. Appl. Microbiol.* 27:85-123.
Hynes et al. (1994) "Duplication of the Lantibiotic Structural Gene in M-type 49 Group A *Streptococcus* Strains Producing *Streptococcin* A-M49," *Appl. Environ. Microbiol.* 60:4207-4209.
Hynes et al. (1993) "Cloning of the Gene Encoding Streptococcin A-FF22, a Novel Lantibiotic Produced by Streptococcus Pyogenes, and Determination of its Nucleotide Sequence," *Appl. Environ. Microbiol.* 59:1969-1971.
Imperiali, B. (1988) "Synthetic Fluoropeptides as Pharmacologically Useful Compounds," *Adv. Biotechnol. Processes* 10:97-129.
Ingram, L.C. (1969) "Synthesis of the Antibiotic Nisin: Formation of Lanthionine and Beta-methyl-lanthionine," *Biochim. Biophys. Acta.* 184:216-219.
Jack et al. (2000) "Lantibiotics and Microcins: Polypeptides with Unusual Chemical Diversity," *Curr. Opin. Chem. Biol.* 4:310-317.
Jack et al. (1995) "The Genetics of Lantibiotic Biosynthesis," *BioEssays* 17:793-802.
Jameson et al. (1995) "Fluorescence Anisotropy Applied to Biomolecular Interactions," *Methods Enzymol.* 246:283.
Jarrett et al. (1997) "Changes in Protonation Associated with Substrate Binding and Cob(I)alamin Formation in Cobalamin-Dependent Methionine Synthase," *Biochemistry* 36:15739-15748.
Jung, G. (1991) "Lantibiotics-Ribosomally Synthesized Biologically Active Polypeptides Containing Sulfide Bridges and a,b-dehydroamino Acids," *Angew. Chem. Intl. Ed. Engl.* 30:1051-1068.
Kalmokoff et al. (1999) "Evidence for Production of a New Lantibiotic (butyrivibriocin OR79A) by the Ruminal Anaerobe Butyrivibrio Fibrisolvens OR79: Characterization of the Structural Gene Encoding Butyrivibriocin OR79A," *Appl. Environ. Microbiol.* 65:2128-2135.
Kelleher et al. (1998) "Regioselectivity and Chemoselectivity Analysis of Oxazole and Thiazole Ring Formation by the Peptide-Heterocyclizing Microcin B17 Synthetase Using High-Resolution MS/MS," *J. Am. Chem. Soc.* 120:9716-9717.
Kelleher et al. (1999) "Posttranslational Heterocyclization of Cysteine and Serine Residues in the Antibiotic Microcin B17: Distributivity and Directionality," *Biochemistry* 38:15623-15630.
Kelleher, N.L. (2000) "From Primary Structure to Function: Biological Insights from Large-Molecule Mass Spectra," *Chem. Biol.* 7:R37-R45.
Kenyon et al. (1977) "Novel Sulfhydryl Reagents," *Methods Enzymol.* 47:407-430.
Kido et al. (1983) "Isolation and Characterization of Ancovenin, a New Inhibitor of Angiotensin I Converting Enzyme, Produced by Actinomycetes," *J. Antibiot.* (Tokyo) 36:1295129-9.
Kiesau et al. (1997) "Evidence for a Multimeric Subtilin Synthetase Complex," *J. Bacteriol.* 179:1475-1481.
Kitazume et al. (1991) "Stereocontrolled Synthesis of 4,4,4-trifluorothreonine," *Tetrahedron Asym.* 2:235-238.
Klaenhammer, T.R. (1993) "Genetics of Bacteriocins Produced by Lactic Acid Bacteria," *FEMS Microbiol. Rev.* 12:39-85.
Kleinnijenhuis et al. (2003) "Localization of Intramolecular Monosulfide Bridges in Lantibiotics Determined with Electron Capture Induced Dissociation," *Anal. Chem.* 75:3219-3225.
Koide et al. (1993) "Synthetic Study on Selenocystine-Containing Peptides," *Chem. Pharm. Bull.* 41:502-506.
Koide et al. (1993) "Syntheses and Biological Activities of Selenium Analogs of .Alpha.-Rat Atrial Natriuretic Peptide," *Chem. Pharm. Bull.* 41:1596-1600.
Koksch et al. (1996) "Synthesis and Incorporation of A-trifluoromethyl-Substituted Amino Acids into Peptides," *ACS Symp. Ser.* 639:42-58.
Koksch et al. (1997) "Proteolytically Stable Peptides by Incorporation of Alpha-Tfm Amino Acids," *J. Pept. Sci.* 3:157-167.
Kollonitsch et al. (1978) "Selective Inhibitors of Biosynthesis of aminergic neurotransmitters," *Nature* 274:906-908.
Koponen et al. (2002) "NisB is Required for the Dehydration and NisC for the Lanthionine Formation in the Post-Translational Modification of Nisin," *Microbiol.* 148:3561-3568.
Krull et al. (2000) "Biochemical Structural Analysis of the Lantibiotic Mutacin II," *J. Biol. Chem.* 275:15845-15850.
Kuipers et al. (1996) "Protein Engineering of Lantibiotics," *Antonie van Leeuwenhoek* 69:161-169.
Kuipers et al. (1992) "Engineering Dehydrated Amino Acid Residues in the Antimicrobial Peptide Nisin," *J. Biol. Chem.* 267:24340-12346.
Kuipers et al. (1995) "Autoregulation of Nisin Biosynthesis in *Lactococcus lactis* by Signal Transduction," *J. Biol. Chem.* 270:27299-27304.
Kuipers et al. (1993) "Biosynthesis and Secretion of a Precursor of Nisin Z by *Lactococcus lactis*, Directed by the Leader Peptide of the Homologous Lantibiotic Subtilin from *Bacillus subtilis*," *FEMS Lett.* 330:23-27.
Kukhar, V. (1994) "Fluorine-Containing Amino Acids," *J. Fluor. Chem.* 69, 199-205.
Kupke et al. (1996) "Expression, Purification, and Characterization of EpiC, an Enzyme Involved in the Biosynthesis of the Lantibiotic Epiderm, and Sequence Analysis of *Staphylococcus epidermidis* epiC Mutants," *J. Bacteriol.* 178:1335-1340.

Kupke et al. (1996) "Post-Translational Modifications of Lantibiotics," *Antonie van Leeuwenhuek* 69:139-150.
Lam et al. (1991) "A New Type of Synthetic Peptide Library for Identifying Ligand-Binding Activity," *Nature* 354:82-84.
Lane et al. (1977) "Synthetic Analogues of the Active Sites of Iron-Sulfur Proteins. 14. Synthesis, Properties, and Structures of bis(o-xylyl-.alpha.,.alpha.'-dithiolato)ferrate(II,III) Anions, Analogs of Oxidized and Reduced Rubredoxin Sites," *J. Am. Chem. Soc.* 99:84-98.
Lemieux et al. (1998) "Chemoselective Ligation Reactions with Proteins, Oligosaccharides and Cells," *TIBTECH* 16:506-513.
Levy, S.B. (2000) "The Future of Antibiotics: Facing Antibiotic Resistance," *Clin. Microbiol. Infect.* 6 supp 3:101-106.
Li et al. (1996) "From Peptide Precursors to Oxazole and Thiazole-Containing Peptide Antibiotics: Microcin B17 Synthase," *Science* 274:1188-1193.
Limbert et al. (1991) "Chemotherapeutic Properties of Mersacidin in vitro and in vivo," In *Nisin and Novel Lantibiotics* (G. Jung and H.-G. Sahl, Ed.), pp. 448-456, ESCOM, Leiden, The Netherlands.
Liptak et al. (1994) "Fast Atom Bombardment Mass Spectrometry of Some Lantibiotics," *Biol Mass Spectrom* 23:701-706.
Liu et al. (1992) "Enhancement of the Chemical and Antimicrobial Properties of Subtilin by Site-Directed Mutagenesis," *J. Biol. Chem.* 267:25078-25085.
Liu et al. (1993) "The Antimicrobial Effect of a Structural Variant of Subtilin Against Outgrowing *Bacillus cereus* T Spores and Vegetative Cells Occurs by Different Mechanisms," *Appl. Environ. Microbiol.* 59:648-651.
Madison et al. (1997) "The Leader Peptide is Essential for the Post-Translational Modification of the DNA-Gyrase Inhibitor Microcin B17," *Mol. Microbiol.* 23:161-168.
Marcille et al. (2002) "Distribution of Genes Encoding the Trypsin-Dependent Lantibiotic Ruminococcin A Among Bacteria Isolated from Human Fecal Microbiota," *Appl. Environ. Microbiol.* 68:3424-3431.
Maret et al. (1993) "Cobalt as Probe and Label of Proteins," *Methods Enzymol.* 226:52-71.
Marki et al. (1991) "Mode of Action of the Lanthionine-Containing Peptide Antibiotics Duramycin, Duramycin B and C, and Cinnamycin as Indirect Inhibitors of Phospholipase A2," *Biochem. Pharmacol.* 42:2027-2035.
Matthews et al. (1997) "Enzyme-Catalyzed Methyl Transfers to Thiols: The Role of Zinc," *Curr. Opin. Chem. Biol.* 1:332-339.
Mathis et al. (1997) "Pre-Steady-State Study of Recombinant Sesquiterpene Cyclases," *Biochemistry* 36:8340-8348.
May et al. (1978) "Preparation and Properties of Cobalt(II) Rubredoxin," *Biochemistry* 17:3333-3338.
Mayer et al. (2001) "Characterization of Rat LANCL1, a Novel Member of the Lanthionine Synthetase C-like Protein Family, Highly Expressed in Testis and Brain," *Gene* 269:73-80.
Mayer et al. (2001) "Organization and Chromosomal Localization of the Human and Mouse Genes Coding for LanC-like Protein 1 (LANCL1)," *Cytogenet. Cell Genet.* 93:100-104.
Mayer et al. (2001) "Molecular Cloning, Characterization, and Tissue-Specific Expression of Human LANCL2, a Novel Member of the LanC-like Protein Family," *DNA Seq.* 12:161-166.
McAuliffe et al. (2001) "Lantibiotics: Structure Biosynthesis and Mode of Action," *FEMS Microbiol. Rev.* 25:285-308.
McAuliffe et al. (2000) "Each Peptide of the Two-Component Lantibiotic Lacticin 3147 Requires a Separate Modification Enzyme for Activity," *Microbiol.* 146:2147-2154.
McCaskill et al. (1997) "Prospects for the Bioengineering of Isoprenoid Biosynthesis," *Adv. Biochem. Eng. Biotechnol.* 55:107-146.
McLafferty et al. (1999) "Techview: Biochemistry. Biomolecule Mass Spectrometry," *Science* 284:1289-1290.
McLaughlin et al. (1999) "Nucleotide Sequence of the Streptococcin A-FF22 Lantibiotic Regulation: Model for Production of the Lantibiotic SA-FF22 by Strains of *Streptococcus pyogenesm*" *FEMS Microbiol. Lett.* 175(2):171-177.
Meyer et al. (2000) "Oxidosqualene Cyclase Residues that Promote Formation of Cycloartenol, Lanosterol, and Parkeol," *Angew. Chem. Int. Ed. Engl.* 39:4090-4092.
Meyer et al. (1994) "Sequence Analysis of Lantibiotics: Chemical Derivatization Procedures Allow a Fast Access to Complete Edman Degradation," *Anal. Biochem.* 223:185-190.
Meyer et al. (1995),"Nucleotide Sequence of the Lantibiotic Pep5 Biosynthetic Gene Cluster and Functional Analysis of PepP and PepC," *Eur. J. Biochem.* 232:478-489.
Milne et al. (1998) "ATP/GTP Hydrolysis is Required for Oxazole and Thiazole Biosynthesis in the Peptide Antibiotic Microcin B17," *Biochemistry* 37:13250-13261.
Mitra et al. (1983) "Synthesis and 19F Spectra of Tetra-L-alanine Analogs Containing Selectively Incorporated 3-fluoro-L-alanine Residues," *Int. J. Peptide Prot. Res.* 22:494-501.
Moll et al. (1999) "Bacteriocins: Mechanism of Membrane Insertion and Pre Formation," *Antonie van Leewenhoek* 76:185-198.
Moll et al. (1996) "Mechanism of Lantibiotic-Induced Pore-Formation," *Antonie van Leeuwenhoek* 69:185-191.
Moroder et al. (1996) "Oxidative Folding of Cystine-Rich Peptides vs Regioselective Cysteine Pairing Strategies," *Biopolymers* 40:207-234.
Morris et al. (1981) "Inhibition of *Bacillus cereus* Spore Outgrowth by Covalent Modification of a Sulfhydryl Group by Nitrosothiol and Iodoacetate," *J. Bacteriol.* 148:465-471.
Muir et al. (1998) "Expressed Protein Ligation: A General Method for Protein Engineering," *Proc. Natl. Acad. Sci. USA* 95:6705-6710.
Mullins et al. (1999) "Channeling of Ammonia Through the Intermolecular Tunnel Contained Within Carbamoyl Phosphate Synthetase," *J. Am. Chem. Soc.* 121:3803-3804.
Myers et al. (1992) "Zinc Binding by the Methylation Signaling Domain of the *Escherichia coli* Ada Protein," *Biochemistry* 31:4541-4547.
Myers et al. (1993) "Repair of DNA Methylphosphotriesters Through a Metalloactivated Cysteine Nucleophile," *Science* 261:1164-1167.
Nair et al. (1996) "Unexpected Binding Mode of the Sulfonamide Fluorophore 5-Dimethylamino-1-naphthalene Sulfonamide to Human Carbonic Anhydrase II. Implications for the Development of a Zinc Biosensor," *J. Biol. Chem.* 271:1003-1007.
Nair et al. (1995) "Structural Basis of Inhibitor Affinity to Variants of Human Carbonic Anhydrase II," *Biochemistry* 34:3981-3989.
Nair et al. (1993) "Structural Consequences of Hydrophilic Amino Acid Substitutions in the Hydrophobic Pocket of Human Carbonic Anhydrase II," *Biochemistry* 32:4506-4514.
Nair et al. (1993) "Crystallographic Studies of Azide Binding to Human Carbonic Anhydrase II," *Eur. J. Biochem.* 213:507-515.
Nair et al. (1991) "Structural Properties of Human Carbonic Anhydrase II at pH 9.5," *Biochem. Biophys. Res. Commun.* 181:579-584.
Nair et al. (1991) "Altering the Mouth of a Hydrophobic Pocket. Structure and Kinetics of Human Carbonic Anhydrase II Mutants at Residue Val-121," *J. Biol. Chem.* 266:17320-17325.
Nakajima et al. (1983) "Studies on 2-Aziridinecarboxylic acid. IX. Convenient Synthesis of Optically Active S-alkylcysteine, Threo-S-alkyl-b-methylcysteine, and Lanthionine Derivatives Via the Ring Opening Reaction of Aziridine by Several Thiols," *Bull. Chem. Soc. Jpn.* 56:520-522.
Navaratna et al. (1999) "Identification of Genes Encoding Two-Component Lantibiotic Production in *Staphylococcus aureus* C55 and Other Phage Group II *S. Aureus* Strains and Demonstration of an Association with the Exfoliative Toxin B Gene," *Infect. Immun.* 67:4268-4271.
Neis et al. (1997) "Effect of Leader Peptide Mutations on Biosynthesis of the Lantibiotic Pep5," *FEMS Microbiol. Lett.* 149:249-255.
Nes et al. (2000) "Class II Antimicrobial Peptides from Lactic Acid Bacteria," *Biopolymers* 55:50-61.
Nes et al. (1996) "Novel Lantibiotics and Their Pre-Peptides," *Antonie van Leewenhoek* 69:89-97.
Nissen-Meyer et al. (1997) "Ribosomally Synthesized Antomicrobial Peptides: Their Function, Structure, Biogenesis, and Mechanism of Action," *Arch. Microbiol.* 167:67-77.
Norgrady (1985) "Pro-drugs and Soft Drugs," In; *Medicinal Chemistry a Biochemical Approach*, Oxford University Press, New York, pp. 388-392.

Okeley et al. (2003) "SpaC and NisC, The Cyclases Involved in Subtilin and Nisin Biosythesis, are Zinc Proteins," *Biochem.* 42:13613-13624.
Okeley et al. (2000) "Facile Chemoselective Synthesis of Dehydroalanine-Containing Peptides." *Org. Lett.* 2:3603-3606.
Okeley et al. (2000) "Novel Cofactors via Post-Translational Modifications of Enzyme Active Stress," *Chem. Biol.* 7:R159-R171.
O'Sullivan et al. (2002) "Elevated Enzyme Release from Lactococcal Starter Cultures on Exposure to the Lantibiotic Lacticin 481, Produced by *Lactococcus lactis* DPC5552," *J. Dairy Sci* 85:2130-2140.
O'Sullivan et al. (2003) "Generation of Food-Grade Lactococcal Starters Which Produce the Lantibiotics Lacticin 3147 and Lacticin 481," *Appl. Environ. Microbiol.* 69:3681-3685.
O'Sullivan et al. (2002) "Potential of Bacteriocin-Producing Lactic Acid Bacteria for Improvements in Food Safety and Quality," *Biochimie.* 84:593-604.
Pansare et al. (1989) "Synthesis and Reactivity of B-lactones Derived from L-Threonine and Related Amino Acids," *Org. Chem.* 54:2311-2316.
Park et al. (2003) "Lanthionine Synthetase Components C-like 2 Increases Cellular Sensitivity to Adriamycin by Decreasing the Expression of P-glycoprotein Through a Transcription-Mediated Mechanism," *Cancer Res* 63:723-727.
Peariso et al. (1998) "Characterization of the Zinc Binding Site in Methionine Synthase Enzymes of *Escherichia coli*: The Role of Zinc in the Methylation of Homocysteine," *J. Am. Chem. Soc.* 120:8410-8416.
Peariso et al. (2001) "Characterization of the Zinc Sites in Cobalamin-Independent and Cobalamin-Dependent Methionine Synthase Using Zinc and Selenium X-ray Absorption Spectroscopy," *Biochemistry* 40:987-993.
Peng et al. (2001) "Structural Characterization of a Pentadienyl Radical Intermediate Formed During Catalysis by Prostaglandin Synthase-2," *J. Am. Chem. Soc.* 123:3609-3610.
Peng et al. (2002) "Synthesis of Isotopically Labeled Arachidonic Acids to Probe the Reaction Mechanism of Prostaglandin H Synthase," *J. Am. Chem. Soc.* 124:10785-10796.
Peng at al. (2003) "An Unusual Isotope Effect on Substrate Inhibition in the Oxidation of Arachidonic Acid by Lipoxygenase," *J. Am. Chem. Soc.* in press.
Peschel et al. (1996) "Inducible Production and Cellular Location of the Epidermin Biosythetic Enzyme EpiB Using an Improved *Staphylococcal* Expression System," *FEMS Microbiol. Lett.* 137:279-284.
Peter et al. (1983) "Use of Endoproteinase Lys-C from Lysobacter Enzymogenes in Protein Sequence Analysis," *Anal. Biochem.* 134(2):347-354.
Piard et al. (1993) "Structure, Organization, and Expression of the Ict Gene for Lacticin 481, a Novel Lantibiotic Produced by *Lactococcus lactis*," *J. Biol. Chem.* 268:16361-16368.
Piard et al. (1992) "Purification and Partial Characterization of Lacticin 481, a Lanthionine-Containing Bacteriocin Produced by *Lactococcus Lactis* Subsp. *lactis* CNRZ 481," *Appl. Environ. Microbiol.* 58:279-284.
Piard et al. (1990) "Evidence for a Bacteriocin Produced by *Lactococcus lactis* CNRZ 481," Neth. *Milk and Dairy J.* 44:143-158.
Piettre et al. (1987) "Synthesis of Fluorinated Vinylsulfides and Selenides," *Tetrahedron* 43:4309-4319.
Pridmore et al. (1996) "Variacin, a New Lanthionine-Containing Bacteriocin Produced by *Micrococcus varians*: Comparison to Lacticin 481 of *Lactococcus lactis*," *Appl. Environ. Microbiol.* 62:1799-1802.
Purrington et al. (1987) "The Preparation of a-Fluorosulfoxides and Vinyl Fluorides," *Tetrahedron Lett.* 28:3901-3904.
Qiu et al. (1994) "Zinc-free and Reduced T4 Gene 32 Protein Binds Single-Stranded DNA Weakly and Fails to Stimulate UvsX-catalyzed Homologous Pairing," *J. Biol. Chem.* 269:2773-2781.
Radisky et al. (2000) "Squalene Synthase: Steady-State, Pre-Steady-State, and Isotope-Trapping Studies," *Biochemistry* 39:1748-1760.
Raushel et al. (1979) "Determination of Rate-limiting Steps of *Escherichia coli* Carbamoyl-Phosphate Synthase. Rapid Quench and Isotope Partitioning Experiments," *Biochemistry* 18:3424-3429.
Rayman et al. (1981) "Nisin: A Possible Alternative or Adjunct to Nitrite in the Preservation of Meats," *Appl. Environ. Microbiol.* 41:375-380.
Reis et al. (1994) "Producer Immunity Towards the Lantibiotic Pep5: Identification of the Immunity Gene Pepl and Localization and Functional Analysis of its Gene Product," *Appl. Environ. Microbiol.* 60:2876-2883.
Rincé et al. (1997) "Characterization of the Lacticin 481 Operon: The *Lactococcus lactis* Genes IctF. IctE and IctG Encode a Putative ABC Transporter Ivolved in Bacteriocin Immunity," *Appl. Environ. Microbiol.* 63:4252-4260.
Rince et al. (1994) "Cloning, Expression, and Nucleotide Sequence of Genes Involved in Production of Lactococcin DR, a Bacteriocin from *Lactococcus lactis* Subsp. *lactis*," *Appl. Environ. Microbiol.* 60:1652-1657.
Roehm et al. (1998) "Selectivity of Methylation of Metal-Bound Cysteinates and Its Consequences," *J. Am. Chem. Soc.* 120:13083-13087.
Roepstorff et al. (1984) "Proposal for a Common Nomenclature for Sequence Ions in Mass Spectra of Peptides," *Biomed. Mass Spectrom.* 11:601.
Rollema et al. (1995) "Improvement of Solubility and Stability of the Antimicrobial Peptide Nisin by Protein Engineering," *Appl. Environ. Microbiol.* 61:2873-2878.
Rose, I.A. (1980) "The Isotope Trapping Method: Desorption Rates of Productive E.S Complexes," *Methods Enzymol.* 64:47-59.
Rose et al. (1974) "Determination of the Rate of Hexokinase-Glucose Dissociation by the Isotope-Trapping Method," *J. Biol. Chem.* 249:5163-5168.
Rozema et al. (1999) "Yeast Protein Farnesyltransferase. pKas of Peptide Substrates Bound as Zinc Thiolates," *Biochemistry* 38:13138-13146.
Ryan et al. (1999) "Extensive Post-Translational Modification, Including Serine to D-Alanine Conversion, in the Two-Component Lantibiotic, Lacticin 3147," *J. Biol. Chem.* 274:37544-37550.
Saderholm et al. (2000) "Role of Metals in the Reaction Catalyzed by Protein Farnesyltransferase," *Biochemistry* 39:12398-12405.
Sahl et al. (1998) "Lantibiotics: Biosynthesis and Biological Activities of Uniquely Modified Peptides from Gram-Positive Bacteria," *Annu. Rev. Microbiol.* 52:41-79.
Sahl et al. (1995) "Biosynthesis and Biological Activities of Lantibiotics with Unique Post-Translational Modifications," *Eur. J. Biochem.* 230:827-853.
Sahl, H.-G. (1991) "Pore Formation in Bacterial Membranes by Cationic Lantibiotics," In *Nisin and novel Lantibiotics* (G. Jung and H.-G. Sahl, Ed.), pp. 347-358, ESCOM, Leiden, The Netherlands.
Sashihara et al. (2000) "A Novel Lantibiotic, Nukacin ISK-1, of *Staphylococcus warneri* ISK-1: Cloning of the Structural Gene and Identification of the Structure," *Biosci. Biotechnol. Biochem.* 64(11):2420-2428.
Schmidt et al. (2001) "Evolution of Enzymatic Activities in the Enolase Superfamily: Functional Assignment of Unknown Proteins in *Bacillus subtilis* and *Escherichia coli* L-Ala-D/L-Glu Epimerases," *Biochemistry* 40:15707-15715.
Schnell et al. (1988) "Peptide Sequence of Epidermin, A Ribosomally Synthesized Antibiotic with four Sulphide-Rings," *Nature* 333:276-278.
Schnell et al. (1992) "Analysis of Genes Involved in the Biosythesis of the Lantibiotic Epidermin," *Eur. J. Biochem.* 204:57-68.
Sen et al. (1999) "Post-Translational Modification of Nisin. The Involvement of NisB in the Dehydration Process," *Eur. J. Biochem.* 137:279-284.
Senko et al. (1996) "Electrospray Ionization Fourier Transform Ion Cyclotron Resonance at 9.4 T," *Rapid Commun. Mass Spectrom.* 10:1824-1828.
Shey et al. (2002) "Mechanistic Investigation of a Novel Vitamin B12-Catalyzed Carbon-Carbon Bond Forming Reaction," *J. Org. Chem.* 67:837-846.
Shey et al. (2000) "Mechanistic Studies on the Vitamin B12-Catalyzed Dechlorination of Chlorinated Alkenes," *J. Am. Chem. Soc.* 122:12403-12404.

Siegers et al. (1996) "Biosynthesis of Lantibiotic Nisin. Post-translational Modification of its Prepeptide Occurs at a Multimeric Membrane-Associated Lanthionine Synthetase Complex," *J. Biol. Chem.* 271:12294-12301.
Siezen et al. (1996) "Comparison of Lantibiotic Gene Clusters and Encoded Proteins," *Antonie van Leeuwenhoek* 69:171-184.
Silverman et al. (1977) "Mechanism of Inactivation of Gamma-Cystathionase by Beta,Beta,Beta-Trifluoroalanine," *Biochemistry* 16:5515-5520.
Silverman et al. (1976) "Inactivation of Pyridoxal Phosphate Dependent Enzymes by Mono- and Polyhaloalanines," *Biochemistry* 15:4718-4723.
Skaugen et al. (1997) "Organization and Expression of a Gene Cluster Involved in the Biosynthesis of the Lantibiotic Lactocin S," *Mol. Gen. Genet.* 253:674-686.
Smith et al. (1975) "Simple Alkanethiol Groups for Temporary Blocking of Sulfhydryl Groups of Enzymes," *Biochemistry* 14:766-771.
Soloshonok, V.A. (1996) "Practical Synthesis of Enantiopure Fluoroamino Acids of Biological Interest by Asymmetric Aldol Reactions," *ACS Symp. Ser.* 639:26-41.
Spee, et al. (1993) "Efficient Random Mutagenesis Method with Adjustable Mutation Frequency by use of PCR and dITP," *Nucleic Acids Res.* 21:777-778.
Stadtman, T.C. (1991) "Biosynthesis and Function of Selenocysteine-Containing Enzymes," *J. Biol. Chem.* 266:16257-16260.
Stadtman, T.C. (1996) "Selenocysteine," *Annu. Rev. Biochem.* 65:83-100.
Swartz, M.N. (1994) "Hospital-Aquired Infections: Diseases with Increasingly Limited Therapies," *Proc. Natl. Acad. Sci. USA* 91:2420-2427.
Szekat et al. (2003) "Construction of an Expression System for Site-Directed Mutogenesis of the Lantibiotic Mersacidin," *Appl. Environ. Microbiol.* 69:3777-3783.
Tagg et al. (1971) "Assay System for Bacteriocins," *Appl. Microbiol.* 21:943.
Tellier et al. (1991) "Introduction Stereoselective Du Groupement Trifluoromethyle Dans Des Systemes Insatures," *Tetrahedron Lett.* 32:5963-5964.
Thuault et al. (1991) "Inhibition of *Clostridium tyrobutyricum* by Bacteriocin-like Substances Produced by Lactic Acid Bacteria," *J Dairy Sci* 74:1145-1150.
Tormay et al. (1994) "Genes Coding for the Selenocysteine-Inserting tRNA Species from Desulfomicrobium Baculatum and Clostridium Thermoaceticum: Structural and Evolutionary Implications," *J. Bacteriol.* 176:1268-1274.
Udwary et al. (2002) "A Method for Prediction of the Locations of Linker Regions Within Large Multifunctional Proteins, and Application to a Type I Polyketide Synthase," *J. Mol. Biol.* 323:585-598.
Uguen et al. (2002) "The LcnC Homologue Cannot Replace LctT in Lacticin 481 Export," *FEMS Microbiol. Lett.* 208:99-103.
Uguen et al. (2000) "Lantibiotic Biosynthesis: Interactions Between Prelacticin 481 and its Putative Modification Enzyme, LctM," *J. Bacteriol.* 182:5262-5266.
Vallee et al. (1990) "Active-Site Zinc Ligands and Activated Water of Zinc Enzymes," *Proc. Natl. Acad. Sci. U. S. A.* 87:220-224.
Vallee et al. (1993) "Zinc: Biological Functions and Coordination Motifs," *Acc. Chem. Res.* 26:543-551.
van Kraaij et al. (1999) "Lantibiotics: Biosynthesis, Mode of Action and Applications," *Nat. Prod. Rep.* 16:575-587.
van der Hooven et al. (1996) "The Structure of the Lantibiotic Lanticin 481 Produced by *Lactococcus lactis*: Location of the Thioether Bridges," *FEBS Lett.* 391:317-322.
van der Meer et al. (1994) "Influence of Amino Acid Substtutions in the Nisin Leader Peptide on Biosynthesis and Secretion of Nisin by *Lactococcus lactis*," *J. Biol. Chem.* 269:3555-3562.
Venema et al. (1995) "Functional Analysis of the Pediocin Operon of *Pediococcus acidilactici* PAC1.0: PedB is the Immunity Protein and PedD is the Precursor Processing Enzyme," *Mol. Microbiol.* 17:515-522.
Vrtis et al. (2001) "Phosphite Dehydrogenase: An Unusual Phosphoryl Transfer Reaction," *J. Am. Chem. Soc.* 123:2672-2673.
Vrtis et al. (2002) "Phosphite Dehydrogenase, A Versatile Cofactor Regeneration Enzyme," *Angew. Chem. Int. Ed. Engl.* 41:3257-3259.
Walsh, C. (1982) "Suicide Substrates: Mechanism Based Enzyme Inactivators," *Tetrahedron* 38:871-909.
Wang et al. (1981) "Characteristics of Beta, Beta-difluoroalanine and Beta, Beta, Beta—trifluoroalanine as Suicide Substrates for *Escherichia coli* B Alanine Racemase," *Biochemistry* 20:7539-7546.
Wang et al. (1978) "Suicide Substrates for the Alanine Racemase of *Escherichia coli* B," *Biochemistry* 17:1313-1321.
Wang et al. (1981) "Mechanism-Based Inactivation of Serine Transhydroxymethylases by D- fluoroalanine and Related Amino Acids," *J. Biol. Chem.* 256:6917-6926.
Weil et al. (1990) "Biosynthesis of the Lantibiotic Pep5. Isolation and Characterization of a Prepeptide Containing Dehydroamino Acids," *Eur. J. Biochem.* 194:217-223.
Widdick et al. (2003) "Cloning and Engineering of the Cinnamycin Biosynthetic Gene Cluster from *Streptomyces cinnamoneus cinnamoneus* DSM 40005," *Proc. Natl. Acad. Sci. USA* 100(7):4316-4321.
Wiedemann et al. (2001) "Specific Binding of Nisin to the Peptidoglycan Precursor Lipid II Combines Pore Formation and Inhibition of Cell Wall Biosynthesis for Potent Antibiotic Activity," *J. Biol. Chem.* 276:1772-1779.
Wilkinson et al. (1979) "Isotope Trapping Studies of Yeast Hexokinase During Steady State Catalysis. A Combined Rapid Quench and Isotope Trapping Technique," *J. Biol. Chem.* 254:12567-12572.
Woodruff et al. (1998) "Sequence Analysis of mutA and mutB Genes Involved in the Biosynthesis of the Lantibiotic Mutacin II in *Streptococcus mutans*," *Gene* 206(1):37-43.
Xie et al. (2002) "Heterologous Expression and Purification of SpaB Involved in Subtilin Biosynthesis," *Biochem. Biophys. Res. Commun.* 295:952-957.
Xie et al. (2001) "Homemade Cofactors: Self-Processing in Galactose Oxidase," *Proc. Natl. Acad. Sci. USA* 98:12863-12865.
Xie et al. (2004) "Lacticin 481: in Vitro Reconstitution of Lantibiotic Synthase Activity," *Science* 303:679-681.
Yamazaki et al. (1991) "Preparation and Evaluation of Optically Active 4,4-Difluorothreonine as a Potent Novel Antitumor Material," *Bioorg. Med. Chem. Lett.* 1:271-276.
Zhou et al. (2003) "Chemical and Enzymatic Synthesis of Fluorinated Dehydroalanine-Containing Peptides," *ChemBioChem* :1206-1215.
Zhou et al. (2002) "Biomimetic Stereoselective Formulation of Methyllanhionine," *Org. Lett./* 4:1335-1338.
Zhou et al. (2001) "Synthesis of 2-Amino-3flouro-acrylic Acid Containing Peptides," *Org. Lett.* 3:593-596.
Zhou et al. (1999) "Identification of the Zinc Ligands in Cobalamin-Independent Methionine Synthase (MetE) from *Escherichia coli*," *Biochemistry* 38:15915-15926.
Zhu et al. (2003) "Biomimetic Studies on the Mechanism of Stereoselective Lanthionine Formation," *Org. Biomol. Chem.* 1:3304-3315.
Zhu et al. (2001) "Convergent Synthesis of Peptide Conjugates Using Dehydroalanines for Chemoselective Ligations," *Org. Lett.* 3(8):1189-1192.

* cited by examiner lacticin 481

| | |
|---|---|
| His₆-LctA | His₆-tag-MKEQNSPNLLQRVTRSELDLILGA-KGCSGVIFISHECRMNSHQFVFTCC |
| His₆-LctA(5-51) | His₆-tag-M----NSPNLLQRVTRSELDLILGA-KGCSGVIFISHECRMNSHQFVFTCC |
| His₆-LctA(10-51) | His₆-tag-M---------LQRVTRSELDLILGA-KGCSGVIFISHECRMNSHQFVFTCC |
| His₆-LctA(25-51) | His₆-tag-M------------------------KGCSGVIFISHECRMNSHQFVFTCC |
| His₆-LctA(1-37) | His₆-tag-MKEQNSPNLLQRVTRSELDLILGA-KGCSGVIFISHE |
| His₆-LctA(1-38) | His₆-tag-MKEQNSPNLLQRVTRSELDLILGA-KGCSGVIFISHEC |
| His₆-LctA(1-38)C38U | His₆-tag-MKEQNSPNLLQRVTRSELDLILGA-KGCSGVIFISHEU |
| His₆-LctA-T48S | His₆-tag-MKEQNSPNLLQRVTRSELDLILGA-KGCSGVIFISHECRMNSHQFVFSCC |
| His₆-LctA-C49S | His₆-tag-MKEQNSPNLLQRVTRSELDLILGA-KGCSGVIFISHECRMNSHQFVFTCS |

Figures 8, 9:
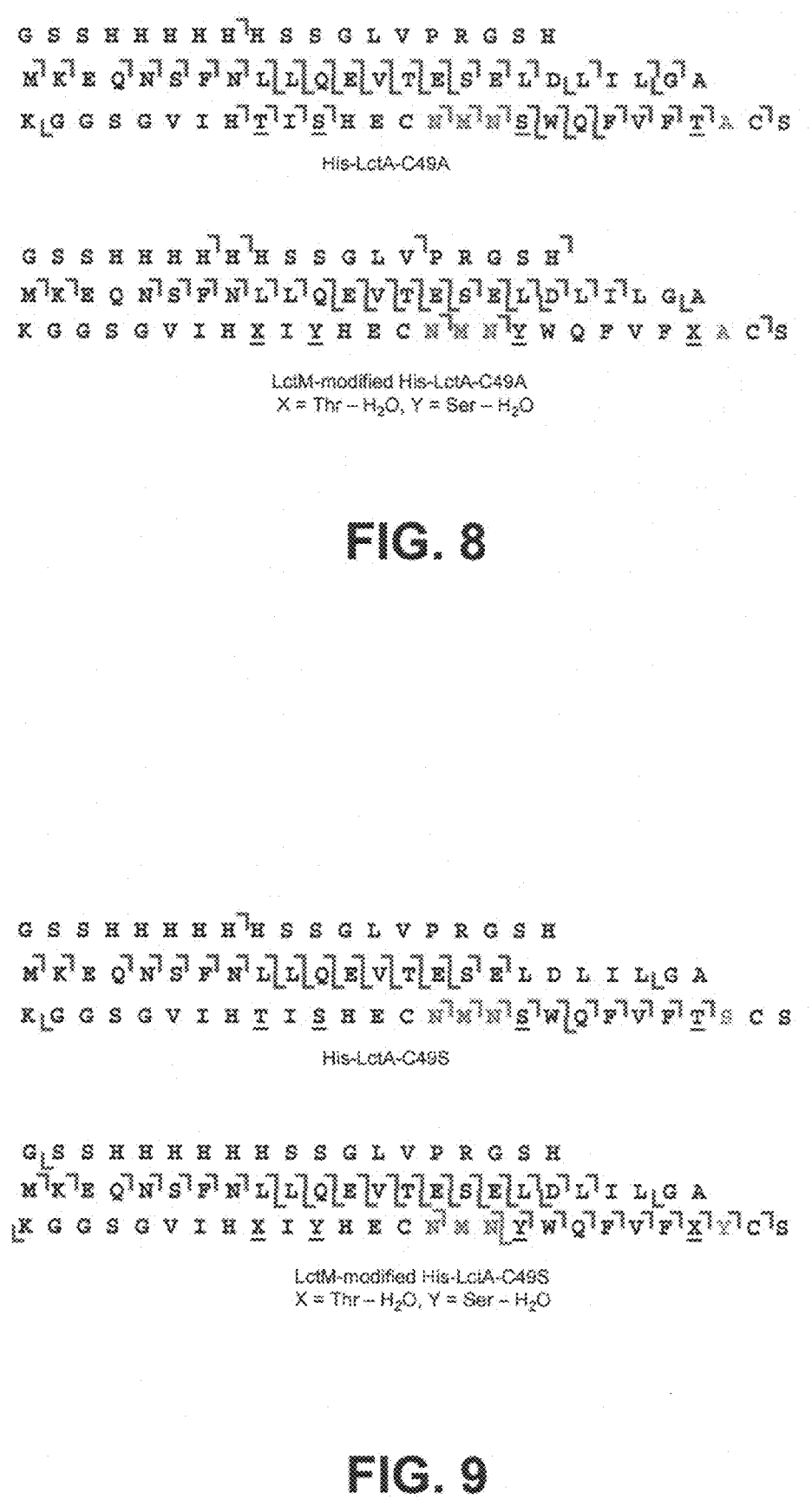

His-LctA-C49A

G S S H H H H H H S S G L V P R G S H
M K E Q N S F N L L Q E V T E S E L D L I L G A
K G G S G V I H X I Y H E C N M N Y W Q F V F X A C S

LctM-modified His-LctA-C49A
X = Thr − $H_2O$, Y = Ser − $H_2O$

His-LctA-C49S

G S S H H H H H H S S G L V P R G S H
M K E Q N S F N L L Q E V T E S E L D L I L G A
K G G S G V I H X I Y H E C N M N Y W Q F V F X Y C S

LctM-modified His-LctA-C49S
X = Thr − $H_2O$, Y = Ser − $H_2O$

FIG. 9 meso-Lanthionine (La)
Methyl Lanthionine (MeLa)
Nisin
Dehydroalanine (Dha)
Dehydrobutyrine (Dhb)
Subtilin

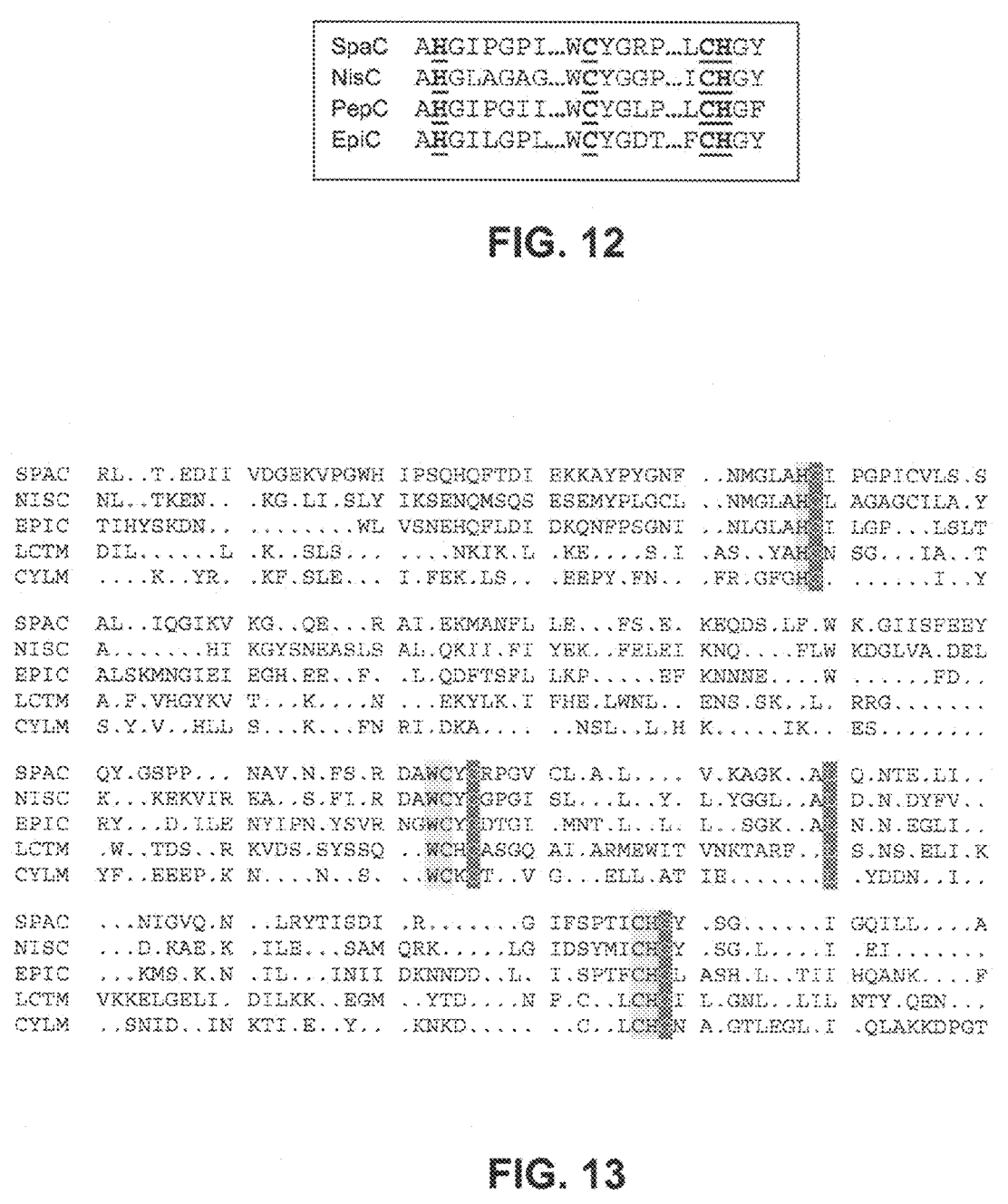

```
SpaC  AHGIPGPI...WCYGRP...LCHGY
NisC  AHGLAGAG...WCYGGP...ICHGY
PepC  AHGIPGII...WCYGLP...LCHGF
EpiC  AHGILGPL...WCYGDT...FCHGY
```

FIG. 12

```
SPAC  RL..T.EDII VDGEKVPGWH IPSQHQFTDI EKKAYPYGNF ..NMGLAHGI PGPICVLS.S
NISC  NL..TKEN.. .KG.LI.SLY IKSENQMSQS ESEMYPLGCL ..NMGLAHGL AGAGCILA.Y
EPIC  TIHYSKDN.. ........WL VSNEHQFLDI DKQNFPSGNI ..NLGLAHGI LGP...LSLT
LCTM  DIL......L .K..SLS... ....NKIK.L .KE...S.I .AS..YAHGN SG...IA..T
CYLM  ....K..YR. .KF.SLE... I.FEK.LS.. .EEPY.FN.. .FR.GFGHG. ......I..Y

SPAC  AL..IQGIKV KG..QE...R AI.EKMANFL LE...FS.E. KEQDS.LF.W K.GIISFEEY
NISC  A.......HI KGYSNEASLS AL.QKII.FI YEK..FELEI KNQ....FLW KDGLVA.DEL
EPIC  ALSKMNGIEI EGH.EE..F. .L.QDFTSFL LKP.....EF KNNNE....W ......FD..
LCTM  A.F.VHGYKV T...K....N ...EKYLK.I FHE.LWNL.. ENS.SK..L. RRG.......
CYLM  S.Y.V..HLL S...K...FN RI.DKA.... ..NSL..L.H K.....IK.. ES........

SPAC  QY.GSPP... NAV.N.FS.R DAWCYGRPGV CL.A.L.... V.KAGK..A[illegible] Q.NTE.LI..
NISC  K...KEKVIR EA..S.FI.R DAWCYGGPGI SL...L..Y. L.YGGL..A[illegible] D.N.DYFV..
EPIC  RY...D.ILE NYIPN.YSVR NGWCYGDTGI .MNT.L..L. L..SGK..A[illegible] N.N.EGLI..
LCTM  .W..TDS..R KVDS.SYSSQ ..WCHGASGQ AI.ARMEWIT VNKTARF..[illegible] S.NS.ELI.K
CYLM  YF..EEEP.K N....N..S. ..WCKGT..V G...ELL.AT IE.......[illegible] .YDDN..I..

SPAC  ...NIGVQ.N ..LRYTISDI .R.......G IFSPTICHGY .SG......I GQILL....A
NISC  ...D.KAE.K .ILE...SAM QRK.....LG IDSYMICHGY .SG.L....I .EI.......
EPIC  ...KMS.K.N .IL...INII DKNNDD..L. I.SPTFCHGL ASH.L..TII HQANK....F
LCTM  VKKELGELI. DILKK..EGM ..YTD....N F.C..LCHGI L.GNL..LIL NTY.QEN...
CYLM  ..SNID..IN KTI.E..Y.. .KNKD..... ..C..LCHGN A.GTLEGL.I .QLAKKDPGT
```

FIG. 13

Left. MALDI-MS analysis of the His -LctA substrate (blue) and the products obtained after incubation with LctM (red). Right. HPLC trace showing major peaks for substrate and product in addition to incompletely dehydrated peptides.

```
                         Protease cleavage site
              Leader peptides              |   structural region
         1   4    9     13      18        24v
51
LctA     -MKEQNSFNLL-QEV  TESEL  DLILGA--KGGSGVIHTISHECNMNSWQFVFTCCS
RumA     ---MRNDVLTLTNPM  EEKEL  EQILGG----GNGVLKTISHECNMNTWQFLFTCC-
VarA     ---MTNAFQAL-DEV  TDAEL  DAILGG----GSGVIPTISHECHMNSFQFVFTCCS
ScnA''   -MTKEHEIINSIQEV  SLEEL  DQIIGA---GKNGVFKTISHECHLNTWAFLATCCS
ScnA     -MEKNNEVINSIQEV  SLEEL  DQIIGA---GKNGVFKTISHECHLNTWAFLATCCS
MutA     MNKLNSNAVVSLNEV  SDSEL  DTILGG-NRWWQGVVPTVSYECRMNSWQHVFTCC
```

FIG. 17

```
LctT    --------------------- MKIVLQNNEQ DCLLACYSMI LGYFGRDVAI HELYSGEMIP    40
ComA    ---------------MKFGKR H-YRPQVDQM DCGVASLAMV FGYYGSYYFL AHLRELAKTT
LcnC    ---------------MKFKKK N-YTSQVDEM DCGCAALSMI LKSYGTEKSL ASLRLLAGTT
PedD    --------------MWTQKWHK Y-YTAQVDEN DCGLAALNMI LKYYGSDYML AHLRQLAKTT
CvaB    MTNRNFRQIINLLDLRWQRR VPVIHQTETA ECGLACLAMI CGHFGKNIDL IYLRRKFNLS

LctT    PDGLSVSYLK NINMKHQVSM HVYKTDK-KN SPNKIFYPKM LPVIIQWNON HFVVVTKIYR    99
ComA    MDGTTALGLV KVAEEIGFET RAIKADMTLF DLPDLTFPFV AHVLKEGKLL HYYVVTGQDK
LcnC    IEGTSALGIK KAGEGLGFVV QVLRADASLF EMKKVPYPFI AHVIKNQKYP HYYVITGANK
PedD    ADGTTVLGLV KAAKHLNLNA EAVRADMDAL TASQLPLPVI VHVFKKNKLP HYYVVYQVTE
CvaB    ARGATLAGIN GIAEQLGMAT RALSLELDEL RVLKTP---- --CILHWDFS HFVVLVSVKR

LctT    KNVTLIDP-- AIGKVKYNYN DFMKKFSGYI ITLSPNSSFT KKKRIS--EI IFPLKKIPKN   155
ComA    DSIHIADPDP GVKLTKLPRE RFEEEWTGVT LFMAPSPDYK PHKEQK--NG LSFIPILVKQ
LcnC    NSVPIADPDP TVKMTKLSKE VFLSEWTGIS LFLSPTPSYQ PTKEKT-SSL LSFIPIITRQ
PedD    NDLIIGDPDP TVKTTKISKS QFAKEWTQIA IIIAPTVKYK PIKESR-HTL IDLVPLLIKQ
CvaB    NRYVLHDPAR GIRY--ISRE EMSRYFTGVA LEVWPGSEFQ SETLQTRISL RSLINSIYGI
```

FIG. 18

Enzymatic Radical Chemistry
prostaglandin synthase (cyclooxygenase)
lipoxygenase
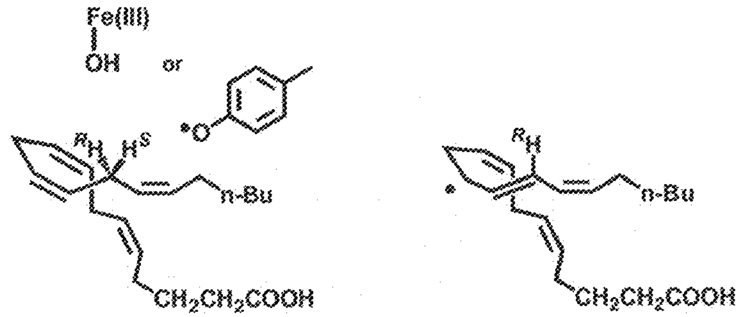
Vitamin $B_{12}$-catalyzed dechlorination of perchloroethylene
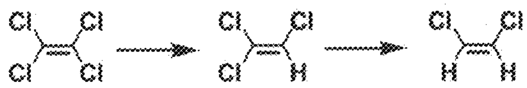
Enzymatic Phosphorus Redox Chemistry
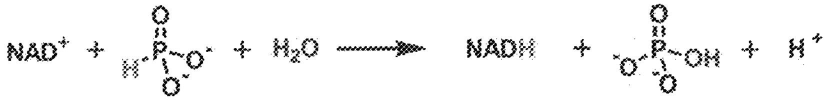
FIG. 19 penicillin

Erythromycin vancomycin microcin B17 nisin

Lanthionine
(Ln)

Methyl lanthionine
(MeLn)

Dehydrobutyrine
(Dhb)

Dehydroalanine
(Dha)

Subtilin meso-Lanthionine

Methyl Lanthionine

Nisin $X_n$ = n amino acid peptide subtilin

| Lantibiotic | Modification enzymes | Shape |
|---|---|---|
| **Class I** | | |
| Nisin | NisB/NisC | Linear elongated |
| Subtilin | SpaB/SpaC | Linear elongated |
| Gallidermin | GdmB/GdmC | Linear elongated |
| **Class II** | | |
| Cinnamycin | CinM | globular |
| Mersacidin | MrsM | globular |
| Lacticin 481 | LctM | globular |

FIG. 27 lacticin 481

MKEQNSFNLLQEVTESELDLILGA-KGGSGVIHTISHECNMNSWQFVFTCCS LctA

GSSHHHHHHSSGLVPRGSH-LctA (His-LctA)

LctA-LEHHHHHH (LctA-His)

GSSHHHHHHSSGLVPRGSH-LctA-LEHHHHHH

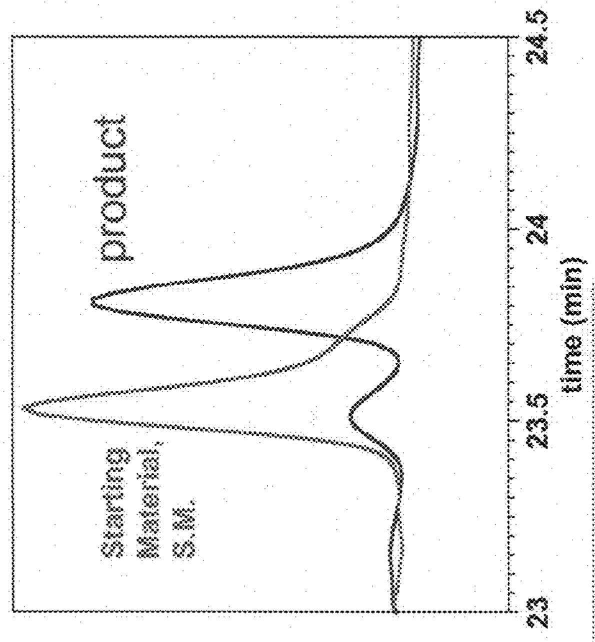
AGLILDLESETVEQLLNFSNQEKM-HSGRPVLGSSHHHHHHSSG
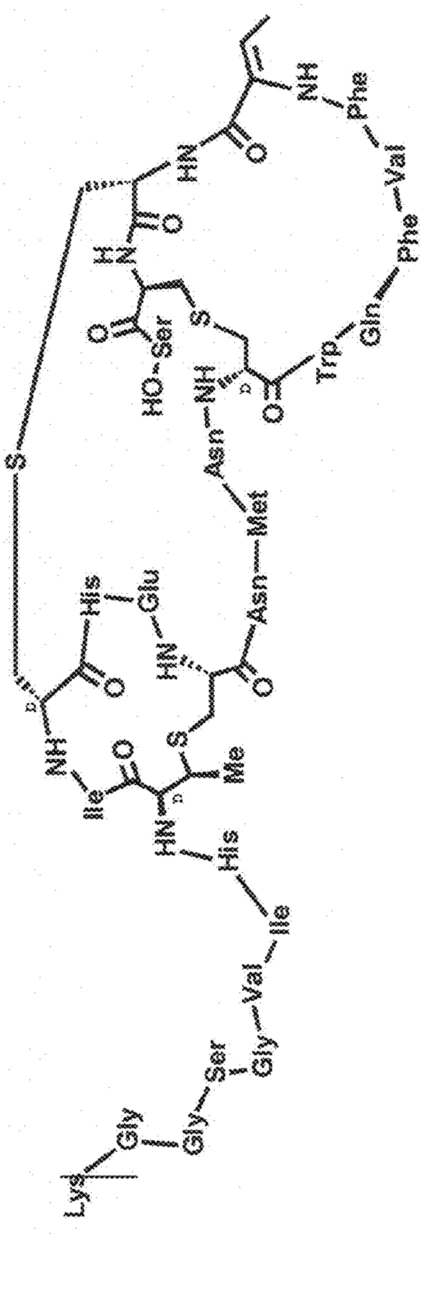
FIG. 35

G S S H H H H H H S S G L V P R G S H

M K E Q N S F N L L Q E V T E S E L D L I L G A

K G G S G V I H T I S H E C N M N S W Q F V F T C C S

Pink symbol - example of fragment seen only prior to cyclization

LctM

LctM is a *bifunctional* enzyme, performing both dehydration and cyclization reactions.

|  | Leader peptide | | | | | propeptide | |
|---|---|---|---|---|---|---|---|
| 1 | 4 | 9 | 13 | 18 | 24 | | 51 |

```
LctA      -MKEQNSFNLL-QEV TESEL DLIILGA--KGGSGVIHTISHECNMNSWQFVFTCCS
RumA      ---MRNDVLTLTNPM EEKEL EQIILGG----GNGVLKTISHECNMNTWQFLFTCC-
VarA      ---MTNAFQAL-DEV TDAEL DAIILGG----GSGVIPTISHECMNSFQFVFTCCS
ScnA''    -MTKEHEIINSIQEV SLEEL DQIIGA----GKNGVFKTISHECHLNTWAFLATCCS
ScnA      -MEKNNEYINSIQEV SLEEL DQIIGA----GKNGVFKTISHECHLNTWAFLATCCS
MutA      MNKLNSNAVVSLNEV SDSEL DTIILGG--NRWWQGVPTVSYECRMNWQHVFTCC-

Consensus      V    EL D ILGG        GV  TISHEC MNTW FLFTCC
                    E   I A                  V   L SF VA
```

↑
Protease cleavage site

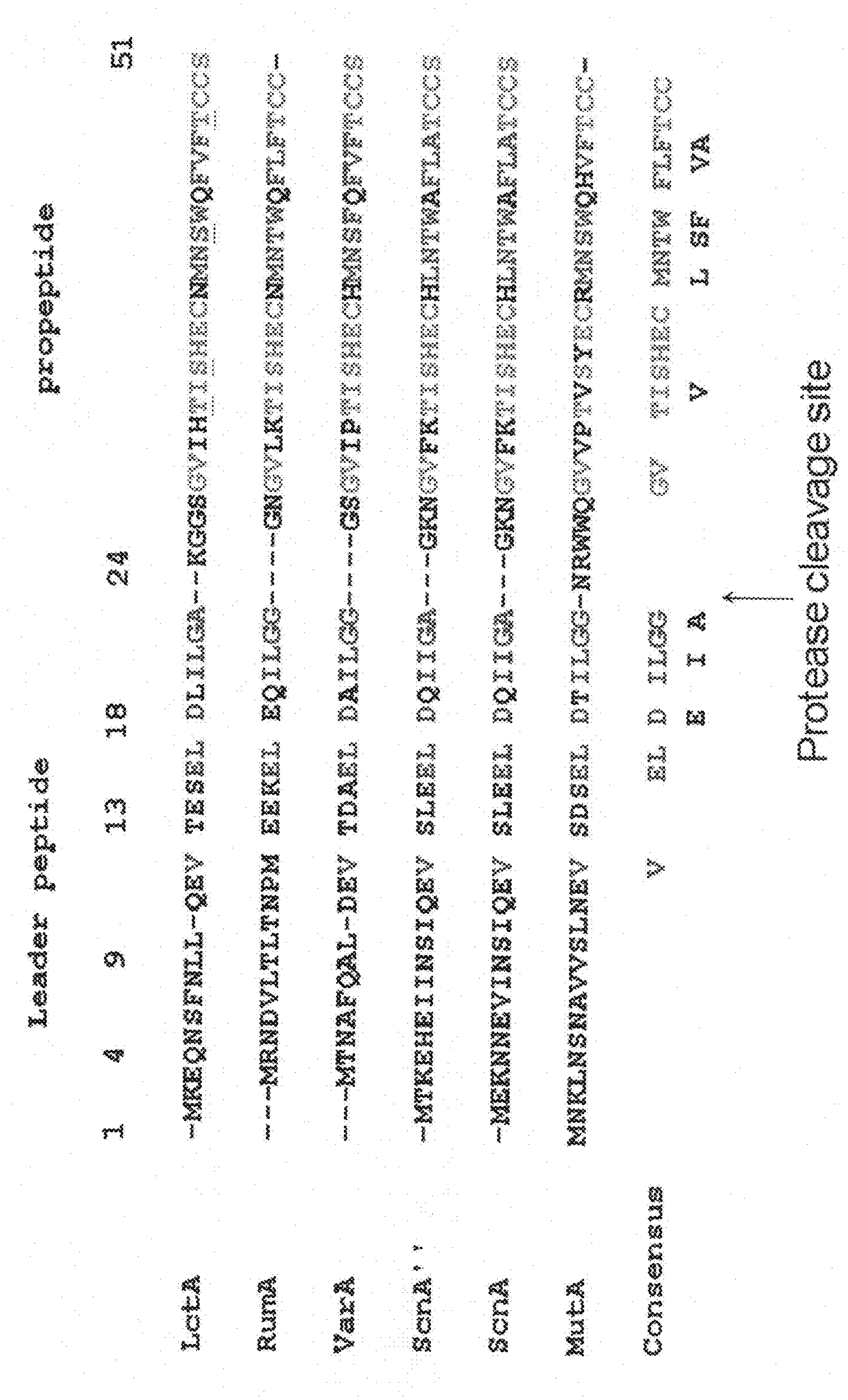

FIG. 40

| | |
|---|---|
| ComA | --------------MKFGKRH-YRPQVDQMDCGVASLAMVFGYYGSYYFLAHLRELAKTT |
| LcnC | --------------MKFKKKN-YTSQVDEMDCGCAALSMILKSYGTEKSLASLRLLAGTT |
| PedD | ------------MWTQKWHKY-YTAQVDENDCGLAALNMILKYYGSDYMLAHLRQLAKTT |
| CvaB | MTNRNFRQIINLLDLRWQRRVPVIHQTETAECGLACLAMICGHFGKNIDLIYLRRKFNLS |
| LctT | --------------------MKIVLQNNEQDCLLACYSMILGYFGRDVAIHELYSGEMIP |
| | |
| ComA | MDGTTALGLVKVAEEIGFETRAIKADMTLFDLPDLTFPFVAHVLKEGKLLHYYVVTGQDK |
| LcnC | IEGTSALGIKKAGEGLGFVVQVLRADASLFEMKKVPYPFIAHVIKNQKYPHYYVITGANK |
| PedD | ADGTTVLGLVKAAKHLNLNAEAVRADMDALTASQLPLPVIVHVFKKNKLPHYYVVYQVTE |
| CvaB | ARGATLAGINGIAEQLGMATRALSLELDELRVLKTP------CILHWDFSHFVVLVSVKR |
| LctT | PDGLSVSYLKNINMKHQVSMHVYKTDK-KNSPNKIFYPKMLPVIIQWNDNHFVVVTKIYR |
| | |
| ComA | DSIHIADPDPGVKLTKLPRERFEEEWTGVTLFMAPSPDYKPHKEQK-NGLLSFIPILVKQ |
| LcnC | NSVFIADPDPTVKMTKLSKEVFLSEWTGISLFLSPTPSYQPTKEKT-SSLLSFIPIITRQ |
| PedD | NDLIIGDPDPTVKTTKISKSQFAKEWTQIAIIIAPTVKYKPIKESR-HTLIDLVPLLIKQ |
| CvaB | NRYVLHDPARGIRY--ISREEMSRYFTGVALEVWPGSEFQSETLQTRISLRSLINSIYGI |
| LctT | KNVTLIDP--AIGKVKYNYNDFMKKFSGYIITLSPNSSFTKKKRIS--EIIFPLKKIFKN |

FIG. 44

His-LctA(1-38)

LctM-modified His-LctA(1-38)
X = Thr – $H_2O$, Y = Ser – $H_2O$

*GSSHHHHHHSSGLVPRGSH* MKEQNSFNLLQEVTESELDLILGA KGGSGVIHTISHE

G S S H H H H H H S S G L V P R G S H

M K E Q N S F N L L Q E V T E S E L D L I L G A

K G G S G V I H T I S H E U

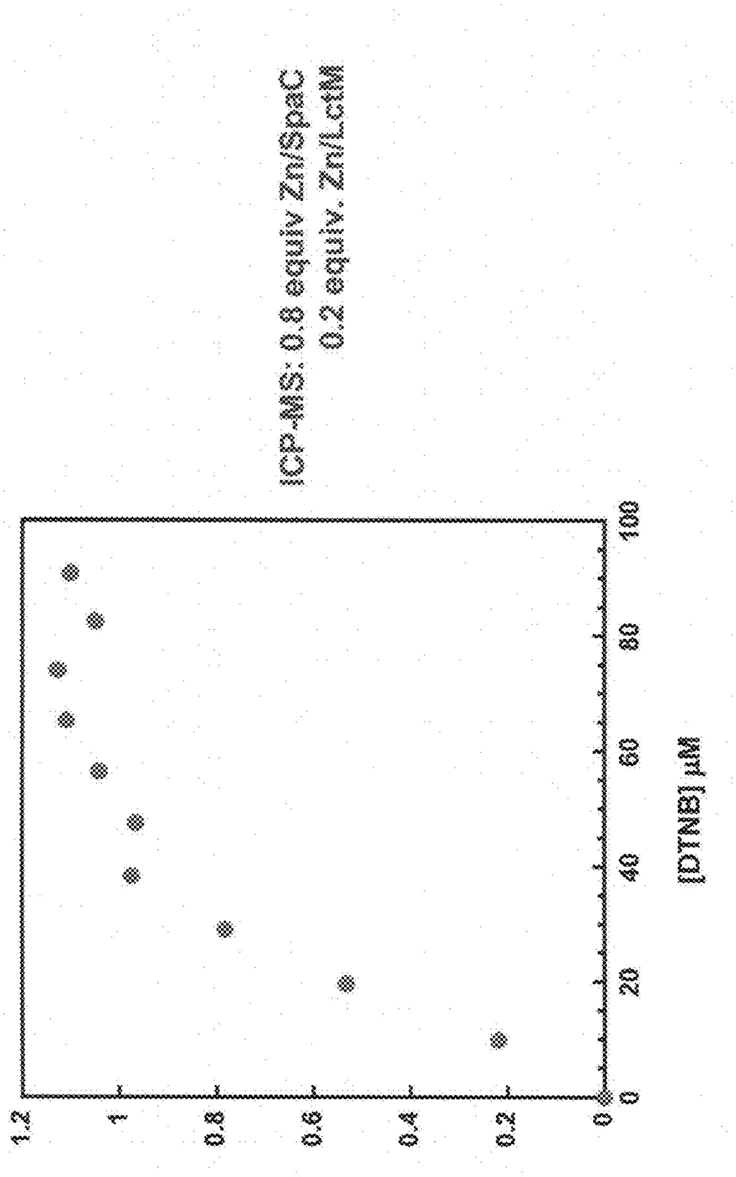
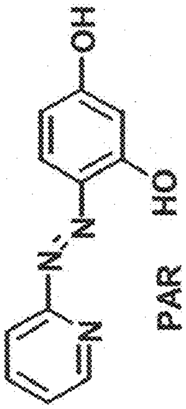
PAR
FIG. 57

```
SpaC QFTDIEKKAY PYGNFNMGLA HGIPGPICVL SSALIQGIKV KGQEAAIEKM ANFLLEFSEK
EpiC QFLDIDKQNF PSGNINLGLA HGILGPLSLT ALSKMNGIEI EGHEEFLQDF TSFLLKPEFK
NisC QMSQSESEMY PLGCLNMGLA HGLAGAGCIL AYAHIKGYSN EASLSALQKI IFIYEKFELE
PepC IKFNNDDYLL DTILSNLGYA HGIPGIINTL CNSYKRGYGI IKTKKILEQS IFTLLQNLKL
LctM ILLKSLSNKI KLKESIASYA HGNSGIATAF ----VHGYKV ---------- -TKNEKYLK-
                     N G A HG  G            G

SpaC EQDSLFWKGI ISFEEYQYGS PPNAVNFSRD AWCYGRPGVC LALVKAGKALQ NTELINIGV
EpiC NNNEWFDR-- --YDILENYI PNYSV---RN GWCYGDTGIM NTLLLSGKALN NEGLIKMSK
NisC IKNQFLWKDG LVADELKKEK VIREASFIRD AWCYGGPGIS LLYLYGGLALD NDYFVDKAE
PepC ENGTIYIP-- ---------N DIESPNDYRD AWCYGLPSVA YTIFNVSSTLK NKSLIELSE
LctM IFHELWNLEN SSKLRRGWTD SRKVDSSYSS QWCHGASGQA IARMEWITVNK TARFLSNSELIKVK
                                   R   WCYG               L  N

SpaC QNLRYTISDI RG----IFSPT ICHGYSGIGQ ILLAVNLLTG QEYFKEELQE IKQ---KIMS
EpiC NILINIIDKN NDD---LISPT FCHGLASHLT IIHQANKFFN LSQVSTYIDT IVR---KIIS
NisC KILESAMQRK LG----IDSYM ICHGYSGLIE ICSLFKRLLN TKKFDSYIEE FNVNSEQILE
PepC SLLHQVFLRS DNATK-LISPT LCHGFSGVVM ISLLMNNNEL SSKYQK---- ------KIIQ
LctM KELGELIDIL KKEGMYTDNFC LCHGILGNLL ILNTYQENFD NKNINLKNE- -------ILN
       L                    CHG       I                            I
```

FIG. 58

Typically used methods:
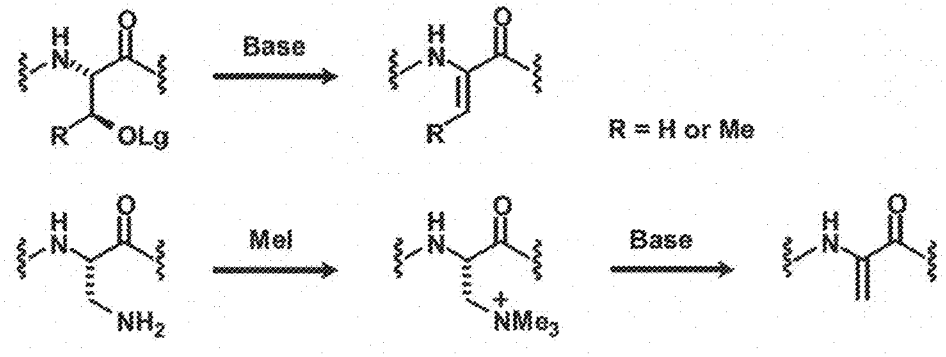
leader peptide
structural region
MSKFDDFDLDVVKVSKQDSKITPQ — WKSESLCTPGCVTGALQTCFLQTLTCNCKISK SpaS
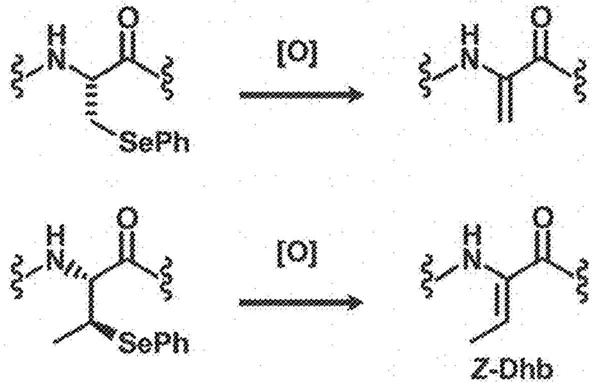
Z-Dhb
FIG. 62

U(Ph)

Dha

| Peptide | Dehydropeptide | Oxidant | Yield (%) |
|---|---|---|---|
| Ac-GLPU(Ph)VIA | Ac-GLPDhaVIA | $H_2O_2$ | 82 |
| Ac-ISVU(Ph)RSTS | Ac-ISVDhaRSTS | $NaIO_4$ | 82 |
| Ac-GGC(StBu)PU(Ph)VIA | Ac-GGC(StBu)PDhaVIA | $NaIO_4$ | 84 |
| LU(Ph)PGC(Trt)VG | LDhaPGC(Trt)VG | $NaIO_4$ | 80 |
| RIAU(Ph)IALC(StBu)K | RIADhaIALC(StBu)K | $NaIO_4$ | 72 |
| AMU(Ph)A | AMDhaA | $NaIO_4$ | 62 |

E-21

2S,3R,6R 2R,3R,6R 2S,3S,6R (22)

2R,3S,6R

Z-21

MNNPLFPEFLSYMKKHDSTVKKSLSFYSENFIDISIFKLFAKALVYLINEKRENQSLIGLTSEEKY
EYFTKHYVLTGIILDEIRTKFPNIVISFHNYFNSLNMLGNQVTSNYLNDHQDLVNLGLVDQSDKIV
SLQVVGDMHNELAVVKVNLTGRSLFYKPHLDNYIVYNEILQLLNSKLPANLKQRQVKSFVSSDHSW
LEEVKRNPLLKENIHNYFSRMGGLIAIAYSLNMTDLHFENIISDGEYPVILDMETICGTTINNNEF
LFTMAQKEVNNKIFDSVLNTGLLPMKGLGSIFGGDVSGMMGGEFTKSFNRIVDNNKDTIHFEKKIE
RLTNMNHLPYYIRNNKEILIKNSPDYLTNIVYGFNSTYDYIQVLKNEIITIIKKYEFLTCRVIFRQ
TAHYSLMLEVLNSPIYQNSKENVLSKLSYSAYSKGVLESEKKQYRWEYPSPTRLNSINILISFNCS
ISSLSPIDNLEIKLSSLSRTDRQFQEKLIRFSLQGNIELYLNPQINLRSSTQNLESNELITRSIND
IKQKIIDNSLVASDGTINWFNVSVGDYDELELEIMDDTIYKGIAGIKLAFLLSSRNFGMSSDKVIL
DRINKSLSFSDYTLNRESFYEGTFGSQLPSYKEISKEDLQNPKQWDALLGASSTIIGIYQNFKINP
TFKEIIEQYADYLVISLQKNSINGYSWFDEEHQDLVNVSFAHGNSGCMTALLISYALLGKSEYLDT
FQKLGKVNKKFMIDCGWEDTRNTDRLSSANWCHGSTGALTSRLLWFKLNKKFNILNEHDIQRVYLE
IDHSVNDIIDKGLSINNFSLCHGIMGNLIALNEYSLAFSNQKIQQLVQSTLISLCSVGMKKDWLCG
VNDLFYNNGLMTGLAGILYGIIKIYYDDNYDQHVLNLSFY

FIG. 70

MHTKFKRNSVWNRSSSISERKVRRSLNTNWDELTNRRFERWKSL
VESDEGIRIEDVLATQNIDEETLKHTINAKEVEFINEGDHQGWLEIIQLVDEQSYKNV
NIEVRKDILFFSFIKPFLKIARGKLEEVLYSHSTKSLIKEELSPSVIDDLLNNLGETL
SAISSRILILELNVARVSGKLRGETSEERASYFNQALLNDPAYVRSIREEYIVLTRLL
ATKTMYWIQNTSDLLVRFHQDKGILESEFSNGQKLGKIISIDTGSGVSDTHNKGKTVA
ILNFETGIKIVYKPRSLEIDVKFNKFVNYLNGKNLSFDLKTVHTLNKKSYGWTQFISY
KECQEELQIGKFYWRIGSYLAILYAMNAVDFHMQNLIADGEYPILVDLESLFHNNSTY
TDTSAFSRAQEHIERSVLRIGLLPRKINSKAGFEGIDLSALGAQEGQVSPHKTSTIVD
RDKDTVRIEEKNFPIPVSQHRPMLHGQIINTVAYEGNIIKGFEETYFLFMKYKQDMLE
QIDSFKGVTVRQILRGTSRYANLLKISLHPDFMRDGLDREMILDKLWLDTKLNPRLNQ
VVNSEKEGLFLGDIPYFTSKPESTNMWDSSGRKINNFFKTSALNETKEKINEMNESDC
HEQVSFIKTAILVIKDSYRKHKVFDINPRLHVFNPKDFFQEAIKIGDFLASRAIEGEQ
LDGQEDVSWIGSFVDNQREDQFKISAANSSLYEGVGGISLFLAYLGRLSNNEKYTKLS
KKALVAVHKNMSASSDLGAFGGIASYLYLLDHLSKLWNDEQLLKNELYSALNKLDSLI
ERDENNDILTGVAGTAVILINLFKRYKEEQILNLITKCGNRLIQNINVMEKGVGWKVP
ANPTPASGFAHGASGIIWALYEIYAITKQTVFKEVAEKALEFERTLFIPEKNNWADIK
LENGQFRNDNFVAWCNGAAGIGLSRILILPHNQNELIKDEAHVAINTTLKYGFEHDQS
LCHGDLGNLDILMYAAENFNKKLSVNVTELSHKILNDIKLRGWLTGFEKNNESPSLMM
GYAGIGLGLLKIFAPVEVPSVLRLQSPLELKL

FIG. 71

MGMGNAYPLDIAARAANLTERLRVVAAAGGEAAVRDNTVELDAF
DRWKADTLAGKLADKFHQESLHRGRPPQHTKDELAGVLSAYRRLELGLDTADDDVRTL
LGELQSAWLPAYRAALDAHDAARDDERADAQPGEEPGWRGFDVYYGRLAKACEPFLRE
LGRGLGAARDAAQGEGAALSPQLAEDIQRHLLDRFELSLAWAVEADANVHCTQAGIDK
AEATREDYLAYLDTTFSDSAAYHRFYLKFPVLGRWLAHTTALLTAFGRDLFDSLAADA
EAIGTEFFGQPVTAFTSLRLGDSDPHAGARTVARVAVVLADGRTGEFFYKPRSVRSEA
ALQDVLARLADDGVVDFATRPVLPRDGYGYEALIPAGRNRVETPEEVTRIYRELGGYL
ALFYVLGGSDLHFENVIVADGHAFVCDAETVLGVHPQGRAQSEGTLLDSVFKTGLLEW
PRAASPGEEAAAEMRISGYAGGEGYDVPVPVARRTGEGLTFAASVVHKTGVHVETSAS
NRVYLGEELVRPEDHVESIMEGFNRVYDWFAEDPDASVDYLMETFSWVTARFINWGTQ
IYAQLLSAARHPRCLTEPLEVDLLANTVRTFPRTWDAEGVLAGREVAAMWQMDVPLFT
AAAHARQLVHGHGDPLSARLDSSPIDHAAARIRRLSQRNREQQSQYIAASLSTGEISS
PAFVATSLDYAARIGDRLCDELRAPAAPAPWTSYQLSGESLAEVDIEADLYQGSAGVV
LFLAYLDQLVPRPAYRKAARQALDHVLVHWDRDRLGAFAGLGGVVYLLTHLHRLWGDE
ELLDLAVRLSDELPARIDEDRHFDILHGAAGLIPVLLGLAQETGGHGIEHAHRCAEHL
LRHAEDDGTTLSWPPSAADETYGNLTGFSHGSGGIGWALIQLGRHTGRSDYIEAGRKA
FAYEDRHVDEQEKDWYDLRINNGSAVKGARHFSNAWCNGAAGIGLARISSWAALDRSD
EQLLRDAQQALSATLRNFPRLKNHTLCHGTSGNAELLLRFARLSDEPAFQLEANVQVQ
ALWRSLDEAGGGAGGGSADFFPGLMIGISGFGMHFLRLAAPDRVPSVLLLDPPSHHEQ

FIG. 72

MNPKELLYSQFDRFPKVVIENNFPELLNESSELIKDVEDEISDY
YRSTLIYLINEKRIEKNLIGDSPESRYEYFNNVLCQNGLIFEEIDRRFPSINQRVMST
IKKCLELINFVKERFTLDFKELRETGYIYSEAQTPKISEVKIKITGDIHNGCGVCILS
YEEQKVVFKKKSSNPNVLLHELNIEVGKFLQKDIDFIPDFLDKGEYFWEKFVSSSPLR
TEEDAKEFYRRMGYLLSYSYILNISDLHFENLISTSFSPKLVDVETVFSVSPYQTVAN
NESTLEIINNSRNSILSTGLLPVSEAGKVFGGDTSGVLGGTLIGEAKIVINHNRDDIH
VEKQKFKTENQDHLPYFIDSKGMKEFLNAEDYVEYIKEGFREVSYFFMNSQDFLKKLY
IKHNDIKTRILFRNTRDYSLVRQLLVSPVYCEQSEILFETMANKLSEQNSRSLCLSEK
KQLLNMDIPYFYSNIDSCDIKDENMIIWNLESSALSEAINKLEKLSEEIINEQIELIE
FSIKTPKALYSTELQEAYQKFEKVSSSENIIKTGIDTLVDIILENESNSLKDDSTNWL
TLKVTDYDAFELVPMDDSLYEGLSGIAISLSEAYDFLDSGRQRRVKECLKRIFSVLSN
SYMKLPNHSFFVGKLGIYSALKRISVVTGQEIQNSIMNYNNLKYTLDVDVLSADFLSS
FPNEITALRNSDIKIDNLTQALDKLKELAIVQKDFISWDKLESNNVSLAHGNLGVEIA
LLYLAGKLESPEALNLFHKAKMFDKHQKLENGWIDKRNSSTSANWCHGSTGVLVARLA
QLKLDDEYSLLSYSERIELENDMKHAAKQILEIGFDMTNFSLCHGTSGNLLALTYYQS
YLTGADSEKLKEILDREYRKLHSFGLENGWMCSFNTKYNVYGLMTGVSGILFSTVKYM
KGDDSLDVLIPNF

FIG. 73

MHKKFCGLYIEYIFEYIIETLKEKEDYLFDSEKIKYVKEIIEKE
IFQRVFKSLLYCMNVERLDGNLSGNTPEERYEMFSNTRYCIEAMGKNFPTMRNQIYDE
MAHKCVYVMEVIRELENNKNKIGRHFGINPGEIVQVQNSGDWHDSECVLIFTFQSQDK
IVYKPTRGENLQFMKGFMDYFFEPEYAEQYIGLCIRKGTWVKFVKHIELTNSRNVERF
YYNYGKVLFVAYILGMNDIHYENLIACGEYPVITDVETIFSSYLFFDTHTFLYDAQYK
AVKELLYGTMATGMLPIFSMTDYFGGDVSCLSNKGIQLIVEKIKNEYRDDMYICTAPE
MIVEYKHLPNHTIDPLMYGKQIVQGFEEAENNFGEKKVEIINYILNNMGKVESRIILN
MTKGYSKIVRIKSDPRYRHEPELFGHLLTTLKRTNQFNPEVYEQEVTELCRSNIPSFY
WKMDMNCVYGLNLGQKKKILDLPIFTKERLSEILEYQINIQMLEKQKQLIYDAIVSNI
ALGIEYEKLKISVKQHVDIHVKKVLRRNIDQNCIVGSDGTISWLGLMVNDKEQLEYAM
LDWSLYSGIIGLGYMYISEYDKEPDVLAKDMLQRIFCTLAKSYDLGVFKEYDISYFCG
LTGIYAFLKQIKDRNIIEPDIIEKYIKNIQEAIRNNIVKTSSYDTLAGIHSAVIYYFG
CYEQDIFSREILSSIEEYFLNSFKIDDMKRNFNYASFAHGYSGVMTSIMCMLQHKYDI
KLEKILCELWKEEKELYVEKFIWKDMRAHHIVHSHYWCHGSVGIMMARLIWKKFGFDK
KFAEDIEEENLEEILSKYKEELLNKKFQSKNYSLCHGNFALIDFLISYRKIVGTDERI
DAYIEEIIESGQENGYSCVGAPGAINSIGFMVGEAGIQYTENRSENSKLHSVLMLETV

FIG. 74

MNNIKVEQFRGFSNFILKKYSKQELNTLIDWNYLRSIILDICGK
SLIVLINEKRLNKKLNGNTPEERYKYFDEELCEKGIIYEELNKSYPSIINDLEQTLNS
YFSFLKEIENKFNQEKKKLLEANLIKTEKETICHISILGDLHGGKAVTKVTTDKSQLL
YKPRSLENDSFFLEFLEFMYSFQKNEISTYYKYKFIDYKDHGWMEYIEKQPTSKNKIN
MYYKRLGYLLSIGYLLNISDLHFENILCSSNFPILIDLETIFHTSIYESKFRNLATKN
IEDKAANSVFATGMLPISKKDKKYGGDISGILGGVFNKHERTISNPNRDDIKFEKRLV
RVKRNDHIPFYMENDKKRRFSPEVFIEDIQEGFKYGYELFLNNRKEILHYIKKTSSEV
EVRILPRSTIEYSVLIQAAKSPLYANKRKSLFNKLEEYGENLLSDKLINSEIKQIETL
SVPYFYTKVQSVSVKDIKNNTVHHLLKNPLNVFLEKTQRYSLKDLLFQCKLIKFSLES
QNKLFIDGNGFINYGYEIVNSDNIDDAIDNLVSIIINNAVIDEKDGSVNWMNLGISKG
EEIIFESLSDDLYKGLSGIGIALLKYYEINKNLKDMSRLKKILSSIYSSILSNINTNS
SKEKDLSFFNGEIGKIAFLYNYQIEFKENCDSSKNYMKHILGIILSSEFEMNDIIAGL
PGIISYLYNQEIFSKELVIMGDRLLKDLDNNPTMAYYAHGKSGVMVSLLYLYDLTKDK
KYLVKFHQEWKKENTLKLEIGWKDVRQNEETYSVSWCNGVTGQLISRLVALEIHDKVK
IFDAVNKKLMQKEIEELLYLLKEEGLEQNNFCLCHGVMGNLLVLNYYQKKFENTNIHL
ANKIDSHFYSVANFGLNKGWICGLGNNFYSFSIMTGISGILYAFLKYKTKDTELGILL
PNI

FIG. 75

LtnM1

MKFNKNVFPEINETDFDNNIKPLLDELESRITIPQEELSFSSIN
DDLFRELTRNEEYPYQSICTIVANIVMDDGSEIWRKDIFVDSNSVREAVCDILSQTLF
LYFIRCFSEQIKDIRKTDEDKESTYNRYINLLFSSNFKIFSDEYPVLWYRTIRIIKNR
WYSIKKSLLLTQKHRVEIDKQLDIPHKMKIKGLKIGGDTHNGGATVTTIFFEKGYKLI
YKPRSTSGEFSYKKFIEKINPYLKKDMGAIKAIDFGEYGFSEYIECNTDEEDMKQVGQ
LAFFMYLLNASDMHYSNVIWTKQGPVPIDLETLFQPDRIRKGLKQSETNAYHKMEKSV
YGTGIIPISLSVKGKKGEVDVGFSGIRDERSSSPFRVLEILDGFSSDIKIVWKKQQKS
SSSKNNLIVDHKKEREILQRAQSVVEGFQETSKIFMKHREEFISIILDSFENIKIRYI
HNMTFRYEQLLRTLTDAEPAQKIELDRLLLSRTGILSISSSPYISLSECQQMWQGDVP
YFYSKFSSKSIFDTNGFVDEIELTPRQAFIIKAESITNDEVDFQSKIIKLAFMARLSD
PHTTNDNKLNKKVIIESNQQSNSSESGNKAILFLSDLLKNNVLEDRYSHLPKTWIGPV
ARDGGLGWAPGVLGYDLYSGRTGPALALAAAGRVLKDKDSIELSADIFNKSSQILQEK
TYDFRNLFASGIGGFSGITGLFWALNAAGNILNNDDWIKTSNQSMLLLNENMLKVDKN
FFDLISGNSGAIGMMYLTNPNFYLSRSKINDILLTTDCLITEMEKDETSGLAHGVSQI
LWFLSIMMQRQPSSEIKIRATIVDNIIKKKYTNSYGEIECYYPTDGHSKSTSWCNGTS
GILVAYIEGYKANIVDKSSVYHIINQINVEQLQHDNIPIMCHGSLGVYESLKYASKYF
EIETKYLLDVMRNGGCSSQEVLKYYGKGNGRYPLSPGLMAGQSGALLHCCKLEDNDIS
VSPISLMT

FIG. 76

LtnM2

MDPSIKKLVDSIIEFYKKDIYLAYKELEREIKNIDKTIYNTSND
EILRIFKESLISIITDDIYRLSIKTFIYEFHKFRIDNGFPAVKDSESAFNYYISTFDV
KTIARWFEKFPMLESIISSSIKNDCTFMVDVCVNFILDLSECEKINLISEDSRLITIS
SSNSDPHNGGTRVLFFRFHNGDTILYKPRSLTVDKLISNIFEEVFEFDATNSKNPIPK
VLDRGTYGWQEFIEKKSISSSEIKQAYYNLGIFSSIFTVLGSTDIHDENLIFKGTTPY
FIDLETALSPRIRYEGNEENLFYRMSSSLFTSIVGTTIIPAKLAVHSQEIMIGAINTP
AKQKTKKDGFNIINFGTDAVDIAKQNIEVERIANPMRIKNNIVNDPLPYQNIFTRGFK
EGIKSIILKKGSIISILNNFNSPIRYIMRPTAKYYLILDAAVFPENLYSEQTLNKTLN
YLKPPKIVENSLISKQLFLAEKRILSEGDIPSFYVLGKEKNIRAQNFISEQIFEETAV
DNAIQILESISQDWVNFNERLIAEGFSYIREQSRGYLSSDFENSDIFKSSLTETKKSG
YTAMLKTIISMSVKTSENKKIGWLPGIYDDYPISYMSAAFCSFHDSGGIITLLEHHFG
HCSPEYNEMKRGLLELGKMLKINNSNLSIISGSESLEFLYTHREVECLELEYILNNSA
EIMGDVFLGKLGLYLILASYLKTDLKIFQDFSIICQKNLEFKKFGIAHGELGYLWTIF
RIQNKLKNKNACLSIYHEVLNIYKGKRIESVGWCNGLSGILMILSEMSTVLEKNQDYL
FKLANLSTKLNEESVDLSVCHGASGVLQTLLFVYSNTNDKRYLSLANKYWKKVLDNSI
KYGFYNGERDKDYLLGYFQGWSGFTDSALLLDKYNNNEQVWIPINLSSDIYQHNLNNC
KEKNYEGDGCHKS

FIG. 77

MKKKTYQFEKFLKNTFDQFSIKQNEVLVEDDLNDIIMNVCGKAL
VLMINEKREMNLLMGNTPEERYQYFENEYSSTGKAFEEIKDKFPVIYIDLKNSINSYL
KLVSQIMKDFKKDYSLLVERKIIEEHSTISTMKIKGDLHNGKAVIEITTNKSKLIYKP
KSLSNDVFFNNFLKYMDSFFIKEGKSTKYKENFYLVNTLDMKTYGWVEYVDKKPINSF
EEARNYYRKIGVLLSVAYTLNLTDLHFENVISQGENPCIIDLETMFNMPMFVKDYKNE
SRNIINGKIMDSVVSTGMLPVLGIDSLFGGDPSGILGGTFSKEERVIINPFRDDIKFQ
KIVVRSVFKDHIPFFNNNNEKRYCKPKDYVNDIIKGFEKTYKIIVKNKEKILGFLKKE
SSSVTCRILFRNTMEYSVLLNAAKSPVYSNKREEIFEKLSTFNRGLGNDIIKSEISQI
NTLSIPYFNCQVDSNLIKNMDGETIFEHTLTPFKCFLSKYRRLCVDDMEQQVKLIRFS
IQSQEQLFKDGEQFSLYKKQKGSQEDLLIAINELSSILENNAYIGTSDDTINWMSLGI
ADNDQILFESLENDIYKGISGIGLALLEYYEFYPNINTKKILKLIYKNISKDFINTNN
EPQNYGFYVGLIGEYSFLRKYEKVFHKTSSCNILKNILKDFTPEKCQTILPSDDVIAG
EAGIIIYISNLNNYLEYRDEIDILLKSLSNKIKLKESIASYAHGNSGIATAFVHGYKV
TKNEKYLKIFHELWNLENSSKLRRGWTDSRKVDSSYSSQWCHGASGQAIARMEWITVN
KTARFLSNSELIKVKKELGELIDILKKEGMYTDNFCLCHGILGNLLILNTYQENFDNK
NINLKNEILNNYYSVCNYGLNKGWICGLGTEFYSYGLMTGISGILYGLIRQVKQKNNF
GVLMPYVD

FIG. 78A

MGSSHHHHHHSSGLVPRGSHMAS

FIG. 78B atg ggc agc agc cat cat cat cat cat cac agc agc ggc ctg gtg ccg cgc ggc agc cat atg gct
agc

FIG. 79A

```
  1 atgaaaatag ttttacaaaa taatgagcag gattgtttgc tagcatgcta ttcaatgata
 61 ttgggatatt ttggtaggga tgttgcaata catgagcttt atagtgggga aatgatcccg
121 cctgatggct tgtctgtttc atatttaaaa aatattaata tgaagcatca agttagtatg
181 catgtttata agactgataa aaagaattct ccaaataaga tattctatcc aaagatgctg
241 cctgtaatta tacaatggaa tgataatcat tttgttgtag taactaagat ttacagaaaa
301 aatgtaacac tcattgaccc tgcaataggt aaagtgaagt ataactataa tgattttatg
361 aaaaaatttt ctggttatat tattacttta tcaccgaata gttcttttac aaagaaaaaa
421 agaataagtg aaattatctt tccactaaaa
```

FIG. 79B

MKIVLQNNEQDCLLACYSMILGYFGRDVAIHELYSGEMIPPDGLSVSYLKNINMKHQVSMHVYK
TDKKNSPNKIFYPKMLPVIIQWNDNHFVVVTKIYRKNVTLIDPAIGKVKYNYNDFMKKFSGYII
TLSPNSSFTKKKRISEIIFPLK

FIG. 79C (atg) ggc agc agc cat cat cat cat cat cac agc agc ggc ctg gtg ccg cgc ggc agc cat

FIG. 80A

```
  1 atgaaagaac aaaactcttt taatcttctt caagaagtga cagaaagtga attggacctt
 61 attttaggtg caaaaggcgg cagtggagtt attcatacaa tttctcatga atgtaatatg
121 aatagctggc aatttgtatt tacttgctgc tcttaa
```

FIG. 80B

```
   1 gtgaaaaaaa agacttacca atttgaaaaa tttttaaaaa atacttttga tcaattttct
  61 attaagcaaa atgaagttct ggttgaagat gatttaaacg atataattat gaacgtttgt
 121 ggaaaagcac ttgttttgat gataaatgaa aaaagagaaa tgaatctatt aatgggcaat
 181 acaccagagg aaaggtacca atattttgaa aatgagtatt cgagtacagg taaagctttt
 241 gaagaaataa aagataaatt tccagtaata tatattgatt taaaaaattc tataaattct
 301 tatttaaagt tggtttcaca aataatgaaa gattttaaaa aagattactc acttctagta
 361 gaacgtaaga ttattgagga acattcgact atttcgacta tgaaaataaa aggtgattta
 421 cataatggga aggctgttat agaaattact actaacaaaa gtaaattaat ttataaacca
 481 aagtcattaa gtaatgatgt gtttttaac aatttttga agtatatgga tagttttttt
 541 attaaagagg gaaaaagcac taaatataaa gaaaattttt atttggtaaa cacgcttgat
 601 atgaagacat atggatgggt tgaatacgta gataaaaaac caatcaattc atttgaggaa
 661 gcaagaaatt attatagaaa aattggagta cttttatcag ttgcttatac tttaaattta
 721 actgacttac attttgaaaa tgtgatctca caaggagaaa atccttgtat tattgaccta
 781 gagactatgt ttaacatgcc tatgtttgta aaagattata aaaatgaatc tcgtaatatt
 841 attaatggaa agattatgga ttcggtagtc tcaacaggaa tgttaccagt cttaggaata
 901 gatagtttgt ttgggggga tcctagtgga attttaggtg gtacattttc taaagaagaa
 961 cgagtgatca taaatccatt tagagatgac ataaaatttc aaaaaatagt tgtacgatct
1021 gtattcaaag atcatattcc tttttttaac aataataatg agaaaagata ttgtaagccc
1081 aaagactatg ttaatgatat tataaaggg tttgaaaaaa catataaaat aatcgttaaa
1141 aataaggaaa aaatattagg gtttctaaaa aaagaatcta gtagtgttac ctgtagaata
1201 ttatttagaa atacgatgga atactcagtt ttattaaatg cagcaaagtc gcctgtatat
1261 tcaaacaaaa gagaagaaat ttttgaaaaa ttatcaactt ttaatcgagg acttggaaat
1321 gatattatta aatcagagat aagtcaaata aacactttat caatccccta tttcaattgt
1381 caagtagact caaacttaat aaagaatatg gatggagaaa caatatttga gcatactctc
1441 accccattca aatgtttcct atcaaaatat agaagactgt gtgtagatga tatggaacaa
1501 caagttaagc taatccgatt ttcaattcaa agtcaagaac agctttttaa agatggggaa
1561 cagttcagtt tatataagaa acaaaaaggt tcacaagaag atttattgat tgcgataaat
1621 gagctttcaa gtatcttaga aaacaatgca tatattggta caagcgatga taccataaat
1681 tggatgagtt taggaattgc tgataatgat cagatactct ttgaaagtct tgaaaatgat
1741 atatataagg gaatatcagg aataggctta gccttattgg aatattatga attttatcca
1801 aatatcaaca caaaaaaaat actaaaatta atatataaaa atatatcaaa agattttatt
1861 aatacaaata atgagcccca aaattatgga ttctatgttg gcttaatagg tgagtatagt
1921 tttttgagaa aatacgaaaa agtatttcac aaaacaagta gttgcaacat tttaaagaac
1981 attttaaaag attttactcc cgagaagtgt caaacaatac taccttcaga tgacgtaata
2041 gccggagaag cgggaattat tatttacatt tcaaatctca ataattacct agaatacaga
2101 gatgaaattg atattctatt gaaaagttta tcaaataaga taaaattaaa agaaagtatt
2161 gcaagttatg ctcatggtaa tagtggtata gcaacagctt ttgtacatgg atataaggtt
2221 actaaaaatg aaaaatatct taagatattc catgaacttt ggaatttaga aaattctagt
2281 aaactgagaa gaggttggac agattcaaga aaagttgata gttcatactc ttcacagtgg
2341 tgtcacggtg catcgggaca agctatagca agaatggagt ggattactgt aaacaaaaca
2401 gctagatttc ttagtaactc tgaactaatt aaggttaaaa aagagctagg ggaattaatt
2461 gatatcttaa aaaaagaggg aatgtataca gataattttt gtctatgcca tggtatttta
2521 ggaaatctat taattttaaa tacctatcaa gagaatttg ataataagaa tatcaatcta
2581 aagaatgaaa ttttaaacaa ctattactct gtttgtaact atggtttaaa taaaggatgg
2641 atttgtggct taggtacaga attttattct tatgggctta tgacaggaat atctggtata
2701 ttatatggac tgattcggca agtaaaacaa aaaaataatt ttggagtctt aatgccatat
2761 gttgattaa
```

FIG. 81

```
   1 atgaaaaaaa agacttacca atttgaaaaa tttttaaaaa atacttttga tcaattttct
  61 attaagcaaa atgaagttct ggttgaagat gatttaaacg atataattat gaacgtttgt
 121 ggaaaagcac ttgttttgat gataaatgaa aaaagagaaa tgaatctatt aatgggcaat
 181 acaccagagg aaaggtacca atattttgaa aatgagtatt cgagtacagg taaagctttt
 241 gaagaaataa aagataaatt tccagtaata tatattgatt taaaaaattc tataaattct
 301 tatttaaagt tggtttcaca aataatgaaa gattttaaaa aagattactc acttctagta
 361 gaacgtaaga ttattgagga acattcgact atttcgacta tgaaaataaa aggtgattta
 421 cataatggga aggctgttat agaaattact actaacaaaa gtaaattaat ttataaacca
 481 aagtcattaa gtaatgatgt gtttttttaac aatttttttga agtatatgga tagttttttt
 541 attaaagagg gaaaaagcac taaatataaa gaaaattttt atttggtaaa cacgcttgat
 601 atgaagacat atggatgggt tgaatacgta gataaaaaac caatcaattc atttgaggaa
 661 gcaagaaatt attatagaaa aattggagta cttttatcag ttgcttatac tttaaattta
 721 actgacttac attttgaaaa tgtgatctca caaggagaaa atccttgtat tattgaccta
 781 gagactatgt ttaacatgcc tatgtttgta aaagattata aaaatgaatc tcgtaatatt
 841 attaatggaa agattatgga ttcggtagtc tcaacaggaa tgttaccagt cttaggaata
 901 gatagtttgt ttgggggga tcctagtgga attttaggtg gtacattttc taaagaagaa
 961 cgagtgatca taaatccatt tagagatgac ataaaatttc aaaaaatagt tgtacgatct
1021 gtattcaaag atcatattcc ttttttttaac aataataatg agaaaagata ttgtaagccc
1081 aaagactatg ttaatgatat tataaaaggg tttgaaaaaa catataaaat aatcgttaaa
1141 aataaggaaa aaatattagg gtttctaaaa aaagaatcta gtagtgttac ctgtagaata
1201 ttatttagaa atacgatgga atactcagtt ttattaaatg cagcaaagtc gcctgtatat
1261 tcaaacaaaa gagaagaaat ttttgaaaaa ttatcaactt ttaatcgagg acttggaaat
1321 gatattatta aatcagagat aagtcaaata aacactttat caatccccta tttcaattgt
1381 caagtagact caaacttaat aaagaatatg gatggagaaa caatatttga gcatactctc
1441 accccattca aatgtttcct atcaaaatat agaagactgt gtgtagatga tatggaacaa
1501 caagttaagc taatccgatt ttcaattcaa agtcaagaac agctttttaa agatggggaa
1561 cagttcagtt tatataagaa acaaaaaggt tcacaagaag atttattgat tgcgataaat
1621 gagctttcaa gtatcttaga aaacaatgca tatattggta caagcgatga taccataaat
1681 tggatgagtt taggaattgc tgataatgat cagatactct ttgaaagtct tgaaaatgat
1741 atatataagg gaatatcagg aataggctta gccttattgg aatattatga attttatcca
1801 aatatcaaca caaaaaaaat actaaaatta atatataaaa atatatcaaa agattttatt
1861 aatacaaata atgagcccca aaattatgga ttctatgttg gcttaatagg tgagtatagt
1921 tttttgagaa aatacgaaaa agtatttcac aaaacaagta gttgcaacat tttaaagaac
1981 attttaaaag attttactcc cgagaagtgt caaacaatac taccttcaga tgacgtaata
2041 gccggagaag cgggaattat tatttacatt tcaaatctca ataattacct agaatacaga
2101 gatgaaattg atattctatt gaaaagttta tcaaataaga taaaattaaa agaaagtatt
2161 gcaagttatg ctcatggtaa tagtggtata gcaacagctt ttgtacatgg atataaggtt
2221 actaaaaatg aaaaatatct taagatattc catgaacttt ggaatttaga aaattctagt
2281 aaactgagaa gaggttggac agattcaaga aaagttgata gttcatactc ttcacagtgg
2341 tgtcacggtg catcgggaca agctatagca agaatggagt ggattactgt aaacaaaaca
2401 gctagatttc ttagtaactc tgaactaatt aaggttaaaa aagagctagg ggaattaatt
2461 gatatcttaa aaaaagaggg aatgtataca gataattttt gtctatgcca tggtatttta
2521 ggaaatctat taattttaaa tacctatcaa gagaattttg ataataagaa tatcaatcta
2581 aagaatgaaa ttttaaacaa ctattactct gtttgtaact atggtttaaa taaaggatgg
2641 atttgtggct taggtacaga attttattct tatgggctta tgacaggaat atctggtata
2701 ttatatggac tgattcggca agtaaaacaa aaaaataatt ttggagtctt aatgccatat
2761 gttgattaa
```

FIG. 82

SEQUENCE LISTING

<160> NUMBER OF SEQ ID NOS: 134

<210> SEQ ID NO 1
<211> LENGTH: 5
<212> TYPE: PRT
<213> ORGANISM: Artificial Sequence
<220> FEATURE:
<223> OTHER INFORMATION: Synthetic or consensus peptide
<220> FEATURE:
<221> NAME/KEY: MISC_FEATURE
<222> LOCATION: (1)..(2)
<223> OTHER INFORMATION: X is isoleucine or leucine
<220> FEATURE:
<221> NAME/KEY: MISC_FEATURE
<222> LOCATION: (5)..(5)
<223> OTHER INFORMATION: X is any amino acid

<400> SEQUENCE: 1

```
Xaa Xaa Gly Gly Xaa
1               5
```

<210> SEQ ID NO 2
<211> LENGTH: 5
<212> TYPE: PRT
<213> ORGANISM: Artificial Sequence
<220> FEATURE:
<223> OTHER INFORMATION: Synthetic or consensus peptide
<220> FEATURE:
<221> NAME/KEY: MISC_FEATURE
<222> LOCATION: (1)..(2)
<223> OTHER INFORMATION: X is isoleucine or leucine
<220> FEATURE:
<221> NAME/KEY: MISC_FEATURE
<222> LOCATION: (5)..(5)
<223> OTHER INFORMATION: X is any amino acid

<400> SEQUENCE: 2

```
Xaa Xaa Gly Ala Xaa
1               5
```

<210> SEQ ID NO 3
<211> LENGTH: 51
<212> TYPE: PRT
<213> ORGANISM: Artificial Sequence
<220> FEATURE:
<223> OTHER INFORMATION: Synthetic construct

<400> SEQUENCE: 3

```
Met Lys Glu Gln Asn Ser Phe Asn Leu Leu Gln Glu Val Thr Glu Ser
1               5                   10                  15

Glu Leu Asp Leu Ile Leu Gly Ala Lys Gly Gly Ser Gly Val Ile His
            20                  25                  30

Thr Ile Ser His Glu Cys Asn Met Asn Ser Trp Gln Phe Val Phe Thr
        35                  40                  45

Cys Cys Ser
    50
```

<210> SEQ ID NO 4
<211> LENGTH: 70
<212> TYPE: PRT
<213> ORGANISM: Artificial Sequence
<220> FEATURE:
<223> OTHER INFORMATION: Synthetic construct

<400> SEQUENCE: 4

```
Gly Ser Ser His His His His His His Ser Ser Gly Leu Val Pro Arg
```

-continued

```
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Thr Cys Cys Ser
65                  70
```

<210> SEQ ID NO 5
<211> LENGTH: 67
<212> TYPE: PRT
<213> ORGANISM: Artificial Sequence
<220> FEATURE:
<223> OTHER INFORMATION: Synthetic construct

<400> SEQUENCE: 5

```
Gly Ser Ser His His His His His His Ser Ser Gly Leu Val Pro Arg
1               5                   10                  15

Gly Ser His Met Asn Ser Phe Asn Leu Leu Gln Glu Val Thr Glu Ser
            20                  25                  30

Glu Leu Asp Leu Ile Leu Gly Ala Lys Gly Gly Ser Gly Val Ile His
        35                  40                  45

Thr Ile Ser His Glu Cys Asn Met Asn Ser Trp Gln Phe Val Phe Thr
    50                  55                  60

Cys Cys Ser
65
```

<210> SEQ ID NO 6
<211> LENGTH: 62
<212> TYPE: PRT
<213> ORGANISM: Artificial Sequence
<220> FEATURE:
<223> OTHER INFORMATION: Synthetic construct

<400> SEQUENCE: 6

```
Gly Ser Ser His His His His His His Ser Ser Gly Leu Val Pro Arg
1               5                   10                  15

Gly Ser His Met Leu Gln Glu Val Thr Glu Ser Glu Leu Asp Leu Ile
            20                  25                  30

Leu Gly Ala Lys Gly Gly Ser Gly Val Ile His Thr Ile Ser His Glu
        35                  40                  45

Cys Asn Met Asn Ser Trp Gln Phe Val Phe Thr Cys Cys Ser
    50                  55                  60
```

<210> SEQ ID NO 7
<211> LENGTH: 47
<212> TYPE: PRT
<213> ORGANISM: Artificial Sequence
<220> FEATURE:
<223> OTHER INFORMATION: Synthetic construct

<400> SEQUENCE: 7

```
Gly Ser Ser His His His His His His Ser Ser Gly Leu Val Pro Arg
1               5                   10                  15

Gly Ser His Met Lys Gly Gly Ser Gly Val Ile His Thr Ile Ser His
            20                  25                  30

Glu Cys Asn Met Asn Ser Trp Gln Phe Val Phe Thr Cys Cys Ser
        35                  40                  45
```

-continued

<210> SEQ ID NO 8
<211> LENGTH: 56
<212> TYPE: PRT
<213> ORGANISM: Artificial Sequence
<220> FEATURE:
<223> OTHER INFORMATION: Synthetic construct

<400> SEQUENCE: 8

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu
    50                  55
```

<210> SEQ ID NO 9
<211> LENGTH: 57
<212> TYPE: PRT
<213> ORGANISM: Artificial Sequence
<220> FEATURE:
<223> OTHER INFORMATION: Synthetic construct

<400> SEQUENCE: 9

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys
    50                  55
```

<210> SEQ ID NO 10
<211> LENGTH: 57
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (57)..(57)
<223> OTHER INFORMATION: X=selenocysteine, abbreviated elsewhere in the application as U or Sec

<400> SEQUENCE: 10

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Xaa
    50                  55
```

<210> SEQ ID NO 11
<211> LENGTH: 70
<212> TYPE: PRT
<213> ORGANISM: Artificial Sequence
<220> FEATURE:
<223> OTHER INFORMATION: Synthetic construct

<400> SEQUENCE: 11

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Ser Cys Cys Ser
65                  70

<210> SEQ ID NO 12
<211> LENGTH: 70
<212> TYPE: PRT
<213> ORGANISM: Artificial Sequence
<220> FEATURE:
<223> OTHER INFORMATION: Synthetic construct

<400> SEQUENCE: 12

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Thr Ser Cys Ser
65                  70

<210> SEQ ID NO 13
<211> LENGTH: 70
<212> TYPE: PRT
<213> ORGANISM: Artificial Sequence
<220> FEATURE:
<223> OTHER INFORMATION: Synthetic construct

<400> SEQUENCE: 13

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Thr Ala Cys Ser
65                  70

<210> SEQ ID NO 14
<211> LENGTH: 30
<212> TYPE: DNA
<213> ORGANISM: Artificial Sequence
<220> FEATURE:
<223> OTHER INFORMATION: Synthetic construct

<400> SEQUENCE: 14
cgactagcta gcatgaaaaa aaagacttac                                    30

-continued

<210> SEQ ID NO 15
<211> LENGTH: 27
<212> TYPE: DNA
<213> ORGANISM: Artificial Sequence
<220> FEATURE:
<223> OTHER INFORMATION: Synthetic construct

<400> SEQUENCE: 15
ccgctcgagt taatcaacat atggcat 27

<210> SEQ ID NO 16
<211> LENGTH: 34
<212> TYPE: DNA
<213> ORGANISM: Artificial Sequence
<220> FEATURE:
<223> OTHER INFORMATION: Synthetic construct

<400> SEQUENCE: 16
gggaattcca tatgaaagaa caaaactctt ttaa 34

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
cgcggatcct taagagcagc aagta 25

<210> SEQ ID NO 18
<211> LENGTH: 2769
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(2769)

<400> SEQUENCE: 18

```
atg aaa aaa aag act tac caa ttt gaa aaa ttt tta aaa aat act ttt       48
Met Lys Lys Lys Thr Tyr Gln Phe Glu Lys Phe Leu Lys Asn Thr Phe
1               5                   10                  15

gat caa ttt tct att aag caa aat gaa gtt ctg gtt gaa gat gat tta       96
Asp Gln Phe Ser Ile Lys Gln Asn Glu Val Leu Val Glu Asp Asp Leu
            20                  25                  30

aac gat ata att atg aac gtt tgt gga aaa gca ctt gtt ttg atg ata      144
Asn Asp Ile Ile Met Asn Val Cys Gly Lys Ala Leu Val Leu Met Ile
        35                  40                  45

aat gaa aaa aga gaa atg aat cta tta atg ggc aat aca cca gag gaa      192
Asn Glu Lys Arg Glu Met Asn Leu Leu Met Gly Asn Thr Pro Glu Glu
    50                  55                  60

agg tac caa tat ttt gaa aat gag tat tcg agt aca ggt aaa gct ttt      240
Arg Tyr Gln Tyr Phe Glu Asn Glu Tyr Ser Ser Thr Gly Lys Ala Phe
65                  70                  75                  80

gaa gaa ata aaa gat aaa ttt cca gta ata tat att gat tta aaa aat      288
Glu Glu Ile Lys Asp Lys Phe Pro Val Ile Tyr Ile Asp Leu Lys Asn
                85                  90                  95

tct ata aat tct tat tta aag ttg gtt tca caa ata atg aaa gat ttt      336
Ser Ile Asn Ser Tyr Leu Lys Leu Val Ser Gln Ile Met Lys Asp Phe
            100                 105                 110

aaa aaa gat tac tca ctt cta gta gaa cgt aag att att gag gaa cat      384
```

-continued

```
Lys Lys Asp Tyr Ser Leu Leu Val Glu Arg Lys Ile Ile Glu Glu His
        115                 120                 125

tcg act att tcg act atg aaa ata aaa ggt gat tta cat aat ggg aag      432
Ser Thr Ile Ser Thr Met Lys Ile Lys Gly Asp Leu His Asn Gly Lys
    130                 135                 140

gct gtt ata gaa att act act aac aga agt aaa tta att tat aaa cca      480
Ala Val Ile Glu Ile Thr Thr Asn Arg Ser Lys Leu Ile Tyr Lys Pro
145                 150                 155                 160

aag tca tta agt aat gat gtg ttt ttt aac aat ttt ttg aag tat atg      528
Lys Ser Leu Ser Asn Asp Val Phe Phe Asn Asn Phe Leu Lys Tyr Met
                165                 170                 175

gat agt ttt ttt att aaa gag gga aaa ggc act aaa tat aaa gaa aat      576
Asp Ser Phe Phe Ile Lys Glu Gly Lys Gly Thr Lys Tyr Lys Glu Asn
            180                 185                 190

ttt tat ttg gta aac acg ctt gat atg aag aca tat gga tgg gtt gaa      624
Phe Tyr Leu Val Asn Thr Leu Asp Met Lys Thr Tyr Gly Trp Val Glu
        195                 200                 205

tac gta gat aaa aaa cca atc aat tca ttt gag gaa gca aga aat tat      672
Tyr Val Asp Lys Lys Pro Ile Asn Ser Phe Glu Glu Ala Arg Asn Tyr
    210                 215                 220

tat aga aaa att gga gta ctt tta tca gtt gct tat act tta aat tta      720
Tyr Arg Lys Ile Gly Val Leu Leu Ser Val Ala Tyr Thr Leu Asn Leu
225                 230                 235                 240

act gac tta cat ttt gaa aat gtg atc tca caa gga gaa aat cct tgt      768
Thr Asp Leu His Phe Glu Asn Val Ile Ser Gln Gly Glu Asn Pro Cys
                245                 250                 255

att att gac cta gag act atg ttt aac atg cct atg ttt gta aaa ggt      816
Ile Ile Asp Leu Glu Thr Met Phe Asn Met Pro Met Phe Val Lys Gly
            260                 265                 270

tat aaa aat gaa tct cgt aat att att aat gga aag att atg gat tcg      864
Tyr Lys Asn Glu Ser Arg Asn Ile Ile Asn Gly Lys Ile Met Asp Ser
        275                 280                 285

gta gtc tca aca gga atg tta cca gtc tta gga ata gat agt ttg ttt      912
Val Val Ser Thr Gly Met Leu Pro Val Leu Gly Ile Asp Ser Leu Phe
    290                 295                 300

ggg ggg gat cct agt gga att tta ggt ggt aca ttt tct aaa gaa gaa      960
Gly Gly Asp Pro Ser Gly Ile Leu Gly Gly Thr Phe Ser Lys Glu Glu
305                 310                 315                 320

cga gtg atc ata aat cca ttt aga gat gac ata aaa ttt caa aaa ata     1008
Arg Val Ile Ile Asn Pro Phe Arg Asp Asp Ile Lys Phe Gln Lys Ile
                325                 330                 335

gtt gta cga tct gta ttc aaa gat cat att cct ttt ttt aac aat aat     1056
Val Val Arg Ser Val Phe Lys Asp His Ile Pro Phe Phe Asn Asn Asn
            340                 345                 350

aat gag aaa aga tat tgt aag ccc aaa gac tat gtt aat gat att ata     1104
Asn Glu Lys Arg Tyr Cys Lys Pro Lys Asp Tyr Val Asn Asp Ile Ile
        355                 360                 365

aaa ggg ttt gaa aaa aca tat aaa ata atc gtt aaa aat aag gaa aaa     1152
Lys Gly Phe Glu Lys Thr Tyr Lys Ile Ile Val Lys Asn Lys Glu Lys
    370                 375                 380

ata tta ggg ttt cta aaa aaa gaa tct agt agt gtt acc tgt aga ata     1200
Ile Leu Gly Phe Leu Lys Lys Glu Ser Ser Ser Val Thr Cys Arg Ile
385                 390                 395                 400

tta ttt aga aat acg atg gaa tac tca gtt tta tta aat gca gca aag     1248
Leu Phe Arg Asn Thr Met Glu Tyr Ser Val Leu Leu Asn Ala Ala Lys
                405                 410                 415

tcg cct gta tat tca aac aaa aga gaa gaa att ttt gaa aaa tta tca     1296
Ser Pro Val Tyr Ser Asn Lys Arg Glu Glu Ile Phe Glu Lys Leu Ser
            420                 425                 430
```

-continued

```
act ttt aat cga gga ctt gga aat gat att att aaa tca gag ata agt      1344
Thr Phe Asn Arg Gly Leu Gly Asn Asp Ile Ile Lys Ser Glu Ile Ser
        435                 440                 445

caa ata aac act tta tca atc ccc tat ttc aat tgt caa gta gac tca      1392
Gln Ile Asn Thr Leu Ser Ile Pro Tyr Phe Asn Cys Gln Val Asp Ser
    450                 455                 460

aac tta ata aag aat atg gat gga gaa aca ata ttt gag cat act ctc      1440
Asn Leu Ile Lys Asn Met Asp Gly Glu Thr Ile Phe Glu His Thr Leu
465                 470                 475                 480

acc cca ttc aaa tgt ttc cta tca aaa tat aga aga ctg tgt gta gat      1488
Thr Pro Phe Lys Cys Phe Leu Ser Lys Tyr Arg Arg Leu Cys Val Asp
                485                 490                 495

gat atg gaa caa caa gtt aag cta atc cga ttt tca att caa agt caa      1536
Asp Met Glu Gln Gln Val Lys Leu Ile Arg Phe Ser Ile Gln Ser Gln
            500                 505                 510

gaa cag ctt ttt aaa gat ggg gaa cag ttc agt tta tat aag aaa caa      1584
Glu Gln Leu Phe Lys Asp Gly Glu Gln Phe Ser Leu Tyr Lys Lys Gln
        515                 520                 525

aaa ggt tca caa gaa gat tta ttg att gcg ata aat gag ctt tca agt      1632
Lys Gly Ser Gln Glu Asp Leu Leu Ile Ala Ile Asn Glu Leu Ser Ser
    530                 535                 540

atc tta gaa aac aat gca tat att ggt aca agc gat gat acc ata aat      1680
Ile Leu Glu Asn Asn Ala Tyr Ile Gly Thr Ser Asp Asp Thr Ile Asn
545                 550                 555                 560

tgg atg agt tta gga att gct gat aat gat cag ata ctc ttt gaa agt      1728
Trp Met Ser Leu Gly Ile Ala Asp Asn Asp Gln Ile Leu Phe Glu Ser
                565                 570                 575

ctt gaa aat gat ata tat aag gga ata tca gga ata ggc tta gcc tta      1776
Leu Glu Asn Asp Ile Tyr Lys Gly Ile Ser Gly Ile Gly Leu Ala Leu
            580                 585                 590

ttg gaa tat tat gaa ttt tat cca aat atc aac aca aaa aaa ata cta      1824
Leu Glu Tyr Tyr Glu Phe Tyr Pro Asn Ile Asn Thr Lys Lys Ile Leu
        595                 600                 605

aaa tta ata tat aaa aat ata tca aaa gat ttt att aat aca aat aat      1872
Lys Leu Ile Tyr Lys Asn Ile Ser Lys Asp Phe Ile Asn Thr Asn Asn
    610                 615                 620

gag ccc caa aat tat gga ttc tat gtt ggc tta ata ggt gag tat agt      1920
Glu Pro Gln Asn Tyr Gly Phe Tyr Val Gly Leu Ile Gly Glu Tyr Ser
625                 630                 635                 640

ttt ttg aga aaa tac gaa aaa gta ttt cac aaa aca agt agt tgc aac      1968
Phe Leu Arg Lys Tyr Glu Lys Val Phe His Lys Thr Ser Ser Cys Asn
                645                 650                 655

att tta aag aac att tta aaa gat ttt act ccc gag aag tgt caa aca      2016
Ile Leu Lys Asn Ile Leu Lys Asp Phe Thr Pro Glu Lys Cys Gln Thr
            660                 665                 670

ata cta cct tca gat gac gta ata gcc gga gaa gcg gga att att att      2064
Ile Leu Pro Ser Asp Asp Val Ile Ala Gly Glu Ala Gly Ile Ile Ile
        675                 680                 685

tac att tca aat ctc aat aat tac cta gaa tac aga gat gaa att gat      2112
Tyr Ile Ser Asn Leu Asn Asn Tyr Leu Glu Tyr Arg Asp Glu Ile Asp
    690                 695                 700

att cta ttg aaa agt tta tca aat aag ata aaa tta aaa gaa agt att      2160
Ile Leu Leu Lys Ser Leu Ser Asn Lys Ile Lys Leu Lys Glu Ser Ile
705                 710                 715                 720

gca agt tat gct cat ggt aat agt ggt ata gca aca gct ttt gta cat      2208
Ala Ser Tyr Ala His Gly Asn Ser Gly Ile Ala Thr Ala Phe Val His
                725                 730                 735

gga tat aag gtt act aaa aat gaa aaa tat ctt aag ata ttc cat gaa      2256
Gly Tyr Lys Val Thr Lys Asn Glu Lys Tyr Leu Lys Ile Phe His Glu
            740                 745                 750
```

-continued

```
ctt tgg aat tta gaa aat tct agt aaa ctg aga aga ggt tgg aca gat      2304
Leu Trp Asn Leu Glu Asn Ser Ser Lys Leu Arg Arg Gly Trp Thr Asp
        755                 760                 765

tca aga aaa gtt gat agt tca tac tct tca cag tgg tgt cac ggt gca      2352
Ser Arg Lys Val Asp Ser Ser Tyr Ser Ser Gln Trp Cys His Gly Ala
    770                 775                 780

tcg gga caa gct ata gca aga atg gag tgg att act gta aac aaa aca      2400
Ser Gly Gln Ala Ile Ala Arg Met Glu Trp Ile Thr Val Asn Lys Thr
785                 790                 795                 800

gct aga ttt ctt agt aac tct gaa cta att aag gtt aaa aaa gag cta      2448
Ala Arg Phe Leu Ser Asn Ser Glu Leu Ile Lys Val Lys Lys Glu Leu
                805                 810                 815

ggg gaa tta att gat atc tta aaa aaa gag gga atg tat aca gat aat      2496
Gly Glu Leu Ile Asp Ile Leu Lys Lys Glu Gly Met Tyr Thr Asp Asn
            820                 825                 830

ttt tgt cta tgc cat ggt att tta gga aat cta tta att tta aat acc      2544
Phe Cys Leu Cys His Gly Ile Leu Gly Asn Leu Leu Ile Leu Asn Thr
        835                 840                 845

tat caa gag aat ttt gat aat aag aat atc aat cta aag aat gaa att      2592
Tyr Gln Glu Asn Phe Asp Asn Lys Asn Ile Asn Leu Lys Asn Glu Ile
    850                 855                 860

tta aac aac tat tac tct gtt tgt aac tat ggt tta aat aaa gga tgg      2640
Leu Asn Asn Tyr Tyr Ser Val Cys Asn Tyr Gly Leu Asn Lys Gly Trp
865                 870                 875                 880

att tgt ggc tta ggt aca gaa ttt tat tct tat ggg ctt atg aca gga      2688
Ile Cys Gly Leu Gly Thr Glu Phe Tyr Ser Tyr Gly Leu Met Thr Gly
                885                 890                 895

ata tct ggt ata tta tat gga ctg att cgg caa gta aaa caa aaa aat      2736
Ile Ser Gly Ile Leu Tyr Gly Leu Ile Arg Gln Val Lys Gln Lys Asn
            900                 905                 910

aat ttt gga gtc tta atg cca tat gtt gat taa                          2769
Asn Phe Gly Val Leu Met Pro Tyr Val Asp
        915                 920


<210> SEQ ID NO 19
<211> LENGTH: 922
<212> TYPE: PRT
<213> ORGANISM: Artificial Sequence
<220> FEATURE:
<223> OTHER INFORMATION: Synthetic Construct

<400> SEQUENCE: 19

Met Lys Lys Lys Thr Tyr Gln Phe Glu Lys Phe Leu Lys Asn Thr Phe
1               5                   10                  15

Asp Gln Phe Ser Ile Lys Gln Asn Glu Val Leu Val Glu Asp Asp Leu
            20                  25                  30

Asn Asp Ile Ile Met Asn Val Cys Gly Lys Ala Leu Val Leu Met Ile
        35                  40                  45

Asn Glu Lys Arg Glu Met Asn Leu Leu Met Gly Asn Thr Pro Glu Glu
    50                  55                  60

Arg Tyr Gln Tyr Phe Glu Asn Glu Tyr Ser Ser Thr Gly Lys Ala Phe
65                  70                  75                  80

Glu Glu Ile Lys Asp Lys Phe Pro Val Ile Tyr Ile Asp Leu Lys Asn
                85                  90                  95

Ser Ile Asn Ser Tyr Leu Lys Leu Val Ser Gln Ile Met Lys Asp Phe
            100                 105                 110

Lys Lys Asp Tyr Ser Leu Leu Val Glu Arg Lys Ile Ile Glu Glu His
        115                 120                 125
```

-continued

```
Ser Thr Ile Ser Thr Met Lys Ile Lys Gly Asp Leu His Asn Gly Lys
    130                 135                 140

Ala Val Ile Glu Ile Thr Thr Asn Arg Ser Lys Leu Ile Tyr Lys Pro
145                 150                 155                 160

Lys Ser Leu Ser Asn Asp Val Phe Phe Asn Asn Phe Leu Lys Tyr Met
                165                 170                 175

Asp Ser Phe Phe Ile Lys Glu Gly Lys Gly Thr Lys Tyr Lys Glu Asn
            180                 185                 190

Phe Tyr Leu Val Asn Thr Leu Asp Met Lys Thr Tyr Gly Trp Val Glu
        195                 200                 205

Tyr Val Asp Lys Lys Pro Ile Asn Ser Phe Glu Glu Ala Arg Asn Tyr
    210                 215                 220

Tyr Arg Lys Ile Gly Val Leu Leu Ser Val Ala Tyr Thr Leu Asn Leu
225                 230                 235                 240

Thr Asp Leu His Phe Glu Asn Val Ile Ser Gln Gly Glu Asn Pro Cys
                245                 250                 255

Ile Ile Asp Leu Glu Thr Met Phe Asn Met Pro Met Phe Val Lys Gly
            260                 265                 270

Tyr Lys Asn Glu Ser Arg Asn Ile Ile Asn Gly Lys Ile Met Asp Ser
        275                 280                 285

Val Val Ser Thr Gly Met Leu Pro Val Leu Gly Ile Asp Ser Leu Phe
    290                 295                 300

Gly Gly Asp Pro Ser Gly Ile Leu Gly Gly Thr Phe Ser Lys Glu Glu
305                 310                 315                 320

Arg Val Ile Ile Asn Pro Phe Arg Asp Asp Ile Lys Phe Gln Lys Ile
                325                 330                 335

Val Val Arg Ser Val Phe Lys Asp His Ile Pro Phe Phe Asn Asn Asn
            340                 345                 350

Asn Glu Lys Arg Tyr Cys Lys Pro Lys Asp Tyr Val Asn Asp Ile Ile
        355                 360                 365

Lys Gly Phe Glu Lys Thr Tyr Lys Ile Ile Val Lys Asn Lys Glu Lys
    370                 375                 380

Ile Leu Gly Phe Leu Lys Lys Glu Ser Ser Ser Val Thr Cys Arg Ile
385                 390                 395                 400

Leu Phe Arg Asn Thr Met Glu Tyr Ser Val Leu Leu Asn Ala Ala Lys
                405                 410                 415

Ser Pro Val Tyr Ser Asn Lys Arg Glu Glu Ile Phe Glu Lys Leu Ser
            420                 425                 430

Thr Phe Asn Arg Gly Leu Gly Asn Asp Ile Ile Lys Ser Glu Ile Ser
        435                 440                 445

Gln Ile Asn Thr Leu Ser Ile Pro Tyr Phe Asn Cys Gln Val Asp Ser
    450                 455                 460

Asn Leu Ile Lys Asn Met Asp Gly Glu Thr Ile Phe Glu His Thr Leu
465                 470                 475                 480

Thr Pro Phe Lys Cys Phe Leu Ser Lys Tyr Arg Arg Leu Cys Val Asp
                485                 490                 495

Asp Met Glu Gln Gln Val Lys Leu Ile Arg Phe Ser Ile Gln Ser Gln
            500                 505                 510

Glu Gln Leu Phe Lys Asp Gly Glu Gln Phe Ser Leu Tyr Lys Lys Gln
        515                 520                 525

Lys Gly Ser Gln Glu Asp Leu Leu Ile Ala Ile Asn Glu Leu Ser Ser
    530                 535                 540

Ile Leu Glu Asn Asn Ala Tyr Ile Gly Thr Ser Asp Asp Thr Ile Asn
```

-continued

```
545                 550                 555                 560

Trp Met Ser Leu Gly Ile Ala Asp Asn Asp Gln Ile Leu Phe Glu Ser
                565                 570                 575

Leu Glu Asn Asp Ile Tyr Lys Gly Ile Ser Gly Ile Gly Leu Ala Leu
            580                 585                 590

Leu Glu Tyr Tyr Glu Phe Tyr Pro Asn Ile Asn Thr Lys Lys Ile Leu
        595                 600                 605

Lys Leu Ile Tyr Lys Asn Ile Ser Lys Asp Phe Ile Asn Thr Asn Asn
    610                 615                 620

Glu Pro Gln Asn Tyr Gly Phe Tyr Val Gly Leu Ile Gly Glu Tyr Ser
625                 630                 635                 640

Phe Leu Arg Lys Tyr Glu Lys Val Phe His Lys Thr Ser Ser Cys Asn
                645                 650                 655

Ile Leu Lys Asn Ile Leu Lys Asp Phe Thr Pro Glu Lys Cys Gln Thr
            660                 665                 670

Ile Leu Pro Ser Asp Asp Val Ile Ala Gly Glu Ala Gly Ile Ile Ile
        675                 680                 685

Tyr Ile Ser Asn Leu Asn Asn Tyr Leu Glu Tyr Arg Asp Glu Ile Asp
    690                 695                 700

Ile Leu Leu Lys Ser Leu Ser Asn Lys Ile Lys Leu Lys Glu Ser Ile
705                 710                 715                 720

Ala Ser Tyr Ala His Gly Asn Ser Gly Ile Ala Thr Ala Phe Val His
                725                 730                 735

Gly Tyr Lys Val Thr Lys Asn Glu Lys Tyr Leu Lys Ile Phe His Glu
            740                 745                 750

Leu Trp Asn Leu Glu Asn Ser Ser Lys Leu Arg Arg Gly Trp Thr Asp
        755                 760                 765

Ser Arg Lys Val Asp Ser Ser Tyr Ser Ser Gln Trp Cys His Gly Ala
    770                 775                 780

Ser Gly Gln Ala Ile Ala Arg Met Glu Trp Ile Thr Val Asn Lys Thr
785                 790                 795                 800

Ala Arg Phe Leu Ser Asn Ser Glu Leu Ile Lys Val Lys Lys Glu Leu
                805                 810                 815

Gly Glu Leu Ile Asp Ile Leu Lys Lys Glu Gly Met Tyr Thr Asp Asn
            820                 825                 830

Phe Cys Leu Cys His Gly Ile Leu Gly Asn Leu Leu Ile Leu Asn Thr
        835                 840                 845

Tyr Gln Glu Asn Phe Asp Asn Lys Asn Ile Asn Leu Lys Asn Glu Ile
    850                 855                 860

Leu Asn Asn Tyr Tyr Ser Val Cys Asn Tyr Gly Leu Asn Lys Gly Trp
865                 870                 875                 880

Ile Cys Gly Leu Gly Thr Glu Phe Tyr Ser Tyr Gly Leu Met Thr Gly
                885                 890                 895

Ile Ser Gly Ile Leu Tyr Gly Leu Ile Arg Gln Val Lys Gln Lys Asn
            900                 905                 910

Asn Phe Gly Val Leu Met Pro Tyr Val Asp
        915                 920
```

<210> SEQ ID NO 20
<211> LENGTH: 1062
<212> TYPE: PRT
<213> ORGANISM: Artificial Sequence
<220> FEATURE:
<223> OTHER INFORMATION: Synthetic construct -continued

<400> SEQUENCE: 20

```
Met His Thr Lys Phe Lys Arg Asn Ser Val Trp Asn Arg Ser Ser Ser
1               5                   10                  15

Ile Ser Glu Arg Lys Val Arg Arg Ser Leu Asn Thr Asn Trp Asp Glu
            20                  25                  30

Leu Thr Asn Arg Arg Phe Glu Arg Trp Lys Ser Leu Val Glu Ser Asp
        35                  40                  45

Glu Gly Ile Arg Ile Glu Asp Val Leu Ala Thr Gln Asn Ile Asp Glu
    50                  55                  60

Glu Thr Leu Lys His Thr Ile Asn Ala Lys Glu Val Glu Phe Ile Asn
65                  70                  75                  80

Glu Gly Asp His Gln Gly Trp Leu Glu Ile Ile Gln Leu Val Asp Glu
                85                  90                  95

Gln Ser Tyr Lys Asn Val Asn Ile Glu Val Arg Lys Asp Ile Leu Phe
            100                 105                 110

Phe Ser Phe Ile Lys Pro Phe Leu Lys Ile Ala Arg Gly Lys Leu Glu
        115                 120                 125

Glu Val Leu Tyr Ser His Ser Thr Lys Ser Leu Ile Lys Glu Glu Leu
    130                 135                 140

Ser Pro Ser Val Ile Asp Asp Leu Leu Asn Asn Leu Gly Glu Thr Leu
145                 150                 155                 160

Ser Ala Ile Ser Ser Arg Ile Leu Ile Leu Glu Leu Asn Val Ala Arg
                165                 170                 175

Val Ser Gly Lys Leu Arg Gly Glu Thr Ser Glu Glu Arg Ala Ser Tyr
            180                 185                 190

Phe Asn Gln Ala Leu Leu Asn Asp Pro Ala Tyr Val Arg Ser Ile Arg
        195                 200                 205

Glu Glu Tyr Ile Val Leu Thr Arg Leu Leu Ala Thr Lys Thr Met Tyr
    210                 215                 220

Trp Ile Gln Asn Thr Ser Asp Leu Leu Val Arg Phe His Gln Asp Lys
225                 230                 235                 240

Gly Ile Leu Glu Ser Glu Phe Ser Asn Gly Gln Lys Leu Gly Lys Ile
                245                 250                 255

Ile Ser Ile Asp Thr Gly Ser Gly Val Ser Asp Thr His Asn Lys Gly
            260                 265                 270

Lys Thr Val Ala Ile Leu Asn Phe Glu Thr Gly Ile Lys Ile Val Tyr
        275                 280                 285

Lys Pro Arg Ser Leu Glu Ile Asp Val Lys Phe Asn Lys Phe Val Asn
    290                 295                 300

Tyr Leu Asn Gly Lys Asn Leu Ser Phe Asp Leu Lys Thr Val His Thr
305                 310                 315                 320

Leu Asn Lys Lys Ser Tyr Gly Trp Thr Gln Phe Ile Ser Tyr Lys Glu
                325                 330                 335

Cys Gln Glu Glu Leu Gln Ile Gly Lys Phe Tyr Trp Arg Ile Gly Ser
            340                 345                 350

Tyr Leu Ala Ile Leu Tyr Ala Met Asn Ala Val Asp Phe His Met Gln
        355                 360                 365

Asn Leu Ile Ala Asp Gly Glu Tyr Pro Ile Leu Val Asp Leu Glu Ser
    370                 375                 380

Leu Phe His Asn Asn Ser Thr Tyr Thr Asp Thr Ser Ala Phe Ser Arg
385                 390                 395                 400

Ala Gln Glu His Ile Glu Arg Ser Val Leu Arg Ile Gly Leu Leu Pro
                405                 410                 415
```

-continued

```
Arg Lys Ile Asn Ser Lys Ala Gly Phe Glu Gly Ile Asp Leu Ser Ala
            420                 425                 430

Leu Gly Ala Gln Glu Gly Gln Val Ser Pro His Lys Thr Ser Thr Ile
        435                 440                 445

Val Asp Arg Asp Lys Asp Thr Val Arg Ile Glu Glu Lys Asn Phe Pro
    450                 455                 460

Ile Pro Val Ser Gln His Arg Pro Met Leu His Gly Gln Ile Ile Asn
465                 470                 475                 480

Thr Val Ala Tyr Glu Gly Asn Ile Ile Lys Gly Phe Glu Glu Thr Tyr
                485                 490                 495

Phe Leu Phe Met Lys Tyr Lys Gln Asp Met Leu Glu Gln Ile Asp Ser
            500                 505                 510

Phe Lys Gly Val Thr Val Arg Gln Ile Leu Arg Gly Thr Ser Arg Tyr
        515                 520                 525

Ala Asn Leu Leu Lys Ile Ser Leu His Pro Asp Phe Met Arg Asp Gly
    530                 535                 540

Leu Asp Arg Glu Met Ile Leu Asp Lys Leu Trp Leu Asp Thr Lys Leu
545                 550                 555                 560

Asn Pro Arg Leu Asn Gln Val Val Asn Ser Glu Lys Glu Gly Leu Phe
                565                 570                 575

Leu Gly Asp Ile Pro Tyr Phe Thr Ser Lys Pro Glu Ser Thr Asn Met
            580                 585                 590

Trp Asp Ser Ser Gly Arg Lys Ile Asn Asn Phe Phe Lys Thr Ser Ala
        595                 600                 605

Leu Asn Glu Thr Lys Glu Lys Ile Asn Glu Met Asn Glu Ser Asp Cys
    610                 615                 620

His Glu Gln Val Ser Phe Ile Lys Thr Ala Ile Leu Val Ile Lys Asp
625                 630                 635                 640

Ser Tyr Arg Lys His Lys Val Phe Asp Ile Asn Pro Arg Leu His Val
                645                 650                 655

Phe Asn Pro Lys Asp Phe Phe Gln Glu Ala Ile Lys Ile Gly Asp Phe
            660                 665                 670

Leu Ala Ser Arg Ala Ile Glu Gly Glu Gln Leu Asp Gly Gln Glu Asp
        675                 680                 685

Val Ser Trp Ile Gly Ser Phe Val Asp Asn Gln Arg Glu Asp Gln Phe
    690                 695                 700

Lys Ile Ser Ala Ala Asn Ser Ser Leu Tyr Glu Gly Val Gly Gly Ile
705                 710                 715                 720

Ser Leu Phe Leu Ala Tyr Leu Gly Arg Leu Ser Asn Asn Glu Lys Tyr
                725                 730                 735

Thr Lys Leu Ser Lys Lys Ala Leu Val Ala Val His Lys Asn Met Ser
            740                 745                 750

Ala Ser Ser Asp Leu Gly Ala Phe Gly Gly Ile Ala Ser Tyr Leu Tyr
        755                 760                 765

Leu Leu Asp His Leu Ser Lys Leu Trp Asn Asp Glu Gln Leu Leu Lys
    770                 775                 780

Asn Glu Leu Tyr Ser Ala Leu Asn Lys Leu Asp Ser Leu Ile Glu Arg
785                 790                 795                 800

Asp Glu Asn Asn Asp Ile Leu Thr Gly Val Ala Gly Thr Ala Val Ile
                805                 810                 815

Leu Ile Asn Leu Phe Lys Arg Tyr Lys Glu Glu Gln Ile Leu Asn Leu
            820                 825                 830
```

-continued

```
Ile Thr Lys Cys Gly Asn Arg Leu Ile Gln Asn Ile Asn Val Met Glu
        835                 840                 845

Lys Gly Val Gly Trp Lys Val Pro Ala Asn Pro Thr Pro Ala Ser Gly
    850                 855                 860

Phe Ala His Gly Ala Ser Gly Ile Ile Trp Ala Leu Tyr Glu Ile Tyr
865                 870                 875                 880

Ala Ile Thr Lys Gln Thr Val Phe Lys Glu Val Ala Glu Lys Ala Leu
                885                 890                 895

Glu Phe Glu Arg Thr Leu Phe Ile Pro Glu Lys Asn Asn Trp Ala Asp
            900                 905                 910

Ile Lys Leu Glu Asn Gly Gln Phe Arg Asn Asp Asn Phe Val Ala Trp
        915                 920                 925

Cys Asn Gly Ala Ala Gly Ile Gly Leu Ser Arg Ile Leu Ile Leu Pro
    930                 935                 940

His Asn Gln Asn Glu Leu Ile Lys Asp Glu Ala His Val Ala Ile Asn
945                 950                 955                 960

Thr Thr Leu Lys Tyr Gly Phe Glu His Asp Gln Ser Leu Cys His Gly
                965                 970                 975

Asp Leu Gly Asn Leu Asp Ile Leu Met Tyr Ala Ala Glu Asn Phe Asn
            980                 985                 990

Lys Lys Leu Ser Val Asn Val Thr  Glu Leu Ser His Lys  Ile Leu Asn
        995                 1000                 1005

Asp Ile  Lys Leu Arg Gly Trp  Leu Thr Gly Phe Glu  Lys Asn Asn
    1010                 1015                 1020

Glu Ser  Pro Ser Leu Met Met  Gly Tyr Ala Gly Ile  Gly Leu Gly
    1025                 1030                 1035

Leu Leu  Lys Ile Phe Ala Pro  Val Glu Val Pro Ser  Val Leu Arg
    1040                 1045                 1050

Leu Gln  Ser Pro Leu Glu Leu  Lys Leu
    1055                 1060


<210> SEQ ID NO 21
<211> LENGTH: 898
<212> TYPE: PRT
<213> ORGANISM: Artificial Sequence
<220> FEATURE:
<223> OTHER INFORMATION: Synthetic construct

<400> SEQUENCE: 21

Met Asn Asn Pro Leu Phe Pro Glu Phe Leu Ser Tyr Met Lys Lys His
1               5                   10                  15

Asp Ser Thr Val Lys Lys Ser Leu Ser Phe Tyr Ser Glu Asn Phe Ile
            20                  25                  30

Asp Ile Ser Ile Phe Lys Leu Phe Ala Lys Ala Leu Val Tyr Leu Ile
        35                  40                  45

Asn Glu Lys Arg Glu Asn Gln Ser Leu Ile Gly Leu Thr Ser Glu Glu
    50                  55                  60

Lys Tyr Glu Tyr Phe Thr Lys His Tyr Val Leu Thr Gly Ile Ile Leu
65                  70                  75                  80

Asp Glu Ile Arg Thr Lys Phe Pro Asn Ile Val Ile Ser Phe His Asn
                85                  90                  95

Tyr Phe Asn Ser Leu Asn Met Leu Gly Asn Gln Val Thr Ser Asn Tyr
            100                 105                 110

Leu Asn Asp His Gln Asp Leu Val Asn Leu Gly Leu Val Asp Gln Ser
        115                 120                 125
```

-continued

```
Asp Lys Ile Val Ser Leu Gln Val Val Gly Asp Met His Asn Glu Leu
    130                 135                 140

Ala Val Val Lys Val Asn Leu Thr Gly Arg Ser Leu Phe Tyr Lys Pro
145                 150                 155                 160

His Leu Asp Asn Tyr Ile Val Tyr Asn Glu Ile Leu Gln Leu Leu Asn
                165                 170                 175

Ser Lys Leu Pro Ala Asn Leu Lys Gln Arg Gln Val Lys Ser Phe Val
            180                 185                 190

Ser Ser Asp His Ser Trp Leu Glu Glu Val Lys Arg Asn Pro Leu Leu
        195                 200                 205

Lys Glu Asn Ile His Asn Tyr Phe Ser Arg Met Gly Gly Leu Ile Ala
    210                 215                 220

Ile Ala Tyr Ser Leu Asn Met Thr Asp Leu His Phe Glu Asn Ile Ile
225                 230                 235                 240

Ser Asp Gly Glu Tyr Pro Val Ile Leu Asp Met Glu Thr Ile Cys Gly
                245                 250                 255

Thr Thr Ile Asn Asn Asn Glu Phe Leu Phe Thr Met Ala Gln Lys Glu
            260                 265                 270

Val Asn Asn Lys Ile Phe Asp Ser Val Leu Asn Thr Gly Leu Leu Pro
        275                 280                 285

Met Lys Gly Leu Gly Ser Ile Phe Gly Gly Asp Val Ser Gly Met Met
    290                 295                 300

Gly Gly Glu Phe Thr Lys Ser Phe Asn Arg Ile Val Asp Asn Asn Lys
305                 310                 315                 320

Asp Thr Ile His Phe Glu Lys Lys Ile Glu Arg Leu Thr Asn Met Asn
                325                 330                 335

His Leu Pro Tyr Tyr Ile Arg Asn Asn Lys Glu Ile Leu Ile Lys Asn
            340                 345                 350

Ser Pro Asp Tyr Leu Thr Asn Ile Val Tyr Gly Phe Asn Ser Thr Tyr
        355                 360                 365

Asp Tyr Ile Gln Val Leu Lys Asn Glu Ile Ile Thr Ile Ile Lys Lys
    370                 375                 380

Tyr Glu Phe Leu Thr Cys Arg Val Ile Phe Arg Gln Thr Ala His Tyr
385                 390                 395                 400

Ser Leu Met Leu Glu Val Leu Asn Ser Pro Ile Tyr Gln Asn Ser Lys
                405                 410                 415

Glu Asn Val Leu Ser Lys Leu Ser Tyr Ser Ala Tyr Ser Lys Gly Val
            420                 425                 430

Leu Glu Ser Glu Lys Lys Gln Tyr Arg Trp Glu Tyr Pro Ser Pro Thr
        435                 440                 445

Arg Leu Asn Ser Ile Asn Ile Leu Ile Ser Phe Asn Cys Ser Ile Ser
    450                 455                 460

Ser Leu Ser Pro Ile Asp Asn Leu Glu Ile Lys Leu Ser Ser Leu Ser
465                 470                 475                 480

Arg Thr Asp Arg Gln Phe Gln Glu Lys Leu Ile Arg Phe Ser Leu Gln
                485                 490                 495

Gly Asn Ile Glu Leu Tyr Leu Asn Pro Gln Ile Asn Leu Arg Ser Ser
            500                 505                 510

Thr Gln Asn Leu Glu Ser Asn Glu Leu Ile Thr Arg Ser Ile Asn Asp
        515                 520                 525

Ile Lys Gln Lys Ile Ile Asp Asn Ser Leu Val Ala Ser Asp Gly Thr
    530                 535                 540

Ile Asn Trp Phe Asn Val Ser Val Gly Asp Tyr Asp Glu Leu Glu Leu
```

-continued 545 550 555 560

Glu Ile Met Asp Asp Thr Ile Tyr Lys Gly Ile Ala Gly Ile Lys Leu
565 570 575

Ala Phe Leu Leu Ser Ser Arg Asn Phe Gly Met Ser Ser Asp Lys Val
580 585 590

Ile Leu Asp Arg Ile Asn Lys Ser Leu Ser Phe Ser Asp Tyr Thr Leu
595 600 605

Asn Arg Glu Ser Phe Tyr Glu Gly Thr Phe Gly Ser Gln Leu Pro Ser
610 615 620

Tyr Lys Glu Ile Ser Lys Glu Asp Leu Gln Asn Pro Lys Gln Trp Asp
625 630 635 640

Ala Leu Leu Gly Ala Ser Ser Thr Ile Ile Gly Ile Tyr Gln Asn Phe
645 650 655

Lys Ile Asn Pro Thr Phe Lys Glu Ile Ile Glu Gln Tyr Ala Asp Tyr
660 665 670

Leu Val Ile Ser Leu Gln Lys Asn Ser Ile Asn Gly Tyr Ser Trp Phe
675 680 685

Asp Glu Glu His Gln Asp Leu Val Asn Val Ser Phe Ala His Gly Asn
690 695 700

Ser Gly Cys Met Thr Ala Leu Leu Ile Ser Tyr Ala Leu Leu Gly Lys
705 710 715 720

Ser Glu Tyr Leu Asp Thr Phe Gln Lys Leu Gly Lys Val Asn Lys Lys
725 730 735

Phe Met Ile Asp Cys Gly Trp Glu Asp Thr Arg Asn Thr Asp Arg Leu
740 745 750

Ser Ser Ala Asn Trp Cys His Gly Ser Thr Gly Ala Leu Thr Ser Arg
755 760 765

Leu Leu Trp Phe Lys Leu Asn Lys Lys Phe Asn Ile Leu Asn Glu His
770 775 780

Asp Ile Gln Arg Val Tyr Leu Glu Ile Asp His Ser Val Asn Asp Ile
785 790 795 800

Ile Asp Lys Gly Leu Ser Ile Asn Asn Phe Ser Leu Cys His Gly Ile
805 810 815

Met Gly Asn Leu Ile Ala Leu Asn Glu Tyr Ser Leu Ala Phe Ser Asn
820 825 830

Gln Lys Ile Gln Gln Leu Val Gln Ser Thr Leu Ile Ser Leu Cys Ser
835 840 845

Val Gly Met Lys Lys Asp Trp Leu Cys Gly Val Asn Asp Leu Phe Tyr
850 855 860

Asn Asn Gly Leu Met Thr Gly Leu Ala Gly Ile Leu Tyr Gly Ile Ile
865 870 875 880

Lys Ile Tyr Tyr Asp Asp Asn Tyr Asp Gln His Val Leu Asn Leu Ser
885 890 895

Phe Tyr

<210> SEQ ID NO 22
<211> LENGTH: 1088
<212> TYPE: PRT
<213> ORGANISM: Artificial Sequence
<220> FEATURE:
<223> OTHER INFORMATION: Synthetic construct

<400> SEQUENCE: 22

Met Gly Met Gly Asn Ala Tyr Pro Leu Asp Ile Ala Ala Arg Ala Ala
1 5 10 15

-continued

```
Asn Leu Thr Glu Arg Leu Arg Val Val Ala Ala Ala Gly Gly Glu Ala
            20                  25                  30

Ala Val Arg Asp Asn Thr Val Glu Leu Asp Ala Phe Asp Arg Trp Lys
        35                  40                  45

Ala Asp Thr Leu Ala Gly Lys Leu Ala Asp Lys Phe His Gln Glu Ser
    50                  55                  60

Leu His Arg Gly Arg Pro Pro Gln His Thr Lys Asp Glu Leu Ala Gly
65                  70                  75                  80

Val Leu Ser Ala Tyr Arg Arg Leu Glu Leu Gly Leu Asp Thr Ala Asp
                85                  90                  95

Asp Asp Val Arg Thr Leu Leu Gly Glu Leu Gln Ser Ala Trp Leu Pro
            100                 105                 110

Ala Tyr Arg Ala Ala Leu Asp Ala His Asp Ala Ala Arg Asp Asp Glu
        115                 120                 125

Arg Ala Asp Ala Gln Pro Gly Glu Glu Pro Gly Trp Arg Gly Phe Asp
    130                 135                 140

Val Tyr Tyr Gly Arg Leu Ala Lys Ala Cys Glu Pro Phe Leu Arg Glu
145                 150                 155                 160

Leu Gly Arg Gly Leu Gly Ala Ala Arg Asp Ala Ala Gln Gly Glu Gly
                165                 170                 175

Ala Ala Leu Ser Pro Gln Leu Ala Glu Asp Ile Gln Arg His Leu Leu
            180                 185                 190

Asp Arg Phe Glu Leu Ser Leu Ala Trp Ala Val Glu Ala Asp Ala Asn
        195                 200                 205

Val His Cys Thr Gln Ala Gly Ile Asp Lys Ala Glu Ala Thr Arg Glu
    210                 215                 220

Asp Tyr Leu Ala Tyr Leu Asp Thr Thr Phe Ser Asp Ser Ala Ala Tyr
225                 230                 235                 240

His Arg Phe Tyr Leu Lys Phe Pro Val Leu Gly Arg Trp Leu Ala His
                245                 250                 255

Thr Thr Ala Leu Leu Thr Ala Phe Gly Arg Asp Leu Phe Asp Ser Leu
            260                 265                 270

Ala Ala Asp Ala Glu Ala Ile Gly Thr Glu Phe Phe Gly Gln Pro Val
        275                 280                 285

Thr Ala Phe Thr Ser Leu Arg Leu Gly Asp Ser Asp Pro His Ala Gly
    290                 295                 300

Ala Arg Thr Val Ala Arg Val Ala Val Val Leu Ala Asp Gly Arg Thr
305                 310                 315                 320

Gly Glu Phe Phe Tyr Lys Pro Arg Ser Val Arg Ser Glu Ala Ala Leu
                325                 330                 335

Gln Asp Val Leu Ala Arg Leu Ala Asp Asp Gly Val Val Asp Phe Ala
            340                 345                 350

Thr Arg Pro Val Leu Pro Arg Asp Gly Tyr Gly Tyr Glu Ala Leu Ile
        355                 360                 365

Pro Ala Gly Arg Asn Arg Val Glu Thr Pro Glu Glu Val Thr Arg Ile
    370                 375                 380

Tyr Arg Glu Leu Gly Gly Tyr Leu Ala Leu Phe Tyr Val Leu Gly Gly
385                 390                 395                 400

Ser Asp Leu His Phe Glu Asn Val Ile Val Ala Asp Gly His Ala Phe
                405                 410                 415

Val Cys Asp Ala Glu Thr Val Leu Gly Val His Pro Gln Gly Arg Ala
            420                 425                 430
```

-continued

```
Gln Ser Glu Gly Thr Leu Leu Asp Ser Val Phe Lys Thr Gly Leu Leu
        435                 440                 445

Glu Trp Pro Arg Ala Ala Ser Pro Gly Glu Glu Ala Ala Ala Glu Met
    450                 455                 460

Arg Ile Ser Gly Tyr Ala Gly Gly Glu Gly Tyr Asp Val Pro Val Pro
465                 470                 475                 480

Val Ala Arg Arg Thr Gly Glu Gly Leu Thr Phe Ala Ala Ser Val Val
                485                 490                 495

His Lys Thr Gly Val His Val Glu Thr Ser Ala Ser Asn Arg Val Tyr
            500                 505                 510

Leu Gly Glu Glu Leu Val Arg Pro Glu Asp His Val Glu Ser Ile Met
        515                 520                 525

Glu Gly Phe Asn Arg Val Tyr Asp Trp Phe Ala Glu Asp Pro Asp Ala
    530                 535                 540

Ser Val Asp Tyr Leu Met Glu Thr Phe Ser Trp Val Thr Ala Arg Phe
545                 550                 555                 560

Ile Asn Trp Gly Thr Gln Ile Tyr Ala Gln Leu Leu Ser Ala Ala Arg
                565                 570                 575

His Pro Arg Cys Leu Thr Glu Pro Leu Glu Val Asp Leu Leu Ala Asn
            580                 585                 590

Thr Val Arg Thr Phe Pro Arg Thr Trp Asp Ala Glu Gly Val Leu Ala
        595                 600                 605

Gly Arg Glu Val Ala Ala Met Trp Gln Met Asp Val Pro Leu Phe Thr
    610                 615                 620

Ala Ala Ala His Ala Arg Gln Leu Val His Gly His Gly Asp Pro Leu
625                 630                 635                 640

Ser Ala Arg Leu Asp Ser Ser Pro Ile Asp His Ala Ala Ala Arg Ile
                645                 650                 655

Arg Arg Leu Ser Gln Arg Asn Arg Glu Gln Gln Ser Gln Tyr Ile Ala
            660                 665                 670

Ala Ser Leu Ser Thr Gly Glu Ile Ser Ser Pro Ala Phe Val Ala Thr
        675                 680                 685

Ser Leu Asp Tyr Ala Ala Arg Ile Gly Asp Arg Leu Cys Asp Glu Leu
    690                 695                 700

Arg Ala Pro Ala Ala Pro Ala Pro Trp Thr Ser Tyr Gln Leu Ser Gly
705                 710                 715                 720

Glu Ser Leu Ala Glu Val Asp Ile Glu Ala Asp Leu Tyr Gln Gly Ser
                725                 730                 735

Ala Gly Val Val Leu Phe Leu Ala Tyr Leu Asp Gln Leu Val Pro Arg
            740                 745                 750

Pro Ala Tyr Arg Lys Ala Ala Arg Gln Ala Leu Asp His Val Leu Val
        755                 760                 765

His Trp Asp Arg Asp Arg Leu Gly Ala Phe Ala Gly Leu Gly Gly Val
    770                 775                 780

Val Tyr Leu Leu Thr His Leu His Arg Leu Trp Gly Asp Glu Glu Leu
785                 790                 795                 800

Leu Asp Leu Ala Val Arg Leu Ser Asp Glu Leu Pro Ala Arg Ile Asp
                805                 810                 815

Glu Asp Arg His Phe Asp Ile Leu His Gly Ala Ala Gly Leu Ile Pro
            820                 825                 830

Val Leu Leu Gly Leu Ala Gln Glu Thr Gly Gly His Gly Ile Glu His
        835                 840                 845

Ala His Arg Cys Ala Glu His Leu Leu Arg His Ala Glu Asp Asp Gly
```

-continued

```
    850                 855                 860

Thr Thr Leu Ser Trp Pro Pro Ser Ala Ala Asp Glu Thr Tyr Gly Asn
865                 870                 875                 880

Leu Thr Gly Phe Ser His Gly Ser Gly Gly Ile Gly Trp Ala Leu Ile
                885                 890                 895

Gln Leu Gly Arg His Thr Gly Arg Ser Asp Tyr Ile Glu Ala Gly Arg
            900                 905                 910

Lys Ala Phe Ala Tyr Glu Asp Arg His Val Asp Glu Gln Glu Lys Asp
        915                 920                 925

Trp Tyr Asp Leu Arg Ile Asn Asn Gly Ser Ala Val Lys Gly Ala Arg
    930                 935                 940

His Phe Ser Asn Ala Trp Cys Asn Gly Ala Ala Gly Ile Gly Leu Ala
945                 950                 955                 960

Arg Ile Ser Ser Trp Ala Ala Leu Asp Arg Ser Asp Glu Gln Leu Leu
                965                 970                 975

Arg Asp Ala Gln Gln Ala Leu Ser Ala Thr Leu Arg Asn Phe Pro Arg
            980                 985                 990

Leu Lys Asn His Thr Leu Cys His  Gly Thr Ser Gly Asn  Ala Glu Leu
        995                 1000                1005

Leu Leu  Arg Phe Ala Arg Leu  Ser Asp Glu Pro Ala  Phe Gln Leu
    1010                1015                1020

Glu Ala  Asn Val Gln Val Gln  Ala Leu Trp Arg Ser  Leu Asp Glu
    1025                1030                1035

Ala Gly  Gly Gly Ala Gly Gly  Gly Ser Ala Asp Phe  Phe Pro Gly
    1040                1045                1050

Leu Met  Ile Gly Ile Ser Gly  Phe Gly Met His Phe  Leu Arg Leu
    1055                1060                1065

Ala Ala  Pro Asp Arg Val Pro  Ser Val Leu Leu Leu  Asp Pro Pro
    1070                1075                1080

Ser His  His Glu Gln
    1085


<210> SEQ ID NO 23
<211> LENGTH: 927
<212> TYPE: PRT
<213> ORGANISM: Artificial Sequence
<220> FEATURE:
<223> OTHER INFORMATION: Synthetic construct

<400> SEQUENCE: 23

Met Asn Pro Lys Glu Leu Leu Tyr Ser Gln Phe Asp Arg Phe Pro Lys
1               5                   10                  15

Val Val Ile Glu Asn Asn Phe Pro Glu Leu Leu Asn Glu Ser Ser Glu
            20                  25                  30

Leu Ile Lys Asp Val Glu Asp Glu Ile Ser Asp Tyr Tyr Arg Ser Thr
        35                  40                  45

Leu Ile Tyr Leu Ile Asn Glu Lys Arg Ile Glu Lys Asn Leu Ile Gly
    50                  55                  60

Asp Ser Pro Glu Ser Arg Tyr Glu Tyr Phe Asn Asn Val Leu Cys Gln
65                  70                  75                  80

Asn Gly Leu Ile Phe Glu Glu Ile Asp Arg Arg Phe Pro Ser Ile Asn
                85                  90                  95

Gln Arg Val Met Ser Thr Ile Lys Lys Cys Leu Glu Leu Ile Asn Phe
            100                 105                 110

Val Lys Glu Arg Phe Thr Leu Asp Phe Lys Glu Leu Arg Glu Thr Gly
```

-continued

```
        115                 120                 125

Tyr Ile Tyr Ser Glu Ala Gln Thr Pro Lys Ile Ser Glu Val Lys Ile
    130                 135                 140

Lys Ile Thr Gly Asp Ile His Asn Gly Cys Gly Val Cys Ile Leu Ser
145                 150                 155                 160

Tyr Glu Glu Gln Lys Val Val Phe Lys Lys Lys Ser Ser Asn Pro Asn
                165                 170                 175

Val Leu Leu His Glu Leu Asn Ile Glu Val Gly Lys Phe Leu Gln Lys
            180                 185                 190

Asp Ile Asp Phe Ile Pro Asp Phe Leu Asp Lys Gly Glu Tyr Phe Trp
        195                 200                 205

Glu Lys Phe Val Ser Ser Ser Pro Leu Arg Thr Glu Glu Asp Ala Lys
    210                 215                 220

Glu Phe Tyr Arg Arg Met Gly Tyr Leu Leu Ser Tyr Ser Tyr Ile Leu
225                 230                 235                 240

Asn Ile Ser Asp Leu His Phe Glu Asn Leu Ile Ser Thr Ser Phe Ser
                245                 250                 255

Pro Lys Leu Val Asp Val Glu Thr Val Phe Ser Val Ser Pro Tyr Gln
            260                 265                 270

Thr Val Ala Asn Asn Glu Ser Thr Leu Glu Ile Ile Asn Asn Ser Arg
        275                 280                 285

Asn Ser Ile Leu Ser Thr Gly Leu Leu Pro Val Ser Glu Ala Gly Lys
    290                 295                 300

Val Phe Gly Gly Asp Thr Ser Gly Val Leu Gly Gly Thr Leu Ile Gly
305                 310                 315                 320

Glu Ala Lys Ile Val Ile Asn His Asn Arg Asp Asp Ile His Val Glu
                325                 330                 335

Lys Gln Lys Phe Lys Thr Glu Asn Gln Asp His Leu Pro Tyr Phe Ile
            340                 345                 350

Asp Ser Lys Gly Met Lys Glu Phe Leu Asn Ala Glu Asp Tyr Val Glu
        355                 360                 365

Tyr Ile Lys Glu Gly Phe Arg Glu Val Ser Tyr Phe Phe Met Asn Ser
    370                 375                 380

Gln Asp Phe Leu Lys Lys Leu Tyr Ile Lys His Asn Asp Ile Lys Thr
385                 390                 395                 400

Arg Ile Leu Phe Arg Asn Thr Arg Asp Tyr Ser Leu Val Arg Gln Leu
                405                 410                 415

Leu Val Ser Pro Val Tyr Cys Glu Gln Ser Glu Ile Leu Phe Glu Thr
            420                 425                 430

Met Ala Asn Lys Leu Ser Glu Gln Asn Ser Arg Ser Leu Cys Leu Ser
        435                 440                 445

Glu Lys Lys Gln Leu Leu Asn Met Asp Ile Pro Tyr Phe Tyr Ser Asn
    450                 455                 460

Ile Asp Ser Cys Asp Ile Lys Asp Glu Asn Met Ile Ile Trp Asn Leu
465                 470                 475                 480

Glu Ser Ser Ala Leu Ser Glu Ala Ile Asn Lys Leu Glu Lys Leu Ser
                485                 490                 495

Glu Glu Ile Ile Asn Glu Gln Ile Glu Leu Ile Glu Phe Ser Ile Lys
            500                 505                 510

Thr Pro Lys Ala Leu Tyr Ser Thr Glu Leu Gln Glu Ala Tyr Gln Lys
        515                 520                 525

Phe Glu Lys Val Ser Ser Ser Glu Asn Ile Ile Lys Thr Gly Ile Asp
    530                 535                 540
```

-continued

```
Thr Leu Val Asp Ile Ile Leu Glu Asn Glu Ser Asn Ser Leu Lys Asp
545                 550                 555                 560

Asp Ser Thr Asn Trp Leu Thr Leu Lys Val Thr Asp Tyr Asp Ala Phe
                565                 570                 575

Glu Leu Val Pro Met Asp Asp Ser Leu Tyr Glu Gly Leu Ser Gly Ile
            580                 585                 590

Ala Ile Ser Leu Ser Glu Ala Tyr Asp Phe Leu Asp Ser Gly Arg Gln
        595                 600                 605

Arg Arg Val Lys Glu Cys Leu Lys Arg Ile Phe Ser Val Leu Ser Asn
    610                 615                 620

Ser Tyr Met Lys Leu Pro Asn His Ser Phe Phe Val Gly Lys Leu Gly
625                 630                 635                 640

Ile Tyr Ser Ala Leu Lys Arg Ile Ser Val Val Thr Gly Gln Glu Ile
                645                 650                 655

Gln Asn Ser Ile Met Asn Tyr Asn Asn Leu Lys Tyr Thr Leu Asp Val
            660                 665                 670

Asp Val Leu Ser Ala Asp Phe Leu Ser Ser Phe Pro Asn Glu Ile Thr
        675                 680                 685

Ala Leu Arg Asn Ser Asp Ile Lys Ile Asp Asn Leu Thr Gln Ala Leu
    690                 695                 700

Asp Lys Leu Lys Glu Leu Ala Ile Val Gln Lys Asp Phe Ile Ser Trp
705                 710                 715                 720

Asp Lys Leu Glu Ser Asn Asn Val Ser Leu Ala His Gly Asn Leu Gly
                725                 730                 735

Val Glu Ile Ala Leu Leu Tyr Leu Ala Gly Lys Leu Glu Ser Pro Glu
            740                 745                 750

Ala Leu Asn Leu Phe His Lys Ala Lys Met Phe Asp Lys His Gln Lys
        755                 760                 765

Leu Glu Asn Gly Trp Ile Asp Lys Arg Asn Ser Ser Thr Ser Ala Asn
    770                 775                 780

Trp Cys His Gly Ser Thr Gly Val Leu Val Ala Arg Leu Ala Gln Leu
785                 790                 795                 800

Lys Leu Asp Asp Glu Tyr Ser Leu Leu Ser Tyr Ser Glu Arg Ile Glu
                805                 810                 815

Leu Glu Asn Asp Met Lys His Ala Ala Lys Gln Ile Leu Glu Ile Gly
            820                 825                 830

Phe Asp Met Thr Asn Phe Ser Leu Cys His Gly Thr Ser Gly Asn Leu
        835                 840                 845

Leu Ala Leu Thr Tyr Tyr Gln Ser Tyr Leu Thr Gly Ala Asp Ser Glu
    850                 855                 860

Lys Leu Lys Glu Ile Leu Asp Arg Glu Tyr Arg Lys Leu His Ser Phe
865                 870                 875                 880

Gly Leu Glu Asn Gly Trp Met Cys Ser Phe Asn Thr Lys Tyr Asn Val
                885                 890                 895

Tyr Gly Leu Met Thr Gly Val Ser Gly Ile Leu Phe Ser Thr Val Lys
            900                 905                 910

Tyr Met Lys Gly Asp Asp Ser Leu Asp Val Leu Ile Pro Asn Phe
        915                 920                 925
```

<210> SEQ ID NO 24
<211> LENGTH: 914
<212> TYPE: PRT
<213> ORGANISM: Artificial Sequence
<220> FEATURE:

-continued

<223> OTHER INFORMATION: Synthetic construct

<400> SEQUENCE: 24

```
Met His Lys Lys Phe Cys Gly Leu Tyr Ile Glu Tyr Ile Phe Glu Tyr
1               5                   10                  15

Ile Ile Glu Thr Leu Lys Glu Lys Glu Asp Tyr Leu Phe Asp Ser Glu
            20                  25                  30

Lys Ile Lys Tyr Val Lys Glu Ile Ile Glu Lys Glu Ile Phe Gln Arg
        35                  40                  45

Val Phe Lys Ser Leu Leu Tyr Cys Met Asn Val Glu Arg Leu Asp Gly
    50                  55                  60

Asn Leu Ser Gly Asn Thr Pro Glu Glu Arg Tyr Glu Met Phe Ser Asn
65                  70                  75                  80

Thr Arg Tyr Cys Ile Glu Ala Met Gly Lys Asn Phe Pro Thr Met Arg
                85                  90                  95

Asn Gln Ile Tyr Asp Glu Met Ala His Lys Cys Val Tyr Val Met Glu
            100                 105                 110

Val Ile Arg Glu Leu Glu Asn Asn Lys Asn Lys Ile Gly Arg His Phe
        115                 120                 125

Gly Ile Asn Pro Gly Glu Ile Val Gln Val Gln Asn Ser Gly Asp Trp
    130                 135                 140

His Asp Ser Glu Cys Val Leu Ile Phe Thr Phe Gln Ser Gln Asp Lys
145                 150                 155                 160

Ile Val Tyr Lys Pro Thr Arg Gly Glu Asn Leu Gln Phe Met Lys Gly
                165                 170                 175

Phe Met Asp Tyr Phe Phe Glu Pro Glu Tyr Ala Glu Gln Tyr Ile Gly
            180                 185                 190

Leu Cys Ile Arg Lys Gly Thr Trp Val Lys Phe Val Lys His Ile Glu
        195                 200                 205

Leu Thr Asn Ser Arg Asn Val Glu Arg Phe Tyr Tyr Asn Tyr Gly Lys
    210                 215                 220

Val Leu Phe Val Ala Tyr Ile Leu Gly Met Asn Asp Ile His Tyr Glu
225                 230                 235                 240

Asn Leu Ile Ala Cys Gly Glu Tyr Pro Val Ile Thr Asp Val Glu Thr
                245                 250                 255

Ile Phe Ser Ser Tyr Leu Phe Phe Asp Thr His Thr Phe Leu Tyr Asp
            260                 265                 270

Ala Gln Tyr Lys Ala Val Lys Glu Leu Leu Tyr Gly Thr Met Ala Thr
        275                 280                 285

Gly Met Leu Pro Ile Phe Ser Met Thr Asp Tyr Phe Gly Gly Asp Val
    290                 295                 300

Ser Cys Leu Ser Asn Lys Gly Ile Gln Leu Ile Val Glu Lys Ile Lys
305                 310                 315                 320

Asn Glu Tyr Arg Asp Asp Met Tyr Ile Cys Thr Ala Pro Glu Met Ile
                325                 330                 335

Val Glu Tyr Lys His Leu Pro Asn His Thr Ile Asp Pro Leu Met Tyr
            340                 345                 350

Gly Lys Gln Ile Val Gln Gly Phe Glu Glu Ala Glu Asn Asn Phe Gly
        355                 360                 365

Glu Lys Lys Val Glu Ile Ile Asn Tyr Ile Leu Asn Asn Met Gly Lys
    370                 375                 380

Val Glu Ser Arg Ile Ile Leu Asn Met Thr Lys Gly Tyr Ser Lys Ile
385                 390                 395                 400
```

-continued

```
Val Arg Ile Lys Ser Asp Pro Arg Tyr Arg His Glu Pro Glu Leu Phe
                405                 410                 415

Gly His Leu Leu Thr Thr Leu Lys Arg Thr Asn Gln Phe Asn Pro Glu
            420                 425                 430

Val Tyr Glu Gln Glu Val Thr Glu Leu Cys Arg Ser Asn Ile Pro Ser
        435                 440                 445

Phe Tyr Trp Lys Met Asp Met Asn Cys Val Tyr Gly Leu Asn Leu Gly
    450                 455                 460

Gln Lys Lys Lys Ile Leu Asp Leu Pro Ile Phe Thr Lys Glu Arg Leu
465                 470                 475                 480

Ser Glu Ile Leu Glu Tyr Gln Ile Asn Ile Gln Met Leu Glu Lys Gln
                485                 490                 495

Lys Gln Leu Ile Tyr Asp Ala Ile Val Ser Asn Ile Ala Leu Gly Ile
            500                 505                 510

Glu Tyr Glu Lys Leu Lys Ile Ser Val Lys Gln His Val Asp Ile His
        515                 520                 525

Val Lys Lys Val Leu Arg Arg Asn Ile Asp Gln Asn Cys Ile Val Gly
    530                 535                 540

Ser Asp Gly Thr Ile Ser Trp Leu Gly Leu Met Val Asn Asp Lys Glu
545                 550                 555                 560

Gln Leu Glu Tyr Ala Met Leu Asp Trp Ser Leu Tyr Ser Gly Ile Ile
                565                 570                 575

Gly Leu Gly Tyr Met Tyr Ile Ser Glu Tyr Asp Lys Glu Pro Asp Val
            580                 585                 590

Leu Ala Lys Asp Met Leu Gln Arg Ile Phe Cys Thr Leu Ala Lys Ser
        595                 600                 605

Tyr Asp Leu Gly Val Phe Lys Glu Tyr Asp Ile Ser Tyr Phe Cys Gly
    610                 615                 620

Leu Thr Gly Ile Tyr Ala Phe Leu Lys Gln Ile Lys Asp Arg Asn Ile
625                 630                 635                 640

Ile Glu Pro Asp Ile Ile Glu Lys Tyr Ile Lys Asn Ile Gln Glu Ala
                645                 650                 655

Ile Arg Asn Asn Ile Val Lys Thr Ser Ser Tyr Asp Thr Leu Ala Gly
            660                 665                 670

Ile His Ser Ala Val Ile Tyr Tyr Phe Gly Cys Tyr Glu Gln Asp Ile
        675                 680                 685

Phe Ser Arg Glu Ile Leu Ser Ser Ile Glu Glu Tyr Phe Leu Asn Ser
    690                 695                 700

Phe Lys Ile Asp Asp Met Lys Arg Asn Phe Asn Tyr Ala Ser Phe Ala
705                 710                 715                 720

His Gly Tyr Ser Gly Val Met Thr Ser Ile Met Cys Met Leu Gln His
                725                 730                 735

Lys Tyr Asp Ile Lys Leu Glu Lys Ile Leu Cys Glu Leu Trp Lys Glu
            740                 745                 750

Glu Lys Glu Leu Tyr Val Glu Lys Phe Ile Trp Lys Asp Met Arg Ala
        755                 760                 765

His His Ile Val His Ser His Tyr Trp Cys His Gly Ser Val Gly Ile
    770                 775                 780

Met Met Ala Arg Leu Ile Trp Lys Lys Phe Gly Phe Asp Lys Lys Phe
785                 790                 795                 800

Ala Glu Asp Ile Glu Glu Glu Asn Leu Glu Glu Ile Leu Ser Lys Tyr
                805                 810                 815

Lys Glu Glu Leu Leu Asn Lys Lys Phe Gln Ser Lys Asn Tyr Ser Leu
```

-continued

```
            820                 825                 830

Cys His Gly Asn Phe Ala Leu Ile Asp Phe Leu Ile Ser Tyr Arg Lys
        835                 840                 845

Ile Val Gly Thr Asp Glu Arg Ile Asp Ala Tyr Ile Glu Glu Ile Ile
    850                 855                 860

Glu Ser Gly Gln Glu Asn Gly Tyr Ser Cys Val Gly Ala Pro Gly Ala
865                 870                 875                 880

Ile Asn Ser Ile Gly Phe Met Val Gly Glu Ala Gly Ile Gln Tyr Thr
                885                 890                 895

Glu Asn Arg Ser Glu Asn Ser Lys Leu His Ser Val Leu Met Leu Glu
            900                 905                 910

Thr Val


<210> SEQ ID NO 25
<211> LENGTH: 980
<212> TYPE: PRT
<213> ORGANISM: Artificial Sequence
<220> FEATURE:
<223> OTHER INFORMATION: Synthetic construct

<400> SEQUENCE: 25

Met Lys Phe Asn Lys Asn Val Phe Pro Glu Ile Asn Glu Thr Asp Phe
1               5                   10                  15

Asp Asn Asn Ile Lys Pro Leu Leu Asp Glu Leu Glu Ser Arg Ile Thr
            20                  25                  30

Ile Pro Gln Glu Glu Leu Ser Phe Ser Ser Ile Asn Asp Asp Leu Phe
        35                  40                  45

Arg Glu Leu Thr Arg Asn Glu Glu Tyr Pro Tyr Gln Ser Ile Cys Thr
    50                  55                  60

Ile Val Ala Asn Ile Val Met Asp Asp Gly Ser Glu Ile Trp Arg Lys
65                  70                  75                  80

Asp Ile Phe Val Asp Ser Asn Ser Val Arg Glu Ala Val Cys Asp Ile
                85                  90                  95

Leu Ser Gln Thr Leu Phe Leu Tyr Phe Ile Arg Cys Phe Ser Glu Gln
            100                 105                 110

Ile Lys Asp Ile Arg Lys Thr Asp Glu Asp Lys Glu Ser Thr Tyr Asn
        115                 120                 125

Arg Tyr Ile Asn Leu Leu Phe Ser Ser Asn Phe Lys Ile Phe Ser Asp
    130                 135                 140

Glu Tyr Pro Val Leu Trp Tyr Arg Thr Ile Arg Ile Ile Lys Asn Arg
145                 150                 155                 160

Trp Tyr Ser Ile Lys Lys Ser Leu Leu Leu Thr Gln Lys His Arg Val
                165                 170                 175

Glu Ile Asp Lys Gln Leu Asp Ile Pro His Lys Met Lys Ile Lys Gly
            180                 185                 190

Leu Lys Ile Gly Gly Asp Thr His Asn Gly Gly Ala Thr Val Thr Thr
        195                 200                 205

Ile Phe Phe Glu Lys Gly Tyr Lys Leu Ile Tyr Lys Pro Arg Ser Thr
    210                 215                 220

Ser Gly Glu Phe Ser Tyr Lys Lys Phe Ile Glu Lys Ile Asn Pro Tyr
225                 230                 235                 240

Leu Lys Lys Asp Met Gly Ala Ile Lys Ala Ile Asp Phe Gly Glu Tyr
                245                 250                 255

Gly Phe Ser Glu Tyr Ile Glu Cys Asn Thr Asp Glu Glu Asp Met Lys
            260                 265                 270
```

-continued

```
Gln Val Gly Gln Leu Ala Phe Phe Met Tyr Leu Leu Asn Ala Ser Asp
        275                 280                 285

Met His Tyr Ser Asn Val Ile Trp Thr Lys Gln Gly Pro Val Pro Ile
    290                 295                 300

Asp Leu Glu Thr Leu Phe Gln Pro Asp Arg Ile Arg Lys Gly Leu Lys
305                 310                 315                 320

Gln Ser Glu Thr Asn Ala Tyr His Lys Met Glu Lys Ser Val Tyr Gly
                325                 330                 335

Thr Gly Ile Ile Pro Ile Ser Leu Ser Val Lys Gly Lys Lys Gly Glu
            340                 345                 350

Val Asp Val Gly Phe Ser Gly Ile Arg Asp Glu Arg Ser Ser Ser Pro
        355                 360                 365

Phe Arg Val Leu Glu Ile Leu Asp Gly Phe Ser Ser Asp Ile Lys Ile
    370                 375                 380

Val Trp Lys Lys Gln Gln Lys Ser Ser Ser Ser Lys Asn Asn Leu Ile
385                 390                 395                 400

Val Asp His Lys Lys Glu Arg Glu Ile Leu Gln Arg Ala Gln Ser Val
                405                 410                 415

Val Glu Gly Phe Gln Glu Thr Ser Lys Ile Phe Met Lys His Arg Glu
            420                 425                 430

Glu Phe Ile Ser Ile Ile Leu Asp Ser Phe Glu Asn Ile Lys Ile Arg
        435                 440                 445

Tyr Ile His Asn Met Thr Phe Arg Tyr Glu Gln Leu Leu Arg Thr Leu
    450                 455                 460

Thr Asp Ala Glu Pro Ala Gln Lys Ile Glu Leu Asp Arg Leu Leu Leu
465                 470                 475                 480

Ser Arg Thr Gly Ile Leu Ser Ile Ser Ser Ser Pro Tyr Ile Ser Leu
                485                 490                 495

Ser Glu Cys Gln Gln Met Trp Gln Gly Asp Val Pro Tyr Phe Tyr Ser
            500                 505                 510

Lys Phe Ser Ser Lys Ser Ile Phe Asp Thr Asn Gly Phe Val Asp Glu
        515                 520                 525

Ile Glu Leu Thr Pro Arg Gln Ala Phe Ile Ile Lys Ala Glu Ser Ile
    530                 535                 540

Thr Asn Asp Glu Val Asp Phe Gln Ser Lys Ile Ile Lys Leu Ala Phe
545                 550                 555                 560

Met Ala Arg Leu Ser Asp Pro His Thr Thr Asn Asp Asn Lys Leu Asn
                565                 570                 575

Lys Lys Val Ile Ile Glu Ser Asn Gln Gln Ser Asn Ser Ser Glu Ser
            580                 585                 590

Gly Asn Lys Ala Ile Leu Phe Leu Ser Asp Leu Leu Lys Asn Asn Val
        595                 600                 605

Leu Glu Asp Arg Tyr Ser His Leu Pro Lys Thr Trp Ile Gly Pro Val
    610                 615                 620

Ala Arg Asp Gly Gly Leu Gly Trp Ala Pro Gly Val Leu Gly Tyr Asp
625                 630                 635                 640

Leu Tyr Ser Gly Arg Thr Gly Pro Ala Leu Ala Leu Ala Ala Ala Gly
                645                 650                 655

Arg Val Leu Lys Asp Lys Asp Ser Ile Glu Leu Ser Ala Asp Ile Phe
            660                 665                 670

Asn Lys Ser Ser Gln Ile Leu Gln Glu Lys Thr Tyr Asp Phe Arg Asn
        675                 680                 685
```

-continued

```
Leu Phe Ala Ser Gly Ile Gly Gly Phe Ser Gly Ile Thr Gly Leu Phe
    690                 695                 700

Trp Ala Leu Asn Ala Ala Gly Asn Ile Leu Asn Asn Asp Asp Trp Ile
705                 710                 715                 720

Lys Thr Ser Asn Gln Ser Met Leu Leu Leu Asn Glu Asn Met Leu Lys
                725                 730                 735

Val Asp Lys Asn Phe Phe Asp Leu Ile Ser Gly Asn Ser Gly Ala Ile
            740                 745                 750

Gly Met Met Tyr Leu Thr Asn Pro Asn Phe Tyr Leu Ser Arg Ser Lys
        755                 760                 765

Ile Asn Asp Ile Leu Leu Thr Thr Asp Cys Leu Ile Thr Glu Met Glu
    770                 775                 780

Lys Asp Glu Thr Ser Gly Leu Ala His Gly Val Ser Gln Ile Leu Trp
785                 790                 795                 800

Phe Leu Ser Ile Met Met Gln Arg Gln Pro Ser Ser Glu Ile Lys Ile
                805                 810                 815

Arg Ala Thr Ile Val Asp Asn Ile Ile Lys Lys Lys Tyr Thr Asn Ser
            820                 825                 830

Tyr Gly Glu Ile Glu Cys Tyr Tyr Pro Thr Asp Gly His Ser Lys Ser
        835                 840                 845

Thr Ser Trp Cys Asn Gly Thr Ser Gly Ile Leu Val Ala Tyr Ile Glu
    850                 855                 860

Gly Tyr Lys Ala Asn Ile Val Asp Lys Ser Ser Val Tyr His Ile Ile
865                 870                 875                 880

Asn Gln Ile Asn Val Glu Gln Leu Gln His Asp Asn Ile Pro Ile Met
                885                 890                 895

Cys His Gly Ser Leu Gly Val Tyr Glu Ser Leu Lys Tyr Ala Ser Lys
            900                 905                 910

Tyr Phe Glu Ile Glu Thr Lys Tyr Leu Leu Asp Val Met Arg Asn Gly
        915                 920                 925

Gly Cys Ser Ser Gln Glu Val Leu Lys Tyr Tyr Gly Lys Gly Asn Gly
    930                 935                 940

Arg Tyr Pro Leu Ser Pro Gly Leu Met Ala Gly Gln Ser Gly Ala Leu
945                 950                 955                 960

Leu His Cys Cys Lys Leu Glu Asp Asn Asp Ile Ser Val Ser Pro Ile
                965                 970                 975

Ser Leu Met Thr
            980


<210> SEQ ID NO 26
<211> LENGTH: 927
<212> TYPE: PRT
<213> ORGANISM: Artificial Sequence
<220> FEATURE:
<223> OTHER INFORMATION: Synthetic construct

<400> SEQUENCE: 26

Met Asp Pro Ser Ile Lys Lys Leu Val Asp Ser Ile Ile Glu Phe Tyr
1               5                   10                  15

Lys Lys Asp Ile Tyr Leu Ala Tyr Lys Glu Leu Glu Arg Glu Ile Lys
            20                  25                  30

Asn Ile Asp Lys Thr Ile Tyr Asn Thr Ser Asn Asp Glu Ile Leu Arg
        35                  40                  45

Ile Phe Lys Glu Ser Leu Ile Ser Ile Ile Thr Asp Asp Ile Tyr Arg
    50                  55                  60
```

-continued

```
Leu Ser Ile Lys Thr Phe Ile Tyr Glu Phe His Lys Phe Arg Ile Asp
65                  70                  75                  80

Asn Gly Phe Pro Ala Val Lys Asp Ser Glu Ser Ala Phe Asn Tyr Tyr
                85                  90                  95

Ile Ser Thr Phe Asp Val Lys Thr Ile Ala Arg Trp Phe Glu Lys Phe
            100                 105                 110

Pro Met Leu Glu Ser Ile Ile Ser Ser Ser Ile Lys Asn Asp Cys Thr
        115                 120                 125

Phe Met Val Asp Val Cys Val Asn Phe Ile Leu Asp Leu Ser Glu Cys
    130                 135                 140

Glu Lys Ile Asn Leu Ile Ser Glu Asp Ser Arg Leu Ile Thr Ile Ser
145                 150                 155                 160

Ser Ser Asn Ser Asp Pro His Asn Gly Gly Thr Arg Val Leu Phe Phe
                165                 170                 175

Arg Phe His Asn Gly Asp Thr Ile Leu Tyr Lys Pro Arg Ser Leu Thr
            180                 185                 190

Val Asp Lys Leu Ile Ser Asn Ile Phe Glu Glu Val Phe Glu Phe Asp
        195                 200                 205

Ala Thr Asn Ser Lys Asn Pro Ile Pro Lys Val Leu Asp Arg Gly Thr
    210                 215                 220

Tyr Gly Trp Gln Glu Phe Ile Glu Lys Lys Ser Ile Ser Ser Ser Glu
225                 230                 235                 240

Ile Lys Gln Ala Tyr Tyr Asn Leu Gly Ile Phe Ser Ser Ile Phe Thr
                245                 250                 255

Val Leu Gly Ser Thr Asp Ile His Asp Glu Asn Leu Ile Phe Lys Gly
            260                 265                 270

Thr Thr Pro Tyr Phe Ile Asp Leu Glu Thr Ala Leu Ser Pro Arg Ile
        275                 280                 285

Arg Tyr Glu Gly Asn Glu Glu Asn Leu Phe Tyr Arg Met Ser Ser Ser
    290                 295                 300

Leu Phe Thr Ser Ile Val Gly Thr Thr Ile Ile Pro Ala Lys Leu Ala
305                 310                 315                 320

Val His Ser Gln Glu Ile Met Ile Gly Ala Ile Asn Thr Pro Ala Lys
                325                 330                 335

Gln Lys Thr Lys Lys Asp Gly Phe Asn Ile Ile Asn Phe Gly Thr Asp
            340                 345                 350

Ala Val Asp Ile Ala Lys Gln Asn Ile Glu Val Glu Arg Ile Ala Asn
        355                 360                 365

Pro Met Arg Ile Lys Asn Asn Ile Val Asn Asp Pro Leu Pro Tyr Gln
    370                 375                 380

Asn Ile Phe Thr Arg Gly Phe Lys Glu Gly Ile Lys Ser Ile Ile Leu
385                 390                 395                 400

Lys Lys Gly Ser Ile Ile Ser Ile Leu Asn Asn Phe Asn Ser Pro Ile
                405                 410                 415

Arg Tyr Ile Met Arg Pro Thr Ala Lys Tyr Tyr Leu Ile Leu Asp Ala
            420                 425                 430

Ala Val Phe Pro Glu Asn Leu Tyr Ser Glu Gln Thr Leu Asn Lys Thr
        435                 440                 445

Leu Asn Tyr Leu Lys Pro Pro Lys Ile Val Glu Asn Ser Leu Ile Ser
    450                 455                 460

Lys Gln Leu Phe Leu Ala Glu Lys Arg Ile Leu Ser Glu Gly Asp Ile
465                 470                 475                 480

Pro Ser Phe Tyr Val Leu Gly Lys Glu Lys Asn Ile Arg Ala Gln Asn
```

-continued

```
                485                 490                 495

Phe Ile Ser Glu Gln Ile Phe Glu Glu Thr Ala Val Asp Asn Ala Ile
            500                 505                 510

Gln Ile Leu Glu Ser Ile Ser Gln Asp Trp Val Asn Phe Asn Glu Arg
        515                 520                 525

Leu Ile Ala Glu Gly Phe Ser Tyr Ile Arg Glu Gln Ser Arg Gly Tyr
    530                 535                 540

Leu Ser Ser Asp Phe Glu Asn Ser Asp Ile Phe Lys Ser Ser Leu Thr
545                 550                 555                 560

Glu Thr Lys Lys Ser Gly Tyr Thr Ala Met Leu Lys Thr Ile Ile Ser
                565                 570                 575

Met Ser Val Lys Thr Ser Glu Asn Lys Lys Ile Gly Trp Leu Pro Gly
            580                 585                 590

Ile Tyr Asp Asp Tyr Pro Ile Ser Tyr Met Ser Ala Ala Phe Cys Ser
        595                 600                 605

Phe His Asp Ser Gly Gly Ile Ile Thr Leu Leu Glu His His Phe Gly
    610                 615                 620

His Cys Ser Pro Glu Tyr Asn Glu Met Lys Arg Gly Leu Leu Glu Leu
625                 630                 635                 640

Gly Lys Met Leu Lys Ile Asn Asn Ser Asn Leu Ser Ile Ile Ser Gly
                645                 650                 655

Ser Glu Ser Leu Glu Phe Leu Tyr Thr His Arg Glu Val Glu Cys Leu
            660                 665                 670

Glu Leu Glu Tyr Ile Leu Asn Asn Ser Ala Glu Ile Met Gly Asp Val
        675                 680                 685

Phe Leu Gly Lys Leu Gly Leu Tyr Leu Ile Leu Ala Ser Tyr Leu Lys
    690                 695                 700

Thr Asp Leu Lys Ile Phe Gln Asp Phe Ser Ile Ile Cys Gln Lys Asn
705                 710                 715                 720

Leu Glu Phe Lys Lys Phe Gly Ile Ala His Gly Glu Leu Gly Tyr Leu
                725                 730                 735

Trp Thr Ile Phe Arg Ile Gln Asn Lys Leu Lys Asn Lys Asn Ala Cys
            740                 745                 750

Leu Ser Ile Tyr His Glu Val Leu Asn Ile Tyr Lys Gly Lys Arg Ile
        755                 760                 765

Glu Ser Val Gly Trp Cys Asn Gly Leu Ser Gly Ile Leu Met Ile Leu
    770                 775                 780

Ser Glu Met Ser Thr Val Leu Glu Lys Asn Gln Asp Tyr Leu Phe Lys
785                 790                 795                 800

Leu Ala Asn Leu Ser Thr Lys Leu Asn Glu Glu Ser Val Asp Leu Ser
                805                 810                 815

Val Cys His Gly Ala Ser Gly Val Leu Gln Thr Leu Leu Phe Val Tyr
            820                 825                 830

Ser Asn Thr Asn Asp Lys Arg Tyr Leu Ser Leu Ala Asn Lys Tyr Trp
        835                 840                 845

Lys Lys Val Leu Asp Asn Ser Ile Lys Tyr Gly Phe Tyr Asn Gly Glu
    850                 855                 860

Arg Asp Lys Asp Tyr Leu Leu Gly Tyr Phe Gln Gly Trp Ser Gly Phe
865                 870                 875                 880

Thr Asp Ser Ala Leu Leu Leu Asp Lys Tyr Asn Asn Asn Glu Gln Val
                885                 890                 895

Trp Ile Pro Ile Asn Leu Ser Ser Asp Ile Tyr Gln His Asn Leu Asn
            900                 905                 910
```

Asn Cys Lys Glu Lys Asn Tyr Glu Gly Asp Gly Cys His Lys Ser
915 920 925

<210> SEQ ID NO 27
<211> LENGTH: 917
<212> TYPE: PRT
<213> ORGANISM: Artificial Sequence
<220> FEATURE:
<223> OTHER INFORMATION: Synthetic construct

<400> SEQUENCE: 27

Met Asn Asn Ile Lys Val Glu Gln Phe Arg Gly Phe Ser Asn Phe Ile
1 5 10 15

Leu Lys Lys Tyr Ser Lys Gln Glu Leu Asn Thr Leu Ile Asp Trp Asn
20 25 30

Tyr Leu Arg Ser Ile Ile Leu Asp Ile Cys Gly Lys Ser Leu Ile Val
35 40 45

Leu Ile Asn Glu Lys Arg Leu Asn Lys Lys Leu Asn Gly Asn Thr Pro
50 55 60

Glu Glu Arg Tyr Lys Tyr Phe Asp Glu Glu Leu Cys Glu Lys Gly Ile
65 70 75 80

Ile Tyr Glu Glu Leu Asn Lys Ser Tyr Pro Ser Ile Ile Asn Asp Leu
85 90 95

Glu Gln Thr Leu Asn Ser Tyr Phe Ser Phe Leu Lys Glu Ile Glu Asn
100 105 110

Lys Phe Asn Gln Glu Lys Lys Lys Leu Leu Glu Ala Asn Leu Ile Lys
115 120 125

Thr Glu Lys Glu Thr Ile Cys His Ile Ser Ile Leu Gly Asp Leu His
130 135 140

Gly Gly Lys Ala Val Thr Lys Val Thr Thr Asp Lys Ser Gln Leu Leu
145 150 155 160

Tyr Lys Pro Arg Ser Leu Glu Asn Asp Ser Phe Phe Leu Glu Phe Leu
165 170 175

Glu Phe Met Tyr Ser Phe Gln Lys Asn Glu Ile Ser Thr Tyr Tyr Lys
180 185 190

Tyr Lys Phe Ile Asp Tyr Lys Asp His Gly Trp Met Glu Tyr Ile Glu
195 200 205

Lys Gln Pro Thr Ser Lys Asn Lys Ile Asn Met Tyr Tyr Lys Arg Leu
210 215 220

Gly Tyr Leu Leu Ser Ile Gly Tyr Leu Leu Asn Ile Ser Asp Leu His
225 230 235 240

Phe Glu Asn Ile Leu Cys Ser Ser Asn Phe Pro Ile Leu Ile Asp Leu
245 250 255

Glu Thr Ile Phe His Thr Ser Ile Tyr Glu Ser Lys Phe Arg Asn Leu
260 265 270

Ala Thr Lys Asn Ile Glu Asp Lys Ala Ala Asn Ser Val Phe Ala Thr
275 280 285

Gly Met Leu Pro Ile Ser Lys Lys Asp Lys Lys Tyr Gly Gly Asp Ile
290 295 300

Ser Gly Ile Leu Gly Gly Val Phe Asn Lys His Glu Arg Thr Ile Ser
305 310 315 320

Asn Pro Asn Arg Asp Asp Ile Lys Phe Glu Lys Arg Leu Val Arg Val
325 330 335

Lys Arg Asn Asp His Ile Pro Phe Tyr Met Glu Asn Asp Lys Lys Arg
340 345 350

-continued

```
Arg Phe Ser Pro Glu Val Phe Ile Glu Asp Ile Gln Glu Gly Phe Lys
        355                 360                 365

Tyr Gly Tyr Glu Leu Phe Leu Asn Asn Arg Lys Glu Ile Leu His Tyr
    370                 375                 380

Ile Lys Lys Thr Ser Ser Glu Val Glu Val Arg Ile Leu Pro Arg Ser
385                 390                 395                 400

Thr Ile Glu Tyr Ser Val Leu Ile Gln Ala Ala Lys Ser Pro Leu Tyr
                405                 410                 415

Ala Asn Lys Arg Lys Ser Leu Phe Asn Lys Leu Glu Glu Tyr Gly Glu
            420                 425                 430

Asn Leu Leu Ser Asp Lys Leu Ile Asn Ser Glu Ile Lys Gln Ile Glu
        435                 440                 445

Thr Leu Ser Val Pro Tyr Phe Tyr Thr Lys Val Gln Ser Val Ser Val
    450                 455                 460

Lys Asp Ile Lys Asn Asn Thr Val His His Leu Leu Lys Asn Pro Leu
465                 470                 475                 480

Asn Val Phe Leu Glu Lys Thr Gln Arg Tyr Ser Leu Lys Asp Leu Leu
                485                 490                 495

Phe Gln Cys Lys Leu Ile Lys Phe Ser Leu Glu Ser Gln Asn Lys Leu
            500                 505                 510

Phe Ile Asp Gly Asn Gly Phe Ile Asn Tyr Gly Tyr Glu Ile Val Asn
        515                 520                 525

Ser Asp Asn Ile Asp Asp Ala Ile Asp Asn Leu Val Ser Ile Ile Ile
    530                 535                 540

Asn Asn Ala Val Ile Asp Glu Lys Asp Gly Ser Val Asn Trp Met Asn
545                 550                 555                 560

Leu Gly Ile Ser Lys Gly Glu Glu Ile Ile Phe Glu Ser Leu Ser Asp
                565                 570                 575

Asp Leu Tyr Lys Gly Leu Ser Gly Ile Gly Ile Ala Leu Leu Lys Tyr
            580                 585                 590

Tyr Glu Ile Asn Lys Asn Leu Lys Asp Met Ser Arg Leu Lys Lys Ile
        595                 600                 605

Leu Ser Ser Ile Tyr Ser Ser Ile Leu Ser Asn Ile Asn Thr Asn Ser
    610                 615                 620

Ser Lys Glu Lys Asp Leu Ser Phe Phe Asn Gly Glu Ile Gly Lys Ile
625                 630                 635                 640

Ala Phe Leu Tyr Asn Tyr Gln Ile Glu Phe Lys Glu Asn Cys Asp Ser
                645                 650                 655

Ser Lys Asn Tyr Met Lys His Ile Leu Gly Ile Ile Leu Ser Ser Glu
            660                 665                 670

Phe Glu Met Asn Asp Ile Ile Ala Gly Leu Pro Gly Ile Ile Ser Tyr
        675                 680                 685

Leu Tyr Asn Gln Glu Ile Phe Ser Lys Glu Leu Val Ile Met Gly Asp
    690                 695                 700

Arg Leu Leu Lys Asp Leu Asp Asn Asn Pro Thr Met Ala Tyr Tyr Ala
705                 710                 715                 720

His Gly Lys Ser Gly Val Met Val Ser Leu Leu Tyr Leu Tyr Asp Leu
                725                 730                 735

Thr Lys Asp Lys Lys Tyr Leu Val Lys Phe His Gln Glu Trp Lys Lys
            740                 745                 750

Glu Asn Thr Leu Lys Leu Glu Ile Gly Trp Lys Asp Val Arg Gln Asn
        755                 760                 765
```

-continued

```
Glu Glu Thr Tyr Ser Val Ser Trp Cys Asn Gly Val Thr Gly Gln Leu
    770                 775                 780

Ile Ser Arg Leu Val Ala Leu Glu Ile His Asp Lys Val Lys Ile Phe
785                 790                 795                 800

Asp Ala Val Asn Lys Lys Leu Met Gln Lys Glu Ile Glu Glu Leu Leu
                805                 810                 815

Tyr Leu Leu Lys Glu Glu Gly Leu Glu Gln Asn Asn Phe Cys Leu Cys
            820                 825                 830

His Gly Val Met Gly Asn Leu Leu Val Leu Asn Tyr Tyr Gln Lys Lys
        835                 840                 845

Phe Glu Asn Thr Asn Ile His Leu Ala Asn Lys Ile Asp Ser His Phe
    850                 855                 860

Tyr Ser Val Ala Asn Phe Gly Leu Asn Lys Gly Trp Ile Cys Gly Leu
865                 870                 875                 880

Gly Asn Asn Phe Tyr Ser Phe Ser Ile Met Thr Gly Ile Ser Gly Ile
                885                 890                 895

Leu Tyr Ala Phe Leu Lys Tyr Lys Thr Lys Asp Thr Glu Leu Gly Ile
            900                 905                 910

Leu Leu Pro Asn Ile
        915
```

<210> SEQ ID NO 28
<211> LENGTH: 450
<212> TYPE: DNA
<213> ORGANISM: Artificial Sequence
<220> FEATURE:
<223> OTHER INFORMATION: Synthetic construct

<400> SEQUENCE: 28

```
atgaaaatag ttttacaaaa taatgagcag gattgtttgc tagcatgcta ttcaatgata     60

ttgggatatt ttggtaggga tgttgcaata catgagcttt atagtgggga aatgatcccg    120

cctgatggct tgtctgtttc atatttaaaa aatattaata tgaagcatca agttagtatg    180

catgtttata agactgataa aaagaattct ccaaataaga tattctatcc aaagatgctg    240

cctgtaatta tacaatggaa tgataatcat tttgttgtag taactaagat ttacagaaaa    300

aatgtaacac tcattgaccc tgcaataggt aaagtgaagt ataactataa tgattttatg    360

aaaaaatttt ctggttatat tattacttta tcaccgaata gttcttttac aaagaaaaaa    420

agaataagtg aaattatctt tccactaaaa                                     450
```

<210> SEQ ID NO 29
<211> LENGTH: 155
<212> TYPE: PRT
<213> ORGANISM: Artificial Sequence
<220> FEATURE:
<223> OTHER INFORMATION: Synthetic construct

<400> SEQUENCE: 29

```
Met Lys Ile Val Leu Gln Asn Asn Glu Gln Asp Cys Leu Leu Ala Cys
1               5                   10                  15

Tyr Ser Met Ile Leu Gly Tyr Phe Gly Arg Asp Val Ala Ile His Glu
            20                  25                  30

Leu Tyr Ser Gly Glu Met Ile Pro Pro Asp Gly Leu Ser Val Ser Tyr
        35                  40                  45

Leu Lys Asn Ile Asn Met Lys His Gln Val Ser Met His Val Tyr Lys
    50                  55                  60

Thr Asp Lys Lys Asn Ser Pro Asn Lys Ile Phe Tyr Pro Lys Met Leu
```

-continued

```
65                  70                  75                  80

Pro Val Ile Ile Gln Trp Asn Asp Asn His Phe Val Val Val Thr Lys
                85                  90                  95

Ile Tyr Arg Lys Asn Val Thr Leu Ile Asp Pro Ala Ile Gly Lys Val
            100                 105                 110

Lys Tyr Asn Tyr Asn Asp Phe Met Lys Lys Phe Ser Gly Tyr Ile Ile
        115                 120                 125

Thr Leu Ser Pro Asn Ser Ser Phe Thr Lys Lys Lys Arg Ile Ser Glu
    130                 135                 140

Ile Ile Phe Pro Leu Lys Lys Ile Phe Lys Asn
145                 150                 155


<210> SEQ ID NO 30
<211> LENGTH: 36
<212> TYPE: DNA
<213> ORGANISM: Artificial Sequence
<220> FEATURE:
<223> OTHER INFORMATION: Synthetic construct

<400> SEQUENCE: 30

attcgcggat ccatgaaaat agttttacaa aataat                              36


<210> SEQ ID NO 31
<211> LENGTH: 36
<212> TYPE: DNA
<213> ORGANISM: Artificial Sequence
<220> FEATURE:
<223> OTHER INFORMATION: Synthetic construct

<400> SEQUENCE: 31

aaaccgctcg agttatttta gtggaaagat aatttc                              36


<210> SEQ ID NO 32
<211> LENGTH: 5
<212> TYPE: PRT
<213> ORGANISM: Artificial Sequence
<220> FEATURE:
<223> OTHER INFORMATION: Synthetic construct

<400> SEQUENCE: 32

Ile Leu Gly Ala Lys
1               5


<210> SEQ ID NO 33
<211> LENGTH: 5
<212> TYPE: PRT
<213> ORGANISM: Artificial Sequence
<220> FEATURE:
<223> OTHER INFORMATION: Synthetic construct

<400> SEQUENCE: 33

Ile Leu Gly Gly Gly
1               5


<210> SEQ ID NO 34
<211> LENGTH: 5
<212> TYPE: PRT
<213> ORGANISM: Artificial Sequence
<220> FEATURE:
<223> OTHER INFORMATION: Synthetic construct

<400> SEQUENCE: 34

Ile Leu Gly Gly Gly
1               5
```

-continued

<210> SEQ ID NO 35
<211> LENGTH: 5
<212> TYPE: PRT
<213> ORGANISM: Artificial Sequence
<220> FEATURE:
<223> OTHER INFORMATION: Artificial

<400> SEQUENCE: 35

Ile Ile Gly Ala Gly
1 5

<210> SEQ ID NO 36
<211> LENGTH: 5
<212> TYPE: PRT
<213> ORGANISM: Artificial Sequence
<220> FEATURE:
<223> OTHER INFORMATION: Synthetic construct

<400> SEQUENCE: 36

Ile Ile Gly Ala Gly
1 5

<210> SEQ ID NO 37
<211> LENGTH: 5
<212> TYPE: PRT
<213> ORGANISM: Artificial Sequence
<220> FEATURE:
<223> OTHER INFORMATION: Synthetic construct

<400> SEQUENCE: 37

Ile Leu Gly Gly Asn
1 5

<210> SEQ ID NO 38
<211> LENGTH: 2769
<212> TYPE: DNA
<213> ORGANISM: Artificial Sequence
<220> FEATURE:
<223> OTHER INFORMATION: Synthetic construct

<400> SEQUENCE: 38
gtgaaaaaaa agacttacca atttgaaaaa tttttaaaaa atacttttga tcaattttct 60
attaagcaaa atgaagttct ggttgaagat gatttaaacg atataattat gaacgtttgt 120
ggaaaagcac ttgttttgat gataaatgaa aaaagagaaa tgaatctatt aatgggcaat 180
acaccagagg aaaggtacca atattttgaa aatgagtatt cgagtacagg taaagctttt 240
gaagaaataa aagataaatt tccagtaata tatattgatt taaaaaattc tataaattct 300
tatttaaagt tggtttcaca aataatgaaa gattttaaaa aagattactc acttctagta 360
gaacgtaaga ttattgagga acattcgact atttcgacta tgaaaataaa aggtgattta 420
cataatggga aggctgttat agaaattact actaacaaaa gtaaattaat ttataaacca 480
aagtcattaa gtaatgatgt gttttttaac aattttttga agtatatgga tagttttttt 540
attaaagagg gaaaaagcac taaatataaa gaaaattttt atttggtaaa cacgcttgat 600
atgaagacat atggatgggt tgaatacgta gataaaaaac caatcaattc atttgaggaa 660
gcaagaaatt attatagaaa aattggagta cttttatcag ttgcttatac tttaaattta 720
actgacttac attttgaaaa tgtgatctca caaggagaaa atccttgtat tattgaccta 780
gagactatgt ttaacatgcc tatgtttgta aaagattata aaaatgaatc tcgtaatatt 840
attaatggaa agattatgga ttcggtagtc tcaacaggaa tgttaccagt cttaggaata 900

-continued

```
gatagtttgt ttggggggga tcctagtgga attttaggtg gtacattttc taaagaagaa    960
cgagtgatca taaatccatt tagagatgac ataaaatttc aaaaaatagt tgtacgatct   1020
gtattcaaag atcatattcc ttttttaac aataataatg agaaaagata ttgtaagccc    1080
aaagactatg ttaatgatat tataaaaggg tttgaaaaaa catataaaat aatcgttaaa   1140
aataaggaaa aaatattagg gtttctaaaa aaagaatcta gtagtgttac ctgtagaata   1200
ttatttagaa atacgatgga atactcagtt ttattaaatg cagcaaagtc gcctgtatat   1260
tcaaacaaaa gagaagaaat ttttgaaaaa ttatcaactt ttaatcgagg acttggaaat   1320
gatattatta aatcagagat aagtcaaata aacactttat caatccccta tttcaattgt   1380
caagtagact caaacttaat aaagaatatg gatggagaaa caatatttga gcatactctc   1440
accccattca aatgtttcct atcaaaatat agaagactgt gtgtagatga tatggaacaa   1500
caagttaagc taatccgatt ttcaattcaa agtcaagaac agctttttaa agatggggaa   1560
cagttcagtt tatataagaa acaaaaaggt tcacaagaag atttattgat tgcgataaat   1620
gagctttcaa gtatcttaga aaacaatgca tatattggta caagcgatga taccataaat   1680
tggatgagtt taggaattgc tgataatgat cagatactct ttgaaagtct tgaaaatgat   1740
atatataagg gaatatcagg aataggctta gccttattgg aatattatga attttatcca   1800
aatatcaaca caaaaaaaat actaaaatta atatataaaa atatatcaaa agattttatt   1860
aatacaaata atgagcccca aaattatgga ttctatgttg gcttaatagg tgagtatagt   1920
tttttgagaa aatacgaaaa agtatttcac aaaacaagta gttgcaacat tttaaagaac   1980
attttaaaag attttactcc cgagaagtgt caaacaatac taccttcaga tgacgtaata   2040
gccggagaag cgggaattat tatttacatt tcaaatctca ataattacct agaatacaga   2100
gatgaaattg atattctatt gaaaagttta tcaaataaga taaaattaaa agaaagtatt   2160
gcaagttatg ctcatggtaa tagtggtata gcaacagctt ttgtacatgg atataaggtt   2220
actaaaaatg aaaaatatct taagatattc catgaacttt ggaatttaga aaattctagt   2280
aaactgagaa gaggttggac agattcaaga aaagttgata gttcatactc ttcacagtgg   2340
tgtcacggtg catcgggaca agctatagca agaatggagt ggattactgt aaacaaaaca   2400
gctagatttc ttagtaactc tgaactaatt aaggttaaaa aagagctagg ggaattaatt   2460
gatatcttaa aaaaagaggg aatgtataca gataattttt gtctatgcca tggtatttta   2520
ggaaatctat taattttaaa tacctatcaa gagaatttg ataataagaa tatcaatcta    2580
aagaatgaaa ttttaaacaa ctattactct gtttgtaact atggtttaaa taaaggatgg   2640
atttgtggct taggtacaga attttattct tatgggctta tgacaggaat atctggtata   2700
ttatatggac tgattcggca agtaaaacaa aaaaataatt ttggagtctt aatgccatat   2760
gttgattaa                                                           2769
```

<210> SEQ ID NO 39
<211> LENGTH: 2769
<212> TYPE: DNA
<213> ORGANISM: Artificial Sequence
<220> FEATURE:
<223> OTHER INFORMATION: Synthetic construct

<400> SEQUENCE: 39

```
atgaaaaaaa agacttacca atttgaaaaa tttttaaaaa atacttttga tcaattttct     60
attaagcaaa atgaagttct ggttgaagat gatttaaacg atataattat gaacgtttgt    120
```

-continued

```
ggaaaagcac ttgttttgat gataaatgaa aaaagagaaa tgaatctatt aatgggcaat    180
acaccagagg aaaggtacca atattttgaa aatgagtatt cgagtacagg taaagctttt    240
gaagaaataa aagataaatt tccagtaata tatattgatt taaaaaattc tataaattct    300
tatttaaagt tggtttcaca aataatgaaa gattttaaaa aagattactc acttctagta    360
gaacgtaaga ttattgagga acattcgact atttcgacta tgaaaataaa aggtgattta    420
cataatggga aggctgttat agaaattact actaacaaaa gtaaattaat ttataaacca    480
aagtcattaa gtaatgatgt gtttttaac aatttttga agtatatgga tagttttttt    540
attaaagagg gaaaaagcac taaatataaa gaaaattttt atttggtaaa cacgcttgat    600
atgaagacat atggatgggt tgaatacgta gataaaaaac caatcaattc atttgaggaa    660
gcaagaaatt attatagaaa aattggagta cttttatcag ttgcttatac tttaaattta    720
actgacttac attttgaaaa tgtgatctca caaggagaaa atccttgtat tattgaccta    780
gagactatgt ttaacatgcc tatgtttgta aaagattata aaaatgaatc tcgtaatatt    840
attaatggaa agattatgga ttcggtagtc tcaacaggaa tgttaccagt cttaggaata    900
gatagtttgt ttgggggga tcctagtgga attttaggtg gtacattttc taaagaagaa    960
cgagtgatca taaatccatt tagagatgac ataaaatttc aaaaaatagt tgtacgatct   1020
gtattcaaag atcatattcc tttttttaac aataataatg agaaaagata ttgtaagccc   1080
aaagactatg ttaatgatat tataaaaggg tttgaaaaaa catataaaat aatcgttaaa   1140
aataaggaaa aaatattagg gtttctaaaa aaagaatcta gtagtgttac ctgtagaata   1200
ttatttagaa atacgatgga atactcagtt ttattaaatg cagcaaagtc gcctgtatat   1260
tcaaacaaaa gagaagaaat ttttgaaaaa ttatcaactt ttaatcgagg acttggaaat   1320
gatattatta aatcagagat aagtcaaata aacactttat caatccccta tttcaattgt   1380
caagtagact caaacttaat aaagaatatg gatggagaaa caatatttga gcatactctc   1440
accccattca aatgtttcct atcaaaatat agaagactgt gtgtagatga tatggaacaa   1500
caagttaagc taatccgatt ttcaattcaa agtcaagaac agcttttaa agatggggaa   1560
cagttcagtt tatataagaa acaaaaaggt tcacaagaag atttattgat tgcgataaat   1620
gagctttcaa gtatcttaga aaacaatgca tatattggta caagcgatga taccataaat   1680
tggatgagtt taggaattgc tgataatgat cagatactct ttgaaagtct tgaaaatgat   1740
atatataagg gaatatcagg aataggctta gccttattgg aatattatga attttatcca   1800
aatatcaaca caaaaaaaat actaaaatta atatataaaa atatatcaaa agattttatt   1860
aatacaaata atgagcccca aaattatgga ttctatgttg gcttaatagg tgagtatagt   1920
tttttgagaa aatacgaaaa agtatttcac aaaacaagta gttgcaacat tttaaagaac   1980
attttaaaag attttactcc cgagaagtgt caaacaatac taccttcaga tgacgtaata   2040
gccggagaag cgggaattat tatttacatt tcaaatctca ataattacct agaatacaga   2100
gatgaaattg atattctatt gaaaagttta tcaaataaga taaaattaaa agaaagtatt   2160
gcaagttatg ctcatggtaa tagtggtata gcaacagctt ttgtacatgg atataaggtt   2220
actaaaaatg aaaaatatct taagatattc catgaacttt ggaatttaga aaattctagt   2280
aaactgagaa gaggttggac agattcaaga aaagttgata gttcatactc ttcacagtgg   2340
tgtcacggtg catcgggaca agctatagca agaatggagt ggattactgt aaacaaaaca   2400
gctagatttc ttagtaactc tgaactaatt aaggttaaaa aagagctagg ggaattaatt   2460
gatatcttaa aaaaagaggg aatgtataca gataattttt gtctatgcca tggtatttta   2520
```

-continued

```
ggaaatctat taattttaaa tacctatcaa gagaattttg ataataagaa tatcaatcta   2580

aagaatgaaa ttttaaacaa ctattactct gtttgtaact atggtttaaa taaaggatgg   2640

atttgtggct taggtacaga attttattct tatgggctta tgacaggaat atctggtata   2700

ttatatggac tgattcggca agtaaaacaa aaaaataatt ttggagtctt aatgccatat   2760

gttgattaa                                                           2769


<210> SEQ ID NO 40
<211> LENGTH: 922
<212> TYPE: PRT
<213> ORGANISM: Artificial Sequence
<220> FEATURE:
<223> OTHER INFORMATION: Synthetic construct

<400> SEQUENCE: 40

Met Lys Lys Lys Thr Tyr Gln Phe Glu Lys Phe Leu Lys Asn Thr Phe
1               5                   10                  15

Asp Gln Phe Ser Ile Lys Gln Asn Glu Val Leu Val Glu Asp Asp Leu
            20                  25                  30

Asn Asp Ile Ile Met Asn Val Cys Gly Lys Ala Leu Val Leu Met Ile
        35                  40                  45

Asn Glu Lys Arg Glu Met Asn Leu Leu Met Gly Asn Thr Pro Glu Glu
    50                  55                  60

Arg Tyr Gln Tyr Phe Glu Asn Glu Tyr Ser Ser Thr Gly Lys Ala Phe
65                  70                  75                  80

Glu Glu Ile Lys Asp Lys Phe Pro Val Ile Tyr Ile Asp Leu Lys Asn
                85                  90                  95

Ser Ile Asn Ser Tyr Leu Lys Leu Val Ser Gln Ile Met Lys Asp Phe
            100                 105                 110

Lys Lys Asp Tyr Ser Leu Leu Val Glu Arg Lys Ile Ile Glu Glu His
        115                 120                 125

Ser Thr Ile Ser Thr Met Lys Ile Lys Gly Asp Leu His Asn Gly Lys
    130                 135                 140

Ala Val Ile Glu Ile Thr Thr Asn Lys Ser Lys Leu Ile Tyr Lys Pro
145                 150                 155                 160

Lys Ser Leu Ser Asn Asp Val Phe Phe Asn Asn Phe Leu Lys Tyr Met
                165                 170                 175

Asp Ser Phe Phe Ile Lys Glu Gly Lys Ser Thr Lys Tyr Lys Glu Asn
            180                 185                 190

Phe Tyr Leu Val Asn Thr Leu Asp Met Lys Thr Tyr Gly Trp Val Glu
        195                 200                 205

Tyr Val Asp Lys Lys Pro Ile Asn Ser Phe Glu Glu Ala Arg Asn Tyr
    210                 215                 220

Tyr Arg Lys Ile Gly Val Leu Leu Ser Val Ala Tyr Thr Leu Asn Leu
225                 230                 235                 240

Thr Asp Leu His Phe Glu Asn Val Ile Ser Gln Gly Glu Asn Pro Cys
                245                 250                 255

Ile Ile Asp Leu Glu Thr Met Phe Asn Met Pro Met Phe Val Lys Asp
            260                 265                 270

Tyr Lys Asn Glu Ser Arg Asn Ile Ile Asn Gly Lys Ile Met Asp Ser
        275                 280                 285

Val Val Ser Thr Gly Met Leu Pro Val Leu Gly Ile Asp Ser Leu Phe
    290                 295                 300

Gly Gly Asp Pro Ser Gly Ile Leu Gly Gly Thr Phe Ser Lys Glu Glu
```

-continued

```
305                 310                 315                 320

Arg Val Ile Ile Asn Pro Phe Arg Asp Asp Ile Lys Phe Gln Lys Ile
                325                 330                 335

Val Val Arg Ser Val Phe Lys Asp His Ile Pro Phe Phe Asn Asn Asn
            340                 345                 350

Asn Glu Lys Arg Tyr Cys Lys Pro Lys Asp Tyr Val Asn Asp Ile Ile
        355                 360                 365

Lys Gly Phe Glu Lys Thr Tyr Lys Ile Ile Val Lys Asn Lys Glu Lys
    370                 375                 380

Ile Leu Gly Phe Leu Lys Lys Glu Ser Ser Ser Val Thr Cys Arg Ile
385                 390                 395                 400

Leu Phe Arg Asn Thr Met Glu Tyr Ser Val Leu Leu Asn Ala Ala Lys
                405                 410                 415

Ser Pro Val Tyr Ser Asn Lys Arg Glu Glu Ile Phe Glu Lys Leu Ser
            420                 425                 430

Thr Phe Asn Arg Gly Leu Gly Asn Asp Ile Ile Lys Ser Glu Ile Ser
        435                 440                 445

Gln Ile Asn Thr Leu Ser Ile Pro Tyr Phe Asn Cys Gln Val Asp Ser
    450                 455                 460

Asn Leu Ile Lys Asn Met Asp Gly Glu Thr Ile Phe Glu His Thr Leu
465                 470                 475                 480

Thr Pro Phe Lys Cys Phe Leu Ser Lys Tyr Arg Arg Leu Cys Val Asp
                485                 490                 495

Asp Met Glu Gln Gln Val Lys Leu Ile Arg Phe Ser Ile Gln Ser Gln
            500                 505                 510

Glu Gln Leu Phe Lys Asp Gly Glu Gln Phe Ser Leu Tyr Lys Lys Gln
        515                 520                 525

Lys Gly Ser Gln Glu Asp Leu Leu Ile Ala Ile Asn Glu Leu Ser Ser
    530                 535                 540

Ile Leu Glu Asn Asn Ala Tyr Ile Gly Thr Ser Asp Asp Thr Ile Asn
545                 550                 555                 560

Trp Met Ser Leu Gly Ile Ala Asp Asn Asp Gln Ile Leu Phe Glu Ser
                565                 570                 575

Leu Glu Asn Asp Ile Tyr Lys Gly Ile Ser Gly Ile Gly Leu Ala Leu
            580                 585                 590

Leu Glu Tyr Tyr Glu Phe Tyr Pro Asn Ile Asn Thr Lys Lys Ile Leu
        595                 600                 605

Lys Leu Ile Tyr Lys Asn Ile Ser Lys Asp Phe Ile Asn Thr Asn Asn
    610                 615                 620

Glu Pro Gln Asn Tyr Gly Phe Tyr Val Gly Leu Ile Gly Glu Tyr Ser
625                 630                 635                 640

Phe Leu Arg Lys Tyr Glu Lys Val Phe His Lys Thr Ser Ser Cys Asn
                645                 650                 655

Ile Leu Lys Asn Ile Leu Lys Asp Phe Thr Pro Glu Lys Cys Gln Thr
            660                 665                 670

Ile Leu Pro Ser Asp Asp Val Ile Ala Gly Glu Ala Gly Ile Ile Ile
        675                 680                 685

Tyr Ile Ser Asn Leu Asn Asn Tyr Leu Glu Tyr Arg Asp Glu Ile Asp
    690                 695                 700

Ile Leu Leu Lys Ser Leu Ser Asn Lys Ile Lys Leu Lys Glu Ser Ile
705                 710                 715                 720

Ala Ser Tyr Ala His Gly Asn Ser Gly Ile Ala Thr Ala Phe Val His
                725                 730                 735
```

-continued

```
Gly Tyr Lys Val Thr Lys Asn Glu Lys Tyr Leu Lys Ile Phe His Glu
            740                 745                 750

Leu Trp Asn Leu Glu Asn Ser Ser Lys Leu Arg Arg Gly Trp Thr Asp
        755                 760                 765

Ser Arg Lys Val Asp Ser Ser Tyr Ser Ser Gln Trp Cys His Gly Ala
    770                 775                 780

Ser Gly Gln Ala Ile Ala Arg Met Glu Trp Ile Thr Val Asn Lys Thr
785                 790                 795                 800

Ala Arg Phe Leu Ser Asn Ser Glu Leu Ile Lys Val Lys Lys Glu Leu
                805                 810                 815

Gly Glu Leu Ile Asp Ile Leu Lys Lys Glu Gly Met Tyr Thr Asp Asn
            820                 825                 830

Phe Cys Leu Cys His Gly Ile Leu Gly Asn Leu Leu Ile Leu Asn Thr
        835                 840                 845

Tyr Gln Glu Asn Phe Asp Asn Lys Asn Ile Asn Leu Lys Asn Glu Ile
    850                 855                 860

Leu Asn Asn Tyr Tyr Ser Val Cys Asn Tyr Gly Leu Asn Lys Gly Trp
865                 870                 875                 880

Ile Cys Gly Leu Gly Thr Glu Phe Tyr Ser Tyr Gly Leu Met Thr Gly
                885                 890                 895

Ile Ser Gly Ile Leu Tyr Gly Leu Ile Arg Gln Val Lys Gln Lys Asn
            900                 905                 910

Asn Phe Gly Val Leu Met Pro Tyr Val Asp
        915                 920


<210> SEQ ID NO 41
<211> LENGTH: 69
<212> TYPE: DNA
<213> ORGANISM: Artificial Sequence
<220> FEATURE:
<223> OTHER INFORMATION: Artificial

<400> SEQUENCE: 41

atgggcagca gccatcatca tcatcatcac agcagcggcc tggtgccgcg cggcagccat     60

atggctagc                                                             69


<210> SEQ ID NO 42
<211> LENGTH: 23
<212> TYPE: PRT
<213> ORGANISM: Artificial Sequence
<220> FEATURE:
<223> OTHER INFORMATION: Artificial

<400> SEQUENCE: 42

Met Gly Ser Ser His His His His His His Ser Ser Gly Leu Val Pro
1               5                   10                  15

Arg Gly Ser His Met Ala Ser
            20


<210> SEQ ID NO 43
<211> LENGTH: 60
<212> TYPE: DNA
<213> ORGANISM: Artificial Sequence
<220> FEATURE:
<223> OTHER INFORMATION: Artificial

<400> SEQUENCE: 43

atgggcagca gccatcatca tcatcatcac agcagcggcc tggtgccgcg cggcagccat     60
```

-continued

<210> SEQ ID NO 44
<211> LENGTH: 156
<212> TYPE: DNA
<213> ORGANISM: Artificial Sequence
<220> FEATURE:
<223> OTHER INFORMATION: Synthetic construct

<400> SEQUENCE: 44
atgaaagaac aaaactcttt taatcttctt caagaagtga cagaaagtga attggacctt 60
attttaggtg caaaaggcgg cagtggagtt attcatacaa tttctcatga atgtaatatg 120
aatagctggc aatttgtatt tacttgctgc tcttaa 156

<210> SEQ ID NO 45
<211> LENGTH: 63
<212> TYPE: PRT
<213> ORGANISM: Artificial Sequence
<220> FEATURE:
<223> OTHER INFORMATION: Artificial

<400> SEQUENCE: 45

Gly Ser Ser His His His His His His Ser Ser Gly Leu Val Pro Arg
1 5 10 15

Gly Ser His Met Lys Glu Gln Asn Ser Phe Asn Leu Leu Gln Glu Val
20 25 30

Thr Glu Ser Glu Leu Asp Leu Ile Leu Gly Ala Lys Gly Gly Cys Gly
35 40 45

Val Ile His Thr Ile Ser His Glu Cys Val Ile Ser His Glu Ala
50 55 60

<210> SEQ ID NO 46
<211> LENGTH: 68
<212> TYPE: PRT
<213> ORGANISM: Artificial Sequence
<220> FEATURE:
<223> OTHER INFORMATION: Artificial

<400> SEQUENCE: 46

Gly Ser Ser His His His His His His Ser Ser Gly Leu Val Pro Arg
1 5 10 15

Gly Ser His Met Lys Glu Gln Asn Ser Phe Asn Leu Leu Gln Glu Val
20 25 30

Thr Glu Ser Glu Leu Asp Leu Ile Leu Gly Ala Lys Gly Gly Cys Gly
35 40 45

Val Ile His Thr Ile Ser His Glu Cys Val Ile Ser His Ile Ser His
50 55 60

Ile Ser His Ala
65

<210> SEQ ID NO 47
<211> LENGTH: 73
<212> TYPE: PRT
<213> ORGANISM: Artificial Sequence
<220> FEATURE:
<223> OTHER INFORMATION: Artificial

<400> SEQUENCE: 47

Gly Ser Ser His His His His His His Ser Ser Gly Leu Val Pro Arg
1 5 10 15

Gly Ser His Met Leu Glu Met Lys Glu Gln Asn Ser Phe Asn Leu Leu
20 25 30

-continued

```
Gln Glu Val Thr Glu Ser Glu Leu Asp Leu Ile Leu Gly Ala Asn Arg
        35                  40                  45

Trp Trp Gln Gly Val Val Pro Thr Val Ser Tyr Glu Cys Arg Met Asn
    50                  55                  60

Ser Trp Gln His Val Phe Thr Cys Cys
65                  70
```

<210> SEQ ID NO 48
<211> LENGTH: 225
<212> TYPE: DNA
<213> ORGANISM: Artificial Sequence
<220> FEATURE:
<223> OTHER INFORMATION: Artificial

<400> SEQUENCE: 48

```
atgggcagca gccatcatca tcatcatcac agcagcggcc tggtgccgcg cggcagccat     60

atgctcgaga tgaaagaaca aaactctttt aatcttcttc aagaagtgac agaaagtgaa    120

ttggacctta ttttaggtgc aaatcgttgg tggcaaggtg ttgtgccaac ggtctcatat    180

gagtgtcgca tgaattcatg gcaacatgtt ttcacttgct gttaa                    225
```

<210> SEQ ID NO 49
<211> LENGTH: 70
<212> TYPE: PRT
<213> ORGANISM: Artificial Sequence
<220> FEATURE:
<223> OTHER INFORMATION: Artificial

<400> SEQUENCE: 49

```
Gly Ser Ser His His His His His His Ser Ser Gly Leu Val Pro Arg
1               5                   10                  15

Gly Ser His Met Leu Glu Met Lys Glu Gln Asn Ser Phe Asn Leu Leu
            20                  25                  30

Gln Glu Val Thr Glu Ser Glu Leu Asp Leu Ile Leu Gly Ala Gly Asn
        35                  40                  45

Gly Val Leu Lys Thr Ile Ser His Glu Cys Asn Met Asn Thr Trp Gln
    50                  55                  60

Phe Leu Phe Thr Cys Cys
65                  70
```

<210> SEQ ID NO 50
<211> LENGTH: 216
<212> TYPE: DNA
<213> ORGANISM: Artificial Sequence
<220> FEATURE:
<223> OTHER INFORMATION: Artificial

<400> SEQUENCE: 50

```
atgggcagca gccatcatca tcatcatcac agcagcggcc tggtgccgcg cggcagccat     60

atgctcgaga tgaaagaaca aaactctttt aatcttcttc aagaagtgac agaaagtgaa    120

ttggacctta ttttaggtgc aggtaatggt gttcttaaaa ctatttctca tgaatgtaat    180

atgaatactt ggcaatttct ttttacttgt tgttaa                              216
```

<210> SEQ ID NO 51
<211> LENGTH: 75
<212> TYPE: PRT
<213> ORGANISM: Artificial
<220> FEATURE:
<223> OTHER INFORMATION: Artificial

<400> SEQUENCE: 51

-continued

```
Gly Ser Ser His His His His His His Ser Ser Gly Leu Val Pro Arg
1               5                   10                  15

Gly Ser His Met Leu Glu Met Asn Lys Leu Asn Ser Asn Ala Val Val
            20                  25                  30

Ser Leu Asn Glu Val Ser Asp Ser Glu Leu Asp Thr Ile Leu Gly Gly
        35                  40                  45

Asn Arg Trp Trp Gln Gly Val Val Pro Thr Val Ser Tyr Glu Cys Arg
    50                  55                  60

Met Asn Ser Trp Gln His Val Phe Thr Cys Cys
65                  70                  75
```

<210> SEQ ID NO 52
<211> LENGTH: 231
<212> TYPE: DNA
<213> ORGANISM: Artificial Sequence
<220> FEATURE:
<223> OTHER INFORMATION: Artificial

<400> SEQUENCE: 52

```
atgggcagca gccatcatca tcatcatcac agcagcggcc tggtgccgcg cggcagccat      60

atgctcgaga tgaacaagtt aaacagtaac gcagtagttt ctttgaatga agtttcagat     120

tctgaattgg atactatttt gggtggtaat cgttggtggc aaggtgttgt gccaacggtc     180

tcatatgagt gtcgcatgaa ttcatggcaa catgttttca cttgctgtta a              231
```

<210> SEQ ID NO 53
<211> LENGTH: 74
<212> TYPE: PRT
<213> ORGANISM: Artificial Sequence
<220> FEATURE:
<223> OTHER INFORMATION: Artificial

<400> SEQUENCE: 53

```
Gly Ser Ser His His His His His His Ser Ser Gly Leu Val Pro Arg
1               5                   10                  15

Gly Ser His Met Leu Glu Met Lys Glu Gln Asn Ser Phe Asn Leu Leu
            20                  25                  30

Gln Glu Val Thr Glu Ser Glu Leu Asp Leu Ile Leu Gly Ala Lys Asn
        35                  40                  45

Arg Trp Trp Gln Gly Val Val Pro Thr Val Ser Tyr Glu Cys Arg Met
    50                  55                  60

Asn Ser Trp Gln His Val Phe Thr Cys Cys
65                  70
```

<210> SEQ ID NO 54
<211> LENGTH: 228
<212> TYPE: DNA
<213> ORGANISM: Artificial Sequence
<220> FEATURE:
<223> OTHER INFORMATION: Artificial

<400> SEQUENCE: 54

```
atgggcagca gccatcatca tcatcatcac agcagcggcc tggtgccgcg cggcagccat      60

atgctcgaga tgaaagaaca aaactctttt aatcttcttc aagaagtgac agaaagtgaa     120

ttggacctta ttttaggtgc aaagaatcgt tggtggcaag gtgttgtgcc aacggtctca     180

tatgagtgtc gcatgaattc atggcaacat gttttcactt gctgttaa                  228
```

<210> SEQ ID NO 55

-continued

<211> LENGTH: 62
<212> TYPE: PRT
<213> ORGANISM: Artificial Sequence
<220> FEATURE:
<223> OTHER INFORMATION: Artificial
<220> FEATURE:
<221> NAME/KEY: MISC_FEATURE
<222> LOCATION: (59)..(59)
<223> OTHER INFORMATION: X=norleucine, Nle

<400> SEQUENCE: 55

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Xaa Asn Ser Ala
    50                  55                  60
```

<210> SEQ ID NO 56
<211> LENGTH: 57
<212> TYPE: PRT
<213> ORGANISM: Artificial Sequence
<220> FEATURE:
<223> OTHER INFORMATION: Artificial
<220> FEATURE:
<221> NAME/KEY: MISC_FEATURE
<222> LOCATION: (57)..(57)
<223> OTHER INFORMATION: X=L-homocysteine

<400> SEQUENCE: 56

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Xaa
    50                  55
```

<210> SEQ ID NO 57
<211> LENGTH: 57
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (57)..(57)
<223> OTHER INFORMATION: X=D-homocysteine

<400> SEQUENCE: 57

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Xaa
    50                  55
```

<210> SEQ ID NO 58
<211> LENGTH: 57

-continued

<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (57)..(57)
<223> OTHER INFORMATION: X=(BETA-3-L-CYSTEINE)

<400> SEQUENCE: 58

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Xaa
    50                  55
```

<210> SEQ ID NO 59
<211> LENGTH: 62
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (61)..(61)
<223> OTHER INFORMATION: S residue has been phosphorylated chemically.

<400> SEQUENCE: 59

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Ala
    50                  55                  60
```

<210> SEQ ID NO 60
<211> LENGTH: 57
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (52)..(52)
<223> OTHER INFORMATION: T residue has been phosphorylated chemically.

<400> SEQUENCE: 60

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Cys Gly
        35                  40                  45

Val Ile His Thr Ile Ser His Glu Ala
    50                  55
```

<210> SEQ ID NO 61
<211> LENGTH: 70
<212> TYPE: PRT

-continued

<213> ORGANISM: Artificial Sequence
<220> FEATURE:
<223> OTHER INFORMATION: Synthetic construct

<400> SEQUENCE: 61

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Asp Lys Gly Gly Ser Gly
        35                  40                  45

Val Ile His Thr Ile Ser His Glu Cys Asn Met Asn Ser Trp Gln Phe
    50                  55                  60

Val Phe Thr Cys Cys Ser
65                  70
```

<210> SEQ ID NO 62
<211> LENGTH: 70
<212> TYPE: PRT
<213> ORGANISM: Artificial Sequence
<220> FEATURE:
<223> OTHER INFORMATION: Synthetic construct

<400> SEQUENCE: 62

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Val Ala Lys Gly Gly Ser Gly
        35                  40                  45

Val Ile His Thr Ile Ser His Glu Cys Asn Met Asn Ser Trp Gln Phe
    50                  55                  60

Val Phe Thr Cys Cys Ser
65                  70
```

<210> SEQ ID NO 63
<211> LENGTH: 70
<212> TYPE: PRT
<213> ORGANISM: Artificial Sequence
<220> FEATURE:
<223> OTHER INFORMATION: Artificial

<400> SEQUENCE: 63

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Gln Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Thr Cys Cys Ser
65                  70
```

<210> SEQ ID NO 64
<211> LENGTH: 70
<212> TYPE: PRT
<213> ORGANISM: Artificial Sequence
<220> FEATURE:
<223> OTHER INFORMATION: Artificial -continued

<400> SEQUENCE: 64

Gly Ser Ser His His His His His His Ser Ser Gly Leu Val Pro Arg
1 5 10 15

Gly Ser His Met Lys Glu Gln Asn Ser Phe Asn Leu Leu Gln Glu Val
20 25 30

Thr Glu Ser Glu Glu Asp Leu Ile Leu Gly Ala Lys Gly Gly Ser Gly
35 40 45

Val Ile His Thr Ile Ser His Glu Cys Asn Met Asn Ser Trp Gln Phe
50 55 60

Val Phe Thr Cys Cys Ser
65 70

<210> SEQ ID NO 65
<211> LENGTH: 70
<212> TYPE: PRT
<213> ORGANISM: Artificial Sequence
<220> FEATURE:
<223> OTHER INFORMATION: Artificial

<400> SEQUENCE: 65

Gly Ser Ser His His His His His His Ser Ser Gly Leu Val Pro Arg
1 5 10 15

Gly Ser His Met Lys Glu Gln Asn Ser Phe Asn Leu Leu Gln Glu Val
20 25 30

Thr Glu Ser Glu Leu Asp Leu Ile Leu Gly Ala Lys Gly Gly Cys Gly
35 40 45

Val Ile His Thr Ile Ser His Glu Cys Asn Met Asn Ser Trp Gln Phe
50 55 60

Val Phe Thr Cys Cys Ser
65 70

<210> SEQ ID NO 66
<211> LENGTH: 922
<212> TYPE: PRT
<213> ORGANISM: Artificial Sequence
<220> FEATURE:
<223> OTHER INFORMATION: Synthetic construct

<400> SEQUENCE: 66

Met Lys Lys Lys Thr Tyr Gln Phe Glu Lys Phe Leu Lys Asn Thr Phe
1 5 10 15

Asp Gln Phe Ser Ile Lys Gln Asn Glu Val Leu Val Glu Asp Asp Leu
20 25 30

Asn Asp Ile Ile Met Asn Val Cys Gly Lys Ala Leu Val Leu Met Ile
35 40 45

Asn Glu Lys Arg Glu Met Asn Leu Leu Met Gly Asn Thr Pro Glu Glu
50 55 60

Arg Tyr Gln Tyr Phe Glu Asn Glu Tyr Ser Ser Thr Gly Lys Ala Phe
65 70 75 80

Glu Glu Ile Lys Asp Lys Phe Pro Val Ile Tyr Ile Asp Leu Lys Asn
85 90 95

Ser Ile Asn Ser Tyr Leu Lys Leu Val Ser Gln Ile Met Lys Asp Phe
100 105 110

Lys Lys Asp Tyr Ser Leu Leu Val Glu Arg Lys Ile Ile Glu Glu His
115 120 125

Ser Thr Ile Ser Thr Met Lys Ile Lys Gly Asp Leu His Asn Gly Lys
130 135 140

-continued

```
Ala Val Ile Glu Ile Thr Thr Asn Arg Ser Lys Leu Ile Tyr Lys Pro
145                 150                 155                 160

Lys Ser Leu Ser Asn Asp Val Phe Phe Asn Asn Phe Leu Lys Tyr Met
                165                 170                 175

Asp Ser Phe Phe Ile Lys Glu Gly Lys Gly Thr Lys Tyr Lys Glu Asn
            180                 185                 190

Phe Tyr Leu Val Asn Thr Leu Asp Met Lys Thr Tyr Gly Trp Val Glu
        195                 200                 205

Tyr Val Asp Lys Lys Pro Ile Asn Ser Phe Glu Glu Ala Arg Asn Tyr
    210                 215                 220

Tyr Arg Lys Ile Gly Val Leu Leu Ser Val Ala Tyr Thr Leu Asn Leu
225                 230                 235                 240

Thr Asp Leu His Phe Glu Asn Val Ile Ser Gln Gly Glu Asn Pro Cys
                245                 250                 255

Ile Ile Asp Leu Glu Thr Met Phe Asn Met Pro Met Phe Val Lys Gly
            260                 265                 270

Tyr Lys Asn Glu Ser Arg Asn Ile Ile Asn Gly Lys Ile Met Asp Ser
        275                 280                 285

Val Val Ser Thr Gly Met Leu Pro Val Leu Gly Ile Asp Ser Leu Phe
    290                 295                 300

Gly Gly Asp Pro Ser Gly Ile Leu Gly Gly Thr Phe Ser Lys Glu Glu
305                 310                 315                 320

Arg Val Ile Ile Asn Pro Phe Arg Asp Asp Ile Lys Phe Gln Lys Ile
                325                 330                 335

Val Val Arg Ser Val Phe Lys Asp His Ile Pro Phe Phe Asn Asn Asn
            340                 345                 350

Asn Glu Lys Arg Tyr Cys Lys Pro Lys Asp Tyr Val Asn Asp Ile Ile
        355                 360                 365

Lys Gly Phe Glu Lys Thr Tyr Lys Ile Ile Val Lys Asn Lys Glu Lys
    370                 375                 380

Ile Leu Gly Phe Leu Lys Lys Glu Ser Ser Ser Val Thr Cys Arg Ile
385                 390                 395                 400

Leu Phe Arg Asn Thr Met Glu Tyr Ser Val Leu Leu Asn Ala Ala Lys
                405                 410                 415

Ser Pro Val Tyr Ser Asn Lys Arg Glu Glu Ile Phe Glu Lys Leu Ser
            420                 425                 430

Thr Phe Asn Arg Gly Leu Gly Asn Asp Ile Ile Lys Ser Glu Ile Ser
        435                 440                 445

Gln Ile Asn Thr Leu Ser Ile Pro Tyr Phe Asn Cys Gln Val Asp Ser
    450                 455                 460

Asn Leu Ile Lys Asn Met Asp Gly Glu Thr Ile Phe Glu His Thr Leu
465                 470                 475                 480

Thr Pro Phe Lys Cys Phe Leu Ser Lys Tyr Arg Arg Leu Cys Val Asp
                485                 490                 495

Asp Met Glu Gln Gln Val Lys Leu Ile Arg Phe Ser Ile Gln Ser Gln
            500                 505                 510

Glu Gln Leu Phe Lys Asp Gly Glu Gln Phe Ser Leu Tyr Lys Lys Gln
        515                 520                 525

Lys Gly Ser Gln Glu Asp Leu Leu Ile Ala Ile Asn Glu Leu Ser Ser
    530                 535                 540

Ile Leu Glu Asn Asn Ala Tyr Ile Gly Thr Ser Asp Asp Thr Ile Asn
545                 550                 555                 560

Trp Met Ser Leu Gly Ile Ala Asp Asn Asp Gln Ile Leu Phe Glu Ser
```

-continued

```
                565                 570                 575

Leu Glu Asn Asp Ile Tyr Lys Gly Ile Ser Gly Ile Gly Leu Ala Leu
            580                 585                 590

Leu Glu Tyr Tyr Glu Phe Tyr Pro Asn Ile Asn Thr Lys Lys Ile Leu
        595                 600                 605

Lys Leu Ile Tyr Lys Asn Ile Ser Lys Asp Phe Ile Asn Thr Asn Asn
    610                 615                 620

Glu Pro Gln Asn Tyr Gly Phe Tyr Val Gly Leu Ile Gly Glu Tyr Ser
625                 630                 635                 640

Phe Leu Arg Lys Tyr Glu Lys Val Phe His Lys Thr Ser Ser Cys Asn
                645                 650                 655

Ile Leu Lys Asn Ile Leu Lys Asp Phe Thr Pro Glu Lys Cys Gln Thr
            660                 665                 670

Ile Leu Pro Ser Asp Asp Val Ile Ala Gly Glu Ala Gly Ile Ile Ile
        675                 680                 685

Tyr Ile Ser Asn Leu Asn Asn Tyr Leu Glu Tyr Arg Asp Glu Ile Asp
    690                 695                 700

Ile Leu Leu Lys Ser Leu Ser Asn Lys Ile Lys Leu Lys Glu Ser Ile
705                 710                 715                 720

Ala Ser Tyr Ala His Gly Asn Ser Gly Ile Ala Thr Ala Phe Val His
                725                 730                 735

Gly Tyr Lys Val Thr Lys Asn Glu Lys Tyr Leu Lys Ile Phe His Glu
            740                 745                 750

Leu Trp Asn Leu Glu Asn Ser Ser Lys Leu Arg Arg Gly Trp Thr Asp
        755                 760                 765

Ser Arg Lys Val Asp Ser Ser Tyr Ser Ser Gln Trp Cys His Gly Ala
    770                 775                 780

Ser Gly Gln Ala Ile Ala Arg Met Glu Trp Ile Thr Val Asn Lys Thr
785                 790                 795                 800

Ala Arg Phe Leu Ser Asn Ser Glu Leu Ile Lys Val Lys Lys Glu Leu
                805                 810                 815

Gly Glu Leu Ile Asp Ile Leu Lys Lys Glu Gly Met Tyr Thr Asp Asn
            820                 825                 830

Phe Cys Leu Cys His Gly Ile Leu Gly Asn Leu Leu Ile Leu Asn Thr
        835                 840                 845

Tyr Gln Glu Asn Phe Asp Asn Lys Asn Ile Asn Leu Lys Asn Glu Ile
    850                 855                 860

Leu Asn Asn Tyr Tyr Ser Val Cys Asn Tyr Gly Leu Asn Lys Gly Trp
865                 870                 875                 880

Ile Cys Gly Leu Gly Thr Glu Phe Tyr Ser Tyr Gly Leu Met Thr Gly
                885                 890                 895

Ile Ser Gly Ile Leu Tyr Gly Leu Ile Arg Gln Val Lys Gln Lys Asn
            900                 905                 910

Asn Phe Gly Val Leu Met Pro Tyr Val Asp
        915                 920


<210> SEQ ID NO 67
<211> LENGTH: 56
<212> TYPE: PRT
<213> ORGANISM: Artificial Sequence
<220> FEATURE:
<223> OTHER INFORMATION: Synthetic construct

<400> SEQUENCE: 67

Met Ser Lys Phe Asp Asp Phe Asp Leu Asp Val Val Lys Val Ser Lys
```

-continued

```
1               5                   10                  15

Gln Asp Ser Lys Ile Thr Pro Gln Trp Lys Ser Glu Ser Leu Cys Thr
            20                  25                  30

Pro Gly Cys Val Thr Gly Ala Leu Gln Thr Cys Phe Leu Gln Thr Leu
        35                  40                  45

Thr Cys Asn Cys Lys Ile Ser Lys
    50                  55


<210> SEQ ID NO 68
<211> LENGTH: 441
<212> TYPE: PRT
<213> ORGANISM: Artificial Sequence
<220> FEATURE:
<223> OTHER INFORMATION: Synthetic construct

<400> SEQUENCE: 68

Met Glu Arg Gly Thr Val Ser Arg Ile Glu Val Glu Ile Val Lys Glu
1               5                   10                  15

Met Ala Arg Gln Ile Ser Asn Tyr Asp Lys Val Leu Glu Ile Val Asn
            20                  25                  30

Gln Lys Asp Asn Phe Arg Ser Ile Gly Glu Val Pro Leu Ile Pro Trp
        35                  40                  45

Lys Ser Thr Ala Leu Ser His Gly Ile Pro Gly Ile Cys Met Leu Tyr
    50                  55                  60

Gly Glu Leu His Ala His Phe Pro Glu Glu Gly Trp Asp Asp Ile Gly
65                  70                  75                  80

His Gln Tyr Leu Ser Ile Leu Val Asn Glu Ile Lys Glu Lys Gly Leu
                85                  90                  95

His Thr Pro Ser Met Phe Ser Gly Ala Ala Gly Ile Gly Leu Ala Ala
            100                 105                 110

Ile Cys Leu Ser Gln Arg Phe Thr Tyr Tyr Asn Gly Leu Ile Ser Asp
        115                 120                 125

Ile Asn Glu Tyr Leu Ala Glu Thr Val Pro Gln Leu Leu Thr Glu Phe
    130                 135                 140

Asp Gln Arg Gln Val Cys Met Ser Asp Tyr Asp Val Ile Glu Gly Val
145                 150                 155                 160

Ser Gly Ile Ala Asn Tyr Leu Leu Leu Phe Gln Glu Asp Lys Ala Met
                165                 170                 175

Gly Asp Leu Leu Ile Asp Ile Leu Lys Tyr Leu Val Arg Leu Thr Glu
            180                 185                 190

Asp Ile Ile Val Asp Gly Glu Lys Val Pro Gly Trp His Ile Pro Ser
        195                 200                 205

Gln His Gln Phe Thr Asp Ile Glu Lys Lys Ala Tyr Pro Tyr Gly Asn
    210                 215                 220

Phe Asn Met Gly Leu Ala His Gly Ile Pro Gly Pro Ile Cys Val Leu
225                 230                 235                 240

Ser Ser Ala Leu Ile Gln Gly Ile Lys Val Lys Gly Gln Glu Ala Ala
                245                 250                 255

Ile Glu Lys Met Ala Asn Phe Leu Leu Glu Phe Ser Glu Lys Glu Gln
            260                 265                 270

Asp Ser Leu Phe Trp Lys Gly Ile Ile Ser Phe Glu Glu Tyr Gln Tyr
        275                 280                 285

Gly Ser Pro Pro Asn Ala Val Asn Phe Ser Arg Asp Ala Trp Cys Tyr
    290                 295                 300

Gly Arg Pro Gly Val Cys Leu Ala Leu Val Lys Ala Gly Lys Ala Leu
```

-continued 305 310 315 320

Gln Asn Thr Glu Leu Ile Asn Ile Gly Val Gln Asn Leu Arg Tyr Thr
325 330 335

Ile Ser Asp Ile Arg Gly Ile Phe Ser Pro Thr Ile Cys His Gly Tyr
340 345 350

Ser Gly Ile Gly Gln Ile Leu Leu Ala Val Asn Leu Leu Thr Gly Gln
355 360 365

Glu Tyr Phe Lys Glu Glu Leu Gln Glu Ile Lys Gln Lys Ile Met Ser
370 375 380

Tyr Tyr Asp Lys Asp Tyr Ile Phe Gly Phe His Asn Tyr Glu Ser Met
385 390 395 400

Glu Gly Glu Glu Ala Val Pro Leu Gln Tyr Val Gly Leu Leu Asp Gly
405 410 415

Ala Val Gly Val Gly Leu Gly Val Leu Asn Met Glu Leu Gly Ser Lys
420 425 430

Thr Asp Trp Thr Lys Ala Leu Leu Ile
435 440

<210> SEQ ID NO 69
<211> LENGTH: 418
<212> TYPE: PRT
<213> ORGANISM: Artificial Sequence
<220> FEATURE:
<223> OTHER INFORMATION: Synthetic construct

<400> SEQUENCE: 69

Met Arg Ile Met Met Asn Lys Lys Asn Ile Lys Arg Asn Val Glu Lys
1 5 10 15

Ile Ile Ala Gln Trp Asp Glu Arg Thr Arg Lys Asn Lys Glu Asn Phe
20 25 30

Asp Phe Gly Glu Leu Thr Leu Ser Thr Gly Leu Pro Gly Ile Ile Leu
35 40 45

Met Leu Ala Glu Leu Lys Asn Lys Asp Asn Ser Lys Ile Tyr Gln Lys
50 55 60

Lys Ile Asp Asn Tyr Ile Glu Tyr Ile Val Ser Lys Leu Ser Thr Tyr
65 70 75 80

Gly Leu Leu Thr Gly Ser Leu Tyr Ser Gly Ala Ala Gly Ile Ala Leu
85 90 95

Ser Ile Leu His Leu Arg Glu Asp Asp Glu Lys Tyr Lys Asn Leu Leu
100 105 110

Asp Ser Leu Asn Arg Tyr Ile Glu Tyr Phe Val Ile Glu Lys Ile Glu
115 120 125

Gly Phe Asn Leu Glu Asn Ile Thr Pro Pro Asp Tyr Asp Val Ile Glu
130 135 140

Gly Leu Ser Gly Ile Leu Ser Tyr Leu Leu Leu Ile Asn Asp Glu Gln
145 150 155 160

Tyr Asp Asp Leu Lys Ile Leu Ile Ile Asn Phe Leu Ser Asn Leu Thr
165 170 175

Lys Glu Asn Lys Gly Leu Ile Ser Leu Tyr Ile Lys Ser Glu Asn Gln
180 185 190

Met Ser Gln Ser Glu Ser Glu Met Tyr Pro Leu Gly Cys Leu Asn Met
195 200 205

Gly Leu Ala His Gly Leu Ala Gly Ala Gly Cys Ile Leu Ala Tyr Ala
210 215 220

His Ile Lys Gly Tyr Ser Asn Glu Ala Ser Leu Ser Ala Leu Gln Lys

-continued

```
225                 230                 235                 240

Ile Ile Phe Ile Tyr Glu Lys Phe Glu Leu Glu Ile Lys Asn Gln Phe
                245                 250                 255

Leu Trp Lys Asp Gly Leu Val Ala Asp Glu Leu Lys Lys Glu Lys Val
            260                 265                 270

Ile Arg Glu Ala Ser Phe Ile Arg Asp Ala Trp Cys Tyr Gly Gly Pro
        275                 280                 285

Gly Ile Ser Leu Leu Tyr Leu Tyr Gly Gly Leu Ala Leu Asp Asn Asp
    290                 295                 300

Tyr Phe Val Asp Lys Ala Glu Lys Ile Leu Glu Ser Ala Met Gln Arg
305                 310                 315                 320

Lys Leu Gly Ile Asp Ser Tyr Met Ile Cys His Gly Tyr Ser Gly Leu
                325                 330                 335

Ile Glu Ile Cys Ser Leu Phe Lys Arg Leu Leu Asn Thr Lys Lys Phe
            340                 345                 350

Asp Ser Tyr Ile Glu Glu Phe Asn Val Asn Ser Glu Gln Ile Leu Glu
        355                 360                 365

Glu Tyr Gly Asp Glu Ser Gly Thr Gly Phe Leu Glu Gly Ile Ser Gly
    370                 375                 380

Cys Ile Leu Val Leu Ser Lys Phe Glu Tyr Ser Ile Asn Phe Thr Tyr
385                 390                 395                 400

Trp Arg Gln Ala Leu Leu Leu Phe Asp Asp Phe Leu Lys Gly Gly Lys
                405                 410                 415

Arg Lys


<210> SEQ ID NO 70
<211> LENGTH: 60
<212> TYPE: PRT
<213> ORGANISM: Artificial Sequence
<220> FEATURE:
<223> OTHER INFORMATION: Synthetic construct

<400> SEQUENCE: 70

Met Lys Asn Asn Lys Asn Leu Phe Asp Leu Glu Ile Lys Lys Glu Thr
1               5                   10                  15

Ser Gln Asn Thr Asp Glu Leu Glu Pro Gln Thr Ala Gly Pro Ala Ile
            20                  25                  30

Arg Ala Ser Val Lys Gln Cys Gln Lys Thr Leu Lys Ala Thr Arg Leu
        35                  40                  45

Phe Thr Val Ser Cys Lys Gly Lys Asn Gly Cys Lys
    50                  55                  60


<210> SEQ ID NO 71
<211> LENGTH: 455
<212> TYPE: PRT
<213> ORGANISM: Artificial Sequence
<220> FEATURE:
<223> OTHER INFORMATION: Synthetic construct

<400> SEQUENCE: 71

Met Ala Val Leu Tyr Thr Cys Val Val Ile Glu Tyr Ser Val Leu Ile
1               5                   10                  15

Leu Lys Lys Lys Asn Leu Phe Tyr Leu Phe Leu Met Lys Leu Gln Lys
            20                  25                  30

Leu Lys Asn Ile Gly Met Val Val Ile Asn Ile Asn Asn Ile Lys Lys
        35                  40                  45

Ile Leu Glu Asn Lys Ile Thr Phe Leu Ser Asp Ile Glu Lys Ala Thr
```

-continued

```
    50                  55                  60

Tyr Ile Ile Glu Asn Gln Ser Glu Tyr Trp Asp Pro Tyr Thr Leu Ser
65                  70                  75                  80

His Gly Tyr Pro Gly Ile Ile Leu Phe Leu Ser Ala Ser Glu Lys Val
                85                  90                  95

Phe His Lys Asp Leu Glu Lys Val Ile His Gln Tyr Ile Arg Lys Leu
            100                 105                 110

Gly Pro Tyr Leu Glu Ser Gly Ile Asp Gly Phe Ser Leu Phe Ser Gly
        115                 120                 125

Leu Ser Gly Ile Gly Phe Ala Leu Asp Ile Ala Ser Asp Lys Gln Tyr
    130                 135                 140

Ser Tyr Gln Ser Ile Leu Glu Gln Ile Asp Asn Leu Leu Val Gln Tyr
145                 150                 155                 160

Val Phe Asp Phe Leu Asn Asn Asp Ala Leu Glu Val Thr Pro Thr Asn
                165                 170                 175

Tyr Asp Ile Ile Gln Gly Phe Ser Gly Ile Gly Arg Tyr Leu Leu Asn
            180                 185                 190

Arg Ile Ser Tyr Asn Tyr Asn Ala Lys Lys Ala Leu Lys His Ile Leu
        195                 200                 205

Asn Tyr Phe Lys Thr Ile His Tyr Ser Lys Asp Asn Trp Leu Val Ser
    210                 215                 220

Asn Glu His Gln Phe Leu Asp Ile Asp Lys Gln Asn Phe Pro Ser Gly
225                 230                 235                 240

Asn Ile Asn Leu Gly Leu Ala His Gly Ile Leu Gly Pro Leu Ser Leu
                245                 250                 255

Thr Ala Leu Ser Lys Met Asn Gly Ile Glu Ile Glu Gly His Glu Glu
            260                 265                 270

Phe Leu Gln Asp Phe Thr Ser Phe Leu Leu Lys Pro Glu Phe Lys Asn
        275                 280                 285

Asn Asn Glu Trp Phe Asp Arg Tyr Asp Ile Leu Glu Asn Tyr Ile Pro
    290                 295                 300

Asn Tyr Ser Val Arg Asn Gly Trp Cys Tyr Gly Asp Thr Gly Ile Met
305                 310                 315                 320

Asn Thr Leu Leu Leu Ser Gly Lys Ala Leu Asn Asn Glu Gly Leu Ile
                325                 330                 335

Lys Met Ser Lys Asn Ile Leu Ile Asn Ile Ile Asp Lys Asn Asn Asp
            340                 345                 350

Asp Leu Ile Ser Pro Thr Phe Cys His Gly Leu Ala Ser His Leu Thr
        355                 360                 365

Ile Ile His Gln Ala Asn Lys Phe Phe Asn Leu Ser Gln Val Ser Thr
    370                 375                 380

Tyr Ile Asp Thr Ile Val Arg Lys Ile Ile Ser His Tyr Ser Glu Glu
385                 390                 395                 400

Ser Ser Phe Met Phe Gln Asp Ile Glu Tyr Ser Tyr Gly Gln Lys Ile
                405                 410                 415

Tyr Lys Asn Lys Val Gly Ile Leu Glu Gly Glu Leu Gly Val Leu Leu
            420                 425                 430

Ala Leu Leu Asp Tyr Ile Asp Thr Gln Asn Gln Ser Arg Lys Asn Trp
        435                 440                 445

Lys Asn Met Phe Leu Ile Thr
    450                 455
```

<210> SEQ ID NO 72

-continued

<211> LENGTH: 993
<212> TYPE: PRT
<213> ORGANISM: Artificial Sequence
<220> FEATURE:
<223> OTHER INFORMATION: Synthetic construct

<400> SEQUENCE: 72

```
Met Glu Asp Asn Leu Ile Asn Val Leu Ser Ile Asn Glu Arg Cys Phe
1               5                   10                  15

Leu Leu Lys Gln Ser Gly Asn Glu Lys Tyr Asp Ile Lys Asn Leu Gln
            20                  25                  30

Ala Trp Lys Glu Arg Lys Ser Val Leu Lys Gln Asp Asp Leu Asp Tyr
        35                  40                  45

Leu Ile Lys Tyr Lys Tyr Glu Ser Leu Asp Asn Phe Gly Leu Gly Ile
    50                  55                  60

Thr Pro Ile Glu Asn Phe Pro Asp Lys Glu Val Ala Ile Gln Tyr Ile
65                  70                  75                  80

Lys Asp Gln Ser Trp Tyr Ile Phe Phe Glu Ser Ile Leu Asp Ser Tyr
                85                  90                  95

Asn Asp Ser Glu Glu Gln Leu Leu Glu Val Asp Ala Ser Tyr Pro Phe
            100                 105                 110

Arg Tyr Phe Leu Gln Tyr Ala Arg Leu Phe Leu Leu Asp Leu Asn Ser
        115                 120                 125

Glu Leu Asn Ile Cys Thr Lys Glu Phe Ile Ile Asn Leu Leu Glu Ile
    130                 135                 140

Leu Thr Gln Glu Leu Ile His Leu Thr Ser Lys Thr Leu Val Leu Asp
145                 150                 155                 160

Leu His Thr Phe Lys Lys Asn Glu Pro Leu Lys Gly Asn Asp Ser Ser
                165                 170                 175

Lys Arg Phe Ile Tyr Tyr Leu Lys Lys Arg Phe Asn Ser Lys Lys Asp
            180                 185                 190

Ile Ile Ala Phe Tyr Thr Cys Tyr Pro Glu Leu Met Arg Ile Thr Val
        195                 200                 205

Val Arg Met Arg Tyr Phe Leu Asp Asn Thr Lys Gln Met Leu Ile Arg
    210                 215                 220

Val Thr Glu Asp Leu Pro Ser Ile Gln Asn Cys Phe Asn Ile Gln Ser
225                 230                 235                 240

Ser Glu Leu Asn Ser Ile Ser Glu Ser Gln Gly Asp Ser His Ser Arg
                245                 250                 255

Gly Lys Thr Val Ser Thr Leu Thr Phe Ser Asp Gly Lys Lys Ile Val
            260                 265                 270

Tyr Lys Pro Lys Ile Asn Ser Glu Asn Lys Leu Arg Asp Phe Phe Glu
        275                 280                 285

Phe Leu Asn Lys Glu Leu Glu Ala Asp Ile Tyr Ile Val Lys Lys Val
    290                 295                 300

Thr Arg Asn Thr Tyr Phe Tyr Glu Glu Tyr Ile Asp Asn Ile Glu Ile
305                 310                 315                 320

Asn Asn Ile Glu Glu Val Lys Lys Tyr Tyr Glu Arg Tyr Gly Lys Leu
                325                 330                 335

Ile Gly Ile Ala Phe Leu Phe Asn Val Thr Asp Leu His Tyr Glu Asn
            340                 345                 350

Ile Ile Ala His Gly Glu Tyr Pro Val Ile Ile Asp Asn Glu Thr Phe
        355                 360                 365

Phe Gln Gln Asn Ile Pro Ile Glu Phe Gly Asn Ser Ala Thr Val Asp
    370                 375                 380
```

-continued

```
Ala Lys Tyr Lys Tyr Leu Asp Ser Ile Met Val Thr Gly Leu Val Pro
385                 390                 395                 400

Tyr Leu Ala Met Lys Asp Lys Ser Asp Ser Lys Asp Glu Gly Val Asn
                405                 410                 415

Leu Ser Ala Leu Asn Phe Lys Glu Gln Ser Val Pro Phe Lys Ile Leu
            420                 425                 430

Lys Ile Lys Asn Thr Phe Thr Asp Glu Met Arg Phe Glu Tyr Gln Thr
        435                 440                 445

His Ile Met Asp Thr Ala Lys Asn Thr Pro Ile Met Asn Asn Glu Lys
    450                 455                 460

Ile Ser Phe Ile Ser Tyr Glu Lys Tyr Ile Val Thr Gly Met Lys Ser
465                 470                 475                 480

Ile Leu Met Lys Ala Lys Asp Ser Lys Lys Lys Ile Leu Ala Tyr Ile
                485                 490                 495

Asn Asn Asn Leu Gln Asn Leu Ile Val Arg Asn Val Ile Arg Pro Thr
            500                 505                 510

Gln Arg Tyr Ala Asp Met Leu Glu Phe Ser Tyr His Pro Asn Cys Phe
        515                 520                 525

Ser Asn Ala Ile Glu Arg Glu Lys Val Leu His Asn Met Trp Ala Tyr
    530                 535                 540

Pro Tyr Lys Asn Lys Lys Val Val His Tyr Glu Phe Ser Asp Leu Ile
545                 550                 555                 560

Asp Gly Asp Ile Pro Ile Phe Tyr Asn Asn Ile Ser Lys Thr Ser Leu
                565                 570                 575

Ile Ala Ser Asp Gly Cys Leu Val Glu Asp Phe Tyr Gln Glu Ser Ala
            580                 585                 590

Leu Asn Arg Cys Leu Asn Lys Ile Asn Asp Leu Cys Asp Glu Asp Ile
        595                 600                 605

Ser Ile Gln Thr Val Trp Leu Glu Ile Ala Leu Asn Ile Tyr Asn Pro
    610                 615                 620

Tyr Lys Tyr Ile Asn Asp Leu Lys Asn Gln Asn Ser Asn Lys Tyr Ile
625                 630                 635                 640

Tyr Thr Gly Leu Glu Leu Asn Gly Lys Ile Ile Gln Ala Cys Gln Lys
                645                 650                 655

Ile Glu Lys Lys Ile Phe Lys Arg Ala Ile Phe Asn Lys Lys Thr Asn
            660                 665                 670

Thr Val Asn Trp Ile Asp Ile Lys Leu Asp Gln Asp Trp Asn Val Gly
        675                 680                 685

Ile Leu Asn Asn Asn Met Tyr Asp Gly Leu Pro Gly Ile Phe Ile Phe
    690                 695                 700

Tyr Val Ala Leu Lys Tyr Ile Thr Lys Asn His Lys Tyr Asp Tyr Val
705                 710                 715                 720

Ile Glu Cys Ile Lys Asn Ser Ile Tyr Thr Ile Pro Ser Glu Asp Ile
                725                 730                 735

Leu Ser Ala Phe Phe Gly Lys Gly Ser Leu Ile Tyr Pro Leu Leu Val
            740                 745                 750

Asp Tyr Arg Leu Asn Asn Asp Ile Asn Ser Leu Asn Val Ala Val Glu
        755                 760                 765

Ile Ala Asp Met Leu Ile Glu Lys Lys Pro Ile Asn Asn Gly Glu Leu
    770                 775                 780

Lys Asn Asp Trp Ile His Gly His Asn Ser Ile Ile Lys Val Leu Leu
785                 790                 795                 800
```

-continued

```
Leu Leu Ser Glu Ile Thr Glu Asp Glu Lys Tyr Arg Lys Phe Ser Leu
                805                 810                 815

Glu Ile Phe Glu Lys Leu Ser Glu Glu Pro Tyr Phe Asn Phe Arg Gly
            820                 825                 830

Phe Gly His Gly Ile Tyr Ser Tyr Val His Leu Leu Ser Lys Phe Asn
        835                 840                 845

Arg Ile Asp Lys Ala Asn Ser Leu Leu His Lys Ile Lys Glu Ser Tyr
    850                 855                 860

Phe Glu Glu Glu Pro Lys Asn Asn Ser Trp Cys Lys Gly Thr Val Gly
865                 870                 875                 880

Glu Leu Leu Ala Thr Ile Glu Leu Tyr Asp Asp Asn Ile Ser Asn Ile
                885                 890                 895

Asp Ile Asn Lys Thr Ile Glu Tyr Lys Asn Lys Asp Cys Leu Cys His
            900                 905                 910

Gly Asn Ala Gly Thr Leu Glu Gly Leu Ile Gln Leu Ala Lys Lys Asp
        915                 920                 925

Pro Glu Thr Tyr Gln Tyr Lys Lys Asn Lys Leu Ile Ser Tyr Met Leu
    930                 935                 940

Lys Tyr Phe Glu Lys Asn Asn Thr Leu Lys Val Ala Gly Ser Glu Tyr
945                 950                 955                 960

Leu Glu Ser Leu Gly Phe Phe Val Gly Ile Ser Gly Val Gly Tyr Glu
                965                 970                 975

Leu Leu Arg Asn Leu Asp Ser Glu Ile Pro Asn Ala Leu Leu Phe Glu
            980                 985                 990

Leu


<210> SEQ ID NO 73
<211> LENGTH: 47
<212> TYPE: PRT
<213> ORGANISM: Artificial Sequence
<220> FEATURE:
<223> OTHER INFORMATION: Synthetic construct

<400> SEQUENCE: 73

Met Thr Asn Ala Phe Gln Ala Leu Asp Glu Val Thr Asp Ala Glu Leu
1               5                   10                  15

Asp Ala Ile Leu Gly Gly Gly Ser Gly Val Ile Pro Thr Ile Ser His
            20                  25                  30

Glu Cys His Met Asn Ser Phe Gln Phe Val Phe Thr Cys Cys Ser
        35                  40                  45


<210> SEQ ID NO 74
<211> LENGTH: 70
<212> TYPE: PRT
<213> ORGANISM: Artificial Sequence
<220> FEATURE:
<223> OTHER INFORMATION: Synthetic construct

<400> SEQUENCE: 74

Gly Ser Ser His His His His His His Ser Ser Gly Leu Val Pro Arg
1               5                   10                  15

Gly Ser His Met Leu Glu Met Lys Glu Gln Asn Ser Phe Asn Leu Leu
            20                  25                  30

Gln Glu Val Thr Glu Ser Glu Leu Asp Leu Ile Leu Gly Ala Gly Asn
        35                  40                  45

Gly Val Leu Lys Thr Ile Ser His Glu Cys Asn Met Asn Thr Trp Gln
    50                  55                  60
```

-continued

```
Phe Leu Phe Thr Cys Cys
65                  70


<210> SEQ ID NO 75
<211> LENGTH: 51
<212> TYPE: PRT
<213> ORGANISM: Artificial Sequence
<220> FEATURE:
<223> OTHER INFORMATION: Synthetic construct

<400> SEQUENCE: 75

Met Thr Lys Glu His Glu Ile Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50


<210> SEQ ID NO 76
<211> LENGTH: 51
<212> TYPE: PRT
<213> ORGANISM: Artificial Sequence
<220> FEATURE:
<223> OTHER INFORMATION: Synthetic construct

<400> SEQUENCE: 76

Met Glu Lys Asn Asn Glu Val Ile Asn Ser Ile Gln Glu Val Ser Leu
1               5                   10                  15

Glu Glu Leu Asp Gln Ile Ile Gly Ala Gly Lys Asn Gly Val Phe Lys
            20                  25                  30

Thr Ile Ser His Glu Cys His Leu Asn Thr Trp Ala Phe Leu Ala Thr
        35                  40                  45

Cys Cys Ser
    50


<210> SEQ ID NO 77
<211> LENGTH: 717
<212> TYPE: PRT
<213> ORGANISM: Artificial Sequence
<220> FEATURE:
<223> OTHER INFORMATION: Synthetic construct

<400> SEQUENCE: 77

Met Lys Phe Gly Lys Arg His Tyr Arg Pro Gln Val Asp Gln Met Asp
1               5                   10                  15

Cys Gly Val Ala Ser Leu Ala Met Val Phe Gly Tyr Tyr Gly Ser Tyr
            20                  25                  30

Tyr Phe Leu Ala His Leu Arg Glu Leu Ala Lys Thr Thr Met Asp Gly
        35                  40                  45

Thr Thr Ala Leu Gly Leu Val Lys Val Ala Glu Glu Ile Gly Phe Glu
    50                  55                  60

Thr Arg Ala Ile Lys Ala Asp Met Thr Leu Phe Asp Leu Pro Asp Leu
65                  70                  75                  80

Thr Phe Pro Phe Val Ala His Val Leu Lys Glu Gly Lys Leu Leu His
                85                  90                  95

Tyr Tyr Val Val Thr Gly Gln Asp Lys Asp Ser Ile His Ile Ala Asp
            100                 105                 110

Pro Asp Pro Gly Val Lys Leu Thr Lys Leu Pro Arg Glu Arg Phe Glu
```

-continued

```
        115                 120                 125

Glu Glu Trp Thr Gly Val Thr Leu Phe Met Ala Pro Ser Pro Asp Tyr
    130                 135                 140

Lys Pro His Lys Glu Gln Lys Asn Gly Leu Leu Ser Phe Ile Pro Ile
145                 150                 155                 160

Leu Val Lys Gln Arg Gly Leu Ile Ala Asn Ile Val Leu Ala Thr Leu
                165                 170                 175

Leu Val Thr Val Ile Asn Ile Val Gly Ser Tyr Tyr Leu Gln Ser Ile
            180                 185                 190

Ile Asp Thr Tyr Val Pro Asp Gln Met Arg Ser Thr Leu Gly Ile Ile
        195                 200                 205

Ser Ile Gly Leu Val Ile Val Tyr Ile Leu Gln Gln Ile Leu Ser Tyr
    210                 215                 220

Ala Gln Glu Tyr Leu Leu Leu Val Leu Gly Gln Arg Leu Ser Ile Asp
225                 230                 235                 240

Val Ile Leu Ser Tyr Ile Lys His Val Phe His Leu Pro Met Ser Phe
                245                 250                 255

Phe Ala Thr Arg Arg Thr Gly Glu Ile Val Ser Arg Phe Thr Asp Ala
            260                 265                 270

Asn Ser Ile Ile Asp Ala Leu Ala Ser Thr Ile Leu Ser Ile Phe Leu
        275                 280                 285

Asp Val Ser Thr Val Val Ile Ile Ser Leu Val Leu Phe Ser Gln Asn
    290                 295                 300

Thr Asn Leu Phe Phe Met Thr Leu Leu Ala Leu Pro Ile Tyr Thr Val
305                 310                 315                 320

Ile Ile Phe Ala Phe Met Lys Pro Phe Glu Lys Met Asn Arg Asp Thr
                325                 330                 335

Met Glu Ala Asn Ala Val Leu Ser Ser Ser Ile Ile Glu Asp Ile Asn
            340                 345                 350

Gly Ile Glu Thr Ile Lys Ser Leu Thr Ser Glu Ser Gln Arg Tyr Gln
        355                 360                 365

Lys Ile Asp Lys Glu Phe Val Asp Tyr Leu Lys Lys Ser Phe Thr Tyr
    370                 375                 380

Ser Arg Ala Glu Ser Gln Gln Lys Ala Leu Lys Lys Val Ala His Leu
385                 390                 395                 400

Leu Leu Asn Val Gly Ile Leu Trp Met Gly Ala Val Leu Val Met Asp
                405                 410                 415

Gly Lys Met Ser Leu Gly Gln Leu Ile Thr Tyr Asn Thr Leu Leu Val
            420                 425                 430

Tyr Phe Thr Asn Pro Leu Glu Asn Ile Ile Asn Leu Gln Thr Lys Leu
        435                 440                 445

Gln Thr Ala Gln Val Ala Asn Asn Arg Leu Asn Glu Val Tyr Leu Val
    450                 455                 460

Ala Ser Glu Phe Glu Glu Lys Lys Thr Val Glu Asp Leu Ser Leu Met
465                 470                 475                 480

Lys Gly Asp Met Thr Phe Lys Gln Val His Tyr Lys Tyr Gly Tyr Gly
                485                 490                 495

Arg Asp Val Leu Ser Asp Ile Asn Leu Thr Val Pro Gln Gly Ser Lys
            500                 505                 510

Val Ala Phe Val Gly Ile Ser Gly Ser Gly Lys Thr Thr Leu Ala Lys
        515                 520                 525

Met Met Val Asn Phe Tyr Asp Pro Ser Gln Gly Glu Ile Ser Leu Gly
    530                 535                 540
```

-continued

```
Gly Val Asn Leu Asn Gln Ile Asp Lys Lys Ala Leu Arg Gln Tyr Ile
545                 550                 555                 560

Asn Tyr Leu Pro Gln Gln Pro Tyr Val Phe Asn Gly Thr Ile Leu Glu
                565                 570                 575

Asn Leu Leu Leu Gly Ala Lys Glu Gly Thr Thr Gln Glu Asp Ile Leu
            580                 585                 590

Arg Ala Val Glu Leu Ala Glu Ile Arg Glu Asp Ile Glu Arg Met Pro
        595                 600                 605

Leu Asn Tyr Gln Thr Glu Leu Thr Ser Asp Gly Ala Gly Ile Ser Gly
    610                 615                 620

Gly Gln Arg Gln Arg Ile Ala Leu Ala Arg Ala Leu Leu Thr Asp Ala
625                 630                 635                 640

Pro Val Leu Ile Leu Asp Glu Ala Thr Ser Ser Leu Asp Ile Leu Thr
                645                 650                 655

Glu Lys Arg Ile Val Asp Asn Leu Ile Ala Leu Asp Lys Thr Leu Ile
            660                 665                 670

Phe Ile Ala His Arg Leu Thr Ile Ala Glu Arg Thr Glu Lys Val Val
        675                 680                 685

Val Leu Asp Gln Gly Lys Ile Val Glu Glu Gly Lys His Ala Asp Leu
    690                 695                 700

Leu Ala Gln Gly Gly Phe Tyr Ala His Leu Val Asn Ser
705                 710                 715


<210> SEQ ID NO 78
<211> LENGTH: 715
<212> TYPE: PRT
<213> ORGANISM: Artificial Sequence
<220> FEATURE:
<223> OTHER INFORMATION: Synthetic construct

<400> SEQUENCE: 78

Met Lys Phe Lys Lys Lys Asn Tyr Thr Ser Gln Val Asp Glu Met Asp
1               5                   10                  15

Cys Gly Cys Ala Ala Leu Ser Met Ile Leu Lys Ser Tyr Gly Thr Glu
            20                  25                  30

Lys Ser Leu Ala Ser Leu Arg Leu Leu Ala Gly Thr Thr Ile Glu Gly
        35                  40                  45

Thr Ser Ala Leu Gly Ile Lys Lys Ala Ala Glu Ile Leu Glu Phe Ser
    50                  55                  60

Val Gln Ala Leu Arg Thr Asp Ala Ser Leu Phe Glu Met Lys Asn Ala
65                  70                  75                  80

Pro Tyr Pro Phe Ile Ala His Val Ile Lys Asp Gln Lys Tyr Pro His
                85                  90                  95

Tyr Tyr Val Ile Thr Gly Ala Asn Lys Asn Ser Val Phe Ile Ala Asp
            100                 105                 110

Pro Asp Pro Thr Ile Lys Met Thr Lys Leu Ser Lys Glu Ala Phe Leu
        115                 120                 125

Ser Glu Trp Thr Gly Ile Ser Leu Phe Leu Ser Thr Thr Pro Ser Tyr
    130                 135                 140

His Pro Thr Lys Glu Lys Ala Ser Ser Leu Leu Ser Phe Ile Pro Ile
145                 150                 155                 160

Ile Thr Arg Gln Lys Lys Val Ile Leu Asn Ile Val Ile Ala Ser Phe
                165                 170                 175

Ile Val Thr Leu Ile Asn Ile Leu Gly Ser Tyr Tyr Leu Gln Ser Met
            180                 185                 190
```

-continued

```
Ile Asp Ser Tyr Ile Pro Asn Ala Leu Met Gly Thr Leu Gly Ile Ile
        195                 200                 205

Ser Val Gly Leu Leu Leu Thr Tyr Ile Ile Gln Gln Val Leu Glu Phe
    210                 215                 220

Ala Lys Ala Phe Leu Leu Asn Val Leu Ser Gln Arg Leu Ala Ile Asp
225                 230                 235                 240

Val Ile Leu Ser Tyr Ile Arg His Ile Phe Gln Leu Pro Met Ser Phe
                245                 250                 255

Phe Ser Thr Arg Arg Thr Gly Glu Ile Thr Ser Arg Phe Ser Asp Ala
            260                 265                 270

Ser Ser Ile Leu Asp Ala Ile Ala Ser Thr Ile Leu Ser Leu Phe Leu
        275                 280                 285

Asp Leu Thr Ile Val Val Met Thr Gly Leu Ile Leu Gly Leu Gln Asn
    290                 295                 300

Met Gln Leu Phe Leu Leu Val Leu Leu Ala Ile Pro Leu Tyr Ile Val
305                 310                 315                 320

Val Ile Ile Ile Phe Thr Pro Leu Phe Glu Lys Gln Asn His Glu Val
                325                 330                 335

Met Gln Thr Asn Ala Val Leu Asn Ser Ser Ile Ile Glu Asp Ile Asn
            340                 345                 350

Gly Ile Glu Thr Ile Lys Ala Leu Ala Ser Glu Gln Glu Arg Tyr Gln
        355                 360                 365

Lys Ile Asp Tyr Glu Phe Ala Ser Tyr Leu Lys Lys Ala Phe Thr Leu
    370                 375                 380

Gln Lys Ser Glu Ala Ile Gln Gly Leu Ile Lys Ala Ile Ile Gln Leu
385                 390                 395                 400

Thr Leu Ser Val Thr Ile Leu Trp Phe Gly Ala Thr Leu Val Ile Ser
                405                 410                 415

Gln Lys Ile Thr Leu Gly Gln Leu Ile Thr Phe Asn Ala Leu Leu Ser
            420                 425                 430

Tyr Phe Thr Asn Pro Ile Thr Asn Ile Ile Asn Leu Gln Thr Lys Leu
        435                 440                 445

Gln Lys Ala Arg Val Ala Asn Glu Arg Leu Asn Glu Val Tyr Leu Val
    450                 455                 460

Pro Ser Glu Phe Glu Glu Lys Lys Thr Glu Leu Ser Leu Ser His Phe
465                 470                 475                 480

Asn Leu Asn Met Ser Asp Ile Ser Tyr Gln Tyr Gly Phe Gly Arg Lys
                485                 490                 495

Val Leu Ser Glu Ile Glu Leu Ser Ile Lys Glu Asn Glu Lys Leu Thr
            500                 505                 510

Ile Val Gly Met Ser Gly Ser Gly Lys Ser Thr Leu Val Lys Leu Leu
        515                 520                 525

Val Asn Phe Phe Gln Pro Thr Ser Gly Thr Ile Thr Leu Gly Gly Ile
    530                 535                 540

Asp Leu Gln Gln Phe Asp Lys His Gln Leu Arg Arg Leu Ile Asn Tyr
545                 550                 555                 560

Leu Pro Gln Gln Pro Tyr Ile Phe Thr Gly Ser Ile Leu Asp Asn Leu
                565                 570                 575

Leu Leu Gly Ala Asn Glu Asn Ala Ser Gln Glu Glu Ile Leu Lys Ala
            580                 585                 590

Val Glu Leu Ala Glu Ile Arg Ala Asp Ile Glu Gln Met Gln Leu Gly
        595                 600                 605
```

-continued

```
Tyr Gln Thr Glu Leu Ser Ser Asp Ala Ser Ser Leu Ser Gly Gly Gln
    610                 615                 620

Lys Gln Arg Ile Ala Leu Ala Arg Ala Leu Leu Ser Pro Ala Lys Ile
625                 630                 635                 640

Leu Ile Leu Asp Glu Ala Thr Ser Asn Leu Asp Met Ile Thr Glu Lys
                645                 650                 655

Lys Ile Leu Lys Asn Leu Leu Pro Leu Asp Lys Thr Ile Ile Phe Ile
            660                 665                 670

Ala His Arg Leu Ser Val Ala Glu Met Ser His Arg Ile Ile Val Val
        675                 680                 685

Asp Gln Gly Lys Val Ile Glu Ser Gly Ser His Val Asp Leu Leu Ala
    690                 695                 700

Gln Asn Gly Phe Tyr Glu Gln Leu Tyr His Asn
705                 710                 715


<210> SEQ ID NO 79
<211> LENGTH: 724
<212> TYPE: PRT
<213> ORGANISM: Artificial Sequence
<220> FEATURE:
<223> OTHER INFORMATION: Synthetic construct

<400> SEQUENCE: 79

Met Trp Thr Gln Lys Trp His Lys Tyr Tyr Thr Ala Gln Val Asp Glu
1               5                   10                  15

Asn Asp Cys Gly Leu Ala Ala Leu Asn Met Ile Leu Lys Tyr Tyr Gly
            20                  25                  30

Ser Asp Tyr Met Leu Ala His Leu Arg Gln Leu Ala Lys Thr Thr Ala
        35                  40                  45

Asp Gly Thr Thr Val Leu Gly Leu Val Lys Ala Ala Lys His Leu Asn
    50                  55                  60

Leu Asn Ala Glu Ala Val Arg Ala Asp Met Asp Ala Leu Thr Ala Ser
65                  70                  75                  80

Gln Leu Pro Leu Pro Val Ile Val His Val Phe Lys Lys Asn Lys Leu
                85                  90                  95

Pro His Tyr Tyr Val Val Tyr Gln Val Thr Glu Asn Asp Leu Ile Ile
            100                 105                 110

Gly Asp Pro Asp Pro Thr Val Lys Thr Thr Lys Ile Ser Lys Ser Gln
        115                 120                 125

Phe Ala Lys Glu Trp Thr Gln Ile Ala Ile Ile Ile Ala Pro Thr Val
    130                 135                 140

Lys Tyr Lys Pro Ile Lys Glu Ser Arg His Thr Leu Ile Asp Leu Val
145                 150                 155                 160

Pro Leu Leu Ile Lys Gln Lys Arg Leu Ile Gly Leu Ile Ile Thr Ala
                165                 170                 175

Ala Ala Ile Thr Thr Leu Ile Ser Ile Ala Gly Ala Tyr Phe Phe Gln
            180                 185                 190

Leu Ile Ile Asp Thr Tyr Leu Pro His Leu Met Thr Asn Arg Leu Ser
        195                 200                 205

Leu Val Ala Ile Gly Leu Ile Val Ala Tyr Ala Phe Gln Ala Ile Ile
    210                 215                 220

Asn Tyr Ile Gln Ser Phe Phe Thr Ile Val Leu Gly Gln Arg Leu Met
225                 230                 235                 240

Ile Asp Ile Val Leu Lys Tyr Val His His Leu Phe Asp Leu Pro Met
                245                 250                 255
```

-continued

```
Asn Phe Phe Thr Thr Arg His Val Gly Glu Met Thr Ser Arg Phe Ser
            260                 265                 270

Asp Ala Ser Lys Ile Ile Asp Ala Leu Gly Ser Thr Thr Leu Thr Leu
        275                 280                 285

Phe Leu Asp Met Trp Ile Leu Leu Ala Val Gly Leu Phe Leu Ala Tyr
    290                 295                 300

Gln Asn Ile Asn Leu Phe Leu Cys Ser Leu Val Val Val Pro Ile Tyr
305                 310                 315                 320

Ile Ser Ile Val Trp Leu Phe Lys Lys Thr Phe Asn Arg Leu Asn Gln
                325                 330                 335

Asp Thr Met Glu Ser Asn Ala Val Leu Asn Ser Ala Ile Ile Glu Ser
            340                 345                 350

Leu Ser Gly Ile Glu Thr Ile Lys Ser Leu Thr Gly Glu Ala Thr Thr
        355                 360                 365

Lys Lys Lys Ile Asp Thr Leu Phe Ser Asp Leu Leu His Lys Asn Leu
    370                 375                 380

Ala Tyr Gln Lys Ala Asp Gln Gly Gln Gln Ala Ile Lys Ala Ala Thr
385                 390                 395                 400

Lys Leu Ile Leu Thr Ile Val Ile Leu Trp Trp Gly Thr Phe Phe Val
                405                 410                 415

Met Arg His Gln Leu Ser Leu Gly Gln Leu Leu Thr Tyr Asn Ala Leu
            420                 425                 430

Leu Ala Tyr Phe Leu Thr Pro Leu Glu Asn Ile Ile Asn Leu Gln Pro
        435                 440                 445

Lys Leu Gln Ala Ala Arg Val Ala Asn Asn Arg Leu Asn Glu Val Tyr
    450                 455                 460

Leu Val Glu Ser Glu Phe Ser Lys Ser Arg Glu Ile Thr Ala Leu Glu
465                 470                 475                 480

Gln Leu Asn Gly Asp Ile Glu Val Asn His Val Ser Phe Asn Tyr Gly
                485                 490                 495

Tyr Cys Ser Asn Ile Leu Glu Asp Val Ser Leu Thr Ile Pro His His
            500                 505                 510

Gln Lys Ile Thr Ile Val Gly Met Ser Gly Ser Gly Lys Thr Thr Leu
        515                 520                 525

Ala Lys Leu Leu Val Gly Phe Phe Glu Pro Gln Glu Gln His Gly Glu
    530                 535                 540

Ile Gln Ile Asn His His Asn Ile Ser Asp Ile Ser Arg Thr Ile Leu
545                 550                 555                 560

Arg Gln Tyr Ile Asn Tyr Val Pro Gln Glu Pro Phe Ile Phe Ser Gly
                565                 570                 575

Ser Val Leu Glu Asn Leu Leu Leu Gly Ser Arg Pro Gly Val Thr Gln
            580                 585                 590

Gln Met Ile Asp Gln Ala Cys Ser Phe Ala Glu Ile Lys Thr Asp Ile
        595                 600                 605

Glu Asn Leu Pro Gln Gly Tyr His Thr Arg Leu Ser Glu Ser Gly Phe
    610                 615                 620

Asn Leu Ser Gly Gly Gln Lys Gln Arg Leu Ser Ile Ala Arg Ala Leu
625                 630                 635                 640

Leu Ser Pro Ala Gln Cys Phe Ile Phe Asp Glu Ser Thr Ser Asn Leu
                645                 650                 655

Asp Thr Ile Thr Glu His Lys Ile Val Ser Lys Leu Leu Phe Met Lys
            660                 665                 670

Asp Lys Thr Ile Ile Phe Val Ala His Arg Leu Asn Ile Ala Ser Gln
```

-continued

```
        675                 680                 685

Thr Asp Lys Val Val Val Leu Asp His Gly Lys Ile Val Glu Gln Gly
    690                 695                 700

Ser His Arg Gln Leu Leu Asn Tyr Asn Gly Tyr Tyr Ala Arg Leu Ile
705                 710                 715                 720

His Asn Gln Glu


<210> SEQ ID NO 80
<211> LENGTH: 698
<212> TYPE: PRT
<213> ORGANISM: Artificial Sequence
<220> FEATURE:
<223> OTHER INFORMATION: Synthetic construct

<400> SEQUENCE: 80

Met Thr Asn Arg Asn Phe Arg Gln Ile Ile Asn Leu Leu Asp Leu Arg
1               5                   10                  15

Trp Gln Arg Arg Val Pro Val Ile His Gln Thr Glu Thr Ala Glu Cys
            20                  25                  30

Gly Leu Ala Cys Leu Ala Met Ile Cys Gly His Phe Gly Lys Asn Ile
        35                  40                  45

Asp Leu Ile Tyr Leu Arg Arg Lys Phe Asn Leu Ser Ala Arg Gly Ala
    50                  55                  60

Thr Leu Ala Gly Ile Asn Gly Ile Ala Glu Gln Leu Gly Met Ala Thr
65                  70                  75                  80

Arg Ala Leu Ser Leu Glu Leu Asp Glu Leu Arg Val Leu Lys Thr Pro
                85                  90                  95

Cys Ile Leu His Trp Asp Phe Ser His Phe Val Val Leu Val Ser Val
            100                 105                 110

Lys Arg Asn Arg Tyr Val Leu His Asp Pro Ala Arg Gly Ile Arg Tyr
        115                 120                 125

Ile Ser Arg Glu Glu Met Ser Arg Tyr Phe Thr Gly Val Ala Leu Glu
    130                 135                 140

Val Trp Pro Gly Ser Glu Phe Gln Ser Glu Thr Leu Gln Thr Arg Ile
145                 150                 155                 160

Ser Leu Arg Ser Leu Ile Asn Ser Ile Tyr Gly Ile Lys Arg Thr Leu
                165                 170                 175

Ala Lys Ile Phe Cys Leu Ser Val Val Ile Glu Ala Ile Asn Leu Leu
            180                 185                 190

Met Pro Val Gly Thr Gln Leu Val Met Asp His Ala Ile Pro Ala Gly
        195                 200                 205

Asp Arg Gly Leu Leu Thr Leu Ile Ser Ala Ala Leu Met Phe Phe Ile
    210                 215                 220

Leu Leu Lys Ala Ala Thr Ser Thr Leu Arg Ala Trp Ser Ser Leu Val
225                 230                 235                 240

Met Ser Thr Leu Ile Asn Val Gln Trp Gln Ser Gly Leu Phe Asp His
                245                 250                 255

Leu Leu Arg Leu Pro Leu Ala Phe Phe Glu Arg Arg Lys Leu Gly Asp
            260                 265                 270

Ile Gln Ser Arg Phe Asp Ser Leu Asp Thr Leu Arg Ala Thr Phe Thr
        275                 280                 285

Thr Ser Val Ile Gly Phe Ile Met Asp Ser Ile Met Val Val Gly Val
    290                 295                 300

Cys Val Met Met Leu Leu Tyr Gly Gly Tyr Leu Thr Trp Ile Val Leu
305                 310                 315                 320
```

-continued

```
Cys Phe Thr Thr Ile Tyr Ile Phe Ile Arg Leu Val Thr Tyr Gly Asn
                325                 330                 335

Tyr Arg Gln Ile Ser Glu Glu Cys Leu Val Arg Glu Ala Arg Ala Ala
            340                 345                 350

Ser Tyr Phe Met Glu Thr Leu Tyr Gly Ile Ala Thr Val Lys Ile Gln
        355                 360                 365

Gly Met Val Gly Ile Arg Gly Ala His Trp Leu Asn Met Lys Ile Asp
    370                 375                 380

Ala Ile Asn Ser Gly Ile Lys Leu Thr Arg Met Asp Leu Leu Phe Gly
385                 390                 395                 400

Gly Ile Asn Thr Phe Val Thr Ala Cys Asp Gln Ile Val Ile Leu Trp
                405                 410                 415

Leu Gly Ala Gly Leu Val Ile Asp Asn Gln Met Thr Ile Gly Met Phe
            420                 425                 430

Val Ala Phe Ser Ser Phe Arg Gly Gln Phe Ser Glu Arg Val Ala Ser
        435                 440                 445

Leu Thr Ser Phe Leu Leu Gln Leu Arg Ile Met Ser Leu His Asn Glu
    450                 455                 460

Arg Ile Ala Asp Ile Ala Leu His Glu Lys Glu Glu Lys Lys Pro Glu
465                 470                 475                 480

Ile Glu Ile Val Ala Asp Met Gly Pro Ile Ser Leu Glu Thr Asn Gly
                485                 490                 495

Leu Ser Tyr Arg Tyr Asp Ser Gln Ser Ala Pro Ile Phe Ser Ala Leu
            500                 505                 510

Ser Leu Ser Val Ala Pro Gly Glu Ser Val Ala Ile Thr Gly Ala Ser
        515                 520                 525

Gly Ala Gly Lys Thr Thr Leu Met Lys Val Leu Cys Gly Leu Phe Glu
    530                 535                 540

Pro Asp Ser Gly Arg Val Leu Ile Asn Gly Ile Asp Ile Arg Gln Ile
545                 550                 555                 560

Gly Ile Asn Asn Tyr His Arg Met Ile Ala Cys Val Met Gln Asp Asp
                565                 570                 575

Arg Leu Phe Ser Gly Ser Ile Arg Glu Asn Ile Cys Gly Phe Ala Glu
            580                 585                 590

Glu Met Asp Glu Glu Trp Met Val Glu Cys Ala Arg Ala Ser His Ile
        595                 600                 605

His Asp Val Ile Met Asn Met Pro Met Gly Tyr Glu Thr Leu Ile Gly
    610                 615                 620

Glu Leu Gly Glu Gly Leu Ser Gly Gly Gln Lys Gln Arg Ile Phe Ile
625                 630                 635                 640

Ala Arg Ala Leu Tyr Arg Lys Pro Gly Ile Leu Phe Met Asp Glu Ala
                645                 650                 655

Thr Ser Ala Leu Asp Ser Glu Ser Glu His Phe Val Asn Val Ala Ile
            660                 665                 670

Lys Asn Met Asn Ile Thr Arg Val Ile Ile Ala His Arg Glu Thr Thr
        675                 680                 685

Leu Arg Thr Val Asp Arg Val Ile Ser Ile
    690                 695
```

<210> SEQ ID NO 81
<211> LENGTH: 57
<212> TYPE: PRT
<213> ORGANISM: Artificial Sequence
<220> FEATURE:

-continued

<223> OTHER INFORMATION: Synthetic construct

<400> SEQUENCE: 81

Met Ser Thr Lys Asp Phe Asn Leu Asp Leu Val Ser Val Ser Lys Lys
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met Gly Cys Asn Met Lys Thr Ala Thr
        35                  40                  45

Cys His Cys Ser Ile His Val Ser Lys
    50                  55

<210> SEQ ID NO 82
<211> LENGTH: 56
<212> TYPE: PRT
<213> ORGANISM: Artificial Sequence
<220> FEATURE:
<223> OTHER INFORMATION: Synthetic construct: dehydration product of SEQ ID NO :67.
<220> FEATURE:
<221> NAME/KEY: MISC_FEATURE
<222> LOCATION: (1)..(56)
<223> OTHER INFORMATION: At positions 27, 29 and 55 Xaa is didehydroalanine and at positions 32, 37, 42, 47 and 49 Xaa is didehydrobutyrine.

<400> SEQUENCE: 82

Met Ser Lys Phe Asp Asp Phe Asp Leu Asp Val Val Lys Val Ser Lys
1               5                   10                  15

Gln Asp Ser Lys Ile Thr Pro Gln Trp Lys Xaa Glu Xaa Leu Cys Xaa
            20                  25                  30

Pro Gly Cys Val Xaa Gly Ala Leu Met Xaa Cys Phe Leu Gln Xaa Leu
        35                  40                  45

Xaa Cys Asn Cys Lys Ile Xaa Lys
    50                  55

<210> SEQ ID NO 83
<211> LENGTH: 70
<212> TYPE: PRT
<213> ORGANISM: Artificial Sequence
<220> FEATURE:
<223> OTHER INFORMATION: Synthetic construct

<400> SEQUENCE: 83

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Ala Cys Cys Ser
65                  70

<210> SEQ ID NO 84
<211> LENGTH: 70
<212> TYPE: PRT
<213> ORGANISM: Artificial Sequence
<220> FEATURE:
<223> OTHER INFORMATION: Synthetic construct

<400> SEQUENCE: 84

-continued

```
Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Thr Ile Ser His Glu Cys Asn Met Asn Ser Trp Gln Phe
    50                  55                  60

Val Phe Thr Cys Ala Ser
65                  70
```

<210> SEQ ID NO 85
<211> LENGTH: 30
<212> TYPE: DNA
<213> ORGANISM: Artificial Sequence
<220> FEATURE:
<223> OTHER INFORMATION: Synthetic construct

<400> SEQUENCE: 85
gggaattcca tatgaactct tttaatcttc 30

<210> SEQ ID NO 86
<211> LENGTH: 25
<212> TYPE: DNA
<213> ORGANISM: Artificial Sequence
<220> FEATURE:
<223> OTHER INFORMATION: Synthetic construct

<400> SEQUENCE: 86
cgcggatcct taagagcagc aagta 25

<210> SEQ ID NO 87
<211> LENGTH: 29
<212> TYPE: DNA
<213> ORGANISM: Artificial Sequence
<220> FEATURE:
<223> OTHER INFORMATION: Synthetic construct

<400> SEQUENCE: 87
gggaattcca tatgcttcaa gaagtgaca 29

<210> SEQ ID NO 88
<211> LENGTH: 25
<212> TYPE: DNA
<213> ORGANISM: Artificial Sequence
<220> FEATURE:
<223> OTHER INFORMATION: Synthetic construct

<400> SEQUENCE: 88
cgcggatcct taagagcagc aagta 25

<210> SEQ ID NO 89
<211> LENGTH: 29
<212> TYPE: DNA
<213> ORGANISM: Artificial Sequence
<220> FEATURE:
<223> OTHER INFORMATION: Synthetic construct

<400> SEQUENCE: 89
gggaattcca tatgaaaggc ggcagtgga 29

<210> SEQ ID NO 90
<211> LENGTH: 19

-continued

<212> TYPE: DNA
<213> ORGANISM: Artificial Sequence
<220> FEATURE:
<223> OTHER INFORMATION: Synthetic construct

<400> SEQUENCE: 90
gctagttatt gctcagcgg 19

<210> SEQ ID NO 91
<211> LENGTH: 34
<212> TYPE: DNA
<213> ORGANISM: Artificial Sequence
<220> FEATURE:
<223> OTHER INFORMATION: Synthetic construct

<400> SEQUENCE: 91
gggaattcca tatgaaagaa caaaactctt ttaa 34

<210> SEQ ID NO 92
<211> LENGTH: 30
<212> TYPE: DNA
<213> ORGANISM: Artificial Sequence
<220> FEATURE:
<223> OTHER INFORMATION: Synthetic construct

<400> SEQUENCE: 92
atatgctctt ccgcattcat gagaaattgt 30

<210> SEQ ID NO 93
<211> LENGTH: 34
<212> TYPE: DNA
<213> ORGANISM: Artificial Sequence
<220> FEATURE:
<223> OTHER INFORMATION: Synthetic construct

<400> SEQUENCE: 93
gggaattcca tatgaaagaa caaaactctt ttaa 34

<210> SEQ ID NO 94
<211> LENGTH: 25
<212> TYPE: DNA
<213> ORGANISM: Artificial Sequence
<220> FEATURE:
<223> OTHER INFORMATION: Synthetic construct

<400> SEQUENCE: 94
cgcggatcct taagagcagc aagaa 25

<210> SEQ ID NO 95
<211> LENGTH: 34
<212> TYPE: DNA
<213> ORGANISM: Artificial Sequence
<220> FEATURE:
<223> OTHER INFORMATION: Synthetic construct

<400> SEQUENCE: 95
gggaattcca tatgaaagaa caaaactctt ttaa 34

<210> SEQ ID NO 96
<211> LENGTH: 25
<212> TYPE: DNA
<213> ORGANISM: Artificial Sequence
<220> FEATURE:
<223> OTHER INFORMATION: Synthetic construct

<400> SEQUENCE: 96

-continued cgcggatcct taagagcagc atgca 25

<210> SEQ ID NO 97
<211> LENGTH: 34
<212> TYPE: DNA
<213> ORGANISM: Artificial Sequence
<220> FEATURE:
<223> OTHER INFORMATION: Synthetic construct

<400> SEQUENCE: 97
gggaattcca tatgaaagaa caaaactctt ttaa 34

<210> SEQ ID NO 98
<211> LENGTH: 25
<212> TYPE: DNA
<213> ORGANISM: Artificial Sequence
<220> FEATURE:
<223> OTHER INFORMATION: Synthetic construct

<400> SEQUENCE: 98
cgcggatcct taagagcatg cagta 25

<210> SEQ ID NO 99
<211> LENGTH: 34
<212> TYPE: DNA
<213> ORGANISM: Artificial Sequence
<220> FEATURE:
<223> OTHER INFORMATION: Synthetic construct

<400> SEQUENCE: 99
gggaattcca tatgaaagaa caaaactctt ttaa 34

<210> SEQ ID NO 100
<211> LENGTH: 25
<212> TYPE: DNA
<213> ORGANISM: Artificial Sequence
<220> FEATURE:
<223> OTHER INFORMATION: Synthetic construct

<400> SEQUENCE: 100
cgcggatcct taagagcagc tagta 25

<210> SEQ ID NO 101
<211> LENGTH: 12323
<212> TYPE: DNA
<213> ORGANISM: Artificial Sequence
<220> FEATURE:
<223> OTHER INFORMATION: Synthetic construct

<400> SEQUENCE: 101
ctaattgaca ttgttatact tagatggcgg actcggaaag gtaattttaa atcttgtgcc 60
aattcccggc tgactatata tatcaatatt tcccccatgt gccttgataa tttgttgagc 120
aatagccatt cctaatccag tccctgagtt atttgacgta gcgcttgtcc ctctgaaata 180
ccgatcaaat aaacattcga ccgtctcttc gtccattcct atcccatcgt cttctattat 240
aatttgtatt tcattgtcat gtaacacgtc ctgatataat atgaccttta ttttagtgcc 300
cggaggatta tgtttaatac aattagcaat caagttttca actgcacgct ttaggtacct 360
ttcatccata ttaaaaagta tcttattgtg actggattct aaagcgaatc tcttattttc 420
tgactccggt agcagcttca ttttttctaa agtgtcatga attactttca ctacgttttt 480
ttcttcaaga tggattggaa gcgactcatt tttcaattga aaagttaagt tgaaatcttc 540
aatcagcttt tccatatatt cgacacgttc ttccattatt aaggaaaaat cacgcacttg 600

-continued

```
ctgattttcc cactcatatt catttgaaga taaaagaacc gtatatccct taataaccga    660
aagaggggtt tttaaatcat gtgagacacc ggccatccac tcttctcgtg tcttttccaa    720
taattctcgc tcagccttat tcctttgaag cgttgaggta agttcagaca gagcctgcat    780
taattcttga taggtcttat atccagattt attatgtcta tatttgcttg aatgaaactt    840
ccaatcataa ggttcttcat atttttcttt agacaaattc tcaatccaag atacaataaa    900
cagcagggga gcacctagtt tttttccgta aaatattgca atgacaatcc ctgccataat    960
aatagaaaca atccacaagt tattcaccca atagaaaaaa gggttatttt tttccatcgg   1020
ctttcccaat acccatgtta aatcctgatt gtttttcgtt tcataccacg tagataattg   1080
ataacctttt ttggcaggat acatgtaatc tgatattaac tctccaagaa tataatgctt   1140
aggtatattt tgaggtttat taaaagaaaa aacctcatct ccttgttcat ctaaaatttg   1200
aatccacatc cggttctcta ataaatcttc ttttgctttc gtatttattg aaaattgttt   1260
atctgcaaca actgtttggt caacaatttt ttttaaggat aagtgcggcg tttccatttt   1320
attctgacct aagacgaggc tgaaaaatat gatactgccc acaatgagca caccccaaat   1380
aaacatgagt aaaaaaagtc tcgatacgaa gtaaaatgct atcctatttc tcagcttcaa   1440
aataaatcct catctatagg ctctgcttca aatatatagc cctgtcctcg aaccgtttta   1500
atccatctag gtctgctcgg gtcttcctct aatttttcac gtaatcgtct tacatgtacc   1560
attacagtac tatctccgcc ataaaactcc ccccacacat ctttataaat ttggtgttta   1620
cttaaaattt gattgggatg ttcacagaaa taaatcagaa gtttcatttc ctgagcaggg   1680
caatctattc ttgtcccgtt aacaacaagt cttccggtat tgggatctat tttaaaatat   1740
tcataatcgt atacctgttt tagagggtaa gaagaagaga gttgagtcgt tctctttaat   1800
tgggctttta cacgagctac aatttctagt ggattaaatg gtttagtaat atagtcatct   1860
cccccaaaac taaacccttg caatttatct aaatctgttg tttttgccgt taagaagagt   1920
atcggcacat ttgtatgcga gcgtattttg ctgcataagg tgaagccatc agtgtccgga   1980
agcatgacat ctaataaaat aatatttgga agttcctgat cgattttcag aagggtttcg   2040
ctccctgtca tagctgtgga aatattgctg aaaccttcct tttcaaagca agttattaat   2100
aagtttaaga tatgttcgtc atcatccacc atgaggattt tgttctcttc taacgtcata   2160
agttaccctc ctttttattt cttattttat atgagatcaa tgacataaag gtcagaaaag   2220
gaaagaattt aactttcgtt aagggttcag aatattcttt cgaattttta accttgatat   2280
tcaggtatca atataactac atacagaaaa taaaccaggg atgtcgttaa gtgaatgttt   2340
aggaagagtt tcgtttgtgt ttaaagaaca tcgcttatga taaaagtgag gtgagagaca   2400
aatgaatgat caaatagtgg taacacacga tctgactaaa aagtataaaa agcatacttc   2460
tgttgatgga ttaaacttaa ggattaggcg tggcgaaatt tatggttttc ttggaccgaa   2520
tggtgctggt aaaacaacaa ccatccgaat gttattaggt ttaattaaac caacaaaagg   2580
aaacatcgaa atctttggcc aaaacctaaa caagaatcgt ttgcagatat tgcaaagaat   2640
cgggtcactg gtagaatctc caacttatta tggtaattta acaggttacg aaaacttaga   2700
agctgttagg aggttacgag gacttccgga acaacaggtc aatgaagtat tggaaactgt   2760
aaggttatct aaagtagcaa atcgactgac taaggagtat tcccttggaa tgaaacaacg   2820
tttgggaatt gcagttgccc tgttaagcag tcctgattta ttaattctgg atgaaccgac   2880
aaatggttta gatccatccg gtatccaaga aataagagag ctaattaaag aattgcctaa   2940
```

-continued

```
atcgggaatg agtgttattg tatccagcca cttattgagt gaaatagatc aaatggctac   3000
tcaagtggga attatcaaca atggaaaaat gatttttcag gactcgattg caagtttaca   3060
tcaaaaaaga aaaccactat taaaagtcgg tgttagtgac gtaatcgaag caaaaacaat   3120
attaaacagg aaaggattaa aggttgattt acaaaaaaat tatttgtggc tgtctcaaac   3180
agaaccggaa ttcgtttcag aaatcaattc catacttctt cattcagggc tgtctgtatt   3240
tcgacttgaa gaaaagacac gatcacttga ggatattttt ttagaattaa ccggtacaga   3300
gggaagtcta tgaaaaagtt attatgggca gatcaattaa aactgaaacg ttcgtcgtta   3360
ttgattgtag tcttattggt cccttactca ttatagcata tgagttggta aatcttactt   3420
atcgatctga atacgtggaa aaacaagctg aaatgttcca tgctggatca atgtggatgt   3480
atttactgta tgataacagt ttgttatttg gtctgggttt tccattagcc gccacacttt   3540
ctgcgtcaat aatagcaaat atagagcatc aagcaaacgg atggaagcaa accctttctt   3600
ttcctgtatc tagaatgcga atttatgtaa gtaaatttat ttgcttagta gtcagtttat   3660
ttatttcgtc aacaatcttc ttgctcggca tggtactgct gggcaaactg gtaggattcg   3720
aaggtagtgt accttgggga cttttgtttg gagatagtta cagcatgtta gttacagtac   3780
tgcctataat ggcattccag atatggttat ctatggtgtt tagcaaccaa gcattctcaa   3840
ttcttgtagg atcagtatca tctataatgg gtttgttttt ggcagctgct caatcaacga   3900
gatggtttcc gctggcttat cctagtcaat cttcgacagt cattctgcag tatgaaggta   3960
taggatataa cccagatctt tcatcttacc tttgcattag ccttttctta gggataatta   4020
tattatttct aggctctatt cattttgcta aacgggatgc tttgtaaaaa ggaggcgaaa   4080
tacttgaaaa acattttatt tgtagaacgt ttaaagctta agcgatcaaa gttatggatc   4140
atctacttat tagggccttt gttaggtgta tccctggcat acactaactt tattaaaaac   4200
tataaccttt ttatgaatcc cggagacaat ccctgggtag aggcttggac acaagttgcc   4260
ttatttatgg gccctttgt attgcctatc gtagtgggaa ttttcgccgc ccttgtttgc   4320
aggggggaac atgtaggagg cggttggaaa cagcttctag ccttaccagt caaacactca   4380
gatatctttc tgggaaagtt tctaacagtg gtccgcatga tattcattag tatgtccatt   4440
ttaatcctct tatttattgg attcggttat atgttaggca taagcgggag tcttccttta   4500
cttacaattc taggttatgg aattagaggg atcttagctt gtttaccatt aattttattg   4560
cagcttattg tttcaatcag gtctaaaaca tttggcatac cactcgctgt tagcattgtt   4620
tttacattac cggccattat tattgccagt acaccattag gtcaagtata tccatggaca   4680
cagcctatgt tagcaatgtc acccgaagat gaatcaccga ttcaatcaaa tttcctgttt   4740
tactcaatta tggtaataac gtgtctcggt ctcctggttt acggaataag aagttttact   4800
aaacgagacc ttacgtaggg tatatgcggt ataaacttat gagaattcga gacaaggtaa   4860
actaatttga ctagcgctat gtaaaacaga aatttatatg aaggtaagac taaatctttt   4920
tggttgtatt ctttgaaact aaacgactaa tggaaaaggt gatgtttcaa agcataagac   4980
ataagaaata taaagatatc ttaagactct ttatttaaac attttttaca tttaataata   5040
tctcttccat ttttttgatt atgagttaat ataatactat acttaataag ggggtgaata   5100
caatgagtca agaagctatc attcgttcat ggaaagatcc tttttcccgt gaaaattcta   5160
cacaaaatcc agctggtaac ccattcagtg agctgaaaga agcacaaatg gataagttag   5220
taggtgcggg agacatggaa gcagcatgta cttttacatt gcctggtggc ggcggtgttt   5280
gtactctaac ttctgaatgt atttgttaat ttgatttata taggctgttt cccttcagaa   5340
```

-continued

```
ggaacagcct atattttatt atataaacta ttagaaaatt cttaaaaaac aggagggtaa   5400
atcattgggg aaaactctcg tttgttcaga aaatagctat ttccaagcat atatgaatca   5460
tttattaacg ccagatagta atgaaataat aaatgttaac acattggatg aactaaaaca   5520
aataatatcc aaagaaaatt tttcctctgt aatcatcgat acttgccacc ctaatgactt   5580
agtgttgcaa ctgataaaat cgatatcttg cccagtcata atacttaact ccttagaaac   5640
taacgtttca gattataacc ctggtccaat attaaatcaa ataaataatg tttcaaccct   5700
aaaacataat gtttttcaat tgtctttcac aactttttc gacgttggaa agcattgtat   5760
ttggaaaaag aatgaatata tccctctagc aatacaagaa tttaaaattt tatatttgct   5820
ttatttaaat tcaaataaaa tagtctgttc tgaagaactt attgaatatg ctgaccttac   5880
tggtaggtca agtctttatg tacacattag ttctcttaga gaaaaagtag aggataaccc   5940
tggagatcca aagattcttc aaacaaagtt tggaaaaggg tacctcttat ctgacagtac   6000
atatatttgt cttgaaaaaa aagcagactc aaaaaatgtc gtgtaaaaag gatgacccaa   6060
aaatcatttt aaaatgactt ttgagtcatc ccatttatgt tagtgagggg tgttttgttc   6120
tttctttaaa accttttttct attgctaata aagctttgtc gggtgtaatt agaccacgat   6180
taggttttct tgtacccgtc gcaatctcaa acgccataat ttcaactggt tcaataacaa   6240
tatgcccatc ttttcttaat tgttcaatat tcctggaaac aactgtttta ttccacatta   6300
aatcgttcat attaggaaag aaaatagtgt tatgtggatg agctaataca gtagttgcaa   6360
ctaaattcat tgctacacca ttagcagttt gtcctaagat gttcgctgta gctggaataa   6420
tgcaatatat gtccgcccag cggccaattt ctacgtggct atgtcttttt ccgttttccc   6480
catgttctga gtatacatgg tcacaaaaat aagaaacagt atgagctgga ataaggtctt   6540
ccgctgtttt tgtcataaca acccttattt ccttaaagaa gcttttaaaa tataagagat   6600
acgaggagat gccgacagat gagattgatc cgcaaatccc gatcaataac tttttatctt   6660
ttaatattga aatactcatt tttttctccc tctgtaaatt ttaaacaatc atactacaca   6720
attattcttt ttgtggtgtt tattccaaat attaaatatt cttaataaac acatataaaa   6780
taaacctaaa cttcttttaa aattctttta acttttaaat ggctctgcta tatttatgga   6840
taattaagga atattaattg ttcaaattta ttaaaaatga ggtgttcaat atgcatacaa   6900
aattcaaacg gaattcggta tggaataggt cttcttcgat aagtgaaaga aaagtaaggc   6960
gttcacttaa tactaattgg gatgaactaa caaacagacg cttcgaaaga tggaaaagcc   7020
ttgttgaaag tgatgagggg attcgaattg aggatgtatt agccacccaa aatattgacg   7080
aagaaaccct aaagcatact atcaatgcaa aagaagtgga atttattaat gaaggtgatc   7140
atcaaggatg gcttgaaatt attcagctag ttgatgaaca atcctataaa aatgtaaata   7200
tagaagttag aaaagatatt ctcttcttta gttttataaa accatttttg aaaatagcaa   7260
gaggcaaatt agaggaagta ttatattctc actctactaa atctctgata aaggaagaac   7320
ttagtccgtc ggtaattgat gatttactta ataatcttgg tgaaacttta tcagctataa   7380
gtagtcggat attaatattg gagttaaatg tagcaagggt atcaggaaag ctgcggggtg   7440
aaacttctga agaacgagcc tcttatttca atcaagccct tttaaatgac ccggcatatg   7500
ttcgatcaat tcgagaagaa tacatagttt taacaaggct gttagcaaca aaaacaatgt   7560
attggattca aaatacttct gatctccttg taagatttca tcaggataaa gggatattag   7620
aatctgagtt tagtaatggt caaaaattag ggaaaattat ttccatcgat acaggaagtg   7680
```

-continued

```
gcgtctcaga tactcataac aaaggaaaaa cagtcgccat tttaaacttt gaaactggaa   7740
ttaaaattgt gtataagcct cgttcattag aaatagacgt aaaatttaat aaatttgtaa   7800
attatctaaa tggtaaaaat ttaagttttg acttaaaaac tgtacacaca cttaacaaaa   7860
aatcttatgg atggacgcag tttatctctt ataaagaatg tcaggaagaa ctgcaaattg   7920
gaaagtttta ttggcgtatt ggaagttatt tggctatctt atatgcaatg aatgcggtag   7980
attttcatat gcaaaattta attgctgatg gagaatatcc tattttagtt gatttagaat   8040
ctttatttca taataattct acgtatacag ataccagtgc ttttagtcgc gcacaagaac   8100
atattgaacg gtcagtttta cgaattgggt tattaccgag aaaaataaat agtaaagctg   8160
gatttgaagg aattgacctt agtgcattag gtgcacaaga aggacaagta tctccgcata   8220
aaaccagtac aatagttgat cgagataaag atacagtcag gatagaagaa aaaaactttc   8280
caattccagt tagtcagcat agacctatgc tgcatggaca aatcattaat actgttgctt   8340
acgaaggaaa tattataaaa ggatttgaag aaacctactt ccttttcatg aaatataaac   8400
aagacatgct cgaacaaata gattctttta aaggggttac tgtaagacaa atattgcgtg   8460
gtacatctcg ctatgcaaac cttctgaaaa taagtttaca tccagatttc atgagagacg   8520
gcttagatcg tgaaatgatt ttagataaat tgtggctaga tacaaaattg aatccacgat   8580
tgaaccaagt tgtaaatagt gaaaaggaag gcttattcct tggggatatc ccatatttca   8640
caagcaagcc tgaatctaca aatatgtggg attccagcgg tcgaaaaatc aacaattttt   8700
ttaaaacaag tgccttaaat gagacaaagg aaaaaataaa tgaaatgaat gaaagtgact   8760
gtcatgaaca agtaagcttt ataaaaacag ctattttagt aattaaggat tcttatcgta   8820
aacataaagt atttgatata aatcctcgat tacacgtttt taacccaaaa gatttttttc   8880
aagaagctat taaaatcgga gactttcttg ctagtagggc gattgaaggt gaacagttag   8940
atggacaaga ggatgtatct tggatcggat cgtttgttga caatcaacga gaggatcaat   9000
tcaagatttc agctgcaaat agttcattat acgagggtgt aggtggtatt tctctcttcc   9060
ttgcttattt aggtcgcctc tctaacaatg aaaaatacac caaactatct aaaaaagctt   9120
tagtggcagt acacaaaaat atgtctgcat ctagtgattt aggtgccttt gggggaattg   9180
cttcttacct ttatttgttg gatcatttat caaaattatg gaatgatgaa caactattga   9240
aaaacgaact ttattctgcc ctcaacaaat tagattcttt gatcgaaagg gatgaaaaca   9300
acgatatttt aacaggggtg gctgggacag cagttatttt aataaatttg tttaaacggt   9360
ataaagaaga acaaatctta aacttgatta caaaatgcgg aaatcgtctt attcaaaata   9420
taaacgttat ggaaaaggga gttggatgga aagtcccggc aaacccaacg ccagcctccg   9480
gatttgctca tggtgcctca ggaattatat gggctcttta tgagatttac gcaattacta   9540
agcaaactgt atttaaagag gtagctgaaa aagcgttaga atttgaaaga actttgttta   9600
ttccggaaaa aaacaattgg gcagatatta aacttgaaaa cggacagttt cgaaatgata   9660
attttgttgc ttggtgtaat ggcgcagcag gcataggatt aagtaggata ttgatcctgc   9720
cacacaatca aaatgaattg ataaaagatg aagcacatgt cgcaattaat acaaccctaa   9780
aatatggttt tgaacatgat caatctttat gccatggtga tttaggtaat ctggacatcc   9840
ttatgtacgc agcggaaaac tttaataaaa agttaagcgt aaatgtaaca gaactaagcc   9900
ataaaatttt aaatgatata aagctcagag gatggttaac tggatttgaa aaaaataacg   9960
aatccccatc cttaatgatg gggtatgcag gtataggact tggattgctt aagatttttg  10020
caccagtcga agtgccatca gttttgagac tccaatcacc tttagaacta aaattgtaaa  10080
```

-continued

```
attaaaatga gccttacttt gttaaggctc tatttcttag aggtgatcca atgagaagaa  10140
gagttcctct agtaaggcaa atgggacaat atgagtgtgg gcccgcctgt ctcaccatga  10200
ttttaagtta ttatgggagt actatatctc taaataaaat aagtgaacaa tgtgatgccc  10260
aaagaaatgg cgtatctgta tccattttaa aatcagtatc agaatattat gggcttaact  10320
gcaaagtata ccaagtttcg tttaaagatt tgaaaaaata tatcaattca tatcttccct  10380
gcatcatatt ttgggatgaa cggcactttg tggttttaga acagattaaa aaaggtcttt  10440
ttcatataat tgaccccaac agaggaaaat tgaaattatc cgaagaagaa tttaaaagac  10500
attatagcaa ggtaatcttg acttttaaga agtcagataa atttaaagag atgatgccat  10560
cacccgcagc aaagtattat ttacgttata tagttaaaag ccgtactatt gtttcactta  10620
tcattctctt ttcactgatc acacaagtag tcttcttagc cgttcctttt ttaattaaat  10680
atttagtgga tcattcttta ataagtaaat caacaaattc ttttctattt ttaggaattg  10740
tagtcatcat agcagttttt atattgggac ttgttatgtt tatccgcaat tatttcacaa  10800
ttaaacttca agctattata agtaaaagca tctcaaacga ttttgtggaa catttattaa  10860
aattacctct caatttttat gaaaatcgaa caaccggtga tattgcaatg agagtaagta  10920
acatttccat gataagggag attatagcta agaatggagc aacaatagta ctagatatta  10980
ttactttgat ttcatttttt attgctatgt taactcaatc atttaaactt gcattttttg  11040
ctattggatt ggcaattatt caattcttac taatgatgat tttgattcca agaataaaaa  11100
atttaatcca taatgactta tcaattcaaa caaccacaca aagtttttta gtggaagctc  11160
taagagctat cacttttatt aaatcaaatg gtttagatca ttctatccta acaaagtggt  11220
caaattacta tgataaacaa atcgaagcat tttcacagcg ataccactta gacgctataa  11280
tggatagcat aagtgtaagc atccgatatt gtgcacccct tctcttatta tggtttggat  11340
caaaagaagt tatcaccgga aatttaacac tcggaggctt attagggttt agcagcttag  11400
gaacatcttt cttgttgccg attgcttctt taataacagg catgcaacaa tttcaattgg  11460
tcggtgacac ttttgaacga atgcaagatg ttatggaaac tgagcccgaa caaatcaacc  11520
aaacttcaat aattgaaact gaactatcaa aacaagatat aaaacttgaa aatgtcacat  11580
ttacacatca tagcttacat attcttaaag aagtttcatt aaacattaag tcaggtacta  11640
aattagctct cgtaggccgt acaggtagtg gaaagacaac tttatcaaga attatactgg  11700
ggttatacaa acccactaag ggaaaagtat tttatggtga acaggacttg aagaatttaa  11760
acctttacga gctccgaaaa caaatggggg tcgtattaca agaaagcttt cttttcaatg  11820
atactattgc aaacaatata gctggattta aaagcttatc tcaggataaa attgaacaag  11880
cagcaaagag agtgcagtta catgaagata taataagaat gccaatggga tataacacaa  11940
ttatcgggga aaatggcagt atgttatcag gagggcagcg tcagcgcata gcaatagcaa  12000
gagctatcgt cgataaccct tctgtagtca ttttagatga aataacaagt aacttggata  12060
cattaacaga gcatgaaatt gacgaatact ttgcaaaatc aaatattacc cgtattgtaa  12120
taactcatcg tcttttaagt agccaagact ctgatttaat agtggtatta gatcaaggaa  12180
aaatagtcga aaaaggaaaa catcaagagt tattagagaa aaagggatac tattataact  12240
tatggataaa acaagtaggg gatagacaga aagctacgct gcaaaagccc tttttcctca  12300
atgagcaaac tggcaaaact tga                                          12323
```

<210> SEQ ID NO 102

-continued

<211> LENGTH: 3480
<212> TYPE: DNA
<213> ORGANISM: Artificial Sequence
<220> FEATURE:
<223> OTHER INFORMATION: Synthetic construct

<400> SEQUENCE: 102
ttaaaaaagg tgatggctta cctgaatggc aaaagtactg atttatcgga tattgaagac 60
tatattagac tggttgagca gctgggtaat cctacactgg ctatgttttt aagaactaat 120
ttggaacaga ttatgatgaa aagttaacct aaggacgata aaaggcaccg aactactgag 180
gtagtcgatg cctttctttt gggagaattt aaagcaacgt attttaccat atagctgctt 240
acaataatgg cagaaacaac aatggcaagc aaatggcgag ataaataatt ctttttaaca 300
taggattccc aacctccttc atacttattt tactaagaaa tttttgtaaa atagcatatt 360
cgcaaatatg aaaaaatttt ttaaaaattt catatttgcg aatttcttaa tagtggtaaa 420
aaagatggta aactgtaaat gtaaaatatt tgatcaaaat tttacatttt aagcaataaa 480
gtgaggtgtt ttattatgaa caagttaaac agtaacgcag tagtttcttt gaatgaagtt 540
tcagattctg aattggatac tattttgggt ggtaatcgtt ggtggcaagg tgttgtgcca 600
acggtctcat atgagtgtcg catgaattca tggcaacatg ttttcacttg ctgttaaaaa 660
attaaaaatt ataacggggg gcttaagctg tagcttgagt ccttttttatc aaaaaggaga 720 aatttatgaa caacccgtta ttccctgaat tcttatcata catgaaaaaa catgattcga 780
ctgtaaaaaa gtcgttatcc ttctacagtg aaaattttat tgatataagt atttttaaat 840
tgttcgctaa agctcttgtt tatttaatta atgaaaagcg agaaaatcaa tctttgattg 900
gtttaacctc ggaagaaaaa tatgaatatt tcactaagca ctatgtactt accggaataa 960
tattagatga aattcgtact aaatttccta atatcgttat ttcatttcat aattacttta 1020
actcattaaa tatgctagga aatcaggtta catctaacta cttaaatgac caccaggacc 1080
ttgttaatct tggtttagta gatcaatctg ataagattgt cagccttcaa gtagtaggcg 1140
atatgcataa tgaattagcg gtcgttaaag ttaatttgac aggtcgttct ttattttata 1200
aaccgcattt agataattac attgtctata atgagattct tcaattactg aattctaaat 1260
taccggctaa tcttaaacaa agacaagtta aatcctttgt ttcttcagac cattcttggc 1320
ttgaagaagt taaaagaaat ccgttattaa aagaaaacat ccataattat ttttctcgaa 1380
tgggagggtt aattgcaatt gcttattctc tcaatatgac cgatttacat tttgaaaata 1440
tcataagtga cggtgaatat ccagttattc tggacatgga gaccatttgt ggtacaacta 1500
taaataataa tgaattttta tttaccatgg ctcaaaaaga agtaaataat aagatatttg 1560
attctgtgct aaatacaggc ttattaccta tgaaaggctt aggaagtatt tttggtggtg 1620
atgtcagtgg tatgatgggg ggtgagttta ccaagagttt taatcgcata gtagataaca 1680
ataaagatac tattcatttt gaaaaaaaga ttgaacgttt aactaatatg aatcatcttc 1740
catattacat cagaaataat aaagagatac ttatcaaaaa ttcaccagat tatctaacaa 1800
atatagttta tggttttaat tccacatatg actatattca agttttaaaa aatgaaataa 1860
taactatcat aaaaaaatat gaatttctaa catgtcgcgt catttttaga caaactgccc 1920
actattcgct aatgctagaa gtattaaatt ctccaattta tcaaaatagc aaagaaaatg 1980
ttttgagtaa attatcttac tcagcttatt ccaaaggtgt tctggaatct gaaaagaaac 2040
aatataggtg ggaatatccc tctcccacaa ggttgaattc catcaatata ttgatcagct 2100
tcaactgttc aattagtagc ttaagtccaa tagacaattt agaaattaaa ttatcgagtc 2160
tttcaagaac agatagacaa tttcaagaga agctgattcg gttctcgcta caaggaaata 2220
tagaattata tttaaatcca caaattaacc taagaagtag tactcagaat cttgagtcta 2280
atgagttgat aacacgctct atcaatgata ttaagcaaaa aattattgat aattcattag 2340
ttgcatctga cgggacgatt aattggttta atgtaagtgt cggagattat gacgaattag 2400
aattagagat aatggatgat actatataca agggaatcgc aggaatcaag ttagccttcc 2460
ttctaagtag tcgtaatttt ggtatgagta gtgacaaagt gattcttgac agaattaaca 2520
agagtttaag tttcagtgac tataccctga atcgtgaatc attttatgaa ggaacttttg 2580
gaagtcagtt gccctcgtat aaagagattt ctaaggaaga tctacaaaat cctaaacagt 2640
gggatgcttt attaggtgct tctagcacta ttataggaat ttatcaaaac tttaaaatta 2700
atcctacttt caaagaaatt attgaacaat atgctgatta tttagttata tctttacaaa 2760
agaacagtat taacggatat tcttggtttg acgaagaaca tcaagatttg gtaaatgtta 2820
gttttgcaca tggtaattca ggatgtatga ctgccttgtt aatttcttat gctctattag 2880
gtaaatcaga atatttagat acgtttcaaa agcttgggaa agtgaacaaa aaattcatga 2940
tagattgtgg atgggaggat acacgtaata ctgatagatt gtcttcagct aattggtgtc 3000
atggaagtac gggcgcttta acctctagac ttttatggtt taaactaaat aagaaattta 3060
atattcttaa tgaacatgat atccaacggg tttatcttga aattgaccac tctgtcaatg 3120
atataattga taaagggtta tcaattaata atttttcact ttgtcacggt attatgggta 3180
acttgattgc tctaaacgaa tacagcctcg ctttctccaa tcagaagatc caacaattag 3240
ttcagagtac tttgatttca ttatgctcag tagggatgaa aaaagattgg ctctgtggtg 3300
tcaatgacct gttttacaat aatggtttaa tgacaggcct agctggcatt ttatatggaa 3360
tcataaaaat atattatgat gataattacg accagcatgt cttaaatctt tcattttact 3420
aaaatataat tctcgaaagg aaaagagctt aactctcttt tagaggtcat tataaattga 3480

<210> SEQ ID NO 103
<211> LENGTH: 17083
<212> TYPE: DNA
<213> ORGANISM: Artificial Sequence
<220> FEATURE:
<223> OTHER INFORMATION: Synthetic construct

<400> SEQUENCE: 103
ggatcccggg ccgttcgccc agcacgagcc ccacacccag cgggaccgcg acgccgccga 60
gcgcgccgag gggggaaacc acgcccatgg ggcccagggc cagggccttg tagaaggcga 120
gcatcgccgc cgggccgacg acgccggccg ccaccgcgta ccagagctgg ggcccggcct 180
cggaccagcc gccggtgccg atcacgatcg cgcccagggc gaggacggcc agcagctggg 240
agaccaggac cacggtcagg gcgggcatgc gccgggtgag cagcccgccg ccgaagtcgg 300
ccagccccca catgaggctg gtggccaggg cgaagaccgg tgtcatgggg gagacctcgc 360
agtacagtgt gatgaacggt ggcgtccacg acaccgtagt acacgatact cgacttacga 420
gaataatatt ttggacggga tggatcgacc gacgtgacgg acctcgacca gctcacgcaa 480
tcgctcgccc gcaacctcaa gcgctggcgc ggtgagcgcc acttcaccct cgacgccctg 540
gcggcccgct ccggcgtcag ccgcggcatg atcatccaga tcgagcaggc ccggacgaac 600
cccagcgtcg gcaccacggt gaagctcgcc gacgccctgg gcgtcagcat caccacgctg 660
ctcgactacg agcagggcgc ccgcgtgcgg ctcgtgcccg aggagcaggt ggtgcgcatg 720

-continued

```
tggtccaccg aggcgggcag ccacacctca ctgctcgtcg gcgccgatgt gcgcggccca     780
ctggagctgt gggactggcg cctcgtgtcc ggcgacagca gcgtctcgga cccccacccg     840
cccggcacgg tcgagatgct gaccgtacgg tcgggccgcc tcacgctcgt cgtcgacggc     900
gaggagcacg aggtcgccgc cggcacctcg gccaccttcg aggccgacgc cccgcacacc     960
taccgcaacg acggcaccga gcccgtcgag atgacgatgg tggtggccgt cccgcccgcg    1020
ggctgacccc cgagcgcacg gggcccgccg ggagacgtcg agcgacgctc tcccggcggg    1080
cccctgtgcg tggtggctcc gtgcgccggt gaagacggtg ctcccgaagg cggtgctccc    1140
gaaggcggtg ttccggaagg cggtgctccc gaagacggtg ctcctgaaag cggagtgaaa    1200
ccgtagtgaa agcggacgct cctagtgtcg ttctcaccgg gaaccgactg gatggggaaa    1260
cgggccatga aaagtgccaa ggaaccgacg atctaccagg acgtggatat catccgccgc    1320
atccaggagc tcatggttct gtgctccttg ctgccgcccg acggcaagct gcgtgaagcg    1380
ctggagttcg ctctctcgct ccacgaggag ccggtactgg cccggatcac tcccctcacc    1440
aatctccatc ccttcgcgac gaaagcctgg ctggagtccc tgtggctcgg cgacggcgtt    1500
tccagcgagg agaaggagct ggtcgcctgg cagaacaaca gcgacaacat gggaccggcc    1560
attcgtgaac tcaagaatgc cgaacagcaa tccggcatca ggctggtcgc acagctgacg    1620
tcctgacacc cgccgggtgc cggattcac ctcaacatcg gaggtaagcc atgaccgctt     1680
cgattcttca gcagtccgtc gtggacgccg acttccgcgc ggcgctgctc gagaaccccg    1740
ccgccttcgg cgcttccgcc gcggccctgc ccacgcccgt cgaggcccag gaccaggcgt    1800
cccttgactt ctggaccaag gacatcgccg ccacggaagc cttcgcctgc cgccagagct    1860
gcagcttcgg cccgttcacc ttcgtgtgcg acggcaacac caagtaagtg gctgctgcct    1920
ctaggcggta atgctcgccc ggtgcgatga cgcggtgggc cggtgacctg ccggcccacc    1980
gcgttgcgcc gcgcggcggc gcccctgcca cgagggtcac gaggctcctt cgacttcgac    2040
cgcaggagaa attcgcatat gggtatgggt aacgcgtatc cgctggacat cgcagcacgg    2100
gcggccaatc tgaccgaacg gttacgggtc gtggccgcgg cgggcggcga ggcggccgtg    2160
cgggacaaca cggtcgagct cgacgccttc gaccgctgga aggccgacac gctggccgga    2220
aaactggccg acaagttcca ccaggaatcg ctccaccgcg gccggccgcc ccagcacacc    2280
aaggacgaac tcgccggcgt gctgtccgcc taccgtcgtc tggaactcgg cctggacacc    2340
gcggacgacg acgtccggac gcttctcggc gagctgcaga gcgcctggct gcccgcctac    2400
cgtgcggccc tcgacgccca cgacgccgcc cgcgacgacg aacgggccga cgcacagccg    2460
ggcgaggagc ccggctggcg cgggttcgac gtgtactacg gccggctggc gaaggcgtgc    2520
gagccgttcc tgcgcgaact gggtcgcggc ctgggcgccg cgcgcgacgc cgcacagggc    2580
gaaggcgccg cgctctcccc gcagttggcc gaggacatcc agcgccacct gctcgaccgc    2640
ttcgagctga gcctggcctg ggccgtggag gccgacgcca acgtgcactg cacgcaggcc    2700
gggatcgaca aggccgaggc cacccgcgag gactacctcg cctacctcga caccacgttc    2760
tccgacagcg ccgcctacca ccgcttctac ctgaagttcc ccgtgctcgg ccgctggctc    2820
gcccacacca ccgccctgct caccgcgttc ggccgcgacc tcttcgacag cctggccgcc    2880
gacgcggagg ccatcggcac cgaattcttc gggcagcccg tcaccgcgtt cacctcgctg    2940
cgcctcggcg actccgaccc ccacgcgggc gcgcgcaccg tcgcccgcgt cgccgtcgtg    3000
ctcgccgacg gacgcaccgg cgaattcttc tacaagccgc gcagcgtccg gtccgaggcg    3060
gcgctccagg acgtcctcgc caggctggcg gacgacgggg tcgtcgactt cgcgacccgg    3120
```

-continued

```
cccgtcctgc cccgggacgg ctacggctac gaggcgctga tccccgccgg ccgcaaccgc   3180
gtcgagaccc ccgaagaagt cacccggatc taccgggaac tgggcggcta cctggcgctg   3240
ttctacgtcc tgggcggcag cgacctccac ttcgagaacg tcatcgtcgc cgacggacac   3300
gccttcgtct gcgacgccga gaccgtcctc ggcgtccacc cccaggggcg ggcacagtcg   3360
gagggcaccc tcctcgactc cgtcttcaag accggactcc tcgaatggcc gcgcgccgcg   3420
agcccgggcg aggaggccgc cgccgagatg cgcatcagcg gctacgcggg cggcgagggc   3480
tacgacgtcc ccgtcccggt ggcccgccgc accggcgagg ggctcacctt cgcggcctcc   3540
gtcgtgcaca agaccggcgt ccacgtcgag accagcgcct ccaaccgcgt ctacctcggc   3600
gaggagctcg tgcgtcccga ggaccacgtc gagtcgatca tggagggctt caaccgcgtc   3660
tacgactggt tcgccgagga ccccgacgcg tccgtcgact acctgatgga gacgttcagc   3720
tgggtcaccg cccgcttcat caactggggc acccagatct acgcccagct gctgagcgcc   3780
gcccgccacc cgcgctgcct caccgaaccc ctcgaagtgg acctgctcgc caacaccgtc   3840
cgcaccttcc cccgcacctg ggacgccgag ggcgtcctgg ccggacggga agtggccgcc   3900
atgtggcaga tggacgtgcc gctgttcacc gcggccgccc acgccaggca actcgtccac   3960
gggcacggcg acccgctgtc cgcgcgcctg gacagctccc cgatcgacca cgcggccgcc   4020
cgcatccggc ggctgtcgca gcggaaccgt gaacagcaga gccagtacat cgccgccagc   4080
ctctcgaccg gcgagatcag cagccccgcc ttcgtcgcca cctccctgga ctacgcggcc   4140
aggatcggcg accgcctgtg cgacgagctg cgggcccccg ccgcccccgc cccctggacc   4200
tcctaccagc tgtccggcga gtccctcgcc gaagtggaca tcgaggccga cctctaccag   4260
ggctccgccg gcgtcgtcct cttcctcgcc tacctcgacc agctcgtgcc ccgccccgcg   4320
taccgcaagg ccgcccggca ggccctcgac cacgtcctcg tccactggga ccgcgaccgg   4380
ctcggcgcct tcgccggact cggcggcgtc gtctacctcc tcacccacct gcaccgcctg   4440
tggggcgacg aggagctcct cgacctggcc gtgcggctca gcgacgagct gcccgcgcgc   4500
atcgacgagg accggcactt cgacatcctg cacggcgcgg ccggcctcat ccccgtcctg   4560
ctcggcctgg cccaggagac cggcggccac ggcatcgagc acgcccaccg ctgcgccgaa   4620
cacctgctgc gccacgccga ggacgacggc accaccctca gctggccccc ctccgcggcc   4680
gacgagacgt acggcaacct caccggcttc tcgcacggct ccggcggcat cggctgggcg   4740
ctcatccagc tcggccggca caccggccgg tccgactaca tcgaggccgg gcgcaaggcg   4800
ttcgcctacg aggaccggca cgtcgacgag caggagaagg actggtacga cctgcggatc   4860
aacaacggat ccgcggtcaa gggcgcccgt cacttctcca acgcctggtg caacggcgcg   4920
gcgggcatcg gcctcgcccg catcagcagc tgggccgcgc tcgaccgcag cgacgaacaa   4980
ctgctgcgcg acgcacagca ggccctgtcg gcgaccctcc ggaacttccc ccgcctgaag   5040
aaccacaccc tgtgccacgg cacctccggc aacgccgaac tcctcctgcg cttcgcccgg   5100
ctgagcgacg aacccgcctt ccagctggag gccaacgtcc aggtccaggc gctgtggcgg   5160
agcctcgacg aggccggcgg cggcgccggc gggggcagcg ccgacttctt cccgggactg   5220
atgatcggca tctccgggtt cggcatgcac ttcctgcgac tggcggcccc ggaccgcgtc   5280
ccgtccgtgc tgctcctcga cccgccgtcg caccacgaac agtaaggagt ggctccacca   5340
tggccctgaa gacctgcgag gaattcctgc gcgacgccct cgacccggcc cggttcgggc   5400
gcgagatgaa ggcggtcacg gaggtaccgg agatcgtcga gctcggccgc cgccacggct   5460
```

-continued

```
acggcttcac cgcggaggag ttcctgacga aggccatgac cttcgacggc acggcggcgg   5520
gcggcacggc cgcgggcggc ccggaggcgg gcgggcaaca ggccccccgg cagaccccgc   5580
cccccgggac ccctgcgaac ggcgcgccgg caccggccac cgccaccagc ttcgcccact   5640
acgagtaccg tctggacgac ctcccggagt tcgcgcccgt cgtggccgag ctgccccggc   5700
tcaaggtcat gccaccctcc gcccgcctgg accggttcgc cgggcacttc cgcgaggagg   5760
acgcccggac cgtctccacc tcgcccgccg accccgccta ccaggcatgg caccgcgacc   5820
tcgccgcgcg gggctggcag gacgagggcg ccgcgcccgg cgccccgcgc cgcgacttcc   5880
acctcgtcaa cctggacgaa cacgtcgact acccgggcta cgaggactac ttcgccgcga   5940
agacgcgggt cgtggccgcc ctggagaacc tcttcggcgg cgaggtgcgg gcctcgggct   6000
ccatgtggta tccgccgtcg agctaccggc tctggcacac caacgcggac cagccgggat   6060
ggcgcatgta cctggtggac gtggaccggc ccttcgccga ccccggccag acctccttct   6120
tccgctacct ccacccgcgc acccgcgaga tcgtcaccct caccgagagc ccgcgcatcg   6180
tgcgcttctt caaggtggag caggacccgg agaagctctt ctggcactgc atcgccaacc   6240
ccacggaccg gcaccgctgg agcttcggct acgtcgtgcc ggagacctgg atggacgccc   6300
tccgccacca cggctgaccc ggcacccgtc gtccgcgcac cgcgcggcac caaggaggag   6360
cgatgttcgg agcaggaccg cggacggcgc gggggcccgc ggcggggacg gacggcgacg   6420
ccgcccaccg aagcggccgg ccggcaccgg ccgccggggc cgctggcggc ccgacggccg   6480
ggtccggtcc gccggccgtc ctggcgcggg ggctgggcaa gtcgtacgcg ggagtggaag   6540
ccgtgcgcgg catcgacctg accgtcgccc agggcgagac cttcggcttc ctcggcccca   6600
acggggcggg caagaccacg acgatctcga tgctgaccac cctcgccacg cccaccacgg   6660
gccggatcga gatcgcgggc cacgacaccc gcaccgcacc ccagcaggtg cgccgcaacc   6720
tcgggctggt cttccaggag accacgctcg acccggagct gacggccgtg gagaacctgc   6780
gcttccacgc cgacctctac gcactgccgc gggccggcct ggccgggcgc atcgccgaga   6840
tgctggagct cgtcgggctc tccgcccgcg gcgacagcct cgggcgcacc ttctccggcg   6900
gcatgcagcg ccgcctggag atcgcccgcg gcctgctgca ccggccgcgc ctgctcttcc   6960
tcgacgagcc gaccatcggg ctcgacccgc agacccgcgc ccaggtgtgg gcgcacctgg   7020
ccgaggtccg cgagcgcgag gcgacgacca tcttcctcac cacgcactac ctcgacgagg   7080
ccgagcagtg cgaccgcatc gccatcatcg acgacggccg gatcgtcgcc cagggcagcc   7140
cggccgagct gaagtccgtc atcggcgcgg accgggtgga cctgcgcacc ggtgacgaca   7200
tggccgcggc cgccctgctg cacgagcgct tcggcctggc ggcggtccgg ggcccgaacg   7260
gcctgagcgt caaggtcgcg gaaggcgccc ggctcgtccc ggcgctgtgc gccgccctcg   7320
acgtggccgt ctacgaggtg acggtcaccc gccccagcct cgacgacgtc ttcctccacc   7380
acacggggcg cggcatccgt gacgacgccc tgcccggcgc ggcgggcacg gcaggcacag   7440
ccgaaccgtc ggactcagga gacagcacat gacgcacgcc acggtcgccc tgcccgcggc   7500
cgaccgccac gcccccggcc ggctcgccgc cgaatggcgc gcgggcagca tggtgtggcg   7560
gcgcgaaatg atccacttcc tgcgctcgcg cgccgggatc gccgtctccc tgctgcagcc   7620
gctgctgttc ctctacgtgc tgggcatcgg cctgtcccgg atgttcagcg gcgccggctc   7680
gtcggacgac tacatgatct tcctcttccc cggtgtgctg gtgatggcgg cacaggcccc   7740
ggcgatctcg gtgggagcct cgatcgtctg ggaccggcag agcggcttcc tgcgcgagat   7800
gctggtggcc cccgtccgcc gcagcaccct gctgatcggc aagtgcctgg gcggcgccac   7860
```

-continued

```
cgtcgccgcc tgccagggcg cggtcgtcct ggccagcgcg ggcctggtgg gcgtgcccta   7920
ccgcgtcgac ctcttcgccg ccctgctggc cgaactcctg ctcgcctccc tggcgatgac   7980
ggtcctcggc gcggtgatcg ccgtgcggat ccagcggatc cagacgttcc acacagcgct   8040
gaccgtcctg acggcaccga tggtcttcct gtcggggctg atgttccccg tcagcgccat   8100
gccggcctgg atggcggcgc tcaccctggt caaccccctg acctacgccg tggacgccat   8160
gcgtcagacg atcacggcct tccaccccgc gcccgcggcc ggggcatcgg gtgcgcccat   8220
cttcgacccc gtctcctggg gcggctggga cgtaccgccg ggcctgtcgg tggtgctggt   8280
ggccgtgttc tcggccctgg ccctggcggc ggcctcccgg cgcttctccc gcaccgactg   8340
acggcgttcg cggaccgact gaaaacaccg tcgttcccac gcgtccaacc gtggatcatc   8400
actcacgtcc agcgcccgga ttcacatctg aggagacatc accatgcgta gcaccagacg   8460
cctttcgtta cgtcgccgtt ccgccctgct gatgggcgcc gcctccctcg cggcgccggc   8520
gctgctgacg gtccaggccg gcgaggcgca ggcgttcggc acgatcaact cgctgggcca   8580
gcgcgccgag cacgagcgca tcacccgggc ggcgctggcc tgcgccgccg gcacgtcgtc   8640
cgacggatcg tgcttcgagg cccggtcgat cgatcaagtg gccggtcaca cggggacgtt   8700
cggggccgtc gggtcgccgg actcggacga gatcttcacc cccgaggcgc actgcgacga   8760
cgccgactac ctcacggcct ccggctaccc gcgcacccgt cagcaggcca gcgaccagct   8820
cgtcgcctgc atatccaagc tgcagggacg tttcagccag ggcgtcgccg ccggctcggg   8880
caccctgaac ggggacggca cggtctcccc gggcaacagc gacctgtccc aggactgcac   8940
cttcaccggc ggcgtccccg ggcgcggcaa gtgcaacgcc atcgagggct tcggccgggc   9000
cctgcacggt gtgcaggact tctactcgca cagcaactgg gcggacaagg cggaccccaa   9060
ccaggccgtg ggcgtcaaca acccgcccgg cctcaacatg tcgggccccg ccccactgct   9120
ctcgctcaag agcggccgcc ctccggcggc ctcctcggtg ccggcgcagc tgtccacggg   9180
ctgtttctcg ctcaacccct ggggctgctc gggccgggtg acccacagca ccctcaacaa   9240
ggacaccggc ctgatcgacc cggccagcgg cgccaccagt gacccgacga cgaaccgcgg   9300
caggatcacc ggcaacttcg accgcgccgt caagggtgcc attgccgaca cccgccgtca   9360
gtgggccgac ttccggaccg cgctgaccga gcgctacggc caggagcgcg gccagcgcat   9420
cgcctgcgtc ctgacgcacg acaaccccgt gcgcgactgc cgctgatccc tcgcggcccc   9480
gcgtcccgcc ggcccggtgc tccgcgccgg gccggccggc acgcaccgga ccggtcctcg   9540
cgggtcaggc gtcgccgtac gcctcgccgc cgagctccag cacggccgtc ccggcggtgg   9600
tgtccgccag ccaggcccgg aacccctcga cgtcggcctc gggcagcccg atcccgatgc   9660
gcacgccctc gccgtaggcc acctcgcgca cctcgcgccc ggtggcccgc aggtcgttct   9720
gcagcttccc ggcccgctgg tggtcgaccg tgaccgtggc cagccggaag cgcttgtggg   9780
tcaccgtgcc gagctcgtcg agggcctcgc cgaccactcc gccgtacgcc cggatcagac   9840
cgcccgcgcc gagcttgacg ccgccgaagt agcgggtgac gaccgccacg acgtagcgca   9900
tgtcgcgccg gaggagcatc tgcagcatgg gcacgcccgc ggtgccccgg ggctcgccgt   9960
cgtcgctggc cttctggacc gagccgtcgg cgccgaggac gtacgcccag cagtggtgcc  10020
gcgcggtcgg gtgctccttg cggatgcgcg cgaggaacgc ctgcgcctcc tcctcggtgg  10080
cggcgggcgc gagcgcgcag atgaagcgcg acctgctgat ctcgatctcg tgcacgcctt  10140
cgagcgcgac cgtgcggtac tcgtcctgca ttccgccagc ctagacgtct ccgcggcgcc  10200
```

-continued

```
gcccggaccc gggaatggtc cggcgaccta gatcgttgag ccggcatgtt cgcagaaccg  10260
gggatcatcc agaagatcat cgaggggacc ggcgacacct gggcgctggt cggcctctcc  10320
gccaacgagc agcgcgccgc gtacggcgtc gccgaggtgc tccagcgcca cggcaagcgc  10380
atcgttcccg tccaccccaa ggccgagacg gtccacggcg agctgggcta cgcctccctc  10440
gccgacatcc ccttcgacgt cgacgtcgtg gacgtcttcg tccggtccga gctcgcgggt  10500
gccgtcgcgg acgaggcggt agagatcggc gccaaggccg tctggttcca gctcggggtg  10560
atcgacgagg aggcgtacga ccgcacgcgc ggggcgggcc tgctgatggt catggaccgc  10620
tgcccggcga tcgaactcgg ccggccgcgg ggacgggcgg tctgacatct tcctgcgaag  10680
gtctccgcga acggttgtgc gaccatgccg gattcccttg gaatgtgctc ctcagtcctt  10740
ttggtcaagg agtacagatg cgcaagtccc ttgctgttgc ggccgcttcg gcggttgccg  10800
gcctcacgct gatggccggc accccggcga acgcggcgcc ggccgccgcc accaccgtac  10860
cgagctgtgt gacgtctacc ttctcgacgc cgttcttcgc gatggtccgc gtcgacatgg  10920
agaacaagtg caccaccgag cagcgggtga agccgtcgtt caactacgag ctgaaggacg  10980
ttccgtgcta cgccctgcag cccggtcaga aggcggtgtt cagccgggac gtgatcttcg  11040
cctccgggta cacgttcgcc ggcctcgtca gctgctgaca cccggcccgt agcggtcacg  11100
gctcacaccg tcacaccgtc agtcccgcgt cgcgggcgca cagcgccgcc tgcaccctgt  11160
tgccgacctc cagggcggcc aggatgcggc tgacgtgagc cttgaccgtg ctctcccgca  11220
tgcccaggcc gtcggcgatc tccgcattgg aggcgccggc ggccaggagc cccaggacgt  11280
ccgactcgcg gggggtcagc cgcgccaggc gctgctgggc ggcttggaca tcgcgggacg  11340
ccgtgcggtg gtagcggtcg accagacggc gggccgcggc ggggtggagc atggcctggc  11400
ccgccgcgac gacctgtatc gcccggatga tctcggccgg atcggtgtcc ttgaggagga  11460
agcccgaggc gccggccgcc agcgcgtcgt acacgtactg gtcgaggtcg aacgtggtca  11520
gcatgacgac ttccggcggg ctgggcagcg cgcgcagccg ctcggtggcc gctatcccgt  11580
ccatgcgcgg catccggacg tccatcaggg ccacgtccac gcgcagggca ccggcccgct  11640
ggacggcttc gaggccgtcg cccgcctgtg ccacgacctc aatgccgggg acgtcgtcga  11700
ggatgtcggc gagggccagc cggaccaggc tgtcgtcgtc gacgatcaat gtacggatca  11760
tgccgctccc ggcgcgaggt gttcttcgac agtgctgacg gggatgtcgg cggcgatgtt  11820
ccagccaccg ccccccgaag gtccgtagtc cagccggccg cccagcgccg tgacgcgctc  11880
ggccagtccg accagcccgt agccgctgct gaccggcggc tccccggcgg cggacgccgg  11940
gtcgccggcg cggttgtgca cctcgacgct ggaggccggg ggaccgtagc gcacgacgac  12000
ccgcacgggg gccccgggag cgtgcttgcg ggcgttggtc agcgcctcct gcaccagccg  12060
gtggacggcg aggcggtgac tggccgggag cggcccggcc gcgccctcga cgaccgcgtc  12120
gatctcctgg ccggccgcgc gcgcctcgtc gaagagggcg ggcagctcgc gcagccccgg  12180
gacgcgctgc ccctgcagct ccgggtggtc gggatcgcgc aggacgccca ggacgtcccg  12240
caggtcgccc agggcctcgg tggaagtggt gcgcagcagt gcgagccggt ccgccacggg  12300
ctcgggaagg gtggcggccc gccgctgcag ggctccggcg tgcagggcca gcaggctcag  12360
ccggtgggcg agcacgtcgt gcatctcggc ggcgatgcgg gcccgttcgc tcagccgcgc  12420
ctgcttggcg cgcagctcgc gctcgacgcg caggtgctcg acctgcgccg tcaggctcgc  12480
ctccagccgc ctacggctgt ccgcccacag ccccagcacc atgacgaggg cgaacggcag  12540
cacggggccg tacgcacggg tgctccacag caactgctcc ggctgcgcga accagttgcc  12600
```

-continued

```
ggccagcgcc accgcggcac acgcacagcc cagcgcgcgc cacccgcgcg aggcgaggta  12660
gaagagcatg accagcaggg gcagcagggc gcccaccacg accgcggcgc agacggtcac  12720
caccaccgtg accaacggga cgcggtagcg caccgccaag gagaggctgc cgacggcggc  12780
gacggccgtg tccgggcccc acagcgtggc gccggccccc acgtaggcgt tctgtacggc  12840
cagcacaccc acggcggcga ccagcagcgc ctccgcccat cccggccacc ttcggtcgtc  12900
cgcactcagc acgggtaaat cgtagtcacc caccgttttt gatccctccg ccagtcggcc  12960
tacgctaccc cctactttcg taccgatcga gcgtcgcaca acggccgatg gtgcgccccg  13020
cggcggcccc tagtttcatg gtcatggatc tgacgcaagc caactccacg cccgtacagc  13080
cgcgttcggc caccgggctg gccttcctcc gcgaggcgac ccgcaccttc cgcaccaccg  13140
gcgcgatcgc gccgagcagc cggcagctcg ccgagcggct ggccgcgccc ctcgcccctg  13200
cgagcagact gcgccggccc accgcggtgc tggaggtcgg cgccggcacg gggccggtga  13260
cccgggttct ggccggtgcc gtgggccccg ccgaccggct cgacgtcgtc gagatcaacc  13320
cccgcttcgt cgagatcctc aacggcgccc tgcgcacgga ccccgccatg tcggcggcct  13380
cggaccgcat ccggatcatc cccgagtcga tcaccgagat gcccatcgac cacagctacg  13440
acgtcgtcgt ctcctgcctg ccgttcacca acttcgcgcc ggagacggtc aggtccatcc  13500
tggaccgcta cctgtcggtg ctcgtgccgg gcggacacct gacgttcttc ggctacctcg  13560
gcacccacgc cacccgctcg ctgctcagca gccggaagga ggccgcccgc caccgcgaag  13620
tgaccgacct gctgcacgac ttcacccgcc gctacgccag ccggcagagt gtcgtgtggc  13680
gcaacatccc gcccgcccgg gtgtggcacg tgcgcgcccc cgagcacgcc acccgggcgg  13740
cggacgccgc ctgatgccca ccgcggacga gctgttgcac ggagtgccgc ccgcggccgc  13800
gtacggtctc gtgctcggcc tggtgctcct cgaatcggtg ctgctgctcg gttcgttcgt  13860
gcccacgctc agcctgatgc tgtgcgccgg ggtcctggca caggagggaa cgctgcggct  13920
gcccctggtg gtgctgtgcg ccacgacggg ggtggtggcc ggtgacctgc tcgcgcagcg  13980
caccgggcgc cgcctcggcc ccggcctgcg gcgctcccgg ctggggaggc ggctgcccga  14040
ggcggcctgg gagcgcgcct ggtcggtgct ccagcgccgc ggcggccccg cgctgctggt  14100
ctgccgcttc gtgccggtcg tgcggacctt cgcgccgcac ctggcgggcg ccgccggcat  14160
gccgtaccgg cggctggccc cgtacagcct ggtggcgggc ctggtctggg cgggcgggga  14220
agccggtgcg ggatacgtgc tgggcgcctc ctacgaccgg ctgaccgcgc cgggcggcgg  14280
gctgcccacg gtctgcgccg ccgccggcgt cctgctggcg gcagcggcgg ggctgctcgt  14340
gcaccgccgg cgcgcgcgcc gggcggtggg cggctcaggc cgagcgggcc agcgacaggc  14400
tgacgtcggt gcgcaggatc gcgacgtgca gatgacgcag ctcgcgcccg gggtccaccc  14460
cgagctcgtc gcggaagacg ccgctgacct ccgcgtacgc ggccagggcc tcgcccctgc  14520
ggccgcagcg gtagagggcg agcatcagcc gctgccacag gctctcgcgc agcgggtact  14580
tcgcggtcag cgtccgcagg tcgccgacga tctcgtcgtg gcggccgagg gcgaggcagg  14640
cgtcgtggta gcgctcgatg gcccggatcc actcctccat cagccccggc accacgtccc  14700
ggtggagcgc gtccgagcgc acgccgccga gcggctggcc gtgccagagg gccagtgcct  14760
cggtgagggc ggagtgctcc agtgcgcggt cgccgagctc ggcggcgagc cgggcgcggg  14820
cggcggattc acggaaaaga gtgagatcca gacagccggt ggggacctcg atcaggtaac  14880
cgctgggcga ggtgtgcagc agtccggaga gccccgcgcc ggctgcgtcc aggctctgtc  14940
```

-continued

```
gtaagcgggt gaggagggtg tgcagggcgg ggcgcgggct gtgcggcagc tcgtcgcccc  15000

acaccaggtc cacgagtttc tcgaccggga cgatctcgcc cgggtgcacg agcagggccg  15060

ccaggaggga ccgttgccgg ccgctgggta gcgaaacgtt tttcctgccc accgtgacgc  15120

tcagtggtcc gagaactcgg aaggatattg cccggttcat gaactctccc cttcgctcat  15180

cgagccgcac cctgaagacg gctggggact gccgtgtccg ctgtccactc aagcggacgt  15240

cgcggtcagc aagcgtacgg tgcgtacaga gttggttgtc aactatggcg tatgaatgtc  15300

agggttgtct ggcgttatcc atacgctcaa gcggacagaa acagtcgacc gggcaacaac  15360

tcccggggga gggacggggc atgagcgaca gtcgaccggc accggaccgc aacgaccggc  15420

cacttctgcg ccagttcgac cagcggctca gtgaactgat cgccaccacc gccggggccg  15480

aggggaacaa gcgccccgga tacgcgcgcc tggccaagga gatccgcgac accaccggcc  15540

ggaccatctc cggcacctac ctgtgggagc tggccaccgg gaagaagcgc aacgtcacgc  15600

tcgaacagct cgacgtcctc gcggagttct tcggtgtgcc cccggagtac ttcctcgacg  15660

acgagaccgg ccgccgcatc gacgaccgcc gaagactggc catcgccctg cgcgacgcca  15720

aggtgcgcaa cctcgccctg cgcgcggacg ggctctcgcc cgactgcctg gacgcgctga  15780

tcgccatggt gaacgaggcg cgcaagaccc agaacctgtc gtccatcgac gatgacgacg  15840

acaccgccac cacccttact tcttcagggt agtcaacgac ccgacgccgg tcccgtgggc  15900

ctggaggacc gatgccacgc cgtacgtacg tcgcctaccg ccgctgcctg agaaagggtc  15960

aacgggaacc cgagatgccg tacacgagcg acgccgccct ccgtcgacgc tgccgggccc  16020

tgctggcccg cgtcagcctg cccgagccgt tctccgtcga ggtcctgtgc cggcacctcg  16080

gcgaacagcg cggccggccc atccacctgc acccgctgcc ggaacaggcc gccctggccg  16140

gggcctgcgg cctgtggctc gccaccgcca ccgacgacca catcttccac gagcgccaca  16200

ccgtccgccc gcaccaggag cacatcgtcc tccacgagat cggccacatg ctcttcgacc  16260

accactcgct ggccccggcc ggcggcccgg cgggcgccct cctggccgac ctcgaccccc  16320

ggctcatccg ccgtctcctc gcgcgcacca actactccac gcgccaggaa cgcgaggcgg  16380

agatgctcgc cagcctgatc cgcaccagcg tccgcgccgg caccggggaa cggccgccgg  16440

gcgcgctggg ccggctgcag gcggcgctgg gcgtggtcgg gtcccatggc cgctgacgtc  16500

ctcgattccg tcctggggac caccgggctg gtgtgcctgt ggaccgcggt ggtcctgcga  16560

tgtccctacg ccgtgcgcca ccccgcacag cgcggactgt ggctggcggt ggccacggcg  16620

gccctggcga tgaccctcac cacctccatc ggctccgtcg tccccgaagc ggcgctcggg  16680

ctcgccggca acctcaccgg catggtctcc gcgggcgccg tcctcggctt cgtcatcacg  16740

atcatgggcg ggcggcgcct gcacacctgg gcctgcggca cggtcgccgc cacggccctc  16800

gccctgaccg tcctcggcgt cacctcccgg gcccacctct cctacggcac catcgccgag  16860

atcccgccca ccgccaccgc ctaccggctg ctgctgatcg gcacccacct ggccgtgaac  16920

gcggcctgca tcgcggtgtg ctggcggtac gggagggggc ccagccgctc cccgctcgcc  16980

ctcggcctgc ggctcttcgg catcggcacc gtcctggcgg agctgtactg gctgcgcctg  17040

ttcgccggcc tcttcaccac ctccgacgcc ctcctgcggt acc                    17083
```

<210> SEQ ID NO 104
<211> LENGTH: 11650
<212> TYPE: DNA
<213> ORGANISM: Artificial Sequence
<220> FEATURE:
<223> OTHER INFORMATION: Synthetic construct -continued

<400> SEQUENCE: 104

```
ctagatagga atagacttgc tttttaatag atcttagtga tttatttgca gtagtgtcta     60
tcacaccaaa tactaaataa tgatttttaa aaattttttc atagttgata ttatctccga    120
taataatatt tgcaatcgtg aagaaagagc ctaaaaaata aatattctga ataacagaaa    180
gctaaagtca ttatttttta cttatgtttc ggattttaat ctctgcttta tcaaaaaatt    240
ttgttaagtg tttagtgatt caatagggag ggtaattact gtttggaagt actgcccttg    300
tgtacttgta attatcatgt ttccatcatg taaatcaata atttgtttag aaattttcaa    360
tcccatacca ctccttcgaa cgcctgacat atcaaaatta aattcttcaa tcttattgat    420
atttttttagt ctttcaggag aagttcctat accattatca cgaatagtaa tcgaaaaaca    480
atcttcaggt agatattcta aaatgatttt aatgtcgcaa ccagaatgat tatgaagtac    540
tgaattataa attaggttat gaacaactct agaaatgaga gctttttcaa tatacatttt    600
cttacctaat agtttagaat caggaatgaa ttcaaaattg aagtcttccc aaatttcttg    660
attgataatc tgaatgatta tttctttgaa gaaagggatt atatcaacaa tctcatggtt    720
tagttttaag tttccgtttg ttaatcgagc aaatatattt aaatcgttta ggagattttg    780
aatgtagtga ctttcaacta aggtgggttt caaatgttta aggaattcgt catcatttgt    840
tttttcaatg gctaaggaag tgttagatac aattactgaa agtggtgtct ttatatcatg    900
tgctattcca gaaatccaat tctccttgaa ttcttcgttt tcacgaagtt gctgatttgc    960
tgagttaata gcaagtgtta atttatctaa ttctcgtaca gatttgacct gagtattaat   1020
tccatttggt aatttagtaa ttgcgttaat gataggttta atgttacgat ttaaaaaagt   1080
aacagaataa atgtaaagaa ataggcagaa caaacagttt gcaaatatga tagacaaaat   1140
aaggattgga aaaatttgaa ctctatttag ttcgaaataa ttactactat aacgtattat   1200
actgtctttt ggaaaagcaa tgatgtaaat atcattatct tttatttgcg taaatacagg   1260
atagtctttt aggtaaaatc tagaaaatcg tatagcatct gcaaaatcga attgattttc   1320
tataatctga ggtttattaa tattaaattt ttcttttcca ttatctttgt caataatcat   1380
tatccataac tttttatcat caatgagttg tttagcttta gaactaacat tatatttacc   1440
attagaagat agagtgattt cagatgagac agtttcgatt atagtagatg cagactgctg   1500
acttcggata taattggtag cagttattaa cagtatgacg tcaattatta taataaagaa   1560
aaatgatagg ataaatttta gtatattttt cttgaaaata ttcatgctat attccttata   1620
gtttatataa ctagtttata accaagccct tttacagtaa taagatgatt tggcttagat   1680
ggagttatct cgattttttc tctgatattg cgaatatgta ccataagtga tttttcgtag   1740
ccaaggctct caagtcccca aacggtatca caaatcgatt cagttgatgc aatataattt   1800
ttatttgaaa ataattttcg taggatttgt atttctgttg gagtgagtga caaatgttga   1860
ccattttttt caacacttgc attgtttaag tctatggtac aatttgttag ctcaattagt   1920
tccgattcat ctttataagc ccttctcaac agtgcaataa tacgatatgt taaagatttg   1980
ggaagaaatg gcttcgtaac ataatcatcc cctccggatt caagtcctcg aatttcatca   2040
tcaggattgt ttttggctgt taaaaagaga attggcacat ctgaatattt cctaatgtat   2100
tttgcaagta agtgcccttc tccatctggt agcataacat ctaaaataat gagatcaatt   2160
ttagaaactg agaagatatc aattccttcg cttatactat aagcacagct gatattcttg   2220
aaatcccgac tgataagtac ctctttaatt gatttgctaa gtgcgacatc atcgtcgaca   2280
```

-continued

```
atcaatatgc gtttattcaa taattgagac tcaaaattca tacaatacct cctaaagtgt   2340
aataaaatta taccataaag attatagata taagagaata agtaggactt gtgttgtata   2400
atcttaaaat taaatttatg ttttctttat tctgtcttaa agttatcatc ttaaaataag   2460
gttgtaacaa agaggaaggc acctatcctt ctgaagaaag ttaaatgagg tatagaaaat   2520
ggaaaaaaat aatgaagtaa tcaactctat tcaagaagtt agtcttgaag aactcgatca   2580
aattatcggt gctggaaaaa atggtgtgtt taaaacaatt tctcatgagt gtcatttgaa   2640
tacatgggca ttccttgcta cttgttgttc ataaaactct actgttcagg tgtctttgat   2700
gttacataaa aaaagagggg gacctctttt tttatttgca ttgacatagg tagaaaattt   2760
aatttaactt tagttttcct taatattgtc tttatgtaac aaatttaaaa tcaatgtata   2820
aagaaaacaa atttcgagtt ctactcgatg tcatataaat gaggtaaaga attatggaag   2880
aaaaaatgtg cctaggtgct ttgaatgcgt tacaagaatt tcagattgag gaattggata   2940
accttttggg aggaagaggg catggtgtca atacaatttc agctgaatgt cgttggaata   3000
gtttacaggc aatttttact tgttgttaat atgtttagga gtaaagaata tgaatccaaa   3060
agaactgtta tatagccaat ttgatagatt cccaaaagta gttattgaaa ataatttccc   3120
agaattgcta aatgaaagta gtgagctgat taaggatgtt gaagatgaaa tttctgatta   3180
ttatcgttcc actcttattt acctaataaa tgaaaaaaga attgagaaaa acctaattgg   3240
agattctcca gagtcacgct atgaatactt taataatgta ctatgtcaga atggcttaat   3300
ttttgaagaa attgatagac gtttcccttc tattaatcag cgtgtaatga gtactatcaa   3360
gaaatgtttg gaattaatta attttgtaaa ggaaagattt actttagatt tcaaagagtt   3420
gagagagaca ggctatatct atagtgaagc tcagactcca aaaattagtg aagtcaaaat   3480
caaaataact ggagatattc acaatggttg tggagtctgc attttgagtt atgaagaaca   3540
aaaagtagtt tttaagaaaa aatcatcaaa tcccaatgtt ctcttgcatg aactgaatat   3600
agaagttggt aaattcttac agaaagatat agactttatc cctgattttt tagataaagg   3660
agagtatttt tgggaaaaat ttgtatcaag ttctccgtta agaaccgagg aggatgcaaa   3720
ggaattttat cgtaggatgg gttacttatt atcatattct tacatattga atatctctga   3780
tttgcatttt gaaaatctga tttctacaag cttttctcct aagttagttg atgttgagac   3840
agtttttttca gttagcccct atcaaactgt tgcaaataac gagtcaacat tggagataat   3900
taataatagt agaaattcga tattatcaac aggtttgctt cctgtttctg aagctggtaa   3960
agtttttgga ggagatacta gtggtgttct aggaggcacc ttaattggag aggcaaaaat   4020
cgtcatcaat cataaccgag atgatattca tgttgaaaaa caaaagttta aaacagaaaa   4080
ccaggatcat ttgccttact ttattgattc gaagggaatg aaagaatttc ttaatgctga   4140
agattatgtt gaatatatca aagaagggtt ccgtgaagtc agctactttt tcatgaattc   4200
acaagatttt ttaaagaagc tttatattaa gcataatgat ataaagacta gaattttgtt   4260
cagaaataca agagattata gcttagtgcg ccaattgcta gtttctcctg tttattgtga   4320
gcaatccgag attttatttg aaacaatggc caataaattg tctgaacaaa atagtcgtag   4380
tttatgtcta tcagaaaaga aacagctttt aaatatggat atcccttatt tttactcaaa   4440
tattgatagt tgtgatataa aggatgaaaa catgattatt tggaaccttg aaagttctgc   4500
tttaagcgaa gcaatcaata aattagaaaa attgagtgaa gaaatcataa atgagcaaat   4560
tgaattaatt gagttttcta tcaaaactcc taaagcttta tatagtacgg aacttcaaga   4620
ggcatatcaa aaatttgaga aggttagtag cagtgaaaat ataataaaaa ctggtattga   4680
```

-continued

```
tactctagtt gatattattt tggaaaatga aagcaactct ctaaaagacg atagtacaaa   4740
ctggctcacc ttgaaagtta cagattatga tgcttttgag ttagttccga tggatgactc   4800
tctttatgaa ggtttgtctg gaatagcaat ttctttatca gaggcttatg attttctaga   4860
ctcaggaaga caaagaaggg ttaaagaatg tctaaaacga attttttcgg tattatctaa   4920
ttcctatatg aaattaccaa atcattcttt ttttgtgggg aagctgggaa tttactcagc   4980
tttaaaacga attagtgttg ttacaggaca agagattcaa aattctatca tgaattataa   5040
taatctcaaa tatacattgg atgtagatgt tttaagtgct gattttctat caagttttcc   5100
taatgaaatc actgctttga gaaattcgga tattaagata gataatctta ctcaggcact   5160
agacaaactt aaagagttgg caattgttca aaaggatttt attagttggg ataagttaga   5220
gtcgaataat gttagtcttg cacatggtaa tttaggagtt gaaatagcgt tactttattt   5280
agctggaaag ttagaaagtc ctgaggcact aaatttattt cataaagcaa aaatgtttga   5340
taaacatcaa aaattggaaa acggctggat agacaaaaga aattcctcga ctagtgccaa   5400
ctggtgtcat ggttcaacag gagtattagt tgcaaggtta gcacagttaa aactagatga   5460
tgaatatagc cttctttctt attctgaacg gatagaatta gagaatgata tgaagcatgc   5520
tgctaaacag attcttgaaa ttggttttga tatgacaaac ttttcacttt gccatggaac   5580
cagtggaaat ttgctggcac ttacttacta ccaatcatat ttaacaggag ctgattcaga   5640
gaagttaaaa gaaattttgg atagagagta tagaaaactg cattcttttg gcctggaaaa   5700
cggctggatg tgtagtttta atacaaaata taatgtttat gggttaatga caggtgtgtc   5760
aggaatatta ttttctacag taaagtacat gaagggtgat gattccctag atgtgttgat   5820
tcccaatttc taagagatag acaggaatat gagatatgaa tattattttg caaaacaatg   5880
aggaggattg tctcttagct tgttatacaa tgttacttaa tgatttagga cataaagttc   5940
cattatatga aatttatgat aaagatacat tgcctgcaga tggtctaaat gtctcatatc   6000
ttttgtcact aagtgacaga tttggggtga aaataaatgc ttatcatgcc tcttttgatg   6060
aattactaaa agtatacgga gaaaagaagc aaagaatgat tcttcattgg aataatgatc   6120
attttgtggt tcttgaaaaa attacgtcaa ataaaacagt tatagttgac ccagccattg   6180
gtcgtattaa gtatagccgt gatgaatttt taactcacta ctcggaaact atggtgtcag   6240
ttaacaaaag aaataatttt cacccccaaa catataagaa aatcttttgg aagtatttca   6300
aacagacctt acaattaaaa ccgattgcat tattcttgtt gtcactcctg tttattcaag   6360
ttagtgtttt actgttctca gtcattttaa gacaaatgtt agctgaagat ttcaagtttg   6420
gtatcagcct attcctttta ggtgcagtat taatttttca attattaggt tattttataa   6480
agaatggtgc attagataga tataatacag actttgataa atattacagt aaagagttgt   6540
ttcaaagatt attacaaaaa cctttacttt attttagaaa tcatctaagt gggggagtat   6600
ctgaaaaaat tagttttaaa tcaacactta gggacaatgt tactttaaaa attattccat   6660
catgtgtaag tttgatttca gctattatta tctttgcata tctgatgact atatctatta   6720
agttgtcggt gatattaatc ttgatgattg cttcatatag tataatctct actctattgt   6780
atcataggca aaacgagtat aatcagacat atttacagta cttaattgat tttaactcag   6840
agttacaaac agatcttgat gacattgact atataaaaat aatgagaaga gagaaaactg   6900
ttttccattc ctggatggag caaaataatc aagtcactaa gaagtatccg cagattctta   6960
aaattgaaaa tctttcacaa cttattggaa ctatttttaa ctacattagt ctatcctcaa   7020
```

-continued

```
taattgttat cgcagtatat tataagggtt atattaattt atcccttcct gatctattag   7080
tttatcaaac tagtatttct ttattgatat cgcaaattga acaagtaaaa ggggcagtat   7140
ttgaagaaat tcgattgggg gtatatgcag aaaaacaaag tgatttatta aaagaaactt   7200
cacctatcgg tgtacctagt tcacagtcag acgattattt aatcaaaact aaaaatttga   7260
acttttctta tggtaaaaac ccaatctata gtgatgtgaa tttaacaatc agtaaaggag   7320
aaaagattgc cattgtaggt aaatctggta gcgggaagtc aactttacta ttaatgttag   7380
caggtatcac ctatgatgga tctcttgaat atggcatcga aaaattcaaa gacaatctaa   7440
gagttgttct tcaaaatatg acacctagaa aggggactgt cttagaaaac ttagagtgga   7500
ctttagatga tgtaactcca ctttaccaag tattgaatga tacaacagct gatgaagtta   7560
tagcacgatt accaaataag attcactcta gactcttaaa acaaggaaaa aatttatcag   7620
gtggacaaat ccagaagtta ctcatagcaa aatcactttt aaaagaaaat tcaattattt   7680
tttgggacga ggctttcagt aatttagatg aacaaagtaa gaacaaaatt tacgataatg   7740
ttttacaaaa caatagatat tcagacagaa ctatgttaat cgttagtcat catttagata   7800
ttgtcaatta tgttgattct attattttta ttgataatga aactggtaag gttattaaag   7860
atactcatga acatcttatg gaaacaaatg ttaactatac aaatttcatt acttccaaaa   7920
attaagagaa tgtttctctt ttcttaatgt tatctttaag ttgcttagat acaataatgt   7980
tgtaatagaa ggaaaggaag agactcattg aagggtctta ttatggggtt attaacatga   8040
aaaatgctat tgaattaaga aaactttcta aggtctatca ggatattact acggtagatt   8100
tagaaaagat tacggttcgt gaaggcgaga tttacggttt tcttggaccg aatggtgcag   8160
gaaaaacaac aacaatgaaa atgattttgt cactagtttc tccaacacta ggagaaattc   8220
ttataaatgg tgaagatata aaggggaacc acgcttattt gagggtaatc ggttcaatga   8280
ttgaggaacc ctcctattat ccaaatttaa caggttacga gaatctacta gtctttcaaa   8340
aaatggtagg ttttgatgaa agtaatatct ggccgacttt ggcattggtt ggtttagcag   8400
aggaaaataa ccgaaaaaaa cttgtgaaag cctactcttt aggcatgaag caacggttag   8460
ccttggcttt tgctctggtt aaaaaaccaa aaatcttgtt attagatgaa cctactaatg   8520
gacttgatcc ggctggaatt catgaaattc gcgagttaat tgtaaaatta gctaaggaga   8580
aagggctaac agtatttatc tcaagtcaaa ttttatccga aattgagcat atagctgacc   8640
gagtaggcat tataaatcat gggagactgg tttatgaagg ggaaattgaa gcaataaaat   8700
caaatacttg gattgagatt ggcgggggatt tctcgcaaaa taatattgtt caaagtttaa   8760
ttaattacgg acaggttgaa gtgctaggag cttcagcaag tcatgttaag tttaaaaata   8820
ttgataatga caaattagca gatgtaggga cttatttaat tgaaaatgac tatcggattt   8880
tccgagttgt tagggaaagc gagaatttag aagacatttt tcctctcttt aactaaggag   8940
gtttgaaatg ataaaagcaa tacagattga attattaaaa agtaagcgta cgaaatcttt   9000
tatgatttct ttcattatga tgttagtagc agcgacgtgg tcattgttag cagcctcaag   9060
aagtattgat attcctaaat tacggactat cggattgttc tttaataatt tacaagctaa   9120
ttctattttt ttacctattg caacttgcct atttgtttca cgtattgttg gtaatgaaaa   9180
agaaggtagt acatttaaac ttcaagaagc aaataataca aatctaatta taatatttac   9240
tcgcaaattg attttcacaa attctgtctt tctacttttg aatattttcc aagtcttgat   9300
tgtttatcta aatgtactaa gatatgatat ccaagttcca atttggactc tgattttaca   9360
agtagtaggt ttaacgatgt ccagttttac tttaatcact ctctttcttt atttatcaat   9420
```

-continued aattttagaa aaacaaggga ttcttttagg aattggattt ttatcaggtt ttttcggtat 9480
gattacctcc cagactttaa agtggattaa ccttattttt ccgtttggag gatcgagttt 9540
tttagcacta tatagaataa agattttaaa ttccagtgat agtttagatt atattttttc 9600
ttgggacaaa agcgtgcctt taaattatac tttatacctt atttactgcg taatgatcta 9660
tagcgtagtt aagtatttac tgaaaaagaa gaaaggggac aataatgaat gattatttca 9720
aagcggagtg gctaaaaact cgcaaaggag ctattttagc agtgggatta tatttcttgt 9780
tctatctagt ttcattggtt tggcaaattt ctttttgaat tatgaggtac tcattgagga 9840
acaaatgagt agagtactct ggggacagtt aactttctat aatagtcagt tgcttttccc 9900
agctatgtta gcaatattct caggcatgat tattctacct gaatttgagc gaaaaacatt 9960
tgaaatgtta cgtgcaaatc aagtatctgt taaaaagatg cttcttagta agttcttgtt 10020
agctttgcta cttataacag ttatacaagt attattattt gttatatatc ttgtaacact 10080
gaaattgagc cagattccgt ttgtagcaaa agatttactt ttattttttaa gagcaactgt 10140
gctatctgtt attggttcta gctctgttgt aatgattcat agttatatca tggctaaaac 10200
aaaaaatttt tctaaatcag tcgggattgc agctataggt tcattttgtg gattcatatt 10260
tattatgttg ggaggtgtca ttaatcaatt tttcccttat tcccagccaa tgataggtat 10320
acgtagtaga gcgttagtag atatgagcat ttcggagttc gtaatattta tagtggttaa 10380
tgctctatat agttttattt ttttcaaatt gacattacga actttagaga agaatggata 10440
aagtggattt ttatacatta cagaagtaac taaatttata gaaggaaaag gtgagagcat 10500
gtggactaat gtcaaataag tagacagaaa accgtgttat tttattacgt taaactaatt 10560
ttcttctttc tgattagggt ttagtcctag attagccgta tgtgggttgt aattattata 10620
aaaattctca atgtattcaa agcagtctaa ttgaacctgt ttgatatttt gatacttttt 10680
tcggttgatt tgtctatgct ttaaatactt gaaaaatgct tccgttacgg cattatcata 10740
aggatatcca ggtttagaaa aagaatgcat gatagtgttg tcatcaatta tttttctcaa 10800
ttccctggcc ttaaattgtg acccttggtc ggaatgaaag agaagtgttc cttcaatctt 10860
tcttttatta agagctaatt ctagagtgtc acatgctaac tttgcatcca tatgatgact 10920
cagtttccaa gcaatacatt ttctagaata gagatcaagt attgcgcaga gatagacata 10980
tttcttatat ccaatagaaa tataggtgaa gtcagtagac catacttgat ttggtttgtc 11040
aggattaaat ttctggttga gtaagttttg aggatacgtt ttttgagtcc ttttaagagc 11100
tgtttttggc ttaacggtag ccattttagg aagcgccata ttcttcatca gacggtaaat 11160
tcttccttca gagattttttg tgtcgtagtc tctttgaaga atgactttga tagacttcac 11220
accaagtctt ttgttcgctt tggtataaat ctcaagtatt tgttttttat aaatttgatt 11280
atccaattct cttttggagg gcttatgttt tagaaattta tagtaagtgg agcgattgac 11340
acgtaaaaca cgacacaagg ttgttgtggc gtgttcaaag cgtaaccgat agacagcgag 11400
gagtcttact ttaagttttg catgaatatg gcacttgctt ttttttagga taaggttctc 11460
ctcttcaagc tgcgcattac gtttttgtag cccttgtatt tgcttggcag taagtacaga 11520
attatcttcg agtttgactt gggaatactg tttgatccat tttgcaagcg cagaagcgga 11580
taccccatag tctttacaga gttcagaccg agtttttcca gtttgataaa ggttaacaag 11640
agattgtttg 11650

<210> SEQ ID NO 105

-continued

<211> LENGTH: 12802
<212> TYPE: DNA
<213> ORGANISM: Artificial Sequence
<220> FEATURE:
<223> OTHER INFORMATION: Synthetic construct

<400> SEQUENCE: 105
gatcgtaaga atattattta tgggcataac atgaaagatg gcagtatgtt ccatgtgctg 60
agaaattatc aggacattga ttttttcag gagaacacgg gtatggaggt ttatttaccg 120
gataaaagga ttctgaaata tcagattacg gcttgtgagc aggtgccagc ggatagtgaa 180
atttatcagg tagaaaaagg aaacactgag gagaaagagg gaaatgaaat tatattgtct 240
acttgtagtg caaaagcaaa tatccggatt gttataaaag cagagctaga ggcgtaaaat 300
tatcgaaata taatttattt accattatag gcaaaaagga agtagagtaa atctctactt 360
ccgaatcata catcttttc ctatgatata ggtacgagat aaactgataa aagaactagt 420
atgctgaaat acacaaataa accaactttt gcaattgttt gaagattttg ataggatttt 480
actgttcata aagccctctt tttatattca gaaattatta tcgttgactc atctcctacg 540
tggaagcgtt taaaattatt ttattcagaa tatccaatag tacagagttt tgatagcaat 600
tcaggatttg ttttattcaa aaatattgca tggcatgatt ctacttcctg aataagttct 660
ggatcttcga gaccggatag aataatgaaa ggaatgcaga tatttagaga atttactttt 720
tttatgatat ccaatcccgt tccatcgccc ataaaatagt cagaacaaat catatctata 780
tgaattgatt caagaatttg tattgcttct tttacgccag ttgccatata tacatcaaaa 840
tttttctgaa gcaaattgga caacggtttt aaaaagttga tattatcgtc tataagaagt 900 attttttca aaaatacacc tcctagtgta ataataattt cagaggaaca tgttgcctta 960
tgatttaaac gtaagtagta ctgcgaaagc gataattccg gtcattaaca ataaccagaa 1020
aatgctgatt attgttgaaa gaatgtttaa tactctcctg ttttctgcat gacgcacaca 1080
aataatagaa agtactaaac cgactagaat aaataagata tttgcacctg cccatgcagt 1140
ttgtattcca tttgtgagtg ttataccaag gaatgtagga ataagtgttg caagagggag 1200
caggctaaaa acaaatgcgc atatactaag aattttgact ttcttttttt tcatacttaa 1260
ttacctcatt tcttttttcc caaaagcttt aatagataca gccaaaacaa gtacaaatac 1320
aattattgca catggcaaga atggcatgag ttcaaatgta gagtcagaag aaaccgctgt 1380
aaagtcatgt aatgaacaag atacaagata tccactgtaa cagtaaggat aaacaatcca 1440
cagtggggta tttgcaacta agataccagg aattataagt aatagattta aaccaacgga 1500
aagcagtggt ttttcaaata aaaccgtaat tgcccacata gttgctacac atggaagcat 1560
agtaaggaaa agtccaatac accattttag taagtatagt attggtagtg tttcagtaat 1620
tcccatagtg gctgttgcaa taagacctgc gataataaaa acgaccataa aaacagccat 1680
ttccataaag aggtaaaaaa caagaacaca aaatttggcc aaagaaagtg agtatctgct 1740
gacaggtaaa gccagcattt ttaaaatacc gttgttttgt gtttctcgtc cagcaatcat 1800
tacacaaacc acaatcatac taaaaggaag tagataatag gcataaacaa gagcgctttg 1860
gataaacata gcaggccagg catttgtata ttccggagtg aaataagtac ttaggtttgc 1920
aattccagaa ataattacca agataggagc gataaaaata agtggaataa ttttagagcg 1980
ctttactttc ataaattcta tttttagtaa ttcagagaaa ttcatttgtt tgatcctcct 2040
attcataatg ataatttttg gtgagccata gtccaactcc gagaaaagcg aaagtttata 2100
ttaaagagaa gattatgaca gtaggattag gtgaggcatt cagtgcaaca gccggtttta 2160

-continued

```
acattaatac aaatggatga accataaata atatgaattt ggaattggct attgccattc   2220
cacttaggaa gccaccaacg cctatcccga gagaaatcca catattttca aagtgagaag   2280
aaattaataa catgaatgaa agtactggca tggatgtaat aaaggaatat ccagtaaata   2340
caattagcat attcaaatta aatgttccta caggtaaatc agtaatacct atttttagta   2400
gtgcaaggtt ttgtattaag acagcaatta gaagtaacac tgtcaagata acaaacttgc   2460
aaagatacat ggaagaaaca tttataggta gcatatacat tttcttgatt gcttcaccct   2520
taaattccat attataaatc atacatgttg caacaataat tccaaacata tttaaaacca   2580
tgagcattcc atagagttgt gttaataata tgtccattgg agctagcggc aaacttaata   2640
aggtatcctt tctaattatg aaattaagaa aagcgtaagc agctccaaga acccccatgg   2700
ctaaaagaat tggtagtaca ccagtccttt tttctttacg cagttcaatc ataagtgttt   2760
tcataactga gccctcttct ttctagatat attgtcgttt tcaatcatgg aaagaaacat   2820
atcttccaga ttgtcagtag caaatccaga ttgcaaagca gtttgtttta agtcatctaa   2880
actaccttca aaaagcattc ttccatgatt aagaatccca atatcgtcag caatcaattc   2940
aatttcagaa agcatatggg aagagattaa aacagtacaa tcataaaagg taggaagaga   3000
ttttattaaa ttgcgaattt cgtggatgcc ggaagggtct aaaccgttgg tcggctcatc   3060
caaaattaaa attggtggtc tcccgagtaa tgcaccagct aatcccaaac gttgtttcat   3120
gcctaatgag tatttttttg ccagtcgatc accaaactga cttaagccaa ctaaatctaa   3180
agcatcttca actgcatttt ggggtaatcc cagtattctg cgaattatat cgagattttc   3240
gcgaccagtt aggttagcgt aaaaggatgg agcttcaatg aaggagccaa ttcttttcaa   3300
aatagtaagc cggtcatttg gaaattgttt tccatcaatt tggaaacttc cgcttgttgg   3360
agctgttagt cctaaaagca ttttcatagt ggtggatttt cctgcaccat tgggcccaag   3420
gaaaccataa atacttccct ttttgatatg aagtgaaact ttgttgactg aagtgaaatt   3480
tttatatttt tttgtcaact tttctgttgt tataatgtat tccatataaa catctccttt   3540
cgttaatcat atgttacact atgaacctga catttacatt ctcgtatcct tacttttacc   3600
ttactttttg taaaaagtga tcaagaaata tgaaactgtg ttataatagg cacatagata   3660
ggaggtaggt aagatggaca attcatattt aaaaagcaaa aaactgttgt tggtagatga   3720
tgaacccgaa ctattgacaa tgttaacgac tattttgttt gatgatggat ttaattatat   3780
tgtgatggca agtactgtac aagaagcaat ttcaaaagca cgtagcgaaa aaccggattt   3840
gatttttctt gatgttatgt tacctgatgg agacggattc agtttaatgc aacaattacg   3900
gaaatttaca gacgtaccag tgattttttt gactgcaaaa gatgaggcta ctgctaaatt   3960
atctggtttg ggattaggag cagatgacta tatagtgaaa ccgtttatgc cacaggaact   4020
gttgttccgc acatatgcag ttttaaggcg atgctacaaa ggagaggcat taacagtttc   4080
attggatggg tgtattatag attttggacg tgcagaaata aataaaaatg gtgaaattcc   4140
ctctttaaca gctaaggaac atattttatt ggaaacactt gctagaaatg aaggaaagat   4200
tgttactgta gacgttttgt gtgaagcact gtggggagat aatccatttg gctttgagaa   4260
tagtttaaat gcacacattc gaagaattcg agaaaaaatc gaagaggatc cgtcaaaacc   4320
tgtatcgttg attacaataa aaggacttgg atacaaatta aatacaagga agtaacataa   4380
tgaaatcgtt taggacatat atatcaaaac agttgtctgt ttttttggga ttgatttttg   4440
ccttgatatt tttaaatact ataatgtttg gatggacatt ttataatatc atgcataaag   4500
```

-continued

```
attatggttc agaatcaccg cagactatgc tagaagaaac agtttcttct tttgatggaa   4560
cagatatttc aagcaaagtt gcagaaaaat taacccataa caatatttgg gccttttttc   4620
tgaatgagga tggagtagta acatggtcgc acaataaacc gaaaaaggtt ccgaatactt   4680
ataagataaa agatgttgca gtatttgcaa aaggatatat ccaggactat ccagttttta   4740
cttgggaatg tgagggcggg attatggttt tagggtatcc agaagatagt tatacaaaga   4800
ttacaagcaa ttatttttct cttgatgcga taagaaaact acctattttc attttaatta   4860
tgttttgttt ggatatattt cttttattta tagcatattt cttatcaaag agaaaaatca   4920
taaaaactac agaaccaata atcgctgcaa ttaaaaacct ttcagatgga aagtcggttt   4980
cgatttctgt tgatggcgaa ctggtagaaa ttgcagaagg ggtaaatcga gcggcgatta   5040
ttttagatag gcaaaatcaa gccagagcaa attggataag tggagtttct catgatatac   5100
gaacccctct ttcgatgata atgggatatg cacaacggat ttcagatgaa acagagggag   5160
aaagtttaat tcataacgaa gcagtgatta ttcgcaaaca gagtatgaaa ataaaagaat   5220
tagtacaaga tctgaatttg gtatcacagt tagaatattc tatgcaaccg ttaaacaaaa   5280
caaaaattcg tttttcggct ttgttacgta gttatgtggc tgaattattg aatgaaggta   5340
ttcctgaaaa atattctatt aatcttgaag tttcttcatt cgtagagcag ttttggatag   5400
attgtgacga acggcttata acacgagcaa taagcaactt ggtacaaaat agtattcgac   5460
acaacccaaa gggctgtgaa attgtaatta gattagatta tgtagaacat ggatttgaat   5520
tacaaataaa agataacggg attggattat ccgaaaaaag gttacgggaa ttacaagaaa   5580
ttcctcacta tatggagagt acagacgagc gtttggactt acgccatgga ttggggctga   5640
ttattgtaag acaaatagta atagcacatg gaggaaagat aaaaattgat agtgaaccta   5700
atagggggata tactactact atttttcttc caattaatga tttatcaaaa aatcgataag   5760
ttaaaaggca gtttcagtgg gaactgcctt ttaacttgga aaaatttaga aagatggtaa   5820
atattacatg gaagaagggt gaaatttacg agacagaaat atcaaaagaa attcatgata   5880
gtatatgacc ataatcttat ttgagaaaag aaaggagaaa aaaatatgag aaatgatgta   5940
ttaacattaa caaacccaat ggaagaaaaa gaactggagc agatcttggg tggtggtaat   6000
ggtgtgttaa aaacaatcag ccacgaatgc aatatgaata catggcagtt cctgtttaca   6060
tgctgctaaa aaggaggata aacgatatga gaaatgatgt attaacatta acaaatccaa   6120
tggaagaaaa agaactggag cagattttgg gtggcggcaa tggtgtgtta aaaacaatca   6180
gccacgaatg caatatgaac acatggcagt tcctgtttac atgctgctaa aaaaggagga   6240
taaatgatat gagaaatgac gtattaacat taacaaaccc aatggaagaa aaagaactgg   6300
agcagatttt gggtggcggt aatggtgtgt taaaaacaat cagccacgaa tgcaatatga   6360
atacatggca gttcttgttt acatgctgtt aattgcaatt tgaatattac ttctcaaata   6420
agatttactg tacaggctgc ttagattatt ctgagtagcc tgttcttata aaagaagatt   6480
tcctcaaaat acattatggt gtattgaata atatatgagg aattcaaaat aaatattaca   6540
ggaggtaagt atgcataaga agttttgtgg tctttatatt gaatatattt ttgaatacat   6600
catagagaca ttaaaagaga aagaggatta tctttttgat agtgaaaaaa ttaaatatgt   6660
aaaagaaatt attgaaaagg agattttca aagagttttt aaatcgctac tatattgtat   6720
gaatgtagag cgattagatg gaaatttatc tggaaatact ccagaggaac gttatgaaat   6780
gttcagtaat acgagatact gtatagaggc aatgggcaag aattttccaa caatgagaaa   6840
tcaaatatat gacgagatgg cacataaatg tgtatatgta atggaagtaa ttagagaact   6900
```

-continued

```
tgaaaataac aagaataaaa ttggtagaca ttttgggatt aacccgggag aaattgtaca   6960
agtgcaaaat agtggagatt ggcacgatag tgaatgtgtc ttaattttta cattccaatc   7020
tcaagataaa attgtataca aaccaacccg aggagaaaat ttgcaattta tgaaagggtt   7080
tatggactat ttttttgaac cagaatatgc cgaacaatac ataggtttgt gtatcaggaa   7140
aggtacttgg gtaaagtttg tcaagcatat cgaactaaca aattcaagaa atgttgaacg   7200
gttttattat aattacggaa aagtgttatt tgtcgcatat attttaggaa tgaatgacat   7260
tcattatgaa aatcttattg catgtgggga atacccagta attacggacg ttgaaacaat   7320
tttttcctcg tacttatttt ttgatacaca tacattctta tatgacgcac agtataaagc   7380
tgtaaaagaa ttgctctacg gtacaatggc aacagggatg ctaccgattt tttccatgac   7440
ggattatttt ggtggagatg tgagttgttt atcaaataaa ggaatacagt tgattgtaga   7500
aaaaattaaa aatgagtata gagatgatat gtatatttgc actgcaccag agatgatagt   7560
agaatataaa catttgccaa atcatacaat tgatcctttg atgtatggaa aacagattgt   7620
gcaagggttt gaggaagcag aaaataattt tggggagaaa aaggtagaaa tcataaatta   7680
cattttgaat aatatgggaa aagttgagtc acgaattatt ttgaatatga caaaaggcta   7740
ttcaaaaatt gttcgaatta aaagtgatcc aaggtatcgg catgaaccag aattatttgg   7800
acatttgttg acaacattaa aaagaaccaa tcaatttaat cctgaagtat atgaacagga   7860
agttacggaa ctctgccgta gtaatatacc tagtttttat tggaagatgg acatgaattg   7920
tgtatatggt ttgaatttag gacagaaaaa aaagatattg gatcttccta tttttacaaa   7980
agagagatta tcagaaattc ttgaatatca gattaatata caaatgttag aaaaacagaa   8040
acagttaata tatgatgcta ttgtctctaa tatagcatta ggtattgaat atgaaaagtt   8100
gaaaataagt gtgaagcaac atgtggatat tcatgtaaaa aaagtacttc ggagaaatat   8160
tgatcagaat tgcattgtag gttcagatgg aactattagt tggcttggac ttatggtaaa   8220
tgataaagaa cagttagaat atgctatgtt ggattggtct ttatactctg gaattatagg   8280
acttggctat atgtatattt ccgaatatga taaagagcca gatgtattgg caaaagatat   8340
gctacaaaga atattttgta cgctggcaaa atcatatgat ttaggtgttt ttaaagaata   8400
tgatatttct tatttttgcg gattgacagg catttatgcg ttcttgaaac aaattaaaga   8460
ccgaaatata attgagccgg atatcataga aaaatatata aaaaatattc aagaagcaat   8520
aagaaataat attgttaaaa ctagcagtta tgatactttg gcaggaattc attcagcagt   8580
tatttattat tttgggtgtt atgaacaaga catattttcc agagagattt tatcatctat   8640
agaagagtat tttttaaata gttttaaaat tgatgatatg aagagaaact ttaattatgc   8700
aagttttgca catgggtatt caggagttat gacatcaatt atgtgtatgc ttcagcataa   8760
atatgatata aaattagaaa aaattttatg tgagctgtgg aaagaagaaa aagaattgta   8820
tgttgaaaaa tttatatgga aagatatgcg agctcatcat atcgtacatt cacattactg   8880
gtgtcatggt tcagtaggta ttatgatggc aagattgatt tggaaaaaat ttgggtttga   8940
taaaaaattt gctgaagata tagaagagga aaatttagaa gaaatattgt ctaaatataa   9000
agaagaactt cttaataaaa aatttcaatc taaaaaattat tctttatgcc atgggaattt   9060
tgctttaatc gattttctta tttcttatag aaaaattgta ggaactgatg aaagaataga   9120
tgcatatata gaggaaatta ttgagagtgg tcaagaaaat ggatacagtt gtgttggagc   9180
accgggagct ataaactcaa taggatttat ggttggagaa gcaggtattc aatatacaga   9240
```

-continued

```
aaatagaagt gagaattcaa agttgcactc tgttttaatg cttgaaactg tgtaagaaag   9300
tgtggtgata ttagtgaaag ttattttaca aacaaatcaa tctgactgtt tactagcatg   9360
tgctgctatg attatgaata cgcttgggtg caaggtgcca gtatataaat tgattgagaa   9420
gatagaatta tctatggctg gaagtaatat attgcagtta aaagaggcat taggagaata   9480
tggtttttct gtggaaggat ataagattga tgtacagagt ctcaaccaga caataatgcc   9540
agtcattgct tatgtaaaga atggtcattt tattgttctt gacaaaatga gtaaaaatca   9600
gtttactggg gtagatccag caattggacg aattaagtat tcttatgatg aatttcagaa   9660
aatatatagt ggtgtaattg tgaaaatcag aagagtagat gcgggcagaa aatctgagga   9720
ggtaactaga aaaagtctgt taagtttctt agcagataaa agactgtttc ggattttggc   9780
tggtttactt gtaacctcaa tttttacaca ggttgtggca atgagctatt cttatatgta   9840
ttctatggtt ggaaatggtg aaacatatgg gaaagttatg ctattactat gtggggcagt   9900
tattttacta ggaataggaa gtatcatgca aggtgttttg actaaaaaat ttaatatttt   9960
gtatgagcag atatacggaa ataggctagt tgataaactg atgagtaaaa attacaaatt  10020
tttttctttt aggagcaacg gtgatttgct gtataggata aacgcaagag gcatgattaa  10080
agatgctcta ttgctaaaat tggtaccttc tttcatttcg ctatgcacaa ttatttttgt  10140
tcagatttta ttgctagtac aaaatagtct tctaggtata ttatttttag gtgcaattat  10200
tttatattta gttgtatatg taggaacaag taaaatagca tatatggaaa gcaataaata  10260
tacacaaaaa gttatacagt taaatacaac aagtgagaat atcatacgat cagtttcaac  10320
cataaaagtt ttaggtgtta gctcgatttt tactaaaaaa tggcatgaag aaaatcagca  10380
acaagcagag tgttatgggg aattagttgt tattcaaagt tttcaaaata ttttaactaa  10440
tatatttaca tatattgttc caattgcggt gagtatacta agtattgcat gtgatgaaga  10500
aattaacatt tttagtcaaa tggcacttct tccattgtta tacctagtag tacaaaatgt  10560
agtagtgatt gggcaggctt gtaattctat ttacacagtt ttacctaata tagataaagc  10620
gacagagttg ttagatgatg aatttatgca ggacaatgaa cggaaatttg caaaacttga  10680
tggtaataca gcaattcaag ttaatgatat gtcctatcat tatggaagtt tgcaatgttt  10740
ggagaaggtt aatataagaa ttgaaaaagg aaaaaaatat gctgtcgtag gagtttcggg  10800
aagtggtaaa tctacaatgc ttaaaatttt agcaaatctt ttaaatgatt atcacggaga  10860
ggttgtattt gatgaacaat gtagagagaa acctatttat ttagatcagg atacaaccat  10920
tttggatggc agtatattag aaaatgttct ttttggacaa acatgcacaa atgagaggtt  10980
gattcagata agtgaggcga ttggtcttaa tgaagtagta ggtagacagc cacaaaactg  11040
gggaaccgaa attgcaaaag gaaagaattt gtccagggga caggaacaga ggatttgtct  11100
tgcgagatgt ctaatcaaag aggcggatac atatctttta gatgaggcaa ctagtaatat  11160
tgatgtagta gacgaagata aaattatgaa ggcattgatt ggaaatcaag gaattttaga  11220
agaaaagact gtacttattt ctactcacaa gctgagtatg attgattatg tagatgaggt  11280
tatttatata aaaaatggac gggtttatca aggaacacat atgcaattac tccaaaaaga  11340
gaaatcgtat gcagcatttt ttgaaggaaa agttacttaa aatagcggaa taattacatg  11400
ggaaaatttt ggagaataaa agatgatata ttgtaaaaaa caaattctcg ggatttcaat  11460
gaacaagagc atacttgaca attgaatatt gtgcagaaaa agaaagttgt gttcgtgtgt  11520
tccacagaag tagacaggaa ggtagtctta attctagttt gaagacagaa taacactcat  11580
gcaggtggaa tctgtcatag aaagattaag gtactaaaac tgcatgatat aatcccaggc  11640
```

-continued

```
gctcttatgc aaagaaaaat gatgtagata aaatttaaga aaataagata cgaaaagtat  11700
tctgatagtc agtgtgttca ctggtgttaa caggtaagag aaaaattgat cctatccatt  11760
gaataacata tcagcaatca gcgtcaacgt ggattattgc taaaaatagg tgatttttag  11820
aatataaatt tctgtaggtc ttataaaacg aaacatgaag atttcgagaa gatataaaat  11880
gaaagtgagg aaaaaagatg aagtgtaaat tttttaaagt agcagcgtta tgttgcacat  11940
gtatgatggt attggggaat acgatggcag tttacgcaga agaacaacca atggtaataa  12000
gtgaaccgaa tgttacttct tctgaaatgg agaaattgat tgaagtggta ttggatatca  12060
aggaggctaa tccaggaaaa tcagaacagg aaatttttga aattgtttca aaatctttag  12120
aaaatgagag aaaagaaaca agaggaattt cggatatttt ggaatgcttt gacggaaagc  12180
agaaaaagaa attattaatc agatatccgc tagatgcctt gaaagttaat gacgccaaaa  12240
acatagctac tagacagacg gaaagaaagt ttgggcataa tggattagga gatcggagtg  12300
atgcatttag gcatggcatt tggaatgcag aaatgacaat tttaattggg gcagaaaaag  12360
cagaattatt tgcgactgca catgaagaaa aagatacaac aggtgtagag ccggatggtc  12420
acactaaggt agaacataag aatatggatc tgcataacaa taatgttggg agagaaatag  12480
gacttgcaca tccagactta tctgaagagc agatggcaga ttatatatat gatgtaattt  12540
atcaggaaaa tacgccattt gtatggctga atgattaatg caaacaaagg tggtgctaaa  12600
gattaacttt agcatcacct ttttgcaggt agttaattct ataaatcttt ttatagattg  12660
acaggtttaa aaattaaata attgtaaaag aataatattg tgtaaggtat tgtagtaata  12720
aaaaagtacc taaatgagtt gtatatattc ttaaattaag ttgtattcgt atgttaataa  12780
gtcgctttta tgtgtgtatg at                                          12802
```

<210> SEQ ID NO 106
<211> LENGTH: 60232
<212> TYPE: DNA
<213> ORGANISM: Artificial Sequence
<220> FEATURE:
<223> OTHER INFORMATION: Synthetic construct

<400> SEQUENCE: 106

```
tcgcgaattg taaaattaag ttagaaaaat aaaaaggcat ttatggtaca ctcaaattgt     60
atttccgacg aaagaaaaca aaggagtgta accataaatg acctacaaac atcttaccat    120
agacgaactg acaatgatag aatcatatta tcttcaacat aataaaccgg ttgaaatcgc    180
taaccgaatg ggacgtgcta tacaaactat ttataatgta gtcaataagt tcaagcaagg    240
caagactgct cttgattatt ggcaccagta taaagaaaat aagaaaaaat gtggtagaaa    300
agtcattcaa ttacctgctc atgaagtaga ttacattaaa gagaaagtca ctcttggttg    360
gacgcctgac gtcattatcg ggcgaaaaga aaggcctgtt tcatgcggta tgagaacact    420
ttatcgttta ttttctaaag gaatatttga tattgacaca ctaccgatga aaggtaaaag    480
aaaacccaat ggccatcagg aaaaacgggg aaaacaacaa tatcagcgct caatccatga    540
tagacctgat aattatcctg atttcaattc tgagtttggt caccttgaag gtgatacgat    600
cgttggcatt catcataaaa gtgccgtcat tactttagtt gaaagattat ctaaagtaat    660
tatcacgatt aaacccaacg gccgtaaggc attagatatt gaaactgccc ttaatcaatg    720
gttttctcgc ttccctaaaa acttctttaa atctattacg tttgactgtg gaaaagaatt    780
ttctaactgg aaagccatta gtaaccaaca tgatattgat atatattttg cggaccctgg    840
```

-continued

```
aacaccttct caacgcccat taaacgagaa ttctaacggg attctgcgtc gtaatggact    900
gccgaaatca atggatttta gagaagtgaa tcagacattt atttccagtg tcagcaatca    960
acgtaatcat attccaagaa aatcattgaa ttacagaaca ccaattgaga tatttttgag   1020
ctatgtacaa gaagcatttt attctaactt aatttgacaa atcatatata aaaaaactaa   1080
ctaaaaaaaa taaaatagtt agtttttttt atatttatca ggtttatttt cttttatata   1140
atttgagaaa atttttaaaa aatcttctgt ttcgtcaatt gaaagatttt cagtatcaaa   1200
atatttatct agtaaagcac ccttttgtat taattttcga gttctttctt ttcttttttt   1260
tgtactttca aggtattttg atttttttaa aattgaattt tcacgttcaa tttttttctg   1320
aatttcttct tttttagaaa ttaaatttc aagttgatta ctcataagca atcaacctta    1380
aaaattgttt tcagtttttt catgaactga attaatgttt tcatcagaaa cagaatcatt   1440
agatttttca gtttcatcag aaccattttt tccttttaaa aattctgaaa attctttagt   1500
taattctttg attttatcag tagtcaattt tgaataatca agattagaca atttgatgat   1560
ttcatgacct actttgttat caattttttt cttctcgttt ttaatttttt cgtttagctt   1620
atttaatttt tcttgttgtt tttctaaact agataatgtc ataagtacac ctcacttgat   1680
ttttattgac cgtaacaaga taatatcata atcaaaatta tatgtcaaca gattagttgc   1740
taaaaaccaa aaaaaatagt aaaatggaat taagatttag aagcgtcagc agaccgagcg   1800
aagcgaggac aatgcgcact tacacaccac tccaaaattg ggtggtgtaa ttgctcgaaa   1860
aaatggtatc agaagttgcc tttggcaaca acaaataaac aaaaaaacaa gggaaaggag   1920
aaaataaggt atggcaatat ttcacatgaa ttttagtaat attagtgctg gtaagggaag   1980
aagtgcagta gctagtgcaa gttatagaag tggcgaaaaa ctttatagcg aaatggaaaa   2040
taaaacttat ttttataatc gtagtgtcat gcctgaaagt tttatccttt tacctgaaaa   2100
tgcacctgaa tgggctaaag atagacaaaa attatggaac gaagttgaag cagttgaccg   2160
taaagtaaat tcaagatatg caaaagaatt taacgttgct ttgcctattg aattatcaga   2220
agatgaacaa aaagaactat tgaccgaata tgttcaaaaa atatttgttg ataaaggtat   2280
ggttgcagat gttgcaattc atagagatca tgatgaaaac cctcatgctc atgtcatgct   2340
tacaaataga ccttttaatg ctgacggaag ctggggacaa aaagctaaaa aagaatatat   2400
tttagatgaa aatggaaaca aaacttatac agctaatggt catgcaagaa gtagaaaaat   2460
ttggcttgtt gactgggata aagtaggtaa agttgaagaa tggagaaaag catgggcaga   2520
ccatgttaat tctgtttttc aagaaaaaaa tattgatgaa agaattagtg aaaaaacact   2580
agaagcacaa ggtataaatg atattgcaac gcaacacgta ggagtaactg gaaatcgtga   2640
tgaacgtgct gaatttaata aacttgtttt agaaaatata caacataaag cagaactaga   2700
aaaccttgac gaaaaaatca ataatgaact taaagttaag caactaaaaa acttctattc   2760
tttcaacgaa aagaaagtta ttgctgaatt gagtaaagag ttgcatacct ttattgattt   2820
agaacacctt gaagaaaaaa ataaaatgct tttcaactgg aaaaatagtg ttttaattaa   2880
gcaaattgtt ggtaaagatg tttcagaaga attaaacaaa gtcagtcgac aagaattttc   2940
acttgataat gcaaatcgtt tgattgataa agttgtagat agaagtataa aagctatgta   3000
tccgaccgta gatagcaatg ctttttctat gcctgaaaag cgtcaattaa tcagagaaac   3060
agagagcgaa aataaagtat ttactggtgc agagctagac gatagattat caatgattag   3120
agcagatagt ttaaataggc aaatagttgc tttaactaag cgaccattta caagtttaac   3180
tatgctttca aaacaagaaa aatatcatat tgataacatc aataatgttt tagcttatca   3240
```

-continued

```
aggatataac tatgaaaata ttgaaatgtc acatggtaaa attttacgaa attatgaatc   3300
agaagaattt tcaaaagaac tcgatattat tcaacgtagt cttaaacaaa ttaattctat   3360
tgaagaagta agaaaaattg tagaacaaca atattctgtt gttcttggaa caattttccc   3420
tgatagtgaa ttaaataaac taagtttagt tgaaaaagaa aaaacatata atgcagtaat   3480
ctatttcaac ccaacgatca aaaaacttac tcaaagtgaa ttagaaaata ttgttaaaga   3540
accgccaatt ctattttcta caaaagaaca taatcaagga ctttcttatc ttgctggaag   3600
aataagatta gaggatataa acaataaaca tctgacaaga gttttgaaat ttgagggaac   3660
aaaaaaactc tttattggag aagctaaagc agataaaaat attgatcctg aattgctaaa   3720
agaagcaaca aacaggaatg ataaacagtc ctataaaaat gaattttata gagataaaaa   3780
tatggaaaac taccaatcag ttgcctattc agatacaagc ccagcagaat atatgaatcg   3840
tttatttagt ggagttttga ttagtgtttt atataataat gaaaaccaac ataaaaaagg   3900
gttagaagaa gttgaatggg acatggaaag aaaacaccgt gaacatacca aaacaggtgg   3960
tttaagcagg taaaaatagc aaaaaaaata gtaagcaaaa aaatgagcat aatatgctca   4020
tttttgttat acttaattta taaatcaaag aaaggagatg catttgaaaa gttcagagtg   4080
gcacagccta tcaaaagcaa gtgagattct aggaaacgga acatcttatg ttagcttgtg   4140
gttacgtcgg catgaaaaag acatgccaga gggaatggtt attgcgtcag gaaagagcaa   4200
gttaatatca gatcaaggga tcgaatggat aaaaaagaac acaaaaaaag agggcgtcct   4260
cgtaagcaat aaacgtgctt ttgaggataa atatctaata cttccactat tagataaagc   4320
cctaaataac tattttacct tttttaaaaa tttaagtcta ttgttgatat attcaagagt   4380
tactttgaaa gtaggtagat aaatgaaaag tgaaaagtgg caagggataa gcggaacttt   4440
aattcatgat gaaactaaag gaattattat tgataaaaat gaaaaaagtg atagcttaga   4500
ttatttttct gaaaaattaa aaacagacgg aaaaccactt aaagaagtaa gagaaaaaat   4560
gataaaggat agtattaaga gagatctcaa aactaatcct ttgcatttga aagcatggtt   4620
tgataaaaag tatgacagtg ataattctga aaaatctaaa gaaattaatt ctgacaaacc   4680
tactttacaa tataaacaaa taaaaagtga tatttcattt tttggagaaa gtttttttaga   4740
gggtttctta ggtttttatg gttttgaact agataatgca gtttcaagat atgaatcaaa   4800
tcttcaaatc atagaaacaa aggagctggg aatagatgat gaagctaaat attttttagg   4860
tacaagtcaa aaaggagaat ttaaaaaagc aacatctgaa ttgccaagca aaagtattgc   4920
ggaggaagaa ctacaaaaat tcttttcaaa agaaaagaaa caagttcaaa ctcaaagtat   4980
cgaacttaca aaagatactg atgaatgaaa ggagaagttc atgaataaat taggaaaagg   5040
gaaagtcgct aaattagcaa caagtaccct aactgctggt tatcttatgg taatgacagc   5100
acaaacagcg ttcgctgcgg acggtacagc tatacaaggt aagctgacga ccgctgcaaa   5160
cactattaaa ggtattttaa caggaattgt cgttttagta ggtgtctgtg tagctttgtt   5220
tattattata aaacggttgc ctgacgcaga tgatccgaga gagaaatctg aagtttttaa   5280
aagcgtcgga cgggtagcgg ggcttgtagc cctcgcagcc gccattgtat ggctattgcc   5340
ttgggtttac agtcttttaa cttaatataa aaaggagtaa gtcaaatgaa aaaaggtaaa   5400
gaatttattt ttcctgaaaa tgtcgataaa gattatggaa tttggaaaga ttatacctta   5460
aaagattttg gctatggaat tttaacttta ttatgtggtt tagtattcat tgtactgcca   5520
ccatatccct tattttttgt attaggcaag attataattg tcgtaatagc catgacagtt   5580
```

-continued

```
gtcatggcta ttttaacaat aaaacctatt tcttcaagaa aaaatataaa ggttagagat   5640
catctaaggt taaaacgaaa atattctcat agtcagaaat tatattattt aaaaccgcaa   5700
aaaaggggta ttaaagatga atttgaaaaa taaaaaatct aaaaaatcag cattggactg   5760
ggaatatata ccacctaaaa ttaatggcgg taaagaaact attgatgata tgagtttaat   5820
tgtcggaatg tacgataact atcaagtaac taaaacagga aatttagtag gaatacttga   5880
agtaagtggt attaatcttg atttattaaa tgataacgaa caacaagatg tctttaatga   5940
ttacggagct ttccttatga gtacattagg agagggagta gatgatactt tacaattcat   6000
agaacctacc ataccagtta atatgacagc atatattaat ggactaaaac gtaagtattt   6060
agatttaaaa ttaaaccacc ctgaacaaga atttaaaata aacttgctgg caagttattt   6120
agatcatttc acaacagttc aaaattcaaa aaatatgaca acaaaacagc atttattgat   6180
tgtcaaagtg aaaataaaag ataagtcagt tgagagttta gatttagcag taaataatct   6240
tgatgaaaaa attaatcaag tgaagcgtga tttagaaaat gcactagctg attttgactt   6300
aacagctaag attttaccaa gtcaagaagt gctggaagtg ctgaaaaacc ttattaattt   6360
taaaggatag gaggtaagga tatgaattta agtgataaag ttatggactt aattatgcct   6420
aactcaaaaa agaaaaatga aattattgta gatgaagaac aagagcaaaa gaaaagtaag   6480
caagataatt ttatggaatc aatcgaccgt gacagtctac actcactttt tccttttagc   6540
tgggaacaat acccaactta tgttcaatca ggcgaaaatt tcatgagaac aattgcaatt   6600
gctgattatc cgaagcgtgt ttatggaaat tggttatcag aattaaaaag aaaaaaaggc   6660
tcaattgata ttgttcagta cattgatagt gcaagtaaca attcaatgat tacttactac   6720
aaaaaaacaa ttcaaaataa agaagctcaa ttgttaaata cctttgatcc atataaacaa   6780
aaggtattaa aaaattacat tgatagtgcc aatatgcaat tagacaagta tttagataat   6840
tctactacct ttgtttatca acacatgctt gtatatttaa gagcagattc tctagctgaa   6900
ttagatgatt taacagaaaa tgttagaaat acacttatca aattacagat gaagcctttg   6960
ataccagtaa aagcaacttt tcaagggttt tggtctacaa tgccaattaa tgagaactta   7020
ttaggagatt atacctacaa agaaagcaac acagaagttg ccagtagtat gtttcccttt   7080
gatgacgcag aaattcttga tttaaagcct agaagcgata ttgagggaat aaacaaagat   7140
acaaactcaa taattgctat tgatatgttg gatagaaaca ctacccttaa tcaaaacatg   7200
gtagttattg gaacatctgg agttggtaaa acaacctata tgatccaaaa aatattacgt   7260
tacgcaattc aagattatca aatttatatc attgatcctg aaaatgaata tacaagaata   7320
gttgaatcat taggcggttc agttctacat ttaacatcaa atgcaaaata taaaataaac   7380
cctttacaaa tattttcaga agaaatattg agtgcagatg aagcagtcac taaccttgat   7440
gaattagtaa aagataaaat tcaacgatta aaaggttttt ttgaagtttt aaaagatgat   7500
atgacacaag ttgagaaagc ggttatggat aatatagtaa aaaacgcata tatcaatagt   7560
ggaattttaa aatataaccg tctaaacgaa attaagaatg agcaatggcc cactcttagc   7620
aacgtttatg acgaactaac aaaattatca gaaaaagatc ctgaaaaatt taaaacaatt   7680
aaagattttt actttatttt aggtagttat acgcatggat caaacacttt gtttgacgga   7740
gcaaccaaca ttaatttaga tacaaaaatt gtatcttttg acttaaaacc attgcaaagc   7800
gaacaagagg tacaagctgg tgcatactta aatacgtttc aatatttatg ggacgaaatc   7860
acaaaagacc gcaaaaaaag aaaaaaattg tttgttgatg aatttcactt tctaactttg   7920
cacaaatcag cgtctacttt cttccaccaa gcctataaac gttttagaaa atataacgct   7980
```

-continued

```
ggggcgattg ctggaacaca acaaattcaa gatgttattg aggggcaaac agatagcgga   8040
caaaatattg gagaagccat tattggtaac agctttacaa aagttttctt tggacttgac   8100
ggtaaagggg tagatgatat tacctcaaaa ttaagaatga acttttctga aaaagaaaag   8160
aaattgttag aacgtagacg acaaggggac gctttaataa tctatggaag ccaacgtgca   8220
tttatgaacg tagagcttac agaggaagaa ttaagactga ttgatccaga agcatataaa   8280
gaaaaatatg atagagaaac agcagaacaa cctagttatc aaaaaagagt tgttctaaca   8340
ccaactgaaa tagaaatgtt gactactacc gaagaaaaag ggggagtaga taatggttaa   8400
gaaaaaatat gacctgttaa atattgaaat tggtactttt aagcggtcta atgataaact   8460
ttcaatcaaa attgataaat cacaatttag atatgatagt ttatctgaat taaatgaatt   8520
aaaaaaacat caagaaaact ttattgactt agatagtatt gttgagcaag aaaatcaagt   8580
catattgact tataaacttt caaaaaatgc taaatctttg aaagaattaa tcaaagaaaa   8640
aaaagcaatt aggacatcaa ttgctaaacg tattatgaac caagatatat tgaaagatga   8700
tacttatcgt atttctttaa acccagcgaa tatatggtat tatcctatga accatgtttg   8760
gtatgtttat aaagccaatg aagctatgcc ctttgatgat aattttagtc cattaatgaa   8820
gtacaaagcc ttagttcttt actgtcttac tggaatagct tacgaaagat tattgaacga   8880
gccgaaagaa gctcttataa ataatcaaga tccaatagtt ttacaagttc taaattctga   8940
aaatatcgaa gatctaaaac ttgcgattaa tagtattgac gattctattt cttatcaaga   9000
atggcaaaaa atagatacaa aagaaaaaaa gactaaaaga aaatttatta tcacagcaag   9060
ctcaattgca attgtcggtt tattattggt tggaatggta cataaaaatg accaaaaaaa   9120
attgatagca ttggaagata agcaaaaaat agaactcaca aaattaaaat attctagcat   9180
ggttcaaagt tcactagaca ataaaaactg gaaagaagct agtgaagcta tgaaaaaagc   9240
tggatatagc aaagaaaagc aaactcaaac ctttttatct ttaaaagagt atcaagaagc   9300
cattaatgca gatccaaaag aattaaatac agtagttaat gaaatttata aaaataatga   9360
tgaaaaggtt gttttagacc tagaattgcc tactggaaca gaagaaaaaa ttgatgatga   9420
actgaaaata gagaaagcta ttgttagtta tgatagtgaa acactagcaa gtcaattatc   9480
ctttgaagaa aacaaagatg ttctgttaag aatgggacaa gcatttttag aaaataatga   9540
tatgcaagac gcacaaagtg ttcaaacaaa actttttggt ttagatgaaa caaaaggcga   9600
ttatcttaaa tctatgattg atctaaaaac agcaacaaat aaagttaaag acagtcagaa   9660
aaaacttgat gaagctaata agattgataa taaagataaa agcaaaggcg acaaagttaa   9720
agttgctaaa tctaatttag atagtgcgaa aaaagatgaa acattggcta aagataaggt   9780
ggatagttta aagaataaag taggtgctta atatgcagat gttttcatta aaatacaaat   9840
ccaaaaaata taaactcatt atctatttat ttgctggctt tattttattt ctgattatgg   9900
ttattgcgtc acttactgga gggttatctc aaaatgattg tgacaataac acaatttcta   9960
tcacagccaa tagtgcgtca caaaaagaaa atgctaaagt tatctatgat tttttagtaa  10020
aaaattatgg agcaactcca caaggagcaa gtggagtttt aggaaactta caacaagaaa  10080
gtcaacttga tccgaagtct attgaaagac cagcagatac attatcagga catgggcttg  10140
cacaatggac tgctggaaga actacaaatt taatggactt tgcaaaaagc aagaataaag  10200
agtgggacaa tttaggttta caacttgaat tttagatag tgaattaaaa ggttcagaaa  10260
aacaagcaat accagcactt aaagcactta gtgtagagca agcaacaata gactggcaaa  10320
```

-continued

```
aattgtttga aagagctggc aaaccagtat tatcaaatcg acttaattat gcaaataaat  10380
ggtttgcaca gtttggtaca agcgatccaa tttcagcaaa tgcacaagat aatgcttcaa  10440
atggagctat tgaaaatgta gcactcaatt gtggtagttt aaacgataca ggaagttcaa  10500
gtgacttagt aaaatcagca aaaacaatga aaggttactt ctactatgtt caagcccacc  10560
caagttcaga cttaggaact gattttaaaa accctaacaa atcagggggg actgactgtt  10620
caggttttat atggcttgct atgaataaat caggttataa agtaccagcg aacatggggt  10680
ggtttactgg atcaatggca agtgacgcta gaggttcaca tcaatattta aaagaaatta  10740
caccaagcca agctaaagct ggcgatattg taattgtgaa tcaaggtata ggagctggaa  10800
acaacggaca taccgctata ttacttgaaa attggcatgg taaagaaaca aaaatcattc  10860
aagagggcgg agatcaaaca ggtcacgtta acgagggaca gtttggaaca tcattttcaa  10920
ttttgctaga cggtggagat gtagttttag caagaccagt cgctaaataa ggaggaaaac  10980
agatgaagcg atcacacata atttcattat ctgtactagg tatattatta gttggttcat  11040
tatcagtaaa cgtaattcaa aattctacaa acaatcatgt aaaaactcaa ttaaaacaac  11100
aagaaaatca aaataaagat attaatcaaa aattatctac aaaatcacga gaaaataaag  11160
ttttaaaaag tgaggtagac ggttttaaaa agtttgaaaa caacaaagat aaaagtcagt  11220
ctgaattaaa ttttaacaat atcactaata agtttttaac tacaatgttt acctttgagc  11280
ctaatactta taataatcgg aaagataatc ttaaagggtt aatttcagat gatttatata  11340
ataaatattt ccctaaaaat actaattatg gggacgcaaa caacgtttca tctaaacttg  11400
ataaagctac aatttatacg caagcaaaac aaggaaatga acttaaagga cttgcagtag  11460
ttacttttga aagtaagagt ggcgataacg aatggaaaaa agaaactgat ttatatcaaa  11520
taaagtttga taccactaat aatcagatta cagatgttca aaatttaggt agtagtttta  11580
aggcaagtga tgttgaataa atggatcaaa ggtattattt cagtagtagt ggctactggc  11640
ttaatatcct atgtagttca taactacatt aattttgtag aaaaaaaaca aaatgtagtc  11700
acaatagata aaaaaaagaa taaaacttta ttcttttatc gtgacgattg caaagactgt  11760
caaaaagtat ttcatcatgt ttattggaaa aatgtattta ataaaaatat agaatttgta  11820
aatatgaatc aaaaaatgaa cagaaaatac attgaagaat atgatttaaa atcagtacct  11880
agctttgtaa ataaaaatga aatttattca ggtacaaaaa tttcagatat agatcatatt  11940
atggagaata acaaatgaaa gataacataa taaaaatcat taaaagtgtt gttccatatc  12000
tcttatcttt attagctgga ctttacttaa tagtaatttt tacaggttca tttatggggt  12060
tagctcaata taaaattgct tttactgaaa aattttcaga tgttttaaaa gaattagctt  12120
tgcacccctt gtcacattat ttagcctata ttcacgaaaa aaaccccctt gctattattt  12180
taagcattgc acttattttg tacctcatct attttgcttt aagaagaaaa aaagcgaaag  12240
gttcatggga aaccgcagat acagaaacac acggtagtgc agactgggga aattctaaag  12300
aactattttc aaaatatttt ggagtaggtc aaaagaaatt aaaggaagat tttgataaca  12360
gtatagatca agaaattatt gataaattga ataaagagag ggtggaagaa tgaacggtac  12420
aattttaggt gttttagata ataaaattat ttatcaagat aatacaacta aacccaatcg  12480
aaatgtcatg gttattggtg gttcaggatc atacaaaaca caatcagtag ttattactaa  12540
tttattcaat gaaacaaaaa attcaattgt ggttacagat ccaaaagggg agctttacga  12600
aaaaaccgct ggaattaaac ttgcacaagg ttatgaagtc catgtagtca attttgcaaa  12660
tatggctcat agtgaccgat acaacccttt tgattatatt gaaagagata ttcaagcgga  12720
```

-continued

```
aagcgtagct acaaaaattg ttcaatcaga gaatgcagag ggtaaaaaag atgtttggtt  12780
tagcacccaa agacagcttt taaaagctct catattgttt gtaatgaaag aacgaagtcc  12840
tgaacagaga aaccttgctg gagttattaa tgttttacaa acttttgata gtgaacctat  12900
caataaagat gaaaatagtg acctcgataa tttattttta gctttaaaaa taacccaccc  12960
agcaaggata gcttatgaac taggctttaa aaaagctaaa ggggatatga aagcaagtat  13020
catttcaagt ttattagcaa caattagtaa gtttactgat gaagaagtat ctaattttac  13080
aagcatttca gattttcatt tacaagatat aggtagaaaa aaaattgttc tttatgtaat  13140
cataccagtt atggataata cctatgaaag ttttatcaat ttgtttttct cacaaatgtt  13200
tgatgaacta tacaagctgg cttcaagcaa cggagcaaaa ctaccacaag aagttgattt  13260
tattcttgat gaatttgtca atttaggtaa atttccaaag tacgaagaat ttttagcaac  13320
ttgtcgtgga tatggaattg gagttacaac gatctgtcaa acacttactc aattacaatc  13380
actttatgga aaagaaaaag ctgaaagtat tttaggaaac catgcggtta aaatatgttt  13440
aaatgcgtca aacgaagcaa cagcaaaata ttttagtgag ttactcggaa aatcaacggt  13500
taaagttgaa actggaagtg aaagcactag tcacagcaaa gaaacaagca ctagtaaaag  13560
tgatagttac agttatacaa gcagacagtt aatgacacct gatgaaatta taagaatgcc  13620
tgatacacaa agtttattaa tatttaccaa tcaaaaacct attaaagcaa caaaagcatt  13680
tcaatttaaa ctttttcctg acgcagatag taaagtcaaa ttagaacaaa ataaatatgt  13740
cggcataact agtaaaagtc aacttgaaaa atacaatgat ctatctgtta aatgggaaga  13800
aaaattacaa agtctaaaaa atataacagt tacagaagaa gaagaaaaag atcttcaaga  13860
taatatagat tcagatttag aagcaatgaa taacgaaaat agcggagtag ataattctac  13920
taccgaaact gataaaatag ctgaaacaga agctaaagaa gtacaagcgg aagaaaaaaa  13980
ctttgatcaa gtagttctat aaaaggagaa tataaaatga aaaaaaagat attaattgca  14040
gttgcggtag cactacttat aattgctggt ggcgttggtt ttaaacttac tcaaaaatct  14100
acacaagaaa ttttgcaatc taaaacatgg acttttaatg cagataaaaa tgacggtaca  14160
ggaacaccaa ccgcaaaatt tagtgagaaa agtttaacac tatcaattat tggacttaat  14220
gatgtttatc aatatgattt aaaaaaagaa aataataaag aaaaaatcac tttcactaaa  14280
aaagatgata tgacaggcga caaagaaatt agagaatttt atatttcaaa aaataatgat  14340
gaatttaaac ttcaagcaat aaataactta gctaaagaag atacaggaaa tgtgaacctt  14400
gtacctaaat aaaagggggag tacgttatgg acaaattgat ttctagtgca attggaaact  14460
ttttaaaaag tacaatgact ggtattttaa aatggatcat gagtattatg actggaacag  14520
tcgatttact agatacaaat ttatcagaaa ttgccaaata ttatgctatt tttctagcgt  14580
tttcaggtgc attagttgtt gcagttgttt tagcaagaat tataacaaca atgttaaaag  14640
aagctgatga tacaacagat gcaacatggg cgaatattgt tatggatagt ttgaaatcgg  14700
cagtatcaat accaataatg gtatttattc aaggtttttt agtaacagca ataacagtac  14760
ctctgattaa atatatcttt gatgacacta aaggtttgtc aatgaaaaca ataaaccatg  14820
caattgatgt ttcaacagga actgataaag gttttggttt aggagtacca ctattgataa  14880
ttgcattctt tttggttgtt atggttgtat tttttgtaaa aataggtgta tttgtagctg  14940
atcttgcctt tttcaattta gcagtacctc ttgtagcagt atcaattgct tctgaaaatt  15000
ttgaatatgc ttcaacatgg tggaaaaaat tagtttatct caatgtatca atcataacgc  15060
```

-continued

```
aaactctatc attagcttta atggtggcta gtttaggact actggataaa ggctggggtt  15120
atcttgcttt tacaattggt ttcggttttt tagttattaa agcaccaaca atcgttcaag  15180
acttgtggca atcaactggt ttaggaaaag caacagttaa cacatctatg agaacattat  15240
caatgatgat gagaaaaaga tagaaaggtt agtttattat gaaaacaata gttttagcag  15300
aaaaaccaag ccaagcgtca gactatgcca acgcttttca aaagcataca aaaaaacagg  15360
gttactttga agtgagtgat cctgttttag caaatgaaac ttttatcaca tacggttttg  15420
gtcatttagt agaattagct agtcctgaac aatatgatac aaaatataaa aaatgggact  15480
tgaaaaattt acctatattt cctgaaaaat ataaattcat tgtacctaaa gataaaaaag  15540
gtcaattctc aattgtatct gacttaataa aagacgcaga tcaaattatt atagcaaccg  15600
atagcgatag agagggcgaa aatattgcgt ggtctatctt gaataaagca aaaattgatt  15660
taaaaagtaa agatattaaa agactttgga tcaattcact tgaaaaagaa tctattttaa  15720
atggttttaa aaatttaaaa gacggttggg aattttacaa cttcttcaaa gaagctcaaa  15780
caagacaaat aagcgattgg ttaatcggta tgaacgcaag ccctttattt actattgaat  15840
tgcagagaaa gggtattaat ggggtttatt caataggacg agtacaaaca ccgacattat  15900
accttgtata taaaagatat ttagagatta aaaattttaa accaacaccc tattttgaaa  15960
ttaatgcaga ggtacaagct ggtgcagata aatttaatgg aaaactagat ccatatatcc  16020
gtttttcaga taaaaataaa ttaaatgatt ttgctaaaga aaaaaatatt aaaagtggag  16080
ttcaagaggg aataattagt gatgttaaaa agaacctaaa aaaatcacaa agccctagac  16140
tattttcgct ttcagattta caaacagaag ttaataaacg gtaccatgca agtgcaagcg  16200
atactttaaa agcagtacaa aaattatatg aacaaaagat tttaacttat cctagaactg  16260
attgtaactt tataactgat aatgaattta attatttaaa agaaaattta tcaaaatata  16320
tttccttttt aaataaagac ataaatttaa acaatacaaa cccaaataag agatatgttg  16380
atagtagtaa agttcaagaa caccacgcta ttatcttgac taaaacagta cctagcaaag  16440
ataattttaa taaattatct gacttagaaa agaaaatata tcaacttgtt ttaaaaacaa  16500
ctttagcaat gtttgctgat ccttttgaat atgaagaaac agttatttta actaaagtaa  16560
atttagctat tttcaaaaca attggtaaaa cacctaaaaa tattggttgg aaagaattgt  16620
ttagcgaaga atcaaaagaa tcaaaagatg atgaaaatct tttaccagca gtaactattg  16680
gagatattgt taaagtagat ttaagtgtag atcaaaagga aactaaaccc ccaatacccct  16740
atacagaggg tactttaatt aaagctatga aaaccgctgg taaagatctt gatgatgaag  16800
aagatcaaga gattttaaaa gatattgagg gaataggaac ggaagcaaca agagcaaata  16860
tccttgaaac tttaaaaaac aaacaatact tactcactga aaaaaataaa cttaccgtta  16920
gtcaacaagg gataacctta tgtaaagcag ttgaattaga acccttactt gctagtgctg  16980
aaatgacagc aaaatgggaa aaagcattaa aacaaatcgg tcaaaagcaa agaacacaag  17040
ataatttttt agaacaaata aaaaaattta ttactaaaat tataaatgac ttaccaaata  17100
aaatgaatga tagctcaatt ttgaatagtc aaattaaaga acaaataacc acccaaaaag  17160
aaattgaaac agaaagtgaa atttcaaatt gtccgatatg taagactgga aaaattttag  17220
ataaaggcaa attttatggt tgctcaaatt ataatgctga tgaaccttgc aaattctcac  17280
tacctaaaaa atggagtgaa aaaacattaa gcaaaacaat tgtgaaagaa ttaattgaaa  17340
aaggcgaaac aaaaaattatt aaaggtttta aaagtaaaaa aactgggaaa aagtttgacg  17400
caaaactaaa actttcagac ggtaaactat catttaattt tgataaagga gaataaatat  17460
```

-continued

```
gaaaaatgaa ctagatgtat tagcaagcga atttcctgtt ttatcagaaa aaggaagtta  17520
taaatattta aaagaagtag ctggaaaagg agagtatttt caagttgcat ggcagaagtt  17580
agaagatgaa tttgtcgctt tatatggaaa gcaagagatc cctattattt ctttaaataa  17640
tgatattctt tttgaggagg aagtttaagt atgccaagta aagaagaagc agaactttgg  17700
aaaaaacaat tagttgaaaa tgcagaaaag aaaataattg aattgactga tagtgatcaa  17760
tttaaaaatt atcttactac attatctaaa tttcactcat acagcataaa taatattaat  17820
ctaatctatt ctcaaaaccc tgacgcaaca catgttgctg gctttaaaca atgggggact  17880
gattttaacc gtaaagttaa taaaggcgaa aaagctatta gaattgcagc accaatcatt  17940
aaaaagttgt cagaagaaga aaagataaaa ctcaaaacaa ctgatgaacg tgctattgtt  18000
ggttatcgtt atatacctgt ttttgatgtt tcacaaacaa gtggagatcc cttaccgtca  18060
gctcgtgatt ttgtaaaaga aaatctttca gaagttgaaa atgttgatgt tttatataaa  18120
tcgttgaaaa actatataaa tcaaaataca gatattaaag tgagtgaaga agtccttagt  18180
gattttgaag taaaaggttt tttcagaccg tctactaatc aaattattat gaatgaatca  18240
gttgataata taactttcaa actcaaaact ttatatcatg aatttgctca tagtcaattg  18300
cacggtttaa attcagaatt tatagatcgt ccaactggat ataaagaaac acaagcggaa  18360
gcagtagcct atattgctat gcaaaacgtt ggaattgata ctagtgaata ttcactagga  18420
tatgttgcaa catgggctaa agataaaact gtaattcaag aagcacttag tgaaattcat  18480
aaagtaagta ataaaacaat tgatatgact aatcacttaa ttcaagaact aggtttagat  18540
caaaacttag caactaaata caagtcatta caaaaagaag caactaaaaa taatagtcct  18600
gaattaaata aaaaaattaa agatactaga gaaaaaatta gtcaaaatac acaaaaagaa  18660
ttaaatgatt ttgctaaaga aaacccaact ttaaaaaagc ctaaaattga aaatgatgaa  18720
caagaattat caagataaaa taaaaaactg acattatcta aaaatagata atgtcagttt  18780
tttatttaac aacctctaaa ctcgtgaagt ttcgatgcta atttctcatt atctttaatg  18840
aatttcatca aaagttcagt tgttattgta aattgagtgt gtgtcttttt ttcttttgtc  18900
ctcaaaattt gaactcctga cggatcagta attgcaaagc tatgaatgat cctgtttctc  18960
gtttcaacta aagagctaaa tatttcttct atatcttttc ctagtttttt tttgttttgt  19020
ttttcggatt cattgattat tgtttttgtt actatctttt ttagatcacc acccatttta  19080
tcaatcaatt cataccaatc atatttatta ttttcgtctg ctcttaatat attttctata  19140
aggaacccat tatttgaatt aaatacatat attgcagtac ctaataattc tctatattct  19200
ttacttgata aggattggtt tgtgtggttc tgttgcaaag tctgtagaat acttcagaac  19260
ttacaacgag aataagttta caggcaatat taccgcttgg aaaagttata acgaaacagt  19320
tccagaaaac tacaaaatca aatactctac tcacaacaaa tatagtgggg ggtggaatta  19380
ttggtcacat gaagtctatt ttcattggac agccggtggc aaataaacac caaaaatatt  19440
gataaatagc ttaaggtgaa aaatctgaaa tttccgaaaa atcggttatt tcagattttt  19500
tattatttgc tctttaccta tcagctatgt ttaactttat tcaggatcac ttcaaaagtc  19560
tcgaaggtat ctatatctaa ctgacacaac caaagcaagt tctttttttc cttataggtc  19620
cagtcaatag tgggattgga ggacatcaga ttattatatc ttgctctttg ttcacttgaa  19680
gccagttgcc atcgtttttt aaatatcatt tcttcttcca ttattgatcc tccaaaaaga  19740
gcgctgcctg aaacttctat aacgggcagc gcaagtctaa tttatgcaga tcagtatagc  19800
```

-continued

```
ataacaaaca aatatgaaaa aaattagaag gtagtaaagg ttctgccgtc ttttgctttg  19860
cttccgttct taatgtgttt cgttatggtc gctctacata atttttcatt tattacacac  19920
tcgtttattg tttggtactc ctttacattg ctattgatca attgattaac atactcaaac  19980
ttatgtgaag agcaagggcc acagaatcga ttctgcggcc cttagatttg ttttaccata  20040
taaatatcta ctttatttaa aatttatcgg gattaaccta gatcacgtta tgttgagtta  20100
taaattattg ttatttaatc caacacggtt ataaatttca tccactatat catttgctat  20160
tttatctgta gagattacaa aatcgctact tttcataatc aattgttcga attctctttt  20220
gtcatttttt atttttttccc aatcatgatt gcttttccca aaggaattat tctctctaga  20280
taaaatgcgc tcatgcatta tttctattgg tgcagtgagc gtaataataa agtctagata  20340
tggatagatt tctttttgat taatagttgt tccggaaaag aaaatatctt catcgttata  20400
cttctgtata tagttaatga ttctatttgt atccatttta cgatcattac tcatatcatc  20460
catatgaatc caaccatcat aatctaaatc tatactatgg ctataggatt tacttatttg  20520
tttgagaata gttgatttcc caactccaga catcccagtt aataacactt ttaccatatc  20580
tctacctcca actaattttt atatgatcat accaatttg aatacttatt accaaaaagg  20640
ttctgttgca aagttttctg ataagtctat tttagtgtaa aatgaataaa aatgacagcg  20700
aggatatatc aatgaactat tttaaaggta aacaatttca aaaagatgtg attattgtcg  20760
ctgttggtta ttatctacgt tacaatctaa gctatcgtga aattcaagaa ctcctttatg  20820
atcgtgggat taacgtttgt cacacaacta tttatcgttg ggtacaagaa tacagtaaag  20880
tcctctatca tctctggaaa aagaaaaata gacagtcctt ctattcgtgg aaaatggatg  20940
aaacttatat caaaatcaaa cgtcgttggc attatctcta tcgtgcaatt gatgcggatg  21000
gattgacttt agacatctgg ctacgcaaga aacgggatac tcaagctgct tatgcgttct  21060
tgaaacgact acataaacag tttggtcaac caagagtaat tgtcacggat aaagcgccct  21120
ctattggttc tgcatttaga aagttacaga gtaacggttt atatactaag acagagcatc  21180
gaaccgtgaa gtatctcaat aacctcattg agcaagacca tcgaccaatc aaacgacgca  21240
ataaatttta tcgaagtcta cgaactgcct caaccacgat taagggcatg gaaacaattc  21300
gaggaatata caaaaagaac cgaagaaatg gaacgctctt cggattttcg gtatctactg  21360
agattaaggt cttaatggga atattagctt acgaacaaga aggattataa accttgtatt  21420
tgatttttaa actttgcaac agaacctaat tagaaaatat ttcacttgtt gccaaactta  21480
caaactaata tagagaaact aaaaaaagtg tgatagataa gaatataatt tgatataatt  21540
agttataggg ttcatttaat gaagaatagg aagaaataaa aatatgtcag ttgatagtta  21600
tttagcaaat ttagcaagtg aaatggtaat tagagatagt aaaaaagagt ccatttctct  21660
ttcaatttca actctacatt ctagattaaa ggagtatttt gggaaagata ttatagatgt  21720
aataaaattc ggctcatata caaggggaac aatcttacct agaagatatg atgataaatc  21780
cgatgtggat atcatgattg tttttaataa tgactatgat tataagcctc aaacttttct  21840
agatcggtta aaaaaatttg ctcaacagaa atatagcact tcatacgtat atcagtctaa  21900
tcctacaata gttttagaat taaatcatat aaagctggag ttagtcccag ctgttaaaat  21960
ctattcatgg agtgatgact actacaacat tccttataac tcttcttctt ggttggttac  22020
tagacccaaa gcttttgata accttttagt agaatgcaat aaaaataatt taaataaaat  22080
caaacctatt gtacgactaa taaaacattg gaatattgta aataactaca gagatgctga  22140
ttcatatcaa ttagaaaaga aaattgcaga agaaatgaaa tactcatatt tttcttgttc  22200
```

-continued

```
aagttattcc gattacataa aacaagcttt acaagtaatc agattgtaca gtagcgaata  22260
tcgtattgat ctagcaatct ctagaatcga taaagcttta aatcttgaag cggaaggata  22320
tccttattct gcagaatctg agataaagaa agtttttcca ggtatataat atatgagcaa  22380
acgtgatgat gtaagtcggt actatgattc gaatgcagca gttcagaaag ttgttactta  22440
ttcttttata gttaatatcg taggttctat ttttacctta ttttcatctg ggactttttt  22500
tcactttata atccttttac agtttatagc ttcttttata aatatacttt ttagttggtt  22560
aacaaatttc attttttttc cagctgctga gagagcaaga agaaaaactt taatagataa  22620
cgcttttgat ttagatacta ccatagatga aacagacggt tactataata atgacttgtc  22680
tccatctgtt gaaaaattaa tactaaatgc ttttgaaagt atctatttta ctctaaatct  22740
atcccagaaa atgattccaa gagaagctat aaaatcgttg ggtgctataa ttgtattaat  22800
aattacttta aatgtcttca ctacaaatga atttcctctt atagtactgc aagtggtctt  22860
ttcgagctct tatattcttg gaatgattaa tctcatatta tattactatc gcttaaaaag  22920
tttgtacgat gatttctata aatgccttat tgcggaaaaa acttgctctg atattacaat  22980
tatttatttg gttagtcttt gcgtggaata tgaaataatt aaaggtagtc aacaaattaa  23040
aatatcatct aaattgttta aagaactgaa tccgaagtta tccgctaact gggataagct  23100
caaaacaaaa tgtatatatt atcataacta acaaaaaaat cattcaatgt atagtaatta  23160
ttgaatgatt tttttgttat tgttaaatag tttgctatga atagtcagta aaaataaact  23220
tttataaaat acctttattt aataagctaa accttctttt ttgcgttgct atactaattc  23280
ctgtttttcg ctcaatcatc ttgttagtca ttccttgctg ctttaactca taagcaaatt  23340
gaatttgttc cttggtaaat ttttgagggc gtccttcttt aaaatttgga tcatgaattt  23400
tagcaaagtt ttttccttcc tgagtcctgg ttacaataag gtctcgttca aactgcgcaa  23460
aagcactgaa gatggtaaaa atcagctgac cagtaggtgt attatcaata agaccaatat  23520
ttaatatatg aactttaatt cctctattaa ataacgattg aacaatttct aaaacttctc  23580
gagtatttct tgctaaccta tctaactttg tcacaattaa agtgtcacca tcctctaact  23640
ttttaagtac tagattaaat tgtggacgtt caactgtagt tccagtaaac ttttcttgga  23700
aaacttcttc tgctcctgct tctttcagaa cttcaatttg agattctaat ttttgttcaa  23760
aagtactgac acgtgcatac ccaattttca tattatgtcc tctatttata accctaagtt  23820
gtgagctggt ttttcgtttg taccataact tgaaagcact tatataaatg aacatagaat  23880
aaattacggg tttatgaaca agaaatgcaa atgattttaa taatcttaat aagaaaagaa  23940
gagtgttcaa aaaatgacca ttttatggac acaaagataa aaaagaaaaa cggaaatggc  24000
tgtttttctt ttttatcttt gtgtctaatt atttaaaagt tgtccaactt atgacttacc  24060
tgtcacttta agcagatatt cccattaata ctttgatttc agtagacacc gaaaatccga  24120
agagcgttcc atttcttcgg ctctttttgt atattcctcg aatagtctcc atacccttaa  24180
tcgtggttga ggcagttcgg agacttcgat aaaatttatt gcgtcgctta ataggatggt  24240
aatcttgttc gattaaatta ttaaggtatt taacggttca atgctcagtt ttaatgtata  24300
aaccgttttt ctgtaacttt ttaaatgcag cgccaatcga tggcgcttta tcggtgacca  24360
taacctttgg ctcaccaaac tgtttccgaa atagttttaa aaaaggcata ggcagcttgg  24420
ggatctcgtt tcttccgcaa ccagatatct agagtaagtc catccgcatc aatcgcacga  24480
tagagatagt gccaatgccc ttttattttg atataggctt catccatttt ccacgaataa  24540
```

-continued

```
aaggactctc tatttttctt tttccagagt tgatagagga ttttactgta ttcttgaacc  24600
caacgataaa tcgtagtatg acaaacattg attccacgat catatagcaa ttcctgaact  24660
tcacgatagc tcagattgta acgcaaataa taacccacag cgacaattat cacatctttt  24720
tggaattggt tgccattgaa atgattcatc ttcctgcctc gctatctttt tccttacatt  24780
ttacactaaa tctaggaaat tagaaaactt cgcaacagaa cctaatattc aatattcaat  24840
aaccgatgcg aataacatca agggaattga aggggttctg tactggatta agaaactcga  24900
agagaaatag gactcttcga gttttcgcag tggcatgaag tttagaatat attcatagca  24960
gtagaaagtt caatatataa atttatgcgg cctttaaata ttgcgacata acacaaaatt  25020
caacttatcg aagttcggtt cttgaaaatg tcaacatgcc aatgagtaaa aatacaatta  25080
tatatgttaa tgtagcaaaa accatttggc tatttgaaag tagagttagt ttttctattt  25140
tattaggcaa ggcaagctgt gtaggaaaat ttaatagatt tatgggattc cattttaaaa  25200
tatttatttg ttttatcatt ccaaacatta ctgtgctaaa tacatttagt ataaaatatc  25260
cagttacacc tatcaaaatg gcaacatttg acttctttaa cattgttgtt attaaaagca  25320
caacacttag taagagccag agtgagagaa aatttgttaa attagtcaat atccaatatt  25380
caattactct ttgatgagaa tttactaata aatcccctaa tttaatttct gagaaaaaaa  25440
tagttttgtt aataaaacta ataaacatta ctaaagtata caaaaaaagt gagtatgaaa  25500
aaatggttaa ccatttactt ataatgattt tttgtctgga atatcctttg ctcagcagca  25560
gtttcagagt accatattca aattccatag atattatagt agatgctttt actattataa  25620
gtagaggaat aaaacttaac gatgcataat tagaaataaa taattctttt ggtataaaat  25680
gagtggggta ttttacggat agtaaggcaa caaaagtatt ttgaactatc aaaaaaataa  25740
tgaaagccca agaactcttt tgtttaaaaa gtttaaccat ttccttttta tattgattaa  25800
tcattgtcta gctccctttc agtaaataaa ttgtaaaaat ctatcttcta aatcttttgt  25860
gtcttttttt ataaattttt tgagtttaat attattttct tttatcaaat ttaagaattg  25920
tttctcgtcg gattcatcta gaagaatatt tataatcgtt tcattttttg aatatggaat  25980
gttattgaat ttaagagttt taaataattt atctttttgg tcagtaatta agcagaatat  26040
ctccttttc ttgaatgttt taaaaggtaa attaagtatt gatttgccgt cttttataat  26100
aactaattgg tcagctactt tttccaactc acttagtaag tgactagata ttacaaaagt  26160
tactccttga tttttttat taattattat gtcacgtaag tcatgaattg actgaatatc  26220
aagtccattc attggttcat ctagaataac tagaattggt ttgtttaaaa gagcgatcgc  26280
aatcgcaagt ttttgcttca ttcccaaaga ataggagctt gctttctcat ctataaaagt  26340
cgttaacttc aattggtcaa taatctcatt aatgtcggat tgagcttcct ttccttttag  26400
aatagaaaag cattgtaagt gctctctacc tgttaaaaaa ggataaattc caggttcttc  26460
aattaaagaa ccaactctag acagtatagg gtggttgttg aaaagtatgt ttattttaga  26520
aatctctatt tcgccactaa atttgattaa tcctagtata gatttcataa tagtagtttt  26580
acctgaacca tttgctccaa ctaaaccgat aatttgagat gtgtttccct taaatgaaac  26640
attttttagt attttttttt ttcttatttg agtgcttaaa ttattaacac taaaaacttc  26700
gatttcttta tccaattact tctcctattt tggttgtttt ccattttgag gaaacttact  26760
taaactactt ttacatgtgc tattgatacc aaattttata aatcactgaa tcaaatcttt  26820
atattattta ttatctttaa tatattttaa aagacaataa atcccaccaa caaggcaaga  26880
aaaaccatat tttaacataa agaatggttg aattaaatat cctttgggaa atattatgtc  26940
```

-continued

```
acatataatt agagtaatta aaacacaata tgcactatat aaacttattt tagttgttct  27000
ttcatctttt ttcccaatct ttgtggaaat tgttacgaaa aaaactacac ttgacataac  27060
aaatataaaa cttaagccta aaagtatatt ataattgttt gctgaacctt ccgcccactc  27120
ttttaatgag taaaaaagag attcagaaaa ggtattgata ttttcattct tcattcttat  27180
gtcctccagg ttcgtaggta aaaatttttg ttatttcaac atcaaaaaag tttgcaattc  27240
ttagcgccaa taacaaagaa ggtgtatagt tccccttctc cataacaaaa attgtttgtt  27300
ttgatacacc aactttatct gccagatcct gctgagataa acgagatagt actctgtact  27360
tatatacaga gttactaata gaatcttgaa attttttttt caaacatttt cctcctatct  27420
atgataatta taaactttag ttatctaaaa gtaaagtaaa gttatatatt tgcggcagtt  27480
ataaaattta aaaaatcaca aaactattaa atatagacaa caaattcttt aatttatgaa  27540
acaaaaaata tatataatcg acatttatgc atggaattaa tgcataattg gaattgtatg  27600
gaatattttg ttttagtgct aatattctat atgcttttct acattcaaac attacattta  27660
aaagtctttg tgttgtttgg agatgattga catggaataa aatgaagagt aaaattaaat  27720
tattataata aggaggttca tatcatgaac aaaaatgaaa ttgaaacaca accagttaca  27780
tggttggaag aagtatctga tcaaaatttt gatgaagatg tatttggtgc gtgtagtact  27840
aacacattct cgctcagtga ttactgggga aataacgggg cttggtgtac actcactcat  27900
gaatgtatgg cttggtgtaa ataagttaat aacaaatttt taattaatta aggagcttta  27960
cgatgaaaga aaaaaatatg aaaaagaatg acactattga attacaattg ggaaaatacc  28020
ttgaagatga tatgattgaa ttagctgaag ggatgagtc tcatggagga acaacaccag  28080
caactcctgc aatctctatt ctcagtgcat atattagtac caatacttgt ccaacaacaa  28140
aatgtacacg tgcttgttaa ttaggagtaa aaaatgaaat ttaacaaaaa tgtttttcca  28200
gaaattaatg agacagactt tgataataat ataaaaccat tattggatga gttagagagt  28260
agaattacta ttcctcaaga agaactatcg ttttcgtcaa taaacgatga tttatttcgg  28320
gagttgacta gaaatgagga atatccctac cagagtatat gtacaatagt ggcaaatata  28380
gttatggatg atggatctga aatttggaga aaagatattt ttgttgattc aaactctgta  28440
agagaagccg tttgtgatat tttgtcacaa acgcttttct tatattttat aagatgtttt  28500
tctgaacaaa ttaaggatat aagaaagacc gatgaggata aagaatcaac atataataga  28560
tacattaatt tactgttttc ttctaatttt aaaatatttt cagatgaata tcctgtactc  28620
tggtatagaa cgattagaat tattaaaaat aggtggtatt ctataaaaaa aagtctttta  28680
cttacacaaa aacacagagt agaaatcgat aaacaattag atataccaca taaaatgaaa  28740
ataaagggat tgaaaattgg gggggatacc cataatggtg gagcaacagt aactacaata  28800
ttctttgaaa aaggatataa attaatttat aaaccaagat ctacatcagg agaattttca  28860
tataaaaaat tcattgagaa gataaatcca tatttaaaaa aagacatggg agcaattaaa  28920
gcgattgatt tcggggagta tggattttca gaatatattg agtgtaatac tgatgaagaa  28980
gatatgaagc aagtgggaca attagccttc tttatgtatc tattaaacgc ttcagatatg  29040
cactatagta atgtgatatg gaccaaacag ggacccgttc caattgattt agaaactcta  29100
tttcaaccag atagaataag gaaaggttta aaacagtcag aaactaatgc ataccataaa  29160
atggagaaat ctgtttacgg cacaggtatc ataccaattt cgttgagtgt aaaaggaaaa  29220
aaaggagaag ttgatgtagg tttctcaggt attagagatg aaagaagctc tagtccattt  29280
```

-continued

```
cgagtgcttg aaatattaga cggatttagt tcagatataa aaatagtttg gaaaaaacaa  29340
caaaaaagta gtagttcaaa aaataattta attgtagacc acaaaaagga acgcgaaatt  29400
ttacaaagag cacaaagtgt tgttgagggt ttccaagaga cttctaaaat atttatgaaa  29460
catagagagg aatttataag tataatacta gactcttttg aaaatataaa aattagatat  29520
attcataata tgacatttcg ttacgagcag ttactgcgaa ctctaacgga tgctgagcca  29580
gcacaaaaaa ttgaattaga caggctactg ctatcaagga ctggtatact aagtatatca  29640
agtagtccgt atatatcttt gtcagaatgc caacaaatgt ggcagggaga tgtcccttat  29700
ttttattcta aattttctag taagagtatt tttgatacta atggttttgt ggatgaaatt  29760
gaactaactc ctagacaggc ttttattatt aaagcagaat ctataactaa tgatgaggtt  29820
gattttcaat ctaaaataat aaaactagct tttatggcta ggctttcaga tcctcataca  29880
actaatgata ataaattaaa taaaaaagtt attattgaat ctaatcagca atctaattct  29940
agtgaaagtg gtaataaagc gatacttttt ctttcagatt tgttaaaaaa taatgtttta  30000
gaagataggt atagccatct acctaaaacg tggataggtc cagtggcaag agatggagga  30060
ttaggatggg ctccaggggt tttggggtac gatttatatt caggaagaac aggtccagcc  30120
ctagctttag cagccgcagg aagagttctg aaagataaag attctattga attgtcagct  30180
gatattttta ataagtcgtc acaaatatta caagaaaaaa catatgattt tagaaattta  30240
tttgcatcag gaataggggg gttttcaggg ataacaggac tgttctgggc tctgaatgca  30300
gctggtaata tattaaataa tgatgactgg ataaaaacat ctaatcagtc tatgctcttg  30360
ttgaatgaaa acatgttaaa agttgataaa aattttttg atttaatttc gggaaatagt  30420
ggtgctattg gaatgatgta tttgacaaac ccaaattttt atttatcaag aagtaaaata  30480
aatgatatat tattaactac cgattgctta attacagaaa tggaaaaaga tgagacatca  30540
ggattagcac atggagtatc acaaatatta tggttcttat caataatgat gcaaaggcaa  30600
cccagcagtg aaataaaaat aagggcaaca atagttgata atataattaa gaaaaaatac  30660
actaattcat atggagaaat agagtgctat tatccaacag atgggcatag taaatctact  30720
tcttggtgta atggaacaag tggtattttg gtagcttaca tagaaggata taaggcgaat  30780
atagttgata aatccagtgt ttatcatatt ataaaccaaa ttaatgtaga gcaacttcaa  30840
catgataata ttcctataat gtgtcatgga agcctaggtg tatatgagtc attaaaatat  30900
gcaagtaaat attttgagat cgaaacaaaa tatttacttg atgtgatgag aaatgggga  30960
tgctcgtcac aagaagtatt aaaatattac ggaaagggaa atggtagata tccattaagt  31020
ccaggtctta tggcgggaca atctggagct ttactacatt gttgcaaact ggaagataat  31080
gatatctcag tatctcctat atctttgatg acataaagta aaatctttct aatctattaa  31140
ttatgaagaa attaaaatca acttttcaag tagcacaaac tgaatgtgga ctttgctgtg  31200
taagaactat attagattat tttggttatg aaactacagt aacaaaatta agaatattaa  31260
aggaaccagg tagagatggg tcaagtttta atgatattag aaagttactt gaacgttttg  31320
gagttgactc caaattatat aaggtaaaag ataatagaat attttcaaca cttcagttac  31380
ctattattat ttattggaag aacgttcatt ttgtttgtgt ggaaagaata tcaaagaaaa  31440
cagtaataat aatggatcca tcagtaggta gaactaaaat gagcctgact gaattttttc  31500
aaaatttttc gggactaata ctaatcccca aaaaaaatac tgaaaaattt aaaaaaaata  31560
ctgataatat tataaacacc tggagaaaaa gttatatttg gccgagtaaa acagcctctc  31620
tttatatgtt aacaggaata ttaagcttgt ttattatagc ttcttcccta ttattacctt  31680
```

-continued tggcaactca gtatagtata gataatttaa tgaaagaaaa tttttctctt attaaaatta 31740
tttcaggatt aggcgcattt tctattttta tgtttattgt ctattatttt agaaccatgt 31800
tgtcaataaa aataatgtat aattttagct ggaatttaat aaatagagcc tttaccagaa 31860
tattatcatt accagcgaag tactttactg taagggcgcc aggcgaaata acgtatcgac 31920
tgggtgccat gaataatatt agagaagtat tagggcctaa gctagtacaa tcagtattag 31980
atgtttttag tactctatta ttattgatat attgtttttg tgtttcaata gttttaggag 32040
gtgtaatttt atcagtatta cttgttatac tcttattttt agtagttact aataactatg 32100
tcactgcagc gacagataaa gaaataagag aaggagggga tgctcaaaat attcaattag 32160
atgctcttgt ctcaattaat aatttaaaat tgggaggata taaggaaata tatcttaatg 32220
attggcgaaa taattataaa tcatttttaa aggcaacagc aaaaagaatg aaaattcaag 32280
atggctatat tggttcatct ctttatatga ttcaagcttt tatgccttta ttactgcttg 32340
taataagttt aaaaatggtt caaataggaa caatttcgtt aggagttgct ctatcaattc 32400
aaacaatttc atccatgatt tttatatatg ctaattcaat tttcaacact ataacgaact 32460
tagcagtttc cacgagatat attgaattag cagatgatat atttgaatat ccattagagg 32520
atgatagtgg aactgaaaaa tgtggaatta cttttggaag cattgttatg aaagatgttg 32580
actttaggta tactccagat agtaaagatg cgttaaaaca tatttcaata gatatcaatg 32640
ctggacaaac tgttgcattg gttggaatat caggttctgg aaaaactact ttaggtaaaa 32700
ttataagtac attattcaag cctagtaagg gacaaatttt ttttgatgga gtagaaataa 32760
aaaatcataa tctagacagt ttgagaaaat atgtcggtta tattcctcag gaagcacact 32820
tacacaatcg aactataatg gaaaatttgc tcctgggttc aaattaccct caacaagaag 32880
ttttaaatta ttgtaattct ctaaaatttc ttgattttat tcaagattta ccaatgggat 32940
atcagacagt tgtttcagaa atgggaggga atctctctgg aggacaaaaa cagagaattc 33000
atattgctag aatattatta caaaaaccaa aattattagt catggatgag gctacttctt 33060
cactagataa tatatctcaa tcagaagttt atgaagcttt ggaaaaggaa attaattgta 33120
caaaagttgt aattgcccac agattggaaa ctatccttaa agcagataaa atttttgttt 33180
tagagaatgg tagaatcatt gagcaaggaa atcatgacga gctattaaat aataaaggaa 33240
tatataagaa aatatatact tctaagtaat ttattatttt ataaataaaa tactataaaa 33300
aaagaaagaa ttatttttgt ggttctgcca catataagta gttaggttag tgaattttgg 33360
acccatcaat aaaaaaatta gtagacagca taatagagtt ttataaaaaa gatatttact 33420
tggcgtacaa agaattagaa agagaaataa aaaatattga caaaacgatt tacaatactt 33480
ctaatgatga aatactgagg atatttaaag aatctttaat ttcaataatt acagatgata 33540
tatacagatt atcaattaaa acattcattt atgaatttca caaatttaga attgataacg 33600
gattcccagc agtaaaagat tctgagagcg catttaacta ttatattagt acatttgatg 33660
taaaaactat tgcgcgttgg ttcgaaaagt tcccgatgtt agaaagtata atttcatcaa 33720
gtataaagaa tgattgtact ttcatggttg atgtgtgtgt taattttatt cttgatttat 33780
ctgaatgtga aaaaataaat cttataagtg aggattcaag attaattact atttcttcct 33840
ctaattccga cccccataat ggaggaacaa gagttttatt ttttaggttt cataatgggg 33900
acactatttt atataaacca agatctttaa cagttgataa actcattagt aatatattcg 33960
aagaagtgtt tgagtttgat gcaactaatt caaaaaatcc gattccaaaa gtcttggata 34020

-continued

```
gaggaaccta tggttggcaa gaatttatag agaagaaaag cataagttct tctgaaatca  34080
agcaagcata ttataattta ggaatttttt catcgatatt tactgtccta gggtcaactg  34140
atatccatga tgaaaatttg atatttaaag gtacaacacc atattttatt gacttagaga  34200
cagccttaag tccaaggatt agatacgaag gtaatgaaga aaatttattt tatagaatgt  34260
cttcgtcact tttcacttcg attgtcggta caacaattat tcctgctaag ttagcagtac  34320
attctcagga aataatgatt ggggctatta atacccctgc taaacaaaaa acaaaaaaag  34380
atgggtttaa tataataaac tttggtactg atgctgttga tattgctaaa caaaatattg  34440
aagttgaaag aatagccaat ccgatgagga tcaaaaataa tatagtgaat gatccgttac  34500
cctaccaaaa tatatttact agaggattta aagaaggtat aaaatctatt attcttaaaa  34560
aaggatctat aattagtatt cttaataatt ttaatagtcc tatacgttat ataatgagac  34620
caactgccaa atactattta attttagatg cggcagtatt tccagaaaat ttatatagtg  34680
aacaaactct taataaaact ctgaattatc tcaaacctcc caagattgta gaaaattcgc  34740
ttatctcaaa acaactcttc ttagctgaaa aaagaatact atctgaagga gatattccca  34800
gtttttatgt actaggaaaa gaaaaaaata ttagagcaca gaattttatt tcagaacaga  34860
tatttgaaga aactgctgtt gataatgcaa tccaaatatt agaatcaata tctcaagatt  34920
gggtaaattt caatgagaga ttgattgcag aggggttttc atatattagg gaacaatcaa  34980
gaggatatct ttcaagtgac tttgaaaatt cagatatatt taaaagttct cttactgaaa  35040
ctaaaaaatc agggtacacc gcaatgctga aaactatcat aagcatgtct gttaaaactt  35100
cagaaaataa aaaaataggc tggctacctg gtatatatga cgattatcca atttcttata  35160
tgtctgcagc attttgctca tttcatgatt ctggtggaat aattacttta ttggagcatc  35220
acttcggtca ctgtagtcca gaatataacg aaatgaaacg tgggttatta gagttaggaa  35280
aaatgttgaa aattaataat tcaaatttat ctattatttc gggttctgag tccttagaat  35340
ttttatatac ccatagagaa gttgaatgtc ttgaactaga atatatactg aataattctg  35400
ctgagattat gggagatgtt tttttgggaa aattgggact atacttaatt ttagctagtt  35460
acttaaagac agacttaaaa atttttcaag atttttcgat aatttgtcaa aaaaatcttg  35520
aatttaaaaa atttggcatt gctcatggag agttgggata tttatggact atttttagaa  35580
tacaaaataa attgaaaaat aaaaatgctt gtctctctat atatcatgag gttcttaata  35640
tttataaagg caaaagaatt gaaagtgttg gatggtgcaa tggcctttca ggaattctaa  35700
tgattttaag tgaaatgtct actgtacttg aaaaaaacca agattatttg tttaaactag  35760
caaacttaag cacaaaatta aatgaggaaa gcgtagatct ttcggtatgt catggagcat  35820
caggtgtact tcagaccctt ctttttgttt acagtaacac aaatgataaa agatatttaa  35880
gcttggcaaa taaatattgg aaaaaggtgt tagataattc tatcaagtat ggcttttata  35940
atggagaaag ggataaagat tatttattgg gatatttcca agggtggagt ggttttacag  36000
attctgcttt attattggat aaatataata ataatgaaca ggtatggatt ccaataaact  36060
tgagttcaga tatttatcaa cataatttaa acaactgtaa ggagaaaaat tatgaaggcg  36120
atggttgcca taaatcctaa atttaaacat aaaataaaat atacgaattt gggaagtaca  36180
aagtttgggg agacaactat taattttggg ttggttgatt tacctaaacc aaaatttgat  36240
aataaaagta aggataatag taattttgtt cttgtaaaaa ttaatgcaat atcttgtaat  36300
tttagagata aaggaatatt attagataat tatgaaaaac ttattgctag tgatcaatta  36360
taccttcctt ttgggtcaga attttcaggg atagtggtag attatggtac taatgtaaac  36420
```

-continued

```
tgtttctcta ttaatcaaag agtaattcca gactgttcct atcctaaaga aaataataat  36480
atacgtccag gaattccgac aaactttgct tcattgggtt ggctaagaat tcataaagat  36540
aagctattga atgcaccaag agaattaacg gatagcgaag cagcttgttt tcctttaggg  36600
gttcaaactg cccattcaat gatacgtcgt tcaaatattt tacaatctcc tgatcctaaa  36660
cccctaatat ttagtgcaaa gtctgcaact tctttgttca ttattaaaga attactggca  36720
catggtataa aaccgacatg tttatcaact tctaaatgga accaaaaaga gcttaaaagt  36780
attttgggat ctgaagtaag aaatgattat tcttgttttg aaaaagatca tacttttttt  36840
acccatgtat ttgatccatt ttttgatgtt aatattgaaa aagctgtaaa tttactatca  36900
atatacggta cttatataac ttgtgggtta aatagtcaac atccatccct ttccaatagc  36960
aaacttgatg aattagaatg taatttaaga agttcaatac ttggcgctat tgttaaagat  37020
atttcaatta taggaaactg tttagggata aaaagtgatt tagaagaacc aattgccatg  37080
ttagagtcta aaattgattt aaagccaatt ttagattccg aatactcact atcagatggg  37140
ttaaaattta ttgaaaaatc attttttgat tcatcaaaat ttggaaagtg tgtgctgaga  37200
tatgatactt cttatgatac ataactatac gttattttga gagacaccga acaaatgaaa  37260
aaccatttta gatcccaagc gatcattata atggtttttt tatatacgtg acatatctgg  37320
agtaatgatg tctacttgga acttttcatg aaagtcacat ttaaaaagtg taaaaccgta  37380
gacaccagag tagcgtcata gatcattttt agtcgtacct tcaatgtgaa ggtaaacaag  37440
atgctttttg aattcattag gacattagtt cttttacaaa gatgaataaa aggctaaaca  37500
tctttactat tgccctatac ttaagactta agcatgtata cccattaaca tcatattttc  37560
agtcggcccc caaaaaacta agggtgtccc actaatccat aaaagtatcc tagaaaattt  37620
agactgtttg aattgaataa agatagaatt ttttggatgg ccaacagagc atacctggtt  37680
ccctttatag ggattgtaat attattgaat ctttaagagg ccaactaaat tgagcaacca  37740
aagaatggaa ttatgaaata ttattaacga tttttgaaca tggaaatagt aaataacatc  37800
ctactttatg cttaatattg ggtattactt tgtcaaatta tgatattttc ggaaaattat  37860
aaacgtaaag aaaaaagtat actcttaact tacaacatga ttattaagaa tgtacttttt  37920
atttaaaaat atttttaact gattatttag aactttttat cttaattgac aaaagcttcc  37980
atctataaac tcagatagtc ctatctagta ttatggtaaa aattctcaga atatcttgtc  38040
ttcaagtctt caatatctag atgatgctcg gataacattt cttgtaatgt ctcgtcagag  38100
atattttgca aattatagga atgtaaatta tcaataaaac tttttatatt attttttaaa  38160
gacctcagtt ttccctttct gataatttca acttcatgct caaaatctgc ttgatatgag  38220
agctttttcg tcggaataat aagaaatctt gatacagata cagtatcacc atattcagat  38280
ttaaaccaag cacaatggtt attcatttga cctgcttcat gcttgctaat ttcttcacga  38340
gtatcggaca cctgattttt acattcaaag ataaagtaat ggttatcaac gccacaccaa  38400
aggttatcag ggccttttct tatgtcttta tcaggtctct gactaataaa acccaagata  38460
tcgccaattt tctgcaaaga tgcttcaaat ttatttgaat ttactccaaa agacaagtta  38520
tctaatattt catttgtagt taattgtaat tcctcatagt tctcaaattt tattagaaaa  38580
tctctaactt tagatagacg gttttggtct atataagata ctttctgata tgtaactcct  38640
gttttaggct ttaggagttg attgttattt ttaaaagcaa ttttctgcag tttatttgat  38700
ttaattcttt ctttttata atagaatctt gctagttgct gcaaatacca gccttttcc   38760
```

-continued

```
aactcatcac aggtgtattt atcaatatag ctttgtagct tttcacaagc agatttataa  38820
tcatctatca aaaaagtttt ctcgatatca cgttctattt ccagtttttc gtataagctg  38880
aagtcagtag tataatcagt tattgttgcc atctcatcta cataatattg cttccaactt  38940
tcgtctcgac ctgcactttg cttaataaga gatttaataa tctcaaaatc atcttgattt  39000
tggtcctcct cgtcttcatt cgtcatttct gcaatagata atcctatatc aatttgtttt  39060
tttgtctgtg cagaaaaata ttttctggag acaatacttc tgatgaattt tactaaatct  39120
gaaccaatta ttataattac acagtaatct ttttcaccac gaacaccccg tcctaatcct  39180
tgttctattt tttgtgcaat tcttttattc attatctcac tagaaggtcg gcatgcttct  39240
tcatatctat cagacaaact gttaaaatat ggaatagaat caataattaa aattcgacag  39300
gtctcatctg gtaagtcaat accatcatat ctattattta ttactaaaag attttgaaga  39360
ctattgtttt ttattttatc tatcttttcc attatatttt gtgaagttgc gacagtgcct  39420
cctgctactt gatactgctt tgctttagct gtactcggaa ccaatgcaac accaccaaaa  39480
ttattatatt ttgccttaga gaacttagta ataataagat ttctatctaa gttatcacgg  39540
attaaagaag gaacaataat catcttttct cctgaccatt tttgagaatt agtaaccaga  39600
ggacttttaa cagcgttaat gttaaagtcc agtcctttga taaaaaatga atcatcttgt  39660
gtagttgcgg acattaaaat tctatgtttt gcttttgaaa atgttggaaa atcattcaca  39720
ttcgggtagt aaggtgatat ttcaatttta gatgaagtaa tataacaagt gtaatgctca  39780
atggagtctt tcaaaagagg ccatgaaaat tttacttgat tatcgtcaat gtgatgtgaa  39840
agaatttcta aaatgtcact tttttatca taccagctcc aatagggcac attcatcaga  39900
gtgttgtagt ttccgttttt aatatctaag aagcttcctt ccccttgttc aattaaatca  39960
ttttcaaaaa gtgtaagcaa tgaattatac aaattttcat tttggttttt gtcaattgat  40020
attgagaaag catctttaat tgaatctata caagagtgtg aatcatctag gataatcgtt  40080
ccgactggag tgaatttatt gttagtaccg aaaacagaaa gtccattaaa taatttttga  40140
gcatgagtga ttaatatttt ttctccagaa ataaattcat ctgggacacc tatatcttct  40200
atagtacagt aaccaatacc aaatttttcg gcttcggcac agacctgtga aactaaatga  40260
atattaggac atacatatag acaaggacct tcattactgt ttattacaga ctgcagtatt  40320
aacaagccaa tgagggtttt ccctgttcct gtatgaagtt taacaattaa atcccgctct  40380
tcctttcttt gattgtacca tgattcaaga atttcagtct gagcaggtcg taaaggcccc  40440
ttatcacttt ttctatctat tgtttcataa atatcaatgg gatttaccat cttttctatt  40500
tttttcatat ttaatttctt tgaaaaatct accatattaa acctccatta ttaactataa  40560
tttattatag tattttagac tcactaatga aagaagaaac ccatttttgt aaagataaaa  40620
tagtaagata aatcttacta ggcacatttt taaagtttgt atatataata ttatcttact  40680
ttcgggggaa atcgaaaaaa caaatagtag tccgcttctt caatttttta tatatgttta  40740
gaattatctc ctcatcttta atcatagttg gttcacaaca aaattttatg actttcggaa  40800
aaattacgat ttttcgtaca cttatatcaa gcgaaaaccg tactgttgag cgattttata  40860
tttatagagg gtgaaaatcc gcaaaaaatc gccatttatg agaaaaacat tataaaatta  40920
gggcgttttt aatcaaaata ccaggtaatt ttttaaggaa atatgagttg tttatcctca  40980
aattttatga tatttttaaa gagccataaa cataagcaaa aagcatattc tgatttcaca  41040
cacgattcgt caggatatgt tttttattta ctcgatttat catcgcttag tttttgttgt  41100
tgtgatataa tattattaca ttctatttta tccatagaat aattttcttt tatcaactgt  41160
```

-continued

```
cttcctttta gaactccgag ggcagttttt ttattataaa aatgacctcc aaacgttaga  41220
gcttttttc taacatttgg agatcatatc atgaaacgat ttttgatatt ctatttgtgt  41280
gagttataaa agatagctta acccaattga agtaatgagg gcaaaaacca taatgcttaa  41340
aaaactcaag gttgctaaaa taagatatag catactcaga tcattattct tttccttgat  41400
atataaataa agataaaata taaaagataa agttgggatt cctagtagca aaagaactgg  41460
tacaagccag tcaattggta ttattttgct tagtacatca gaaacaaatc gtagagaagc  41520
attcataaat ttaatatgac taaaagaggg tgaggatacc caaagccata cgactaataa  41580
agcaggaagt attcttctta ttttcaaagt attagtacct tcctacctga tagggagcat  41640
atgctggagt aaacaaagcg ggtaaaccag tcggagcaac aactgaatca cttattccgt  41700
acataactgg taaattacct gaaccgaaat aataagcttg ccaaactaat ttagaacagt  41760
agtttggatt tgttacttta agattagatc taactaaata attaatgtgt atgtttttg  41820
ttgcaccacc gtatgtatta taaaagtgag tatctgcata tctagcgact tgacgagcta  41880
aaccagtatt tcttattctg taaacagatg tccattcttt aatatgattt gttatccatt  41940
gtctttttgg gagttgccga ttattatctg agattcccca aaaccaatta ggtcctccag  42000
gcatttctaa aacataaccg tctgcattta ggattgctgc atgaccaatt actcctgtag  42060
gaaagttccc tcctacgatc aagatatcac cagcccttgt atctctgcag aaggcgttga  42120
tattatcttg tgatgaacgt agcatactat ttgaaggagc ttcctctttt gtttgcaaga  42180
ttggtagctt tgtatcagac ataaccccat aattgtttgt cttcaaccat gattcataat  42240
ttattgatga atcatattct ttatattgtt cgtaagaggg tctcatggct gatagttcat  42300
ctttttccca gttagatttt ggataaagat ttgggtcaat aatgttttcg cttactgctt  42360
tgtcataaag acttccaacg tttgtaaatt catcagcatt agcagaaact cctgtcaata  42420
aaaccagagc accaactaat gagatgaggg ttccaatttt tattttttc ataaattccc  42480
tctcttttt gtgactattg cacaagacaa gtataacaaa agaaggatta aaagtgaatc  42540
gttaacttaa attaaactaa aaaaatttgt tgattttatt ctcacttgat tattgttgat  42600
aaggttctgt tgcaaagttt aaaaatcaaa tacaaggttt ataatccttc ttgttcttaa  42660
gctaatattc ccattaagac cttaatctca gtagataccg aaaatccgaa gagcgttcca  42720
tttcttcggt tctttttgta tattcctcga attgtttcca tgcccttaat cgtggttgag  42780
gcagttcgta gacttcgata aaatttattg cgtcgtttga ttggtcgatg gtcttgctca  42840
atgaggttat tgagatactt cacggttcga tgctctgtct tagtatataa accgttactc  42900
tgtaactttc taaatgcaga accaatagag ggcgctttat ccgtgacaat tactcttggt  42960
tgaccaaact gtttatgtag tcgtttcaag aacgcataag cagcttgagt atcccgtttc  43020
ttgcgtagcc agatgtctaa agtcaatcca tccgcatcaa ttgcacgata gagataatgc  43080
caacgacctt tgattttgat ataagtttca tccattttcc acgaatagaa ggactgtcta  43140
tttttctttt tccagagatg atagaggact ttactgtatt cttgtaccca acgataaata  43200
gttgtgtgac aaacgttaat cccacgatca taaaggagtt cttgaatttc acgatagctt  43260
agattgtaac gtagataata accaacagcg acaataatca catctttttg aaattgttta  43320
cctttaaaat agttcattga tatatcctcg ctgtcatttt tattcatttt acactaaaat  43380
agacttatca gaaaactttg caacagaacc agatataaag tcgattacaa aaaaagtcac  43440
aatttaaagt agaaaagcac atcaatatga tgtgcttttt agcttatttt aattaattgt  43500
```

-continued

```
tctatatatt tactttcttg aaaattggag tttccccaag gtttctattt taatgtatta  43560
tacctcagaa gttttatata tacttaaatg tctttttttgt tttgtgttat atcttttgct  43620
ttcattttat ctagttcttt tttgattttc ttctttctag tttgttttcc tccatcatag  43680
ataaaagcca agattagagg gccgaagaat ggcattatta tatccttaaa attaaaacct  43740
aaagctcctt gtgataagaa aaagagtaca aatcctataa acgttaaagg aagaaccatt  43800
cctaaatatt tgttaccgat atacccacag aaagtttgaa aagctataat tgcaactact  43860
aataaaagtt ctaataaatt acccattgat actatcctca tattctctta tgatttcttt  43920
agcagaatcc aaagacactt tttcatcaat caccatctgc attagtttaa ctttgaaaga  43980
atcttgatta taatttttta atttaatttt ttcaataatt ttgtcaactc ttattcttac  44040
agtagggtag ctcacctcat agtcttttgc taactgttta agtgagccag atgcaagaat  44100
gaaccttttt aaaaattctt gctcttcctc ttctaagtct aaaaaccaat tcatatgttc  44160
tcctttttga tccaacttaa ataatgttaa atatatttta acattattta agttaaaagt  44220
aaacaattct ataatattta aattgataat tgaaatagtt cacaacgttg aggtatagaa  44280
tgataaataa aaatacttac atcaactatt atgctttaca aactagtgtt ttgtgttata  44340
atactaatat gtaatgcaag atagttaaga aaaggagtaa aacttgtctc aaacagatat  44400
ttctagtcaa atgcttaaag gaattctaca aggctgtttg ttaattttaa ttaatcaacg  44460
accatattat ggctatgcga tcagtcagga actttcaaag tatgggtttg ctgatattcc  44520
taaaggaaca atttatccat tgctaaccag tatggaaaaa aaaggactaa tccttggtaa  44580
aattgaacca tctaaagaag ggccacaacg aaaatattac tatataacag atactggtaa  44640
acaagcacga aaagtatttc tcactaaatg gaatatactc tcacttagtg tcaatgattt  44700
aattaatgaa agaaggagtg atttatgaac agtgataagt taattaatga aaataatcaa  44760
ctacgggaaa atttaaactc agaaaacaaa cgatactatg aagatttgtt agtctatatt  44820
cgtagtaaat caacgttcaa cagagaaaaa gatgtggaac aacttttgtt agacatgttg  44880
catgacttaa tcgatgctca aagtaatgga gaatctgccg agttctattt tggtagagac  44940
ccaaagtctt tggcagatga gatccttaaa acattaccca aacatttttt tgatattttt  45000
aagatagctt ggtatatcgt gattggttat gttcttttct ttactattcc caatatggtg  45060
gatccttcac ggaaattaga tcttggtaat ttaataatat ttggaatact tggttttata  45120
ttttcaatta cagcttttttg gctaatagga aaagaaacat atcaaacaaa taaaataaaa  45180
aaatacacta gttatgcttt tggtattgta atttttgtta gcctaattat cgggagtatt  45240
tttttaaaaa caccactttc ttttaggata ccgggttggt ggggaattgg tattatctta  45300
atcttattag ttatcacaac aataatattc ataattgagc gtaaacgaat gccatttctg  45360
attactattt atgtcttaat tataattgat gcgatacttg gaattggtag tcgaattccg  45420
atccttgatg atttactaac acaaccaata tcaaaatcaa cggcattatg ggttataata  45480
attggcggac ctattgttgc aattgtatgt ggagtcggaa cttactacta tatcatgaga  45540
aatgaagatt aaagttgaaa caaaaaaaca gattgtttta aaatgtaaat ctgttttttt  45600
gtttggtctg attttatcac accaattatg tgatcagaaa atgaccattt tatgaacact  45660
caaatattga aaaaatatag ctcattttat gtctaattat ttgatagtgg tccattttga  45720
gttgcgttca aatttttagc tcatttacac ctatggttga gcaatttgtg atttttttaac  45780
tttctttata gcaaaaaaga atgcaaacaa gaaatatcct ctgttagaaa aaaagcttct  45840
caaaagagaa actctatact gccccccaac tttgcctgca gtctgagcgt tcaattgaac  45900
```

-continued

```
tctttttttac tggcgaaaaa ttattaatag taaaatcaag aagacaagaa gagacaaaat  45960
agaaataata taaaatgtga gagcgatgcc tattaaattt gcaaaaaaca caaagattgc  46020
tccaccaaat ggtaccgaaa atgtaaaaat agtcgtaatc cctccaccaa ttttccccaa  46080
attttctgaa gaaacatttt ccagaatgag acgattgact ttaggactcg ctttggccga  46140
tatgtaagcc aaagaaaaga gaaatattaa agaaatcaag ccaaaatgag ttaccaaagc  46200
tgcaaaaagt gcaatcatca aaaaagtagc aatcattaat ttgggaagtt cccaatcttt  46260
tagtttatcc cccataataa atgagcctgc gagcattcct agcatcaaaa caacgttaaa  46320
aatcattata gcaatcccgt aattcacaga aaatggatta aattttaaca tggccaagct  46380
ggtcaaaggt ccaatacccg ccaaaataaa gttgataaaa actaatgaaa atactagtac  46440
taaaaaattt gatgaactat ttacagtaaa aacatcacga atttgtgaaa aactctcttt  46500
gatattaaat ttaaactttt catcaaaatt gacagtctta aaagtcaact ttttacggaa  46560
aatcaataaa aagaaaccac tcagtaaata taagatccca ttaatcaaaa cgaccaaaga  46620
aaaggattga tgtgaaagag ccagaatcgt tacacccaaa ggttgtccga taatttctat  46680
aatagatgat aaaccttgga tttgtccaaa tgctggttgt atttcctctg cgcttagatt  46740
attttgtaaa attggtgcgc gtaacccaga tttataactg gtaatcaggt cggtcaaaat  46800
tttcacacca gctatgctcc aaaaactaat ccaatttttc tccatcatca aaaaaatcaa  46860
taaaaagaat aatacggctt gaatccagct cgcacgaatc ataaaatttg ctttattttt  46920
tgttctatcg gccaaaaacc ctgtgtaagc tgcaaatata atcggtaaca aaaggcagag  46980
ttcagctaat gaaatcatca ttttcggatg aggcatgcta ctcgcataaa tcaaaaaaac  47040
aatgttaaat aaactcgttc ccaacataga aaaaatagag ctggacaaca aggaagcaaa  47100
tgttttattt tttctcagta aattcatagt ttcctcctta attctttgat aaatttataa  47160
ccctcataac cttttaaaaa accttcttca taacttttag tataaaaatt atataatttt  47220
ttgtttttga taaataattt gcaagttctt agctgttcat cagcccagct caaatatttt  47280
ttattccccg ttttttgata aaccatcaat aaaaagtatg caattcctga taagcctttc  47340
tcaaaatcca ttgattttga aaatttcaca tccattccat ttgctatttt aataatttgc  47400
ttttcatatt tttcaaaatt ataggtcagc aaaaacaatg ctagaccact agaaccgttt  47460
aataagtagg gagaataact attttcagat aaatgtaaaa atgaatcact taattgtgaa  47520
agtaaatatt caatttttttc atcaattaac ttattttttt taaaaattga taatttccac  47580
aaataacctg ttaaaccatt tagtcctaga ttttcaaatt tattttcttt gataaatgtg  47640
accaagttct ttggttcttc caagtactct ttagaaatat gtaaaaaaac atctgattta  47700
taaaaataaa gtttttttaga aatttctaaa gcctttttgg tagaacttcc agtaaataaa  47760
taagttaata actcagaaat attcgtttta acttcaaatc tttcaaagat tttagcagct  47820
aaaataatcg tttcttcaag gcttctttct tgctgattga acacatttaa ttgaccaact  47880
agaaataaaa tcaactgacc aacttttctt aggtcttttt tcatttccgt caattttgac  47940
caacttttta aatagaatcc ttctgttttt gcagtaactt ttcttgattc atcaaattta  48000
tgagcaaatt ccaaatcaat aaaatgaatt ttattagctt tgtcaatcaa aaaattatca  48060
gggtgaatat catctaatat tacattttta tgatgtgctt cttccaaaat ttcaattaat  48120
tgttgaataa ttgttgaaaa aatcactaat ttatccacgg tcaaattatc aaataaggaa  48180
aagttacttt gaaattctct aagtgtttgt ccatcaataa acttgtaaac ataataatga  48240
```

-continued

```
ttaatccaag cacgaaattt ttcaattggt tgtgaaaaat tagctgaatt taaaaactcg  48300
ctcataagaa attcgttttt gcgcaattct tctgatttta aattcacaaa agttaatata  48360
ttggcccgac tttcttttac aattattttt tgatttttta aagttccaaa ataaatgttt  48420
ccaccattat tttgtcggat aatttttgtc aaatccaaat catttaatct atttttctca  48480
tttagctctt tcttttcttg ataaaaggga tcaactagcc aagctggtaa atcaaaatat  48540
gtttttgaa aatctttcca aattttccca tttcttacga gtgtacagcc atctatattt  48600
tgaaaaaaac caaatcgata aaaaaccgtt ttagaactat gaaaatttct atcacttaaa  48660
atataaactc tgtcaaattt gactaaaatc tctgacaagt cttctagaat cttctctgcg  48720
gcctttatat tttcaggata aattgtaaat aattttccgc tttctgctgg aaattctgtt  48780
ttagaaatat ttttgataaa atcctcacga gttgatagat atttataata taatttttgt  48840
tttaataaat atcttttcgt taaatcaaaa actttttcat aactttcaac tgtcgcagaa  48900
acatgaattt taaagccata ctttggaagt ttatatctct ctgtcgtaaa ataagtaaat  48960
ttttccatat tttttcctta taataaaaac atccggctgt acaaagccag atacttatag  49020
actagctccc tgtaacggga cacatgaaag taataacaat gtcttcttca ttatcaactt  49080
cttttggaag aaggttaagc tcaatcacct gttctttcat tttaaagacc tcctttattt  49140
gataatttta tcttactgca aaaaaatata ctttttgcg atttcctata tataataaaa  49200
aattacaact tttgttgcaa tttttttatt tcttcttgat aaagttttgc tttttctggc  49260
atatagaatt cttcatacgt ttttgcaatc tgttctaaaa tagaaatggc ctctcgaaaa  49320
ttacctgaaa cctcatataa atcagcttct tgtacagcat atgaaattcc aatttcgatg  49380
tttccaatct gcggaattaa agatttaaac ttttctaaat aaaattttac tttttcagtt  49440
tgattatttt gtgccaaaat gtaaattgcg tttctcaaaa tcatcaaaat caagttatta  49500
tctaaattat cttgctccaa aatattatcc agataaaaaa caatggattg actgtcaagt  49560
tgtgtcagcg caatcgcaaa aaattggaga ttagagtatt tccatttttt aatttcataa  49620
aaataattct ctaaaatttc ttgttcaatt atcgtcagtc gttcaaattt tccataattg  49680
attagcattg attttaatgc aattatattt aattgatctt gttttttgct cgtttcacga  49740
tatttttttc gctcctgttc gtacaaattg gctaattcat caatttttcc ggcttgttct  49800
aactttccgg cttgttctaa caagagagtc gtttcatcct tttttaaaag gtctgaaaat  49860
tcattgattg aaacattgat gtttccaatc agagcaaaaa actttcctat cgtcaaatca  49920
cctttgccac attcaaagtg agagagttga gaaattgata ggactccctc acttgcttta  49980
gccaatgaca tttctttttc ttgccttaat tctcgaaaca ctttcccgat ttctgtcttc  50040
atgattttca ttatatcaaa aaaaacataa aaacaacccc cattacctgt ccaatagata  50100
acaggggttg ttttaatagc gttgtatagg ggtcataata taattttaga cccttaatta  50160
ttcttatgaa taggaatcca aatttctgtt atatgatttt ctgacattgg gttaagatca  50220
agtgggtaag attcaaaatc cggagccttt ttttgagtgt aagtggtact tggaaagaaa  50280
gattcataaa tatcttgata cgtttgatga atagcttcag ggactttacc gacagcttta  50340
aatactgccc agtcagaagc aggaagtgta attgtttcta gcttatcagc agttgttttt  50400
tcatcagtgt agaccccaat aaaataatca tacgcctcac cttctcgagg taaacaaata  50460
cctaaaatag tattaggtga gtgctctgat ttttcattaa ttacttgatt aaataaatca  50520
gattcattaa atctatccca aaacttagga atgctagctt gtccgactgt gatattagga  50580
taactttctt taatacccgt gatcatcatt tctggtttgt ttgtaattaa ataattcatt  50640
```

-continued tgaatgcctc cttttatttg gacacgaata gacaacttag ggaaaatagt taactcatgt 50700
tgttctttac gtgccttaga aggagagata ttgaaaagtt gttgaaagct tctgctataa 50760
ctttctgatg aactgtaacc atatttaaaa gcaatatcga ttattttttc atcggtttct 50820
cttaaatcat atagtgattt agaaagacgt ctttttctga tataatcacc taaagttaaa 50880
ccagaaagaa cagaaaaaat cttttgaaaa ttatactcag aaactctagc aagttgctct 50940
attttttca tatcgatgtt atcttctaag tgttcctcaa tgtaattaat aatagcagaa 51000
aattcattca tctatttctc cctctcttct tcttgatact atcataatca atttttttta 51060
aacaaactgg ataaatttg gcaaaaattg ttagatattc cccatggggc tagttgattt 51120
tagaaccgat attttcaatt tttttaaaac cgaatctgat aaccttattg aaaggaacca 51180
agccaacgcc tgtcctccaa aagacattta attcattctc tgataggatc gccttaagta 51240
tttatccaat ttttctcctc gttctctttc aaatgataat atgcttaact ctattataac 51300
aaaagcataa gaaggatgtt gaaggactaa gaatttccct taaatatccc aatttatcag 51360
ttttggtgtt tatttcgatt gtttttcact ctaaaaaaag atataatatc agtaaaactg 51420
atattttga tttaggaggg actatggaac gattaaaatt aaatcaatac tttgactact 51480
cgcttgaacc acgtcgtgcc atcctctttc aagatgtcaa gtctaattat gcttcaattg 51540
aatgcgttca gcgaaattta aatcctctga caacttctct ttgtgtcatg agtcgagcag 51600
atcattctaa agggttaacg cttgcctcta gtccaacctt taaaaaagtt tttggtatga 51660
aaaatgtcag tcgtgccagc gatttacctt ttcttataga aacacgaaag ttcaattatc 51720
cgcaatggta tcgaacacat acagacattc atggacagcg aactgaacca actttgcaat 51780
atgtcgcttt tattgaatct tgggcgaaac gcacgtggat tgttcctcca caaatgcagc 51840
tctatgtgga ctataaaatt gaagtgacag atatcctgac caattatacg tcaattgatg 51900
agattcactc ctactcgatt gatgaatctt ttttggatat cacagaatca ttgaacttct 51960
tctaccctga gattaaaaat cgttatgaac agatgaatcg aattgcttta gacttgcaac 52020
gtgagattcg agataaacta ggactatatg tgactgttgg gatgggagac aaccccttgc 52080
ttgccaaact tgcaatggat aactatgcca agcacaatga taatatgaga gccctaatcc 52140
gttatgaaga tgtccctaat aaactatgga caattcctaa gatgacagat ttctggggaa 52200
tcggaaaacg aactgagaaa cgattaaaca aacttggaat cacttctatc aaagagcttg 52260
cgaatgctga cccacttctc cttaaacaaa atttgggaac aattggactt caacattttt 52320
tccatgcgaa cggcatcgac gaaagcaatg taagggaaaa atatatccct aaaacaacaa 52380
gcttcagcaa ttctcaaatt ctgccacgtg actatcataa gcaaagagaa attgaacttg 52440
tgattaaaga aatggctgag aacttagcga taagattgag aaagggcgga aaactcgcaa 52500
gcaatctttc actttatgca ggagctgctt ctacttctga atactcatct attaaggttt 52560
ctcgcaatat tgaagcaact caaaacacaa aggaattgca agacctcgca atctccttat 52620
ttcgtaaaaa gtacctaggg ggagcgataa gacaaatagg gataagcgga aatcaacttt 52680
ctgatagttc tgttaaacaa ctctctttat ttgaaagtgt tcaagaaaat caaactaata 52740
aaaagcaaga atcactccaa aaagctattg atgagattag agaaacattc gatttcctat 52800
caatacaaaa agcaagtagt ttatccgagg gatcacgtgt catttatcgg aacaaactca 52860
ttggaggtca tgcagcaagt caagacaagg aggaaaaaga tgtcagttga ccgttcatat 52920
agtccctacg aggttattag gatgtatcac gatagaggaa tgatgaaatg gggggcattt 52980

-continued

```
gcgactgggg aattaactga agcccaaaat acttttgaaa aagaaaaaaa agaagataag  53040
ataattcaag cattaccaca tcatctcgtg cttcatcttc ttaaccagtc cttttctaat  53100
caggggcaaa ttaaaattca atatcaagcc aaagataaat taactgaagt ctatggtttt  53160
gtatcagaat ttatcaataa tcaagtaaga gttaaatcaa cggataaaat ctatctcata  53220
tccattgagc aaatcgtaaa tatatcataa aaaaagctat ccttgttgta tattactaca  53280
acaacttgga tagcctttta tatgacgtta agtcaagttt ttagagtaac aaacgtagaa  53340
ttttaatcta tttattttaa gcacttacct tttcaaattg attaggtata agataccta  53400
aactttgatg gattcgtttt gaattataaa aggctcataa gtggagggag aaaatcatga  53460
aatatggata tgctagagta agtacaatag accaaaaact agaatctcaa atcgaacaat  53520
taaagaatgc tggtgcagaa gaaattttcc aagaaaaatt tactggaaca acaaatagtc  53580
gcccagcctt tataaattta ttaaatacat tggaatcagg agatacttta atcattacaa  53640
agctagatcg cttcgcaaga aatactagag aagcattagc aactattcaa gaactttttg  53700
ataaagatat aaaaataccc gaattcctag ttaatttcaa gagactttaa gatattctat  53760
cgggtatcaa gtcatggcta aataatcaac tagcaattcg ggtataaaaa taaatatttt  53820
aaatatggga gtgatagata ataccgcaac tggaaaatta atttttacaa tttttagtgc  53880
ctttgctcaa tttgaaagag atatgattgt tagcagaact caagagggaa aagaatattc  53940
aagaaaaaat aacccaaact ttaaagaggg tagacccaat aaatttacag aagaacaaat  54000
tcaattagct tatgaattaa aacaacaagg aatgacacac aaaatgatcg aacgaaaaac  54060
tggaattagt gtttctactc aaaaaagaag atttaataaa atagtttagt tttttattta  54120
ttaaataaat aaataattaa ataattaaat aaataaattg tttatttttt taattattta  54180
tgttataata gatatagaaa ggtggtagta cattgaaaat cattacattt acagccatta  54240
aaggcggagt tggtaaaaca acactaacac taaattatag cgattggttg gtaaaaaaag  54300
gaaagaaagt tttattaatt gatttagatc atcaatgcaa tttaacaaca atttttcaac  54360
caacacgaag aaataatact attgcagaag catttaaaga tagtgaggaa gcacaagaag  54420
ttatcattga taacattaaa gagaatttag acttagtagc tggttttatt gatttagatg  54480
aactaggaag caaattagaa aacaacagca ataaagaaat gttattattt ctttggttaa  54540
aaaataattt tgaaaaatta aatattggaa gctatgacta tattttaatt gatacacacc  54600
ctgatttttc tacaataaca aaaaatgcag tagcaataag taattattta gttagtccaa  54660
ttacacctag tgaacatgga tattcagcaa aatttgattt agaagctcgt ttagaaaaat  54720
tcagaaaatc tttgtttgat tataaaactg gagaaactta tgttgacgca caattatttt  54780
ttgtagctaa tatgattaaa cataacacca gcacatcaca tgaattgtta agccacataa  54840
aagatgatga aactgttatt tctactattt ctgaaagaga aatttttaat aaagcaacta  54900
ctaaacactt atctattttt gattttgcta aaacccaaga taaaaaagac gataaagttt  54960
taaataatat taatgatagt ttttcaaaaa tatataatca tacaaaataa aggagtttaa  55020
attatgagtt ttgatacatt taacaaagat aaagatgaaa ttgttaaaca gaatttaaaa  55080
gaaacaattg atcctgaacc aaaaaaggaa gatgaaattc acagcgtaat tagttctatt  55140
ttgaagtcta atgatatgaa aagtgaaaaa agaaaatcag tcactttttc attgactgaa  55200
agtcaaataa agaaaattga agaacaagca caaaaacacg gttttaaaac aaaatcaaaa  55260
ctgttagctt atctcataga tcaaatgtaa ctttaaataa ttaattaaat aatttgttta  55320
tttaataatt aaataattag tttatttaat aattaaataa tttgtttatt taataattaa  55380
```

-continued

```
ataatttgtt tagttgaagg aggttctcat gaaaaaattc atggacttat ggctttactt  55440
ttatataagt tgtatctact ttttgccatt aattgctctc atgcgttcta gcaataaaag  55500
tagcaatttc ttattaagaa gattactatt tccctttgaa tatttaattc aaagaagact  55560
tgaaaaaaca acaaattata atcgtggatc aattcgtgcc gttcatattt tcatttggtt  55620
tttcagtatt tttagcttaa tgtttgcgac agcaccgcta attttttttcc acgaaccact  55680
tgaaaatcac accacattat tattatttat tacttactac tgtatgttag ccccattctg  55740
tttttggttt caaccaagaa atctaaaaca ataaaaagga gaactttatg tttatagcaa  55800
ctgacaatca atttacagca agaggaagat tagtagacag tcctcaaatt aatatttcag  55860
aaaaaacagg aaatgctatt gtttcaatca cactagcaca agaacaccct tttaaaaaaa  55920
atgaagctgg ggaaagagaa tctgttttta ttaaatacac cgcaattgat acaaaaaaca  55980
accccattgc cagtcgcatt gcagaatatg tgacaaaagg atcattagtt agtcttattg  56040
gttatcatga cagttacttt aaagaaaatt cagagggtaa aaaagaatat tttgaagtga  56100
aaagaatttc aacttttaga aatgaagaat caaaagaaaa aacattggag cgtagaacta  56160
aagcataata attaataaag gaaagtgatt tttatggaaa aacacaaagt ggacttttac  56220
aatataccga tcgtagacta cttactttca attggagaac cccttgaaag tgttggtcat  56280
aactactatc aacataaaca tcatgatagt ttaaaaatta atcaaaggaa aaactatttt  56340
gtttggaata gtcgttcatc tgaaaaaaat tcacgaggtg gagttgttca gtatatgcag  56400
atcatgcata atttatcttt acaagaaaca ctctcaaaat taagtgaaga tttagacggt  56460
aaagttcttc cagcgatccc taaaaaaagc tatcctaaaa aatttaatta taaagttaaa  56520
gaagctattg tccccataga aacgcaacgc tatttagttg caaaacgaaa aatacctaat  56580
aaaattgttc gcctattttt ttcttatgat ttaatttctc aaaatgaaaa taatgaagtc  56640
atttttaaat ggtttaaagg cgacaaagtt gtaggttttt ctaaacaagg tacgatccca  56700
ctcacagacg aagaaaaaga gaaatatcat actaaaagag atttctttaa atatgttgca  56760
ccaacaacag aagctgatac aatgtggggg tttaattatc ttagtggtga accaaaacat  56820
atctttttct ttgaaagtga gattgattta ttaagttatt attctatttt tgaagaagaa  56880
ttaaacgaaa ctggcaattt ttggttaata tctatcaatg gagttgcgat tgaaaaagtc  56940
tattcatttt ttagatacgg tatagaaaac ttaaatttaa aagaaacttg tcaatctttg  57000
cacgtttgtt ttgataatga tattgctgga aaacaagcct gtaataagtt acagcactta  57060
gaatttaaaa atatcccttt tcaaaatgat ttaccaaaag aatttaaaga ttggaacgaa  57120
gttttacaaa ataaataatt ttaaaagcct ttgaaacttt aaagggcttt ttttgacgct  57180
ttacagagct tttaaggagt tttaaaacga atcaggtaaa ctttattagg actaacactt  57240
aaaagggctt agaaagcaaa atatgagctt ttagagaatc tcttactttt atctttaaat  57300
aatcactttg ctaaccactg atagagaaca tcaagttata ttcaaagcta taaacagttt  57360
attatgcctt agaaagacat atagtcgttt cttatggctt ttaaactgat tcaggtaaag  57420
tttatgaggg taagtgctga aaatcgctta gaacgtaaaa tatgagcttt tatggtttta  57480
atcttttggt tttgaccttt ggtttaaatt tttgaaaaaa ataaaaaaag gcgaagccta  57540
tattaattta tcatatatat tttaatcttt tgttcttttg cgtaaaaaaa aagtgaggtt  57600
tttcaagggt ttacagaata ataaggacag aaaaatcgat gtataaggac agaaaaatcg  57660
atgtataagg acagaaaaat cgatgtataa ggacagggat tgttgtagaa ctgtccttat  57720
```

-continued

```
tatgatataa taaaagcata gagaaattca ctcgcaaaaa tgttttctct atgctaattc  57780
taaaatcact cacaaaggag ttactttcta tgactattat aacagaaaaa gcaaaaaatc  57840
aaaagcaggt actaaccttg aatgaacttg aaaaacgaaa agtagtagag aacaacgctt  57900
taattaccag cgttgctaaa atgcaaaaaa cagctttaaa aatgtttgag ttagccgtat  57960
cttgcattga tacggagaat gtaccagaaa acaatactgt ttatctctca aaagaagaac  58020
tattttcttt ttttgaagtc ggttctaaca gcaagcatac tcaatttaaa gaagcgattg  58080
agatcatgca aaaacaagcc tattttaaaa tcaagtctaa taaaaaacta ggtattgagt  58140
atgaaagcat tgtccctatc ccttatgtta agtggaatga ttacaatgat gaggtaacca  58200
tacaatttag cgaacatatt atgccttatt taattaattt aaaatctgaa tttacacaat  58260
ataaaatttc agaactacaa aaattaaaca gcaagtattc tattattttg tatcgttggt  58320
taaccatgaa ttacaaccag tatgagcatt acagcaataa gggcggacgc agagaagaac  58380
aagtggaaga ataccgcaac ccccaaattt caatacgaga attgcgagaa atgacagata  58440
cggttgaaga gtatcaaaaa atgtcacact ttactacatg ggtactagaa aaaccattag  58500
aagaaataaa tgatcatacc tcgtttaacg tggcttatga caaagtgaaa aaagggcgaa  58560
gtgttgattc tattgtcttt catatcacga aaaaacgtcg agcagacgat aacagctata  58620
agctagaaga taaaactaat caagaagcga aagctgaaaa agaagcaaat gaagataggt  58680
tatatgcaaa agcaatgaaa agcaaatata ctaagttatt gctggaaaat ttccttttat  58740
ccccttatga aatgaccgac ccagcaatca tggctggctt gcaaaaaaat gtttatccaa  58800
agtatgacga actcaaaaca ttacgaggac ttgagggggt caaaaagcat ctctcatacg  58860
ttcgtgagaa gcaagaacct tattcaaaag ggaacattgc aaagtatctt aaaaaggcaa  58920
ttgaacaata cctacctacg gtaaaaaggc aggatataga ttaatgactg aaaaaatgga  58980
cgacctccta aaagcgacaa ctttgagtag gtctgcaaaa taaaagatat aaaagcatgg  59040
aaaaaagcaa ctactaaaaa agtttagtaa ttgctttttt ttttataaaa aatagctgga  59100
atttaaaaaa ataagggcat gaatttcata atcttataaa tctttctttg aaatatccat  59160
tgccttgctt aatagtcgtt attcaatcat gttaacagaa ccccaaatca gaaacaaggg  59220
taaatatact cgcaagctcg cccttgtttc tgctttgaaa ttctgttccc cctcaatcac  59280
aacgaccaaa aacaagcaag gcgaaaaaat ggatcactca aaaaagaaag gacacataat  59340
attatgaaat tcaatatttt tttaaattcc agctaacaac ttcacttcca aacataacaa  59400
aaaaatgaat tttaaaaaca aaaaagaaaa gaaaaaaaac attatgacaa acaacaaaaa  59460
aataagatta gaagatttca aaaatgactg gtttgagggt acagcagaat tacaatatat  59520
caaagcacag gtaagagaag aactcacaaa aaaaggcttt ttaattgata gtagttttga  59580
gtatggcgat aataatgagt gggttggagt atatgcaaga ccccaagaca agccgacagc  59640
gttagaccct tatgacgaag aagaagaaaa agaacaagaa aaatatgcta ttaatggcat  59700
gaagcaagat tttgttgaat ggtttgaatg ggatataaaa aataataatt tagttttata  59760
aaggagctaa aaaaaatgaa taaaaaaatt gaaaaaaaat taaatgaatg ttttgaaaat  59820
aattatagta gttcagtaaa gtttttaata aattatgaaa ttgaaaacgg agcggaaaca  59880
ataaacaaca tgaacgcaga agaaattttt caagattata taaacaacga tagttataca  59940
aaaatctttg atatactaaa ttattttgaa aaataataat ataaaaaatg tctgaaagaa  60000
aaatcaggca ttttttttatt tagtctttaa agactgacaa aataaaaaaa tgcaaaaagg  60060
agagaacgag aaccacgttc acaaaaaacc agtgttttca cgctgatgtg gagcaggaga  60120
```

tataatagca tttggaagct ggtataattt agaattagac gaatgtatag aatatctaaa 60180
aatagtaaaa gaacaaaaaa aaaatgcctg attttagtaa atttatttaa ta 60232

<210> SEQ ID NO 107
<211> LENGTH: 3600
<212> TYPE: DNA
<213> ORGANISM: Artificial Sequence
<220> FEATURE:
<223> OTHER INFORMATION: Synthetic construct

<400> SEQUENCE: 107
gagctcccgc tcgcgctttc tgtcattatg gcaggcttgc gcacggctct cgtcattgcc 60
atcggaatta cagcaatcgg cacatttgtc ggcgccgggg ggctcgggga tatgattgtc 120
cgcggctcaa acgcgacaaa cggaactgcg attattctcg caggcgcgac cccgactgcg 180
gtaatggcca taggagcaga tttgataatg gcctggattg aaaggttctt gaatccggtg 240
aaacaaaaaa gcagaagaaa ggtaataagt gtatagagtt aagcaaaaag gattcttttc 300
tgagagggaa aagagtcctt tttttatggt atttactggg tggatcttga tatttttttg 360
atttttagaa tgtatagtaa aaatagagta ttgtaaatat tttggttcaa atagaataat 420
atggaggact aagcagaggg atgtagaatt gtttttatta agaagcggat aaatatgggg 480
ggctatagac taatatgaaa tccttatata cacctacaga ttattatatg attcgggttc 540
ctttagtaca tcaagactta aaaaatgaga attctcagga tatcgatcag ttattacatg 600
acctttgcaa cgattcatta tttcgggaac aaatactggt atctagcagg acactatatg 660
aaacaataca tactttcctg caagcgccgg ataaattaaa agggaaaaaa aagcgcaact 720
ttcaacaggc tattttgaag tatgcaacaa gaagagcaac aagaaccaca ccttttggcc 780
ttttttcttc agtcggtata gggtcgtttt ctgataaaaa tcacttatct tttaatcaac 840
attcatttta caaaaaggct cgtgttgatt tggagtggct ctaccaatta attagaaaat 900
tggaaaacga atacaccgac cgactttctt ttacattaaa ttccgcttgt tatattaagg 960
gtgaccgggc ttacttgttg tacagcacag atggaaaatc tgaagaagtt agtgttcgtg 1020
cgacatctgt tttctatttg ataaatgaac tgtgtggtga atctgctgca tatcaagata 1080
taatccgttg tttgatagat aactatccaa atactccaat aaataaaatt aatcagtacg 1140
tagcagacct tattgacaaa gagttcctta tatcaaactt acggccgccg atgactgttt 1200
cagatcaatt tcagtattta attgatcaag cggaaagccg ccatattcca aatgaactca 1260
ttcaggcttg taaagacatt caatatcaga tagatgcata taatcggatc actatcggag 1320
agggagagca tcagtattta aatctgattg aaacaatgaa taaactcata aaggcatcat 1380
ctcctctgca agtagacgct gggctggcag actcctccat tcaattagat aatgaaacat 1440
ctctcgccat aagtgaattg gcaagcatgt ttacttatat ggcttctccc tctgccaata 1500
cattagacca cttggaaaaa taccacaatg tatttttgga acgctatgga tatgaaagag 1560
aagttcctct cttagaaatg ctatgttcca gcactggcat tggtgctcct gctacgtaca 1620
cgaatcctgc taatgaattc tttgaagaaa catcatttgg ggagcaattt tcaccggaaa 1680
tgaaacaatt tttcatgaga aagtattttg aatcagttag aaagaaagct cctattcaat 1740
tagacgacga aacattccat agaatttgca actctgaaat tgctgatgag gaaattccat 1800
tatcatttga actcaatttc tttgttaaat tacgaaatgg gagagttaag ctttatttag 1860
gccccaacgt cggatctacc cgcgcaggga aaacatttgg gagattttct catatgtctg 1920

-continued

```
attcaatcag tgaaatcata aagaccttac ataacaagga gaaagagtta acagagtgta   1980

atacgaaagt ttgtgaactg agtattgtgc ctaatcaaac taggtctgga aatgtaacaa   2040

gaaatgtaag ctaccgagaa aaagagatgt ctctttttac gaacagtgct ctgcatctca   2100

atgattccgt caaagctgaa gatattctaa ttggaatcaa taaagaccat aacttttatg   2160

ctagacataa aacaactggc gaaattctgt cttttgagtc aaatcatatg tttaatcctt   2220

tattaatgac caacgctgta cggtttttat tagagatttc aagagatggt aaaagaaaat   2280

ggaatgattt cccgtggttt agtatctata gtgatttcaa gtatattcct gaaatcaaat   2340

ataaagagat aaccttatct tgtgaacaat ggctgatata caaaaatgat ttaagcatgc   2400

actcgaatgc atctctagaa gagataaaat ctcctttttt tgaatttcat cgtacttatg   2460

aactgccgca aacattttat atcgttaacg cagacaatcg attattgatt gatatagaga   2520

atgattgtac tttggatgtt tttttctggg aattgaaaaa aacgaaccat aaccagccat   2580

tacaacttgt ggctgttgag catgatgcag atgcgttaat ggatagaaac caaaatgact   2640

attcgggaga aatcgtcgtt ccgctgctta gaaaacaacc agaaaaacca ttgtatttac   2700

cggttcttaa cgcaatagag ggaagtggtt ccgacagaat aaaaatgcca tttgaagact   2760

ggctgtttat taagctttat tgtaaacaaa caagagaaga agagctaatt gcttttgaaa   2820

tagcggattt ttataaccag atttctgatc aatatccagt cagacatttc tttatgaggt   2880

atcgggatcc aaagcctcat ataagactta gatttaatgg aaaagccgaa gtgctgtaca   2940

gcttgtttcc ccaattattg aattggctga aaagcttaag agaaaaagga ctggtttcag   3000

agtctgttat cactcaatac gagcgggaga tagaacgata tggcgggcta agccttatgg   3060

aggctgcaga acagcttttc tgtgaagaca gcaaagttgt tgaaatgatg attagaatgc   3120

accggatgaa agatattacg ataagcaagg aaattgcagg catggtttcg gttatacagt   3180

ttttagaaca gttcgagcta acgtttgaag aacagttaac ttttttagag agaaattcct   3240

tacagaatga gtatcgtact gaatttaaaa aggatagaga aatgtatatt gaaatatgca   3300

attctgacag agattgggat aatctcaaga aaacaagtga tggcggtatg ttatatgaaa   3360

ctttgaaaac aagaaaaatg gctgcagctc attatgcatt tttaatcaaa aaggcatttg   3420

ataacaaaga tgaagtttat tcacgtatag gaagtatcat ccatctgcat tgcaatcgtt   3480

tattcggaac cgacagagaa ctggaaaata aaattctcac cctatgcaga cattctttat   3540

atgcgcaacg atatcaaaag atgaatggta gtttagcatg gaagtaaagg aacaactgaa   3600
```

<210> SEQ ID NO 108
<211> LENGTH: 7500
<212> TYPE: DNA
<213> ORGANISM: Artificial Sequence
<220> FEATURE:
<223> OTHER INFORMATION: Synthetic construct

<400> SEQUENCE: 108

```
aagcttgtgg gaaagaacat cctcagcctg gcttgattgt ccatactgat caagggagtc     60

aatatacaag ctctcgttat caatctactc ttcgtcaagt cggtgctcaa tctagcatga    120

gtcgtaaagg aaatccctat gacaatgcaa tgatggagtc tttttataag acgctaaaga    180

gggagcttat taatgatgct cattttgaga caagagctga ggctactcaa gaaatattta    240

aatacattga gacctattac aatacaaaaa ggatgcattc aggtcttgat tacaagtctc    300

caaaagactt tgaaaaatat aattcttaaa ttctcttaac tccgtgtcta gtttttcgtt    360

gactttccat tatgcttgga ttttttattg tttaattccc ttttttgtat acaagctcgt    420
```

-continued

```
attcttaaca aataattggc atatcgggtt taaaaatact atgtgtttta aagaatctct    480
catgagtttg acgccaataa cttagattaa aatcattgtc accttatttt taggcacgtt    540
cggcagtaac cttatcaaag gtatctcggt cattaagttt catgatagta tttactattt    600
tgatggtttt tgttattatc caatcgttaa aatgacaaaa acaaatagat aaatagataa    660
atatttatgg ggaggacaag tgaacttatc atgattaatt gtaaacgatt gagttctgat    720
atgtttcaaa ttatgaggaa caacaggagt tggactattc tttaaacgcc tcgacgatac    780
catcactctt cattagccta aaattaacaa gttaaaatca ttagaataat ctcttttaca    840
aaaaatattt atttaagtta tagttgacga atatttaata attttattaa tatcttgatt    900
ttctagttcc tgaataatat agagataggt ttattgagtc ttagacatac ttgaatgacc    960
tagtcttata actatactga caatagaaac attaacaaat ctaaaacagt cttaattcta   1020
tcttgagaaa gtattggtaa taatattatt gtcgataacg cgagcataat aaacggctct   1080
gattaaattc tgaagtttgt tagatacaat gatttcgttc gaaggaacta caaaataaat   1140
tataaggagg cactcaaaat gagtacaaaa gattttaact tggatttggt atctgtttcg   1200
aagaaagatt caggtgcatc accacgcatt acaagtattt cgctatgtac acccggttgt   1260
aaaacaggag ctctgatggg ttgtaacatg aaaacagcaa cttgtcattg tagtattcac   1320
gtaagtaaat aaccaaatca aaggatagta ttttttagtt cagatatgga tactatccta   1380
tttttataag ttatttaggg ttgctaaata gcttataaaa ataaagagag gaaaaaacat   1440
gataaaaagt tcatttaaag ctcaaccgtt tttagtaaga aatacaattt tatgtccaaa   1500
cgataaacgg agttttactg aatatactca agtcattgag actgtaagta aaaataaagt   1560
tttttggaa cagttactac tagctaatcc taaactctat gatgttatgc agaaatataa   1620
tgctggtctg ttaaagaaga aaagggttaa aaaattattt gaatctattt acaagtatta   1680
taagagaagt tatttacgat caactccatt tggattattt agtgaaactt caattggtgt   1740
tttttcgaaa agttcacagt acaagttaat gggaaagact acaaagggta taagattgga   1800
tactcagtgg ttgattcgcc tagttcataa aatggaagta gatttctcaa aaaagttatc   1860
atttactaga aataatgcaa attataagtt tggagatcga gtttttcaag tttataccat   1920
aaatagtagt gagcttgaag aagtaaatat taaatatacg aatgtttatc aaattatttc   1980
tgaattttgt gagaatgact atcaaaaata tgaagatatt tgtgaaactg taacgctttg   2040
ctatggagac gaatatagag aactatcgga acaatatctt ggcagtctga tagttaatca   2100
ttatttgatc tctaatttac aaaaagattt gttgtcagat ttttcttgga acactttttt   2160
gactaaagtt gaagcaatag atgaagataa aaaatatata attcctctga aaaaagttca   2220
aaagtttatt caagaatact cagaaataga aattggtgaa ggtattgaga aactgaaaga   2280
aatatatcag gaaatgtcac aaattcttga gaatgataat tatattcaaa ttgatttaat   2340
tagtgatagt gaaataaatt ttgatgttaa acaaaagcaa caattagaac atttagctga   2400
gtttttagga aatacgacaa aatctgtaag aagaacatat ttggatgact ataaggataa   2460
atttatcgaa aaatatggtg tagatcaaga agtacaaata acagaattat ttgattctac   2520
atttggcata ggagctccat ataattataa tcatcctcga aatgactttt atgagtccga   2580
accgagtact ctatactatt cagaagagga gagagaaaag tacctcagca tgtatgtaga   2640
agccgttaaa aatcataatg taattaatct tgacgactta gagtctcatt atcaaaaaat   2700
ggacttagaa aagaaaagtg aacttcaagg gttagaatta tttttgaatt tggcaaagga   2760
```

-continued

```
gtatgaaaaa gatattttta ttttagggga tatcgttgga aataataatt tgggaggggc   2820
atcaggtaga ttttctgcac tctctccgga gttaacaagt tatcatagaa cgatagtaga   2880
ttctgtcgaa agagaaaatg agaataaaga aattacatcg tgtgaaatag tatttcttcc   2940
agaaaatatc agacatgcta acgttatgca tacatcaatt atgaggagga aagtacttcc   3000
atttttttaca agtacaagtc acaatgaagt tctgttaact aatatctata ttggaataga   3060
cgaaaaagaa aaattttatg cacgagacat ttcaactcaa gaggtattga aattctacat   3120
tacaagcatg tacaataaaa cgttattcag taatgagcta agatttcttt acgaaatttc   3180
attagatgac aagtttggta atttaccttg ggaacttatt tacagagact ttgattatat   3240
tccacgttta gtatttgacg aaatagtaat atctcctgct aaatggaaaa tttggggaag   3300
ggatgtaaat agtaagatga caataagaga acttattcaa agcaaagaaa ttcccaaaga   3360
gttttatatt gtcaatggag ataataaagt ttatttatca cagaaaaacc cattggatat   3420
ggaaatttta gagtcggcga taaagaagag ctcaaaaaga aaagatttta tagagctaca   3480
agaatatttt gaagatgaaa atatcataaa taaaggagaa aaggggagag ttgccgatgt   3540
tgtagtgcct tttattagaa cgagagcatt aggtaatgaa gggagagcat ttataagaga   3600
gaaaagagtt tcggttgaac ggcgtgaaaa attgcccttt aacgagtggc tttatctaaa   3660
gttgtacatt tctataaatc gtcaaaatga atttttactg tcgtatcttc cagatattca   3720
gaaaatagta gcaaacctgg gtggaaatct attcttccta agatatactg atcctaaacc   3780
acatattaga ttgcgtataa aatgttcaga tttatttta gcttacggat ctattcttga   3840
aatcttaaaa aggagtcgga aaaataggat aatgtcaact tttgatattt ctatttatga   3900
tcaagaagta gaaagatatg gtggatttga tactttagag ttatccgaag caatattttg   3960
tgccgattct aaaattattc caaatttgct tacattgata aaagatacta ataatgattg   4020
gaaagtcgat gatgtatcaa tcttggtgaa ttatttatat ctgaaatgct tctttcagaa   4080
tgataacaaa aagattctta attttttgaa tttagttagt actaaaaagg ttaaagaaaa   4140
tgtcaatgaa aagattgaac attatcttaa gcttctgaaa gttaataatc taggtgacca   4200
aatttttat gacaagaatt ttaaagaatt aaagcatgcc ataaaaaatt tatttttaaa   4260
aatgatagct caagatttg aacttcagaa agtttattca attattgaca gtatcattca   4320
tgtccataat aaccgactaa ttggtattga acgagataaa gagaaattaa tttattacac   4380
acttcaaagg ttgtttgttt cggaagaata catgaaatga ggactaatag atggatgaag   4440
tgaaagaatt cacatcaaaa caattttttt atactttact tactcttcca agcaccttga   4500
agttaatttt tcagttggaa aaacgttatg caatttattt aattgtgcta aatgctatca   4560
cagcttttgt tccgttggct agtcttttta tttatcaaga tttaataaac tctgtgctag   4620
gttcagggag acatcttatc aatattatta tcatctattt tattgttcaa gtgataacaa   4680
cagttctggg acagctggaa agttatgtta gtggaaaatt tgatatgcga ctttcttaca   4740
gtatcaatat gcgcctcatg aggactacct catctcttga attaagtgat tatgagcagg   4800
ctgatatgta taatatcata gaaaaagtta ctcaagacag cacttacaag ccttttcagc   4860
tatttaatgc tatcattgtt gagctttcat cgtttatctc attgttatct agtctatttt   4920
ttattggaac atggaacatt ggggtagcaa ttttactcct tattgttcca gtattatctt   4980
tggtactttt tctcagagtg ggacaattag agtttttaat ccagtggcag agagcaagtt   5040
ctgaaagaga aacatggtat attgtatatt tattgactca tgatttttca tttaaagaaa   5100
tcaagttaaa taatattagc aattacttca ttcataaatt tggaaaatta aagaaaggat   5160
```

-continued

```
ttatcaacca agatttagct attgctcgta agaagacata tttcaatatt tttcttgatt   5220
tcattttgaa tttgataaat attcttacga tatttgctat gatcctttcg gtaagagcag   5280
gaaaacttct tataggtaat ttggtaagtc tcatacaagc tatttctaaa atcaatactt   5340
attctcaaac aatgattcaa aatatttaca tcatttataa tactagtttg tttatggaac   5400
aactttttga gtttttaaag agagaaagtg tagttcacaa aaaaatagaa gatactgaaa   5460
tatgcaatca acatatagga actgttaaag taattaattt atcatatgtt taccctaatt   5520
cgaatgcctt tgcactaaag aatatcaatt tatcctttga aaaaggagaa ttaactgcta   5580
ttgtaggaaa aaatggttca gggaaaagta cactagtaaa gataatttca ggattatatc   5640
aaccaactat gggaataatc caatacgaca aaatgagaag tagtttgatg cctgaggagt   5700
tttatcagaa aaacatatcg gtgctgttcc aagattttgt gaagtatgag ttaacgataa   5760
gagagaatat aggattgagt gatttgtctt ctcaatggga agatgagaaa attattaaag   5820
tactagataa tttaggactc gatttttga aaactaataa tcaatatgta cttgatacgc   5880
agttaggaaa ttggtttcaa gaagggcatc aactttcagg aggtcagtgg caaaaaattg   5940
cattagcaag gacattcttt aagaaagctt caatttatat tttagatgaa ccaagtgctg   6000
cactcgatcc tgtagctgaa aaagaaatat ttgattattt tgttgctctt tcggaaaata   6060
atatttcaat tttcatttct catagtttga atgctgccag aaaagcaaat aaaatcgtgg   6120
ttatgaaaga tggacaggtc gaagatgttg gaagtcatga tgtccttctg agaagatgtc   6180
aatactatca agaactttat tattcagagc aatatgagga taatgatgaa taaaaaaaat   6240
ataaaaagaa atgttgaaaa aattattgct caatgggatg agagaactag aaaaaataaa   6300
gaaaacttcg atttcggaga gttgactctc tctacaggat tgcctggtat aattttaatg   6360
ttagcggagt taaaaaataa agataactca aagatatatc agaaaaagat agacaattat   6420
attgaatata ttgttagcaa actttcaaca tatgggcttt taacaggatc actttattcg   6480
ggagcagctg gcattgcatt aagtatccta catttacgag aagatgacga aaaatataag   6540
aatcttcttg atagcctaaa tagatatatc gaatatttcg tcagagaaaa aattgaagga   6600
tttaatttgg aaaacattac tcctcctgat tatgacgtga ttgaaggttt atctgggata   6660
ctttcctatc tattattaat caacgacgag caatatgatg atttgaaaat actcattatc   6720
aatttttat caaatctgac taaagaaaac aatggactaa tatcgcttta catcaaatcg   6780
gagaatcaga tgtctcaatc agaaagtgag atgtatccac taggctgttt gaatatggga   6840
ttagcacatg gacttgctgg agtgggctgt atcttagctt atgcccacat aaaaggatat   6900
agtaatgaag cctcgttgtc agctttgcaa aaaattattt ttatttatga aaagtttgaa   6960
cttgaaagga aaaaacagtt tctatggaaa gatggacttg tagcagatga attaaaaaaa   7020
gagaaagtaa ttagggaagc aagtttcatt agagatgcat ggtgctatgg aggtccaggt   7080
attagtctgc tatacttata cggaggatta gcactggata atgactattt tgtagataaa   7140
gcagaaaaaa tattagagtc agctatgcaa aggaaacttg gtattgattc atatatgatt   7200
tgccatggct attctggttt aatagaaatt tgttctttat ttaagcggct attaaataca   7260
aaaaagtttg attcatacat ggaagaattt aatgttaata gtgagcaaat tcttgaagaa   7320
tacggagatg aaagtggcac gggttttctt gaaggaataa gtggctgtat actggtatta   7380
tcgaaatttg aatattcaat caattttact tattggagac aagcactgtt actttttgac   7440
gatttttga aaggagggaa gaggaaatga gaagatattt aatacttatt gtggccttaa   7500
```

-continued

<210> SEQ ID NO 109
<211> LENGTH: 11740
<212> TYPE: DNA
<213> ORGANISM: Artificial Sequence
<220> FEATURE:
<223> OTHER INFORMATION: Synthetic construct

<400> SEQUENCE: 109
aagctttatc tttaaacttt gaacaaaaaa tcaaatgttc cccccccatc tcttgtaaag 60
gagatggggg aactagatta taagttgttt tcaaaataca atataacgtt atatctgaat 120
tttctaaaac tttaattttt tgtaatagaa ccagattaaa taatccagtt gaattcactt 180
aatgtttgct ttactttttt atacttttct ggagtgattt taaccgtatt attcttaatc 240
gatttcaaaa tatagcattt actatgctta tcgaatatta tatttttaat actttttaaa 300
ggaataagta atgacctact tactaaaata aatccataag aatagagttt tttttctaaa 360
tattttaagg agccattata agaaactgtt tctttgtcat ccaaagtgat aattattttt 420
ctaccgcaac attctgctgt tgtaatttta tcaatttcta aaaaatataa agatttcccc 480
tttttaatgg cgattttttct gtttttaaga ttgttaagat cgaatttttt tctgcatcta 540
tttttgaaat gaagtaagca cttctccaat ttaataggct ctactggttg tattaaatag 600
tcaaaaggat gagcttcaaa acttttatgt gcgtgtttgg aatcagaaga tagaaaaact 660
atttgaatat gtttatgtat agaattgata ttattggcta tatctataaa cttgttgtta 720
tttgtattta tttttaaaaa tattaagtct atatctttct tatctagggt atttttggct 780
tcaatatatt cactaaatgt acctttacat gaaacaaatg agaagtaaga tagatttact 840
tttaaatcct ctctagtact tgcattatcg tctataataa tagcatttat ttttttcata 900
aaatcaattt tcccattcct ttatcaataa aaaattaaaa ccaaccttac ttcattaata 960
tatcacaatt attttttttaa atcattatta ttaaatgaac tttaaaattt ttttaaattg 1020
atagattgta agattatttt gtaaagtata tctgctagac ttcaagtaat tgttgccaat 1080
aaattgcctt cgatgaagtt atcttaataa aagctggaaa gaacaaaata ttaaggtttc 1140
aatactctcc aaaatacaat aactaaagac actatatatg ttttacggtt cataaaaaat 1200
ccgtagttct tttcaaaact acggattttc gccatgccat aatattagta tcatgttaat 1260
caataaaaaa actaaagtaa gtatcactta aagttatttt tactgatttt acaacattcc 1320 ccttttttatg aacaacaagt aaatacaaat tggaaagaat tcatatggca atcgtgtgac 1380
acagttggga ttactcctga ctttttctta gctcctaaga cttcattcaa ttcatcttct 1440
tgaacctctt ctaataaatt tgctacttca atgtccttca taactttaga attttccatg 1500
tttgttacct cctaaattta atatttgtta caagtttaat atcacatgat atttacaaag 1560
tgtaaaattg tataaaccac ttatttatat aattaaaatt tatatttaga gtgataaagt 1620
ggttttctat atgaataaaa taaaaatttg aaacttacaa ttttgttagt tttaggtttt 1680
tccgtttctg ctgcaaaatt tatcttgtag tatgaggtta gattaccaat attagaagta 1740
aagcgaaatt gtagcaagct agttattttt ataacactgt aaaagaggaa tgttcataca 1800
catcaaaact aatttcaaac gtcgaaaaga tatgttaaag caaatttata taatgcgtta 1860
tatgaattat gatagttaat aataggagat gatattaact atgaacaaca ttaaagttga 1920
acaatttaga ggattttcaa attttatttt aaaaaaatac tctaaacaag aacttaacac 1980
attaattgat tggaactact taagatctat tattctagat atttgtggaa aatcattgat 2040
tgttttaatt aatgaaaaaa gattaaacaa aaaactcaat ggaaatactc ctgaagaacg 2100

-continued

```
ctataaatat tttgatgaag aattatgtga aaaagggatt atatatgaag agttaaataa   2160
aagttatcca tcaataataa atgatttaga gcaaacttta aactcatatt tttcgttttt   2220
gaaagaaatc gaaaataaat tcaatcaaga aaaaaagaaa cttttagaag ccaatttaat   2280
aaaaactgaa aaagaaacga tttgtcatat cagtatttta ggagatttac atggaggtaa   2340
agcggtgact aaagtaacca ctgataaatc tcaattatta tataaaccta ggtcattaga   2400
aaatgatagt ttctttttag aattcttaga atttatgtac agttttcaaa aaaatgaaat   2460
atcaacatac tataagtata aattcataga ttataaagac cacggttgga tggaatatat   2520
agaaaagcaa cctacctcta aaaataaaat aaatatgtat tacaaaagat tgggatattt   2580
attgtctata ggatatttat taaatataag tgatttacat ttcgaaaata tactgtgttc   2640
cagtaatttt ccaatattaa ttgatttaga aactatattt catacgtcca tatatgaatc   2700
aaaatttcgt aatttagcta caaagaatat agaagataaa gctgctaatt ctgtattcgc   2760
taccggaatg ttaccgatat ccaaaaaaga caaaaaatac ggtggagata taagtggaat   2820
attaggtgga gtatttaata aacacgaaag aactataagt aatcctaata gagatgatat   2880
aaaattcgaa aagagattag taagagttaa aagaaatgat catatcccat tttatatgga   2940
aaatgataaa aaaaggagat tttctcccga agtatttata gaagatattc aagaaggctt   3000
taaatatggt tacgaattat ttcttaacaa tagaaaagaa atactacatt atataaagaa   3060
aacgtcatca gaagtagaag tgagaatttt accaagaagt acaattgagt actcagtatt   3120
aatacaagct gctaaatcac ctctttatgc aaataagcga aagagcttgt ttaacaaact   3180
agaagagtac ggtgaaaatt tattaagtga taagttaata aattcagaaa taaaacaaat   3240
agaaactctt tcagtaccct atttttatac taaggtccaa agtgtttcgg taaaagatat   3300
taaaaataat acggtacatc acttattgaa aaacccactc aatgtatttt tagaaaaaac   3360
gcaaagatat tctttgaaag atttgttgtt tcaatgtaaa ctaataaaat tttcattaga   3420
aagtcaaaat aaattattta ttgatggtaa tggatttata aattatggat atgaaatagt   3480
aaattcagac aatattgacg atgcaatcga caatttagta agcattataa ttaataatgc   3540
agtcatagat gaaaaagatg gttctgtaaa ttggatgaat ttaggcatat caaaaggaga   3600
agaaataata tttgaaagct tgtcagatga cttatataaa ggattgtcag gaataggaat   3660
agctttatta aaatattatg aaattaacaa aaacttaaaa gatatgagta gactaaaaaa   3720
aatactaagc agtatttatt cttctatatt aagtaatata aatactaatt ctagtaaaga   3780
aaaggattta tctttttta atggtgaaat aggtaaaatc gcatttttat ataattacca   3840
gattgaattt aaagaaaatt gcgacagcag taaaaattat atgaaacata ttttagggat   3900
cattttatct agtgaatttg aaatgaatga cattatagcc ggattaccag gaattatttc   3960
atatttatat aatcaagaaa tattttctaa agaacttgta ataatgggag atagactatt   4020
aaaagactta gacaataatc caactatggc ctactacgct cacggtaaaa gtggggtaat   4080
ggtttcatta ttatatttat atgatttaac taaagacaaa aagtatctag ttaaattcca   4140
tcaggaatgg aaaaaagaaa acacattaaa attggaaata ggatggaaag atgtaagaca   4200
aaatgaagaa acctactctg tatcatggtg taacggagtt acaggacagt taataagtag   4260
actagttgct ttagaaattc atgataaagt aaaaatattt gatgctgtaa ataaaaagtt   4320
aatgcaaaaa gaaattgaag aattacttta tttattgaaa gaagaaggat tagaacaaaa   4380
taatttttgc ctatgtcatg gcgtcatggg aaatttactg gttttaaatt actatcaaaa   4440
```

-continued

```
aaaatttgaa aatacaaaca ttcatttagc caataaaata gacagtcatt tttattcagt   4500
agctaatttt ggtttaaata aaggatggat atgtggctta ggaaataact tttactcttt   4560
tagcattatg acaggaatat caggtatttt atatgctttt ttaaagtata aaactaagga   4620
tactgaatta ggtatattgt taccaaacat ttagtttgga agaaggtgat gacaattgaa   4680
aatcgcatta caaaatagtg accaagactg tctattagcg tgttattcaa tgattttgag   4740
ttattttggt aaaaatgtat ctataaatag tctttacaaa agagagatga taccacctga   4800
tggtctatca atatcttatt tgaaagaatt aaatattaag tacgaactta atatgaaagt   4860
atatagaatt aaagataaag aaaaaacatt ccgagtaata agtaaaataa agaaaccaat   4920
aattgttcat tgggatttaa atcattttgt catagtaaaa aacgttaaaa aaaaccatat   4980
agaaatagtc aacccagaga taggaaaagt aaaaatttca aaagagatgt ttttggaaca   5040
tttttcaaat gttctattaa tgtttgatcc taagagcgat tttccaaagg ataaagaaaa   5100
aattgagttc tttgacgatt taaaaagtgt tttaatgatt aaaaacataa ttcttttttc   5160
attttcagtg atgttagctc aaattgtagc tctaattttt tcaatagttg ttagagatat   5220
aataaatcaa aaatatacat acctaatatc attatcaatg ctattaatga tgattattat   5280
tcaaatattt tctttagttt ttaagcaaaa agctcaaatt aaagagaata aaatatatga   5340
aaaaatcatt tcctataaca tgtttgaagg attatttaac aagcccttat tatactttag   5400
aaatagcaca ataggtactt tgatggaaaa gataaatata aagactacta taagggacaa   5460
catactgctt aaaatattgc catcattctt aaacttcttt tccgttacgg tattgtttat   5520
atatttgtta actgtatcac tgctattatc attattactt ttaggtatgt ccattatata   5580
tttgttaatc agtgtgttta tatatataaa gaaaaatcaa ttgaatattg agtatatgca   5640
gagaactata caatttagtt ctttagctca agaatcatta agtcaaattg atcaaattaa   5700
ggcccaagct caagaatcat caacaataaa taactggaaa gaaaaaagtt ggaatatagt   5760
taactcttat aattcaattt tgaaaattga aggattatca tatactttta atcaaatttt   5820
caattacagt agcataatac ttttaatgat ttttggtatt catcttacaa aatacgggaa   5880
tataaccata gcagatttaa tcttatttca aaccggtatg tctatattta gtttcatctg   5940
ttcacaacta caagacatta cgtttgaaat atcaaaaatt aaagtgtccg gcgagaaaat   6000
caatgactta tttttaaaaa ataatactaa aagaaaagta atcgagcaga aatctaataa   6060
tgctttatca cttaagaatg ttacttttgg ttttgatgaa aaagccccta tattgaaaaa   6120
cattactttc caagtaaaaa aaggtgaaaa agtagctata gtaggagact ccggatcagg   6180
taaaagtact atgttaaatg ttctgttagg tctctataca tgtgatggtg aagtagttta   6240
cggttataga gattttagga aaataacagg ggtcgtctta cagaatatga cgttaagtaa   6300
acaatctatt tataataatt tggtggatga aggaaatgat agcaatatgc aaaaattaaa   6360
ccaaatacta tacgatgtta atattataaa cttgataaat tctttaccta ataaaatata   6420
ttctagtgta tttcaaaatg gaaaaaatct atctggtggt caaattcaaa ggctattaat   6480
tgctaaatct ctatttaata aaaaattaat tttttgggat gaagctttta gcagtttgga   6540
caattacaat cgtataaata tatatagaaa tgttttgaaa aatagtcaat atagcgataa   6600
aactatagta ctcataagtc accatctaga tgttttatca tatgtcgaca aagtaatgtt   6660
tattgaaaac ggaaacgctt tttttggaac acataatgaa ttaattaaaa ataataaaaa   6720
ttatagaaga ttcttagata ctgccaatac taataattaa ggagattcaa ttatgattaa   6780
caatattgta caaacccaaa atttaacaaa aaagttttca gatagttatt cagtagacaa   6840
```

-continued

```
tctatcacta aatattggtt cgaaagaaat atatggattt ttaggtccaa atggtgctgg   6900
taaaagtact acaatgaaaa tgttactagg tctcatgcaa ccaactaaag gtaatattaa   6960
aatattcaat caagatattt caaaaaatag agatgagata ttaatgcatg taggggcatt   7020
aattgaagaa ccttcttatt ataaaaattt aactggttta gaaaatttgc aagttattca   7080
aagattacta aacttacctt ctaaaaatgt taaagaagct ctgaaaattg tacgtttaac   7140
tgaacacaag gataaattag tcaaaaatta ttcattaggt atgaaacaaa ggttaggtat   7200
tgctttagct atagtaaaat ttccaaaact attgatatta gatgaaccta ctaacggctt   7260
agatccttct ggtatacaag aaattagaga attaataaaa tcttttccaa aaacttatgg   7320
aatgactgta cttatatcta gtcatttatt atctgaaatt gaacatatgg ctaatacagt   7380
aggtatcatc aatagaggga aactattgtt tgaaggaaag ttaacagaat tagaagaaca   7440
gaacaaaata ttgataaata ctaacaataa cagtgagagt ataaacttgc ttcaatcaaa   7500
aggatataat ctagaaaata atgaaaaacc tctcctatta gatacaactc aaaaagatat   7560
atctacagcc gttaaattgt tagttaataa taagttcgaa atttaccaag tacaatcagt   7620
tcagaaaagt ttagaagaaa atttatagaa ataactaatg atggaaagga atatttataa   7680
atgttaaaag ctataaattt agaatttttc aaaatgcgga gaagaaaatt tatccttcca   7740
atactactga ttacctttgt tggtatattg tggttttgtg ctatagcaat taaagagtta   7800
aatattactg atacaaagta tggtatttat atgctcattt ctaatattct aactatcgac   7860
agcatgattt atccaatatt aataggtatt ttatgctcaa gacttgcaga tatagaacat   7920
caaggaaaaa cctttcagtt attaaatact agtaaacaaa gtgttttcaa tttgtttact   7980
agtaaagttg gtgtttcgct tattatttta tttgtaattg acattataca attaacgacc   8040
atcttactaa ttgctaattc acataaatatc agtttgaaac tagaaatcat ttcaaaattc   8100
atgctaagtt ttataattgc tagtttcttc ttaatattaa ttcatatggc actttctttc   8160
ttttttgaaa aacaatcagt tagcattgta tcagcattag taggaagttt tttaggatta   8220
gtaacaggag ggatgttgcc ttcatatatt aaaatatttt tgccttggca atattattca   8280
ttactaaatc cagttcataa aaagatggtt cacaaaggat atgaatattc aaataatgac   8340
tattatttta tttacatttt tatttctatt ctagtaatag taattctttt ctttattatt   8400
aaagccttaa taaaaaggag ggatttaaat tgatttcttt attaagcata gaattacgca   8460
aactacaaaa taattatatt ttaatcttct tattagtttt taatatatta agcgtatcta   8520
taggaagtat gatattttat tttaatcaaa gcgcttttcc taattcaaat aatagagatt   8580
taatattgtg gggcaagaa actttatata cttcacaact tttctttccc atactgatag   8640
gtgttttatg ttcaataagt tggcaatttg aggagtctaa taataattgg atgagaatga   8700
aaactatacc tttaaaagaa agtaagatag ttttatcaaa atttttatct cttttcttac   8760
ttactttact aaatcaaatt atattttttg tattattttg tatctcagcc tcaatagtaa   8820
atgtatcctt ggaaggatta cttaaatttc tatactggga ctttataggt tggataggta   8880
cagcatctat tgttgctata caattatatt tgtcagttgc gactagaaat ttcactttct   8940
caattttaat atcaactatt ggtggtgtac taggtcttct aacattgttt attagcaatt   9000
ttatttttaa aatatttcca tattcacaaa ttacagttgg tgtgagagcc agatctttga   9060
tgaacttcac tttttcagaa atgttacttt ttcttataat aaatgtagct tatataacag   9120
tttttttgac acttactact ttaaagctta aaaaaagaga gggttaattt aaaatgaaaa   9180
```

-continued

```
gaaaagacta cttatttttt gtaattgcac ttttaccttt aattagtttg ttattacagt   9240
taatgaaaat ttcacttatc cataattatc aaagtttttt ctctatagtt aatatcatct   9300
gcatactttt tactattgct tattcaatta ttttagttat taatagcaag aaaaagaata   9360
atttgcagaa aacaattctt attttgtcta ttatctatat attaacttta atttttatct   9420
cttttggagt aataattaat atgtttaatt aaaataattt taatagcaaa atactatcaa   9480
aaattttccc acataaaaag tcacgataaa tttatcgtga ctttttaatt gctattcatt   9540
tttacggata ctatgccagt tcaataacct tttttttcta aaaactcatt taaaacatta   9600
tcaacaatcg ctttaataga tgtatcttga tctaatgcca tttgacttaa acgttttttt   9660
aaatttgtat ccacacgcat cgtagtactt ttagaaatag gtttataatt ttcagtatat   9720
ttaactgacg aagtatctat atcatctaaa aatcctgcca ttattttcac tcactttcaa   9780
tcacttgtat tctatctacc aattctatat aaactttatt aaacatgtgt attacttttt   9840
tatcatgcat atctttattt cttataccct cagcaccaaa ttttttaatt ctttctcttt   9900
gataaatttg attttcaaat agagcttgtg aaaatgcagt tttagacata tttaatattt   9960
tctcatccac ttttccactt cgtttaatca aaactgggac agctccaatc aattcaaaag  10020
gcaaattcga ttcatttttt ctatctctta aaaagtttac aaaagacaag ctactttcat  10080
aagctgattg ttgtgtttga aataccataa gaatataatc gcttgcatat acagcattat  10140
tagtaaaatc agagttaata gtcggtggta catcaataaa aatatggtca aaatcataca  10200
tttccctaat cttttctact acattttttta aaatatatct tttcttcaaa atatctgttt  10260
tagaaattat atcagacaaa ttagctaatg aagagtcagc tggtaacaat gataatttag  10320
acgataaccg aatcatacta ttttctaaat ttccggttct aagcatatct ataaacgatt  10380
cattttcctc tggcgcttcg acatatgtcc gtttcataat ttgcgtagcg ttcccctgcg  10440
gatcaaaatc tataagtaat actttcttac catactgctc tgatgctata taagaaagta  10500
ttgttgctac tgttgtttta cctactccgc ctttaaaatt tccaactgtt attacactca  10560
aataaaaacc ccctatgtta catgtaacat gttactaatg tttattcttt ctgtctaatt  10620
taaatcaatt tgctataaat caaaaaagaa ttacttatat atcctatgtt acatgtaaca  10680
tgttactaat gtttattctt tctgtctagt ttaaatcaat ttgctataaa ttaaaaaaga  10740
attacttata tatcctatgt tacatgtaac atgttactaa tgtttattct ttctgtctag  10800
tttaaatcaa tttgctataa attaaaaaag aattacttat atatcccatg ttacatgtaa  10860
catgttactt aagggaaagt tacaatattc tttgttaatt tttcttaaat ttgttactat  10920
gaacttaacg ttcattaata tatttaaaaa gcacttaatc gttggggcga ttaagcgctt  10980
taggtaataa acactatact aacattcact actaaacatt aagaaaagtg ctatctatat  11040
acatttatat attctggatg ctcaaatttc aatccatttt gtagaatcaa ttgtataata  11100
taagtaatat caattcaaga aagatatctt aatttaatta gtattgtgat ttattacctc  11160
aaccctaaat ttatgtgaag aggtatttac tatgactaaa caacgattta caaaactata  11220
taaattctta ttcgaagatt ccacatttaa caaactatca ataaaagcta aattgcttta  11280
tgcattatta accgaacgtc aaaacttatc taagttaagt gccaaacaac atggtattca  11340
atcacaattt attgatgata acggacgttt attctcaatt tatactaata aagaacttat  11400
gaatataatt aatatatctg aacctactgt tattaaccta aaaaagcaac tcattgcatt  11460
tggcttatta gaagaaatac gccttggaaa aaataaaccg aatcgcttat atcctaaaaa  11520
accttatgat gaatatttct atgttcatga tgttgatgaa ttttatcggt taccacattc  11580
```

attattttct aatcctaaat ataagaatct taaagctgag acaattgtcg cttacgctgt 11640
ttacctaagc cgttatgaat atagtgtata caaaaatcat ttttcggata aaagtggtga 11700
aatatattgc catttttcta atgagaaaat ggctgaattc 11740

<210> SEQ ID NO 110
<211> LENGTH: 51
<212> TYPE: PRT
<213> ORGANISM: Artificial Sequence
<220> FEATURE:
<223> OTHER INFORMATION: Synthetic construct: lacticin precursor after first reaction catalyzed by LctM.
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: MISC_FEATURE
<222> LOCATION: (34)..(47)
<223> OTHER INFORMATION: At positions 33 and 48, Xaa represents (Z)-2,3 didehydrobutyrine and at positions 35 and 42 Xaa represents 2,3 didehydroalanine.
<220> FEATURE:
<221> NAME/KEY: misc_feature
<222> LOCATION: (48)..(48)
<223> OTHER INFORMATION: Xaa can be any naturally occurring amino acid

<400> SEQUENCE: 110

Met Lys Glu Gln Asn Ser Phe Asn Leu Leu Gln Glu Val Thr Glu Ser
1 5 10 15

Glu Leu Asp Leu Ile Leu Gly Ala Lys Gly Gly Ser Gly Val Ile His
20 25 30

Xaa Ile Xaa His Glu Cys Asn Met Asn Xaa Trp Gln Phe Val Phe Xaa
35 40 45

Cys Cys Ser
50

<210> SEQ ID NO 111
<211> LENGTH: 57
<212> TYPE: PRT
<213> ORGANISM: Artificial Sequence
<220> FEATURE:
<223> OTHER INFORMATION: Synthetic: product of first reaction of LctM with SEQ ID NO:9.
<220> FEATURE:
<221> NAME/KEY: MISC_FEATURE
<222> LOCATION: (52)..(54)
<223> OTHER INFORMATION: Xaa at position 52 is the dehydration product of the threonine residue (didehydrobutyrine) and Xaa at position 54 is the dehydration production of the serine residue (didehydroalanine) as occurred in SEQ ID NO:9.

<400> SEQUENCE: 111

Gly Ser Ser His His His His His His Ser Ser Gly Leu Val Pro Arg
1 5 10 15

Gly Ser His Met Lys Glu Gln Asn Ser Phe Asn Leu Leu Gln Glu Val
20 25 30

Thr Glu Ser Glu Leu Asp Leu Ile Leu Gly Ala Lys Gly Gly Ser Gly
35 40 45

Val Ile His Xaa Ile Xaa His Glu Cys
50 55

<210> SEQ ID NO 112
<211> LENGTH: 57
<212> TYPE: PRT
<213> ORGANISM: Artificial Sequence -continued

```
<220> FEATURE:
<223> OTHER INFORMATION: Synthetic:  intermediate product of
      LctM-catalzyed dehydration of SEQ ID NO:10.
<220> FEATURE:
<221> NAME/KEY: MISC_FEATURE
<222> LOCATION: (50)..(58)
<223> OTHER INFORMATION: Xaa at position 52 is didehydroalanine, and at
      postiion 54, Xaa is didehydrobutyrine, and at the last position,
      Xaa is selenocysteine.

<400> SEQUENCE: 112

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Xaa Ile Xaa His Glu Xaa
    50                  55


<210> SEQ ID NO 113
<211> LENGTH: 70
<212> TYPE: PRT
<213> ORGANISM: Artificial Sequence
<220> FEATURE:
<223> OTHER INFORMATION: Synthetic:  product of LctM-catalyzed
      dehydration of SEQ ID NO:13.
<220> FEATURE:
<221> NAME/KEY: MISC_FEATURE
<222> LOCATION: (1)..(69)
<223> OTHER INFORMATION: At positions 52 and 67 Xaa is didehydrobutyrine
      and at positions 54 and 61 Xaa is didehydroalanine.

<400> SEQUENCE: 113

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
        35                  40                  45

Val Ile His Xaa Ile Xaa His Glu Cys Asn Met Asn Xaa Trp Gln Phe
    50                  55                  60

Val Phe Xaa Ala Cys Ser
65                  70


<210> SEQ ID NO 114
<211> LENGTH: 70
<212> TYPE: PRT
<213> ORGANISM: Artificial Sequence
<220> FEATURE:
<223> OTHER INFORMATION: Synthetic:  product of LctM-catalyzed
      dehydration of SEQ ID NO:12.
<220> FEATURE:
<221> NAME/KEY: MISC_FEATURE
<222> LOCATION: (1)..(70)
<223> OTHER INFORMATION: At positions 52 and 67, Xaa is
      didehydrobutyrine, and at positions 54, 61 and 68 Xaa is
      didehydroalanine.

<400> SEQUENCE: 114

Gly Ser Ser His His His His His His Ser Ser Gly Leu Val Pro Arg
1               5                   10                  15

Gly Ser His Met Lys Glu Gln Asn Ser Phe Asn Leu Leu Gln Glu Val
            20                  25                  30

Thr Glu Ser Glu Leu Asp Leu Ile Leu Gly Ala Lys Gly Gly Ser Gly
```

-continued

```
        35                  40                  45

Val Ile His Xaa Ile Xaa His Glu Cys Asn Met Asn Xaa Trp Gln Phe
    50                  55                  60

Val Phe Xaa Xaa Cys Ser
65                  70


<210> SEQ ID NO 115
<211> LENGTH: 56
<212> TYPE: PRT
<213> ORGANISM: Artificial Sequence
<220> FEATURE:
<223> OTHER INFORMATION: Synthetic:  product of LctM-catalyzed
      dehydration of SEQ ID NO:67.
<220> FEATURE:
<221> NAME/KEY: MISC_FEATURE
<222> LOCATION: (1)..(56)
<223> OTHER INFORMATION: At positions 27, 29 and 55 Xaa is
      didehydroalanine, and at positions 32, 37, 42, 47 and 49 Xaa is
      didehydrobutyrine.

<400> SEQUENCE: 115

Met Ser Lys Phe Asp Asp Phe Asp Leu Asp Val Val Lys Val Ser Lys
1               5                   10                  15

Gln Asp Ser Lys Ile Thr Pro Gln Trp Lys Xaa Glu Xaa Leu Cys Xaa
            20                  25                  30

Pro Gly Cys Val Xaa Gly Ala Leu Gln Xaa Cys Phe Leu Gln Xaa Leu
        35                  40                  45

Xaa Cys Asn Cys Lys Ile Xaa Lys
    50                  55


<210> SEQ ID NO 116
<211> LENGTH: 8
<212> TYPE: PRT
<213> ORGANISM: Artificial Sequence
<220> FEATURE:
<223> OTHER INFORMATION: Synthetic construct:  C-terminal His tag.

<400> SEQUENCE: 116

Leu Glu His His His His His His
1               5


<210> SEQ ID NO 117
<211> LENGTH: 19
<212> TYPE: PRT
<213> ORGANISM: Artificial Sequence
<220> FEATURE:
<223> OTHER INFORMATION: Synthetic construct:  N-terminal His tag.

<400> SEQUENCE: 117

Gly Ser Ser His His His His His His Ser Ser Gly Leu Val Pro Arg
1               5                   10                  15

Gly Ser His


<210> SEQ ID NO 118
<211> LENGTH: 47
<212> TYPE: PRT
<213> ORGANISM: Artificial Sequence
<220> FEATURE:
<223> OTHER INFORMATION: Synthetic construct:  RumA

<400> SEQUENCE: 118

Met Arg Asn Asp Val Leu Thr Leu Thr Asn Pro Met Glu Glu Lys Glu
1               5                   10                  15

Leu Glu Gln Ile Leu Gly Gly Gly Asn Gly Val Leu Lys Thr Ile Ser
```

-continued

```
            20                  25                  30

His Glu Cys Asn Met Asn Thr Trp Gln Phe Leu Phe Thr Cys Cys
        35                  40                  45


<210> SEQ ID NO 119
<211> LENGTH: 27
<212> TYPE: PRT
<213> ORGANISM: Artificial Sequence
<220> FEATURE:
<223> OTHER INFORMATION: Synthetic construct:  hedratase product of SEQ
      ID NO:3 structural region.
<220> FEATURE:
<221> NAME/KEY: MISC_FEATURE
<222> LOCATION: (1)..(26)
<223> OTHER INFORMATION: Xaa is dehydroalanine.

<400> SEQUENCE: 119

Lys Gly Gly Ser Gly Val Ile His Thr Ile Ser His Glu Cys Asn Met
1               5                   10                  15

Asn Xaa Trp Gln Phe Val Phe Thr Cys Cys Ser
            20                  25


<210> SEQ ID NO 120
<211> LENGTH: 159
<212> TYPE: PRT
<213> ORGANISM: Artificial Sequence
<220> FEATURE:
<223> OTHER INFORMATION: Synthetic construct:  PepC partial sequence.

<400> SEQUENCE: 120

Ile Lys Phe Asn Asn Asp Asp Tyr Leu Leu Asp Thr Ile Leu Ser Asn
1               5                   10                  15

Leu Gly Tyr Ala His Gly Ile Pro Gly Ile Ile Asn Thr Leu Cys Asn
            20                  25                  30

Ser Tyr Lys Arg Gly Tyr Gly Ile Ile Lys Thr Lys Lys Ile Leu Glu
        35                  40                  45

Gln Ser Ile Phe Thr Leu Leu Gln Asn Leu Lys Leu Glu Asn Gly Thr
    50                  55                  60

Ile Tyr Ile Pro Asn Asp Ile Glu Ser Pro Asn Asp Tyr Arg Asp Ala
65                  70                  75                  80

Trp Cys Tyr Gly Leu Pro Ser Val Ala Tyr Thr Ile Phe Asn Val Ser
                85                  90                  95

Ser Thr Leu Lys Asn Lys Ser Leu Ile Glu Leu Ser Glu Ser Leu Leu
            100                 105                 110

His Gln Val Phe Leu Arg Ser Asp Asn Ala Thr Lys Leu Ile Ser Pro
        115                 120                 125

Thr Leu Cys His Gly Phe Ser Gly Val Val Met Ile Ser Leu Leu Met
    130                 135                 140

Asn Asn Asn Glu Leu Ser Ser Lys Tyr Gln Lys Lys Ile Ile Gln
145                 150                 155


<210> SEQ ID NO 121
<211> LENGTH: 5
<212> TYPE: PRT
<213> ORGANISM: Artificial Sequence
<220> FEATURE:
<223> OTHER INFORMATION: Synthetic construct

<400> SEQUENCE: 121

Leu Cys His Gly Tyr
1               5
```

<210> SEQ ID NO 122
<211> LENGTH: 5
<212> TYPE: PRT
<213> ORGANISM: Artificial Sequence
<220> FEATURE:
<223> OTHER INFORMATION: Synthetic construct

<400> SEQUENCE: 122

Phe Cys His Gly Tyr
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: At position 4, Xaa is U(Ph)
<220> FEATURE:
<221> NAME/KEY: MISC_FEATURE
<222> LOCATION: (1)..(1)
<223> OTHER INFORMATION: N-terminal glycine residue is acetylated.

<400> SEQUENCE: 123

Gly Leu Pro Xaa Val Ile Ala
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic construct: dehydropeptide
<220> FEATURE:
<221> NAME/KEY: MISC_FEATURE
<222> LOCATION: (1)..(7)
<223> OTHER INFORMATION: At position 3, Xaa is dehydroalanine.
<220> FEATURE:
<221> NAME/KEY: MISC_FEATURE
<222> LOCATION: (1)..(1)
<223> OTHER INFORMATION: N-terminal glycine residue is acetylated.
<220> FEATURE:
<221> NAME/KEY: MISC_FEATURE
<222> LOCATION: (1)..(7)
<223> OTHER INFORMATION: At position 4, Xaa is dehydroalanine.

<400> SEQUENCE: 124

Gly Leu Pro Xaa Val Ile Ala
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: At position 4, Xaa is U(Ph).
<220> FEATURE:
<221> NAME/KEY: MISC_FEATURE
<222> LOCATION: (1)..(7)
<223> OTHER INFORMATION: N-terminal glycine residue is acetylated.

<400> SEQUENCE: 125

Ile Ser Val Xaa Arg Ser Thr Ser
1               5

-continued

```
<210> SEQ ID NO 126
<211> LENGTH: 8
<212> TYPE: PRT
<213> ORGANISM: Artificial Sequence
<220> FEATURE:
<223> OTHER INFORMATION: Synthetic construct:  dehydropeptide
<220> FEATURE:
<221> NAME/KEY: MISC_FEATURE
<222> LOCATION: (1)..(7)
<223> OTHER INFORMATION: At position 4, Xaa is dehydroalanine
<220> FEATURE:
<221> NAME/KEY: MISC_FEATURE
<222> LOCATION: (1)..(1)
<223> OTHER INFORMATION: N-terminal glycine residue is acetylated.

<400> SEQUENCE: 126

Ile Ser Val Xaa Arg Ser Thr Ser
1               5


<210> SEQ ID NO 127
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: At position 3, C is blocked with StBu
      (tert-butyl disulfide) and at position 5, Xaa is U(Ph).
<220> FEATURE:
<221> NAME/KEY: MISC_FEATURE
<222> LOCATION: (1)..(1)
<223> OTHER INFORMATION: N-terminal glycine residue is acetylated.

<400> SEQUENCE: 127

Gly Gly Xaa Pro Xaa Val Ile Ala
1               5


<210> SEQ ID NO 128
<211> LENGTH: 8
<212> TYPE: PRT
<213> ORGANISM: Artificial Sequence
<220> FEATURE:
<223> OTHER INFORMATION: Synthetic construct:  dehydropeptide
<220> FEATURE:
<221> NAME/KEY: MISC_FEATURE
<222> LOCATION: (1)..(7)
<223> OTHER INFORMATION: At position 3 Xaa is cysteine blocked with StBu
      (tert-butyl disulfide) and at position 5, X is dehydroalanine.
<220> FEATURE:
<221> NAME/KEY: MISC_FEATURE
<222> LOCATION: (1)..(1)
<223> OTHER INFORMATION: N-terminal glycine residue is acetylated.

<400> SEQUENCE: 128

Gly Gly Xaa Pro Xaa Val Ile Ala
1               5


<210> SEQ ID NO 129
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(7)
<223> OTHER INFORMATION: At position 2, Xaa is U(Ph) and at position 6
      Xaa is trityl-cysteine.
```

-continued

<400> SEQUENCE: 129

Leu Xaa Pro Gly Cys Xaa Gly
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic construct: dehydropeptide.
<220> FEATURE:
<221> NAME/KEY: MISC_FEATURE
<222> LOCATION: (1)..(7)
<223> OTHER INFORMATION: At position 2 Xaa is dehydroalanine and at position 5 Xaa is trityl-cysteine.

<400> SEQUENCE: 130

Leu Cys Pro Gly Xaa Val Gly
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(9)
<223> OTHER INFORMATION: At position 4 Xaa is U(Ph) and at position 8 Xaa is trityl-cysteine.

<400> SEQUENCE: 131

Arg Ile Ala Xaa Ile Ala Leu Xaa Lys
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic construct: dehydropeptide
<220> FEATURE:
<221> NAME/KEY: MISC_FEATURE
<222> LOCATION: (1)..(9)
<223> OTHER INFORMATION: At position 4 Xaa is dehydroalanine and at position 8 Xaa is trityl-cysteine.

<400> SEQUENCE: 132

Arg Ile Ala Xaa Ile Ala Leu Xaa Lys
1               5

<210> SEQ ID NO 133
<211> LENGTH: 4
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(4)
<223> OTHER INFORMATION: At position 3 Xaa is U(Ph)

<400> SEQUENCE: 133

Ala Met Xaa Ala
1

<210> SEQ ID NO 134
<211> LENGTH: 4

-continued

```
<212> TYPE: PRT
<213> ORGANISM: Artificial Sequence
<220> FEATURE:
<223> OTHER INFORMATION: Synthetic construct:  dehdropeptide
<220> FEATURE:
<221> NAME/KEY: MISC_FEATURE
<222> LOCATION: (1)..(4)
<223> OTHER INFORMATION: At position 3 Xaa is dehydroalanine.

<400> SEQUENCE: 134

Ala Met Xaa Ala
1
```

COMPOSITIONS AND METHODS FOR DEHYDRATION AND CYCLIZATION OF PEPTIDES, SYNTHETIC COMPOUNDS, AND LANTIBIOTICS

CROSS-REFERENCES TO RELATED APPLICATIONS

This application claims the benefit of U.S. Provisional Application No. 60/536,140, filed Jan. 12, 2004. Each related application(s) is incorporated herein by reference in entirety.

FEDERAL FUNDING

This invention was made, at least in part, with government support under Grant NIH GM 58822 awarded by the National Institutes of Health. The government has certain rights in the invention.

BACKGROUND OF THE INVENTION

Bacteriocins are a large class of genetically encoded antimicrobial peptides in which molecular diversity may be introduced by post-translational modifications. These compounds display diverse and often novel mechanisms of cytotoxicity (2, 3). Ribosomally synthesized peptide antibiotics are amenable to structural variation via site-directed mutagenesis providing access to analogs for structure-function studies. The biosynthesis of the lantibiotics produced by Gram-positive bacteria has long intrigued microbiologists, biochemists, and chemists (1). As illustrated in FIG. 1 for the lantibiotic, lacticin 481 (4), these compounds contain the unusual cyclic thioether amino acids lanthionine (Ln) and/or methyllanthionine (MeLn) as well as 2,3-didehydroalanine (Dha) and (Z)-2,3-didehydrobutyrine (Dhb). The widespread use of the prototypic lantibiotic nisin as an alternative to chemical reagents in food preservation in more than 80 countries for over 40 years without development of significant resistance (5) has spurred research activities directed at understanding lantibiotic biogenesis.

Genetic investigations have indicated that lantibiotics are ribosomally synthesized as precursor peptides (prepeptides), which subsequently undergo post-translational modifications (1). These modifications can include one or more dehydrations and one or more cyclizations, often forming lanthionine or methyllanthionine rings.

In vivo genetic engineering studies aimed at producing novel lantibiotics have focused on site directed mutagenesis of the genes for the precursor peptides (6-9). These investigations have uncovered several limitations including loss of lantibiotic production (10) (11-14). In vitro evaluation of the substrate specificity of purified lantibiotic synthetases can overcome these limitations and allow a detailed study of the molecular logic underlying the formation of the fused cyclic structures. However, despite much effort since the first sequencing of lantibiotic gene clusters (15), the complex biosynthetic process has not proven amenable to in vitro reconstitution.

Many lantibiotics can be grouped as Class I (LanB LanC type as defined herein) or Class II (LanM type as defined herein). Sen et al. disclose that for LanB LanC type lantibiotics such as nisin, no experimental evidence consistent with a dehydration function for LanB proteins has been reported to date (Sen A K et al., 1999, Eur. J. Biochem 261:524-532). Sen et al. further disclose that direct proof for the role of LanB awaits the in vitro dehydration of precursor peptides using the purified enzyme and that problems have been encountered by them and others (Kupke T and Gotz F, 1996, Antonie Van Leeuwenhoek 69:139-150) in various attempts.

In the context of another LanB LanC type lantibiotic, epidermin, Kupke and Gotz disclose that in incubation experiments, EpiC did not react with EpiA (the precursor peptide for epidermin), proepidermin, or with oxidative decarboxylated peptides) despite using various assay conditions (Kupke and Gotz, 1996, J. Bacteriology 178(5):1335-1340). In particular, they disclose that lanthionine formation was not investigated since no dehydrated precursor peptides were available from attempts to examine whether EpiC catalyzes the dehydration of serine and threonine residues of EpiA. In further disclosing the future intention to analyze "whether the catalytic function (dehydration of hydroxy amino acid residues or thioether formation) of EpiB and EpiC depends on (new) cofactors," the implication is that such a useful catalytic function is not yet achieved.

Also in the context of epidermin, Peschel et al. disclose that purified and crude versions of EpiB were used in an in vitro assay for modifications of the purified epidermin precursor (Peschel A et al., 1996, FEMS Micribiology Letters 137:279-284). Despite the fact that the assay conditions were extensively varied in the presence of several potential cofactors and trace elements, no modification of the precursor peptide was detected.

In reviewing the lantibiotic field in the context of LanB LanC proteins, Jack and Jung disclose that "to date, it has not been possible to obtain lantibiotics in vitro using these proteins, and this is clearly one of the great challenges in lantibiotic research" (Jack R W, Jung G, Current Opinion in Chemical Biology 2000, 4:310-317). Sahl and Bierbaum disclose that the N-terminus of LanM enzymes does not display any similarity to the LanB proteins and that the role of LanM proteins in fulfilling the function of LanC or in being involved in the dehydration reaction is a hypothesis that remains to be proven experimentally (Sahl H-G, Bierbaum G, 1998, LANTIBIOTICS: Biosynthesis and Biological Activities of Uniquely Modified Peptides from Gram-Positive Bacteria, Annual Review of Microbiology, Vol. 52, pp. 41-79). Similar to the situation for LanB LanC type lantibiotics, apart from the present invention we are unaware of any prior indication of a successful in vitro biosynthesis for LanM type lantibiotics and therefore, for any lantibiotics.

The ability to successfully develop methods and generate useful compounds, for example any lantibiotics and variants thereof by an in vitro approach, provides an alternative to in vivo approaches. Furthermore, an in vitro approach can lead to different or improved compounds such as lantibiotics. The ability to achieve in vitro dehydration and cyclization of substrates would generally represent a significant advance.

SUMMARY OF THE INVENTION

In general the terms and phrases used herein have their art-recognized meaning, which can be found by reference to standard texts, journal references and contexts known to those skilled in the art. The following definitions are provided to clarify their specific use in the context of the invention.

When used herein, the term "precursor peptide" refers to a peptide that serves as a substrate for a dehydration reaction, cyclization reaction, or both a dehydration reaction and a cyclization reaction. In a preferred embodiment, a precursor peptide can be modified so as to produce a lantibiotic as defined herein. In an embodiment, a precursor peptide is derived from one or more components, where at least one component is a precursor peptide. For example, a first precursor peptide and a second precursor peptide are ligated to generate a third precursor peptide. In an embodiment, a precursor peptide is derived from genetic engineering techniques such as site directed mutagenesis, synthetic techniques, or a combination of techniques.

When used herein, the term "lantibiotic" refers to a biologically active compound that acts so as to modify the ability of a target organism, as defined herein, to develop, grow, proliferate, or otherwise function. The term can optionally include a compound derived by genetic engineering techniques, synthetic techniques, or a combination of techniques. For example, a lantibiotic can be at least partially synthetic and at least partially recombinant; thus the term can include variants of natural lantibiotics. Non-limiting examples of lantibiotics include lacticin 481, Delta-1 lacticin 481, lacticin 3147, cinnamycin, mersacidin, mutacin, streptococcin A-FF22, ruminococcin A, nisin, subtilin, duramycins, ancovenin, epidermin, and nukacin ISK-1. In a preferred embodiment, the target organism is a bacterium and the compound acts to reduce or control growth or proliferation of the bacterium.

When used herein, the term "target organism" refers to bacteria, viruses, fungi, or protozoa. Target organisms may also include a mammal, particularly a human. In the case of a multicellular organism such as a human, the term is meant to broadly convey a cell, tissue, organ, or fluid of the organism, whether in vivo, ex vivo, or in vitro.

When used herein, the term "LanB LanC type lantibiotic" refers to a lantibiotic of Class I, made in connection with LanB and LanC enzymes. In an analogous manner, the term "LanM type lantibiotic" refers to a lantibiotic of Class II, made in connection with a LanM enzyme.

When used herein, the term "LanM enzyme" refers to a polypeptide or fragment thereof capable of acting upon a precursor peptide so as to effect both at least one dehydration reaction and at least one cyclization reaction, only at least one dehydration reaction, or only at least one cyclization reaction. In a preferred embodiment, a LanM enzyme is LctM (SEQ ID NO:40) and is capable of effecting a plurality of dehydration reactions and a plurality of cyclization reactions. In another example, a LanM enzyme is a mutant fragment capable of effecting only a dehydration reaction upon a precursor peptide. In an embodiment, a LanM enzyme can have a protein homology to native LctM of at least about 60%, at least about 70%, at least about 80%, at least about 90%, or at least about 95%.

When used herein, the term "Lan protease" refers to a polypeptide or fragment thereof capable of acting upon a precursor peptide so as to effect cleavage of a leader portion of a precursor peptide. In other conventional contexts which will be apparent to one of ordinary skill in the art, the term may refer to a component of a biosynthetic operon. In an embodiment, the precursor peptide is a lantibiotic precursor peptide. In lantibiotics, a LanT protein can be present wherein the "T" can designate a common transporter function. A subset of LanT enzymes have a LanT enzyme with a protease domain and a protease function. In an embodiment, a Lan protease is LctT (SEQ ID NO:29). In a preferred embodiment, a Lan protease is an LctT fragment comprising a protease domain. In a particular embodiment, LctT is used in connection with lacticin 481 or Delta-1 lacticin 481. In instances where a given LanT protein lacks a protease domain, a protease generally designated LanP can be present. In an embodiment, a Lan protease is a LanP protease. In another preferred embodiment, a Lan protease is Lys-C. In an embodiment, a LctT protease can have a protein homology to native LctT of at least about 60%, at least about 70%, at least about 80%, or at least about 90%. LysC is also known as a commercially available protease that can have applications apart from lantibiotics.

When used herein, the term "synthase" (also referred to as "synthetase") refers to an enzyme involved in synthesis or conversion of a substrate. For example, LctM synthase indicates an enzyme that is capable of acting on a precursor peptide to synthesize a modified peptide product such as a lantibiotic. In embodiments, a synthase (synthetase) is capable of effecting at least one dehydration reaction and at least one cyclization reaction, only at least one dehydration reaction, or only at least one cyclization reaction.

When used herein, the term "derivatized amino acid" refers to any amino acid that is derivatized chemically or biosynthetically. An example of a derivatized amino acid is selenocysteine.

When used herein, the term "non-proteinogenic amino acid" refers to an amino acid that is not incorporated by ribosomal in vivo biosynthesis into a protein.

When used herein, the term "unnatural amino acid" refers to a synthetic amino acid or refers to an amino acid that is typically foreign to a particular organism. Unnatural amino acids can optionally be a subset of non-proteinogenic amino acids.

When used herein, the term "leader portion" refers to a part of a protein molecule. In an embodiment, a leader portion can be longer, shorter, or mutated from a native sequence. For example, in an embodiment wherein His6-LctA(10-51) (SEQ ID NO:6) is used, a truncated leader portion is a sufficient substrate for reaction with LctM; this embodiment also illustrates that a tag, such as a histidine tag useful in affinity purification, can be added to a leader portion.

When used herein, the term "biologically active" refers to an ability to exhibit a biological function. For example, in an embodiment a lantibiotic is biologically active so as to affect a target organism by preventing growth. Although a properly dehydrated precursor peptide of a lantibiotic may serve as a substrate for a chemical reaction (as opposed to a biosynthetic reaction) to induce cyclization, undesirable ring formation can lead to a partial or complete lack of biological activity.

When used herein, the term "vector" refers to a molecular biology tool for use in a recombinant expression system. In a particular embodiment, a vector comprises a deoxynucleotide gene sequence and is adapted for expression in a given host cell such as a Gram positive bacterium or a Gram negative bacterium.

When used herein, the term "insert" refers to a sequence that can be used in connection with a vector. In an embodiment, a vector with an insert is used in a recombinant expression system.

When used herein, the term "effective amount" refers to an amount capable of achieving at least a partial result. For example, an effective amount of a cation allows a reaction to proceed either partially, substantially, or to completion. In a particular example, an effective amount of a LanM enzyme effects dehydration and cyclization of a precursor peptide.

The following abbreviations are applicable: U or Sec, selenocysteine.

The invention provides a composition comprising a purified enzyme capable of effecting dehydration and cyclization of a precursor peptide. In an embodiment, the enzyme is a LanM enzyme. In a particular embodiment, the enzyme is selected from the group consisting of: CinM (SEQ ID NO:22, cinnamycin LanM), MrsM (SEQ ID NO:20, mersacidin LanM), MutM (SEQ ID NO:21, mutacin II LanM), ScnM (SEQ ID NO:23, streptococcin A-FF22 LanM), RumM (SEQ ID NO:24, ruminococcin A LanM), LtnM1 and LtnM2 (SEQ ID NO:25 and SEQ ID NO: 26, lacticin 3147 LanM), LctM (SEQ ID NO:40, lacticin 481 LanM), and NukM (SEQ ID NO:27). In a particularly preferred embodiment, the enzyme is LctM.

The invention provides a method of generating a biologically active compound, comprising reacting a precursor peptide in a reaction mixture comprising said precursor peptide and an effective amount of a purified enzyme capable of effecting dehydration and cyclization of the precursor peptide; and cleaving a leader portion of the precursor peptide; thereby generating a biologically active compound. In an embodiment, the method can achieve dehydration, cyclization, or dehydration and cyclization. In an embodiment, the method can occur in vitro.

In an embodiment, a leader peptide is attached to a protein to allow installation of one or more dehydroalanines into that protein for subsequent modification with a nucleophile or for cyclization, e.g. to stabilize the protein.

In some embodiments of this method, the precursor peptide comprises up to about 70 amino acids. In some embodiments of this method, the precursor peptide has a molecular weight of up to about 10 kiloDaltons. In preferred embodiments, said biologically active compound is a lantibiotic. In an embodiment, said precursor peptide is derived by genetic engineering techniques such as site-directed mutagenesis of a naturally occurring lantibiotic. Other techniques are contemplated such as the use of an expanded genetic code; for example, advances in adapting the machinery for ribosomal protein biosynthesis in an expression system can allow integration of what would otherwise be non-proteinogenic amino acids.

In embodiments of the invention, the precursor peptide comprises at least one non-proteinogenic amino acid, unnatural amino acid, peptoid, beta amino acid, or derivatized amino acid. In a particular embodiment, the precursor peptide comprises selenocysteine. In an embodiment, the derivatized amino acid is a halogenated amino acid. In a particular embodiment, the halogenated amino acid is a fluorinated amino acid.

The invention provides a method of generating a synthetic biologically active compound, wherein said compound comprises at least one non-proteinogenic amino acid, unnatural amino acid, peptoid, beta amino acid, or derivatized amino acid, said method comprising (a) generating a first precursor peptide;

(b) generating a second precursor peptide; wherein said second precursor peptide comprises at least one unnatural amino acid, peptoid, or derivatized amino acid;

(c) combining said first and second precursor peptides so as to produce a third precursor peptide;

(d) reacting said third precursor peptide in a reaction mixture comprising said third precursor peptide and an effective amount of a purified enzyme capable of effecting dehydration and cyclization of the third precursor peptide; and (e) cleaving a leader portion of the precursor peptide; thereby generating a synthetic biologically active compound.

In an embodiment, a second peptide is supplied in trans. In an embodiment, the leader and a synthetic peptide corresponding to the structural peptide contact each other in a reaction mixture in trans (not covalently bound together). In the mixture, the two molecules can bind in or form an active site to effect or affect one or more post-translational modifications. In an embodiment, a post-translational modification can include dehydration, cyclization, or dehydration and cyclization. In a particular embodiment, the trans approach is useful for incorporation of one or more non-proteinogenic amino acids.

In an embodiment of the above method, said combining step comprises ligation, conjugation, or other connection of said first precursor peptide to said second precursor peptide. In an embodiment, said enzyme is selected from the group consisting of CinM (SEQ ID NO:22, cinnamycin LanM), MrsM (SEQ ID NO:20, mersacidin LanM), MutM (SEQ ID NO:21, mutacin II LanM), ScnM (SEQ ID NO:23, streptococcin A-FF22 LanM), RumM (SEQ ID NO:24, rum inococcin A LanM), LtnM1 and LtnM2 (SEQ ID NO:25 and SEQ ID NO: 26, lacticin 3147 LanM) and LctM (SEQ ID NO:40, lacticin 481 LanM). In a particular embodiment, said enzyme is LctM. In an embodiment, said synthetic biologically active compound is a synthetic lantibiotic.

In an embodiment, said synthetic biologically active compound is a synthetic lantibiotic. In an embodiment, the invention provides a lantibiotic produced by the methods of the invention.

In embodiments, the invention provides methods also comprising contacting a target organism with an effective amount of said biologically active compound. In particular embodiments, said effective amount reduces or controls an ability of the target organism to remain viable, develop, grow, metabolize, or proliferate.

In embodiments of methods of the invention, the reaction mixture further comprises an effective amount of a cation. In particular embodiments, the cation is a divalent metal cation. In preferred embodiments, the cation is zinc.

In embodiments of the invention, the precursor peptide is a LanA peptide. In particular embodiments, the precursor peptide is LctA (SEQ ID NO:3).

The invention provides a method of dehydrating a precursor peptide, comprising contacting a precursor peptide with an effective amount of a purified enzyme capable of effecting dehydration and cyclization of the precursor peptide. In an embodiment, the method can occur in vitro.

The invention provides a method of cyclizing a dehydrated precursor peptide, comprising reacting a dehydrated precursor peptide in a reaction mixture comprising said dehydrated precursor peptide and an effective amount of a purified enzyme capable of effecting cyclization of the precursor peptide. In an embodiment, the method can occur in vitro.

The invention provides a method of dehydrating a precursor peptide, comprising reacting a precursor peptide in a reaction mixture comprising said precursor peptide and an effective amount of a purified enzyme capable of effecting dehydration of the precursor peptide. In an embodiment, the method can occur in vitro.

The invention provides a composition comprising a purified Lan protease or fragment thereof. In an embodiment, the fragment can be any fragment of about at least 15 continuos amino acids. In an embodiment, the purified Lan protease can be a mutant Lan protease using mutagenesis techniques known to the art. In an embodiment, mutagenesis is performed and a mutated Lan protease is screened regarding activity, thus achieving mutant Lan proteases with functional activity that is at least partial to or greater than that of a reference Lan protease.

In an embodiment, the invention provides a composition of a purified Lan protease and a precursor peptide. In an embodiment, the precursor peptide has been modified by dehydration, cyclization, or dehydration and cyclization.

In an embodiment, the invention provides a composition comprising a Lan protease domain fragment capable of encoding a Lan protease domain that recognizes a recognition sequence. In an embodiment, the recognition sequence is BBGG-X (SEQ ID NO:1) or BBGA-X (SEQ ID NO:2), wherein B=isoleucine or leucine and X is any amino acid. In an embodiment, the invention provides a composition comprising a protease recognition sequence of BBGG-X (SEQ ID NO:1) or BBGA-X (SEQ ID NO:2), wherein B=isoleucine or leucine and X is any amino acid.

In a particular embodiment, the Lan protease is LctT/Lpd (SEQ ID NO:29) or a fragment thereof. In another embodiment, the Lan protease is Lys-C.

The invention provides a method of purification of a cleavage product of a peptide capable of being cleaved by a Lan protease, comprising:

(a) providing a vector or insert comprising a sequence capable of encoding a Lan protease recognition sequence;

(b) expressing the protease recognition sequence in a peptide;

(c) connecting an end of the peptide to a solid phase support;

(d) contacting the peptide with said Lan protease, thereby cleaving the peptide to form at least one cleavage product; and (e) recovering a cleavage product, thereby achieving purification of a product cleaved by said Lan protease.

In an embodiment, the precursor peptide comprises selenocysteine.

In an embodiment of this purification method, said Lan protease is LctT (SEQ ID NO:29) and said Lan protease recognition sequence is an LctT recognition sequence.

In an embodiment, the invention provides one or more kits for dehydration, cyclization, or dehydration and cyclization of a precursor peptide, comprising a LanM enzyme and a LanM enzyme reaction buffer. The invention provides kits for dehydration and cyclization of a precursor peptide, comprising a LanM enzyme and a LanM enzyme reaction buffer. In a particular embodiment, a kit further comprises a precursor peptide. In a particular embodiment, a kit further comprises a Lan protease. In a particular embodiment of a kit, said LanM enzyme is selected from the group consisting of LctM (SEQ ID NO:40), MrsM (SEQ ID NO:20), CinM (SEQ ID NO:22), MutM (SEQ ID NO:21), ScnM (SEQ ID NO:23), RumM (SEQ ID NO:24), LtnM1 (SEQ ID NO:25), and LtnM2 (SEQ ID NO:26). In a preferred embodiment, said Lan protease is LctT (SEQ ID NO:29) or Lys-C. In a preferred embodiment of a kit, said LanM enzyme is LctM.

In embodiments of the invention, lantibiotics and methods are useful for pharmaceutical applications, agricultural applications, and food industry applications.

In embodiments, a lantibiotic produced by a method of the invention has one or more altered or improved attributes of activity, stability, solubility, or toxicity. For example, a lantibiotic may have altered or improved activity and stability. Regarding an example of the attribute of toxicity, in a pharmaceutical application the toxicity towards the patient is reduced. In an agricultural or food industrial application, the toxicity towards a subject ingesting an agricultural or food product is decreased, or the toxicity towards a desirable microorganism is reduced.

The invention provides a method of screening for a lantibiotic compound, comprising: providing a candidate lantibiotic compound made by a method of this invention; conducting a bioassay for lantibiotic activity; and selecting a lantibiotic compound having lantibiotic activity in said bioassay; thereby screening for a lantibiotic compound. In an embodiment, the invention provides a lantibiotic compound identified by the method of screening.

In an embodiment, the screening method further comprises contacting a target organism with said lantibiotic compound, wherein said target organism is at least partially susceptible to lantibiotic activity. In an embodiment, the method comprises contacting a food or a food precursor with said lantibiotic compound. In an embodiment, the method comprises contacting a patient with said lantibiotic compound. In an embodiment, the method comprises contacting an agricultural product with said lantibiotic compound.

In an embodiment, the invention provides a method of screening for a mutant LanM, comprising (a) providing a mutant LanM via mutagenesis; (b) performing an in vitro dehydration or cyclization assay and optionally an in vivo assay with a precursor peptide; and (c) selecting a mutant LanM that is capable of effecting at least one dehydration reaction and at least one cyclization, only at least one dehydration reaction, or only at least one cyclization reaction; thereby screening for a mutant LanM. In an embodiment, the invention provides a mutant LanM identified by the method. In an embodiment, said LanM is selected from the group consisting of CinM (SEQ ID NO:22, cinnamycin LanM), MrsM (SEQ ID NO:20, mersacidin LanM), MutM (SEQ ID NO:21, mutacin LanM), ScnM (SEQ ID NO:23, streptococcin A-FF22 LanM), RumM (SEQ ID NO:24, ruminococcin A LanM), LtnM1 and LtnM2 (SEQ ID NO:25 and SEQ ID NO: 26, lacticin 3147 LanM), LctM (SEQ ID NO:40, lacticin 481 LanM), and NukM (SEQ ID NO:27). In an embodiment, said LanM is LctM. In an embodiment, a modifying enzyme such as said mutant LanM has a substrate specificity with tolerance for an at least partially synthetic precursor peptide.

In an embodiment, the invention provides a method of producing a lantibiotic in vitro, comprising (a) providing a precursor peptide, (b) reacting the precursor peptide in a reaction mixture in vitro comprising said precursor peptide and an effective amount of an enzyme capable of effecting dehydration and cyclization of the precursor peptide; and (c) cleaving a leader portion of the precursor peptide; thereby producing a lantibiotic in vitro. In an embodiment, the invention provides a lantibiotic produced by the method.

In an embodiment, the invention provides a method of dehydrating and cyclizing a precursor peptide, comprising (a) providing said precursor peptide; (b) providing a purified enzyme capable of effecting dehydration and cyclization of the precursor peptide; and (c) reacting a reaction mixture comprising said precursor peptide and an effective amount of said enzyme; thereby dehydrating and cyclizing said precursor peptide. In an embodiment, the method further comprises the step of cleaving a leader portion of said precursor peptide.

In an embodiment, the invention provides in vitro reconstitution of lantibiotic biosynthesis. In an embodiment, post-translational modification machinery can have low substrate specificity. In an embodiment, an intact leader or structural peptide is not essential. In an embodiment, cyclases contain Zn with two Cys ligands. In an embodiment, peptides have inherent propensity for observed stereochemistry, but regioselectivity is controlled enzymatically. In an embodiment, a peptide does not necessarily drive a desired cyclization when attempted chemically. In an embodiment, one or more alternate rings can form which may be desirable or undesirable.

It is recognized that regardless of the ultimate correctness of any mechanistic explanation or hypothesis, an embodiment of the invention can nonetheless be operative and useful.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4. Sequences of mutants in which either the leader peptide (highlighted in yellow) or propeptide region (highlighted in blue) has been truncated or in which residues that are post-translationally modified have been mutated (yellow font). U=selenocysteine. See SEQ ID NO:4 ($His_6$-LctA); SEQ ID NO:5, ($His_6$-LctA(5-51)); SEQ ID NO:6 ($His_6$-LctA)(10-51); SEQ ID NO:7 ($His_6$-LctA(25-51)); SEQ ID NO:8 ($His_6$-LctA (1-37)); SEQ ID NO:9 ($His_6$-LctA (1-38)); SEQ ID NO:10 ($His_6$-LctA (1-38) C38U); SEQ ID NO:11 ($His_6$-LctA-T48S); and SEQ ID NO:12 ($His_6$-LctA-C49S).

FIG. 8 illustrates Tandem MS on His6-LctA-C49A (SEQ ID NO:13) and the product obtained after LctM-catalyzed modification (SEQ ID NO:113).

FIG. 9 illustrates Tandem MS on His6-LctA-C49S (SEQ ID NO:12) and the product obtained after LctM-catalyzed modification (SEQ ID NO:114).

FIG. 12 illustrates portions of LanC proteins, SpaC (amino acids 230-237, amino acids 302-307 of SEQ ID NO:68, and SEQ ID NO:121), Nis C (amino acids 210-218, amino acids 283-288 and amino acids 329-333 of SEQ ID NO:69), PepC amino acids 20-27, amino acids 81-86 and amino acids 130-134 of SEQ ID NO:120), and EpiC (amino acids 247-254 and amino acids 312-317 of SEQ ID NO:71 and SEQ ID NO:122).

FIG. 13 illustrates partial sequence alignment of a number of LanC proteins with the C-termini of LctM (SEQ ID NO:40, amino acids 704-852) and CylM (SEQ ID NO:72, amino acids 810-931) involved in production of lacticin 481 and cytolysin, respectively. Portions of SpaC, SEQ ID NO:68, amino acids 189-361; NiscC, SEQ ID NO:69, amino acids 174-339; and EpiC, SEQ ID NO:71, amino acids 213-376, are also shown in the alignment. The fully conserved residues are highlighted in color. In addition to the conserved putative metal ligands (yellow, see also FIG. 12), a number of conserved glycine residues are present.

FIG. 17 illustrates sequence alignment of several Type A1 lantibiotic prepeptides. Ser/Thr that are dehydrated in lacticin are shown in red font, fully conserved residues are highlighted in yellow, strongly conserved in magenta. LctA (SEQ ID NO:3) VarA, variacin (59) (SEQ ID NO:73), RumA, ruminococcin A (157) (SEQ ID NO:118), ScnA, streptococcin A-M49 (158) (SEQ ID NO:76), ScnA", streptococcin A-FF22 (159) (SEQ ID NO:75); MutA, mutacin II (114) (SEQ ID NO:51, amino acids 23-75). A BLAST search shows at least 5 other lantibiotic prepeptides with similar homology.

FIG. 18 illustrates alignment of the N-termini of ABC-transporters involved in bacteriocin leader sequence processing. The ATP-binding domain and internal transmembrane segments are omitted. LctT, lacticin 481 transporter (SEQ ID NO:29); ComA, putative *Streptococcus pneumoniae* competence factor transporter (SEQ ID NO:77, amino acids 1-164); LcnC, lactococcin A transporter (SEQ ID NO:78, amino acids 1-164); PedD, pediocin PA-1 transporter (SEQ ID NO:79, amino acids 1-166); CvaB, *E. coli* colicin V transporter (SEQ ID NO:80, amino acids 1-1-172). The LagD sequence can be found in (172).

FIG. 19 illustrates examples of enzyme catalysis.

FIG. 27 denotes attributes of enzymes involved in post translational modifications.

FIG. 35 illustrates results of HPLC analysis (SEQ ID NO:4). Note that the amino acid sequence and chemical structure are given in the carboxyl- to amino-terminal direction.

FIG. 40 illustrates sequence alignments of various precursor peptides, including LctA (SEQ ID NO:3), RumA (SEQ ID NO:118), VarA (SEQ ID NO:73), ScnA" (SEQ ID NO:75), ScnA (SEQ ID NO:76), and MutA (SEQ ID NO:51, amino acids 23-75).

FIG. 44 illustrates LctT sequence analysis of ComA (SEQ ID NO:77, amino acids 1-164), LcnC (SEQ ID NO:78, amino acids 1-164), PedD (SEQ ID NO:79, amino acids 1-166), CvaB (SEQ ID NO:80, amino acids 1-172), and LctT (SEQ ID NO:29).

FIG. 49 illustrates an overview of His-LctA (1-38) (SEQ ID NO:9) modified by LctM.

FIG. 50 illustrates fragments for His-LctA (1-38) (SEQ ID NO:9) and LctM-modified His-LctA (1-38) (SEQ ID NO:114).

FIG. 51 illustrates MS/MS data relating to SEQ ID NO:9.

FIG. 57 illustrates an example of a cyclase containing stoichiometric zinc.

FIG. 58 illustrates a sequence alignment of SpaC (amino acids 211-384 of SEQ ID NO:68), EpiC (amino acids 258-395 of SEQ ID NO:71), NisC (amino acids 192-368 of SEQ ID NO:69), PepC (SEQ ID NONO:120), and LctM (amino acids 705-865 of SEQ ID NO:40) relating to four conserved putative metal ligands.

FIG. 62 illustrates synthesis of dehydroamino acid containing peptides. SpaS, SEQ ID NO:67.

FIG. 70 illustrates a protein sequence for MutM, mutacin II (SEQ ID NO:21).

FIG. 71 illustrates a protein sequence for MrsM, mersacidin (SEQ ID NO:20).

FIG. 72 illustrates a protein sequence for CinM, cinnamycin (SEQ ID NO:22).

FIG. 73 illustrates a protein sequence for ScnM, Streptococcin A-FF22 (SEQ ID NO:23).

FIG. 74 illustrates a protein sequence for RumM, ruminococcin (SEQ ID NO:24).

FIG. 75 illustrates a protein sequence for NukM, nukacin (SEQ ID NO:27).

FIG. 76 illustrates a protein sequence for LtnM1 (SEQ ID NO:25).

FIG. 77 illustrates a protein sequence for LtnM2 (SEQ ID NO:26).

FIG. 78A illustrates a protein sequence for LctM (SEQ ID NO:40) used in Examples 1 to 3. FIG. 78B illustrates an additional amino acid sequence (SEQ ID NO:42) at the N-terminus for the His-tagged protein.

FIG. 79A illustrates a nucleotide sequence including the vector portion coding for the His tag at the N-terminus (bases from pET28 in His-LctM protein) (SEQ ID NO:41). FIG. 79B illustrates a nucleotide sequence (SEQ ID NO:28) and FIG. 79C illustrates an amino acid sequence (SEQ ID NO:29, amino acids 1-150) for an LctT protease domain.

FIG. 80A illustrates a nucleotide sequence of bases from pET15b in His-LctA relating to the His-tag (SEQ ID NO:43). FIG. 80B illustrates an LctA gene nucleotide sequence (SEQ ID NO:44).

FIG. 81 illustrates a nucleotide sequence for the LctM gene with a gtg start codon (SEQ ID NO:38).

FIG. 82 illustrates a nucleotide sequence for the LctM gene with an atg start codon (SEQ ID NO:39).

DETAILED DESCRIPTION OF THE INVENTION

Example 1

LctM, Lacticin 481, and Delta-1 lacticin 481

Reported herein is an active purified lantibiotic synthetase, the LctM enzyme (SEQ ID NO:40) that executes post-translational modifications in the biosynthesis of lacticin 481.

Figure 1:
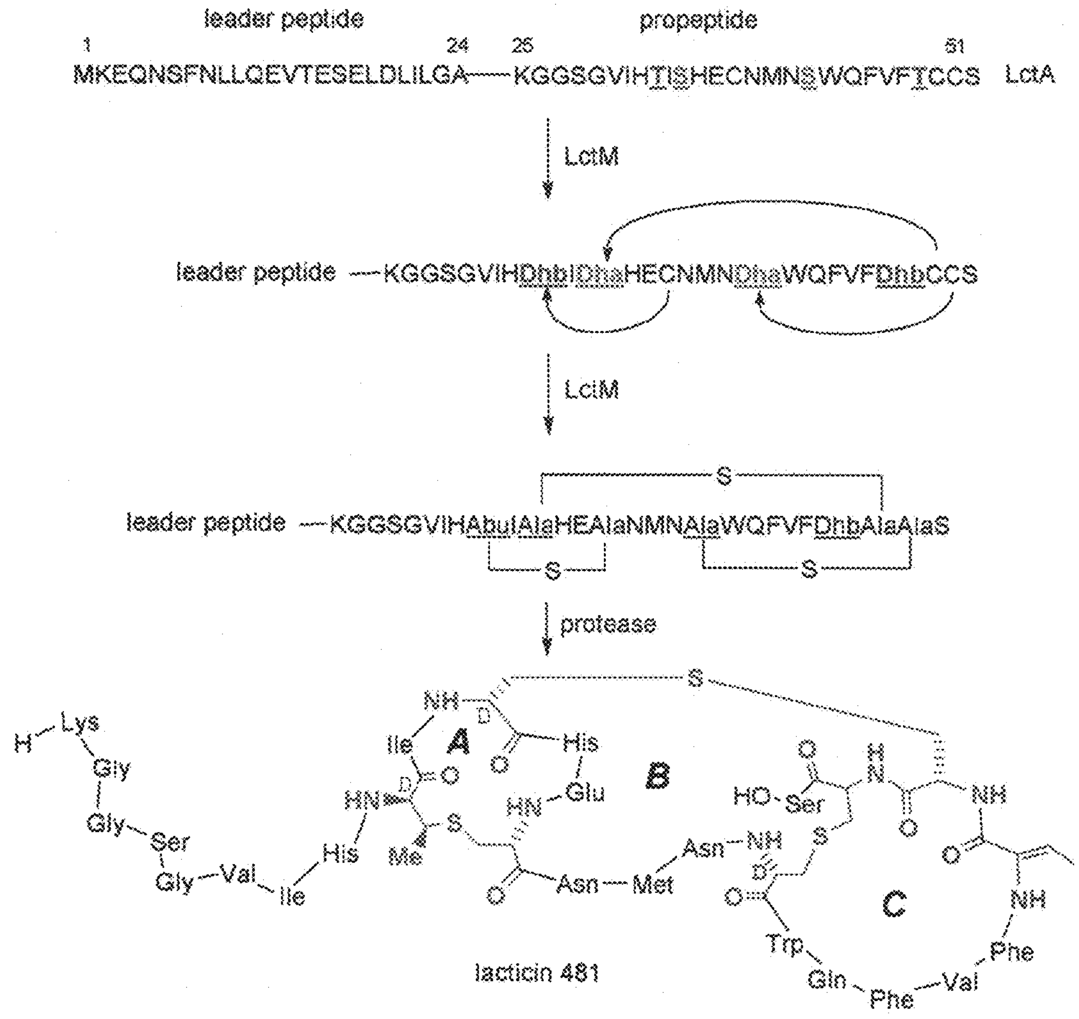
FIG. 1. Representative example of the post-translational maturation process of lantibiotics. The prepeptide LctA (SEQ ID NO:3) is synthesized on ribosomes, followed by LctM (SEQ ID NO:40) catalyzed dehydration of Ser (red) and Thr (blue) residues in the propeptide region of LctA to give the product of SEQ ID NO:110. LctM also catalyzes the conjugate addition of three Cys residues in a regio- and stereospecific manner to three of the Dha (red) and Dhb (blue) residues to generate three cyclic thioethers; one methyllanthionine (purple) and two lanthionines (green) to give the cyclized derivative of SEQ ID NO:110. The leader peptide is proteolytically removed by the N-terminal protease domain of the LctT ABC-type transporter that excretes the final product. Abu refers to 2-aminobutyric acid.

Lacticin 481 is produced by several strains of *Lactococcus lactis*. Its putative biosynthetic pathway is shown in FIG. 1. The biosynthetic operon has been characterized by genetic studies and encompasses six genes, lctAMTFEG (reference 16). The lctA gene encodes the 51-amino acid prepeptide LctA (17) (SEQ ID NO:3). For many lantibiotics the dehydration and cyclization reactions (FIG. 1) are believed to be carried out by two proteins, generically designated LanB and LanC, respectively (1, 18). In the case of lacticin 481, a single enzyme LctM (19) has low levels of sequence homology at its C-terminus to LanC proteins but no similarity to LanB enzymes.

We cloned lctA (SEQ ID NO:44) and lctM (SEQ ID NO:38 for gtg start codon, SEQ ID NO:39 for atg start codon) from *L. lactis* CNRZ 481 and developed high level heterologous expression systems in *E. coli* (20). LctA was expressed with a linker and hexa-histidine tag to its N-terminus (His6-LctA) (21) (SEQ ID NO:4). The peptide was produced in inclusion bodies that were isolated by centrifugation and resolubilized in 6 M guanidinium hydrochloride. The peptide was subsequently purified to homogeneity by immobilized metal affinity chromatography (IMAC) and reverse phase HPLC. LctM (106.7 kDa) was expressed with an N-terminal His6-tag and purified by IMAC followed by cation exchange chromatography resulting in protein of >95 purity.

Figure 2:
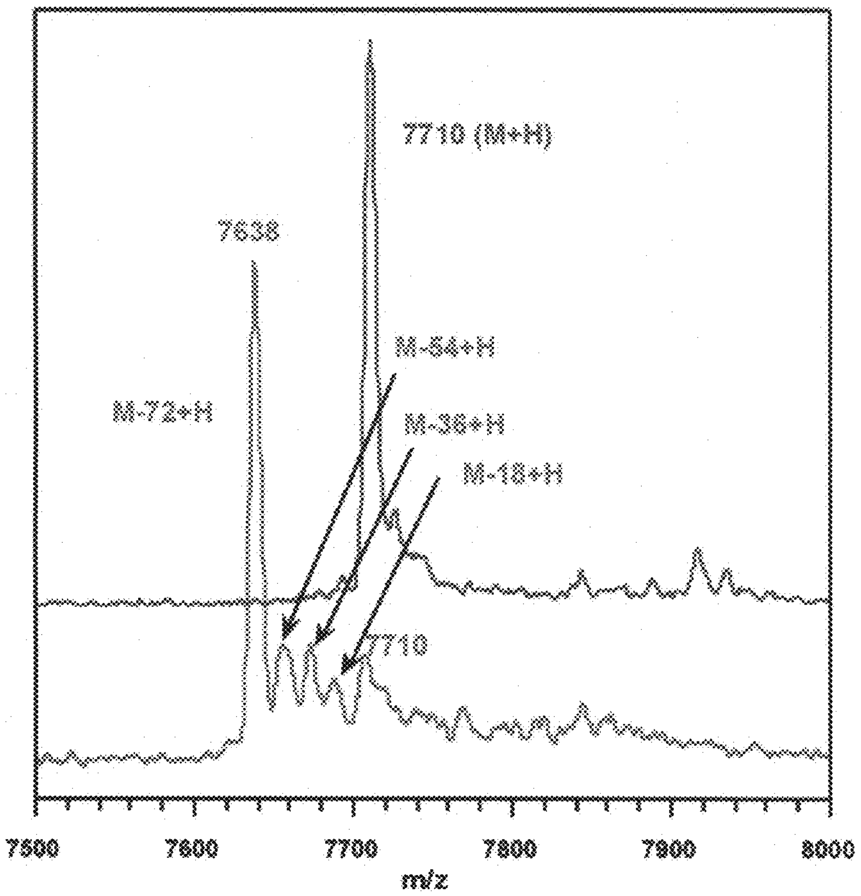
FIG. 2. MALDI-TOF MS analysis of the His6-LctA substrate (blue) and the products obtained after incubation for 2 h with 0.5 microM LctM, 0.5 mM ATP, 5 mM $Mg^{2+}$, 0.36 microM $ZnCl_2$, and 5 mM DTT, pH 7.5 (red).

Incubation of His6-LctA (SEQ ID NO:4) with LctM (SEQ ID NO:40) produced a series of new peaks in the MALDI-TOF mass spectrum of the reaction mixture only when ATP and $Mg^{2+}$ were included in the assay (FIG. 2). EDTA abolished the reaction, consistent with a previous study showing the presence of $Zn^{2+}$ in the putative cyclases involved in the biosynthesis of subtilin and nisin and the presence of four strictly conserved Cys and H is residues in LanC and LanM proteins (22). The new peaks in the mass spectrum correspond to losses of 18, 36, 54, and 72 Da, suggesting the elimination of one to four water molecules, respectively. Isotopic resolution of the starting peptide and the product was achieved by using electrospray ionization Fourier transform mass spectrometry (ESI-FTMS) as depicted in FIG. 3 (insets), verifying the molecular formula of the major dehydration product within 0.07 Da. The process was less efficient with ATP-gamma-S and was completely abolished with the non-hydrolyzable analogs AMP-PCP and AMP-PNP, suggesting that ATP hydrolysis is essential for processing. Analysis of the products revealed the formation of ADP and inorganic phosphate. Due to the very poor solubility of the peptide substrate, we have been unable to determine kinetic parameters.

The experiments described thus far do not establish that thioether formation has occurred since the conjugate addition of Cys residues to Dha/Dhb does not produce a change in mass. Several experiments were performed to demonstrate that the M-72 Da product corresponds to lacticin 481 linked to its leader peptide. Amino acid analysis of the product mixture indicated the presence of lanthionine/methyllanthionine in quantities consistent with the extent to which the M-72 product was formed. The product is generated from a precursor that contains six Ser and three Thr residues in the prepeptide in addition to five Ser residues in the His6-tag linker (21).

Figure 5:
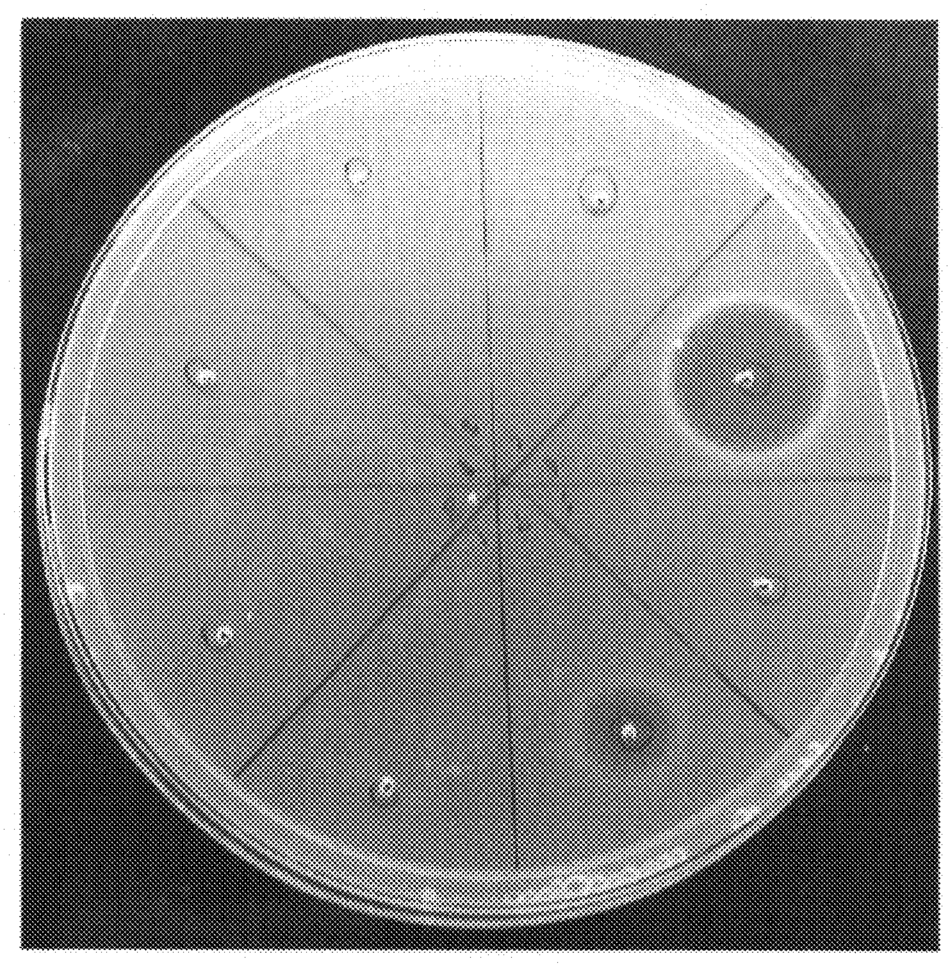
FIG. 5 illustrates a bioassay for lantibiotic activity.

To localize the sites of dehydration, the product was treated with the protease Lys-C resulting in cleavage of the amide bond between Lys25 and Gly26 and removal of the leader sequence and the His6-tag. MALDI-MS analysis of the C-terminal proteolytic fragment confirmed that the dehydrations took place in the propeptide. Lys25 is not conserved in the subclass of lantibiotics that include lacticin 481, and hence its absence was not anticipated to be critical for antimicrobial activity. Indeed, application of the proteolytic fragment to a lacticin 481-sensitive indicator strain (*L. lactis* CNRZ 117) in an agar diffusion assay resulted in a large zone of inhibition (FIG. 5). This proteolytic fragment was designated Delta-1 lacticin 481 to indicate the absence of Lys25. No antimicrobial activity was detected with either His6-LctA or the post-translationally modified product with the leader peptide still attached.

Lys-C was obtained from Sigma (P3428 Endoproteinase Lys-C from Lysobacter enzymogenes). References for Lys-C are: Patent: Endoproteinase-lys-C from bacterial fermentation. (Boehringer Mannheim G.m.b.H., Fed. Rep. Ger.). Belg. (1982), 12 pp. CODEN: BEXXAL BE 890259 A1 19820308 Patent. Application: BE 81-205892 19810908. Priority: DE 80-3034045 19800910. CAN 97:2856 AN 1982:402856 CAPLUS. Reference: E., Peter A.; Weijer, Wicher J.; Beintema, Jaap J. Use of endoproteinase Lys-C from Lysobacter enzymogenes in protein sequence analysis. Analytical Biochemistry (1983), 134(2), 347-54.

To further establish its structure, the M-72 product was analyzed by high resolution tandem mass spectrometry (MS/MS) using an ESI-FTMS instrument (23). Upon treatment with LctM for 1 hour, more than 80% of the substrate was converted to a product decreased in mass by 71.98 Da (FIG. 3A versus FIG. 3B), consistent with four dehydration events (9 ppm error).

Figure 3A:
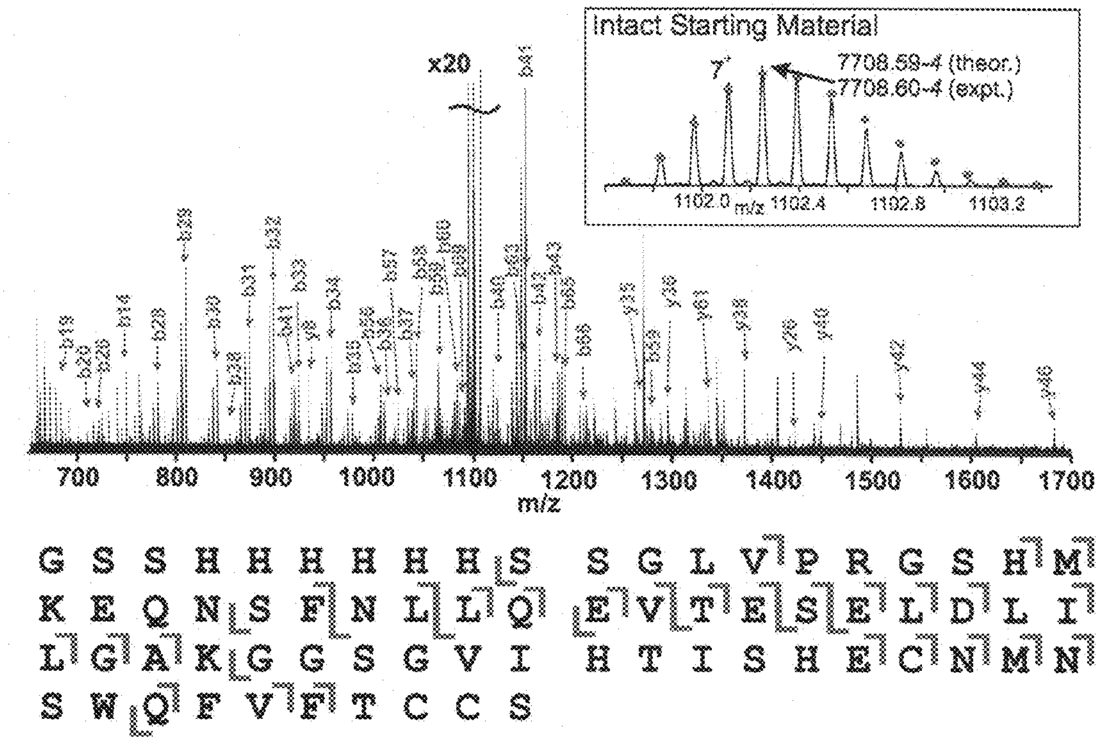
FIG. 3. FT-MS/MS spectra of the substrate His6-LctA (SEQ ID NO:4) (FIG. 3A, 100 scans) and the M-72 product peptide of mass 7636 Da (FIG. 3B, 200 scans). Residues of SEQ ID NO:4 that are dehydrated in lacticin are indicated in red and were assigned on the basis of the y-ion formed upon cleavage between Ile31 and His32. The fragment ions were generated by irradiation with infrared photons and those observed are indicated in blue. The mass difference (in units of 1.0024 Da) between the most abundant isotopic peak and the monoisotopic peak is denoted after the hyphen in italics after each relative molecular weight value ($M_r$). For example, for an Mr value of 7708.59-4, the mass difference is 4 such units.
Figure 3B:
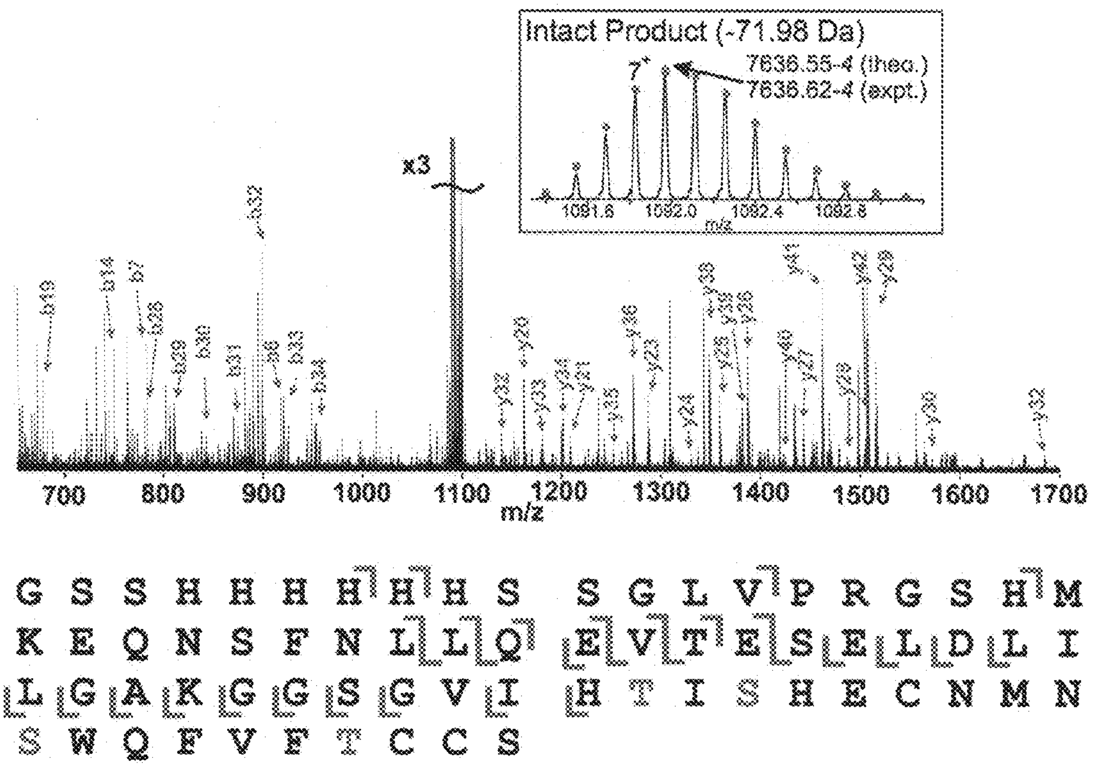

In FIG. 3A, FIG. 3B, and selected other Figures, the depiction of a symbol resembling the letter "L" below and to the left of the position of an amino acid residue signifies a beginning location of a particular observed peptide fragment. The depiction of a symbol resembling an inverted and reversed letter "L" above and to the right of the position of an amino acid residue signifies an ending location of a particular observed peptide fragment.

Inspection of the b- and y-type fragment ions (24) of His6-LctA (SEQ ID NO:4) and the M-72 Da product irradiated with infrared photons shows that the 72 Da is lost from the C-terminal 20 residues consistent with four dehydrations at the expected sites in the propeptide (FIG. 3B). Furthermore, no fragment ions were observed from fragmentation in the C-terminal 20 amino acids in the product, whereas nine such fragments were identified in the corresponding experiment with the substrate. These findings are consistent with three macrocyclic thioethers in this region, which have been shown recently to resist threshold fragmentation methods (25). Collectively, the mass spectrometric studies in conjunction with the biochemical and bioassay results show that the fully processed product consists of lacticin 481 fused to its leader peptide.

A series of LctA mutants was prepared to assess the substrate specificity of LctM for the use of LctM in lantibiotic engineering. Mutants in which three or eight amino acids of the leader sequence were deleted, His6-LctA(5-51) (SEQ ID NO:5) and His6-LctA(10-51) (SEQ ID NO:6) (FIG. 4), were fully processed by LctM. In contrast, His6-LctA(25-51) (SEQ ID NO:7), which represents just the propeptide region, was not processed to dehydrated products. Accordingly, the amino acids at positions 10-24 of the leader peptide are important for the post-translational modification machinery.

In addition to truncation of the leader sequence, LctA analogs were prepared to evaluate the importance of a full length propeptide (FIG. 4). His6-LctA (1-37) (SEQ ID NO:8) was expressed attached to a intein-chitin binding domain (CBD) fusion. After purification using chitin affinity chromatography, His6-LctA(1-37) was cleaved from the intein using beta-mercaptoethanol. The resulting peptide, containing two of the residues that are dehydrated in wild type, was incubated with LctM to provide a product in which two dehydrations had occurred (MALDI-MS).

Example 2

Synthetic Variants of Lantibiotics

Figure 6:
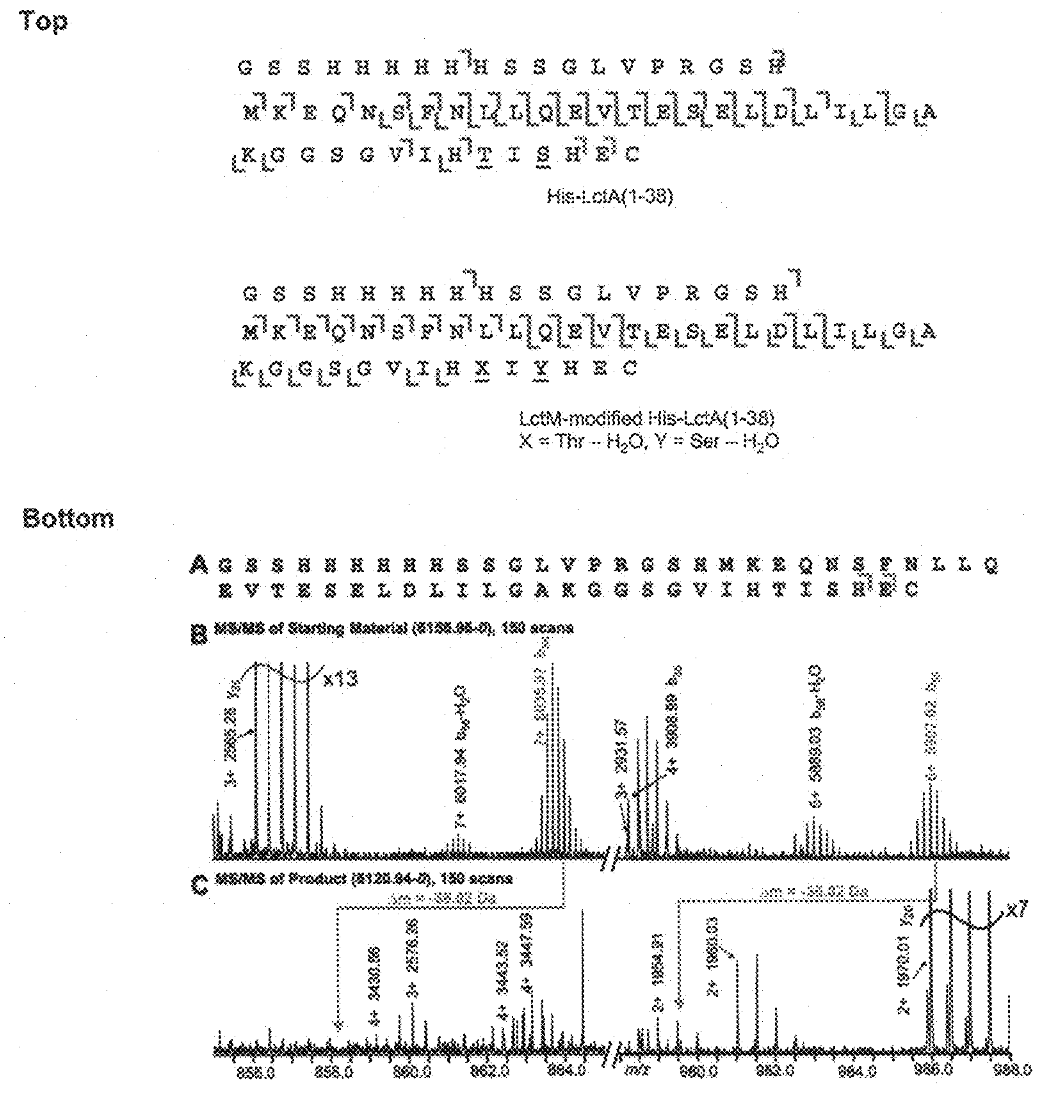
FIG. 6 illustrates results of Tandem MS on His6-LctA(1-38) (SEQ ID NO:9) and the product obtained after LctM-catalyzed modification (SEQ ID NO:111).
Figure 7:
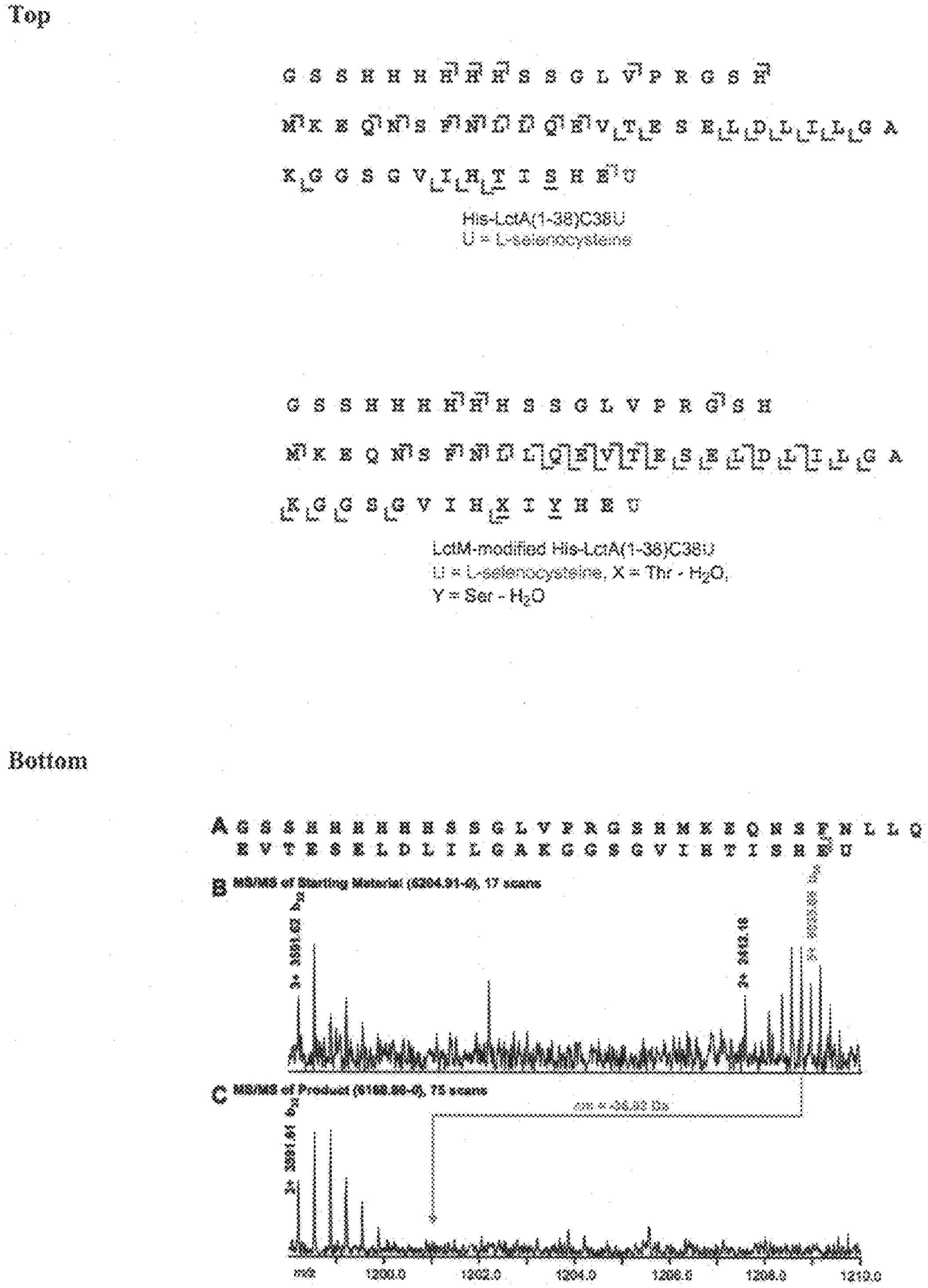
FIG. 7 illustrates results of Tandem MS on His6-LctA(1-38)C38U (SEQ ID NO:10) and the product obtained after LctM-catalyzed modification (SEQ ID NO:112).

To probe cyclization activity for truncated substrates, His6-LctA(1-38) (SEQ ID NO:9) and His6-LctA(1-38) Cys38Sec (SEQ ID NO:10) were produced by expressed protein ligation (EPL) (27) of the His6-LctA(1-37) (SEQ ID NO:8)-intein-CBD fusion with cysteine and selenocysteine (Sec), respectively. His6-LctA(1-38) (SEQ ID NO:9) was converted quantitatively by LctM into a product that was 36.02 Da lower in mass than the starting peptide (ESI-FTMS, FIG. 6). MS/MS analysis using collisionally activated dissociation confirmed that the dehydrations took place from Thr33 and Ser35 and indicated that Cys38 had cyclized (FIG. 6). Hence, these experiments demonstrate that C-terminal truncation of the LctA substrate impairs neither the dehydration nor the cyclization activity of LctM. Similarly, His6-LctA(1-38)Cys38Sec (SEQ ID NO:10) was converted by LctM leading to dehydration of Thr33 and Ser35 and cyclization to produce a selenoether (FIG. 7). This finding illustrates the successful demonstration of combining semisynthetic substrates generated by EPL with the substrate promiscuity of LctM for lantibiotic engineering.

Example 3

Site-Directed Mutagenesis of LctA

A series of LctA point mutants were prepared in which the post-translationally modified residues were replaced by site-directed mutagenesis. As predicted, incubation of His6-LctA-T48A (SEQ ID NO:83) with LctM resulted in only three dehydrations. Unexpectedly, His6-LctA-C49S (SEQ ID NO:12) led to a product with five dehydrations (M-90 Da) in addition to the product with four dehydrations (FIG. 9). Thus, replacement of Cys49 with Ser not only precluded the formation of the B-ring, but also lead to dehydration of the new Ser residue. This dehydration appears to interfere with formation of the C-ring as MS/MS analysis indicates it is not present in the product with five dehydrations (20).

The formation of another lacticin analog lacking the B-ring was investigated in more detail with His6-LctA-C49A (SEQ ID NO:13). MS/MS analysis of the M-72 peptide product indicated the formation of ions resulting from fragmentation of the product peptide between Asn39 and Met40 and between Asn41 and the lanthionine of ring C (20). Such fragmentation is not observed with the product from wt His6-LctA (SEQ ID NO:4) providing an independent confirmation that the B-ring is present in the wt product. Interestingly, assays of LctM with oxidized His6-LctA-C49A (SEQ ID NO:13) in which the two remaining Cys residues (Cys38 & Cys50) were present as a disulfide, resulted in the near quantitative production of a peptide that was 36.09 Da lower in mass than the starting material. MS/MS analysis revealed two dehydrations at Thr33 and Ser35. Upon reduction of the disulfide with DTT and resubmission to LctM, the intermediate peptide was converted to products with three and four dehydrations (data not shown), indicating that LctM can utilize partially dehydrated products as substrates for further processing.

In summary, this work presents the first in vitro reconstitution of the complex series of post-translational modifications carried out by lantibiotic synthetases. The process requires ATP and $Mg^{2+}$. Lacticin 481 synthase shows low specificity with regards to its substrate and provides an excellent system for engineering of lacticin analogs with at least partially synthetic substrates.

Supporting Information for Example 1 to Example 3

Materials and Methods

*E. coli* DH5alpha and BL21(DE3) were used as hosts for cloning and expression, respectively. Transformants were selected by plating on LB agar plates containing 100 micro-g/mL ampicillin (FisherBiotech) and/or 50 micro-g/mL kanamycin (Sigma). pET-15b and pET-28b were obtained from Novagen. pTXB1 was purchased from New England Biolabs (NEB). *E. coli* strains were grown in LB or TB (terrific broth) medium. Lacticin 481 producing strain *Lactococcus lactis* CNRZ 481 was obtained from the Centre National Recherches Zootechniques (CNRZ) culture collection (INRA, Jouy-en-Josas, France) and was cultured in GM17 broth (4% M17 and 0.5 glucose) at 30° C. without aeration for isolating chromosomal DNA.

Restriction enzymes were obtained from either GibcoBRL or NEB. Calf intestinal alkaline phosphatase (CIP) was purchased from Promega. IPTG was purchased from CalBiochem. T4 DNA ligase was obtained from NEB. Primers were purchased from the University of Illinois at Urbana-Champaign (UIUC) Biotechnology Center. dNTPs were obtained from GibcoBRL. DNA polymerases were purchased from GibcoBRL or Stratagene. Chelating Sepharose Fast Flow resin and SP Sepharose Fast Flow resin were purchased from Amersham Pharmacia Biotech. Chitin resin and amylose resin were purchased from NEB. The metal chelating column for the BioCad FPLC system was self-packed using POROS 20 MC resin (metal chelate affinity packing) obtained from PerSeptive Biosystem.

RP-HPLC was performed on either a Rainin system (Dynamax model SD-200 pump and model UV-1 detector), a Beckman Gold system (Model 125 solvent module and model 166 detector), or a Waters system (Model 600 controller, Delta 600 pump, and 2487 dual wavelength absorbance detector) with a Vydac C4 analytical (0.46 cm×25 cm), semi-preparative (1.0 cm×25 cm), or preparative column (2.2 cm×25 cm), or a Waters PrepLCTM 25 mm Module preparative C18 column, monitoring at 220 nm. Solvents for RP-HPLC were solvent A (0.1% TFA in water) and solvent B (0.1% TFA in acetonitrile). MALDI-TOF mass spectrometry was carried out on a Voyager-DE-STR (Applied Biosystem) in the Mass Spectrometry Laboratory, School of Chemical Sciences, UIUC. The instrument has an accuracy of about 0.05% for small to medium sized peptides and proteins when external calibration is used.

Genomic DNA from *L. lactis* CNRZ 481 strain was isolated by the DNAzol method (Molecular Research Center, Inc). Plasmid DNA was isolated using QIAGEN Plasmid Purification Kits (QIAGEN). DNA purification after restriction digestions was performed using QIAquick PCR or gel purification kit (QIAGEN). DNA sequencing was performed using the appropriate primers on an ABI PRISM automated sequence model vision 2.1.1 at the Biotechnology Center of UIUC.

Cloning of LctM

The lctM gene was PCR amplified using the primers 5'-CGACTAGCTAGC-ATGAAAAAAAAGACTTAC-3' (SEQ ID NO:14) and 5'-CCG CTCGAGTTAATCAACATATGGCAT-3' (SEQ ID NO:15). For the lctM gene, see SEQ ID NO:38 (gtg start codon) and SEQ ID NO:39 (atg start codon). For the LctM protein, see SEQ ID NO:40. The PCR product was digested with NheI and XhoI restriction enzymes and ligated into pET28b to generate a His6-tagged (SEQ ID NO:42) LctM construct (pET28b-LctM(NB)H2). The sequence of LctM insert was checked by DNA sequencing.

There are two different bacterial strains that produce lacticin 481 (Lactococcus lactis CNRZ 481 and *Lactococcus lactis* subsp. *lactis* ADRIA 85LO30. Lacticin 481 was originally called lactococcin DR for the latter strain. Upon recognition that lactococcin DR had the same structure as the product of the former strain, the name lacticin 481 was used. The sequence for LctM (SEQ ID NO:40) has been published for *Lactococcus lactis* subsp. *lactis* ADRIA 85LO30. The LctM herein was cloned from *Lactococcus lactis* CNRZ 481. An LctM sequence was reported by A. Rince, A. Dufour, S. Le Pogam, D. Thuault, C. M. Bourgeois, and J.-P. Le Pennec, Appl. Environ. Microbiol. 60:1652-1657, 1994; NCBI Accession number U91581.

Expression and Purification of His$_6$-LctM

BL21(DE3) cells transformed with pET28b-LctM(NB)H2 were grown in TB medium at 37° C. and induced with 0.5 mM IPTG when OD600 nm reached 0.8-0.9. The cells were then continually shaken at 18° C. for 22 h and then harvested. The cell paste was resuspended in start buffer (20 mM Tris, pH 8.3, 1 M NaCl, 10% glycerol) and stored at −80° C. until use. All purification steps were performed at 4° C. Cell paste (11 g) in 50 mL of start buffer was sonicated on ice for 20 min. After centrifugation, the supernatant (48 mL) was loaded onto a POROS20 MC 7.8 mL column at 2 mL/min. The column was washed with 150 mL of start buffer at 2 mL/min. Then the flow rate was increased to 4 mL/min and the column was washed with an additional 100 mL of start buffer, followed by 40 mL of 30 mM imidazole buffer (20 mM Tris, pH 7.2, 100 mM NaCl, 30 mM imidazole), and eluted with 100 mL of a 30 mM to 500 mM imidazole gradient in 20 mM MOPS, pH 7.2, 100 mM NaCl buffer.

The His6-LctM (SEQ ID NO:42, SEQ ID NO:40) containing fractions were combined and directly loaded onto a SP cation exchange column (27 mL, 15 mm diameter) pre-equilibrated with MOPS buffer (20 mM MOPS, pH 7.1, 100 mM NaCl). After the protein samples were loaded, the column was washed with MOPS buffer (~200 mL) at ~2 mL/min until no absorbance was detected at 220 nm in the flow through. His6-LctM protein was then eluted with 20 mM MOPS, pH 7.1, 1 M NaCl. About 20 mg of His6-LctM was obtained (1.16 mg/mL, 19 mL) based on Bradford assay. Mass spectrometric analysis (MALDI) revealed a mass of 109,094±120 (3 determinations) (calcd 109,161). For the His-tagged protein, there is a short additional stretch of amino acids at the N-terminus: MGSSHHHHHHSSGLVPRGSHMAS. See SEQ ID NO:41 (nucleotide sequence with portion for His tag at the N-terminus) and SEQ ID NO:42 (amino acid sequence with His tag at N-terminus).

Cloning of His6-LctA (SEQ ID NO:4)

The lctA gene was amplified using the primers 5'-GGGAATTCCATATG-AAAGAACAAAACTCTTTTAA-3' (SEQ ID NO:16) and 5'-CGC GGATCCTTAAGAGCAGCAAGTA (SEQ ID NO:17). The PCR product was digested with NdeI and BamHI restriction enzymes and ligated into the pET15b vector. The resulting pET15b-LctA#4 plasmid was used for the overexpression of His6-LctA. DNA sequencing revealed a nucleotide change (A33G) leading to a silent mutation (Q11Q).\

Expression and Purification of His6-LctA (SEQ ID NO:4)

BL21(DE3) cells carrying the plasmid pET15b-LctA were induced with 1 mM IPTG at 37° C. at OD600 nm=0.5-0.7, and grown for an additional 3 h. Cells were harvested by centrifugation, and the cell pellet (11 g) was resuspended in 40 mL of start buffer2 (20 mM Na2HPO4, pH 7.5, 500 mM NaCl, 0.5 mM imidazole) and lysed by sonication. After centrifugation, the supernatant was discarded and the pellet was washed twice with start buffer2 to remove trapped proteins. The resulting pellet was resuspended in 10 mL of denaturing buffer (start buffer2 containing 6 M guanidine hydrochloride). The mixture was incubated at rt for 1 h to completely redissolve the protein. The remaining insoluble material was removed by centrifugation and the supernatant was mixed with $Ni^{2+}$-charged chelating resin (~10 mL) at rt for 30 min by rotation in a 50 mL centrifuge tube. The resin mixture was then transferred into a column. The column was drained, washed with denaturing buffer, and 30 mM imidazole buffer containing 6 M guanidine. His6-LctA was eluted with denaturing buffer containing 100 mM EDTA. Fractions containing His6-LctA were concentrated by Amicon ultrafiltration using a YM1 membrane (Millipore). His6-LctA (SEQ ID NO:4) was further purified by RP-HPLC using a C18 preparative column (Waters). The retention time (tR) was 15.5 min using a gradient of 2-100% B over 20 min (B=100% MeCN/0.1% TFA) on a C4 Vydac analytical column. About 32 mg of HPLC purified peptide was obtained (~6.5 mg per liter of culture). MALDI-TOF MS for His6-LctA calcd. 7710

(M+H), found 7710. ESI-FT-MS mass calcd. 7708.59-4, found 7708.60-4 (1 ppm error, external calibration with bovine ubiquitin, 8564.64-5). For all FT-ESI data reported herein, the mass difference (in units of 1.0024 Da) between the most abundant isotopic peak and the monoisotopic peak is denoted as the number following the hyphen after each $M_r$ value.

Activity Assay

The HPLC purified His6-LctA peptide (SEQ ID NO:4) was redissolved in water and the concentration was determined by UV-vis according to the estimated extinction coefficient ($Epsilon_{280\ nm}$=5690) from the ExPASy ProtParam tool. About 10 microL of His6-LctA was mixed with 1 microL of 10× assay buffer (final concentration: 25 mM Tris, 5 mM MgCl2, 5 mM DTT, 0.5 mM ATP, 12.5 microg/mL BSA, pH 7.5) and ~1 microL of $ZnCl_2$ (final conc. 0.36 microM). Peptide precipitation was observed upon addition of the buffer if the peptide concentration was too high. His6-LctM was added (1 microM) and the reaction mixture was incubated at rt for 28 h. Subsequent data (not shown) indicated that an incubation time of 10 minutes achieved substantial reaction progress.

For MALDI MS analysis, 1 microL of the assay sample was mixed with 9 microL of sinapinic acid pre-dissolved in MeCN:H2O (2:1) in 0.1% TFA and 1 microL of the mixture was applied on the MALDI target. MALDI MS calcd. 7710 (M+H), 7638 (M-72+H), found 7638 (M-72+H) as the major peak. Small amounts of species corresponding to 7656 (M-54+H), 7674 (M-36+H), 7692 (M-18+H) and 7710 (M+H) were also observed in MALDI MS. ESI-FT-MS for the major product: mass calcd. 7636.55-4, found 7636.62-4 (9 ppm error, external calibration with bovine ubiquitin, 8564.64-5).

Bioassay for Lantibiotic Activity

The lyophilized assay product (~0.1 microg) was redissolved in 6 microL of Millipore water. To the solution, 4 microL of a solution of Lys-C in 100 mM Tris, pH 8.5 (0.4 ng/microL) was added and the mixture was incubated at 37° C. for 3 h. The resulting mixture was checked by MALDI-TOF MS. Three fragments were expected and two were observed: calcd, 2310 ([1-21]), 2591 ([22-44]), 2773 ([45-70]); found, 2593 ([22-44]), 2775 ([45-70]).

Inhibitory activity was assayed by the solid agar medium test. A GM17 agar plate was seeded with the test strain by mixing 100 mL of liquid GM17 agar at 50° C. with 1.5 mL of an overnight culture. After agar solidification, wells were created in the medium and the samples were added to the wells. The activity of the starting peptide, LctM-product, and the product and starting peptide treated with Lys-C were determined using a solid agar diffusion bioassay with indicator strain *L. lactis* CNRZ 117 (See FIG. 5).

FT-MS/MS Conditions

Samples for MS/MS analysis were resuspended in 78% acetonitrile, 20% water, 2% acetic acid and introduced via electrospray ionization into a custom built 8.5 Tesla Q-FTMS. Data acquisition was performed with the MIDAS datastation and then stored as 512 K data sets. Isopro v3.0 was used to generate theoretical isotopic distributions which were fit to experimental data by least squares to assign the most abundant peak. Instrument specifics have been described previously (S1-Senko et al.). For all FT-ESI data reported herein, the mass difference (in units of 1.0024 Da) between the most abundant isotopic peak and the monoisotopic peak is denoted, following the hyphen and in italics, after each Mr value.

IRMPD: In the FTMS cell the ions of interest were isolated using a stored waveform inverse Fourier transform (SWIFT). After isolation, the selected ions were irradiated with a 75 W $CO_2$ laser which induced fragmentation along the peptide backbone.

Multipole Dissociation For multipole dissociation, ions of interested were first selectively filtered in the quadrupole and then fragmented by lowering the axial offset on the accumulation multipole. The fragment ions were then directed down to the cell via multiple ion guides where they were excited and detected.

Generation of LctA Mutants $His_6$-LctA(5-51) (SEQ ID NO:5). The partial lctA gene (13-156) was amplified using the primers 5'-GGGAATTC CATATGAACTCTTTTAATCTTC-3' (SEQ ID NO:85) and 5'-CGCGGATCCTTAAGAG-CAGCAAGTA-3' (SEQ ID NO:86) with the plasmid pET15b-LctA as the template. The PCR product was gel purified, digested with NdeI and BamHI, and ligated into a pET15b vector. The resulting pET15b-LctA-N5#1 plasmid was used for the overexpression of His6-LctA(5-51). DNA sequencing revealed a nucleotide change (A33G) leading to a silent mutation (Q11Q).

His6-LctA(10-51) (SEQ ID NO:6). The partial lctA gene (28-156) was amplified using the primers 5'-GGGAATTC CATATGCTTCAAGAAGTGACA-3' (SEQ ID NO:87) and 5'-CGCGGATCCTTAA-GAGCAGCAAGTA-3' (SEQ ID NO:88) with genomic DNA as the template. The PCR product was digested with NdeI and BamHI, and ligated into a pET15b vector. The resulting pET15b-LctA-L10#3 plasmid was used for the overexpression of His6-LctA(10-51). DNA sequencing confirmed the desired sequence.

His6-LctA(25-51) (SEQ ID NO:7). The partial lctA gene (73-156) was amplified using the primers 5'-GGGAATTC CATATGAAAGGCGGCAGTGGA-3' (SEQ ID NO:89) and T7 terminator: 5'-GCTAGTTATTGCTCAGCGG-3' (SEQ ID NO:90) with the plasmid pTXB1-LctA as the template. The PCR product was digested with NdeI and BamHI restriction enzymes, and ligated into a pET15b vector. The resulting plasmid was called pET15b-LctA-K25-intein-CBD#2 which was used to obtain the truncated peptide His6-LctA(25-51). DNA sequencing confirmed the presence of the desired sequence.

His6-LctA(1-37) (SEQ ID NO:8). The partial lctA gene (1-111) was amplified using the primers 5'-GGGAATTC CATATGAAAGAACAAAACTCTTTTAA-3' (SEQ ID NO:91) and 5'-ATAT GCTCTTC-CGCATTCATGAGAAATTGT-3' (SEQ ID NO:92) with genomic DNA as the template. The PCR product was digested with NdeI and SapI restriction enzymes, and ligated into a pTXB1 vector. The DNA fragment LctA-37E-intein-CBD was cut out of the resulting pTXB1-LctA-37E plasmid using NdeI and BamHI, and this fragment was ligated into the pET-15b vector. This resulted in the plasmid pET15b-LctA-37E-intein-CBD#2 which was used to obtain the truncated peptide His6-LctA(1-37). The same construct was used to generate the truncated peptides His6-LctA(1-38) and His6-LctA(1-38)C38U by EPL. DNA sequencing revealed a nucleotide change (T48C) leading to a silent mutation (S16S).

His6-LctA-T48S (SEQ ID NO:11). The lctA gene was amplified using the primers 5'-GGGAATTC CATATGAAAGAACAAAACTCTTTTAA-3' (SEQ ID NO:93) and 5'-CGC GGATCC-TTAAGAGCAGCAAGAA-3' (SEQ ID NO:94) with pET15b-LctA as the template. The PCR product was digested with NdeI and BamHI restriction enzymes and ligated into a pET15b vector. The resulting pET15b-LctA-T48S#2 plasmid was used for the overexpression of His6-

LctA-T48S. DNA sequencing revealed a nucleotide change (A33G) leading to a silent mutation (Q11Q) in addition to the desired mutation.

His6-LctA-T48A. The lctA gene was amplified using the primers 5'-GGGAATTC CATATGAAAGAACAAAACTCTTTTAA-3' (SEQ ID NO:95) and 5'-CGCGGATCC-TTAAGAGCAGCATGCA-3' (SEQ ID NO:96) with pET15b-LctA as the template. The PCR product was digested with NdeI and BamHI restriction enzymes and ligated into a pET15b vector. The resulting pET15b-LctA-T48A#6 plasmid was used for the overexpression of His6-LctA-T48A. DNA sequencing revealed a nucleotide change (A33G) leading to a silent mutation (Q11Q) in addition to the desired mutation.

His6-LctA-C49A (SEQ ID NO:13). The lctA gene was amplified using the primers 5'-GGGAATTC CATATGAAAGAACAAAACTCTTTTAA-3' (SEQ ID NO:97) and 5'-CGCGGATCC-TTAAGAGCATGCAGTA-3' (SEQ ID NO:98) with pET15b-LctA as the template. The PCR product was digested with NdeI and BamHI restriction enzymes and ligated into pET15b. The resulting pET15b-LctA-C49A#1 plasmid was used for the overexpression of His6-LctA-C49A. DNA sequencing revealed a nucleotide change (A33G) leading to a silent mutation (Q11Q) in addition to the desired mutation.

His6-LctA-C49S (SEQ ID NO:12). The lctA gene was amplified using the primers 5'-GGGAATTC CATATGAAAGAACAAAACTCTTTTAA-3' (SEQ ID NO:99) and 5'-CGCGGATCC-TTAAGAGCAGCTAGTA-3' (SEQ ID NO:100) with genomic DNA as the template. The PCR product was digested with NdeI and BamHI restriction enzymes and ligated into the pET15b vector. The resulting pET15b-LctA-C49S#4 plasmid was used for the overexpression of His6-LctA-C49S. DNA sequencing matched the published sequence and showed the desired mutation.

General Procedure for Overexpression and Purification of His6-LctA Mutants.

BL21(DE3) cells carrying the corresponding plasmid were induced with 1 mM IPTG at 37° C. at OD600 nm=0.5-0.7, and grown for an additional 3 h. Cells were harvested by centrifugation, and the cell pellet (11 g) was resuspended in 40 mL of the start buffer2 (20 mM Na2HPO4, pH 7.5, 500 mM NaCl, 0.5 mM imidazole) and lysed by sonication. After centrifugation, the supernatant was discarded and the pellet was washed twice with the start buffer2 to remove trapped proteins. The resulting pellet was resuspended in 10 mL of the denaturing buffer (the start buffer2 containing 6 M guanidine hydrochloride). The mixture was incubated at 25° C. for 1 h to completely dissolve the protein. The remaining insoluble material was removed by centrifugation and the supernatant was mixed with Ni2+-charged chelating resin at 25° C. for 30 min by rotation in a 50 mL centrifuge tube (Corning). The resin mixture was then transferred into a column. The column was drained, washed with the denaturing buffer, and 30 mM imidazole buffer containing 4 M guanidine. The peptide was eluted with the buffer containing 50 mM EDTA, 20 mM Tris, pH 6.5, 4 M guanidine. Fractions containing the peptide were collected and purified by RP-HPLC using a C18 preparative column (Waters).

General Procedure for Overexpression and Purification of the Truncated LctA from the Intein System.

BL21(DE3) cells carrying the pET15b-LctA-37E-intein-CBD#2 plasmid were induced with 0.5 mM IPTG at 25° C. at OD600 nm=0.5-0.7, and grown for an additional 6 h. Cells were harvested by centrifugation, and the cell pellet was resuspended in cell lysis buffer (20 mM Tris-HCl, pH 8.0, 1 M NaCl, 1 mM EDTA) and lysed by sonication. After centrifugation, the supernatant containing the truncated peptide was purified by chitin affinity chromatography and subsequent intein mediated cleavage with beta-mercaptoethanol (100 mM) at 25° C. The fractions containing His6-LctA(1-37) were combined, lyophilized, redissolved in minimum solvent and purified further by RP-HPLC. For expressed protein ligation (EPL), the peptide-intein-CBD containing resin was incubated with MESNA (50 mM) and Cys (1 mM) at 25° C. for 15 h before elution. Elution fractions containing the peptide were further purified by RP-HPLC using a C4 Vydac analytical column. The HPLC fractions were lyophilized and analyzed by MALDI-TOF MS.

Overexpression, Preparation and Purification of LctA(1-38)C38U (SEQ ID NO:10).

BL21(DE3) cells carrying the pET15b-LctA-37E-intein-CBD#2 plasmid were induced with 0.5 mM IPTG at 25° C. at OD600=0.6-0.7 and grown for an additional 6 h. Cells were harvested by centrifugation and the cell pellet was resuspended in cell lysis buffer (20 mM Tris-HCl, pH 7.5, 500 mM NaCl, 1 mM EDTA, 0.1% Tween-20) and lysed by sonication. After centrifugation, the supernatant containing the LctA(1-37)-intein-CBD fusion protein was bound to chitin affinity resin with gentle shaking at 4° C. for 2 h. The resin was then washed with wash buffer (20 mM Tris-HCl, pH 7.5, 500 mM NaCl, 1 mM EDTA) until no absorbance was detected at 220 nm in the flow-through. Expressed protein ligation was performed by incubating the resin with bound peptide-intein-CBD with L-selenocysteine, generated in situ by the reduction of L-selenocystine (4 mM) with tris(2-carboxyethyl) phosphine (TCEP) (8 mM), and MESNA (100 mM) for 18 h at 25° C. under argon. Eluted fractions containing the desired peptide were further purified by RP-HPLC using a C4 Vydac analytical column and product fractions were lyophilized and analyzed by MALDI-TOF MS.

Assays with Mutant LctA Peptides.

The assays with the mutant peptides were carried out essentially the same as described above for the wt His6-LctA peptide. Mass spectrometry data is listed below.

His6-LctM assay with His6-LctA(5-51) (SEQ ID NO:5). MALDI-TOF MS calcd. 7324 (M), 7252 (M-72), found 7325 (M+H+), 7252 (M-72), 7270 (M-54), 7288 (M-36).

His6-LctM assay with His6-LctA(10-51) (SEQ ID NO:6). MALDI-TOF MS calcd. 6749 (M), 6677 (M-72), found 6769 (M), 6677 (M-72), 6695 (M-54), 6712 (M-36).

His6-LctM assay with His6-LctA(25-51) (SEQ ID NO:7). MALDI-TOF MS calcd. 5137 (M), 5065 (M-72), found 5134 (M), 5116 (M-18), 5098 (M-36), 5080 (M-54).

His6-LctM assay with His6-LctA(1-38) (SEQ ID NO:9). MALDI-TOF MS calcd. 6161 (M), 6125 (M-36), found 6125 (M-36). ESI-FTMS monoisotopic mass calcd. 6156.98-0 (M), 6120.96-0 (M-36), found 6156.96-0 (M), 6120.94-0 (M-36).

His6-LctM assay with His6-LctA(1-37) (SEQ ID NO:8). MALDI-TOF MS calcd. 6208 (M), 6172 (M-36), found 6210 (M), 6174 (M-36), 6192 (M-18).

His6-LctM assay with His6-LctA-T48S (SEQ ID NO:11). MALDI-TOF MS calcd. 7696 (M), 7624 (M-72), found 7624 (M-72), 7642 (M-54), 7660 (M-36). ESI-FTMS monoisotopic mass calcd. 7690.56-0 (M), 7618.56-0 (M-72), found 7690.50-0 (M+H), 7618.53-0 (M-72).

His6-LctM assay with His6-LctA-T48A (SEQ ID NO:83). MALDI-TOF MS calcd. 7680 (M), 7626 (M-54), found 7624 (M-54), 7680 (M).

His6-LctM assay with His6-LctA-C49A (SEQ ID NO:13). MALDI-TOF MS calcd. 7678 (M), 7606 (M-72), found 7606 (M-72), 7624 (M-54), 7642 (M-36), 7760 (M-72+DTT). ESI- FTMS monoisotopic mass calcd. 7672.61-0 (M), 7600.57-0 (M-72), found 7670.59-0 (M-2; disulfide between Cys38 & Cys50), 7600.59-0 (M-72).

His6-LctM assay with His6-LctA-C49S (SEQ ID NO:12). MALDI-TOF MS calcd. 7694 (M), 7622 (M-72), found 7622 (M-72), 7640 (M-54), 7658 (M-36), 7604 (M-90), 7694 (M), 7758 (M-90+DTT), 7776 (M-72+DTT). ESI-FTMS monoisotopic mass calcd. 7688.60-0 (M), 7616.56-0 (M-72), found 7688.65-0 (M), 7616.50-0 (M-72), 7598.60-0 (M-90).

His6-LctM assay with His6-LctA(1-38)C38U (SEQ ID NO:10). ESI-FTMS monoisotopic mass calcd. 6204.88-0 (M), 6168.86-0 (M-36), found 6204.91-0 (M), 6168.86-0 (M-36).

FIG. 5 illustrates a bioassay for lantibiotic activity. Small aliquots of the following samples were added in the wells: (1) His6-LctA (SEQ ID NO:4), (2) His6-LctA treated with Lys-C, (3) His6-LctA modified by LctM, (4) His6-LctA modified by LctM and treated with Lys-C, (5) cell free broth of *L. lactis* CNRZ 117, (6) cell free broth of *L. lactis* CNRZ 481 containing lacticin 481, (7) 50 mM Tris buffer, pH 8.5, (8) Lys-C in 50 mM Tris buffer, pH 8.5.

FIG. 6 illustrates results of Tandem MS on His6-LctA(1-38) (SEQ ID NO:9) and the product obtained after LctM-catalyzed modification.

Top panel: Sequence of His-LctA(1-38) (SEQ ID NO:9) and its product with key fragments highlighted. The fragmentation pattern of the starting peptide and product is almost identical with exception of the fragments in the C-terminus that are observed for the starting peptide but not in the product as a result of cyclization of the A-ring. The y-ion resulting from fragmentation between Ile31 and His32 localizes the dehydrations to the last 7 residues. Bottom panel (A) Key fragment ions. (B) Fragmentation spectra of His-LctA(1-38) starting material and enzymatic product (−36.02 Da). Formation of the b55 (blue) and b56 (red) ions should be inhibited in the product by the presence of a ring between Dhb33/Dha35 and Cys38. Both the b55 and b56 ions are present with >20 S/N ratio in the starting material. (C) Both of these fragment ions are not observed in key portions of the CAD fragmentation spectrum for the product. If the b55 and b56 ions were observed in the product, they would appear with a −36.02 Da mass shift due to two dehydrations. Overall, panels B and C provide convincing evidence that a thioether ring has been formed. All masses are reported as monoisotopic masses.

FIG. 7 illustrates tandem MS on His6-LctA(1-38)C38U (SEQ ID NO:10) and the product after LctM-catalyzed modification. Top panel: The fragmentation pattern is similar for both the starting peptide and the product with the exception of fragmentation between Glu37 and Sec38 that is absent in the product. This is a result of cyclizaton by LctM catalyzed addition of the selenol side chain of Sec38 to a dehydrated residue. The two dehydrations observed in the product can be localized to the last 6 residues by the y-ion arising from fragmentation between His32 and Thr33. Bottom panel: (A) Key fragment ion. (B) Fragmentation spectrum of the His6-LctA(1-38)C38U starting material showing the b56 ion fragment. (C) Formation of the b56 ion would be inhibited in the product spectrum due to ring formation between Dhb33/Dha35 and Sec38. Indeed the b56 ion fragment is absent in the spectrum of the enzymatic product (−36.02 Da). The red arrow indicates the expected position at Delta-m=−36.02 Da of the b56 ion as a consequence of two dehydrations in the product. The absence of the b56 ion is convincing evidence for thioether ring formation catalyzed by LctM. All masses are reported as monoisotopic masses. Ions corresponding to non-diagnostic fragments are labeled in black.

FIG. 8 illustrates Tandem MS on His6-LctA-C49A (SEQ ID NO:13) and the product obtained after LctM-catalyzed modification. Major differences are seen in the fragmentation pattern of the starting peptide and product in the region of the A- and B-ring. That is fragmentations are observed between His32, Thr33, Ile34, Ser35, and His36 in the starting peptide but not the product as a result of formation of the A-ring. Similarly, fragmentations are observed between Ser42, Trp43, Gln44, Phe45, Val46, Phe47, and Thr48 in the starting peptide but not in the product as a result of formation of the C-ring. However, the fragmentations between Asn39 and Met40 and between Asn41 and Ser42 are observed in both peptides clearly showing the absence of the B-ring.

FIG. 9 illustrates Tandem MS on His6-LctA-C49S (SEQ ID NO:12) and the product obtained after LctM-catalyzed modification. In addition to the M-72 product, a product was formed resulting of loss of 90 Da. MS/MS on this product showed that the newly introduced Ser in the mutant substrate is dehydrated in this peptide. Specifically, the b-ions resulting from fragmentation between Cys50 and residue 49 and between residues 49 and 48 showed unambiguously that residue 49 has lost 18 Da compared to the Ser precursor. Similar inspection of other b-ions in the C-terminal region once more verify dehydration of Thr33, Ser35, Ser42, and Thr48. Of note is that many fragments are generated in the C-terminal 10 amino acids in the product suggesting that the dehydration of Ser49 interferes with formation of the C-ring.

References for Example 1 to Example 3

1. H. G. Sahl, G. Bierbaum, Annu. Rev. Microbiol. 52, 41-79 (1998).
2. E. Breukink et al., Science 286, 2361-2364 (1999).
3. T. R. Klaenhammer, FEMS Microbiol. Rev. 12, 39-85 (1993).
4. H. W. van den Hooven et al., FEBS Lett. 391, 317-22. (1996).
5. J. Delves-Broughton, P. Blackburn, R. J. Evans, J. Hugenholtz, Antonie van Leeuwenhoek 69, 193-202 (1996).
6. W. Liu, J. N. Hansen, J. Biol. Chem. 267, 25078-85 (1992).
7. O. P. Kuipers et al., Antonie van Leeuwenhoek 69, 161-169 (1996).
8. P. Chen et al., Appl. Environ. Microbiol. 64, 2335-40 (1998).
9. C. Szekat, R. W. Jack, D. Skutlarek, H. Farber, G. Bierbaum, Appl. Environ. Microbiol. 69, 3777-83 (2003).
10. Lack of lantibiotic production may be due to disruption of the post-translational modification process, degradation of the non-native peptide product or intermediates, breakdown of self-immunity resulting in shutdown of production, or perturbation of signaling pathways in cases where the bacteriocin acts as a quorum sensor controlling its own expression. See references 11-14.
11. J. R. van der Meer et al., J. Biol. Chem. 269, 3555-62 (1994).
12. O. P. Kuipers, M. M. Beerthuyzen, P. G. de Ruyter, E. J. Luesink, W. M. de Vos, J. Biol. Chem. 270, 27299-27304 (1995).
13. M. Reis, M. Eschbach-Bludau, M. I. Iglesias-Wind, T. Kupke, H. G. Sahl, Appl. Environ. Microbiol. 60, 2876-83 (1994).
14. G. Bierbaum, M. Reis, C. Szekat, H. G. Sahl, Appl. Environ. Microbiol. 60, 4332-8 (1994).
15. N. Schnell et al., Nature 333, 276-278 (1988).
16. A. Rincé, A. Dufour, P. Uguen, J. P. Le Pennec, D. Haras, Appl. Environ. Microbiol. 63, 4252-60. (1997).

17. J. C. Piard, O. P. Kuipers, H. S. Rollema, M. J. Desmazeaud, W. M. de Vos, J. Biol. Chem. 268, 16361-8 (1993).

18. O. Koponen et al., Microbiology 148, 3561-3568 (2002).

19. R. J. Siezen, O. P. Kuipers, W. M. de Vos, Antonie van Leeuwenhoek 69, 171-84. (1996).

20. Materials and methods are available as supporting material on Science Online 21. The sequence of the His6-tag linker is GSSHHHHHHSSGLVPRGSH. The DNA sequences of all constructs were verified and the masses of the expressed gene products were determined by mass spectrometry.

22. N. M. Okeley, M. Paul, J. P. Stasser, N. Blackburn, W. A. van der Donk, Biochemistry 42, 13613-13624 (2003).

23. F. W. McLafferty, E. K. Fridriksson, D. M. Horn, M. A. Lewis, R. A. Zubarev, Science 284, 1289-90. (1999).

24. P. Roepstorff, J. Fohlman, Biomed. Mass Spectrom. 11, 601 (1984).

25. A. J. Kleinnijenhuis, M. C. Duursma, E. Breuking, R. M. A. Heeren, A. J. R. Heck, Anal. Chem. 75, 3219-3225 (2003).

26. Y. M. Li, J. C. Milne, L. L. Madison, R. Kolter, C. T. Walsh, Science 274, 1188-93 (1996).

27. T. W. Muir, D. Sondhi, P. A. Cole, Proc. Natl. Acad. Sci. U.S.A. 95, 6705-10 (1998).

51. M. W. Senko et al., Rapid. Comm. Mass Spectrom. 10, 1824-1828 (1996).

Example 4

Mutants of LctM

An active mutant of LctM was generated. The mutant was a triple mutant with nucleotide changes A458G/A556G/A815G (SEQ ID NO:18), i.e. at each of positions 458, 556, and 815, adenine was changed to guanine. The amino acid changes introduced by A458G/A556G/A815G changes at the nucleotide level are: Lys153Arg, Ser186Gly, and Asp272Gly (SEQ ID NO:19).

Further mutants of LctM are obtained by genetic engineering techniques such as site-directed mutagenesis or random mutagensis. Mutants are evaluated for attributes such as substrate specificity, ability to catalyze dehydration, and ability to catalyze cyclization.

Example 5

Use of LctM to Produce Other Lantibiotics

LctM is used in vitro in the biosynthesis of lantibiotics other than lacticin 481 or variants thereof. For example, according to methods of this invention LctM is used to generate LanM lantibiotics such as mutacin II and variants thereof. LctM is reacted with a precursor peptide of mutacin or a variant thereof and acts to achieve dehydration and cyclization. LctM is similarly used to produce other LanM lantibiotics and variants thereof. LctM is used to generate LanB LanC type lantibiotics by acting upon suitable precursor peptides. For example, LctM is used to generate a nisin lantibiotic by reacting the nisin precursor peptide with LctM to make a modified product. Cleavage of a leader portion of the modified product thus generates an active lantibiotic. In another example, the leader of lacticin 481 is attached to the structural peptide of mutacin II or another lantibiotic; the resulting chimeric substrate is modified by a modifying enzyme such as LctM.

Example 6

Use of LanM Enzymes Other than LctM to Produce Lantibiotics

As an alternative to or in addition to Example 5, a given LanM enzyme is used in vitro in the biosynthesis of a lantibiotic or variant thereof in connection with a precursor peptide corresponding to the organism giving rise to the LanM enzyme. For example, the LanM enzyme CinM is used to act on a corresponding CinA precursor peptide or variant thereof according to the methods herein to generate a cinnamycin lantibiotic or variant thereof. The LanM enzyme MrsM is used to act on a corresponding MrsA precursor peptide or variant thereof according to the methods herein to generate a mersacidin lantibiotic or variant thereof.

In an analogous manner to methods herein employing LctM, other LanM enzymes are manipulated using techniques as known in the art. The nucleotide sequence of a LanM enzyme gene is used to generate an expressed LanM enzyme. Accession numbers of published sequences are retrieved from the National Center for Biotechnology Information (NCBI). A LanM enzyme is selected and used in vitro on its corresponding natural substrate or variant thereof.

Sequence Sources for LanM Enzymes.

The gene cluster including mrsM (SEQ ID NO:101): AJ250862 (Accession number). See Altena, K., Guder, A., Cramer, C. and Bierbaum, G., Biosynthesis of the lantibiotic mersacidin: organization of a type B lantibiotic gene cluster, Appl. Environ. Microbiol. 66 (6), 2565-2571 (2000). See SEQ ID NO:20.

The gene cluster including mutM (SEQ ID NO:102): U40620. See Woodruff, W. A., Novak, J. and Caufield, P. W., Sequence analysis of mutA and mutM genes involved in the biosynthesis of the lantibiotic mutacin II in *Streptococcus mutans, Gene* 206 (1), 37-43 (1998). See SEQ ID NO:21.

The gene cluster including cinM (SEQ ID NO:103): AJ536588. See Widdick, D. A., Dodd, H. M., Barraille, P., White, J., Stein, T. H., Chater, K. F., Gasson, M. J. and Bibb, M. J., Cloning and engineering of the cinnamycin biosynthetic gene cluster from *Streptomyces* cinnamoneus cinnamoneus DSM 40005, Proc. Natl. Acad. Sci. U.S.A. 100 (7), 4316-4321 (2003). See SEQ ID NO:22.

The gene cluster including scnM (SEQ ID NO:104): AF026542. See McLaughlin, R. E., Ferretti, J. J. and Hynes, W. L., Nucleotide sequence of the streptococcin A-FF22 lantibiotic regulon: model for production of the lantibiotic SA-FF22 by strains of *Streptococcus pyogenes*, FEMS Microbiol. Lett. 175 (2), 171-177 (1999). See SEQ ID NO:23.

The gene cluster including rumM (SEQ ID NO:105):NC_005207, AB121757. See Sashihara, T., Kimura, H., Higuchi, T., Adachi, A., Matsusaki, H., Sonomoto, K. and Ishizaki, A., A novel lantibiotic, nukacin ISK-1, of *Staphylococcus warneri* ISK-1: cloning of the structural gene and identification of the structure, Biosci. Biotechnol. Biochem. 64 (11), 2420-2428 (2000). See SEQ ID NO:24.

The sequences of gene cluster including lctnM1 and lctnM2 (SEQ ID NO:106) (ltnM1 and ltnM2): NC_001949, AE001272. See Dougherty, B. A., Hill, C., Weidman, J. F., Richardson, D. R., Venter, J. C., and Ross, R. P., Sequence and analysis of the 60 kb conjugative, bacteriocin-producing plasmid pMRC01 from *Lactococcus lactis* DPC3147, Mol. Microbiol. 29 (4), 1029-1038 (1998). See SEQ ID NO:25 and SEQ ID NO:26.

For NukM, see SEQ ID NO:27.

Example 7

Use of a LanM Enzyme to Make a LanB LanC Type Antibiotic

A LanM enzyme is used according to methods of this invention to act upon a precursor peptide or variant thereof that is derived from an organism capable of making a LanB LanC type lantibiotic. In an example, the LanM enzyme is LctM (SEQ ID NO:40).

Example 8

Electrophilic Substrates for Nucleophile Addition

A dehydrated precursor peptide is generated. First, a precursor peptide is prepared using recombinant or synthetic techniques or a combination of techniques. For example, a precursor peptide having a reduced ability to cyclize is made by designing a recombinant or synthetic peptide so as to lack one or more cysteine residues. Such a peptide is then reacted with a LanM enzyme, particularly LctM, to generate the dehydrated precursor peptide. A dehydrated residue such as dehydroalanine is electrophilic and serves as a target for nucleophilic attack. Thus an electrophilic handle is installed in what otherwise may be an intermediate in an in vitro biosynthesis of a lantibiotic precursor peptide. A nucleophile is then added to the electrophilic substrate. Examples of a nucleophile include a monosaccharide, oligosaccharide, a prenyl group such as farnesyl or geranyl, a fluorescent tag, a spin label, or a radiolabel. As understood in the art, it may be necessary to install or utilize a thiol modification. A nucleophile such as a monosaccharide or oligosaccharide is selected to react with the electrophile substrate, thereby generating a glycoprotein. A glycoprotein serves as a vaccine adjuvant in a tumor therapy. See Convergent Synthesis of Peptide Conjugates Using Dehydroalanines for Chemoselective Ligations Yantao Zhu and Wilfred A. van der Donk, 2001, ORGANIC LETTERS Vol. 3, No. 8 (1189-1192).

Example 9

Identification of a Lan Protease, a Protease Domain of LctT (Lpd)

A Lan protease was identified. The protease domain of LctT (SEQ ID NO:29) was identified by sequence alignment with LanT proteins from other lantibiotic producing organisms. The alignment was used to identify a region of low homology between the proteolytic and transmembrane domains of LctT. This corresponded to 150 amino acids from the N-terminus of LctT. The amino acid sequence is: MKIVLQNNEQDCLLACYSMILGYFGRD-VAIHELYSGEMIPPDGLSVSYLKNINMKHQVS MHVYKTDKKNSPNKIFYPKMLPVI-IQWNDNHFWVTKIYRKNVTLIDPAIGKVKYNYNDF MKKFSGYIITLSPNSSFTKKKRISEIIFPLK (SEQ ID NO:29). The molecular weight of the protein is 17,460 Da. See SEQ ID NO:28 and SEQ ID NO:29.

Cloning of Lpd. The gene corresponding to the N-terminal proteolytic domain of LctT (here forth designated as Lpd) (SEQ ID NO:28) was obtained by PCR with genomic DNA of *Lactococcus lactis* CNRZ 481 employing the forward primer 5'-ATTCGC GGATCCATGAAAATAGTTTTACAAAATAAT-3' (SEQ ID NO:30) and reverse primer 5'-AAACCG CTCGAGTTATTTTAGTGGAAAGATAATTTC-3' (SEQ ID NO:31) incorporating BamHI and XhoI sites, respectively. The PCR product was double digested with BamHI and XhoI and cloned into the pGEX-6P-1 vector (Amersham) that had been similarly reacted to obtain the plasmid pLpd. The correct construct was verified by PCR, restriction digest and sequencing.

Overexpression and purification of GST-Lpd. The Lpd protein (SEQ ID NO:29) was expressed from pGEX-6P-1 vector in BL1(DE3) cells as an N-terminal fusion with the Glutathione S-transferase protein (GST). Purification of the GST-Lpd protein (Mol. wt. ~44 kDa) was achieved by means of affinity chromatography with a reduced glutathione sepharose column (Amersham). After extensive washing with >10 column volumes of binding buffer (1.8 mM $KH_2PO_4$, 10 mM $Na_2HPO_4$, 500 mM KCl, 140 mM NaCl, pH 7.3), the protein was eluted from the column in a buffer consisting of 50 mM Tris-HCl, pH 8.0 and 10 mM reduced L-glutathione. The fractions containing eluted protein were concentrated by Amicon YM-10 ultrafiltration membrane (Millipore) and buffer was exchanged to 20 mM Tris-HCl, pH 7.4, 500 mM NaCl. This yielded GST-Lpd protein at a concentration of 0.5 mg/mL.

Figure 83:
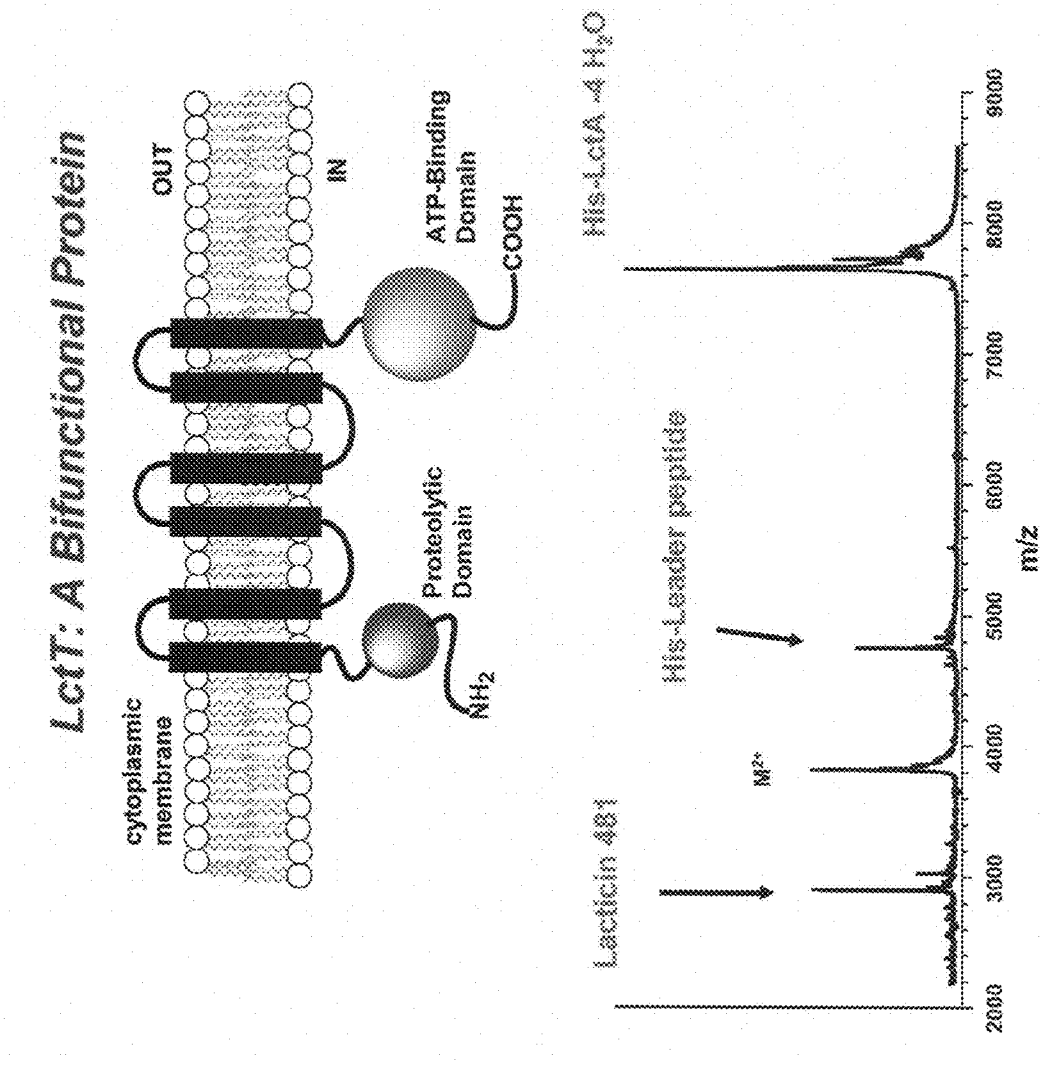
FIG. 83 illustrates LctT as a bifunctional protein along with mass spectrometry data related to proteolysis.

Cleavage of His-LctA and His-pro-Lacticin. The unmodified His-LctA substrate was either directly incubated with GST-Lpd or first modified by LctM prior to incubation with the protease. Assay mixtures typically contained substrate (50-500 μg), GST-Lpd (35-70 μg) and a buffer consisting of 200 mM NaPi, pH 7.5, 200 mM $Na_2SO_4$ and 5 mM DTT. Assays were incubated at 37° C. for 12 h and analyzed by MALDI-TOF MS. Both unmodified and modified His-LctA were substrates for GST-Lpd as determined by MALDI-TOF MS and sensitivity of indicator strain *Lactococcus lactis* 117 towards the modified substrate after cleavage. See FIG. 83 which illustrates LctT as a bifunctional protein including the proteolytic domain.

Recognition sequence of LctT protease domain. Some proteases are called double glycine proteases since they recognize a recognition sequence ending in GG-X (i.e. the protein cleaves at the C-terminal side of the second glycine residue). For the precursor peptide LctA, the relevant sequence is GA-X. Therefore, a Lan protease may cleave both GG-X and GA-X sequences. From alignments, certain lantibiotic precursor peptide sequences have two bulky hydrophobic amino acids before the GG and GA (see Table 1). Thus a recognition sequence for a Lan protease that is a protease domain of LctT is BBGG-X (SEQ ID NO:1) or BBGA-X (SEQ ID NO:2), wherein B=isoleucine or leucine and X is any amino acid.

TABLE 1

| Sequence alignment of protease recognition sequences. | |
| --- | --- |
| Precursor Peptide | Amino Acid Sequence |
| LctA | ILGA-K (SEQ ID NO:32) |
| RumA | ILGG-G (SEQ ID NO:33) |
| VarA | ILGG-G (SEQ ID NO:34) |
| ScnA | IIGA-G (SEQ ID NO:35) |
| ScnA | IIGA-G (SEQ ID NO:36) |
| MutA | ILGG-N (SEQ ID NO:37) |

Example 10

Lantibiotics for Applications in Mammals

Lantibiotics of the invention are used for compositions and methods in applications in mammals, particularly in humans.

In a first category, lantibiotics are administered to a human wherein the target organism is actually a bacterium. Thus the first category is comparable to the pharmaceutical compositions and methods in connection with a traditional antibiotic such as erythromycin.

In a second category, lantibiotics of the invention are used wherein the target organism is actually the mammal. For example, lantibiotics duramycin and cinamycin act as phospholipase A2 inhibitors. Therefore the present invention is used to generate lantibiotics and methods for treatment of a human inflammatory condition (see references 43 and 44 of Example 11). In another example, the lantibiotic ancovenin is an inhibitor of angiotensin converting enzyme (see reference 45 of Example 11). Therefore the present invention is used to generate lantibiotics and methods relating to human disorders in connection with angiotensin converting enzyme.

Example 11

Biosynthetic Enzymes Involved in Lanthionine Formation; Including Combinatorial Synthesis of Precursor Peptides Significant progress regarding in vitro lantibiotic synthesis has been obtained. As described in the preliminary results section, we have been able to achieve in vitro dehydration and cyclization to produce the lantibiotic lacticin 481. This is the first such example, which has been pursued on four continents since the sequencing of the first complete lantibiotic biosynthetic gene clusters in 1988. The lacticin biosynthetic system is a superior choice for our goals because of the postulate that it contains dehydratase and cyclase activity in one protein (LctM, SEQ ID NO:40). We show here that this is indeed the case. We have expressed and purified the LctM protein and incubation with the LctA substrate resulted in full processing of the peptide to the post-translationally modified product. Also, we have established by extensive mass spectrometric experiments in collaboration with the Kelleher lab, that the structure of the product contains all the lanthionine and methyllanthionine rings found in native lacticin 481. We explore the mechanism of lantibiotic biosynthesis, investigate the properties of active protein, and use the active system for in vitro engineering of the structure of lacticin and other compounds.

Lacticin 3147 is a two-component antibiotic comprised of two lantibiotic peptides that are both required for activity. Disruption of either of the structural genes coding for the two prepeptides (ltnA1 or ltnA2) results in mutant strains that are incapable of producing active lacticin 3147. Earlier it was erroneously asserted that “when a synthetic LtnA1 (or LntA2) peptide was added to cell free extracts of these mutants, antibiotic activity was restored.” We initially interpreted an experiment (reported in McAuliffe et al (2000) Microbiology 146, 2147-54) to indicate that the substrates were added, but upon closer inspection the authors use the designation LtnA1 and LtnA2 for the final, post-translationally modified peptides. Hence, not the substrates but the fully processed products were added restoring the two-component lantibiotic. We want to specifically point this out, because it emphasizes that no other reports of in vitro lantibiotic production have been published despite extensive investigations in many laboratories (1-9). Our efforts break open this exciting area for many laboratories.

In disclosing the lacticin 481 system, we provide a blueprint for that and other lantibiotic systems of the LanM and LanB LanC types, including subtilin and nisin systems.

Lantibiotics are a class of ribosomally synthesized peptide antibiotics that are post-translationally modified to their mature structures. These post-translational modifications include dehydration of serine and threonine residues, and subsequent polycyclization through intramolecular Michael additions of cysteine residues to the alpha, beta-unsaturated dehydroalanine (Dha) and dehydrobutyrine (Dhb) residues. Several members of the lantibiotic family have interesting pharmacological properties including binding to lipid II, the target of vancomycin. This report describes the combined use of molecular biology, biochemistry, and organic synthesis to explore the post-translational modifications during the biosynthesis of lacticin 481.

I. Assessment of the Substrate Requirements for Lantibiotic Biosynthesis. In vitro dehydration of lantibiotic prepeptides by the LanB proteins has proven troublesome in six laboratories including our own. Lacticin 481 is a member of the recently described type AII lantibiotics. The producer strains contain only one biosynthetic polypeptide (LanM) that is believed to carry out both dehydration and cyclization reactions. We have expressed and purified the LctM protein involved in the biosynthesis of lacticin 481 and have demonstrated that the protein carries out the posttranslational modifications. No other laboratory has reported in vitro lantibiotic production. This puts us in a prime position to investigate the mechanism of the maturation process. Specific questions asked include (1) does dehydration of all Ser and Thr residues precede the cyclizations or are both reactions tightly coupled, (2) are intermediates that we have observed by mass spectrometry true intermediates or dead-end by-products (3) what is the role of the leader peptide, and (4) what is the substrate specificity in the structural region of the peptides. These issues are addressed with a variety of techniques including mutagenesis, truncation of substrates, and extensive Fourier Transform mass spectrometry.

II. Characterization of the Proteins Involved in Lacticin 481 Maturation. With a functional dehydratase and cyclase in hand, we address a number of important questions. An obvious priority involves structural characterization of LctM using X-ray crystallography. Another important effort focuses on separation of the dehydration and cyclization reactions, either by dissecting the protein by domains or by obtaining site directed mutants that will inactivate the cyclization activity. A third sub-aim focuses on obtaining the protease that removes the leader peptide after post-translational modifications are complete.

III. Investigation of Substrate Binding to LctM. How one protein dehydrates four Ser/Thr residues that are in different sequence contexts and then catalyzes the regio- and stereospecific addition of cysteines to the resulting dehydroamino acids has been an open question in lantibiotic biosynthesis. Obviously, an important clue lies in substrate recognition, which is probed by a variety of methods including X-ray crystallography, EXAFS studies on binding to the Zn site, and determination of binding constants for substrate and substrate/enzyme mutants using surface plasmon resonance spectroscopy.

IV. Protein Engineering to Generate Novel Lacticin Variants. The knowledge obtained in Sections I-III serves as the basis for the second phase of this research program, which uses the biosynthetic enzyme for the preparation of novel lantibiotics. First the steric and electronic tolerance of the enzymes is assessed. This is followed by the incorporation of amino acids designed to answer specific questions about the post-translational modification process including mutants that incorporate peptide fragments from other lantibiotic prepeptides. The structural diversity accessible by these studies is greatly increased by using semi-synthetic substrates prepared by combinatorial parallel synthesis. In addition to the fundamental scientific knowledge that comes forth from these studies, they allow access to molecules with interesting properties that are not easily prepared by either chemical or biological techniques.

B. Background and Significance

B.1 Peptide Antibiotics. Numerous reports of multi-drug resistant bacterial strains have appeared in recent years, with several strains posing the threat of becoming immune against all commercially available antibiotics (10-12). It is evident that in order to prevent potential epidemic outbreaks of infectious diseases, a renewed focus on antibiotic research is highly desired, including the search for new drugs with alternative cellular targets, the investigation of the mechanisms of cytotoxicity and resistance, and the understanding of their biosynthetic pathways. The recent threat of bioterrorism further emphasizes the importance of research in this area.

Gene encoded antimicrobial peptides are a rapidly expanding class of antibiotics with a high level of molecular diversity that is frequently introduced by post-translational modifications (6, 13-19). In addition to their structural divergence, these compounds also display many different and often novel mechanisms of cytotoxicity. As such they are promising as supplements for the rapidly declining arsenal of therapeutic antibiotics, which target only a limited number of cellular processes. An advantage that is unique to ribosomally synthesized peptide antibiotics is that they are amenable to structural variation via site-directed mutagenesis. This potentially allows facile entry into a large number of accessible structures via combinatorial techniques that can be used for structure-function studies or rational drug design. A number of reports have appeared of in vivo production of such novel variants using genetically engineered organisms. However, several disadvantages of this approach have become clear. First, unlike the products of the extensively studied polyketide synthases (20) or the terpenoid biosynthetic pathway (21-24), peptide antibiotics are generally highly susceptible to proteolytic degradation in the cell, particularly when their structures are non-native. Therefore, a large number of compounds varying in degree of degradation are often produced requiring a tedious purification process to obtain novel structures. Furthermore, the structural variation is limited to the physiologically accessible amino acids. Finally, several reports have indicated that variations in the nucleotide sequence of the genes encoding for the antibiotic precursor (prepeptide) can perturb other processes including transcriptional and/or translational regulation and signaling pathways for post-translational modification (25-28). This proposal describes our current and future efforts using a different strategy for the generation of variants of peptide antibiotics that can be used for structure-function studies. In this approach, purified biosynthetic enzymes obtained using recombinant techniques are used in combination with semisynthetic, unnatural prepeptides. Since the experiments in this approach are carried out in vitro, proteolytic or other degradation during the various cellular processes leading to the mature antibiotic is not an issue. Moreover, the number of accessible structures is not limited by the physiological amino acids, while the power of combinatorial techniques can still be applied. As described below, the so-called lantibiotics are a group of peptide antibiotics with interesting chemical and biological properties that are particularly suitable for this approach. Clearly, in addition to exploring the possibility of producing novel structures, the in vitro approach also allows detailed investigation of the mechanism of biosynthesis of lantibiotics, which to date has not been possible. We present in our preliminary results the first in vitro reconstitution of lantibiotic biosynthesis.

Figure 10:
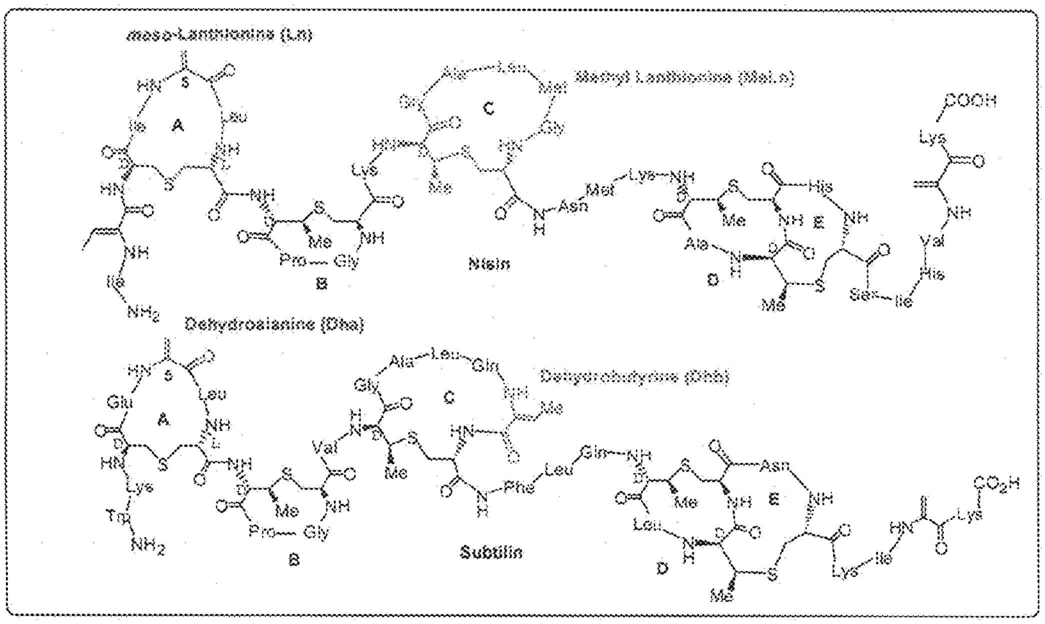
FIG. 10 illustrates the cyclic thioether amino acids lanthionines (Ln) and/or methyllanthionines (MeLn).

B.2 LANTIBIOTICS. The name lantibiotics was introduced in 1988 as an abbreviation for lanthionine-containing antibiotic peptides (29). These compounds all contain the cyclic thioether amino acids lanthionines (Ln) and/or methyllanthionines (MeLn) (FIG. 10).

In addition, lantibiotics often contain the unsaturated amino acids 2,3-didehydroalanine (Dha) and (Z)-2,3-didehydrobutyrine (Dhb) (7-9, 30, 31). The widespread application of the prototype lantibiotic nisin as a safe alternative for chemical reagents in food preservation (>50 countries for over 35 years) (32-34) spurred a rapid expansion of research activities directed at understanding their biogenesis. These studies have indicated that lantibiotics are ribosomally synthesized as precursor peptides (prepeptides), which subsequently undergo post-translational modifications (7, 9, 30, 35, 36). The biosynthesis of lantibiotics distinguishes them from "classical" non-gene encoded peptide antibiotics like gramicidin, which are produced by modular peptide synthetases. Genetic studies have demonstrated that the unsaturated moieties Dha and Dhb are produced by dehydration of serine and threonine residues, respectively, and that the cyclic structures Ln and MeLn are generated by enzyme mediated addition of cysteine residues to a subset of the Dha and Dhb residues (29, 37-39). These cyclizations occur both regio- and stereospecifically in which the original Ser/Thr fragment of the product thioether has the D-configuration and the Cys fragment the L-configuration (FIG. 10). The thioether rings impose important conformational restrictions on the cyclic peptides. In general the lantibiotics can be divided into two types. Type A comprises positively charged, amphiphatic molecules with a screw-like conformation that exert their bactericidal activity by depolarization of energized cytoplasmic membranes via pore formation (18, 40-42). On the other hand, type B lantibiotics are globular in shape and are thought to inhibit specific cellular processes. While much is known about their structures and genetics of biosynthesis, the molecular (chemical) mechanisms of their biosynthesis are poorly understood. The type A compounds nisin and the structurally closely related subtilin have been most extensively studied. In addition, a number of recently isolated type B lantibiotics have attracted considerable attention because of their biological activities. Amongst these are duramycin, which acts as a phospholipase $A_2$ inhibitor (43, 44), ancovenin, a potent inhibitor of angiotensin converting enzyme (45), and mersacidin which exhibits comparable cytotoxic activity against methicillin-resistant *Staphylococcus aureus* (MRSA) as vancomycin without showing cross-resistance (46-48). While the proposed research in principle could be applied to any of the lantibiotics, we will focus our studies on lacticin 481 as we have achieved the first in vitro lantibiotic biosynthetic system for this family member (vide infra). Since most studies in other laboratories have focused on subtilin and nisin, we use these lantibiotics to illustrate the current knowledge in the field.

B.2.a. Proteins Involved in Biosynthesis of Subtilin and Nisin

Nisin is produced by certain strains of *Lactococcus lactis* (34) and subtilin is produced by *Bacillus subtilis* ATCC 6633 (49). The two compounds are structurally closely related, showing 63% sequence identity including 1 Ln and 4 MeLn rings of identical size and position along the peptide chain (FIG. 10). In addition, both contain Dha residues in position 5 and as their penultimate amino acid. Nisin has received much attention recently with the discovery that it binds to lipid II (50-53), a key intermediate in cell wall biosynthesis in Gram-positive bacteria and the target of vancomycin. This finding explained why nisin, which was long considered to be a relatively simple voltage-dependent pore former (18), is three orders of magnitude more potent against biological membranes than against liposomes. Moreover, it also accounts for the high antimicrobial activity of nisin at concentrations (MIC 3.3 nM) where other known pore formers are not active (eg MIC of magainin=0.4 nM) (53, 54). It is now generally believed that nisin acts as a double action antimicrobial that docks onto lipid II prior to assembly to form pores in the cell membrane, and that blocks proper assembly of peptidoglycan (53). Because of its high efficacy at low concentrations, nisin has also received attention as an agent that may enhance the bioavailability of other drugs. Perhaps the most promising aspect of nisin's utility is the fact that there are only very rare reports of nisin resistance despite the fact that it has been used in >50 countries for >35 years as a safe and effective food preservative (32, 34, 51). Binding to lipid II is not restricted to nisin as several other less investigated lantibiotics such as mersacidin and epidermin have recently also been reported to bind to the peptidoglycan biosynthetic intermediate (55). Lacticin 481 is also produced by several strains of the lactic acid bacterium *L. lactis* including a proprietary strain from Nestlé Corp (56-60). *L. lactis* has been declared safe for food applications, and both strains producing nisin and lacticin 481 are used as starter cultures in cheese manufacturing. As such isolated lacticin has been investigated for use in food preservation, enhancer of cheese ripening, and for its activity against *Clostridium tyrobutyricum* (60-64).

Many of the Ian genes involved in the biosynthesis of lantibiotics have been sequenced (7, 9). These studies have demonstrated a high level of similarity in the gene organization for production of the various compounds. The biosynthetic genes (lanBCP), as well as those encoding accessory proteins with functions involving regulation (lanQRK), self-immunity (lanEFGI), and translocation (lanT), are clustered around the gene for the prepeptide (lanA). All prepeptides contain a relatively long N-terminal leader sequence with a net negative charge, which does not undergo post-translational modifications (eg FIG. 11).

It is important to note that the Ser and Thr residues in the structural region are dehydrated without any noticeable consensus sequence. The Ser and Thr residues can be flanked by acidic, basic, and hydrophobic residues. The leader sequence contains Ser and Thr residues but no cysteines, and is proteolytically removed. The role of this leader sequence is at present unclear. Possible functions that have been suggested include signaling for export, protection of the producing strain by keeping the peptides inactive, and providing scaffolds for the post-translational modification machinery (29, 30). Precedent for all three functions can be found in the literature on export proteins, hormones, and microcin biosynthesis, respectively. A number of intriguing but confusing in vivo studies have been conducted with chimeras from the nisin and subtilin leader and structural regions. While expression of the nisin gene in a subtilin producing *Bacillus* strain did not lead to nisin-related modified peptides, a chimera consisting of the subtilin leader and nisin structural gene sequences produced a fully processed product (65). This result suggested that the post-translational modification machinery of the host specifically recognizes the leader sequence. However, when a similar chimera containing a subtilin leader and nisin structural region was expressed in a nisin producing *Lactococcus* strain the structural region was also processed (66). Furthermore, the leader sequences of several other lantibiotics including lacticin 481 have similarity to the leader peptides of bacteriocins that are not post-translationally modified (13, 67). These observations argue against a role of providing a recognition motif for binding of the modifying enzymes. Thus, at present it is unclear whether the leader peptide is required for post-translational modification. We will address this fundamental question in our proposed studies.

It is believed that all essential genes involved in lanthionine biosynthesis have been identified (68, 69). In our laboratory we are predominantly interested in the proteins that catalyze the dehydration and cyclization reactions. The homologous proteins NisB (SEQ ID NO:81) and SpaB (SEQ ID NO:82), and NisC (SEQ ID NO:69) and SpaC (SEQ ID NO:68) are thought to be responsible for these processes during the synthesis of nisin and subtilin, respectively, but a clear assignment of their functions and mode of action is lacking. Recent searches of several sequence databases indicate that neither NisB (SpaB) nor NisC (SpaC) has homology with any known dehydratases, nor with any other proteins. Genetic studies with a producer of the related lantibiotic Pep5 using PepC (SEQ ID NO:70) deletion mutants revealed the production of partially dehydrated peptides but no cyclization products (70, 71). Similar studies have been reported recently for NisC mutants (72). Thus, these observations imply a role for LanC proteins in the cyclization reaction. Aside from our work described in section C, EpiC (SEQ ID NO:71) is the only LanC protein that has been overproduced in *E. coli* (5). It is a soluble protein of 47.9 kDa that did not show any activity with the prepeptide EpiA consistent with this enzyme being involved in cyclization rather than dehydration. From their nucleotide sequences NisB and SpaB are deduced to be hydrophilic proteins of 116 kDa and 115 kDa (1), respectively. Despite their hydrophilic character, the absence of typical trans-membrane segments, and the lack of recognition sites for membrane attachment, immunoblot analysis of SpaB has demonstrated that this protein co-sediments with the membrane fraction of *Bacillus* vesicles (1). Thus, localization at or near the membrane is suggested. EpiB has been expressed in *Staphylococcus carnosus*, and was detected in both the cytosolic and membrane fraction (3). The protein has been partially purified, but no activity has been reported to date (3). Several reports have produced support for the existence of multi-enzyme lantibiotic synthetase complexes using yeast two-hybrid methods or co-immunoprecipitation. For subtilin, these studies have shown that SpaT, SpaB, and SpaC probably are associated in a multimeric complex (73). Similarly, NisB, NisC and NisT have been implicated as part of a larger complex (74). The LanT proteins are homologous with typical dimeric ABC-type transporters.

Genetic Engineering

The cloning of the gene clusters involved in the biosynthesis of many lantibiotics (69) has laid the foundation for genetic protein engineering aimed at in vivo production of novel compounds with potentially interesting properties. Many studies have indicated the feasibility of changing the molecular structures of lantibiotics by mutagenesis of the prepeptide genes (75). So far, engineering of the nisin structure has been most extensively investigated. For instance, replacement of serines by threonines in the structural region of the nisA gene led to the production of Dhb instead of Dha in the mature lantibiotic (76). Even more interesting is the production of a nisin mutant with a Dhb residue in place of Gly after replacement by a Thr codon (75). These studies clearly indicate low substrate specificity for the dehydratase. Removal of the Dha at position 5 by replacement with Ala eliminated nisin's activity against outgrowing spores (75, 77). This result supports a postulate that some of the Dha and/or Dhb structures may be in part responsible for the biological activity of lantibiotics, since they constitute possible sites of covalent modification of their molecular targets (78, 79). In this model, the (Me)Ln structures provide the lantibiotics with their high degree of resistance to proteolytic cleavage, and may help induce the required conformation for molecular recognition by the cellular target(s). Alterations in the Ln and MeLn structures have also been accomplished. Substitution of a Ser with Thr gave MeLn instead of Ln, and replacement of a Thr with Cys produced a disulfide in place of MeLn (75). In addition to changes of the modified residues, several mutants have been reported in which other amino acids in the polypeptide have been replaced (75, 80). Two nisin variants with higher solubility than the parent compound have been reported (81). Despite these important advancements that have contributed to a better understanding of lantibiotic biosynthesis and cytotoxicity, very few mutant lantibiotics have been generated with improved anti-microbial activities. A number of potential explanations could account for this. First of all, it might not come as a surprise that Nature has already optimized the biological activity of these compounds using the same tools, i.e. mutagenesis with 20 amino acids. Furthermore, the structural and functional space that can be sampled using genetic engineering of ribosomally synthesized proteins is currently limited. Another contributing factor to the absence of more potent compounds produced by genetically engineered lantibiotic producers may lie in the breakdown of self-immunity in cases where more active compounds are actually generated. This might lead to either degradation of the intermediates or shutdown of antibiotic production. Indeed, degradation products or incompletely modified peptides are often observed (82). Finally, it has been shown for several lantibiotics that the prepeptide and/or the final product fulfills a regulatory role in lantibiotic production (25-28). Structural variants, however, may lack the ability to induce in vivo synthesis resulting in reduced or abolished production.

The methodology used and proposed in this project is based on purified enzymes and has several conceptual advantages over genetic protein engineering of lantibiotics. 1). The structures of the prepeptides are not limited by the physiological amino acids, only by the ability to design and synthesize the amino acids and incorporate them into peptides using well-developed techniques. In addition, peptide synthesis is particularly amenable to combinatorial techniques thereby dramatically increasing the number and structure of rapidly accessible substrate candidates. 2) Because of the in vitro nature of the approach, degradation of products is not a problem, nor are cytotoxic or regulatory properties of the products a concern. 3) The structural and functional tolerance of the biosynthetic enzymes are explored in much greater detail when unnatural amino acids are utilized in addition to the natural amino acids. 4) Finally, non-peptide structures (peptidomimetics) in part of the substrates can be used in order to produce molecules with higher biological activity.

It should be noted that some advantages of genetic engineering may be lost using the strategy we have adopted. One of the biggest assets of molecular biology is that it produces readily and rapidly renewable sources of manipulated genes and organisms, which is not true for chemically synthesized molecules and purified enzymes. However, the in vivo use of unnatural peptide substrates is at present still largely an unattainable goal, mostly because this suffers to an even higher degree from the same drawbacks as those described above.

Therefore, the strategy described herein is used to extend the tools of lantibiotic engineering beyond their present boundaries.

C. Preliminary Studies and Progress Report

1a. Synthetic methodology for site-specific introduction of dehydroamino acids into peptides.

Facile Chemoselective Synthesis of Dehydroalanine-Containing Peptides. Okeley, N. M.; Zhu, Y.; van der Donk, W. A. *Org. Lett.* 2000, 2, 3603-3606.

Biomimetic Stereoselective Formation of Methyllanthionine. Zhou, H.; van der Donk, W. A. *Org. Lett.* 2002, 4, 1335-1338

Selenocysteine Derivatives for Chemoselective Ligations. Gieselman, M. D.; Zhu, Y.; Zhou, H.; Galonic, D.; van der Donk, W. A. *ChemBioChem* 2002, 3, 709-716

At the outset of our program on the in vitro reconstitution of lantibiotic biosynthesis we realized that the entire project would hinge on the activity of the putatively membrane-bound dehydratases SpaB and NisB. To reduce this risk, we develop new synthetic methodology to introduce dehydroamino acids into peptides in parallel with our studies on the dehydratase. This methodology is very efficient (83). It involves the use of the selenium containing amino acids 1-4.

1

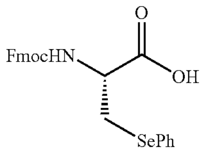

2

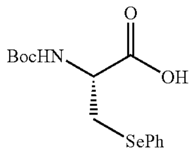

3

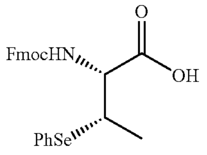

4

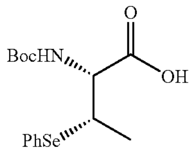

We have demonstrated that these Fmoc or Boc protected monomers can be conveniently incorporated into peptides using automated Solid Phase Peptide Synthesis (SPPS). A series of peptides were prepared to evaluate the compatibility of the oxidative elimination of the selenocysteine derivatives with unprotected side chains of the 20 physiological amino acids. These studies showed that with the exception of cysteine, all functionalities were unaffected by the conditions employed ($NaIO_4$ or $H_2O_2$ as the oxidant) (83). The phenylselenide moieties could also be oxidized chemoselectively in peptides containing methionine and tryptophan as long as the stoichiometry of the oxidant was controlled. Cysteines were also fully compatible when protected with either the bulky trityl group or as the tert-butyldisulfide. The latter group is readily removed with reductants whereas the trityl group can be conveniently converted into disulfides upon treatment with $I_2$. Furthermore, because of the stereospecific syn elimination of selenoxides, compounds 3 and 4 resulted exclusively in formation of the desired Z-Dhb (84). A route to compounds 1-4 is performed on a 25 g scale (85), thus compounds are prepared for precursors for our work on (antibiotics. Thus, our methodology to introduce Dha and Dhb residues into unprotected peptides is developed.

1b. Synthesis of Fluorinated Dehydropeptides

Synthesis of 2-Amino-3-fluoro-acrylic Acid Containing Peptides. Zhou, H.; van der Donk, W. A. *Org. Lett.* 2001, 3, 593-596.

Chemical and Enzymatic Synthesis of Fluorinated Dehydroalanine-Containing Peptides. Zhou, H.; Schmidt, D. M.; Gerlt, J. A.; van der Donk, W. A. *ChemBioChem* 2003, 1206-1215.

The Dha at position 5 of subtilin and nisin has been shown to be indispensable for the inhibition of spore outgrowth in *Bacillus* strains whereas it is not important for cytotoxicity towards stationary and exponential phase cultures, suggesting two different modes of biological activity (77, 78). We note that, although not the focus of our efforts, this inhibition of spore development may be valuable to prevent outgrowth of spores of *Bacillus anthracis*, the infective form of anthrax in past bioterrorist plots. Based on a series of experimental observations it has been suggested that during inhibition of spore development, subtilin becomes covalently linked to a Cys on its target(s) via nucleophilic addition to Dha5 (78, 79). We hypothesized that a fluorinated dehydroalanine at this position renders the lantibiotic more potent for two reasons. First, the dehydroalanine becomes more electrophilic and second, unlike nucleophilic addition to dehydroalanine, which is a reversible process, addition to a fluorinated dehydroalanine results in an irreversible vinyl linkage to the nucleophilic target following fluoride elimination from the enolate intermediate (Scheme 1).

Scheme 1

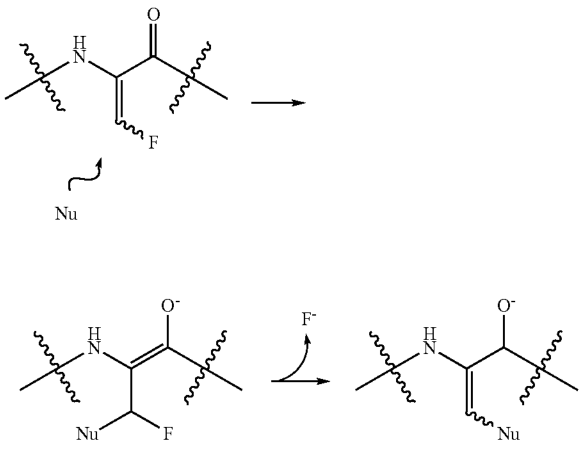

The route to fluorinated dehydroalanines in peptides constitutes a convenient means for preparation of these previously unknown structures (86). We have also shown that interaction of dehydrofluoroalanines with nucleophiles indeed leads to the anticipated rapid elimination of fluoride (86). In addition to this chemical route to fluorinated dehydroalanines, we also devised an enzymatic strategy (87). The protein YcjG catalyzes the epimerization at the alpha-carbon of the C-terminal amino acid in dipeptides (88). Since this process presumably involves an enolate intermediate, we prepared dipeptides containing a difluoroalanine at the C-terminus. Incubation of this peptide with YcjG resulted in the rapid elimination of fluoride as detected by $^{1}H$ and $^{19}F$ NMR spectroscopy as well as a fluoride electrode. The resulting fluorodehydroalanine containing dipeptide proved stable in aqueous solution and can be used as a building block for larger peptides. With two complementary routes to dehydrofluoroalanines, we install this functionality within lantibiotics.

2a. Overexpression and Purification of SpaC and NisC

SpaC and NisC, the Cyclases Involved in Subtilin and Nisin Biosynthesis, are Zinc Proteins. Okeley, N. M.; Paul, M.; Stasser J. P.; Blackburn, N.; van der Donk, W. A., *Biochemistry,* 2003, 42, 13613-13624

The spaC and nisC genes were amplified from genomic DNA of *B. subtilis* and *L. lactis*, respectively. SpaC was overexpressed in *E. coli* as the wild type enzyme, whereas NisC was expressed with an N-terminal $His_6$-tag. SpaC was purified using a three-step protocol and NisC was purified by $Ni^{2+}$-NTA affinity chromatography. Purified SpaC was used to produce both polyclonal and monoclonal antibodies for in vivo localization studies (vide infra). Inductively coupled plasma mass spectrometric (ICP-MS) analysis for the presence of metal ions revealed one equivalent of zinc bound to both SpaC and NisC (89). These findings were corroborated by titration with the metallochromic indicator PAR, which confirmed the presence of 1 equiv. of a divalent metal ion. The metal is released from the protein under denaturing conditions in the presence of DTNB. Alternatively, treatment with methyl methanethiosulfonate (MMTS) or p-hydroxymercuribenzoic acid (HMBA) can release the metal under native conditions. In this case, the protein could be reconstituted with 1 equiv. of zinc. These findings suggest that the metal may be coordinated by cysteine(s). Although the homolog EpiC has been expressed and purified in a previous report (5), no metal analysis was performed. A limited sequence alignment of several LanC proteins obtained from a BLAST search shows only three regions of high homology. These regions include four potential metal ligands, Cys284, Cys330, His212, and His331 (FIG. 12).

If these residues are coordinating the zinc, then its coordination sphere is reminiscent of the zinc sites found in methionine synthase (90, 91) and farnesyl transferase (92-95). These proteins are members of a growing class of metalloproteins that contain a zinc ion surrounded by 3-4 negatively charged ligands, usually including at least two cysteines (96-99). This results in a net negatively charged zinc site that activates a thiol towards alkylation (100). Inspection of the reaction catalyzed by the LanC enzymes reveals a similar possible role for Zn. In farnesyl transferase and methionine synthase the thiol substrate (a cysteine in a peptide and homocysteine, respectively) has been shown to bind to the zinc reducing the $pK_a$ of the thiol (91, 95, 101-103). Similarly, the cysteine residues in the structural region of the lantibiotic prepeptides may coordinate to the metal for activation towards Michael addition. We proposed that both conserved cysteine residues as well as one of the two conserved histidine residues serve as zinc ligands and that the second conserved His functions as a general acid/base that deprotonates the thiol of the substrate or stereospecifically protonates the enolate formed during catalysis (Scheme 2).

Scheme 2

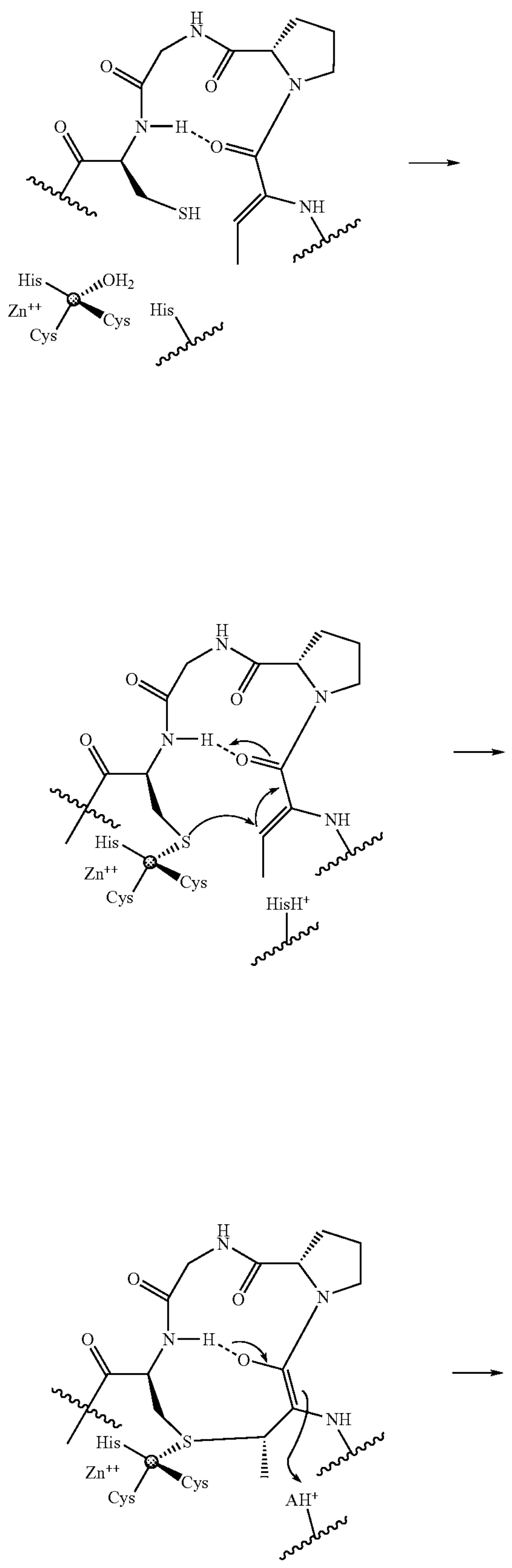

-continued

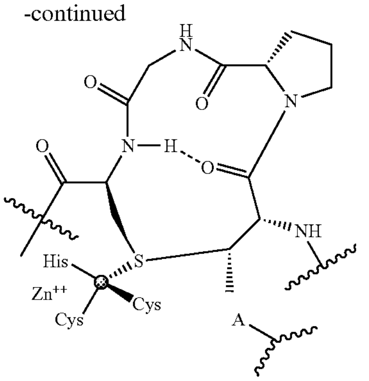

It should be noted that the His cannot function as both the active site acid and base since the observed stereochemistry of the Michael addition precludes this. Water would provide the fourth metal ligand in the resting state of the enzyme as is found in the vast majority of metalloproteins in which the zinc fulfills a catalytic role (104, 105). In collaboration with Dr. Ninian Blackburn at the Oregon Graduate Institute, EXAFS studies on SpaC and SpaC mutants in which the putative Cys ligands were replaced by Ala unambiguously corroborated that two sulfurs and two nitrogen/oxygen ligands were bound to the Zn-site. Note that EXAFS typically cannot distinguish between N/O donors (89). Our characterization of SpaC and NisC as zinc metalloproteins thus provides the first experimentally testable clues as to how the dehydrated substrate is activated towards intramolecular nucleophilic addition.

Interestingly, in the past four years, several reports have shown that mammalian erythrocytes from human and mouse contain proteins with high homology to the LanC proteins (106-109). These proteins, the function of which is currently unknown, have been designated the generic name LANCL for LanC-like proteins (110). LANCL1 (a P40 seven-transmembrane-domain protein) and LANCL2 (testes-specific adriamycin sensitivity protein) are thought to be peptide-modifying enzymes and are expressed in large quantities in the brain and testes where they may have a role in the immune surveillance of these organs. Given the conserved putative metal binding residues, these proteins can be involved in alkylation of thiol substrates.

2b. Biomimetic Cyclization to Form Lanthionines and Methyllanthionines

Facile Chemoselective Synthesis of Dehydroalanine-Containing Peptides. Okeley, N. M.; Zhu, Y.; van der Donk, W. A. *Org. Lett.* 2000, 2, 3603-3606

Biomimetic Stereoselective Formation of Methyllanthionine. Zhou, H.; van der Donk, W. A. *Org. Lett.* 2002, 4, 1335-1338

Biomimetic studies on the mechanism of stereoselective lanthionine formation. Zhu, Y.; Gieselman, M.; Zhou, H.; Averin, O.; van der Donk, W. A. 2003, *Org. Biomol. Chem.* 2003, 1, 3304-3315.

Our methodology to introduce dehydroalanines into peptides described above provided the opportunity to investigate the intrinsic stereoselectivity of lanthionine and methyllanthionine formation. These studies focused on the formation of the B- and E-rings of nisin and subtilin. We showed that these biomimetic cyclizations exclusively produce the D-configuration at the newly formed stereogenic centers of both lanthionine and methyllanthionine, i.e. the same diastereomers are formed as found in the natural products (83, 84). Furthermore, these reactions also exclusively gave the correct stereochemistry at the β-carbon of methyllanthionine (84) (Scheme 3B).

Scheme 3

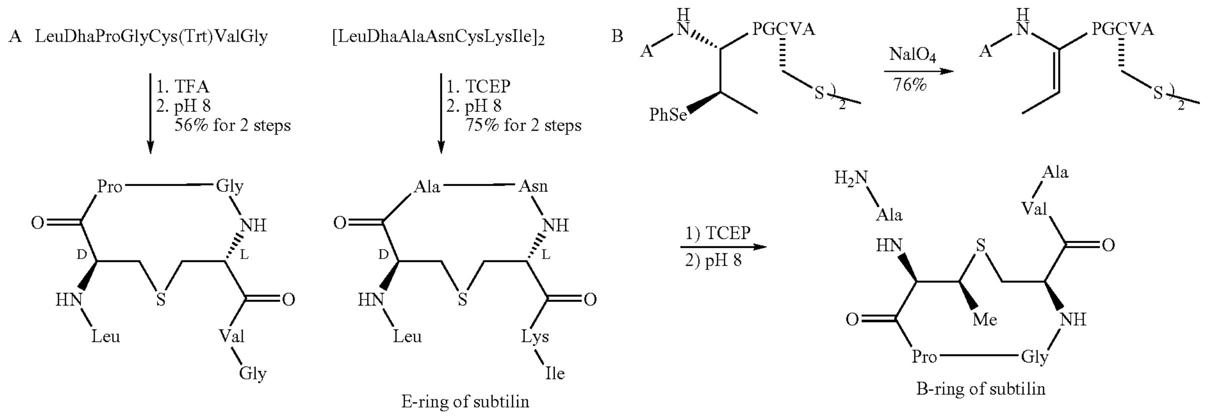

The LanC enzymes do not need to significantly restrict the conformational freedom of the peptide as it already has a natural propensity for the observed product. This is an important point since the LanC proteins have to catalyze the formation of rings of widely different sizes ranging from 4 amino acids (lanthionines B & E, FIG. 10) to a 7 amino acid ring C. It is unlikely that one active site would be able to assure the correct orientation of the peptide backbone for such diverse rings, especially since the backbone changes dramatically with every new ring formed.

Thus, our working model invokes a zinc site that activates the thiol for alkylation and that the intrinsic conformational preference of the peptides together with general acid catalysis by one of the conserved active site histidines assures specific formation of the observed stereocenters. Importantly, a synthetic dehydropeptide precursor to both the A- and B-rings of nisin did not produce the structure found in nisin when subjected to biomimetic cyclization (111). Instead of one Ln and one MeLn, two Ln rings were formed, showing the importance of the biosynthetic enzymes to control the regiochemistry of cyclization.

2c. Overexpression and Purification of SpaB

Heterologous expression and purification of SpaB (SEQ ID NO:82) involved in subtilin biosynthesis. Xie, L.; Chatterjee, C.; Balsara, R.; Okeley, N. M.; van der Donk, W. A. *Biochem. Biophys. Res. Commun.* 2002, 295, 952-7. (Appendix)

The spaB (SEQ ID NO:107) and nisB (SEQ ID NO:108) genes were amplified by PCR from genomic DNA. Initial attempts to heterologously overexpress these 120 kDa proteins in *E. coli* resulted in the recovery of the enzymes in inclusion bodies regardless of the growth conditions and induction protocol. These problems were overcome by the co-expression of the GroEL/ES molecular chaperones, which effected an enormous improvement in the solubility of the SpaB protein (112). His$_6$-SpaB was partially purified (~85% purity) by NTA-Ni$^{2+}$-affinity chromatography. Antibodies generated against the purified protein recognized the wild-type protein in Western blot analysis of subtilin producing *B. subtilis* cells. Localization experiments using Western blot analysis of *B. subtilis* ATCC 6633 showed that the native protein co-localizes with the membrane fraction albeit only loosely (112). This is consistent with the absence of transmembrane segments in the amino acid sequence and with the proposed structure of a membrane associated lantibiotic synthetase complex. Interaction of SpaB and SpaC was observed in co-immunoprecipitation experiments in which purified His$_6$-SpaB was added to cell extracts of subtilin producing cells and precipitated with anti-His-tag antibodies. Western blot analysis with anti-SpaC antibodies revealed coprecipitation of SpaC showing that the heterologously expressed SpaB binds to endogenous SpaC.

Overexpression and Purification of SpaS and Activity Assays with SpaB/SpaC

To assess the activity of the biosynthetic enzymes for subtilin, the 56-amino acid prepeptide SpaS was expressed as a C-terminal intein-chitin binding domain (CBD) fusion. Cleavage from the intein followed by HPLC purification gave the pure peptide. Unfortunately, despite great effort, to date we have been unable to detect any dehydratase activity in a series of assays with SpaB and SpaC. Similar observations have been reported by other laboratories investigating NisB, SpaB, EpiB, and EpiC (1-5). In these studies, both heterologous and homologous expression was performed but in all cases no dehydration activity could be reconstituted. Similarly, cell free extracts of a variety of lantibiotic-producing strains have failed to provide any detectable dehydration activity. It is therefore of great significance that we have been able to achieve in vitro activity in a different system as described in the following section.

3. First In Vitro Reconstitution of Lantibiotic Biosynthesis.

Figure 14:
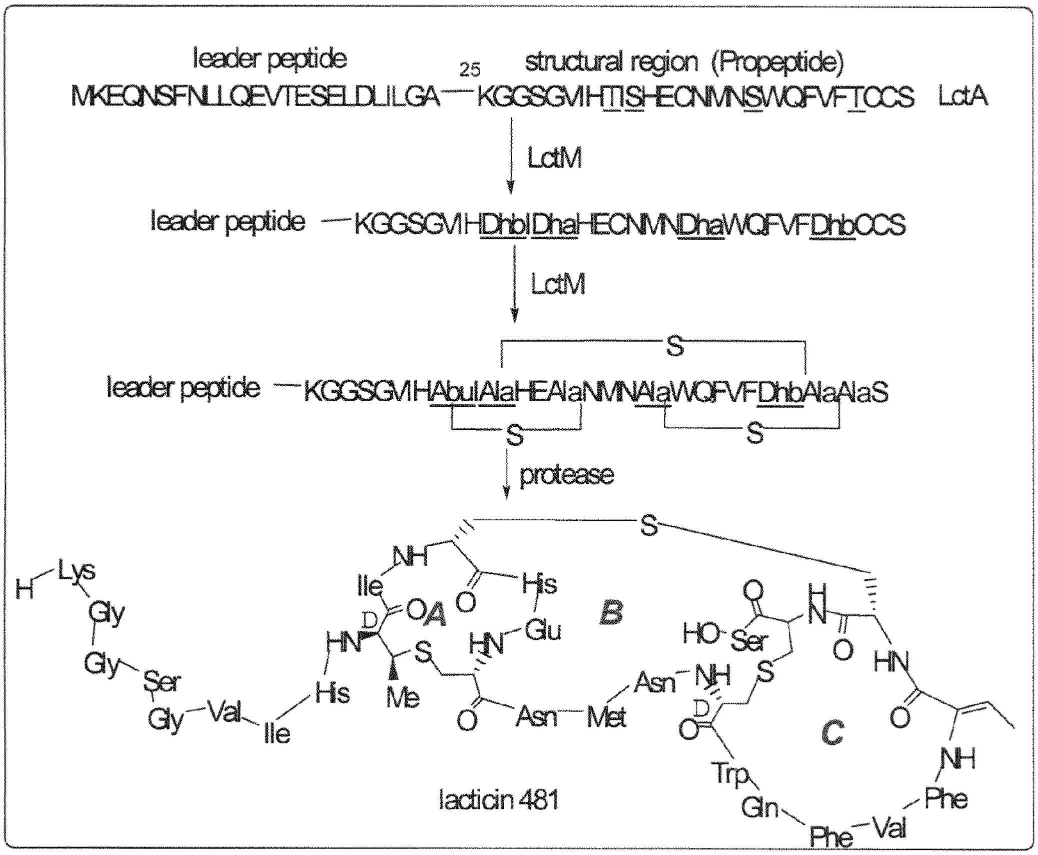
FIG. 14 illustrates steps to the mature lacticin 481 product (SEQ ID NO:110) from LctA (SEQ ID NO:3).
Figure 15:
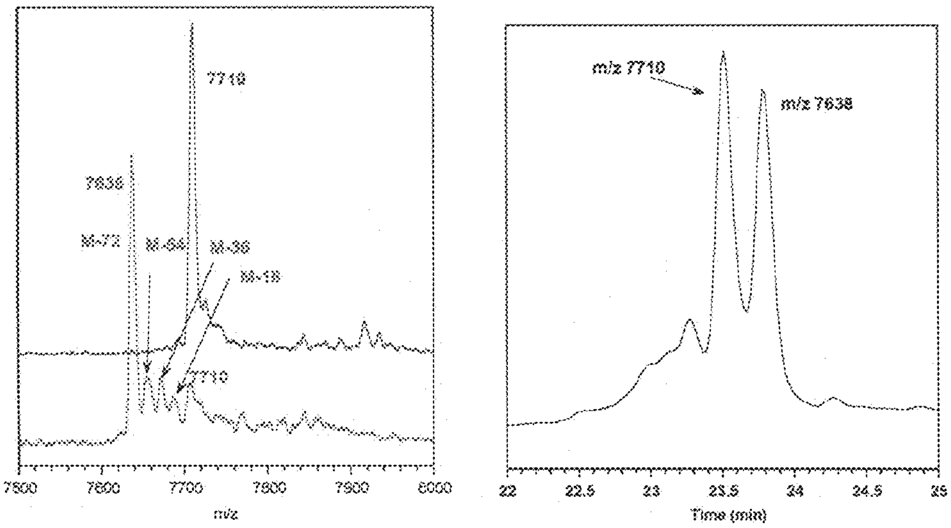
FIG. 15 illustrates MALDI-MS and HPLC data from analysis of His-LctA substrate (SEQ ID NO:4) and products.

In some lantibiotic producing organisms, the lanBC genes are absent (113-120) and a single different gene, lanM, is present instead (9, 121, 122). The LanM proteins have been postulated to carry out both dehydration and cyclization steps. The gene clusters of some of these lantibiotics have been sequenced in recent years. They include mersacidin (120), mutacin II (114, 123), lacticin 481 (58, 67, 113), and the two component antibiotic lacticin 3147 (124). At present, these lantibiotics, designated class AII, have not received the same type of attention as the class AI compounds (including nisin & subtilin). Given our disappointing results with the LanB and LanC enzymes, we proposed in the first submission of this grant renewal that we would change our focus to this class of enzymes. The LanM proteins represent a much better target for in vitro reconstitution of the lantibiotic biosynthetic activity since any complications of protein-protein interactions are simplified. With both post-translational modification reactions combined in one protein, the potential instability of a multi-enzyme complex is eliminated. Hence we obtained a *L. lactis* strain that produces lacticin 481. A BLAST search and subsequent alignment of the LanM proteins showed that they do not share any homology with the LanB proteins nor with any other known proteins. However, at their C-termini they display sequence homology with the LanC proteins including the three putative zinc ligands and the putative active site acid/base histidine (see FIG. 13 for a partial alignment). Analysis of the amino acid sequences indicates that the proteins are overall hydrophilic and that no motifs are present that are found in the Conserved Domain Database at the NCBI. Their average molecular weight is about 105 kDa. The mature lacticin 481 product contains 1 methyllanthionine, 2 lanthionines, and 1 Dhb (FIG. 14). Interestingly, several serines in the structural region are not dehydrated resulting in just four dehydrations and three cyclic thioethers. We cloned lctM and lctA and placed the genes in pET expression vectors. Two variants of LctA were designed, one with an N-terminal His-tag ($His_6$-LctA) and one with a His-tag at the C-terminus (LctA-$His_6$). The constructs also introduce short linkers between the His-tag and the termini of LctA. LctA and LctM were expressed and purified to homogeneity in high yield by IMAC. LctM was incubated with $His_6$-LctA under a variety of conditions producing a new peptide that showed a loss of 72 amu. In other words, four water molecules were eliminated from the parent peptide (FIG. 15). The activity absolutely required exogenous ATP, and $Mg^{2+}$. In addition to the peptide exhibiting loss of 4 water molecules, three other small product peaks are observed that correspond to M-18, M-36, and M-54 (FIG. 15). Incubation of LctM with LctA-$His_6$ also resulted in partial formation of the product of M-72 amu in addition to a larger fraction of incompletely dehydrated peptides (not shown). The observation of intermediates is a very exciting development as it may aid in deducing the processivity of lantibiotic formation (see Experimental Design Section).

The loss of just 4 water molecules from a precursor that contains 6 Ser and 3 Thr in the prepeptide in addition to 5 more serines introduced by the His-tag linker strongly indicates that the product structure is the native lacticin.

Figure 16:
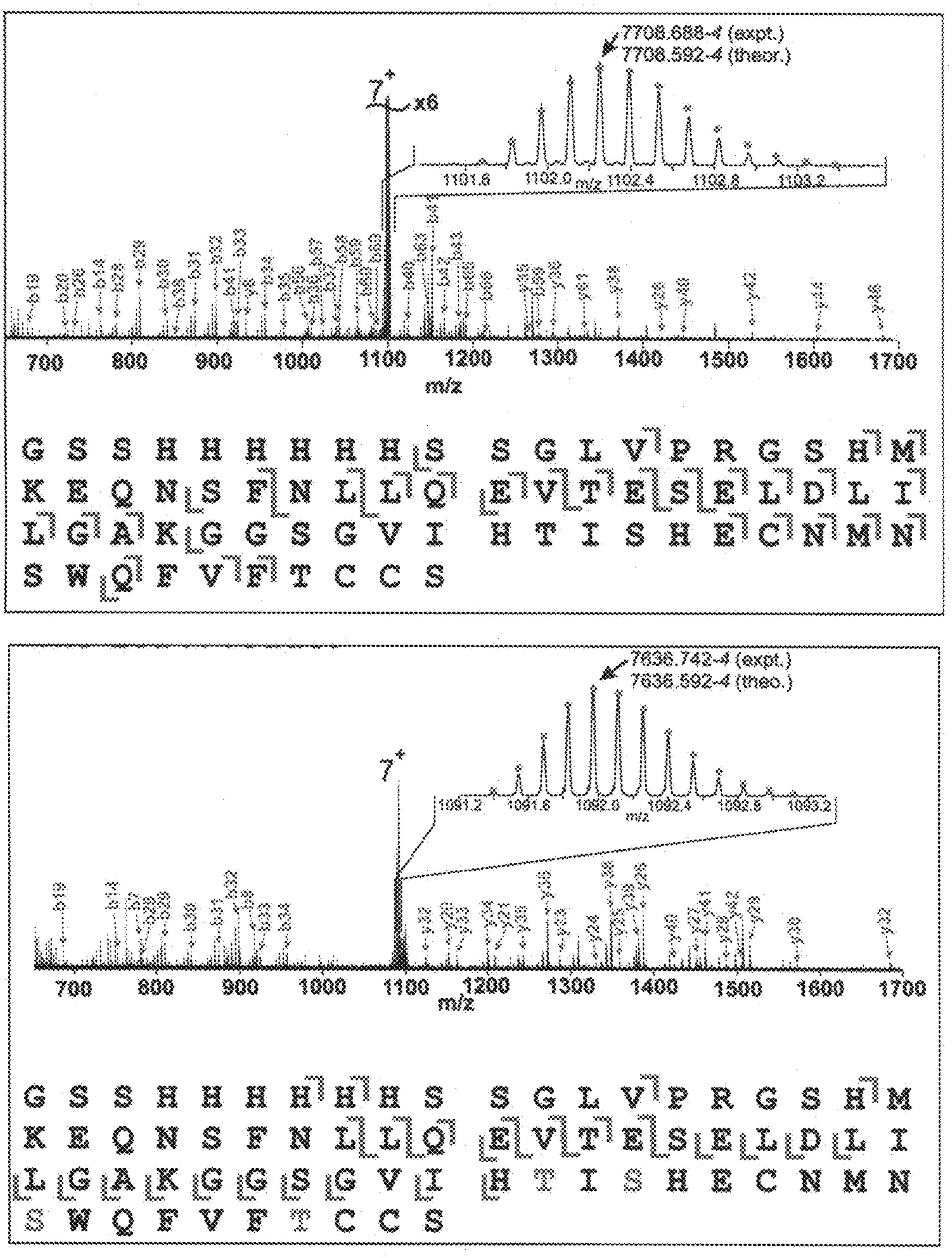
FIG. 16 illustrates FT-MS/MS of the substrate His-LctA (SEQ ID NO:4) (left/top) and the peptide of m/z 7636 (right/bottom). Residues that are dehydrated in lacticin (SEQ ID NO:110) are indicated in red. The fragments observed are indicated in blue. Roepstorff notation is used (b & y-ions) (154).
Figure 20:
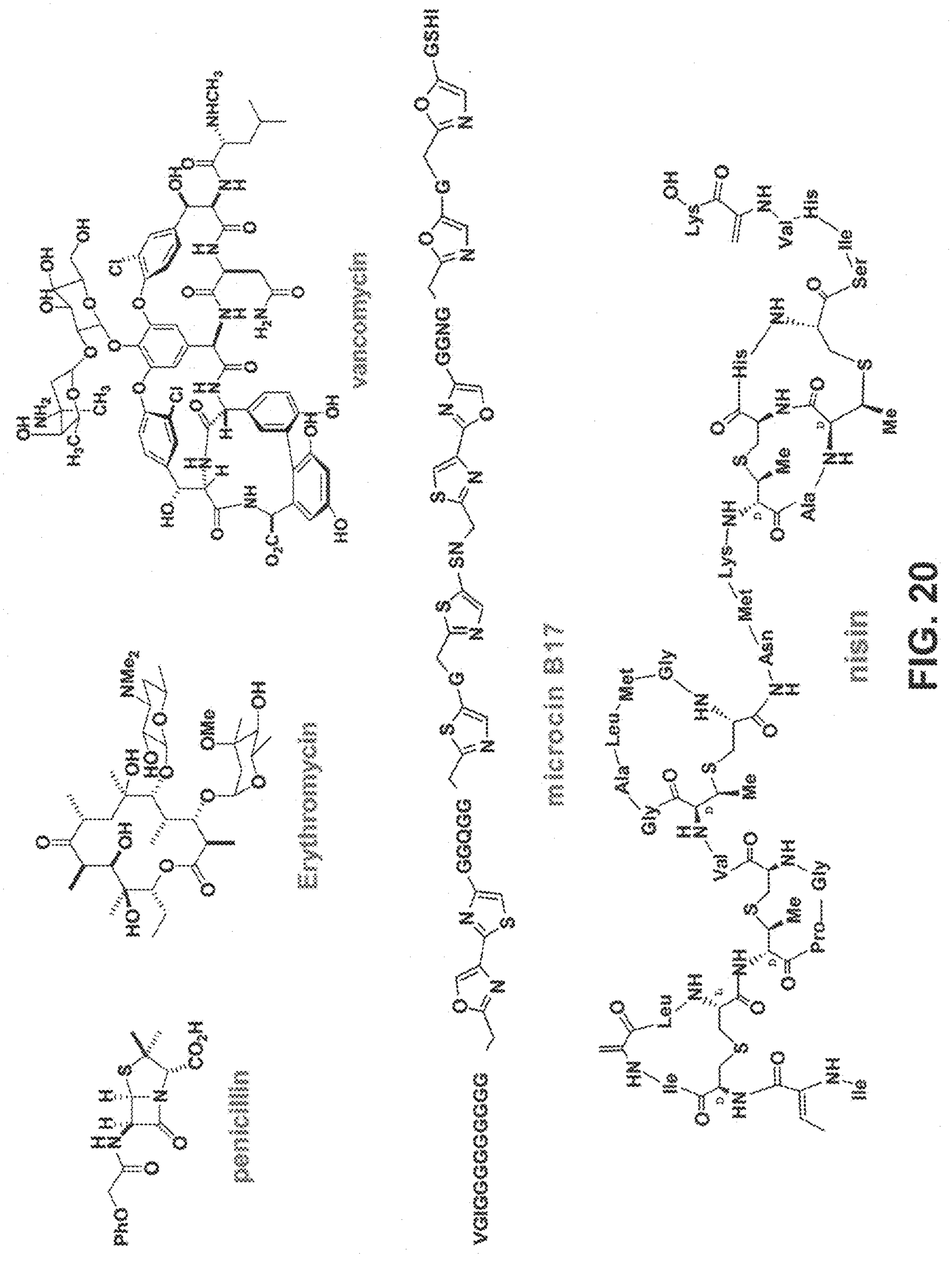
FIG. 20 illustrates structures of antibiotic compounds: penicillin, erythromycin, vancomycin, microcin, and nisin (SEQ ID NO:81).
Figure 21:
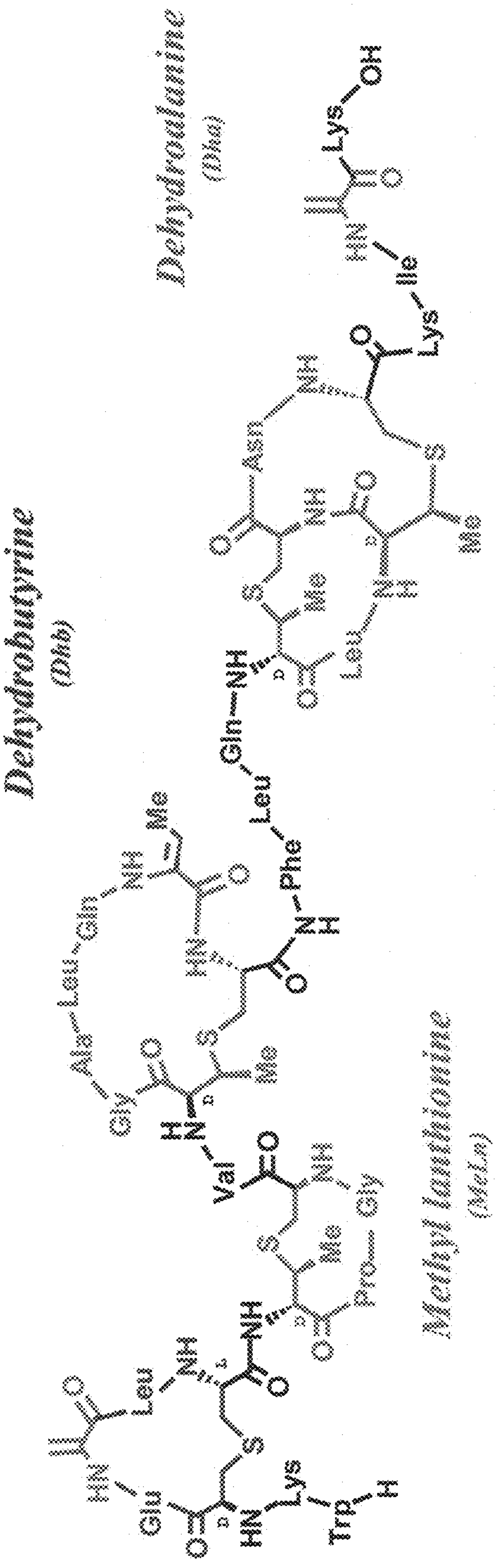
FIG. 21 illustrates subtilin (SEQ ID NO:82) produced by *Bacillus subtilis* ATCC 6633 and structurally closely related to nisin (about 63% sequence identity).
Figure 22:
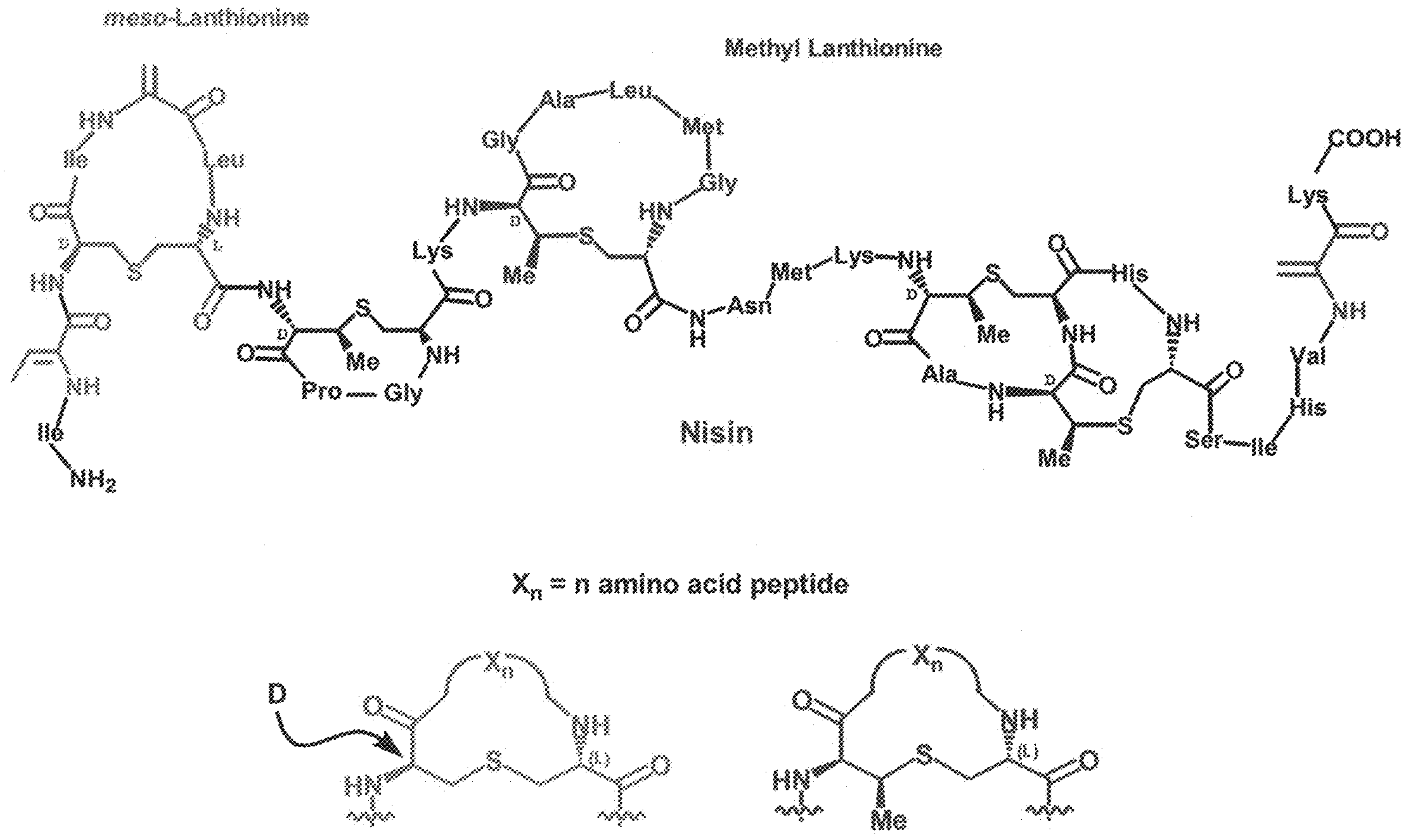
FIG. 22 illustrates post-translational modifications in lantibiotics such as nisin (precursor sequence in SEQ ID NO:81).
Figure 23:
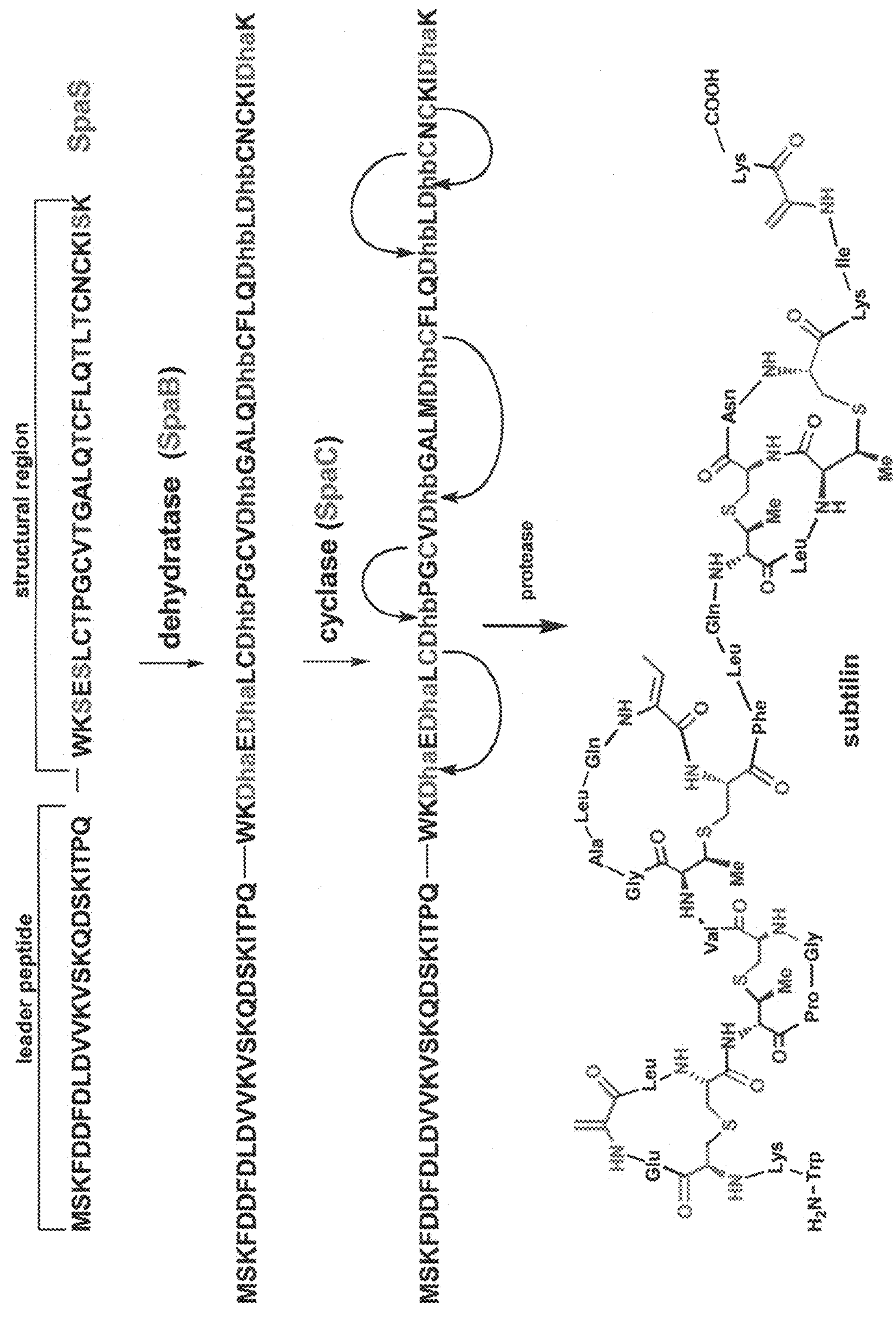
FIG. 23 illustrates steps in subtilin biosynthesis, with dehydration of SEQ ID NO:67 to give intermediate product SEQ ID NO:82.
Figure 24:
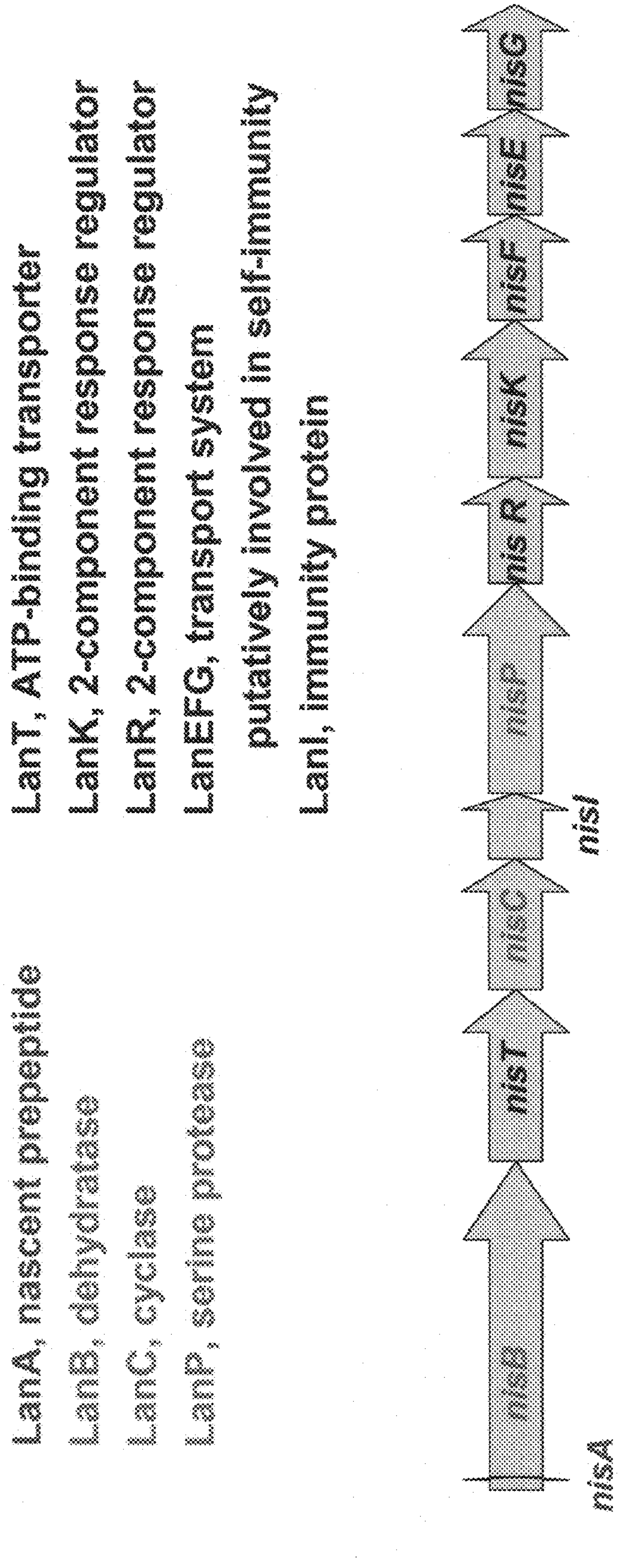
FIG. 24 illustrates examples of gene clusters of biosynthetic enzymes.
Figure 25:
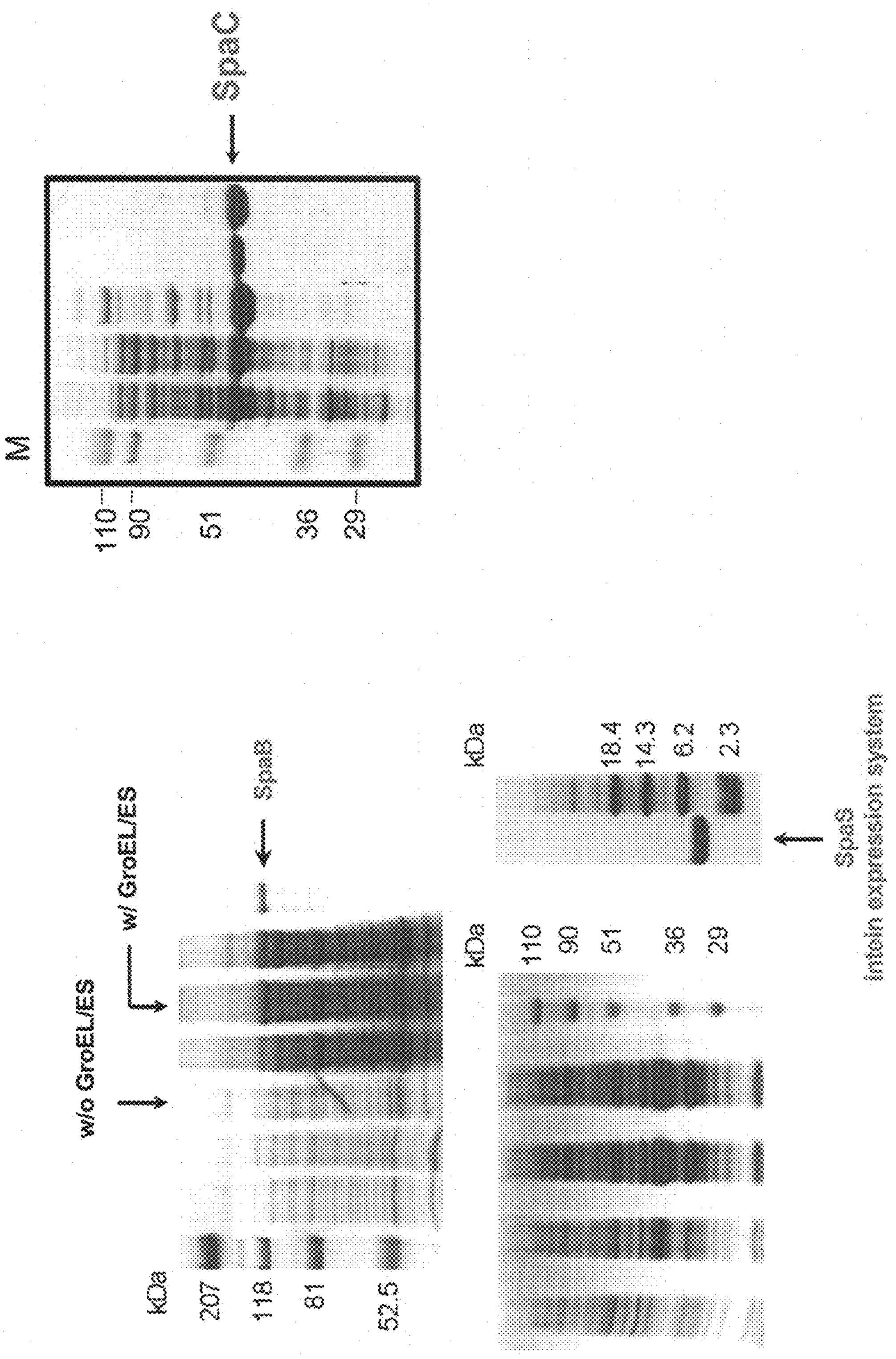
FIG. 25 illustrates aspects of expression and purification of proteins involved in subtilin biosynthesis.
Figure 26:
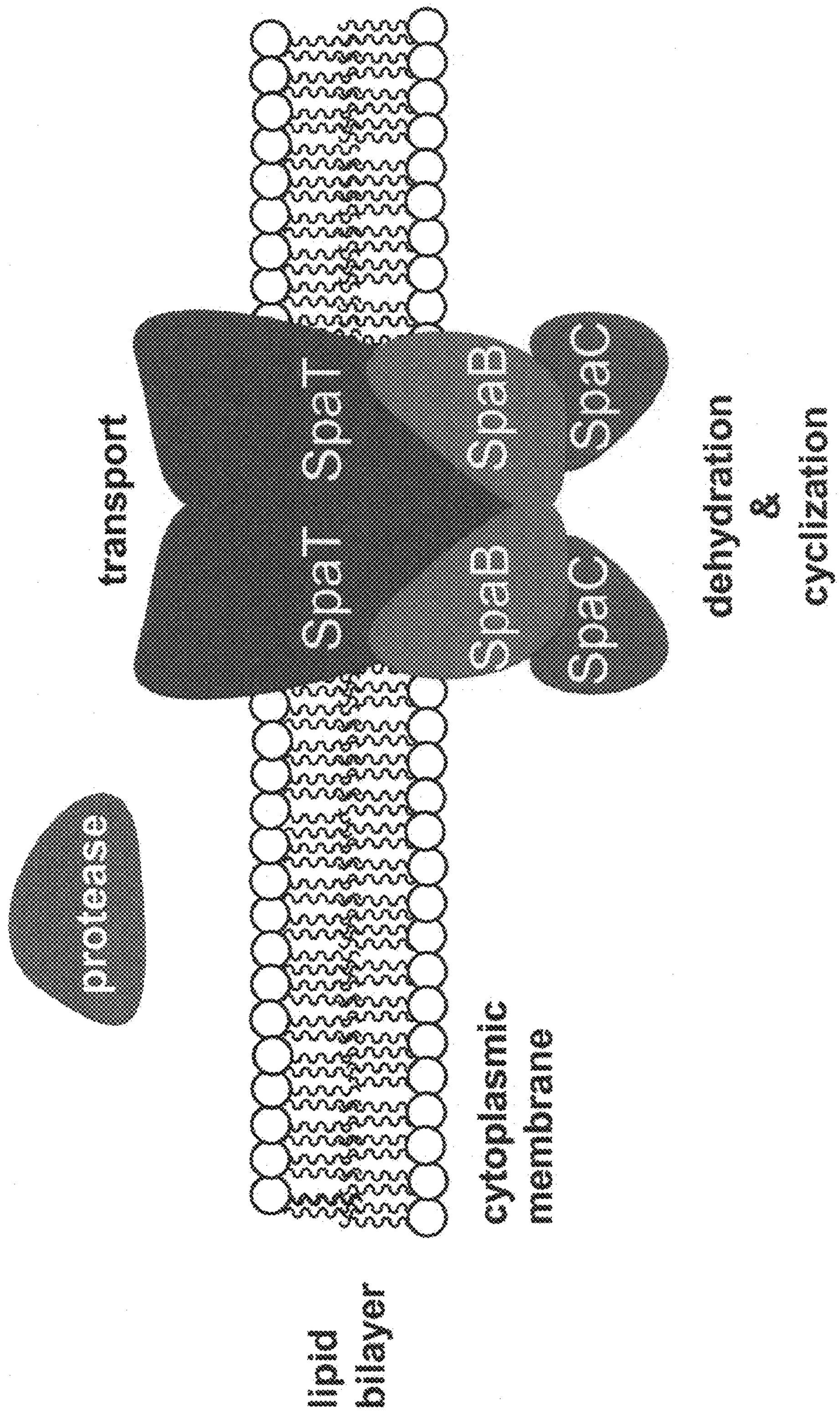
FIG. 26 illustrates the organization of a multi-enzyme complex.
Figure 28:
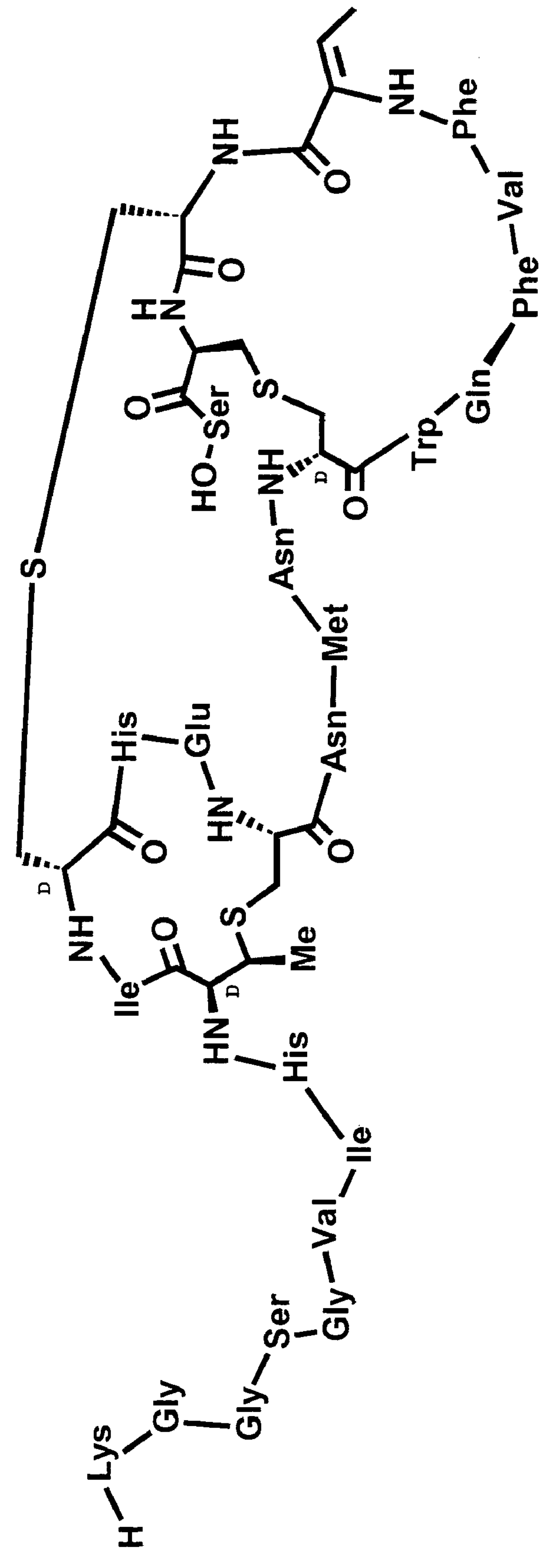
FIG. 28 illustrates lacticin 481 produced by *Lactococcus lactis* CNRZ 481. The molecule has a globular C-terminus and linear N-terminus. This compound has potential uses including use in cheese starter cultures.
Figure 29:
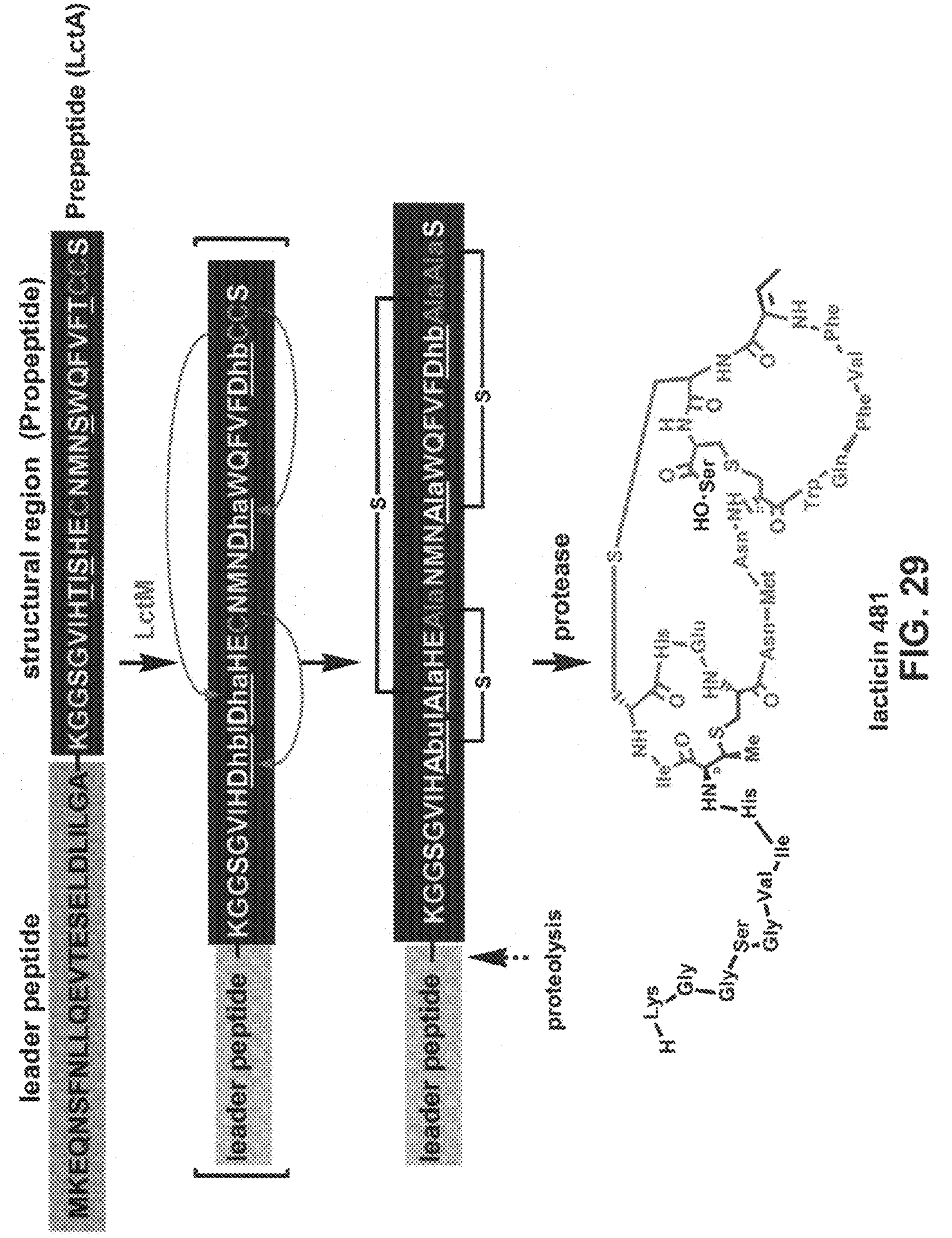
FIG. 29 illustrates the biosynthesis of Lacticin 481, starting from prepeptide LctA (SEQ ID NO:3). The dehydratase intermediate product has the sequence set forth in SEQ ID NO:110.
Figure 30:
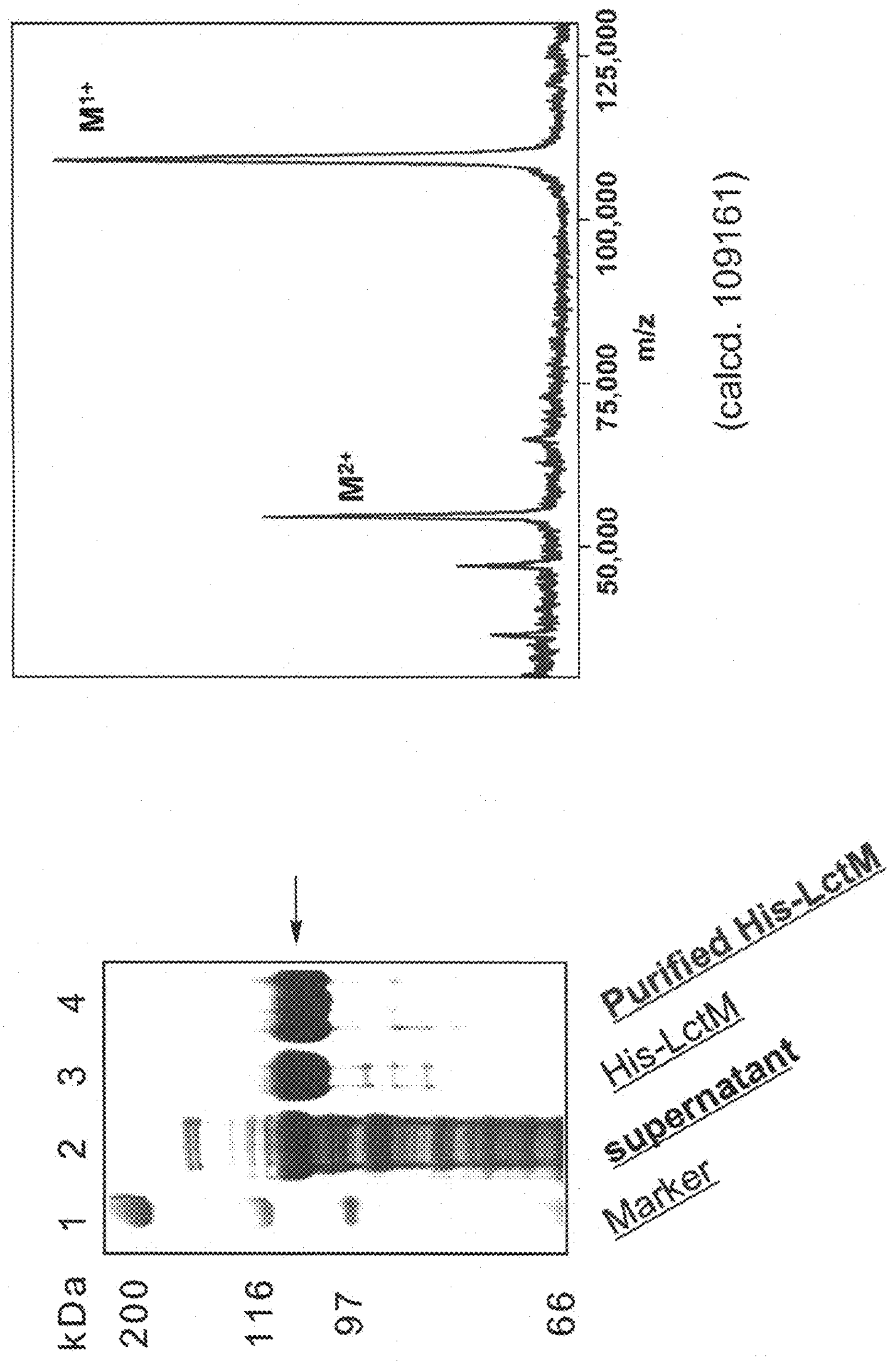
FIG. 30 illustrates purification of LctM, about 106 kDa, cloned and overexpressed as a His-tagged protein.
Figure 31:
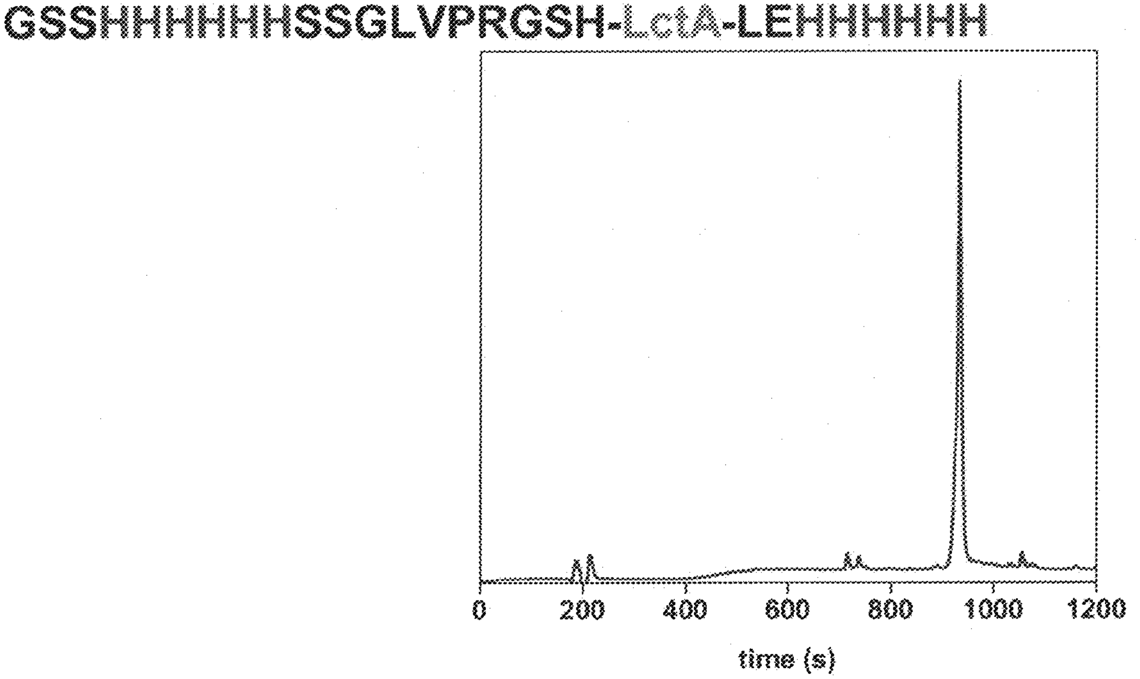
FIG. 31 illustrates permutations of His-tagged LctA (LctA, SEQ ID NO:3; His-LctA, SEQ ID NO:4). The material was expressed as inclusion bodies, resolubilized under denaturing conditions, and HPLC purified. The C-terminal His tag has the sequence set forth in SEQ ID NO:116 and the N-terminal sequence has the sequence set forth in SEQ ID NO:117. The doubly His tagged LctA has the N-terminal His tag sequence of SEQ ID NO:117 and the C-terminal His tag of SEQ ID NO:116.
Figure 32:
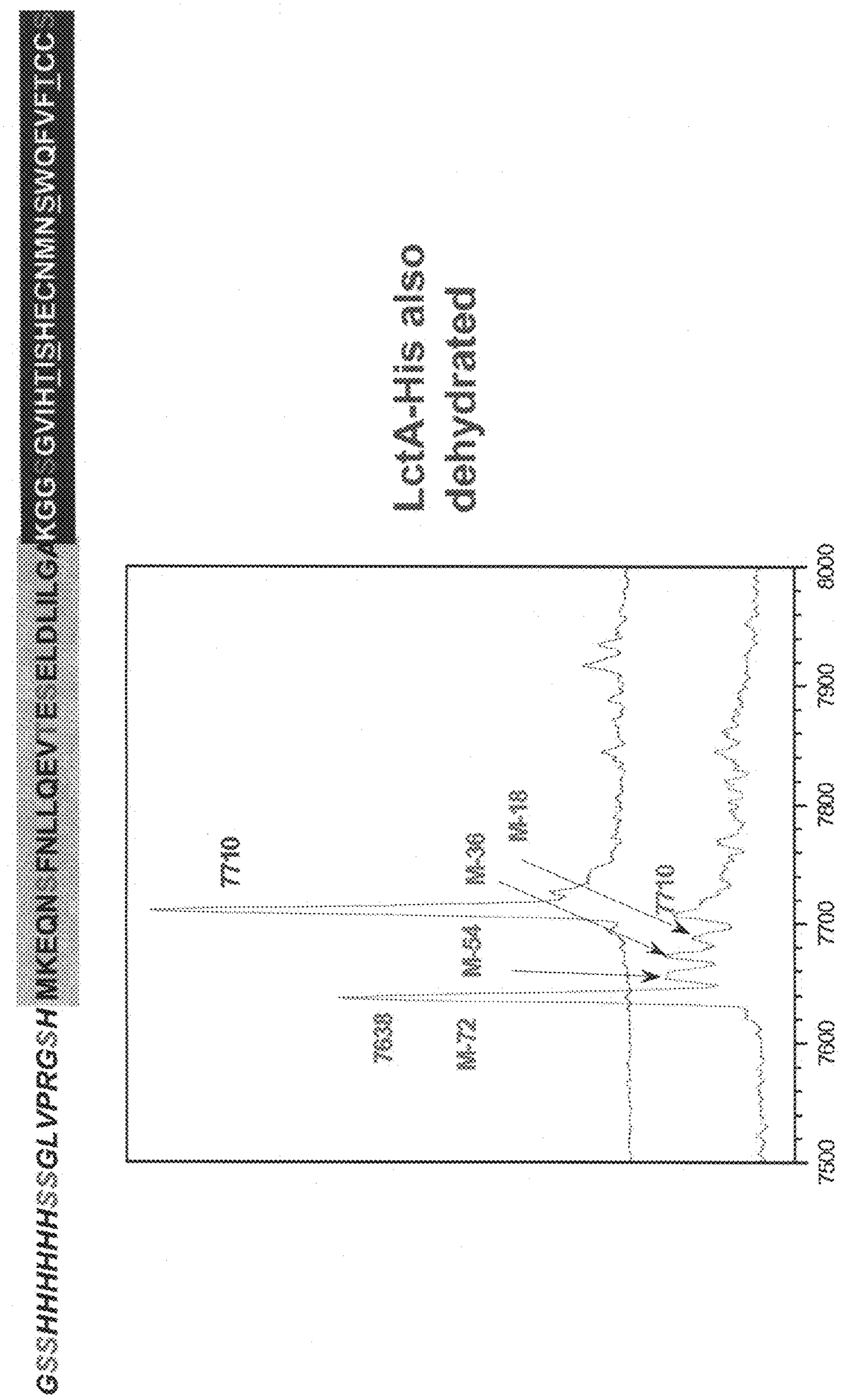
FIG. 32 illustrates an example of an LctA-LctM assay. The conditions involve 5 mM $MgCl_2$, 5 mM DTT, 0.5 mM ATP, pH 7.5, 0.7 μM $Zn^{2+}$ for the assay. $His_6$-LctA-His, SEQ ID NO:4. The results of analysis by mass spectrometry are shown.
Figure 33:
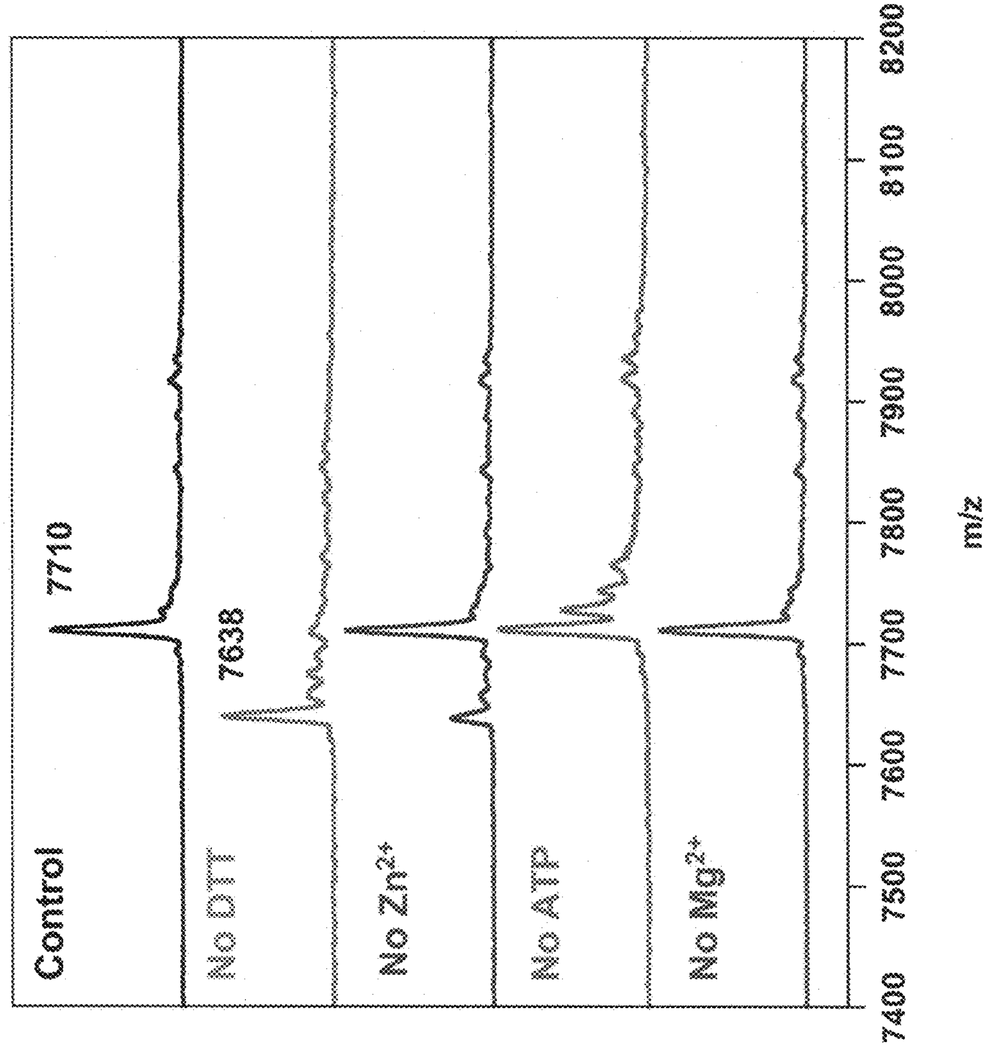
FIG. 33 illustrates testing for identification of required cofactors, indicating that $Mg^{2+}$ and ATP are required cofactors.
Figure 34:
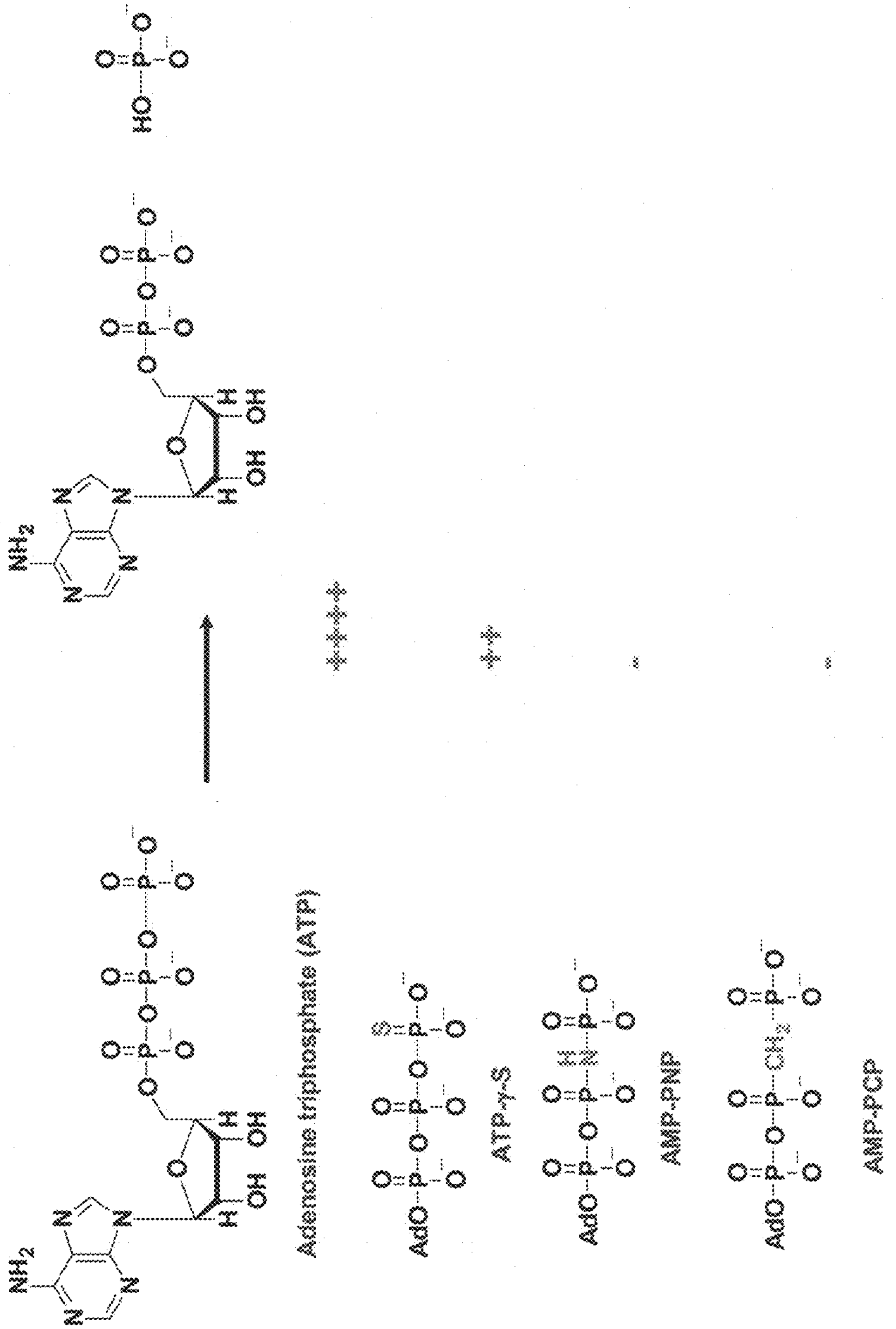
FIG. 34 illustrates results of assays with ATP analogs.
Figure 36:
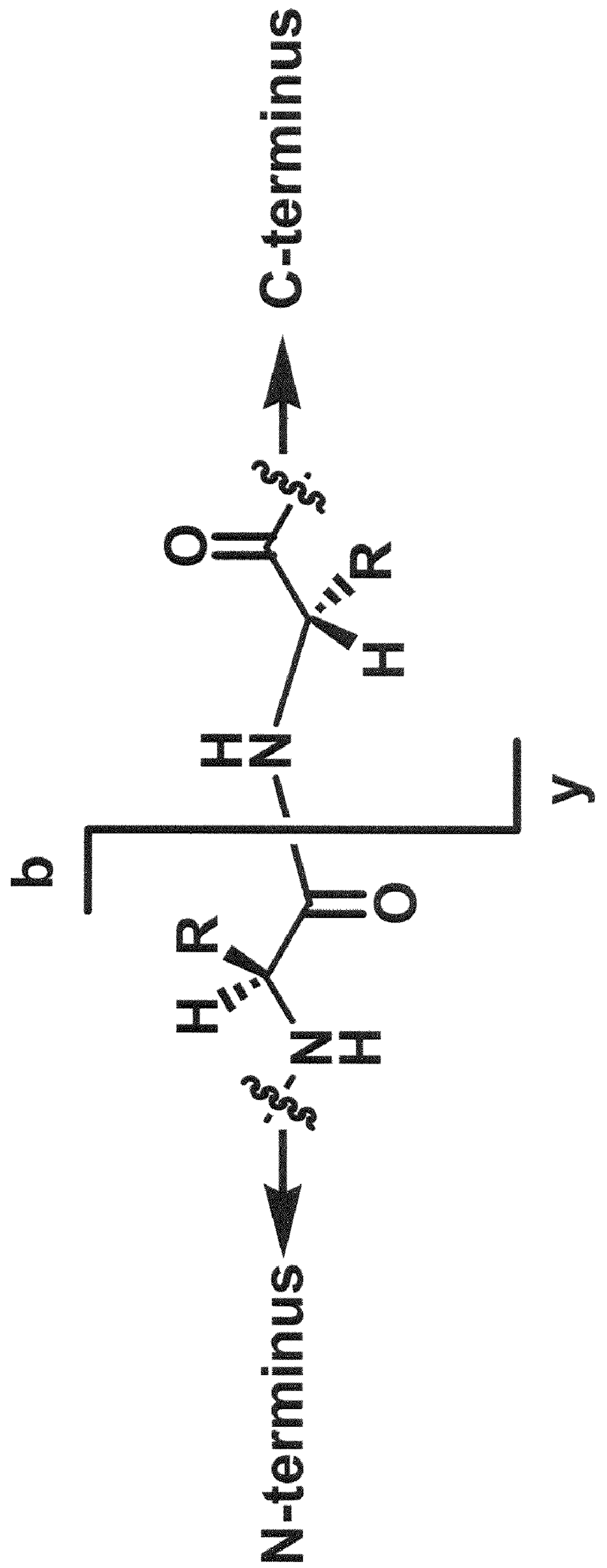
FIG. 36 illustrates a peptide molecule for mass spectrometry analysis, indicating an N-terminus and C-terminus.
Figure 37:
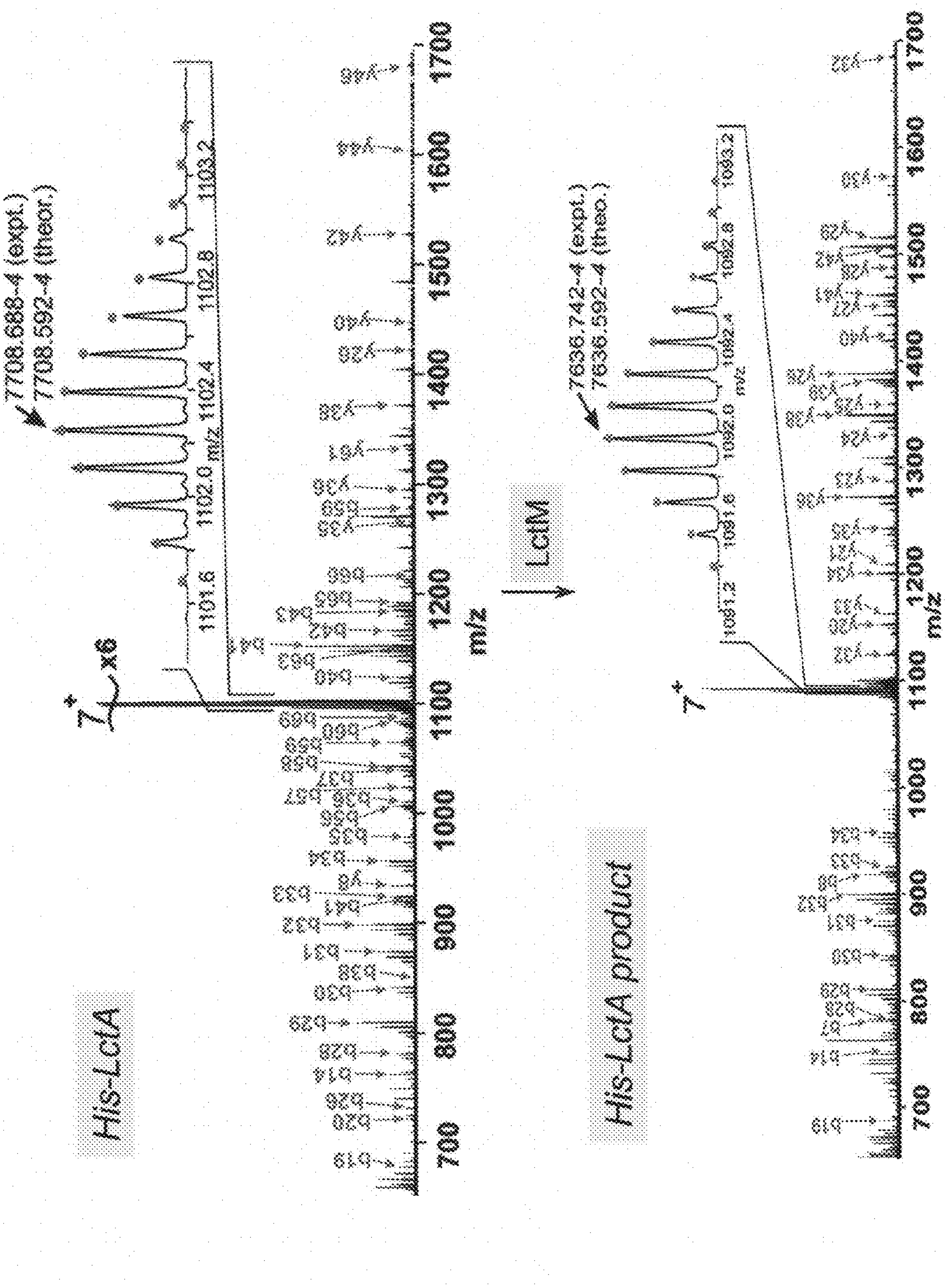
FIG. 37 illustrates data from FT-MS/MS analysis of an assay starting peptide and the product for His-LctA (SEQ ID NO:4).
Figure 38:
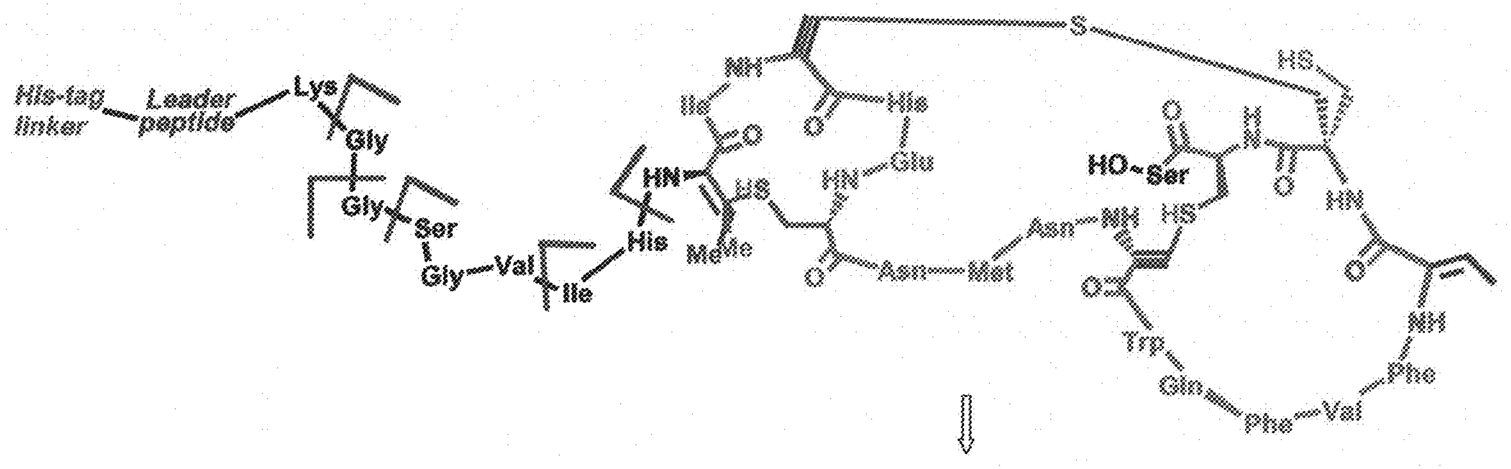
FIG. 38 illustrates MS/MS analysis of an His-LctA (SEQ ID NO:4) LctM assay. LctM is a bifunctional enzyme, performing both dehydration and cyclization reactions.
Figure 39:
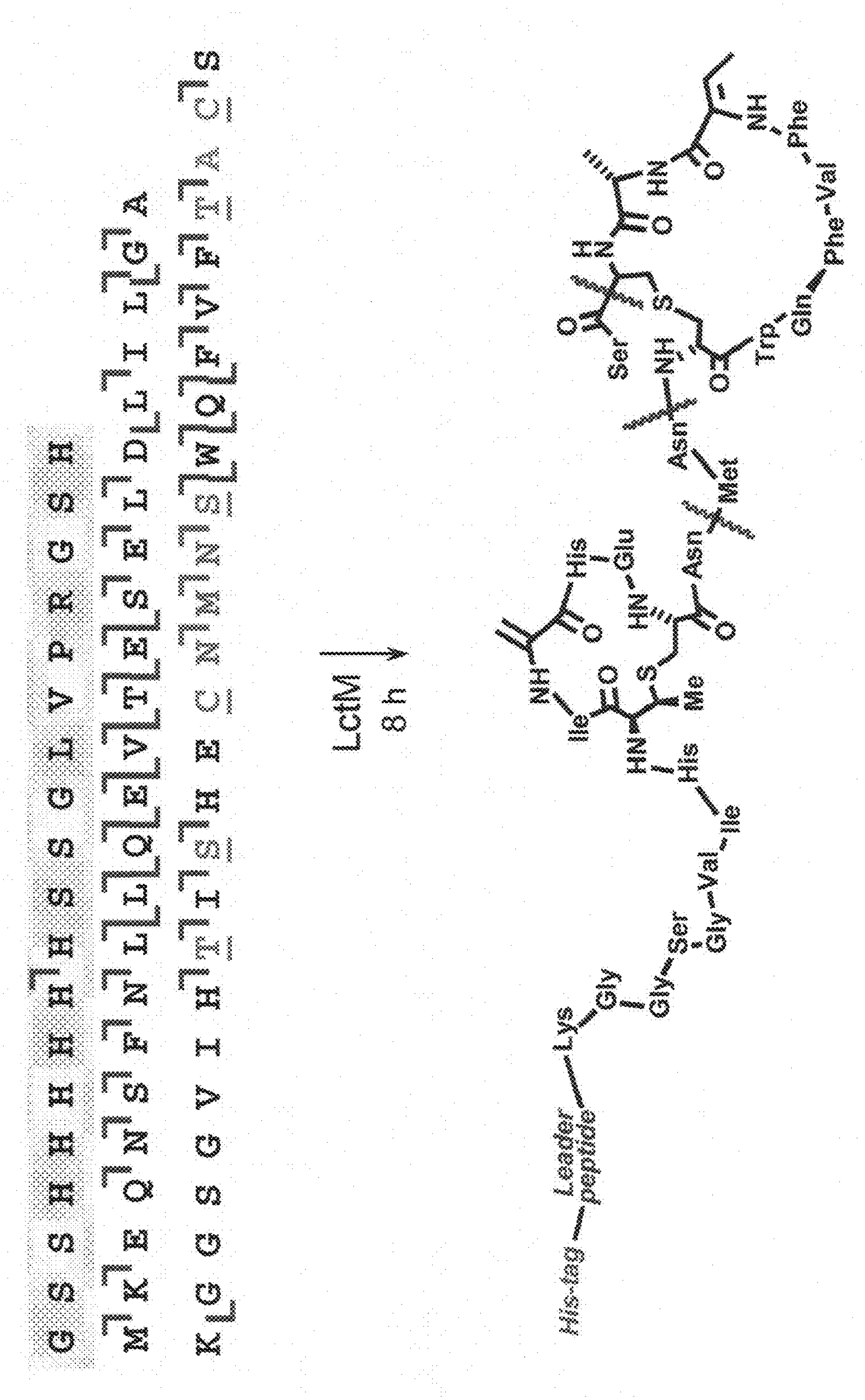
FIG. 39 illustrates MS/MS analysis of an assay product with His-LctA-C49A (SEQ ID NO:13).
Figure 41:
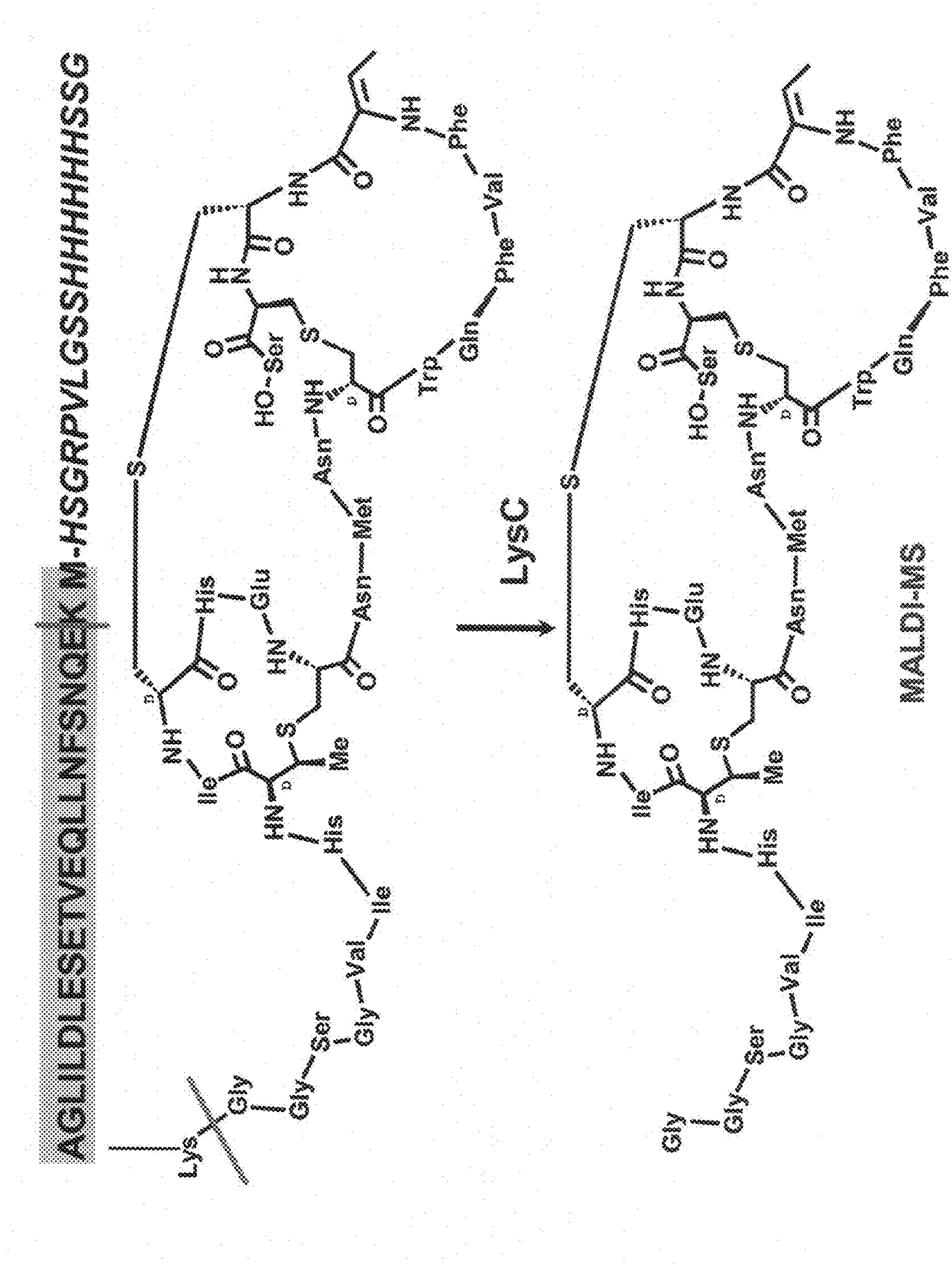
FIG. 41 illustrates the generation of Delta1-lacticin 481 from LctA (SEQ ID NO:4, with amino acids 1-443 shown in the C-terminal to N-terminal direction.
Figure 42:
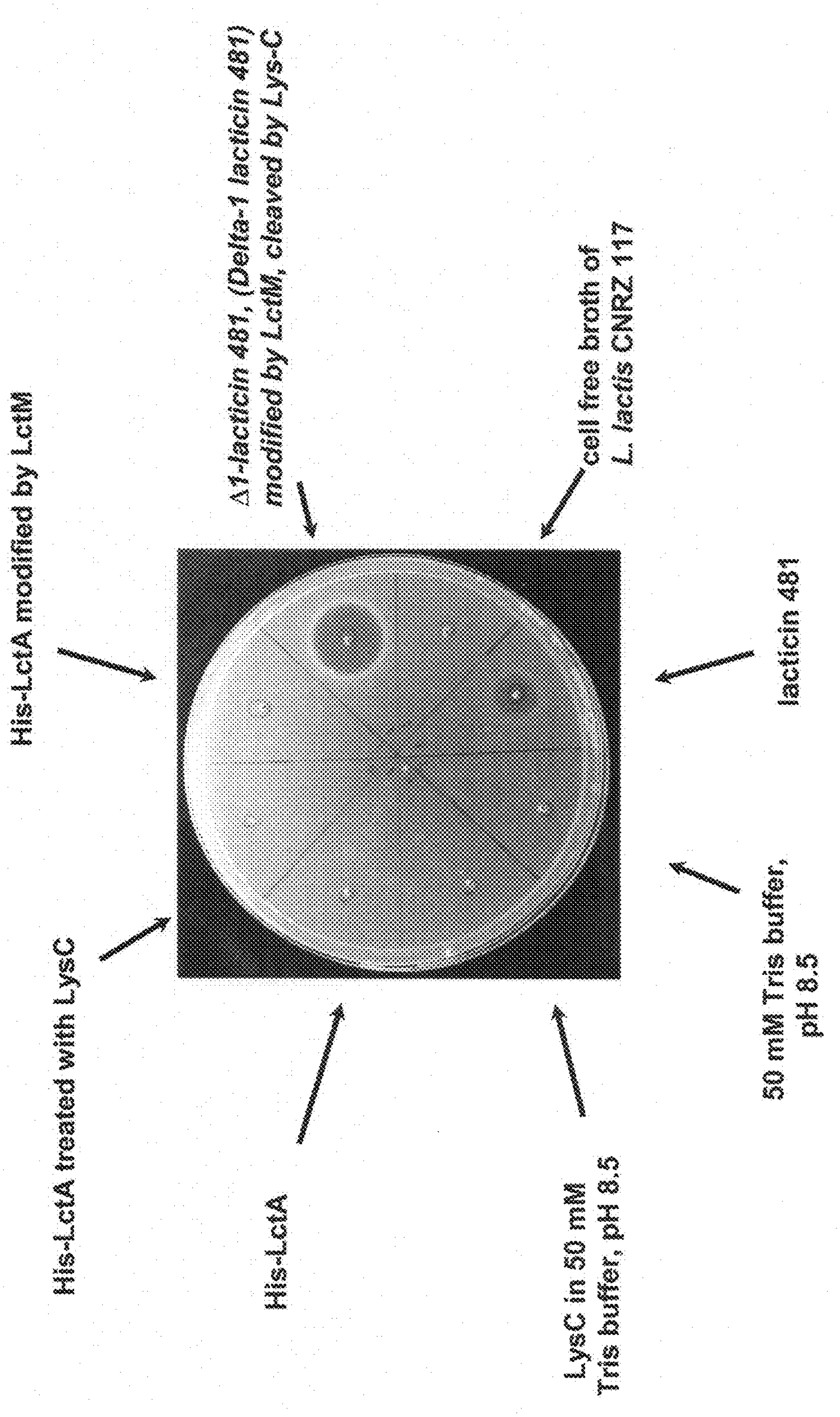
FIG. 42 illustrates a bioassay of Delta1-lacticin 481 against *L. lactis* 117.
Figure 43:
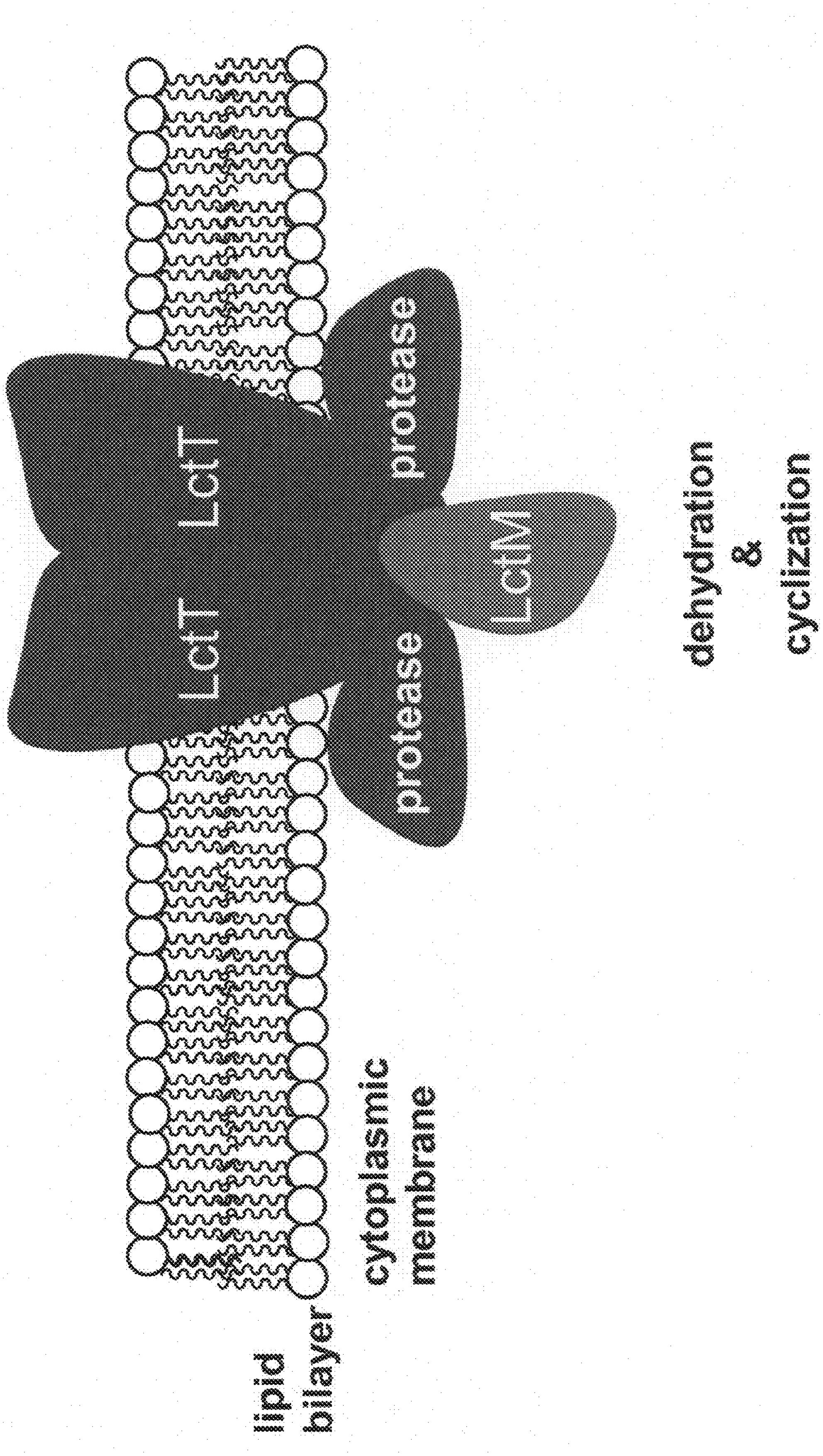
FIG. 43 illustrates a protease involved in lacticin biosynthesis. LctT comprises 691 amino acids and is about 79.8 kDa.

The complete dehydration product was separated from the substrate peptide by HPLC (eg FIG. 15) and both peptides were analyzed by FT-MS to establish the structure of the final product in collaboration with Neil Kelleher's group at UIUC. The observed pattern of fragmentation in MS-MS experiments for the substrate and product is shown in FIG. 16.

The fragments observed present an independent confirmation of the correct sequence of the substrate. Importantly, fragmentation occurs in the substrate in the region of Glu37, Cys38, Asn39, Met40, Asn41 (see also FIG. 14). However, the M-72 product does not show any fragmentation in this region because it is involved in cyclic structures. The reason for this is two-fold. First, it is well known that fragmentation in cyclic peptides is less efficient (125, 126), and second when fragmentation does occur in a cyclic structure, the ring opens, but the overall mass of the fragmentation product will be identical to the parent ion and hence the fragmentation will not be detectable. The observed fragmentation pattern therefore provides very strong support for the product having the ring structures of lacticin 481. Furthermore, amino acid analysis showed the presence of 2 Ln and 1 MeLn. This work presents the very first in vitro biosynthetic system of any lantibiotic. Given the extensive efforts that have been expended towards this goal in numerous laboratories across the globe (see reviews: (6-9)) this is an important achievement. As described in more detail in the experimental design section, we show that lacticin analogs are obtained by mutagenesis of the peptide substrate.

4a. Using Selenocysteines for Chemoselective Ligations

Synthesis of a Selenocysteine-Containing Peptide by Native Chemical Ligation. Gieselman, M. D.; Xie, L.; van der Donk, W. A. *Org. Lett.* 2001, 3, 1331-1334

An Engineered Azurin Variant Containing a Selenocysteine Copper Ligand. Berry, S.; Gieselman, M.; Nilges, M. J.; van der Donk, W. A.; Lu, Y. *J. Am. Chem. Soc.* 2002, 124, 2084-2085

Two uses of the lantibiotic biosynthetic machinery feature the ability to create lantibiotic analogs with unnatural amino acids or to use the dehydratase to introduce dehydroalanines into proteins fused to the lantibiotic leader sequence. The following specific tests probe the feasibility of these approaches: (1) synthetically introduce selenocysteine into the prepeptides and investigate whether the biosynthetic enzymes would generate selenolanthionines in which the thioether bridge(s) are replaced by selenoether bridges, and (2) to evaluate adding external nucleophiles to dehydroalanines. In order to achieve the first goal, we first developed a new route to FmocSec(PMB)-OH (5). This compound is compatible with SPPS and the PMB group can be removed oxidatively or with acid to give unprotected selenopeptides (127-131). The existing route to 5 involved 9 steps (127) that were difficult to scale up to the gram-scale quantities needed for SPPS. Our new route to this compound is shown in Scheme 4 (85).

Scheme 4

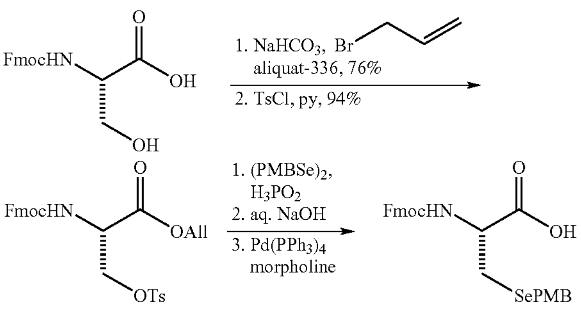

5, 86%

Figure 11:
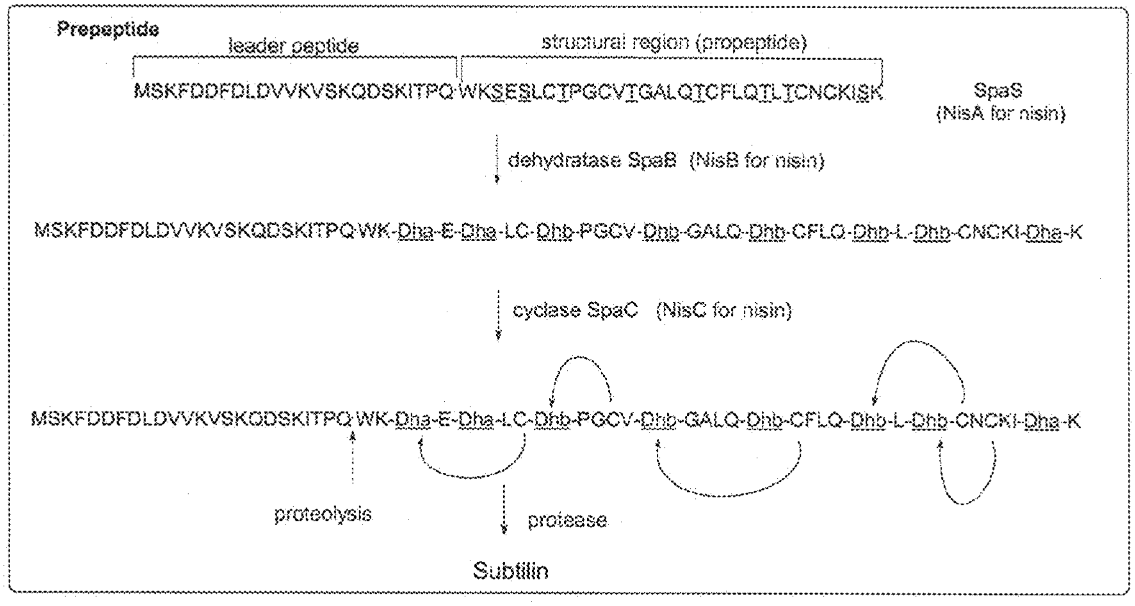
FIG. 11 is a schematic representation of the proposed biosynthesis of subtilin (prepeptide, SpaS, SEQ ID NO:67; product, SEQ ID NO:115) by the dehydratase SpaB and the cyclase SpaC. A similar scheme can be drawn for nisin and a similar scheme is presented for lacticin 481.

The route is significantly shorter, higher yielding, and can be carried out in large scale. A second obstacle to introducing Sec into the lantibiotic prepeptides involves their length of >50 amino acids (FIG. 11 and FIG. 14). Synthesis of lengthy peptides has been significantly improved in recent years by the native chemical ligation technique developed by Kent and coworkers (132, 133). We reported the first example of incorporation of selenocysteine into peptides using native chemical ligation by placing Sec at the point of ligation in peptides prepared with monomer 5 (85, 134). We then extended this methodology to expressed protein ligation (EPL) (135, 136) and replaced the key cysteine copper ligand in the blue copper protein azurin with selenocysteine (137). This study generated the first selenoprotein produced by EPL that behaved significantly different than the wild type enzyme. Having established the synthetic methodology to synthesize Sec-containing peptides and use them for EPL, we generated overexpression constructs in which a truncated prepeptide for lacticin (residues 1-48) is fused to an intein-CBD. This allowed us to overproduce the peptide in *E. coli* and then ligate it to a synthetic tripeptide corresponding to the last three amino acids ($Cys^{49}Cys^{50}Ser^{51}$). One of the Cys residues can be replaced with Sec to create selenolanthionines. Consequently, we have developed the methodology required to prepare Sec-containing prepeptides that are used. Other ligations that are used herein are performed with intein constructs; these include appending a biotinylated synthetic peptide to the C-terminus of expressed lantibiotic prepeptides.

4b. Using Dehydroalanines for Chemoselective Ligations

Zhu, Y.; van der Donk, W. A. *Org. Lett.* 2001, 3, 1189-1192. "Convergent Synthesis of Peptide Conjugates Using Dehydroalanines for Chemoselective Ligations".

Galonic, D.; van der Donk, W. A.; Gin, D. Y. *Chem.-Eur. J.* 2003, 24, 5997-6006. "Oligosaccharide-Peptide Ligation of Glycosyl Thiolates with Dehydropeptides. Synthesis of S-Linked Mucin Glycopeptide Conjugates".

We establish the use of dehydroalanines as electrophilic handles to introduce various functionalities into peptides, and proteins using the dehydratases to generate dehydroalanines in proteins fused to the lantibiotic leader sequence. A few examples of such a chemoselective ligation strategy are shown in Scheme 5 (138).

Scheme 5

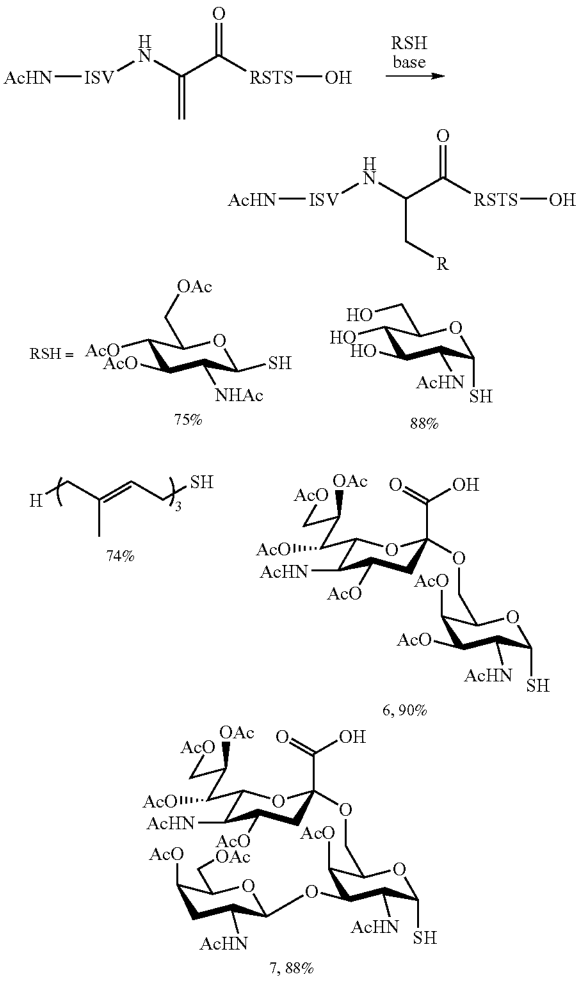

Farnesyl- and geranylgeranylthiol could be conveniently linked to peptides prepared by SPPS. Despite the disadvantage that two diastereomeric products are formed, the overall yield of the route is higher than reported methodologies and perhaps more importantly, the route is significantly simplified as it does not involve complicated protecting group manipulations. The advantage of the chemoselective ligation strategy is even more evident in the addition of thioglycosides to the dehydroalanines. The synthesis of O-linked glycopeptides is an important goal and one of the greatest challenges involves the control of alpha/beta-selectivity of the linkage to Ser/Thr. Since anomeric thioglycosides are configurationally stable and retain their stereochemical integrity during the Michael addition, the route in Scheme 5 provides rapid entry to either alpha-S-linked N-acetylgalactosamine or beta-S-linked N-acetylglucosamine glycopeptides. These are the two stereochemical linkages that are almost exclusively found as the core structure of O-linked glycoproteins. A joint student between the Gin and van der Donk laboratories has recently extended the methodology to several tumor associated antigens such as 6 and 7 (Scheme 5). This approach to the preparation of glycopeptides by chemoselective ligation is particularly attractive because (1) S-linked glycopeptides are closer structural analogs of O-linked peptides than other mimics that have been used for chemoselective ligation strategies (139), and (2) S-linked glycopeptides have been demonstrated to have higher acid and base stability than the corresponding O-linked structures (140). Perhaps the most useful aspect of the strategy involves the capability to perform all steps (SPPS, oxidative elimination and ligation) on the solid support facilitating the use of this technology for combinatorial purposes (111, 138).

We developed the synthetic methodology to introduce Dha and Dhb residues into unprotected peptides and to prepare fluorinated derivatives thereof. Furthermore, our biomimetic studies demonstrated that lanthionine and methyllanthionine formation has an intrinsic propensity to give the stereochemistry observed in the final products. We also showed that we can introduce selenocysteine into proteins, and that we can use ligations to obtain lantibiotic prepeptides in which the leader sequence is overexpressed and the structural region is prepared chemically containing unnatural residues. We cloned, overexpressed and purified the dehydratase and cyclase enzymes for subtilin and nisin biosynthesis, and characterized the cyclases as zinc metalloproteins. And most importantly, we have been able to achieve the first in vitro lantibiotic biosynthetic system. The experimental design describes a multi-faceted approach that uses our knowledge to elucidate the mechanism of lantibiotic biosynthesis as well as to engineer new variants.

D. Experimental Design & Methods.

Our approach towards harnessing the enormous potential of in vitro reconstitution of lantibiotic biosynthesis focuses on lacticin 481. The lessons learned from the work on lacticin are used in parallel to attempt in vitro reconstitution of the subtilin biosynthetic system. These experiments are similar as those described for lacticin. Our studies in Section 1 focus on the substrate requirements for lanthionine formation as well as the kinetics of maturation. Section 2 deals with characterization of the dehydratase/cyclase as well as the protease that removes the leader peptide. Section 3 addresses substrate binding and recognition. Aim 4 explores the use of non-natural substrates and assesses the biological activity of the resulting variants.

Section I. Determine the Substrate Requirements for Lantibiotic Biosynthesis.

I.1 ATP Dependence of Lantibiotic Biosynthesis: Kinetic Assay Development.

The observed activity of the LctM enzyme absolutely requires ATP. We have determined that the products are inorganic phosphate and ADP using known phosphate detection assays (Molecular Probes) as well as ion exchange HPLC to detect ADP. A number of different roles can be envisioned for ATP. It can activate the hydroxyl groups of the Ser and Thr residues by phosphorylation to facilitate dehydration and it can be used as an energy source as found for instance in motor proteins and also for the maturation of microcin B17 (141), another post-translationally modified peptide. In the latter case, decoupling of the ATPase activity is observed. To date we have focused all our efforts on obtaining active protein and characterizing the product. We first determine the stoichiometry of ATP hydrolysis and dehydration and cyclization. ATP hydrolysis is quantitated initially with endpoint assays for both $P_i$ and ADP. In these experiments the peptide substrate is completely processed. The stoichiometry having been determined, and hence it being known whether ATP hydrolysis rates can be used to monitor the kinetics of post-translational modification, we focus on kinetic assays to determine the $k_{cat}$ and $K_m$ for ATP and peptide substrates. GTP, ATP-gammaS, AMP-PCP, AMP-PNP, and ADP-CP are examined for use as substrates and/or inhibitors, the latter being useful for crystallization studies (Section 2). We use continuous assays by using a coupled enzyme approach when the kinetics of ATP hydrolysis are sufficiently fast. In that case, ADP is phosphorylated by pyruvate kinase using phosphoenol pyruvate as phosphoryl donor (Scheme 6).

Scheme 6

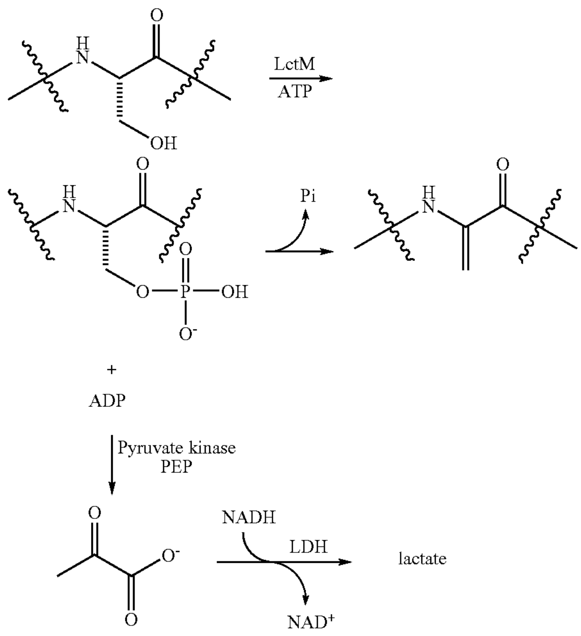

This produces pyruvate, which is reduced with lactate dehydrogenase (LDH) leading to the conversion of NADH to $NAD^+$. This last transformation is conveniently monitored at 340 nm. This strategy for detection of ADP requires identifying the conditions in which the enzymes in the coupled assay are not rate limiting. A complementary fluorescence based phosphate assay (Molecular Probes) is used to corroborate the results of the coupled enzyme assay. If the kinetics are slow, as in other antibiotic biosynthetic enzymes that catalyze complex chemical reactions, coupled enzyme assays do not work well. Hence, discontinuous assays are used. For ADP and phosphate this involves determining their concentrations at set timepoints using the same techniques as described before (HPLC & fluorescence assay); for the peptide it requires quantitative MS analysis since the presence of different intermediates precludes their separation and quantitation by HPLC (eg see FIG. 15). A quantitative MS assay was developed for microcin B17 maturation (141).

I.2 Processivity of Lanthionine Formation: Structural Characterization of Intermediates Mechanism of Cyclization: the Order of Ring Formation The order of ring formation in lantibiotics is investigated. A number of possible scenarios are investigated. These include the generally accepted scheme of global dehydration followed by regioselective cyclization (e.g. FIG. 11 and FIG. 14). However, dehydration of only one specific Ser/Thr residue at a time, followed by ring formation when only that one Dha or Dhb is available for cyclization cannot be ruled out (eg Scheme 7 for lacticin; starting material, "structural region" is given in amino acids 25-51 of SEQ ID NO:3; the Dha-containing structural region is given in SEQ ID NO:110, amino acids; and the sequence of the dehydratase product is given in SEQ ID NO:119).

Scheme 7

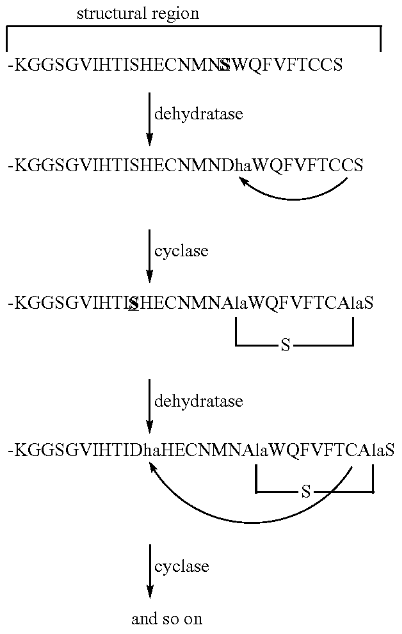

A nice feature of this picture is that it avoids the problem of regioselectivity for the cyclizations. An indirect argument against this mechanism includes the observed accumulation of dehydrated peptides when the LanC genes are disrupted (142). Moreover, in this scenario every cyclization would significantly change the structure of the peptide complicating the task of the dehydratase in each subsequent dehydration. A second question involves the coupling of the dehydration and cyclization activities of LctM, i.e. does the dehydrated substrate produced at the dehydration active site dissociate from the enzyme prior to rebinding at the cyclase active site? If not, one observes either unmodified substrate or completely cyclized product in the steady state phase, but no partially processed dehydropeptides that have not undergone cyclization. With the available activity of the lacticin system both of these questions are experimentally tested for the first time.

The observed peptides with masses of M-18, M-36, and M-54 suggest that intermediates are generated. However, prior to commencing with structural characterization of these intermediates, we first assess whether these structures are true intermediates and not dead-end products that arose for instance from incorrect cyclization and hence termination of the post-translational modification process. As mentioned in the preliminary results section, the LctA substrate with the C-terminal His-tag produces a large amount of partially dehydrated peptides (M-18, M-36, M-54). Using reverse phase and/or anion exchange HPLC, we partially purify the mixture and resubmit the incompletely processed peptides to LctM. When this leads to processing to mature lacticin 481 at a rate similar to the formation of the product with LctA-His, the partially dehydrated peptides are shown to be true intermediates that dissociate from the enzyme. Structural characterization as to whether lanthionines are present in these partially processed peptides answers the question whether the dehydrated peptides dissociate before cyclization. Other experiments that address this issue involve classic pulse-chase or isotope trapping experiments. We first focus on MS structural characterization as described below, and do not describe here these other methodologies (eg see (143-150)).

Another question involves whether the cyclization reactions are carried out in a particular order (eg N-to-C terminus). A non-ordered distributive mechanism on the other hand would feature LctM latching onto the substrate to cyclize one or more thioether rings randomly, then dissociating, before randomly binding again and in a stepwise fashion completing the formation of all five rings. In this case, a distribution of peptides with anywhere between 1-3 rings at various positions is expected at a given time point. Structural characterization of the partially dehydrated peptides discussed above sheds light onto these questions. Hence we determine if lanthionine rings are formed in the partially dehydrated peptides and if so whether they show the expected features of a directional process. These experiments are conducted using mass spectrometry. The maturation process of the antibiotic microcin B17 has similarities with lantibiotic biosynthesis in that a prepeptide containing a leader sequence and a structural region is ribosomally synthesized. The post-translational modifications of microcin B17 involve cyclizations of 4 serines and 4 cysteines onto the carbonyls of the immediately preceding residues in the peptide giving 4 oxazolines and 4 thiazolines. A flavin dependent enzyme subsequently oxidizes these structures to generate the final product containing 4 oxazoles and 4 thiazoles (151). High resolution and tandem-MS was utilized by Dr. Kelleher in the Walsh laboratory to show that the in vitro post-translational modification for microcin B17 proceeds by a distributive yet directional process from N-terminal to C-terminal sites (152, 153). The Kelleher laboratory has the required equipment including an FT-MS instrument to carry out similar studies for lantibiotic maturation.

One important technical difference between the studies on microcin and the investigations described here for lantibiotic formation involves the manner in which the process is monitored. Each modification in microcin leads to a reduction in mass of 20 amu whereas a Michael addition of a cysteine to a Dha residue does not change the mass of the peptide. Three independent approaches are evaluated to render these experiments amenable to MS analysis. The first involves performing the reactions in $D_2O$. After cyclization, this leads to the stoichiometric incorporation of one deuterium at the alpha-position of the former Dha or Dhb residue (Scheme 8).

Scheme 8

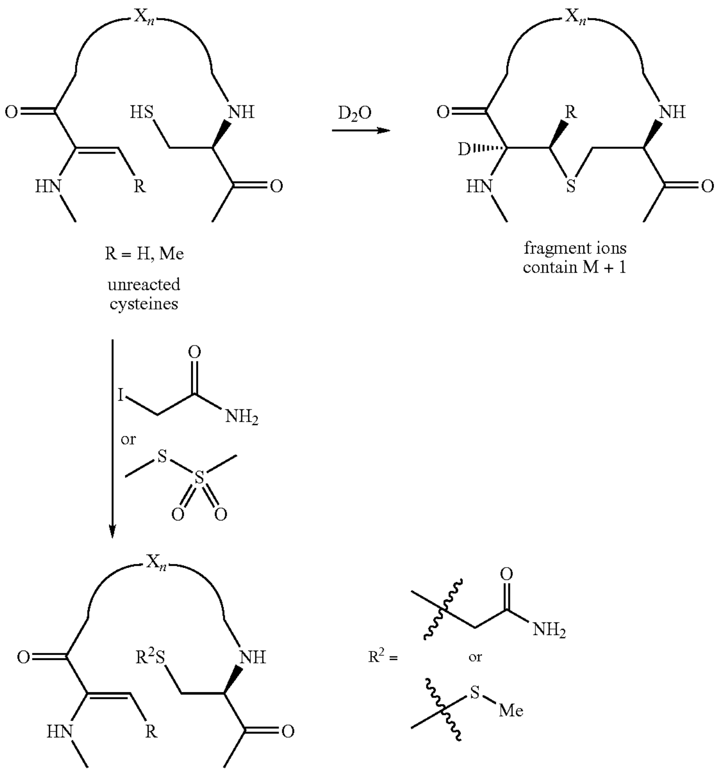

fragment ions contain M + 58 or M + 47

High resolution MS is then utilized to determine the number of rings formed at a given timepoint during the assay by determining the number of deuterium labels. Alternatively, the number of rings formed is determined by modification of unreacted cysteine residues. We have shown previously that the SpaS peptide can be reacted with either iodoacetamide or methane methylthiosulfonate to trap cysteine residues by alkylation or disulfide bond formation. Thus, samples taken from the LctM catalyzed cyclization reaction are treated with one of these reagents and the LctA peptide substrate is analyzed by MS to probe the number of free cysteines and hence the number of rings that have been formed (Scheme 8). Furthermore, tandem MS is used to determine the sites of cysteine modification, and hence also the sites of cyclization. Obviously, a number of controls are carried out in the absence of LctM to verify that the modification of the cysteines with excess reagent is faster than non-enzymatic cyclization. However, our findings have shown that non-enzymatic cyclization is very slow in aqueous solution at pH 7.

We can take advantage of another characteristic of lanthionine rings. Our tandem MS analysis of synthetic peptides containing lanthionine and methyllanthionines rings using a departmental quadrupole-hexapole-quadrupole (QHQ) mass spectrometer showed a typical pattern with an increased intensity of fragment ions generated from cleavage just outside the ring. Hence, it is possible to determine the sites of cyclization simply by inspection of the fragment ions in MS-MS experiments. To further corroborate this useful mass spectrometric technique to assign lanthionine structures, we perform triple MS-MS experiments. Given that the major fragment ions are y- and b-ions (Roepstorff notation (154)), we perform MS on these ions using ESI-ion trap MS. The basic idea is shown in Scheme 9 concentrating in this case on the y-ions but the same arguments also apply for the b-ions.

Scheme 9

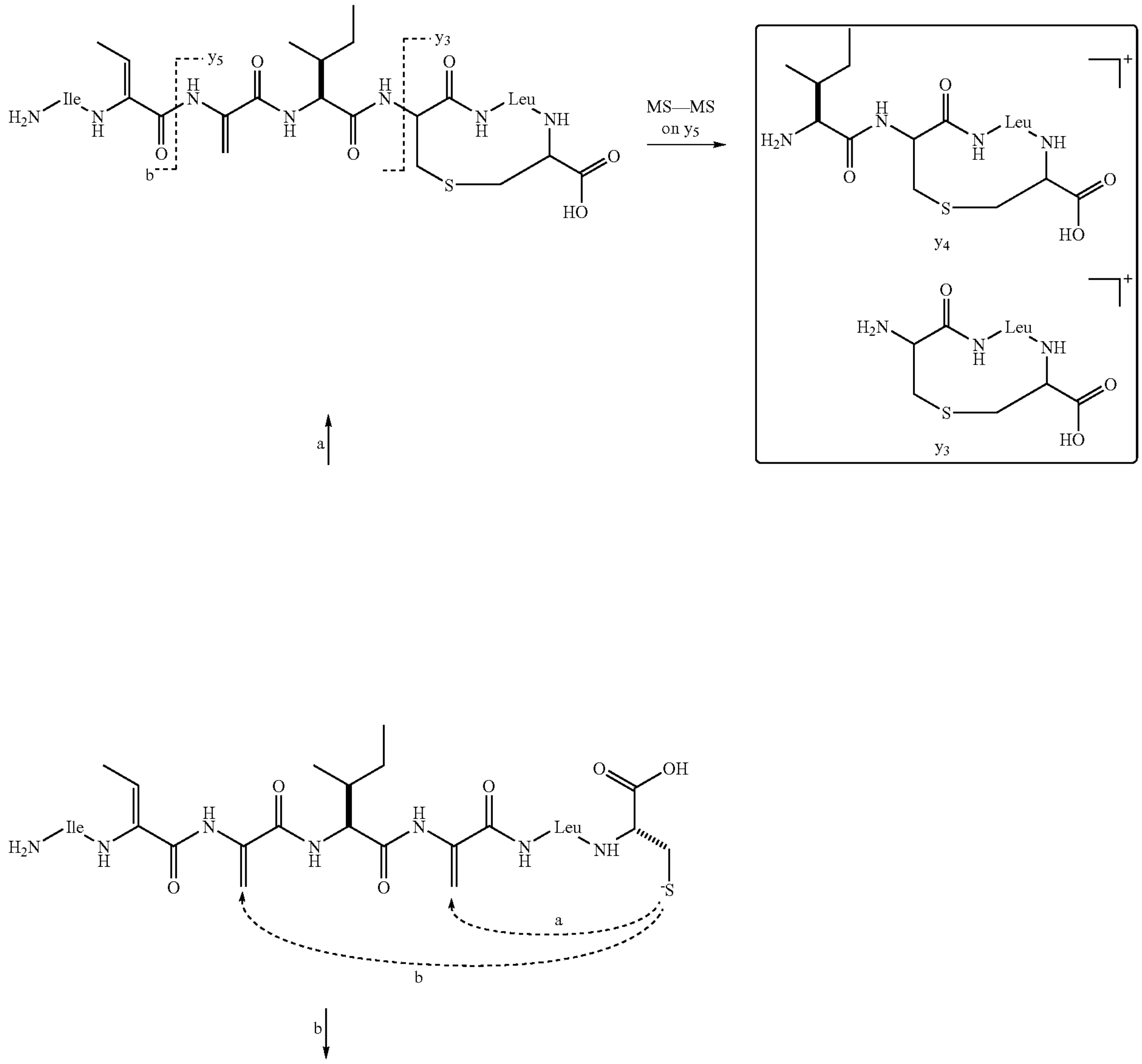

-continued

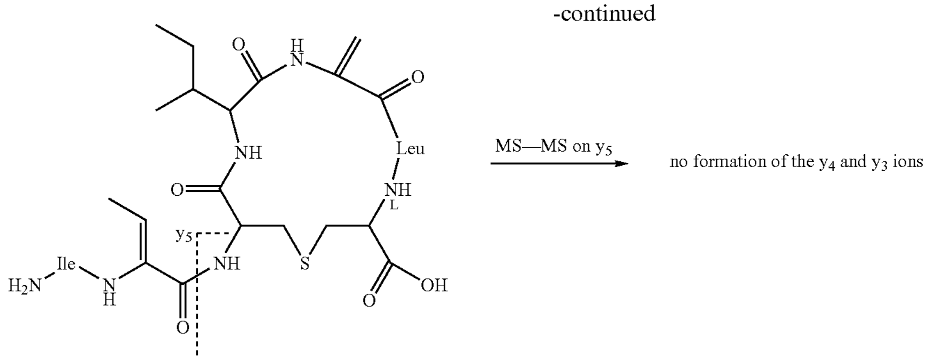

For instance, suppose we want to distinguish between formation of either of the two rings in Scheme 9. First, we anticipate that the $y_3$-ion is the major y-type fragment ion for cyclization via path a, whereas the $y_5$-ion would be the major y-type fragment ion for cyclization via pathway b. This is observed for all synthetic cyclic thioether containing peptides that we have prepared. One complicating factor is that $y_5$ ions can be formed for both cyclic peptides and they have identical masses. So, in addition to relying on the intensity of the $y_5$-ion, we also perform MS-MS on this ion. In the case of pathway a, this results in a typical series of $y_3$ and $y_4$-ions (155). On the other hand, it is clear that fragmentation of the $y_5$-ion in the bottom scenario will not generate the $y_4$- and $y_3$-ions by virtue of the covalent thioether linkage between residues 3 and 6, permitting distinction between pathways a and b. The same logic is applied when one determines where in the peptide cyclic thioethers are formed. The 5-6 kDa peptides are readily analyzed in this way using the ESI-Fourier Transform mass spectrometer in Prof. Kelleher's laboratory. With the methodology for efficient localization of lanthionine rings established, time dependent studies are performed to monitor the formation of the various rings. We note that a study currently in press (156) showed promising results using electron capture induced dissociation (ECD) to localize thioether rings in lantibiotics.

I.3 Use of LctA Mutants.

Interesting studies addressed with the first functional lantibiotic biosynthetic system involves the role of the leader peptide. We first investigate the minimum sequence requirement. Using a molecular biology approach we prepare prepeptides that either contain or lack the leader sequence, or that contain part of the leader sequence. FIG. 17 shows an alignment of the leader and structural regions of lantibiotics with sequence homology to lacticin 481. These prepeptides are members of the so-called GG-group, named after their conserved GG or GA-sequence at the protease cleavage site. Several other conserved regions are present, but the N-terminus shows only weak sequence conservation. Hence we will prepare several truncated prepeptides including Δ1-4, Δ1-9, Δ1-13, Δ1-18, and Δ1-24 (i.e. removal of the entire leader sequence). We have constructed the Δ1-4LctA mutant and found it is fully processed to the corresponding product. This was a first indication that the leader sequence has a different role than that in microcin biosynthesis where the leader was found to be essential for post-translational modification (160). As mentioned in the introduction, other roles for the leader can be envisioned including transport and keeping the peptide inactive until after excretion. The conserved regions in these peptides thus reflect a consensus sequence for the protease or transport system rather than for the dehydratase/cyclase. With the essential region of the leader peptide identified, we turn to truncated peptides that contain the leader sequence but only part of the dehydrated structural region. For instance, fragments 1-38 (precursor to A ring only), 1-49 (A & B rings), and 1-50 (A, B & C rings) are prepared that result in a successively larger number of thioethers formed upon enzyme catalyzed cyclization. The analysis of the products of these enzymatic reactions is carried out using MS as described above. Competitive inhibitory action of LctA1-24 (leader) and LctA 25-51 (structural peptide) is also assessed.

In addition to probing the prepeptide structure by truncations, site directed mutagenesis studies are utilized. Initial targets that we have characterized are T48S, T48A, and C50A. Incubation of T48S with LctM gave rise to a product in which still 4 dehydrations had occurred, indicating that the Dhb at position 48 is now a Dha. MS analysis confirms its location. T48A gave rise to a product in which only 3 dehydrations had taken place, fully consistent with expectations. Perhaps the most interesting mutant is C50A. This mutant can no longer form the C ring. Unexpectedly, however, this mutation also led to a fifth dehydration of Ser52. Most importantly, these results illustrate the promiscuity of LctM for the peptide substrate and indicate the enzyme can access novel structures. Mutants that are generated include T33A (which prevents formation of the A-ring and leave an uncyclized Cys38), S35A (preventing B-ring formation), and S42A (precluding C-ring formation). The corresponding C38A and C49A mutants are also made. Besides probing the range of structures, these experiments also provide important insights into the mechanism of the maturation process, for instance whether formation of a certain ring is essential for proper processing of other rings. For example for a processive mechanism, incompletely processed products can result if the Ser and/or Cys involved in formation of the initial ring are mutated.

In addition to mutants that involve one of the modified residues (Ser/Thr/Cys), we also mutate the conserved GG/GA pair at positions −1 and −2 from the site of proteolytic cleavage.

II. Characterization of the Proteins Involved in Lacticin 481 Maturation

II.1 X-Ray Crystallography of LctM

The availability of a crystal structure of LctM provides very important guidance on the mechanism of catalysis and the mode of substrate binding. At present no structural information has been reported for any proteins involved in lanthionine formation and no sequence homology exists between the proteins in the database and the proteins involved in this process (LanB/C/M). Therefore, we have initiated a collaboration with the laboratory of Satish Nair in the Department of Biochemistry at UIUC. Dr. Nair has much experience in X-ray crystallography of zinc proteins through his studies of carbonic anhydrase (162-167). An effort is dedicated to probing the presence of stable domains by limited proteolysis, evaluating crystallization conditions, and also investigating other proteins involved in lantibiotic biosynthesis (vide infra). These studies provide us with detailed structural information, but do not replace the proposed biophysical experiments described below. A crystal structure provides a static picture whereas most of the proposed experiments described elsewhere in this application provide quantitative information regarding dynamic processes such as binding and catalysis. We note that structural information of the C-terminal region of LctM (LanC-like domain) is valuable for the study of the recently discovered mammalian LANCL proteins that display homology with the LanC proteins (106-109), including the putative zinc ligands.

II.2 Residues Involved in Zinc Binding and ATPase Activity.

Our studies with SpaC and NisC indicate that two conserved cysteines in LctM as well as one or two conserved His residues are candidates for binding Zn. Mutations in SpaC corroborated these roles for the two Cys residues (89), but since the activity of the mutants could not be tested due to the lack of dehydrated substrate, the functional role in catalysis remained ill defined. With active LctM in hand, we initiate studies designed to address this question. We prepare both Cys-to-Ala and Cys-to-Ser single and double mutants and analyze the effect on dehydration and cyclization activity using our MS structural assay of the products. One very exciting outcome involves decoupling of dehydratase and cyclase activities, that is, disruption of the zinc site leads to loss of cyclase activity but not dehydratase activity. The effect of these mutations on ATPase activity is determined, which localizes ATP hydrolysis to the dehydration or cyclization process. Similarly, mutation of the two conserved His residues will be carried out. In the proposed mechanism in Scheme 2, one of these residues is either the active site base that deprotonates the substrate cysteine or the catalytic acid that protonates the enolate intermediate. Mutation of the His residues to Asn and Phe is used to test these mechanistic possibilities. To provide a more detailed look at catalysis of both wild-type LctM and these mutants, their pH-dependent rate profiles are determined, which are used to identify the $pK_a$ of residues that are important in catalysis and substrate binding. In order to simplify the analysis, minimal truncated prepeptide sequences/mutants are used initially in which only one ring structure can be formed (either A-, B-, or C-rings) and the findings with these peptides are used to understand data obtained with full length LctA. As a further improvement aiding these experiments, the dehydrated peptide from the Cys-mutants described above (or using synthesis as described in the Preliminary Results section) is obtained, and dehydropeptides are used as substrates to elucidate the role of the His residues in cyclization in wt and mutant proteins.

Using the His-mutants, we experimentally address whether one of the His residues functions as the proton acceptor during thiolate binding as proposed in Scheme 2. In methionine synthase, binding of homocysteine to the zinc site results in release of a proton into solution as observed using a pH sensitive dye (168). The mechanism in Scheme 2 indicates that no proton is released into solution upon binding of the cysteine in the lantibiotic prepeptide to the metal center. However, mutation of one of the two conserved His residues does not affect the integrity of the zinc center (probed in section II.4) but removes the active site base that accepts the proton from the incoming cysteine. Consequently, substrate binding results in release of a proton into solution with this mutant, similar to the observation in methionine synthase.

II.3 Attempts to Separate Dehydration and Cyclization Activity.

To date, the assignment of dehydratase activity to the LanB enzymes and cyclase activity to the LanC enzymes is largely based on genetic studies as described in the introduction, but proof is still lacking. With an active LctM protein that contains a C-terminal domain that shows homology with the LanC proteins, we attempt to provide unequivocal evidence that this domain in LctM, and hence the LanC proteins, is responsible for the cyclization activity. We use the domain linker analysis tools obtained from Townsend (169) to determine where to separate the cyclization and dehydration domains. Expressing the two domains of the protein independently and demonstrated dehydratase activity for the N-terminal ~470 amino acids and cyclase activity for the C-terminal ~400 amino acids, provides extremely useful tools. Other issues are investigated such as substrate recognition with respect to both leader and structural regions, catalytically essential residues, X-ray crystallography, and the mechanism of dehydration and cyclization (eg ATP dependence). Attempts are also made to generate mutants that can only carry out one of the two reactions as already described for the cyclization reaction in the previous section (i.e. mutation of the Zn ligands). Candidate residues that may be essential for the dehydration are a series of conserved residues in the N-terminal domain of LctM: Lys159, Asp242, His244, Asp259, Glu261, Arg399, and Glu446. The ability of the expressed N-terminal domain or one of the mutations to the metal ligands to produce a dehydratase enzyme, is also useful for the preparation of dehydropeptides, both as substrates for cyclization activity and for synthetic use as described in the introduction.

II.4 Expression and Purification of the Protease that Cleaves the Leader Peptide.

In order to produce novel lantibiotics with interesting biological activities, we provide an efficient means to remove the leader sequence. We first determine the activity of lacticin 481 containing the leader (Section 4), to determine effect of removal of the leader sequence on cytotoxicity (25, 65, 170). Some lantibiotics have dedicated proteases in their biosynthetic operons whereas others do not. Havarstein et al recognized sequence homology between the leader sequences of a large number of non-lantibiotic bacteriocins and a small group of lantibiotics (171). This group was collectively termed double-glycine leader peptides. Subsequently, two laboratories showed that the N-terminal ~150-190 amino acids of the ABC-transporters associated with these non-lantibiotic antimicrobial peptides contain the proteolytic activity that removes the leader concomitant with membrane translocation. This proteolytic domain was shown to be located at the cytoplasmic side of the membrane (172, 173). In vivo protease activity was demonstrated by heterologous expression in *E. coli* of the N-terminal 190 amino acids of PedD involved in pediocin processing (173) and LagD involved in lactococcin G processing. The latter study also overexpressed and purified the N-terminal 150-amino acid domain of LagD in *E. coli* and it was suggested that this domain constitutes a cysteine protease although no sequence homology with any known proteases was found (172). Surprisingly, no follow-up in vitro studies have been reported on characterization of any bacteriocin proteases. FIG. 18 shows an alignment of the N-terminus of the transporter for lacticin 481 (LctT) with several other transporters that process the double-glycine peptides. We will express this domain from LctT in *E. coli* with a C-terminal His-tag as was used for LagD. Once the protease domain is purified, we will test its activity on LctA as well as processed LctA to determine whether the protease requires the post-translational modifications in its substrate. Substrates truncated at either the N-terminus or C-terminus will also be probed. We evaluate whether the enzyme is indeed a Cys-protease using both biochemical techniques and mutagenesis of the apparently conserved His, Cys, and Asp residues that may form the catalytic triad (FIG. 18). It should be noted that the His and Cys are not strictly conserved in all members of this family, thus we can provide novel proteases. In addition, we crystallize this domain, which provides important information regarding substrate recognition. Given the importance of proteolysis of the double-glycine leader sequence in lactic acid bacteriocins (174), these studies provide important insights that are valuable to this entire field.

Section III. Investigation of Substrate Binding to LctM

III.1 Substrate Binding to the Zinc Site

A number of experimental approaches are used to test the proposed substrate activation model in Scheme 2. Alternative roles for the zinc would include a structural function or Lewis acid activation of the carbonyl of the dehydrated electrophiles for conjugate addition by cysteine. We focus on substrate binding. Literature reports on farnesyl transferase show that the cysteine of a truncated peptide substrate binds to the zinc with a micromolar $K_d$ (102, 103). Upon binding the $pK_a$ of the cysteine is decreased such that a thiolate is bound at pH 7. Formation of a similar Zn-thiolate complex between the cyclases and the lantibiotic prepeptide will be investigated in a number of ways, all of which have their own advantages and disadvantages. We initially use prepeptides in which the Ser/Thr residues that are normally dehydrated are mutated to Ala in order to prevent turnover, which complicate analysis. Alternatively, as discussed above a mutant protein is constructed that disrupts cyclization catalysis in which case binding of the dehydrated peptide substrates is monitored.

In order to obtain the binding constant and pKa of prepeptide binding, the zinc 15 is replaced by cobalt. This modification is often used (175, 176) since the ligand to metal charge transfer band (300-400 nm, ϵ900-1300 M−1 cm-1 per Co—S bond (177, 178)) and the d-d visible absorption bands (600-700 nm, ϵ ~500-600 M−1 cm−1) are distinctly removed from the absorption envelope of the protein (175, 179). Furthermore, a clear change in the spectrum is induced upon binding of each consecutive thiolate ligand 20 (180), and the intensity of the bands is indicative of the coordination number (175). Hence we directly monitor binding by a change in both the intensity of the absorption bands and their wavelength maxima. We have shown for SpaC that treatment with phydroxymercuribenzoic acid (HMBA) (181-183) or methyl methanethiosulfonate (MMTS) (184-186) released the zinc without the need for denaturation. We also demonstrated 25 that the protein could be stoichiometrically reconstituted with Zn2+. Under anaerobic conditions and in the presence of TCEP to remove the modification groups from the cysteine introduced by HMBA or MMTS, we should be able to reconstitute LctM with Co2+ as has been demonstrated in a number of other Zn proteins. Concentration and pH dependent titrations can then be performed with the prepeptide or truncated versions 30 thereof to determine the Kd of the substrate and the pKa of the cysteine thiol bound to the metal.

To obtain structural information on the zinc site we have initiated a collaboration with Prof. Ninian Blackburn at OHSU. Our studies with the Blackburn laboratory focus on characterization of the zinc site by extended X-ray absorption fine structure spectroscopy (EXAFS). This project is particularly suited for EXAFS analysis because $Zn^{2+}$ is not photoreducible, allowing characterization of the proteins at low concentrations without side reactions. The power of EXAFS to monitor the zinc site was demonstrated in studies on two other zinc proteins that catalyze cysteine alkylation, the cobalamin dependent and independent methionine synthases (90, 187-189). Binding of either LctA or the dehydrated LctA substrate (prepared using mutant LctM, the dehydration domain (section D.II.3), or synthetically using our methodology) to the protein are analyzed to corroborate a change to a 3 S+1 N/O environment. This not only provides important information on the binding of thiols to the zinc site of LctM, but also lends support for the role of the zinc. The structural data obtained is complementary to the spectroscopic studies described in the previous section. Since EXAFS data are subject to simulation and interpretation, we confirm the conclusions obtained for the wild-type peptides by incorporating selenocysteine into the peptides by the ligation approach we developed. Combined use of the Zn and Se K-edge data provides important information regarding the geometry around the metal and the Lewis acidity of the zinc site (189, 190).

III.2 Fluorescence and SPR Analysis of Substrate Binding to LctM and LctM-Cys/His Mutants Site directed mutants discussed in II.2 that do not assemble a zinc site are analyzed for their ability to still bind the LctA prepeptide. Our model based on our findings on biomimetic lanthionine formation indicates that the metal center provides a low specificity activation site with binding affinity provided elsewhere, most likely by interaction with the leader sequence. The absence of a sequence specific binding site near the active site for cyclization is consistent with the cyclase forming rings of very different sizes and sequences. Thus, disruption of the metal center results in lack of cyclization catalysis at pH 7, but retention of substrate binding. We test this hypothesis in a number of different experiments. As mentioned briefly in the preliminary results section, we have used the expressed protein ligation technique to obtain a purified SpaS peptide with a biotinylated lysine appended through a C18 PEG-linker to its C-terminus, far away from the leader sequence. We use a similar strategy to prepare a LctA peptide for immobilization on a streptavidin-coated chip for use with a surface plasmon resonance (SPR) instrument that is available in the Biotechnology Center at UIUC. We then use this immobilized substrate to test for binding to the wild-type LctM protein as well as the aforementioned mutants. Analysis of the binding curves at different peptide concentrations provides the $K_d$ values. Truncated peptides are also analyzed for substrate binding to further determine the factors governing recognition and to complement the activity assays in Section 1. We can also label the peptide substrate with a fluorescent probe instead of biotin using the intein constructs we have prepared. We then use fluorescent anisotropy binding assays to measure the binding constants as a function of pH to determine the $pK_a$ of the Zn-bound thiolate (191). 2',7'-Difluorofluorescein is used rather than fluorescein since the former has a $pK_a$ of 4.7 (rather than 6.7) (192), which extends the useful range two $pK_a$ units and assures that no complications arise from the need to deconvolute two acid-base equilibria.

III.3 Protein-Substrate Complexes

Structural information on substrate binding provides the most valuable insights into substrate recognition and catalysis. To achieve this, cocrystallization with or diffusion of the prepeptide or truncated versions into LctM crystals are investigated, or, a photoaffinity labeling approach is used to provide insight into the binding site. LctA contains three Phe residues at positions 7, 45, and 47. We have a plasmid construct that fuses LctA1-37 at its C-terminus to intein-CBD, which allows ligation of a synthetic peptide corresponding to LctA38-51 tagged with biotin at the C-terminus, as shown in the preliminary results section. This peptide is synthesized using Fmoc-4-benzoylPhe or Fmoc-4-azidoPhe, well known photoaffinity reagents, to localize the reactive label to positions 45 and/or 47 in the structural region. Alternatively, the label could be located in the leader peptide at position 7 by expressing the intein-construct in an *E. coli* strain that has been modified with a tRNA-tRNA synthetase pair that will biosynthetically incorporate the Phe-analog at position 7 (193). Prof. Tirrell kindly provided the necessary strain for this strategy. Ligation is then performed with synthetic LctA38-51 containing regular Phe residues. These LctA analogs having been prepared, they are incubated with LctM and irradiated using standard techniques. Substrate that has not reacted with the protein is removed by gel filtration chromatography, and the covalently linked LctA-LctM molecules are pulled out by affinity chromatography using streptavidin beads. Fourier-Transform mass spectrometry will be used to determine the site of modification ("top-down" approach) (194, 195), we use the traditional method of proteolysis followed by HPLC purification and MS-MS analysis to identify the labeled residues ("bottom-up" approach). If needed, a radiolabeled residue is incorporated next to Phe45/47 to improve sensitivity in identification.

Section IV. Protein Engineering to Generate Novel Lacticin Variants

IV.1 Bioassays with Lacticin 481 and Analogs.

The assessment of biological activity of all lacticin analogs prepared in this program (Sections I and IV) is carried out via standard techniques. Activity and antagonism studies are performed using an agar diffusion assay (57, 62, 77, 196, 197) at varying concentrations of the peptides and compared to the activity of freshly purified lacticin 481 (67). *L. lactis* IL1835, a known lacticin 481-sensitive Gram-positive bacterial strain, has been obtained and is tested. Additional standard Gram-positive and Gram-negative tester strains are also probed (59), including the industrially important food spoilage bacterium *Clostridium tyrobactericum*. In addition to the agar diffusion assay, growth inhibition are monitored in standard suspension assays (197). Small samples of the analogs are also supplied to the Midwestern Regional Center of Excellence for Biodefense and Emerging Infectious Disease Research for testing against high biolevel strains. The activity of the lacticin variants is also tested against the producing strain to evaluate loss of self immunity.

IV.2 Assessment of the Functional and Steric Tolerance of the Biosynthetic Enzymes.

Genetic protein engineering can be optionally limited to the 20 proteinogenic amino acids. With the size of the structural region of the prepeptide of lacticin 481 (27 a.a.) well within the limit of solid phase peptide synthesis, the pool of available amino acids is increased dramatically when combined with our ligation protocol. Even smaller peptides are amenable to processing by LctM. Our studies with LctA mutants indicate the low substrate specificity of the lantibiotic biosynthetic enzymes. Thus, the natural peptide substrates are altered at specific positions by substitution with unnatural amino acids. These "chemical" mutagenesis studies generate useful compounds and address the structural and chemical requirements of the post-translational modifications. Furthermore, this approach potentially generates analogs of Dha and Dhb that provide additional insight into the in vivo function of these unsaturated residues. These analogs provide an important tool to test whether these unsaturated residues function as sites of covalent attachment to the cellular target (78, 79). The mode of action of lacticin 481 is currently poorly understood. The compound has been shown in a preliminary study to interact with synthetic anionic lipids (198), but in bacteria the observed activity was not consistent with simple pore formation (60). Furthermore, the closely related lantibiotic mutacin II (Lan, MeLan and Dhb in same positions, 60% a.a. identity) interferes with the cell's capability to generate metabolic energy (199).

We determine the substrate tolerance for cyclization and/or dehydration. A number of sterically or electronically diverse amino acids are incorporated into the substrates at the positions of Ser/Thr and Cys using the ligation methodology. Scheme 10 depicts a set of structures that test both the steric and electronic requirements of the LctM catalyzed cyclization.

Scheme 10

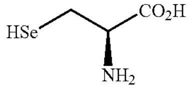

8

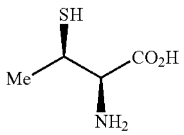

9

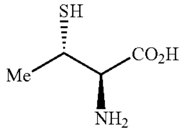

10

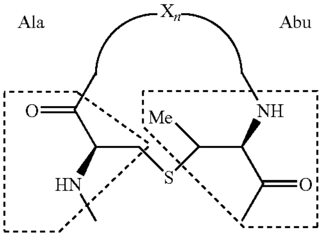

Amino acids are used that are readily available or synthesized (200, 201). Replacement of cysteine residues with selenocysteines is a conservative substitution evaluated for the cyclization reaction. We use a strategy to incorporate Sec into peptides and proteins using expressed protein ligation, and we use this methodology to generate the enzymatic production of selenolanthionines. Other amino acids that are incorporated into the prepeptide (or truncated versions thereof) include homocysteine and β-methyl cysteines 8 or 9 (200, 201, 209, 210). These residues provide "regioisomers" (10) of the natural MeLn structures in lacticin 481. Given the similarity between mutacin II and lacticin 481, we also evaluate LctM's activity with MutA, the prepeptide of mutacin II and with LctA/MutA chimeras. We evaluate the substitution of His8 in lacticin 481 with Pro. In mutacin II, this residue adjacent to the MeLan ring is disclosed as significant for its interference with generation of metabolic energy at the substrate level (199, 211).

IV.3. Design and Synthesis of Mechanism Based Inhibitors

Structure determination of enzyme-substrate complexes constitutes a technique for determining molecular recognition. Due to the reactivity of such complexes, researchers have resorted to enzyme-inhibitor complexes for stability reasons. Suicide inhibitors provide valuable insights into mechanisms of enzymatic reactions. Therefore, several unnatural amino acids that function as potential mechanism based inactivators are incorporated into the peptide substrates for post-translational modification. One class of suicide substrates is those peptides containing amino acids carrying alternative leaving groups at the β-carbon that are incorporated at the positions of Ser/Thr. A number of examples are shown in Scheme 11.

Scheme 11

11

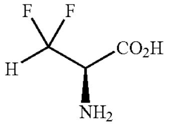

12

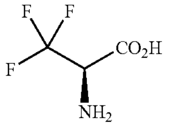

13

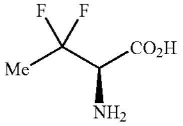

14

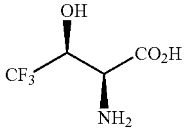

15

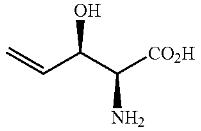

16

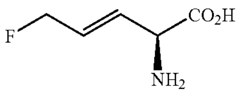

17

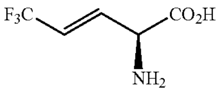

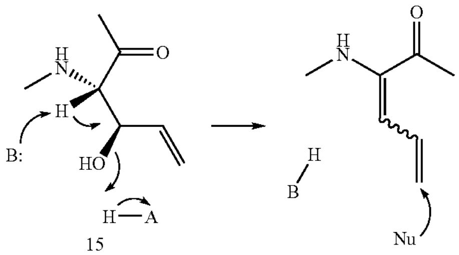

15

-continued

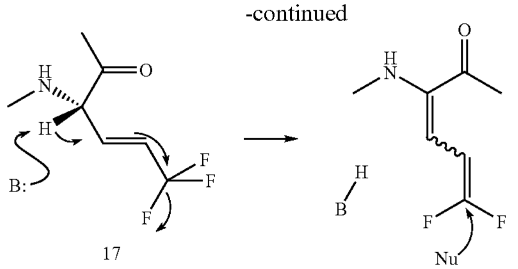

17

Enzymes that generate enolate intermediates, as in the case for the dehydratase activity of LctM, induce elimination of such leaving groups, generating highly reactive electrophilic species. Fluorine substituents are used in particular because of their small size and high leaving group reactivity that does not require acid catalysis. Fluorine substituted Michael acceptors have been previously shown to react irreversibly with active site nucleophiles such as amines, thiols and carboxylates (212-214).

Syntheses of compounds 11 (215, 216), 12 (212, 217, 218), 13 (219), and 14 (220-222) have been reported previously. These fluorinated compounds are of interest as potent suicide substrates for a number of pyridoxal dependent enzymes (212, 215, 217, 223-226). Compounds 15 and 16 have not been previously synthesized, and asymmetric routes are outlined in Scheme 12.

Scheme 12

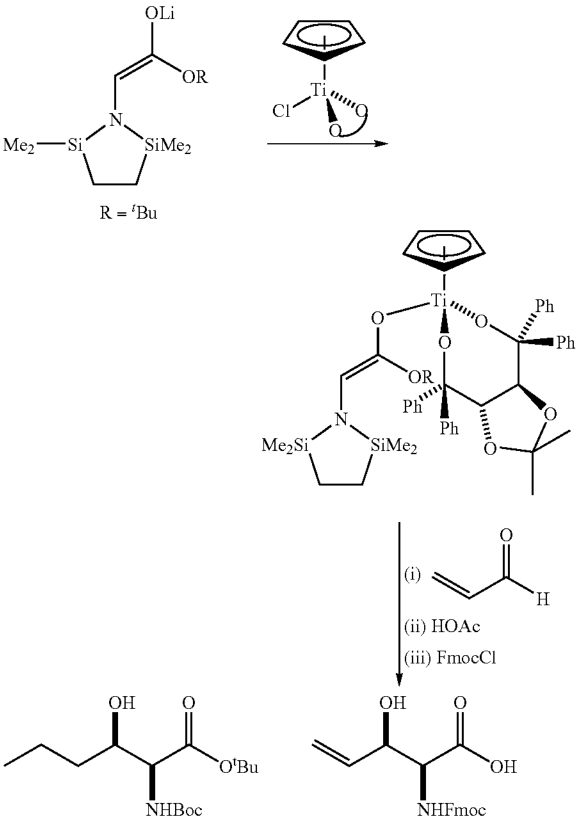

18, 94% ee

15

-continued

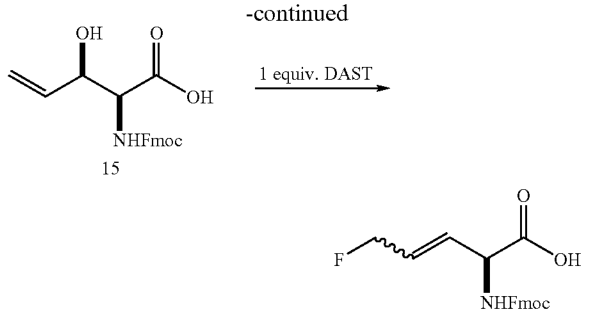

15

16

A tartrate derived ligand has been used to synthesize compound 18 in 94% ee (227). Using acrolein instead of butyraldehyde this methodology gives access to 15. A potentially rapid entry into 16 involves reaction of 15 with DAST. According to literature precedent, allylic alcohols give the $S_N2'$ fluorinated product upon treatment with DAST (228). Fluorinated amino acids are incorporated into synthetic peptides (229-233). Because of the relatively high strength of the carbon-fluorine bond in comparison with other halogens, they are stable to unwanted side reactions. However, the electron withdrawing nature of the fluorines significantly decreases the nucleophilicity of the amino group (e.g. $pK_a$ Ala-$NH_2$=9.87, $pK_a$ 11-$NH_2$=7.25, and pKa 12-$NH_2$=5.91 (215)). As a result these residues are often first incorporated into di- or tripeptides using specialized coupling methods (232), and these peptides can then be used for standard solid phase peptide synthesis when controlling or preventing racemization. Several dipeptides containing 11 are prepared (87).

The amino acids described in this section are designed to inhibit LctM. However, if incubation with LctM leads to lantibiotic products instead of inhibition, they represent novel variants of the natural compounds with biological activity and optionally are also used as tools to investigate the mode of antimicrobial action.

IV.3 Combinatorial Investigation of Substrate Specificity.

The previous two sections have focused on the use of unnatural amino acids to replace Ser/Thr/Cys. To generate variant compounds, understand lacticin's mechanism of cytotoxicity or achieve improvement thereof, preparing more than one peptide at a time is efficient, for example for screening assays or to delineate structure-activity relationships. The lantibiotic biosynthetic precursor peptides are used in combinatorial techniques using SPPS (234, 235). The use of synthetic chemistry expands the structural diversity of the accessible lantibiotics. We generate and evaluate variants of the LctA38-51 segment and develop an efficient screening method. This achieves variation of the structure of both the B- and C-rings (Scheme 13).

Scheme 13

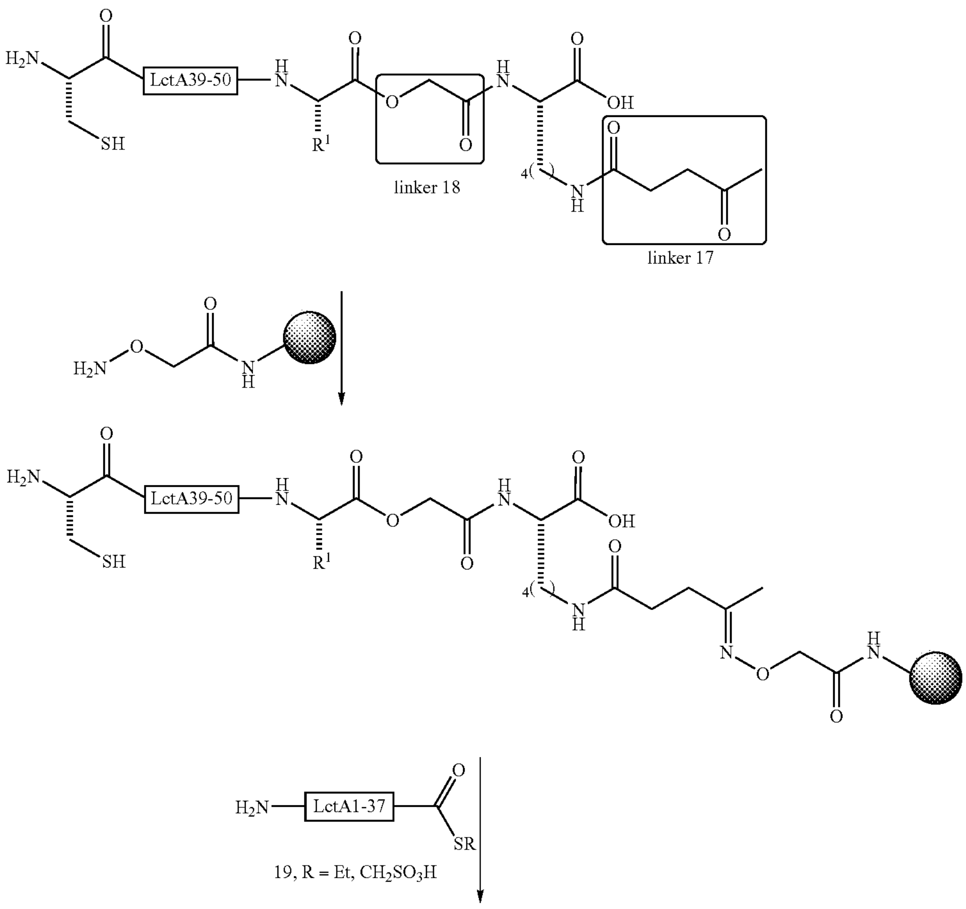

19, R = Et, $CH_2SO_3H$

-continued

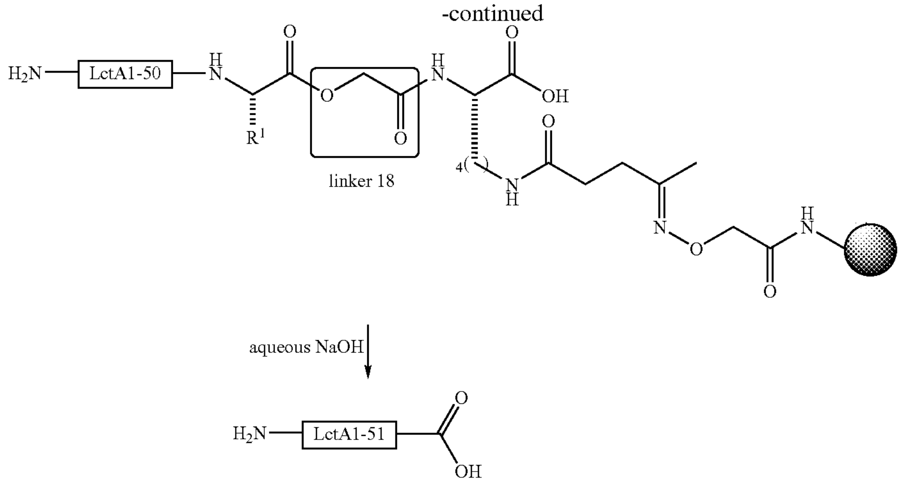

combinatorial library of LctM substrates

Libraries of variants of the 13-mer LctA38-51 are prepared via SPPS incorporating two linkers 17 and 18. Linker 17 has been used previously to efficiently link peptides synthesized on conventional resins to a solid support that is compatible with aqueous solid phase native chemical ligations (cellulose, sepharose) (236, 237). Because of the chemoselective oxime formation, the attachment to the latter support here becomes essentially an affinity purification step which means that optionally no purification is necessary after SPPS. The size of the synthetic peptides (13-mer) is such that purified peptides are obtained. The N-terminal cysteine present on all peptides in the library are used for native chemical ligation with recombinant peptide 19 (LctA1-37), which is obtained in large quantities as the MESNA or ethanethiol thioester by intein chemistry (238). Such solid phase native chemical ligation is high yielding when using water-compatible solid supports (236, 237). After ligation, the peptide is cleaved from the support with aqueous base (236). Hence, the substrate library is optionally prepared without any chromatographic separations. A multiple peptide synthesizer is used to prepare ~1-5 mg of peptides in 96 well format, which translates to 96 LctA analog substrates after ligation and cleavage from the resin. After cleavage from the support we neutralize and redissolve the peptides in the 96-well plate in buffer and add LctM, ATP, $Mg^{2+}$ and $Zn^{2+}$. MS analysis is used to assess the composition of the resulting wells. The protease domain is used to remove the leader peptide. Agar diffusion assays are used with crude products to assess biological activity. Further evaluations are done in quantitative assays with purified products. This approach is relatively high throughput. Using unnatural Fmoc-protected amino acids, new compounds are generated, and the essential structural features for lacticin activity are investigated. Furthermore, lacticin's biological activity is optimized by increasing its interaction with its target, enhancing solubility, improving cellular uptake, and decreasing protease susceptibility. With respect to the latter, the use of peptoids is employed (239). The results of one 96-peptide screen are optionally used in designing a subsequent screen.

References for Example 11 et al

1. Gutowski-Eckel, Z., Klein, C., Siegers, K., Bohm, K., Hammelmann, M., Entian, K.-D. (1994). Growth phase-dependent regulation and membrane localization of SpaB, a protein involved in biosynthesis of the lantibiotic subtilin. Appl. Environ. Microbiol. 60, 1-11.
2. Engelke, G., Gutowski-Eckel, Z., Hammelmann, M., Entian, K.-D. (1992). Biosynthesis of the lantibiotic nisin: genomic organization and membrane localization of the NisB protein. Appl. Environ. Microbiol. 58, 3730-43.
3. Peschel, A., Ottenwälder, B., Götz, F. (1996). Inducible production and cellular location of the epidermin biosynthetic enzyme EpiB using an improved staphylococcal expression system. FEMS Microbiol. Lett. 137, 279-84.
4. Sen, A. K., Narbad, A., Horn, N., Dodd, H. M., Parr, A. J., Colquhoun, I., Gasson, M. J. (1999). Post-translational modification of nisin. The involvement of NisB in the dehydration process. Eur. J. Biochem. 261, 524-32.
5. Kupke, T., Götz, T. (1996). Expression, Purification, and Characterization of EpiC, an Enzyme Involved in the Biosynthesis of the Lantibiotic Epidermin, and Sequence Analysis of *Staphylococcus epidermidis* epiC Mutants. J. Bacteriol. 178, 1335-1340.
6. Jack, R. W., Jung, G. (2000). Lantibiotics and microcins: polypeptides with unusual chemical diversity. Curr. Opin. Chem. Biol. 4, 310-7.
7. Sahl, H. G., Bierbaum, G. (1998). Lantibiotics: biosynthesis and biological activities of uniquely modified peptides from gram-positive bacteria. Annu. Rev. Microbiol. 52, 41-79.
8. van Kraaij, C., de Vos, W. M., Siezen, R. J., Kuipers, O. P. (1999). Lantibiotics: biosynthesis, mode of action and applications. Nat. Prod. Rep. 16, 575-587.
9. McAuliffe, O., Ross, R. P., Hill, C. (2001). Lantibiotics: structure, biosynthesis and mode of action. FEMS Microbiol. Rev. 25, 285-308.
10. Swartz, M. N. (1994). Hospital-Acquired Infections: Diseases with Increasingly Limited Therapies. Proc. Natl. Acad. Sci. USA 91, 2420-2427.
11. Carbon, C. (2000). MRSA and MRSE: is there an answer? Clin Microbiol Infect 6 Suppl 2, 17-22.
12. Levy, S. B. (2000). The future of antibiotics: facing antibiotic resistance. Clin. Microbiol. Infect. 6 Suppl 3, 101-6.
13. Klaenhammer, T. R. (1993). Genetics of bacteriocins produced by lactic acid bacteria. FEMS Microbiol. Rev. 12, 39-85.

14. Nissen-Meyer, J., Nes, I. F. (1997). Ribosomally synthesized antimicrobial peptides: their function, structure, biogenesis, and mechanism of action. Arch. Microbiol. 167, 67-77.

15. Cleveland, J., Montville, T. J., Nes, I. F., Chikindas, M. L. (2001). Bacteriocins: safe, natural antimicrobials for food preservation. Int. J. Food Microbiol. 71, 1-20.

16. Nes, I. F., Holo, H. (2000). Class II antimicrobial peptides from lactic acid bacteria. Biopolymers 55, 50-61.

17. Ennahar, S., Sashihara, T., Sonomoto, K., Ishizaki, A. (2000). Class IIa bacteriocins: biosynthesis, structure and activity. FEMS Microbiol. Rev. 24, 85-106.

18. Moll, G. N., Konings, W. N., Driessen, A. J. (1999). Bacteriocins: mechanism of membrane insertion and pore formation. Antonie van Leeuwenhoek 76, 185-98.

19. Epand, R. M., Vogel, H. J. (1999). Diversity of antimicrobial peptides and their mechanisms of action. Biochim. Biophys. Acta 1462, 11-28.

20. For an in depth discussion of polyketide synthases see the November 1997 issue of Chem. Rev.

21. McCaskill, D., Croteau, R. (1997). Prospects for the bioengineering of isoprenoid biosynthesis. Adv. Biochem. Eng. Biotechnol. 55, 107-46.

22. Herrera, J. B. R., Wilson, W. K., Matsuda, S. P. T. (2000). A tyrosine-to-threonine mutation converts cycloartenol synthase to an oxidosqualene cyclase that forms lanosterol as its major product. J. Am. Chem. Soc. 122, 6765-6766.

23. Meyer, M. M., Segura, N. J. R., Wilson, W. K., Matsuda, S. P. T. (2000). Oxidosqualene cyclase residues that promote formation of cycloartenol, lanosterol, and parkeol. Angew. Chem. Int. Ed. Engl. 39, 4090-4092.

24. Cane, D. E. (1995). Isoprenoid antibiotics. Biotechnology 28, 633-55.

25. van der Meer, J. R., Rollema, H. S., Siezen, R. J., Beerthuyzen, M. M., Kuipers, O. P., de Vos, W. M. (1994). Influence of amino acid substitutions in the nisin leader peptide on biosynthesis and secretion of nisin by *Lactococcus lactis*. J. Biol. Chem. 269, 3555-62.

26. Kuipers, O. P., Beerthuyzen, M. M., de Ruyter, P. G., Luesink, E. J., de Vos, W. M. (1995). Autoregulation of nisin biosynthesis in *Lactococcus lactis* by signal transduction. J. Biol. Chem. 270, 27299-304.

27. Reis, M., Eschbach-Bludau, M., Iglesias-Wind, M. I., Kupke, T., Sahl, H. G. (1994). Producer immunity towards the lantibiotic Pep5: identification of the immunity gene pepl and localization and functional analysis of its gene product. Appl. Environ. Microbiol. 60, 2876-83.

28. Bierbaum, G., Reis, M., Szekat, C., Sahl, H. G. (1994). Construction of an expression system for engineering of the lantibiotic Pep5. Appl. Environ. Microbiol. 60, 4332-8.

29. Schnell, N., Entian, K.-D., Schneider, U., Götz, F., Zahner, H., Kellner, R., Jung, G. (1988). Prepeptide sequence of epidermin, a ribosomally synthesized antibiotic with four sulphide-rings. Nature 333, 276-278.

30. Sahl, H.-G., Jack, R. W., Bierbaum, G. (1995). Biosynthesis and Biological Activities of Lantibiotics with Unique Post-Translational Modifications. Eur. J. Biochem. 230, 827-853.

31. Guder, A., Wiedemann, I., Sahl, H. G. (2000). Posttranslationally modified bacteriocins—the lantibiotics. Biopolymers 55, 62-73.

32. Delves-Broughton, J., Blackburn, P., Evans, R. J., Hugenholtz, J. (1996). Applications of the bacteriocin, nisin. Antonie van Leeuwenhoek 69, 193-202.

33. Rayman, M. K., Aris, B., Hurst, A. (1981). Nisin: a possible alternative or adjunct to nitrite in the preservation of meats. Appl. Environ. Microbiol. 41, 375-80.

34. Hurst, A. (1981). Nisin. Adv. Appl. Microbiol. 27, 85-123.

35. Kupke, T., Götz, F. (1996). Post-Translational Modifications of Lantibiotics. Antonie van Leeuwenhoek 69, 139-150.

36. Nes, I. F., Tagg, J. R. (1996). Novel lantibiotics and their pre-peptides. Antonie van Leeuwenhoek 69, 89-97.

37. Ingram, L. C. (1969). Synthesis of the antibiotic nisin: formation of lanthionine and beta-methyl-lanthionine. Biochim. Biophys. Acta 184, 216-9.

38. Schnell, N., Engelke, G., Augustin, J., Rosenstein, R., Ungermann, V., Götz, F., Entian, K.-D. (1992). Analysis of genes involved in the biosynthesis of the lantibiotic epidermin. Eur. J. Biochem. 204, 57-68.

39. Jung, G. (1991). Lantibiotics-Ribosomally synthesized biologically active polypeptides containing sulfide bridges and a,b-dehydroamino acids. Angew. Chem. Intl. Ed. Engl. 30, 1051-1068.

40. Sahl, H.-G. (1991). Pore formation in baterial membranes by cationic lantibiotics. In Nisin and novel Lantibiotics. (G. Jung and H.-G. Sahl, Ed.), pp 347-358, ESCOM, Leiden, The Netherlands.

41. Driessen, A. J., van den Hooven, H. W., Kuiper, W., van de Kamp, M., Sahl, H. G., Konings, R. N., Konings, W. N. (1995). Mechanistic studies of lantibiotic-induced permeabilization of phospholipid vesicles. Biochemistry 34, 1606-14.

42. Moll, G. N., Roberts, G. C., Konings, W. N., Driessen, A. J. (1996). Mechanism of lantibiotic-induced pore-formation. Antonie van Leeuwenhoek 69, 185-91.

43. Fredenhagen, A., Fendrich, G., Marki, F., Marki, W., Gruner, J., Raschdorf, F., Peter, H. H. (1990). Duramycins B and C, two new lanthionine containing antibiotics as inhibitors of phospholipase A2. Structural revision of duramycin and cinnamycin. J. Antibiot. (Tokyo) 43, 1403-12.

44. Marki, F., Hanni, E., Fredenhagen, A., van Oostrum, J. (1991). Mode of action of the lanthionine-containing peptide antibiotics duramycin, duramycin B and C, and cinnamycin as indirect inhibitors of phospholipase A2. Biochem. Pharmacol. 42, 2027-35.

45. Kido, Y., Hamakado, T., Yoshida, T., Anno, M., Motoki, Y., Wakamiya, T., Shiba, T. (1983). Isolation and characterization of ancovenin, a new inhibitor of angiotensin I converting enzyme, produced by actinomycetes. J. Antibiot. (Tokyo) 36, 1295-9.

46. Chatterjee, S., Chatterjee, D. K., Jani, R. H., Blumbach, J., Ganguli, B. N., Klesel, N., Limbert, M., Seibert, G. (1992). Mersacidin, a new antibiotic from *Bacillus*. In vitro and in vivo antibacterial activity. J. Antibiot. (Tokyo) 45, 839-45.

47. Limbert, M. D., Isert, D., Klesel, N., Markus, A., Seibert, G., Chatterjee, S., Chatterjee, D. K., Jani, R. H., Ganguli, B. N. (1991). Chemotherapeutic properties of mersacidin in vitro and in vivo. In Nisin and novel Lantibiotics. (G. Jung and H.-G. Sahl, Ed.), pp 448-456, ESCOM, Leiden, The Netherlands.

48. Bierbaum, G., Brotz, H., Koller, K. P., Sahl, H. G. (1995). Cloning, sequencing and production of the lantibiotic mersacidin. FEMS Microbiol. Lett. 127, 121-6.

49. Banerjee, S., Hansen, J. N. (1988). Structure and expression of a gene encoding the precursor of subtilin, a small protein antibiotic. J. Biol. Chem. 262, 9508-9514.

50. Breukink, E., Wiedemann, I., van Kraaij, C., Kuipers, O. P., Sahl, H., de Kruijff, B. (1999). Use of the cell wall precursor lipid II by a pore-forming peptide antibiotic. Science 286, 2361-4.

51. Enserink, M. (1999). Promising antibiotic candidate identified. Science 286, 2245, 2247.

52. Breukink, E., de Kruijff, B. (1999). The lantibiotic nisin, a special case or not? Biochim. Biophys. Acta 1462, 223-34.

53. Wiedemann, I., Breukink, E., van Kraaij, C., Kuipers, O. P., Bierbaum, G., de Kruijff, B., Sahl, H. G. (2001). Specific binding of nisin to the peptidoglycan precursor lipid II combines pore formation and inhibition of cell wall biosynthesis for potent antibiotic activity. J. Biol. Chem. 276, 1772-9.

54. Brötz, H., Josten, M., Wiedemann, I., Schneider, U., Gotz, F., Bierbaum, G., Sahl, H.-G. (1998). Role of lipid-bound peptidoglycan precursors in the formation of pores by nisin, epidermin and other lantibiotics. Mol. Microbiol. 30, 317-327.

55. Hechard, Y., Sahl, H. G. (2002). Mode of action of modified and unmodified bacteriocins from Gram-positive bacteria. Biochimie 84, 545-57.

56. Dufour, A., Thuault, D., Boulliou, A., Bourgeois, C. M., Le Pennec, J. P. (1991). Plasmid-encoded determinants for bacteriocin production and immunity in a *Lactococcus lactis* strain and purification of the inhibitory peptide. J Gen Microbiol 137 (Pt 10), 2423-9.

57. Piard, J. C., Muriana, P. M., Desmazeaud, M. J., Klaenhammer, T. R. (1992). Purification and partial characterization of lacticin 481, a lanthionine-containing bacteriocin produced by *Lactococcus lactis* subsp. *lactis* CNRZ 481. Appl. Environ. Microbiol. 58, 279-84.

58. Rince, A., Dufour, A., Le Pogam, S., Thuault, D., Bourgeois, C. M., Le Pennec, J. P. (1994). Cloning, expression, and nucleotide sequence of genes involved in production of lactococcin DR, a bacteriocin from *lactococcus lactis* subsp. *lactis*. Appl. Environ. Microbiol. 60, 1652-7.

59. Pridmore, D., Rekhif, N., Pittet, A. C., Suri, B., Mollet, B. (1996). Variacin, a new lanthionine-containing bacteriocin produced by *Micrococcus* varians: comparison to lacticin 481 of *Lactococcus lactis*. Appl. Environ. Microbiol. 62, 1799-802.

60. O'Sullivan, L., Morgan, S. M., Ross, R. P., Hill, C. (2002). Elevated enzyme release from lactococcal starter cultures on exposure to the lantibiotic lacticin 481, produced by *Lactococcus lactis* DPC5552. J Dairy Sci 85, 2130-40.

61. O'Sullivan, L., Ryan, M. P., Ross, R. P., Hill, C. (2003). Generation of food-grade lactococcal starters which produce the lantibiotics lacticin 3147 and lacticin 481. Appl. Environ. Microbiol. 69, 3681-5.

62. Piard, J. C., Delorme, F., Giraffa, G., Commissaire, J., Desmazeaud, M. (1990). Evidence for a bacteriocin produced by *Lactococcus lactis* CNRZ 481. Neth. Milk and Dairy J. 44, 143-58.

63. Thuault, D., Beliard, E., Le Guern, J., Bourgeois, C. M. (1991). Inhibition of *Clostridium* tyrobutyricum by bacteriocin-like substances produced by lactic acid bacteria. J Dairy Sci 74, 1145-50.

64. O'Sullivan, L., Ross, R. P., Hill, C. (2002). Potential of bacteriocin-producing lactic acid bacteria for improvements in food safety and quality. Biochimie 84, 593-604.

65. Chakicherla, A., Hansen, J. N. (1995). Role of the leader and structural regions of prelantibiotic peptides as assessed by expressing nisin-subtilin chimeras in *Bacillus subtilis* 168, and characterization of their physical, chemical, and antimicrobial properties. J. Biol. Chem. 270, 23533-9.

66. Kuipers, O. P., Rollema, H. S., de Vos, W. M., Siezen, R. J. (1993). Biosynthesis and secretion of a precursor of nisin Z by *Lactococcus lactis*, directed by the leader peptide of the homologous lantibiotic subtilin from *Bacillus subtilis*. FEBS Lett. 330, 23-7.

67. Piard, J. C., Kuipers, O. P., Rollema, H. S., Desmazeaud, M. J., de Vos, W. M. (1993). Structure, organization, and expression of the Id gene for lacticin 481, a novel lantibiotic produced by *Lactococcus lactis*. J. Biol. Chem. 268, 16361-8.

68. Entian, K.-D., de Vos, W. M. (1996). Genetics of subtilin and nisin biosyntheses: biosynthesis of lantibiotics. Antonie van Leeuwenhoek 69, 109-17.

69. Jack, R., Bierbaum, G., Heidrich, C., Sahl, H.-G. (1995). The Genetics of Lantibiotic Biosynthesis. BioEssays 17, 793-802.

70. Meyer, H. E., Heber, M., Eisermann, B., Korte, H., Metzger, J. W., Jung, G. (1994). Sequence analysis of lantibiotics: chemical derivatization procedures allow a fast access to complete Edman degradation. Anal. Biochem. 223, 185-90.

71. Weil, H. P., Beck-Sickinger, A. G., Metzger, J., Stevanovic, S., Jung, G., Josten, M., Sahl, H. G. (1990). Biosynthesis of the lantibiotic Pep5. Isolation and characterization of a prepeptide containing dehydroamino acids. Eur. J. Biochem. 194, 217-23.

72. Koponen, O., Tolonen, M., Qiao, M. Q., Wahlstrom, G., Helin, J., Saris, P. E. J. (2002). NisB is required for the dehydration and NisC for the lanthionine formation in the post-translational modification of nisin. Microbiology 148, 3561-3568.

73. Kiesau, P., Eikmanns, U., Gutowski-Eckel, Z., Weber, S., Hammelmann, M., Entian, K.-D. (1997). Evidence for a multimeric subtilin synthetase complex. J. Bacteriol. 179, 1475-81.

74. Siegers, K., Heinzmann, S., Entian, K.-D. (1996). Biosynthesis of lantibiotic nisin. Posttranslational modification of its prepeptide occurs at a multimeric membrane-associated lanthionine synthetase complex. J. Biol. Chem. 271, 12294-12301.

75. Kuipers, O. P., Bierbaum, G., Ottenwälder, B., Dodd, H. M., Horn, N., Metzger, J., Kupke, T., Gnau, V., Bongers, R., van den Bogaard, P., Kosters, H., Rollema, H. S., de Vos, W. M., Siezen, R. J., Jung, G., Götz, F., Sahl, H. G., Gasson, M. J. (1996). Protein engineering of lantibiotics. Antonie van Leeuwenhoek 69, 161-169.

76. Kuipers, O. P., Rollema, H. S., Yap, W. M., Boot, H. J., Siezen, R. J., de Vos, W. M. (1992). Engineering dehydrated amino acid residues in the antimicrobial peptide nisin. J. Biol. Chem. 267, 24340-6.

77. Chan, W. C., Dodd, H. M., Horn, N., Maclean, K., Lian, L. Y., Bycroft, B. W., Gasson, M. J., Roberts, G. C. (1996). Structure-activity relationships in the peptide antibiotic nisin: role of dehydroalanine 5. Appl. Environ. Microbiol. 62, 2966-9.

78. Liu, W., Hansen, J. N. (1993). The antimicrobial effect of a structural variant of subtilin against outgrowing *Bacillus cereus* T spores and vegetative cells occurs by different mechanisms. Appl. Environ. Microbiol. 59, 648-651.

79. Morris, S. L., Hansen, J. N. (1981). Inhibition of *Bacillus cereus* spore outgrowth by covalent modification of a sulfhydryl group by nitrosothiol and iodoacetate. J. Bacteriol. 148, 465-71.

80. Spee, J. H., de Vos, W. M., Kuipers, O. P. (1993). Efficient random mutagenesis method with adjustable mutation frequency by use of PCR and dITP. Nucleic Acids Res. 21, 777-8.

81. Rollema, H. S., Kuipers, O. P., Both, P., de Vos, W. M., Siezen, R. J. (1995). Improvement of solubility and stability of the antimicrobial peptide nisin by protein engineering. Appl. Environ. Microbiol. 61, 2873-8.

82. Liu, W., Hansen, J. N. (1992). Enhancement of the chemical and antimicrobial properties of subtilin by site-directed mutagenesis. J. Biol. Chem. 267, 25078-85.
83. Okeley, N. M., Zhu, Y., van der Donk, W. A. (2000). Facile Chemoselective Synthesis of Dehydroalanine-Containing Peptides. Org. Lett. 2, 3603-3606.
84. Zhou, H., van der Donk, W. A. (2002). Biomimetic Stereoselective Formation of Methyllanthionine. Org. Lett. 4, 1335-1338.
85. Gieselman, M. D., Xie, L., van der Donk, W. A. (2001). Synthesis of a Selenocysteine-Containing Peptide by Native Chemical Ligation. Org. Lett. 3, 1331-1334.
86. Zhou, H., van der Donk, W. A. (2001). Synthesis of 2-Amino-3-fluoro-acrylic Acid Containing Peptides. Org. Lett. 3, 593-596.
87. Zhou, H., Schmidt, D. M., Gerlt, J. A., van der Donk, W. A. (2003). Chemical and Enzymatic Synthesis of Fluorinated Dehydroalanine-Containing Peptides. Chembiochem in press.
88. Schmidt, D. M., Hubbard, B. K., Gerlt, J. A. (2001). Evolution of enzymatic activities in the enolase superfamily: functional assignment of unknown proteins in *Bacillus subtilis* and *Escherichia coli* as L-Ala-D/L-Glu epimerases. Biochemistry 40, 15707-15.
89. Okeley, N. M., Blackburn, N., van der Donk, W. A. (2003). SpaC and NisC, the Cyclases Involved in Subtilin and Nisin Biosynthesis, are Zinc Proteins. submitted for publication.
90. Gonzalez, J. C., Peariso, K., Penner-Hahn, J. E., Matthews, R. G. (1996). Cobalamin-Independent Methionine Synthase from *Escherichia coli*: A Zinc Metalloenzyme. Biochemistry 35, 12228-12234.
91. Goulding, C. W., Matthews, R. G. (1997). Cobalamin-dependent methionine synthase from *Escherichia coli*: involvement of zinc in homocysteine activation. Biochemistry 36, 15749-57.
92. Casey, P. J., Seabra, M. C. (1996). Protein prenyltransferases. J. Biol. Chem. 271, 5289-92.
93. Fu, H. W., Moomaw, J. F., Moomaw, C. R., Casey, P. J. (1996). Identification of a cysteine residue essential for activity of protein farnesyltransferase. Cys299 is exposed only upon removal of zinc from the enzyme. J. Biol. Chem. 271, 28541-8.
94. Fu, H. W., Beese, L. S., Casey, P. J. (1998). Kinetic analysis of zinc ligand mutants of mammalian protein farnesyltransferase. Biochemistry 37, 4465-72.
95. Huang, C. C., Casey, P. J., Fierke, C. A. (1997). Evidence for a catalytic role of zinc in protein farnesyltransferase. Spectroscopy of Co2+-farnesyltransferase indicates metal coordination of the substrate thiolate. J. Biol. Chem. 272, 20-3.
96. Myers, L. C., Terranova, M. P., Nash, H. M., Markus, M. A., Verdine, G. L. (1992). Zinc binding by the methylation signaling domain of the *Escherichia coli* Ada protein. Biochemistry 31, 4541-7.
97. Myers, L. C., Terranova, M. P., Ferentz, A. E., Wagner, G., Verdine, G. L. (1993). Repair of DNA methylphosphotriesters through a metalloactivated cysteine nucleophile. Science 261, 1164-7.
98. Matthews, R. G., Goulding, C. W. (1997). Enzyme-catalyzed methyl transfers to thiols: the role of zinc. Curr. Opin. Chem. Biol. 1, 332-9.
99. Hightower, K. E., Fierke, C. A. (1999). Zinc-catalyzed sulfur alkylation: insights from protein farnesyltransferase. Curr. Opin. Chem. Biol. 3, 176-181.
100. Bertini, I., Luchinat, C., Rosi, M., Sgamellotti, A., Tarantelli, F. (1990). pKa of zinc-bound water and nucleophilicity of hydroxo-containing species. Ab initio calculations on models for zinc enzymes. Inorg. Chem. 29, 1460-3.
101. Saderholm, M. J., Hightower, K. E., Fierke, C. A. (2000). Role of Metals in the Reaction Catalyzed by Protein Farnesyltransferase. Biochemistry 39, 12398-12405.
102. Hightower, K. E., Huang, C. C., Casey, P. J., Fierke, C. A. (1998). H-Ras peptide and protein substrates bind protein farnesyltransferase as an ionized thiolate. Biochemistry 37, 15555-62.
103. Rozema, D. B., Poulter, C. D. (1999). Yeast protein farnesyltransferase. pKas of peptide substrates bound as zinc thiolates. Biochemistry 38, 13138-13146.
104. Vallee, B. L., Auld, D. S. (1990). Active-site zinc ligands and activated water of zinc enzymes. Proc. Natl. Acad. Sci. U. S. A. 87, 220-4.
105. Vallee, B. L., Auld, D. S. (1993). Zinc: biological functions and coordination motifs. Acc. Chem. Res. 26, 543-51.
106. Bauer, H., Mayer, H., Marchler-Bauer, A., Salzer, U., Prohaska, R. (2000). Characterization of p40/GPR69A as a peripheral membrane protein related to the lantibiotic synthetase component C. Biochem. Biophys. Res. Commun. 275, 69-74.
107. Mayer, H., Bauer, H., Breuss, J., Ziegler, S., Prohaska, R. (2001). Characterization of rat LANCL1, a novel member of the lanthionine synthetase C-like protein family, highly expressed in testis and brain. Gene 269, 73-80.
108. Mayer, H., Bauer, H., Prohaska, R. (2001). Organization and chromosomal localization of the human and mouse genes coding for LanC-like protein 1 (LANCL1). Cytogenet. Cell Genet. 93, 100-4.
109. Mayer, H., Pongratz, M., Prohaska, R. (2001). Molecular cloning, characterization, and tissue-specific expression of human LANCL2, a novel member of the LanC-like protein family. DNA Seq. 12, 161-6.
110. Park, S., James, C. D. (2003). Lanthionine synthetase components C-like 2 increases cellular sensitivity to adriamycin by decreasing the expression of P-glycoprotein through a transcription-mediated mechanism. Cancer Res 63, 723-7.
111. Zhu, Y., Gieselman, M., Zhou, H., Averin, O., van der Donk, W. A. (2003). Biomimetic studies on the mechanism of stereoselective lanthionine formation. submitted.
112. Xie, L., Chatterjee, C., Balsara, R., Okeley, N. M., van der Donk, W. A. (2002). Heterologous expression and purification of SpaB involved in subtilin biosynthesis. Biochem. Biophys. Res. Commun. 295, 952-7.
113. Rince, A., Dufour, A., Uguen, P., Le Pennec, J. P., Haras, D. (1997). Characterization of the lacticin 481 operon: the *Lactococcus lactis* genes IctF, IctE, and IctG encode a putative ABC transporter involved in bacteriocin immunity. Appl. Environ. Microbiol. 63, 4252-60.
114. Woodruff, W. A., Novak, J., Caufield, P. W. (1998). Sequence analysis of mutA and mutM genes involved in the biosynthesis of the lantibiotic mutacin II in *Streptococcus mutans*. Gene 206, 37-43.
115. Dougherty, B. A., Hill, C., Weidman, J. F., Richardson, D. R., Venter, J. C., Ross, R. P. (1998). Sequence and analysis of the 60 kb conjugative, bacteriocin-producing plasmid pMRC01 from *Lactococcus lactis* DPC3147. Mol. Microbiol. 29, 1029-38.
116. Kalmokoff, M. L., Lu, D., Whitford, M. F., Teather, R. M. (1999). Evidence for production of a new lantibiotic (butyrivibriocin OR79A) by the ruminal anaerobe Butyrivibrio fibrisolvens OR79: characterization of the structural gene encoding butyrivibriocin OR79A. Appl. Environ. Microbiol. 65, 2128-35.

117. Navaratna, M. A., Sahl, H. G., Tagg, J. R. (1999). Identification of genes encoding two-component lantibiotic production in *Staphylococcus aureus* C55 and other phage group II *S. aureus* strains and demonstration of an association with the exfoliative toxin B gene. Infect. Immun. 67, 4268-71.

118. McLaughlin, R. E., Ferretti, J. J., Hynes, W. L. (1999). Nucleotide sequence of the streptococcin A-FF22 lantibiotic regulon: model for production of the lantibiotic SA-FF22 by strains of *Streptococcus pyogenes*. FEMS Microbiol. Lett. 175, 171-7.

119. Uguen, P., Le Pennec, J. P., Dufour, A. (2000). Lantibiotic biosynthesis: interactions between prelacticin 481 and its putative modification enzyme, LctM. J. Bacteriol. 182, 5262-6.

120. Altena, K., Guder, A., Cramer, C., Bierbaum, G. (2000). Biosynthesis of the lantibiotic mersacidin: organization of a type B lantibiotic gene cluster. Appl. Environ. Microbiol. 66, 2565-71.

121. Siezen, R. J., Kuipers, O. P., de Vos, W. M. (1996). Comparison of lantibiotic gene clusters and encoded proteins. Antonie van Leeuwenhoek 69, 171-84.

122. Skaugen, M., Abildgaard, C. I., Nes, I. F. (1997). Organization and expression of a gene cluster involved in the biosynthesis of the lantibiotic lactocin S. Mol. Gen. Genet. 253, 674-86.

123. Chen, P., Qi, F., Novak, J., Caufield, P. W. (1999). The specific genes for lantibiotic mutacin II biosynthesis in *Streptococcus mutans* T8 are clustered and can be transferred en bloc. Appl. Environ. Microbiol. 65, 1356-60.

124. Ryan, M. P., Jack, R. W., Josten, M., Sahl, H. G., Jung, G., Ross, R. P., Hill, C. (1999). Extensive post-translational modification, including serine to D-alanine conversion, in the two-component lantibiotic, lacticin 3147. J. Biol. Chem. 274, 37544-50.

125. Barber, M., Elliot, G. J., Bordoli, R. S., Green, B. N., Bycroft, B. W. (1988). Confirmation of the structure of nisin and its major degradation product by FAB-MS and FAB-MS/MS. Experientia 44, 266-70.

126. Liptak, M., Vekey, K., van Dongen, W. D., Heerma, W. (1994). Fast atom bombardment mass spectrometry of some lantibiotics. Biol Mass Spectrom 23, 701-6.

127. Koide, T., Itoh, H., Otaka, A., Yasui, H., Kuroda, M., Esaki, N., Soda, K., Fujii, N. (1993). Synthetic Study on Selenocystine-Containing Peptides. Chem. Pharm. Bull. 41, 502-506.

128. Koide, T., Itoh, H., Otaka, A., Furuya, M., Kitajima, Y., Fujii, N. (1993). Syntheses and biological activities of selenium analogs of .alpha.-rat atrial natriuretic peptide. Chem. Pharm. Bull. 41, 1596-600.

129. Moroder, L., Besse, D., Musiol, H.-J., Rudolph-Bohner, S., Siedler, F. (1996). Oxidative Folding of Cystine-Rich Peptides vs Regioselective Cysteine Pairing Strategies. Biopolymers 40, 207-234.

130. Besse, D., Siedler, F., Diercks, T., Kessler, H., Moroder, L. (1997). The Redox Potential of Selenocystine in Unconstrained Cyclic Peptides. Angew. Chem. Int. Ed. Engl. 36, 883-885.

131. Fiori, S., Pegoraro, S., Rudolph-Bohner, S., Cramer, J., Moroder, L. (2000). Synthesis and conformational analysis of apamin analogues with natural and non-natural cystine/selenosystine connectivities. Biopolymers 53, 550-564.

132. Dawson, P. E., Muir, T. W., Clark-Lewis, I., Kent, S. B. (1994). Synthesis of proteins by native chemical ligation. Science 266, 776-779.

133. Dawson, P. E., Kent, S. B. H. (2000). Synthesis of native proteins by chemical ligation. Annu. Rev. Biochem. 69, 923-960.

134. Gieselman, M. D., Zhu, Y., Zhou, H., Galonic, D., van der Donk, W. A. (2002). Selenocysteine Derivatives for Chemoselective Ligations. Chembiochem 3, 709-716.

135. Muir, T. W., Sondhi, D., Cole, P. A. (1998). Expressed protein ligation: a general method for protein engineering. Proc. Natl. Acad. Sci. U.S.A. 95, 6705-10.

136. Evans, T. C., Benner, J., Xu, M. Q. (1998). Semisynthesis of Cytotoxic Proteins Using a Modified Protein Splicing Element. Protein Sci. 7, 2256-2264.

137. Shey, J., McGinley, C. M., McCauley, K. M., Dearth, A., Young, B., van der Donk, W. A. (2002). Mechanistic Investigation of a Novel Vitamin B12-Catalyzed Carbon-Carbon Bond Forming Reaction. J. Org. Chem. 67, 837-846.

138. Zhu, Y., van der Donk, W. A. (2001). Convergent Synthesis of Peptide Conjugates Using Dehydroalanines for Chemoslective Ligations. Org. Lett. 3, 1189-1192.

139. Lemieux, G. A., Bertozzi, C. R. (1998). Chemoselective ligation reactions with proteins, oligosaccharides and cells. TIBTECH 16, 506-513.

140. Horton, D., Wander, J. D. (1990). In Carbohydrates: Chemistry and Biochemistry. (W. W. Pigman and D. Horton, Ed.), pp 799-842, Academic Press, New York.

141. Milne, J. C., Eliot, A. C., Kelleher, N. L., Walsh, C. T. (1998). ATP/GTP hydrolysis is required for oxazole and thiazole biosynthesis in the peptide antibiotic microcin B17. Biochemistry 37, 13250-61.

142. Meyer, C., Bierbaum, G., Heidrich, C., Reis, M., &fling, J., Iglesias-Wind, M. I., Kempter, C., Molitor, E., Sahl, H.-G. (1995). Nucleotide Sequence of the Lantibiotic Pep5 Biosynthetic Gene Cluster and Functional Analysis of PepP and PepC. Eur. J. Biochem. 232, 478-489.

143. Rose, I. A., O'Connell, E. L., Litwin, S. (1974). Determination of the rate of hexokinase-glucose dissociation by the isotope-trapping method. J. Biol. Chem. 249, 5163-8.

144. Wilkinson, K. D., Rose, I. A. (1979). Isotope trapping studies of yeast hexokinase during steady state catalysis. A combined rapid quench and isotope trapping technique. J. Biol. Chem. 254, 12567-72.

145. Rose, I. A. (1980). The isotope trapping method: desorption rates of productive E. S complexes. Methods Enzymol. 64, 47-59.

146. Radisky, E. S., Poulter, C. D. (2000). Squalene synthase: steady-state, pre-steady-state, and isotope-trapping studies. Biochemistry 39, 1748-60.

147. Mathis, J. R., Back, K., Starks, C., Noel, J., Poulter, C. D., Chappell, J. (1997). Pre-steady-state study of recombinant sesquiterpene cyclases. Biochemistry 36, 8340-8.

148. Mullins, L. S., Raushel, F. M. (1999). Channeling of ammonia through the intermolecular tunnel contained within carbamoyl phosphate synthetase. J. Am. Chem. Soc. 121, 3803-3804.

149. Caperelli, C. A., Frey, W. A., Benkovic, S. J. (1978). Isotope-tapping experiments with rabbit liver fructose bisphosphatase. Biochemistry 17, 1699-704.

150. Raushel, F. M., Villafranca, J. J. (1979). Determination of rate-limiting steps of *Escherichia coli* carbamoyl-phosphate synthase. Rapid quench and isotope partitioning experiments. Biochemistry 18, 3424-9.

151. Li, Y. M., Milne, J. C., Madison, L. L., Kolter, R., Walsh, C. T. (1996). From peptide precursors to oxazole and thiazole-containing peptide antibiotics: microcin B17 synthase. Science 274, 1188-93.

152. Kelleher, N. L., Belshaw, P. J., Walsh, C. T. (1998). Regioselectivity and Chemoselectivity Analysis of Oxazole and Thiazole Ring Formation by the Peptide-Heterocyclizing Microcin B17 Synthetase Using High-Resolution MS/MS. J. Am. Chem. Soc. 120, 9716-9717.
153. Kelleher, N. L., Hendrickson, C. L., Walsh, C. T. (1999). Posttranslational Heterocyclization of Cysteine and Serine Residues in the Antibiotic Microcin B17: Distributivity and Directionality. Biochemistry 38, 15623-15630.
154. Roepstorff, P., Fohlman, J. (1984). Proposal for a common nomenclature for sequence ions in mass spectra of peptides. Biomed Mass Spectrom 11, 601.
155. Krull, R. E., Chen, P., Novak, J., Kirk, M., Barnes, S., Baker, J., Krishna, N. R., Caufield, P. W. (2000). Biochemical structural analysis of the lantibiotic mutacin II. J. Biol. Chem. 275, 15845-50.
156. Kleinnijenhuis, A. J., Duursma, M. C., Bereuking, E., Heeren, R. M. A., Heck, A. J. R. (2003). Localization of Intramolecular Monosulfide Bridges in Lantibiotics Determined with Electron Capture Induced Dissociation. Anal. Chem. asap.
157. Marcille, F., Gomez, A., Joubert, P., Ladire, M., Veau, G., Clara, A., Gavini, F., Willems, A., Fons, M. (2002). Distribution of genes encoding the trypsin-dependent lantibiotic ruminococcin A among bacteria isolated from human fecal microbiota. Appl. Environ. Microbiol. 68, 3424-31.
158. Hynes, W. L., Friend, V. L., Ferretti, J. J. (1994). Duplication of the lantibiotic structural gene in M-type 49 group A *streptococcus* strains producing streptococcin A-M49. Appl. Environ. Microbiol. 60, 4207-9.
159. Hynes, W. L., Ferretti, J. J., Tagg, J. R. (1993). Cloning of the gene encoding Streptococcin A-FF22, a novel lantibiotic produced by *Streptococcus pyogenes*, and determination of its nucleotide sequence. Appl. Environ. Microbiol. 59, 1969-71.
160. Madison, L. L., Vivas, E. I., Li, Y. M., Walsh, C. T., Kolter, R. (1997). The leader peptide is essential for the post-translational modification of the DNA-gyrase inhibitor microcin B17. Mol. Microbiol. 23, 161-8.
161. Chen, P., Qi, F. X., Novak, J., Krull, R. E., Caufield, P. W. (2001). Effect of amino acid substitutions in conserved residues in the leader peptide on biosynthesis of the lantibiotic mutacin II. FEMS Microbiol Lett 195, 139-44.
162. Nair, S. K., Elbaum, D., Christianson, D. W. (1996). Unexpected binding mode of the sulfonamide fluorophore 5-dimethylamino-1-naphthalene sulfonamide to human carbonic anhydrase II. Implications for the development of a zinc biosensor. J. Biol. Chem. 271, 1003-7.
163. Nair, S. K., Krebs, J. F., Christianson, D. W., Fierke, C. A. (1995). Structural basis of inhibitor affinity to variants of human carbonic anhydrase II. Biochemistry 34, 3981-9.
164. Nair, S. K., Christianson, D. W. (1993). Structural consequences of hydrophilic amino acid substitutions in the hydrophobic pocket of human carbonic anhydrase II. Biochemistry 32, 4506-14.
165. Nair, S. K., Christianson, D. W. (1993). Crystallographic studies of azide binding to human carbonic anhydrase II. Eur. J. Biochem. 213, 507-15.
166. Nair, S. K., Christianson, D. W. (1991). Structural properties of human carbonic anhydrase II at pH 9.5. Biochem. Biophys. Res. Commun. 181, 579-84.
167. Nair, S. K., Calderone, T. L., Christianson, D. W., Fierke, C. A. (1991). Altering the mouth of a hydrophobic pocket. Structure and kinetics of human carbonic anhydrase II mutants at residue Val-121. J. Biol. Chem. 266, 17320-5.
168. Jarrett, J. T., Choi, C. Y., Matthews, R. G. (1997). Changes in protonation associated with substrate binding and Cob(I) alamin formation in cobalamin-dependent methionine synthase. Biochemistry 36, 15739-48.
169. Udwary, D. W., Merski, M., Townsend, C. A. (2002). A method for prediction of the locations of linker regions within large multifunctional proteins, and application to a type I polyketide synthase. J. Mol. Biol. 323, 585-98.
170. Neis, S., Bierbaum, G., Josten, M., Pag, U., Kempter, C., Jung, G., SahI, H. G. (1997). Effect of leader peptide mutations on biosynthesis of the lantibiotic Pep5. FEMS Microbiol. Lett. 149, 249-255.
171. Havarstein, L. S., Holo, H., Nes, I. F. (1994). The leader peptide of colicin V shares consensus sequences with leader peptides that are common among peptide bacteriocins produced by gram-positive bacteria. Microbiology 140 (Pt 9), 2383-9.
172. Havarstein, L. S., Diep, D. B., Nes, I. F. (1995). A family of bacteriocin ABC transporters carry out proteolytic processing of their substrates concomitant with export. Mol. Microbiol. 16, 229-40.
173. Venema, K., Kok, J., Marugg, J. D., Toonen, M. Y., Ledeboer, A. M., Venema, G., Chikindas, M. L. (1995). Functional analysis of the pediocin operon of *Pediococcusi* acidilactici PAC1.0: PedB is the immunity protein and PedD is the precursor processing enzyme. Mol. Microbiol. 17, 515-22.
174. Uguen, M., Uguen, P. (2002). The LcnC homologue cannot replace LctT in lacticin 481 export. FEMS Microbiol. Lett. 208, 99-103.
175. Bertini, I., Luchinat, C. (1984). High spin cobalt(II) as a probe for the investigation of metalloproteins. Adv. Inorg. Biochem. 6, 71-111.
176. Maret, W., Vallee, B. L. (1993). Cobalt as probe and label of proteins. Methods Enzymol. 226, 52-71.
177. Lane, R. W., Ibers, J. A., Frankel, R. B., Papaefthymiou, G. C., Holm, R. H. (1977). Synthetic analogs of the active sites of iron-sulfur proteins. 14. Synthesis, properties, and structures of bis(o-xylyl-.alpha.,.alpha.'-dithiolato)ferrate (II, III) anions, analogs of oxidized and reduced rubredoxin sites. J. Am. Chem. Soc. 99, 84-98.
178. May, S. W., Kuo, J. Y. (1978). Preparation and properties of cobalt(II) rubredoxin. Biochemistry 17, 3333-8.
179. Guo, J., Giedroc, D. P. (1997). Zinc Site Redesign in T4 Gene 32 Protein: Structure and Stability of Co(II) Complexes Formed by Wild-Type and Metal Ligand Substitution Mutants. Biochemistry 36, 730-742.
180. Roehm, P. C., Berg, J. M. (1998). Selectivity of Methylation of Metal-Bound Cysteinates and Its Consequences. J. Am. Chem. Soc. 120, 13083-13087.
181. Hunt, J. B., Neece, S. H., Schachman, H. K., Ginsburg, A. (1984). Mercurial-promoted Zn2+ release from *Escherichia coli* aspartate transcarbamoylase. J. Biol. Chem. 259, 14793-803.
182. Hunt, J. B., Neece, S. H., Ginsburg, A. (1985). The use of 4-(2-pyridylazo)resorcinol in studies of zinc release from *Escherichia coli* aspartate transcarbamoylase. Anal. Biochem. 146, 150-7.
183. Giedroc, D. P., Keating, K. M., Williams, K. R., Konigsberg, W. H., Coleman, J. E. (1986). Gene 32 protein, the single-stranded DNA binding protein from bacteriophage T4, is a zinc metalloprotein. Proc. Natl. Acad. Sci. U. S. A. 83, 8452-6.
184. Smith, D. J., Maggio, E. T., Kenyon, G. L. (1975). Simple alkanethiol groups for temporary blocking of sulfhydryl groups of enzymes. Biochemistry 14, 766-71.
185. Kenyon, G. L., Bruice, T. W. (1977). Novel sulfhydryl reagents. Methods Enzymol. 47, 407-30.
186. Qiu, H., Kodadek, T., Giedroc, D. P. (1994). Zinc-free and reduced T4 gene 32 protein binds single-stranded DNA weakly and fails to stimulate UvsX-catalyzed homologous pairing. J. Biol. Chem. 269, 2773-81.
187. Zhou, Z. S., Peariso, K., Penner-Hahn, J. E., Matthews, R. G. (1999). Identification of the Zinc Ligands in Cobalamin-Independent Methionine Synthase (MetE) from *Escherichia coli*. Biochemistry 38, 15915-15926.
188. Peariso, K., Goulding, C. W., Huang, S., Matthews, R. G., Penner-Hahn, J. E. (1998). Characterization of the Zinc Binding Site in Methionine Synthase Enzymes of *Escherichia coli*: The Role of Zinc in the Methylation of Homocysteine. J. Am. Chem. Soc. 120, 8410-8416.
189. Peariso, K., Zhou, Z. S., Smith, A. E., Matthews, R. G., Penner-Hahn, J. E. (2001). Characterization of the Zinc Sites in Cobalamin-Independent and Cobalamin-Dependent Methionine Synthase Using Zinc and Selenium X-ray Absorption Spectroscopy. Biochemistry 40, 987-993.
190. Cramer, S. P., Hille, R. (1985). Arsenite-inhibited xanthine oxidase—determination of the molybdenum-sulfur-arsenic geometry by EXAFS. J. Am. Chem. Soc. 107, 8164-9.
191. Jameson, D. M., Sawyer, W. H. (1995). Fluorescence anisotropy applied to biomolecular interactions. Methods Enzymol. 246, 283.
192. Haugland, R. P. (1996). Handbook of fluorescent probes and research chemicals. Molecular Probes, Eugene, Oreg.
193. Datta, D., Wang, P., Carrico, I. S., Mayo, S. L., Tirrell, D. A. (2002). A designed phenylalanyl-tRNA synthetase variant allows efficient in vivo incorporation of aryl ketone functionality into proteins. J. Am. Chem. Soc. 124, 5652-3.
194. McLafferty, F. W., Fridriksson, E. K., Horn, D. M., Lewis, M. A., Zubarev, R. A. (1999). Techview: biochemistry. Biomolecule mass spectrometry. Science 284, 1289-90.
195. Kelleher, N. L. (2000). From primary structure to function: biological insights from large-molecule mass spectra. Chem. Biol. 7, R37-R45.
196. Tagg, J. R., McGiven, A. R. (1971). Assay system for bacteriocins. Appl. Microbiol. 21, 943.
197. Hirsch, A. (1950). The assay of the antibiotic nisin. J. Gen. Microbiol. 4, 70-83.
198. Demel, R. A., Peelen, T., Siezen, R. J., De Kruijff, B., Kuipers, O. P. (1996). Nisin Z, mutant nisin Z and lacticin 481 interactions with anionic lipids correlate with antimicrobial activity. A monolayer study. Eur. J. Biochem. 235, 267-74.
199. Chikindas, M. L., Novak, J., Driessen, A. J., Konings, W. N., Schilling, K. M., Caufield, P. W. (1995). Mutacin II, a bactericidal antibiotic from *Streptococcus mutans*. Antimicrob Agents Chemother 39, 2656-60.
200. Belokon', Y. N., Sagyan, A. S., Djamgaryan, S. A., Bakhmutov, V. I., Vitt, S. V. (1990). General method for the asymmetric synthesis of anti-diastereomers of b-substituted L-2-aminobutanoic acids via chiral nickel(II) Schiff's Base complexes of dehydroaminobutanoic acid. X-ray crystal and molecular structure of the nickel(II) complex of the Schiff's base from [(benzylprolyl)amino] benzophenone and dehydroaminobutanoic acid. J. Chem. Soc. Perkin Trans. 1 2301-2310.
201. Baldwin, J. E., Adlington, R. M., Moss, N., Robinson, N. (1987). Penicillin biosynthesis: active site mapping with L-a-aminoadipoyl-C-methyl-L-cysteinyl)-D-valine variants. J. Chem. Soc. Chem. Commun. 1664-1667.
202. Böck, A., Forchhammer, K., Heider, J., Baron, C. (1991). Selenoprotein synthesis: an expansion of the genetic code. Trends Biochem. Sci. 16, 463-7.
203. Heider, J., Böck, A. (1993). Selenium metabolism in micro-organisms. Adv. Microb. Physiol. 35, 71-109.
204. Tormay, P., Wilting, R., Heider, J., Böck, A. (1994). Genes coding for the selenocysteine-inserting tRNA species from Desulfomicrobium baculatum and *Clostridium thermoaceticum*: structural and evolutionary implications. J. Bacteriol. 176, 1268-74.
205. Baron, C., Sturchler, C., Wu, X. Q., Gross, H. J., Krol, A., Böck, A. (1994). Eukaryotic selenocysteine inserting tRNA species support selenoprotein isynthesis in *Escherichia coli*. Nucleic Acids Res. 22, 2228-33.
206. Stadtman, T. C. (1991). Biosynthesis and function of selenocysteine-containing enzymes. J. Biol. Chem. 266, 16257-60.
207. Stadtman, T. C. (1996). Selenocysteine. Annu. Rev. Biochem. 65, 83-100.
208. Commans, S., Böck, A. (1999). Selenocysteine inserting tRNAs: an overview. FEMS Microbiol. Rev. 23, 335-51.
209. Nakajima, K., Oda, H., Okawa, K. (1983). Studies on 2-Aziridinecarboxylic acid. IX. Convenient synthesis of optically active S-alkylcysteine, threo-5-alkyl-b-methylcysteine, and lanthionine derivatives via the ring opening reaction of aziridine by several thiols. Bull. Chem. Soc. Jpn. 56, 520-522.
210. Pansare, S. V., Vederas, J. C. (1989). Synthesis and reactivity of b-lactones derived from L-threonine and related amino acids. J. Org. Chem. 54, 2311-2316.
211. Chen, P., Novak, J., Kirk, M., Barnes, S., Qi, F., Caufield, P. W. (1998). Structure-activity study of the lantibiotic mutacin II from *Streptococcus mutans* T8 by a gene replacement strategy. Appl. Environ. Microbiol. 64, 2335-40.
212. Silverman, R. B., Abeles, R. H. (1977). Mechanism of inactivation of gamma-cystathionase by beta,beta,beta-trifluoroalanine. Biochemistry 16, 5515-20.
213. Piettre, S., de Cock, C., Merenyi, R., Viehe, H. G. (1987). Synthesis of fluorinated vinylsulfides and selenides. Tetrahedron 43, 4309-4319.
214. Purrington, S. T., Pittman, J. H. (1987). The preparation of a-fluorosulfoxides and vinyl fluorides. Tetrahedron Lett. 28, 3901-3904.
215. Wang, E. A., Walsh, C. (1981). Characteristics of beta, beta-difluoroalanine and beta, beta, beta-trifluoroalanine as suicide substrates for *Escherichia coli* B alanine racemase. Biochemistry 20, 7539-46.
216. Kukhar, V. (1994). Fluorine-containing amino acids. J. Fluor. Chem. 69, 199-205.
217. Silverman, R. B., Abeles, R. H. (1976). Inactivation of pyridoxal phosphate dependent enzymes by mono- and polyhaloalanines. Biochemistry 15, 4718-23.
218. Amone, A., Bravo, P., Capelli, S., Fronza, G., Meille, S. V., Zanda, M. (1996). New versatile fluorinated chiral building blocks: synthesis and reactivity of optically pure a-(fluoroalkyl)-b-sulfinylenamines. J. Org. Chem. 61, 3375-3387.
219. Ayi, A., Guedj, R., Septe, B. (1995). Enzymatic hydrolysis of methyl 3,3-difluoro-2-amino esters. Synthesis of D- and L-3,3-difluoro-2-amino acids and their derivatives. J. Fluor. Chem. 73, 165-169.
220. Yamazaki, T., Haga, J., Kitazume, T. (1991). Preparation and evaluation of optically active 4,4-difluorothreonine as a potent novel antitumor material. Bioorg. Med. Chem. Lett. 1, 271-276.
221. Kitazume, T., Lin, J. T., Yamazaki, T. (1991). Stereocontrolled synthesis of 4,4,4-trifluorothreonine. Tetrahedron Asym. 2, 235-238.
222. Soloshonok, V. A. (1996). Practical synthesis of enantiopure fluoroamino acids of biological interest by asymmetric aldol reactions. ACS Symp. Ser. 639, 26-41.

223. Kollonitsch, J., Perkins, L. M., Patchett, A. A., Doldouras, G. A., Marburg, S., Duggan, D. E., Maycock, A. L., Aster, S. D. (1978). Selective inhibitors of biosynthesis of aminergic neurotransmitters. Nature 274, 906-8.

224. Wang, E., Walsh, C. (1978). Suicide substrates for the alanine racemase of *Escherichia coli* B. Biochemistry 17, 1313-21.

225. Wang, E. A., Kallen, R., Walsh, C. (1981). Mechanism-based inactivation of serine transhydroxymethylases by D-fluoroalanine and related amino acids. J. Biol. Chem. 256, 6917-26.

226. Walsh, C. (1982). Suicide substrates: mechanism based enzyme inactivators. Tetrahedron 38, 871-909.

227. Duthaler, R. O. (1994). Recent developments in the stereoselective synthesis of α-amino acids. Tetrahedron 50, 1539-1650.

228. Tellier, F., Sauvetre, R. (1991). Introduction stereoselective du groupement trifluoromethyle dans des systemes insatures. Tetrahedron Lett. 32, 5963-5964.

229. Mitra, A. K., Ostashevsky, I., Brewer, C. F. (1983). Synthesis and 19F spectra of tetra-L-alanine analogs containing selectively incorporated 3-fluoro-L-alanine residues. Int. J. Peptide Prot. Res. 22, 494-501.

230. Imperiali, B. (1988). Synthetic fluoropeptides as pharmacologically useful compounds. Adv. Biotechnol. Processes 10, 97-129.

231. Höss, E., Rudolph, M., Seymour, L., Schierlinger, C., Burger, K. (1993). Peptide modification by incorporation of a-trifluoromethyl α-amino acids via trifluoromethyl-substituted acylimines. J. Fluor. Chem. 61, 163-170.

232. Koksch, B., Sewald, N., Jakubke, H.-D., Burger, K. (1996). Synthesis and incorporation of a-trifluoromethyl-substituted amino acids into peptides. ACS Symp. Ser. 639, 42-58.

233. Koksch, B., Sewald, N., Hofmann, H. J., Burger, K., Jakubke, H. D. (1997). Proteolytically stable peptides by incorporation of alpha-Tfm amino acids. J. Pept. Sci. 3, 157-67.

234. Lam, K. S., Salmon, S. E., Hersh, E. M., Hruby, V. J., Kazmierski, W. M., Knapp, R. J. (1991). A new type of synthetic peptide library for identifying ligand-binding activity. Nature 354, 82-4.

235. Houghten, R. A., Pinilla, C., Blondelle, S. E., Appel, J. R., Dooley, C. T., Cuervo, J. H. (1991). Generation and use of synthetic peptide combinatorial libraries for basic research and drug discovery. Nature 354, 84-6.

236. Canne, L. E., Botti, P., Simon, R. J., Chen, Y. J., Dennis, E. A., Kent, S. B. H. (1999). Chemical protein synthesis by solid phase ligation of unprotected peptide segments. J. Am. Chem. Soc. 121, 8720-8727.

237. Brik, A., Keinan, E., Dawson, P. E. (2000). Protein synthesis by solid-phase chemical ligation using a safety catch linker. J. Org. Chem. 65, 3829-3835.

238. Ayers, B., Blaschke, U. K., Camarero, J. A., Cotton, G. J., Holford, M., Muir, T. W. (1999). Introduction of unnatural amino acids into proteins using expressed protein ligation. Biopolymers 51, 343-354.

239. Burkoth, T. S., Fafarman, A. T., Charych, D. H., Connolly, M. D., Zuckermann, R. N. (2003). Incorporation of Unprotected Heterocyclic Side Chains into Peptoid Oligomers via Solid-Phase Submonomer Synthesis. J. Am. Chem. Soc. 125, asap.

240. Shey, J., van der Donk, W. A. (2000). Mechanistic Studies on the Vitamin B12-Catalyzed Dechlorination of Chlorinated Alkenes. J. Am. Chem. Soc. 122, 12403-12404.

241. Peng, S., Okeley, N. M., Tsai, A.-L., Wu, G., Kulmacz, R. J., van der Donk, W. A. (2001). Structural Characterization of a Pentadienyl Radical Intermediate Formed during Catalysis by Prostaglandin synthase-2. J. Am. Chem. Soc. 123, 3609-3610.

242. Peng, S., Okeley, N. M., Tsai, A.-L., Wu, G., Kulmacz, R. J., van der Donk, W. A. (2002). Synthesis of Isotopically Labeled Arachidonic Acids to Probe the Reaction Mechanism of Prostaglandin H Synthase. J. Am. Chem. Soc. 124, 10785-10796.

243. Peng, S., van der Donk, W. A. (2003). An Unusual Isotope Effect on Substrate Inhibition in the Oxidation of Arachidonic Acid by Lipoxygenase. J. Am. Chem. Soc. in press.

244. Vrtis, J. M., White, A., Metcalf, W. W., van der Donk, W. A. (2001). Phosphite Dehydrogenase: An unusual Phosphoryl Transfer Reaction. J. Am. Chem. Soc. 123, 2672-2673.

245. Vrtis, J. M., White, A., Metcalf, W. W., van der Donk, W. A. (2002). Phosphite Dehydrogenase, a New Versatile Cofactor Regeneration Enzyme. Angew. Chem. Int. Ed. Engl. 41, 3257-3259.

Example 12

Modification of Leader Sequence can Result in Dehydration And Cyclization

In this example, a peptide is appended to the leader portion of a precursor peptide. The following substrate is utilized:

GSSHHHHHHSSGLVPRGSHMKEQNSFN-LLQEVTESELDLILGAKGGCGVIHTISHE (CVISHEA) (SEQ ID NO:45). This substrate undergoes three dehydrations. The nucleotide sequence until the parentheses is the same as the sequence provided for LctA1-37. The sequence within the parentheses is added by ligating a chemically prepared peptide. The sequence of this peptide and the location of the last Ser in the peptide is unrelated to currently known lantibiotics, yet this Ser is dehydrated. The next example shows an even more dramatic result.

The following substrate is utilized:

GSSHHHHHHSSGLVPRGSHMKEQNSFN-LLQEVTESELDLILGAKGGCGVIH<u>T</u>I<u>S</u>HE (CVISHIS HISHA) (SEQ ID NO:46). This substrate undergoes five dehydrations. Two dehydrations occur in the region that is derived from lacticin (underlined); three more dehydrations occur in the entirely unrelated peptide that is in parentheses.

Example 13

Use of Lacticin 481 to Effect Modification of Non-Native Substrates

In this example, a given modifying enzyme is used to achieve modification of one or more non-native substrate; in particular, lacticin 481 is used to effect modification of various substrates including mutacin II, Ruminococcin A, and derivatives thereof. The amino acid sequences of the substrates and their nucleotide sequences are shown below. The names of the lantibiotics are mutacin II and Ruminococcin A.

The following nomenclature is used below: LctYyyA means Lct is the leader of lacticin 481, and YyyA is the structural peptide for mutacin II or Ruminococcin A. The first part (a) of each sequence is the His-tag that comes from the plasmid, (b) is the LctA leader, and (c) is the structural region from the other lantibiotic.

For LctMutA, the amino acid sequence (SEQ ID NO:47) is:

```
(a) GSSHHHHHHSSGLVPRGSHMLE;

(b) MKEQNSFNLLQEVTESELDLILGA;
and

(c) NRWWQGVVPTVSYECRMNSWQHVFTCC.
```

The nucleotide sequence (SEQ ID NO:48) is

```
(a) ATGGGCAGCAGCCATCATCATCATCATCACAGCAGCGGCCTGGTGC
CGCGCGGCAGCCATATGCTCGAG;

(b) atgaaagaac aaaactcttt taatcttctt caagaagtga
cagaaagtga;
and

(c) attggacctt attttaggtg caaatcgttg gtggcaaggt
gttgtgccaa cggtctcata tgagtgtcgc atgaattcat
ggcaacatgt tttcacttgc tgttaa
```

We observe the expected 4 dehydrations of LctMutA, and the protease domain of LctT can remove the leader peptide and the His-tag.

For LctRumA, the amino acid sequence (SEQ ID NO:49) is:

```
(a) GSSHHHHHHSSGLVPRGSHMLE;

(b) MKEQNSFNLLQEVTESELDLILGA;
and

(c) GNGVLKTISHECNMNTWQFLFTCC.
```

The nucleotide sequence (SEQ ID NO:50) is:

```
(a) ATGGGCAGCAGCCATCATCATCATCATCACAGCAGCGGCCTGGTGC
CGCGCGGCAGCCATATGCTCGAG;

(b) atgaaagaac aaaactcttt taatcttctt caagaagtga
cagaaagtga;
and

(c) attggacctt attttaggtg caGGTAATGG TGTTCTTAAA
ACTATTTCTC ATGAATGTAA TATGAATACT TGGCAATTTC
TTTTTACTTG TTGTTAA
```

We observed the expected 4 dehydrations of LctRumA.

The substrate MutA was investigated to determine whether LctM requires the Lct leader sequence. For MutA, the amino acid sequence (SEQ ID NO:51) is:

```
(a) GSSHHHHHHSSGLVPRGSHMLE;

(b) MNKLNSNAWSLNEVSDSELDTILGG;
and

(c) NRWWQGWPTVSYECRMNSWQHVFTCC.
```

The nucleotide sequence (SEQ ID NO:52) is

```
(a) ATGGGCAGCAGCCATCATCATCATCATCACAGCAGCGGCCTGGTGC
CGCGCGGCAGCCATATGCTCGAGatg;

(b) aa caagttaaac agtaacgcag tagtttcttt gaatgaagtt
tcagattctg aattggatac tattttgggt ggtaatcgtt
ggtggcaagg tgttgtgcca acggtctcat atgagtgtcg
catgaattca tggcaacatg ttttcacttg ctgttaa
```

We observed 4 dehydrations for substrate MutA. Therefore the Lct leader sequence is not always necessary to achieve modification in vitro.

The substrate LctMutAK was investigated. For LctMutAK, the amino acid sequence (SEQ ID NO:53) is (a)

```
(a) GSSHHHHHHSSGLVPRGSHMLE;

(b) MKEQNSFNLLQEVTESELDLILGA;
and

(c) KNRWWQGWPTVSYECRMNSWQHVFTCC
```

The nucleotide sequence (SEQ ID NO:54) is

```
(a) ATGGGCAGCAGCCATCATCATCATCATCACAGCAGCGGCCTGGTGC
CGCGCGGCAGCCATATGCTCGAG;

(b) atgaaagaac aaaactcttt taatcttctt caagaagtga
cagaaagtga;
and

(c) attggacctt attttaggtg caaagaatcgttg gtggcaaggt
gttgtgccaa cggtctcata tgagtgtcgc atgaattcat
ggcaacatgt tttcacttgc tgttaa
```

We observe 4 dehydrations; here we installed a Lys at the beginning of the MutA structural region which allows us to remove the leader and the His tag using the commercially available protease LysC.

Example 14

Variations of Lacticin Substrates

Certain mutants or substitutions of the lacticin substrate are generated and tested. For example, homocysteine or selenocysteine is used in place of cysteine; the resulting substrate undergoes dehydration, cyclization, or dehydration and cyclization.

SEQ ID NO:55, GSSHHHHHHSSGLVPRGSHMKEQNSFNLLQEVTESELDLILGAKGGSGVIHTISHECN (NIe)NSA, undergoes complete dehydration (-3H2O) and cyclization.

The following three substrates (SEQ ID NO:56, SEQ ID NO:57, and SEQ ID NO:58) undergo two dehydrations as expected as well as one cyclization.

```
                                                  SEQ ID NO:56
GSSHHHHHHSSGLVPRGSHMKEQNSFNLLQEVTESELDLILGAKGGSGVI
HTISHE(L-Homocysteine);

                                                  SEQ ID NO:57
GSSHHHHHHSSGLVPRGSHMKEQNSFNLLQEVTESELDLILGAKGGSGVI
HTISHE(D-Homocysteine);

                                                  SEQ ID NO:58
GSSHHHHHHSSGLVPRGSHMKEQNSFNLLQEVTESELDLILGAKGGSGVI
HTISHE (Beta-3-L-cysteine);
```

SEQ ID NO:59 undergoes all three expected dehydrations. S(PO4) refers to a Ser residue that we have phosphorylated chemically.

SEQ ID NO:59
GSSHHHHHHSSGLVPRGSHMKEQNSFNLLQEVTESELDLILGAKGGSGVIHTISHECNMNS(PO4)A.;

SEQ ID NO:60 undergoes the 2 expected dehydrations.

SEQ ID NO:60
GSSHHHHHHSSGLVPRGSHMKEQNSFNLLQEVTESELDLILGAKGGCGVIHT(PO4)ISHEA.;

The following site-directed mutants have also been generated:

SEQ ID NO:61
GSSHHHHHHSSGLVPRGSHMKEQNSFNLLQEVTESELDLILG(A24D)KGGSGVIHTISHECNMNSWQFVFTCCS;

SEQ ID NO:62
GSSHHHHHHSSGLVPRGSHMKEQNSFNLLQEVTESELDLIL(G23V)AKGGSGVIHTISHECNMNSWQFVFTCCS;

SEQ ID NO:63
GSSHHHHHHSSGLVPRGSHMKEQNSFNLLQEVTESELD(L20Q)ILGAKGGSGVIHTISECNMNSWQFVFTCCS;

SEQ ID NO:64
GSSHHHHHHSSGLVPRGSHMKEQNSFNLLQEVTESE(L18E)DLILGAKGGSGVIHTISHECNMNSWQFVFTCCS;

SEQ ID NO:65
GSSHHHHHHSSGLVPRGSHMKEQNSFNLLQEVTESELDLILGAKGG(S28C)GVIHTISHECNMNSWQFVFTCCS

TABLE 2

Sequence Listing Information.

| SEQ ID NO: | Brief Description | Type |
|---|---|---|
| 1 | Lan protease recognition sequence | PRT |
| 2 | Lan protease recognition sequence | PRT |
| 3 | prepeptide LctA | PRT |
| 4 | His6-LctA | PRT |
| 5 | His6-LctA (5-51) | PRT |
| 6 | His6-LctA(10-51) | PRT |
| 7 | His6-LctA (25-51) | PRT |
| 8 | His6-LctA (1-37) | PRT |
| 9 | His6-LctA (1-38) | PRT |
| 10 | His6-LctA (1-38) C38U (alias C38Sec) | PRT |
| 11 | His6-LctA-T48S | PRT |
| 12 | His6-LctA-C49S | PRT |
| 13 | His6-LctA-C49A | PRT |
| 14 | PCR primer for lctM | DNA |
| 15 | PCR primer for lctM | DNA |
| 16 | PCR primer for lctA | DNA |
| 17 | PCR primer for lctA | DNA |
| 18 | lctM triple mutant A458G/A556G/A815G | DNA |
| 19 | LctM triple mutant Lys153Arg, Ser186Gly, and Asp272Gly; translated from above | PRT |
| 20 | MrsM | PRT |
| 21 | MutM | PRT |
| 22 | CinM | PRT |
| 23 | ScnM | PRT |
| 24 | RumM | PRT |
| 25 | LtnM1 | PRT |
| 26 | LtnM2 | PRT |

TABLE 2-continued

Sequence Listing Information.

| SEQ ID NO: | Brief Description | Type |
|---|---|---|
| 27 | NukM | PRT |
| 28 | lctT protease | DNA |
| 29 | LctT protease | PRT |
| 30 | PCR primer for Lpd/lctT | DNA |
| 31 | PCR primer for Lpd/lctT | DNA |
| 32 | LctA recognition sequence | PRT |
| 33 | RumA recognition sequence | PRT |
| 34 | VarA recognition sequence | PRT |
| 35 | ScnA recognition sequence | PRT |
| 36 | ScnA recognition sequence | PRT |
| 37 | MutA recognition sequence | PRT |
| 38 | lctM gene, gtg start codon | DNA |
| 39 | lctM gene, atg start codon | DNA |
| 40 | LctM | PRT |
| 41 | His tag at the N-terminus; bases from pET28 in His-LctM protein | DNA |
| 42 | His tag at the N-terminus | PRT |
| 43 | Bases from pET15b in His-LctA peptide | DNA |
| 44 | lctA gene | DNA |
| 45 | Appending peptide to the leader; dehydration | PRT |
| 46 | Appending peptide to the leader; multiple dehydrations | PRT |
| 47 | LctMutA | PRT |
| 48 | LctMutA | DNA |
| 49 | LctRumA | PRT |
| 50 | LctRumA | DNA |
| 51 | MutA | PRT |
| 52 | MutA | DNA |
| 53 | LctMutAK | PRT |
| 54 | LctMutAK | DNA |
| 55 | lacticin substrate variant | PRT |
| 56 | lacticin substrate variant | PRT |
| 57 | lacticin substrate variant | PRT |
| 58 | lacticin substrate variant | PRT |
| 59 | lacticin substrate variant | PRT |
| 60 | lacticin substrate variant | PRT |
| 61 | site-directed mutant | PRT |
| 62 | site-directed mutant | PRT |
| 63 | site-directed mutant | PRT |
| 64 | site-directed mutant | PRT |
| 65 | site-directed mutant | PRT |
| 66 | LctM triple mutant | PRT |
| 67 | SpaS | PRT |
| 68 | SpaC | PRT |
| 69 | NisC | PRT |
| 70 | PepC | PRT |
| 71 | EpiC | PRT |
| 72 | CylM | PRT |
| 73 | VarA | PRT |
| 74 | RumA | PRT |
| 75 | ScnA | PRT |
| 76 | ScnA" | PRT |
| 77 | ComA | PRT |
| 78 | LcnC | PRT |
| 79 | PedD | PRT |
| 80 | CvaB | PRT |
| 81 | nisin, NisA | PRT |
| 82 | subtilin, SpaB | PRT |
| 83 | His6-LctA-T48A | PRT |
| 84 | His6-LctA-C50A | PRT |
| 85 | primer1 His6-LctA(5-51) | DNA |
| 86 | primer2 His6-LctA(5-51) | DNA |
| 87 | primer1 His6-LctA(10-51) | DNA |
| 88 | primer2 His6-LctA(10-51) | DNA |
| 89 | primer1 His6-LctA(25-51) | DNA |
| 90 | primer2 His6-LctA(25-51) | DNA |
| 91 | primer1 His6-LctA(1-37) | DNA |
| 92 | primer2 His6-LctA(1-37) | DNA |
| 93 | primer1 His6-LctA-T48S | DNA |
| 94 | primer2 His6-LctA-T48S | DNA |
| 95 | primer1 His6-LctA-T48A | DNA |
| 96 | primer2 His6-LctA-T48A | DNA |
| 97 | primer1 His6-LctA-C49A | DNA |
| 98 | primer2 His6-LctA-C49A | DNA |
| 99 | primer1 His6-LctA-C49S | DNA |

TABLE 2-continued

Sequence Listing Information.

| SEQ ID NO: | Brief Description | Type |
|---|---|---|
| 100 | primer2 His6-LctA-C49S | DNA |
| 101 | mrsM | DNA |
| 102 | mutM | DNA |
| 103 | cinM | DNA |
| 104 | scnM | DNA |
| 105 | rumM | DNA |
| 106 | lctnM1 and LctnM2 | DNA |
| 107 | spaB | DNA |
| 108 | nisB | DNA |
| 109 | nukM | DNA |

STATEMENTS REGARDING INCORPORATION BY REFERENCE AND VARIATIONS

Compounds and methods relevant to the invention can involve prodrugs. For example, prodrugs of compounds are useful in the methods of this invention. Any compound that will be converted in vivo to provide a biologically, pharmaceutically or therapeutically active form of a compound of the invention can be a prodrug. Various examples and forms of prodrugs are well known in the art. Examples of prodrugs are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392).

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Any appendix or appendices hereto are incorporated by reference as part of the specification and/or drawings.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof.

The invention has been described with reference to various specific and preferred embodiments and techniques. However, it should be understood that many variations and modifications may be made while remaining within the spirit and scope of the invention. It will be apparent to one of ordinary skill in the art that compositions, methods, devices, device elements, materials, procedures and techniques other than those specifically described herein can be applied to the practice of the invention as broadly disclosed herein without resort to undue experimentation. All art-known functional equivalents of compositions, methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

REFERENCES

1. Okeley, N. M.; Zhu, Y.; van der Donk, W. A. Org. Lett. 2000, 2, 3603-3606. "Facile Chemoselective Synthesis of Dehydroalanine-Containing Peptides".
2. Okeley, N. M.; van der Donk, W. A. Chem. & Biol. 2000, 7, R159-R171. "Novel Cofactors via Post-translational Modifications of Enzyme Active Sites".
3. Zhou, H.; van der Donk, W. A. Org. Lett. 2001, 3, 593-596. "Synthesis of 2-Amino-3-fluoro-acrylic Acid Containing Peptides".
4. Zhu, Y.; van der Donk, W. A. Org. Lett. 2001, 3, 1189-1192. "Convergent Synthesis of Peptide Conjugates Using Dehydroalanines for Chemoselective Ligations".
5. Xie, L.; van der Donk, W. A. Proc. Natl. Acad. Sci. U.S.A. 2001, 98, 12863-12865. "Homemade cofactors: self-processing in galactose oxidase".
6. Gieselman, M. D.; Xie, L.; van der Donk, W. A. Org. Lett. 2001, 3, 1331-1334. "Synthesis of a Selenocysteine-Containing Peptide by Native Chemical Ligation".
7. Gieselman, M. D.; Zhu, Y.; Zhou, H.; Galonic, D.; van der Donk, W. A. ChemBioChem 2002, 3, 709-716. "Selenocysteine Derivatives for Chemoselective Ligations".
8. Berry, S.; Gieselman, M.; Nilges, M. J.; van der Donk, W. A.; Lu, Y. J. Am. Chem. Soc. 2002, 124, 2084-2085. "An Engineered Azurin Variant Containing a Selenocysteine Copper Ligand".
9. Xie, L.; Chatterjee, C.; Balsara, R.; Okeley, N. M.; van der Donk, W. A. Biochem. Biophys. Res. Commun. 2002, 295, 952-7. "Heterologous expression and purification of SpaB involved in subtilin biosynthesis".
10. Zhou, H.; van der Donk, W. A. Org. Lett. 2002, 4, 1335-1338. "Biomimetic Stereoselective Formation of Methyllanthionine".
11. Galonic, D.; van der Donk, W. A.; Gin, D. Y. *Chem.-Eur. J.* 2003, 24, 5997-6006. "Oligosaccharide-Peptide Ligation of Glycosyl Thiolates with Dehydropeptides. Synthesis of S-Linked Mucin Glycopeptide Conjugates".
12. Zhou, H.; Schmidt, D. M.; Gerlt, J. A.; van der Donk, W. A. ChemBioChem, 2003, 1206-1215 "Chemical and Enzymatic Synthesis of Fluorinated Dehydroalanine-Containing Peptides".
13. Zhu, Y.; Gieselman, M.; Zhou, H.; Okeley, N. M.; Averin, O.; van der Donk, W. A. *Org. Biomol. Chem.* 2003, 1, 3304-3315. "Biomimetic studies on the mechanism of stereoselective lanthionine formation".
14. Okeley, N. M.; Paul, M.; Stasser, J. P. Blackburn, N.; van der Donk, W. A., *Biochemistry,* 2003, 42, 13613-13624. "SpaC and NisC, the Cyclases Involved in Subtilin and Nisin Biosynthesis, are Zinc Proteins".

Gomez et al., 2002. J Bacteriol 184(1):18-28.

Aso et al., on PubMed; Characterization of the gene cluster of *Staphylococcus warneri* ISK-1 encoding biosynthesis and immunity of the lantibiotic, Nukacin ISK-1.

Xie, L.; Miller, L.; Chatterjee, C.; Averin, O.; Kelleher, N. L.; *van der Donk, W. A.* "Lacticin 481: in vitro reconstitution of lantibiotic synthetase activity" *Science,* 2004, 303, 679-681.

The invention claimed is:

1. A method of modifying a lantibiotic precursor peptide by dehydration or dehydration and cyclization, comprising:

(a) providing said lantibiotic precursor peptide;

(b) providing a purified LctM enzyme capable of catalyzing dehydration and cyclization of the lantibiotic precursor peptide, wherein said LctM enzyme has at least 95% sequence identity to SEQ ID NO:40 and enzymatic activity of dehydration or dehydration and cyclization of the lantibiotic precursor peptide of SEQ ID NO:3; and (c) incubating a reaction mixture comprising a divalent metal cation, ATP, said lantibiotic precursor peptide of (a) and said LctM enzyme; thereby modifying said lantibiotic precursor peptide by dehydration or dehydration and cyclization.

2. The method of claim 1, wherein the lantibiotic precursor peptide comprises at least one non-proteinogenic amino acid, unnatural amino acid, beta amino acid, peptoid, or derivatized amino acid.

3. The method of claim 1, wherein the reaction mixture further comprises magnesium.

4. The method of claim 1, wherein the reaction mixture further comprises magnesium and zinc.

5. The method of claim 1, wherein the reaction mixture further comprises magnesium, zinc, and DTT.

6. A method of generating a biologically active lantibiotic compound, comprising:

(a) incubating a reaction mixture comprising a divalent metal ion, ATP, a lantibiotic precursor peptide and a purified LctM enzyme having at least 95% identity to SEQ ID NO:40 and enzymatic activity of dehydration or dehydration and cyclization of the lantibiotic precursor peptide of SEQ ID NO: 3; and (b) cleaving a leader portion of the lantibiotic precursor peptide; thereby generating said biologically active lantibiotic compound.

7. The method of claim 6, wherein said divalent metal cation is zinc or magnesium.

8. A method of modifying a lantibiotic precursor peptide by dehydration or dehydration and cyclization, comprising:

(a) providing said lantibiotic precursor peptide;

(b) providing a purified LctM enzyme capable of catalyzing dehydration and cyclization of the lantibiotic precursor peptide, wherein said LctM enzyme comprises the amino acid sequence as set forth in SEQ ID NO:40; and (c) incubating a reaction mixture comprising a divalent metal cation, ATP, said lantibiotic precursor peptide of (a) and said LctM enzyme; thereby modifying said lantibiotic precursor peptide by dehydration or dehydration and cyclization.

9. The method of claim 8, wherein said LctM enzyme consists of the sequence set forth in SEQ ID NO:40.

10. The method of claim 9 wherein said divalent metal cation is zinc or magnesium.

11. The method of claim 9 wherein the reaction mixture further comprises DTT.

12. The method of claim 9, wherein the reaction mixture further comprises DTT.

13. A method of generating a biologically active lantibiotic compound, comprising:

(a) incubating a reaction mixture comprising a divalent metal ion, ATP, a lantibiotic precursor peptide and a purified LctM enzyme comprising the amino acid sequence as set forth in SEQ ID NO: 40; and (b) cleaving a leader portion of the lantibiotic precursor peptide; thereby generating said biologically active lantibiotic compound.

14. The method of claim 13, wherein said LctM enzyme consists of the sequence set forth in SEQ ID NO:40.

15. The method of claim 13, wherein the lantibiotic precursor peptide comprises at least one non-proteinogenic amino acid, unnatural amino acid, beta amino acid, peptoid, or derivatized amino acid.

16. The method of claim 13, wherein said divalent metal cation is zinc or magnesium.

17. The method of claim 13, wherein said reaction mixture further comprises DTT.

18. The method of claim 9, wherein the lantibiotic precursor peptide comprises at least one non-proteinogenic amino acid, unnatural amino acid, beta amino acid, peptoid, or derivatized amino acid.

* * * * *

UNITED STATES PATENT AND TRADEMARK OFFICE

CERTIFICATE OF CORRECTION

PATENT NO. : 7,785,825 B2
APPLICATION NO. : 11/034275
DATED : August 31, 2010
INVENTOR(S) : van der Donk et al.

Figure 45:
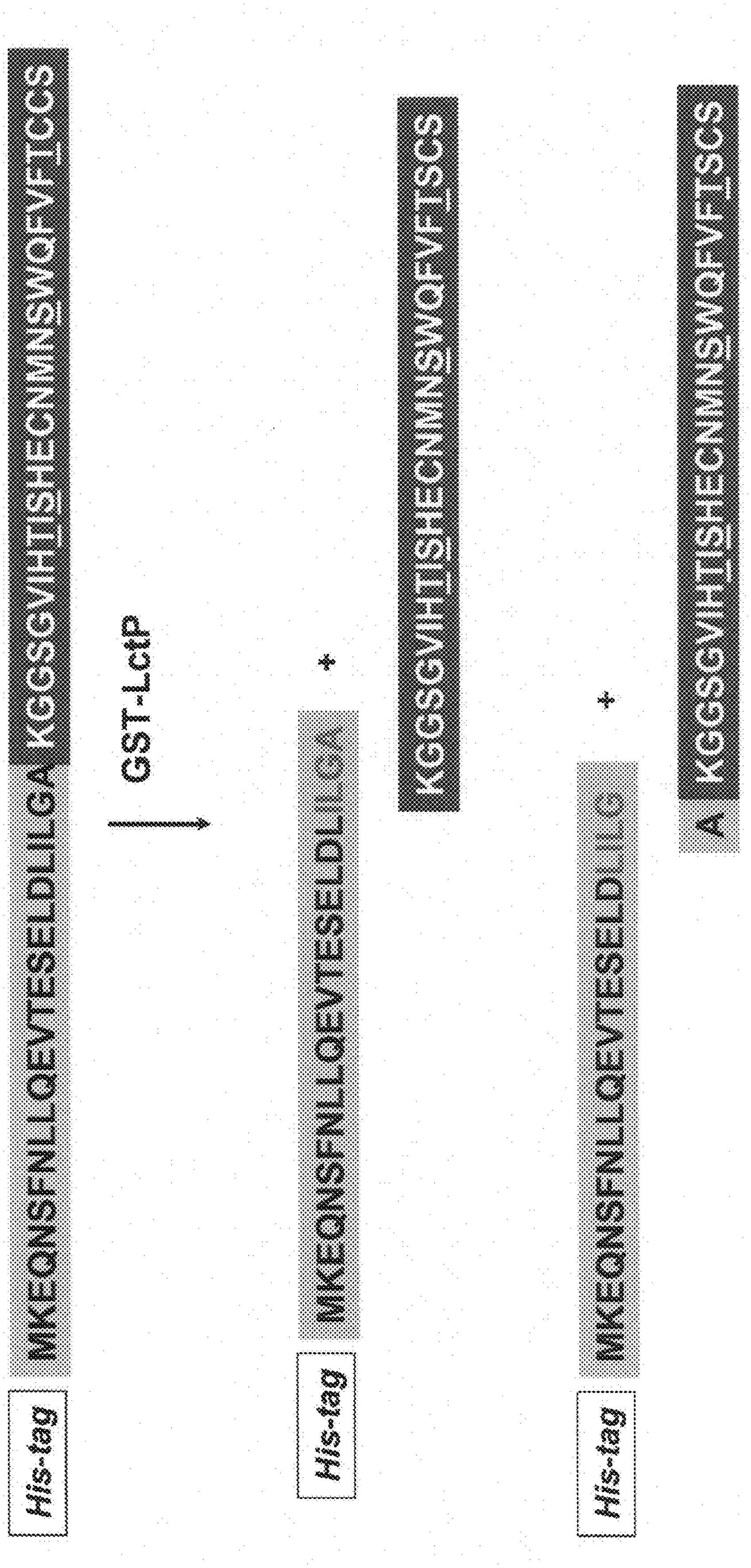
FIG. 45 illustrates an example of lacticin protease activity starting from LctA (SEQ ID NO:3) with a His-tag (SEQ ID NO:4). Products include amino acids 1-43 and amino acids 44-70 and amino acids 1-42 and 43-70, all of SEQ ID NO:4.
Figure 46:
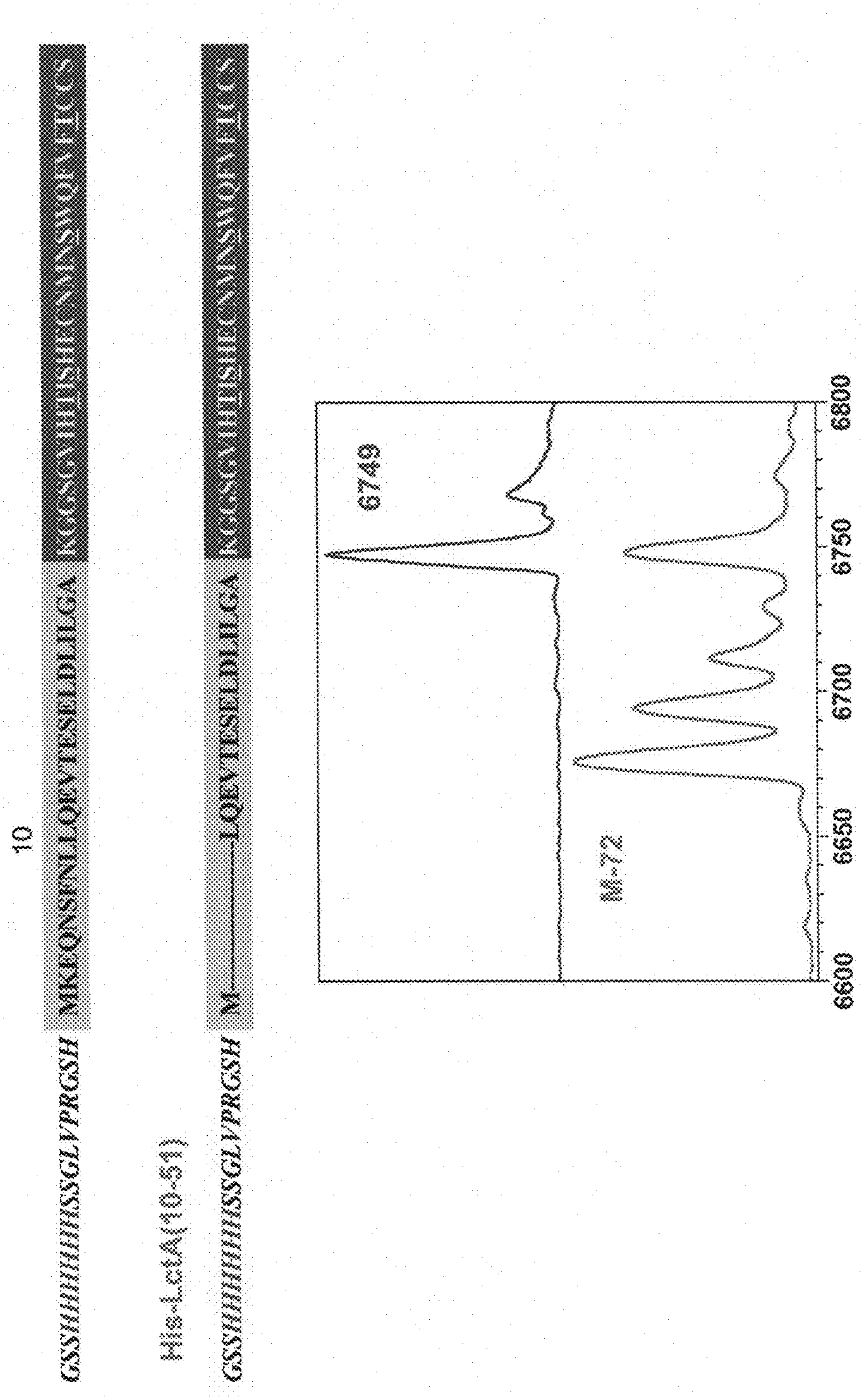
FIG. 46 illustrates His-LctA (SEQ ID NO:4) and a truncated LctA mutant (His-LctA(10-51); SEQ ID NO:6) with N-terminal deletions.
Figure 47:
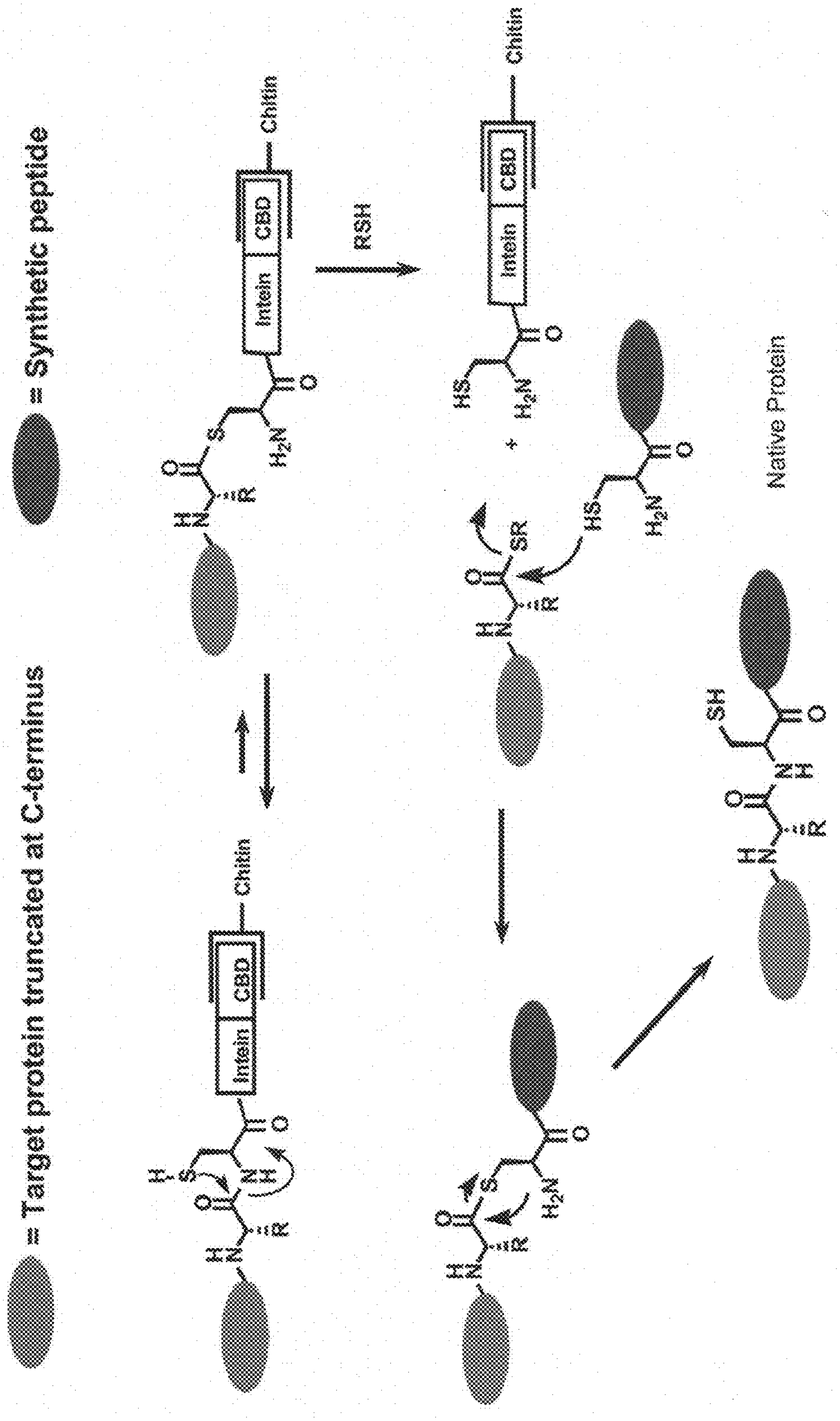
FIG. 47 illustrates expressed protein ligation.
Figure 48:
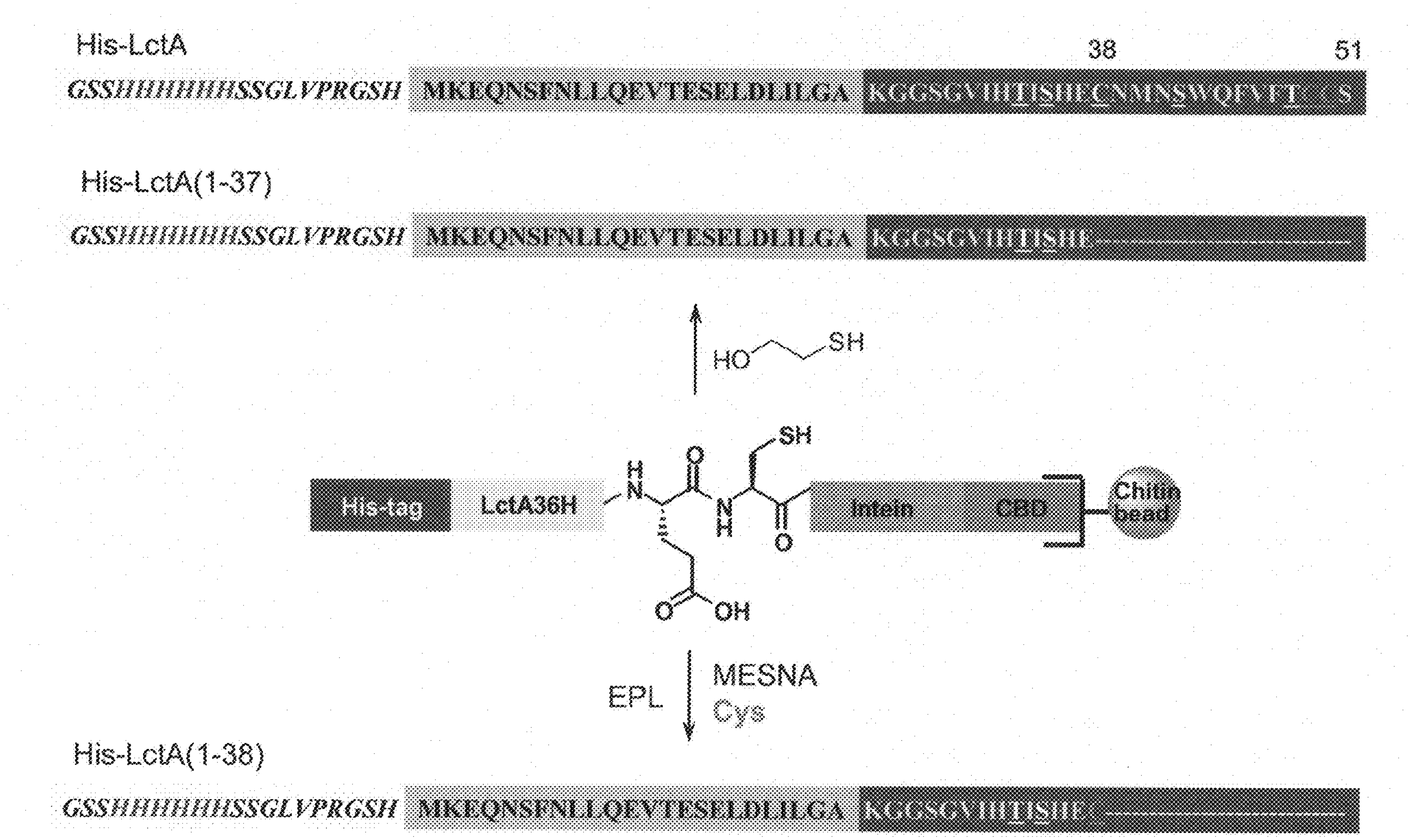
FIG. 48 illustrates a truncated LctA with C-terminal deletions. His-LctA, SEQ ID NO:4; His-LctA(1-37), SEQ ID NO:8; Hist-LctA(1-38), SEQ ID NO:9.
Figure 49:
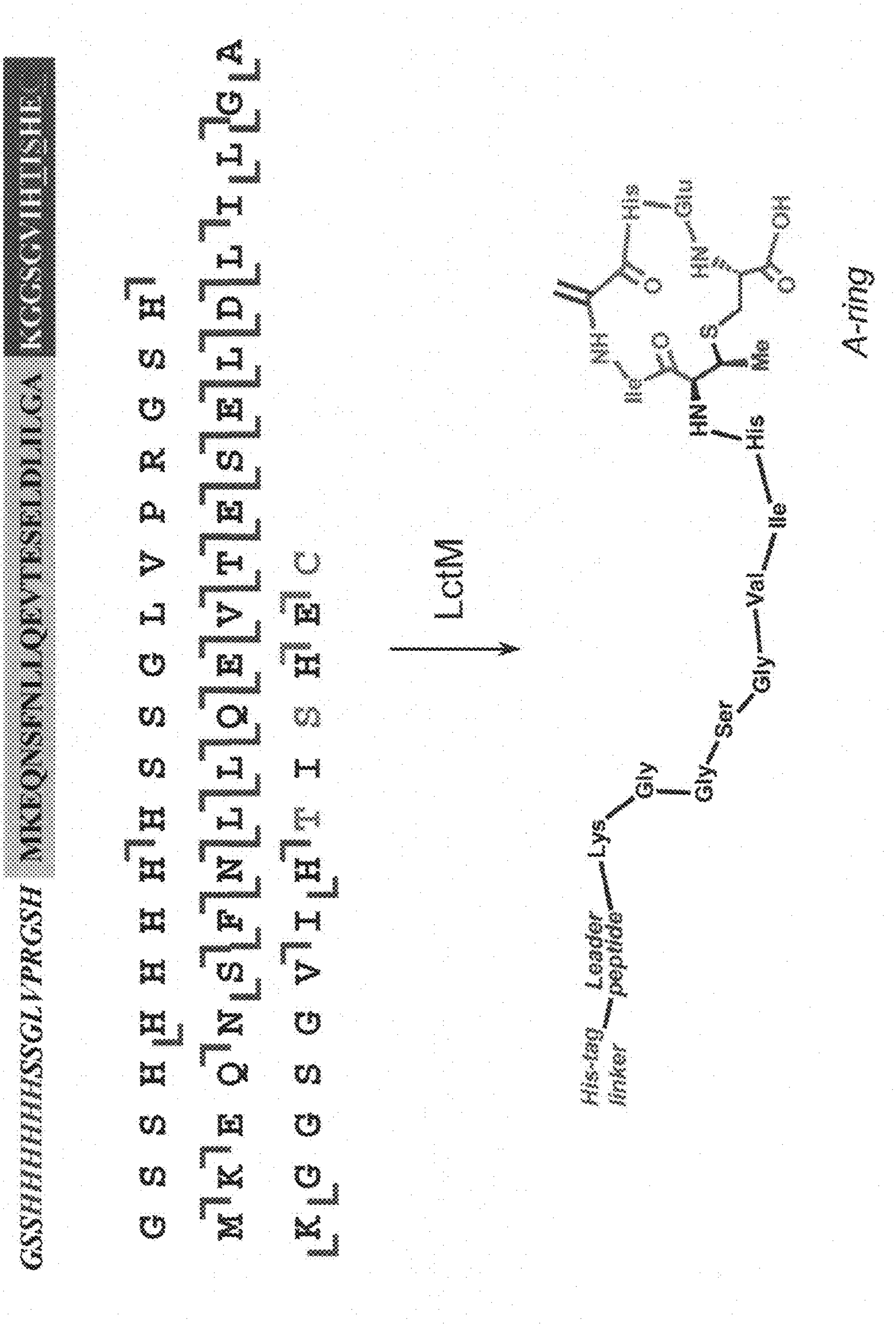
FIGS. 49 to 51 illustrate MS/MS characterization of His-LctA(1-38) (SEQ ID NO:9) product.
Figure 50:
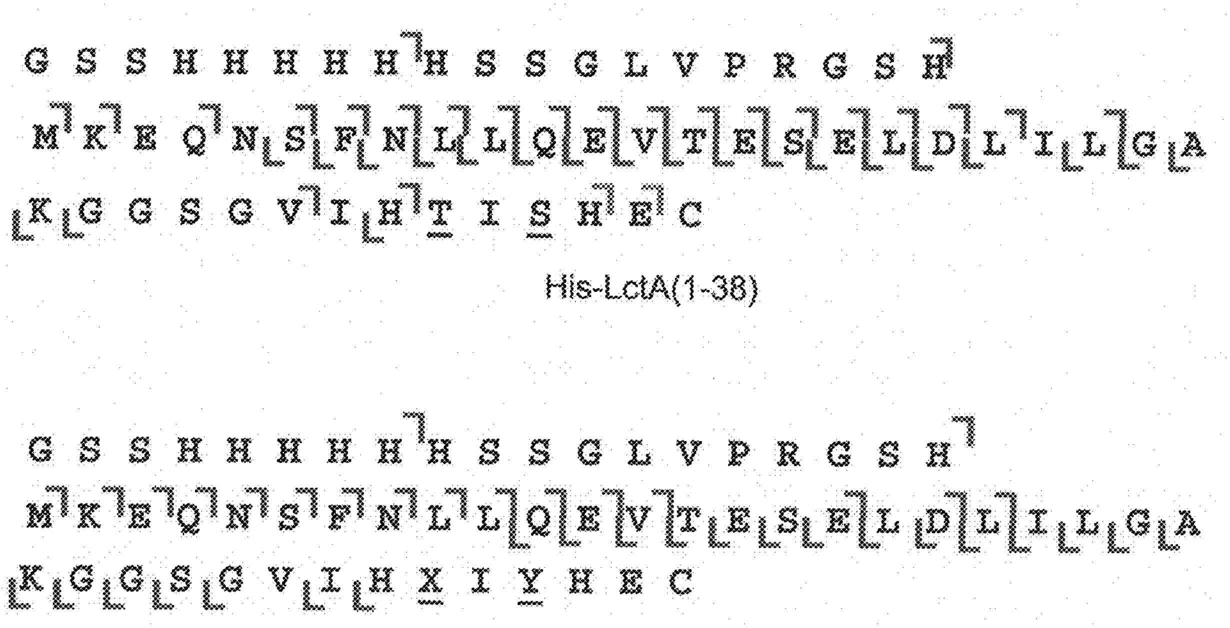
Figure 51:
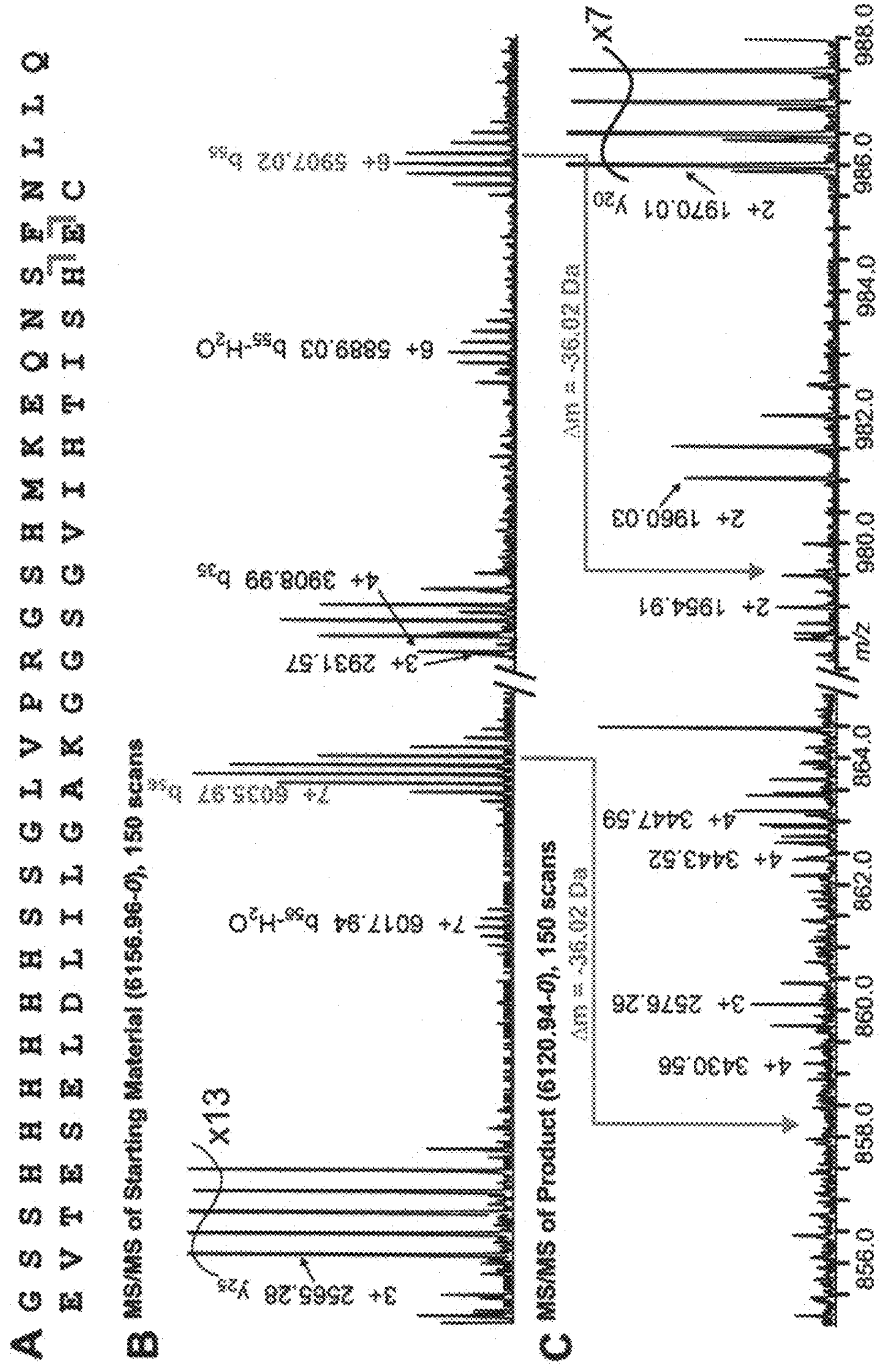
Figure 52:
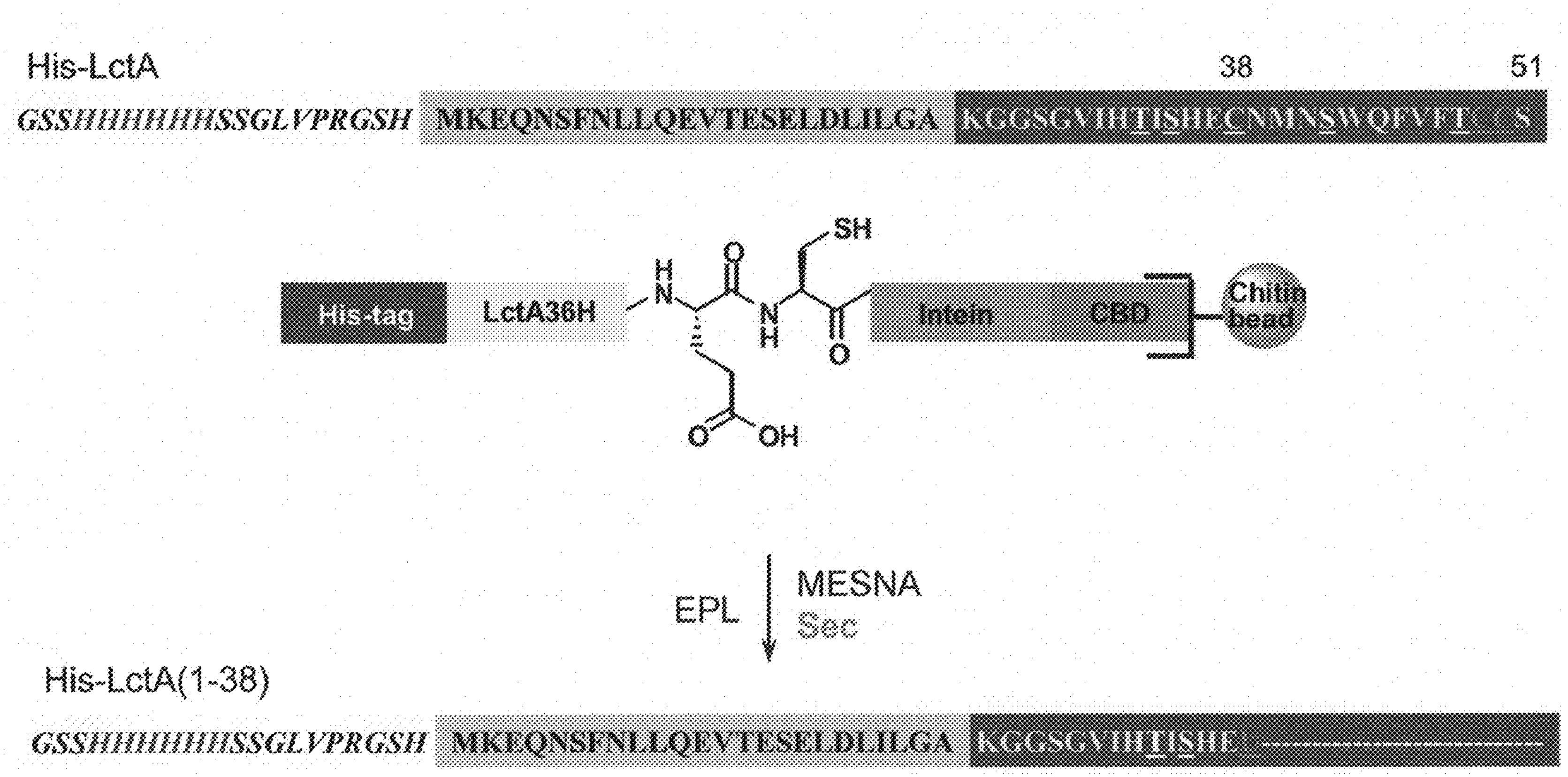
FIG. 52 illustrates a truncated LctA with C-terminal deletions. His-LctA, SEQ ID NO:4; His-LctA(1-38)C38U, SEQ ID NO:10.
Figure 53:
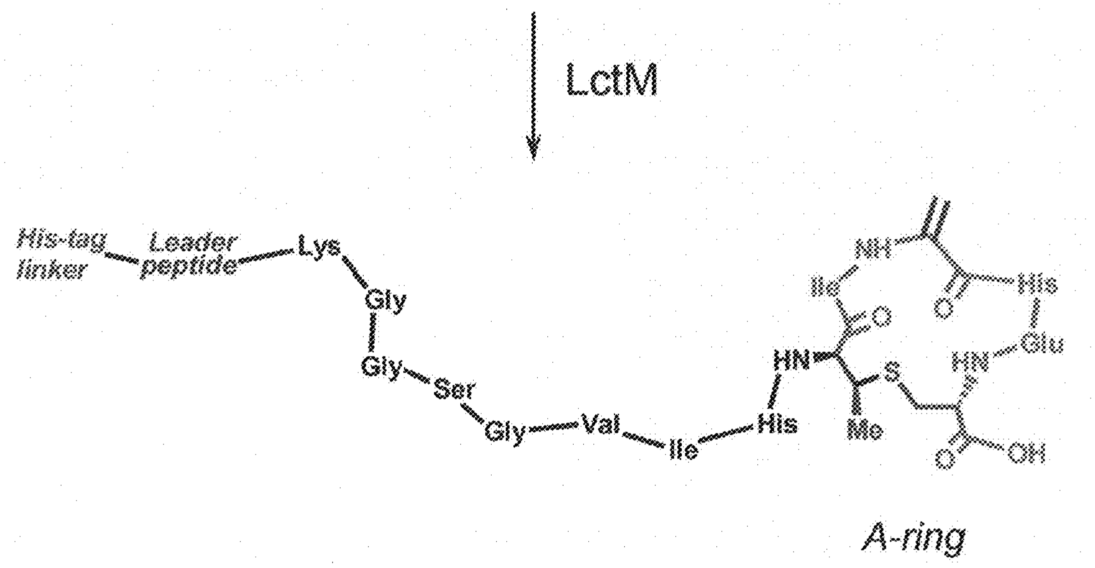
FIG. 53 illustrates characterization of the His-LctA(1-38) C38U, SEQ ID NO:10) product upon modification by LctM.
Figure 54:
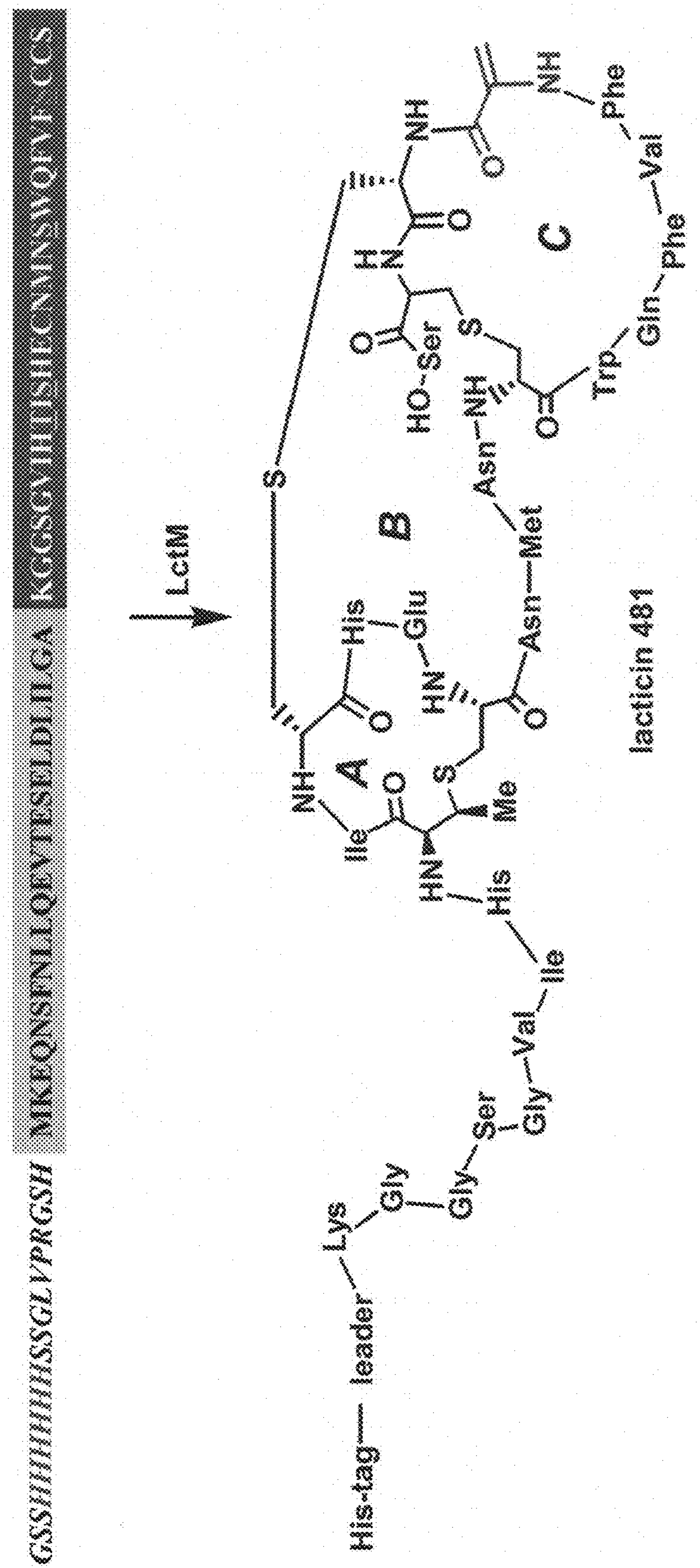
FIG. 54 illustrates a lacticin analog, mutant His-LctA-T48S (SEQ ID NO:11).
Figure 55:
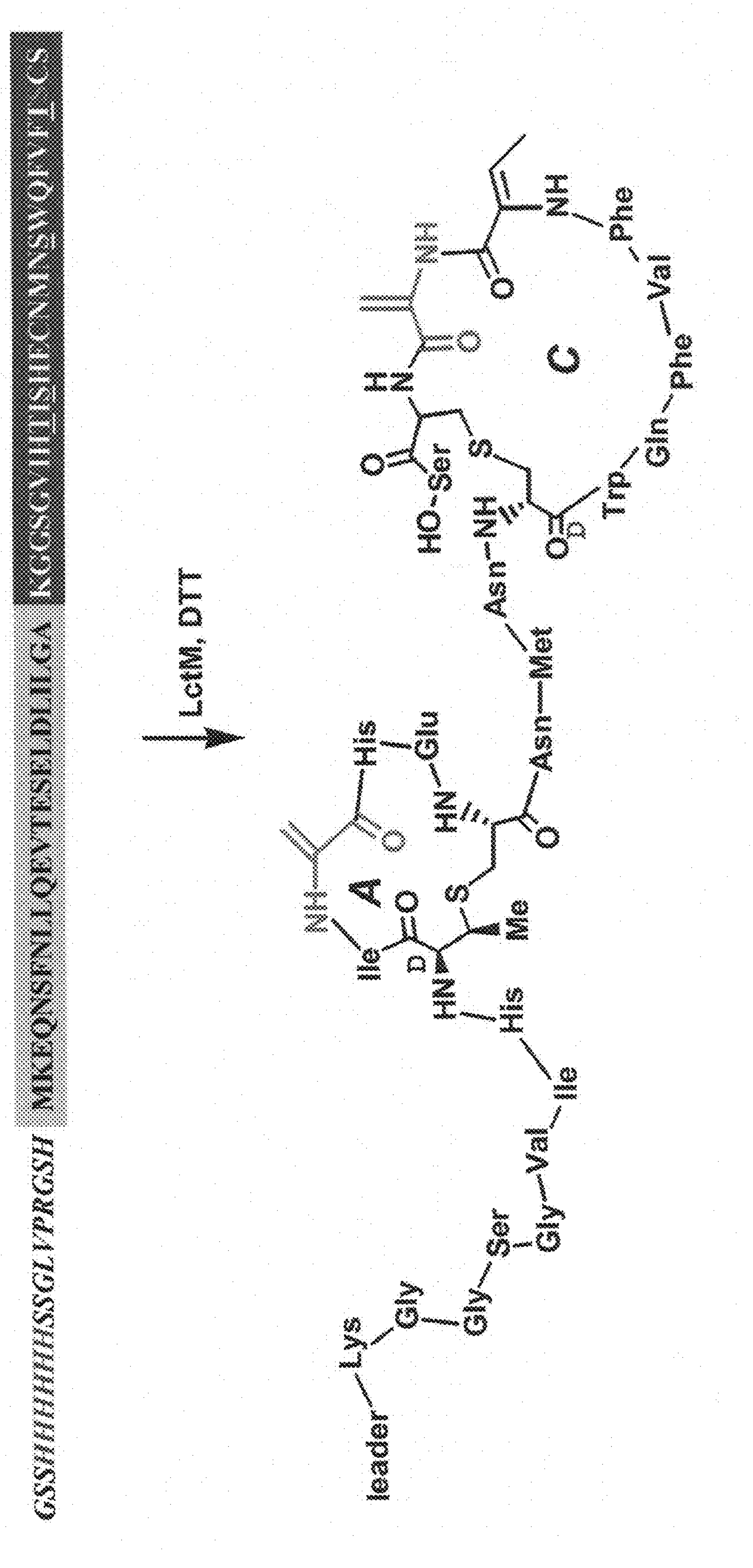
FIG. 55 illustrates a lacticin analog, mutant His-LctA-C49S (SEQ ID NO:12).
Figure 56:
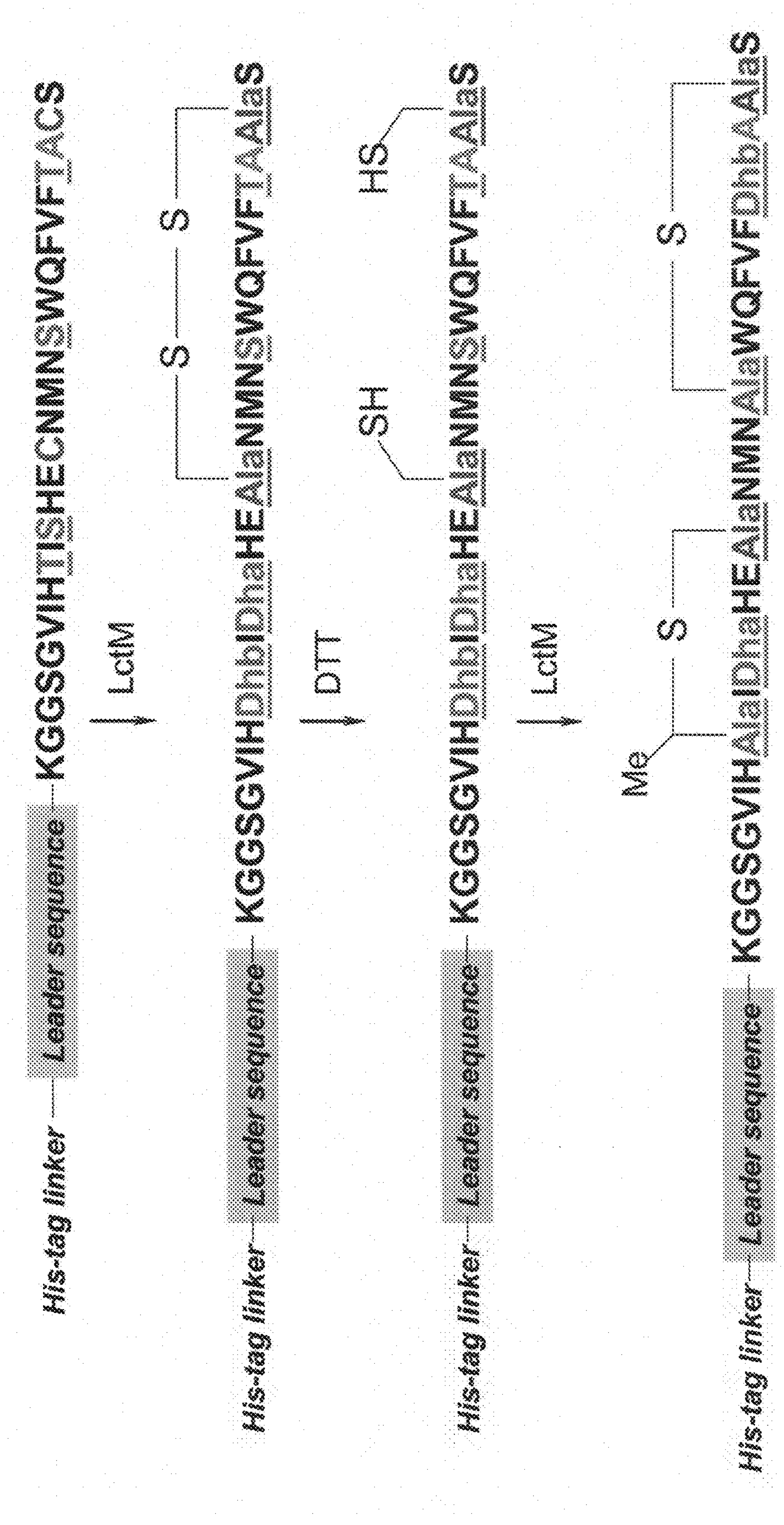
FIG. 56 illustrates a lacticin analog, mutant His-LctA-C49A (SEQ ID NO:13). The LctM-modified product (third line) corresponds to SEQ ID NO:113.
Figure 59:
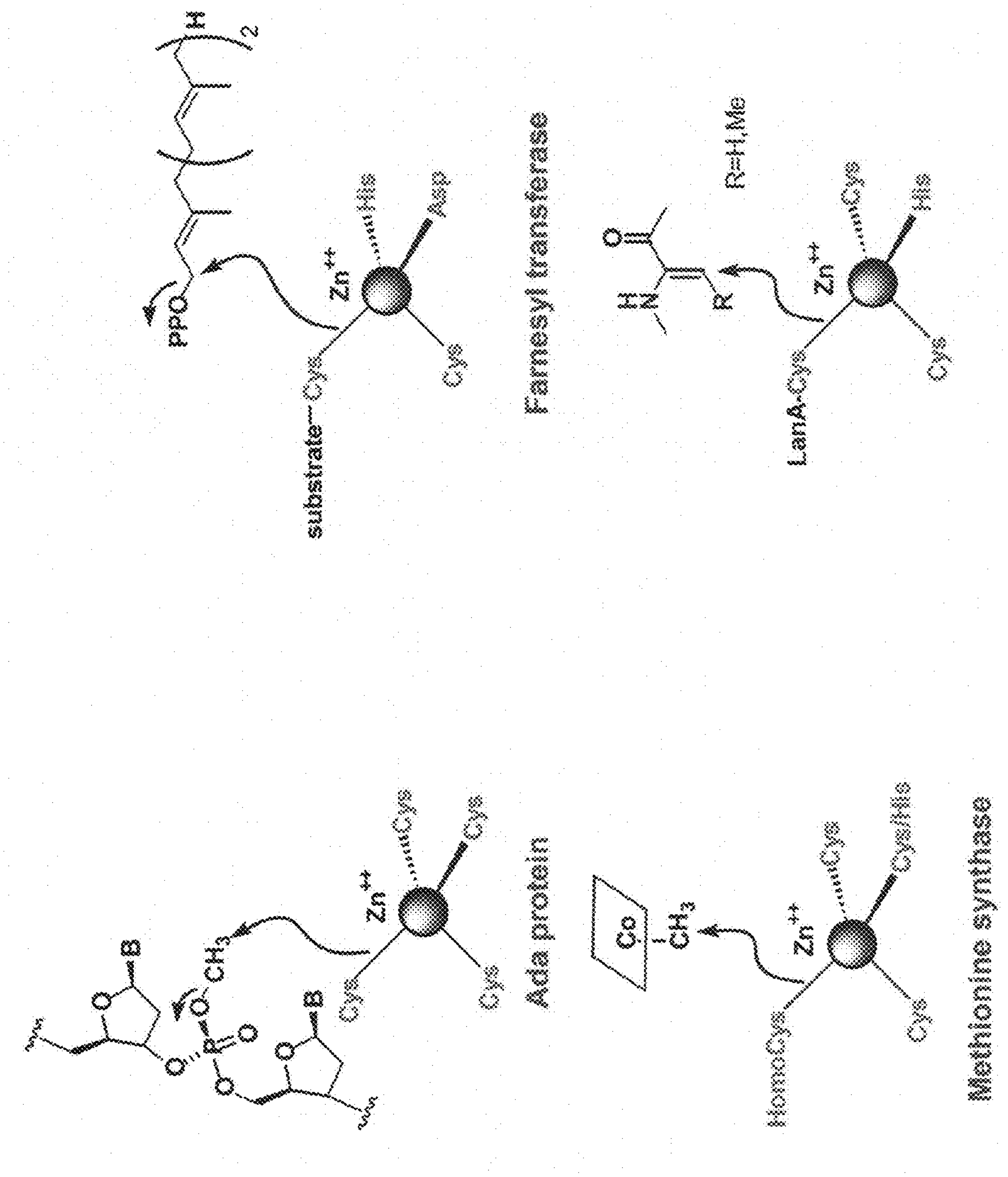
FIG. 59 illustrates a potential role for zinc, Zn, relating to enzyme function.
Figure 60:
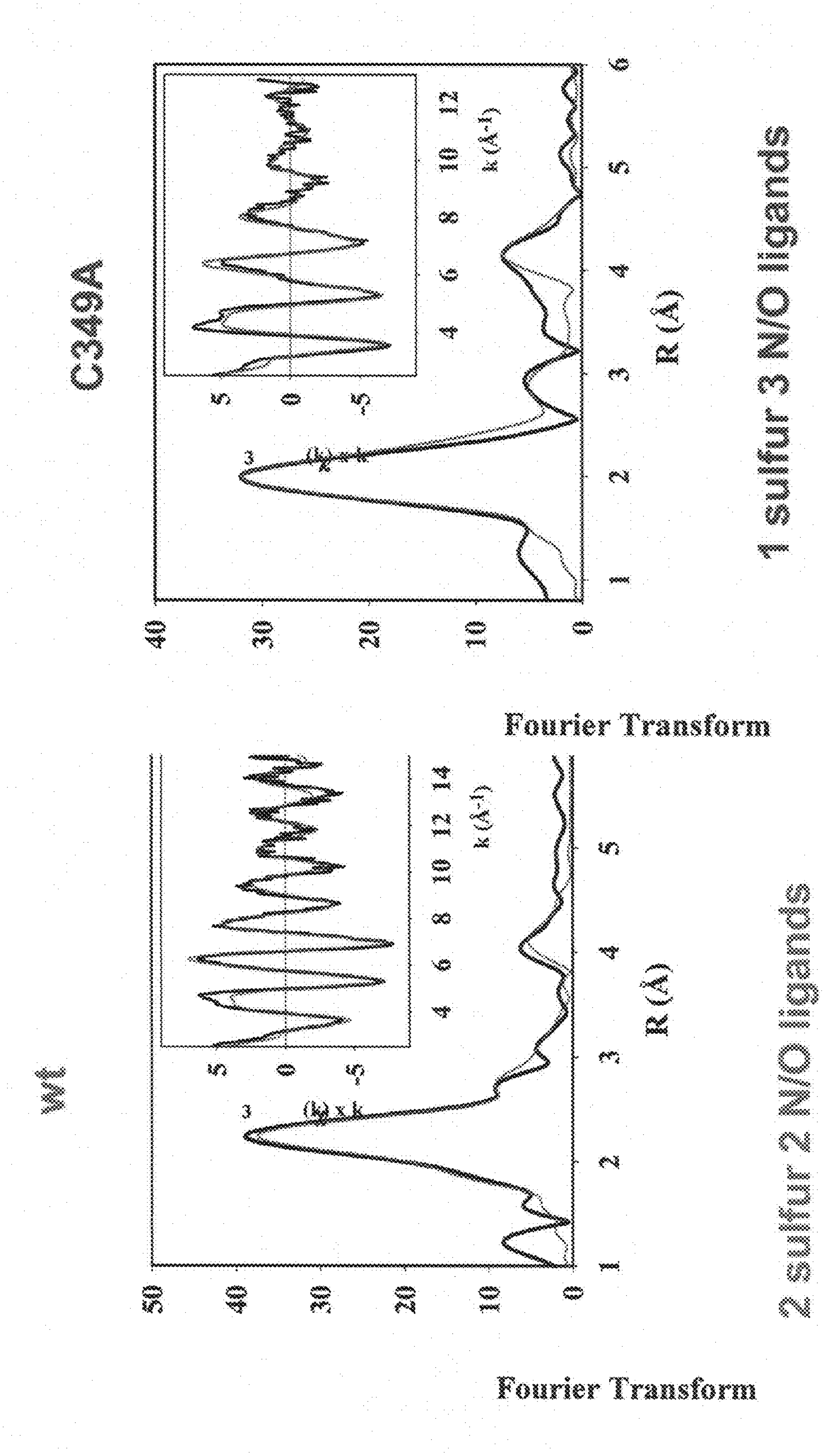
FIG. 60 illustrates data from zinc-edge EXAFS, Extended X-ray Absorption Fine Structure spectroscopy on protein SpaC.
Figure 61:
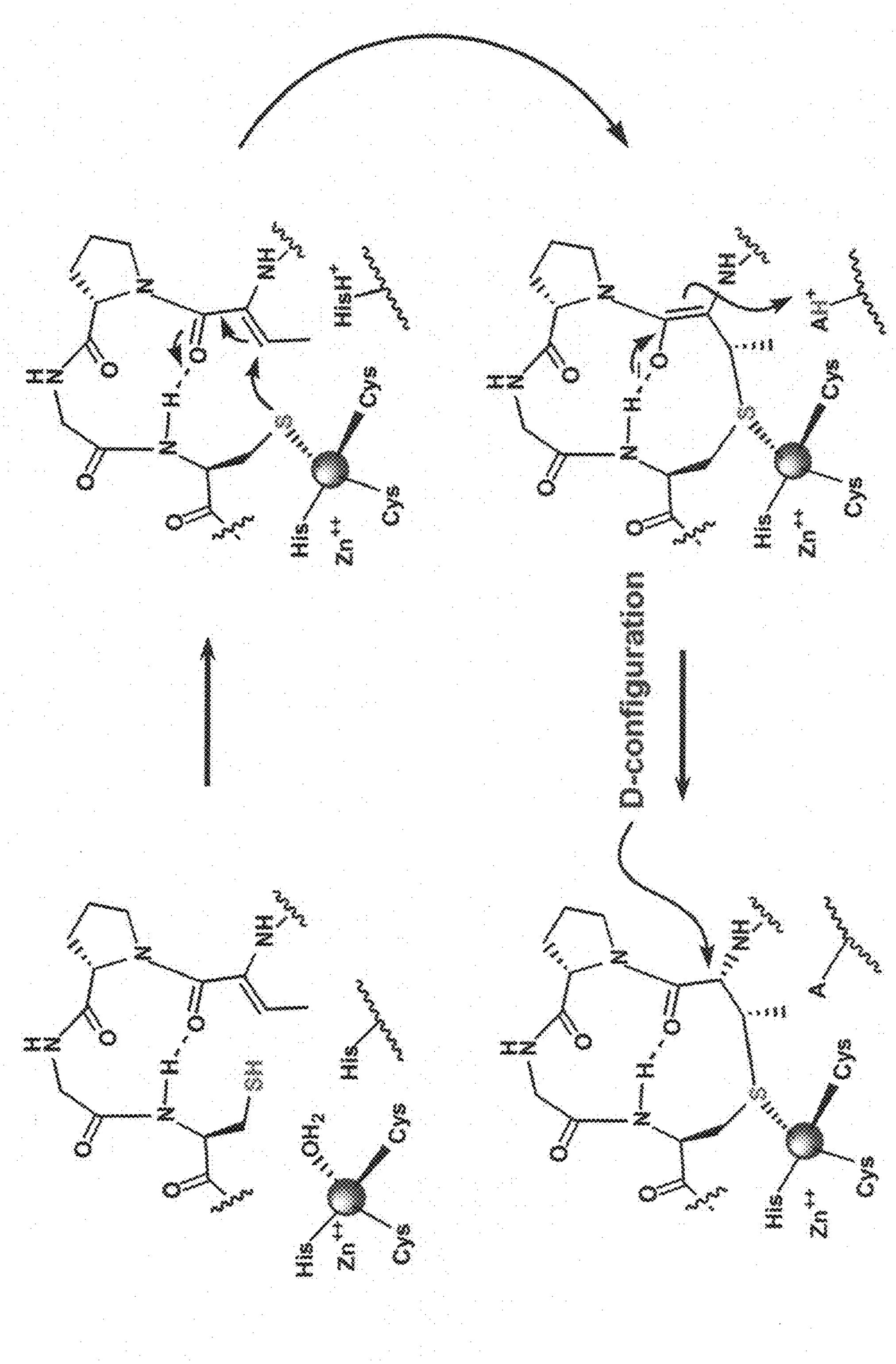
FIG. 61 illustrates proposed substrate activation by zinc.
Figure 63:
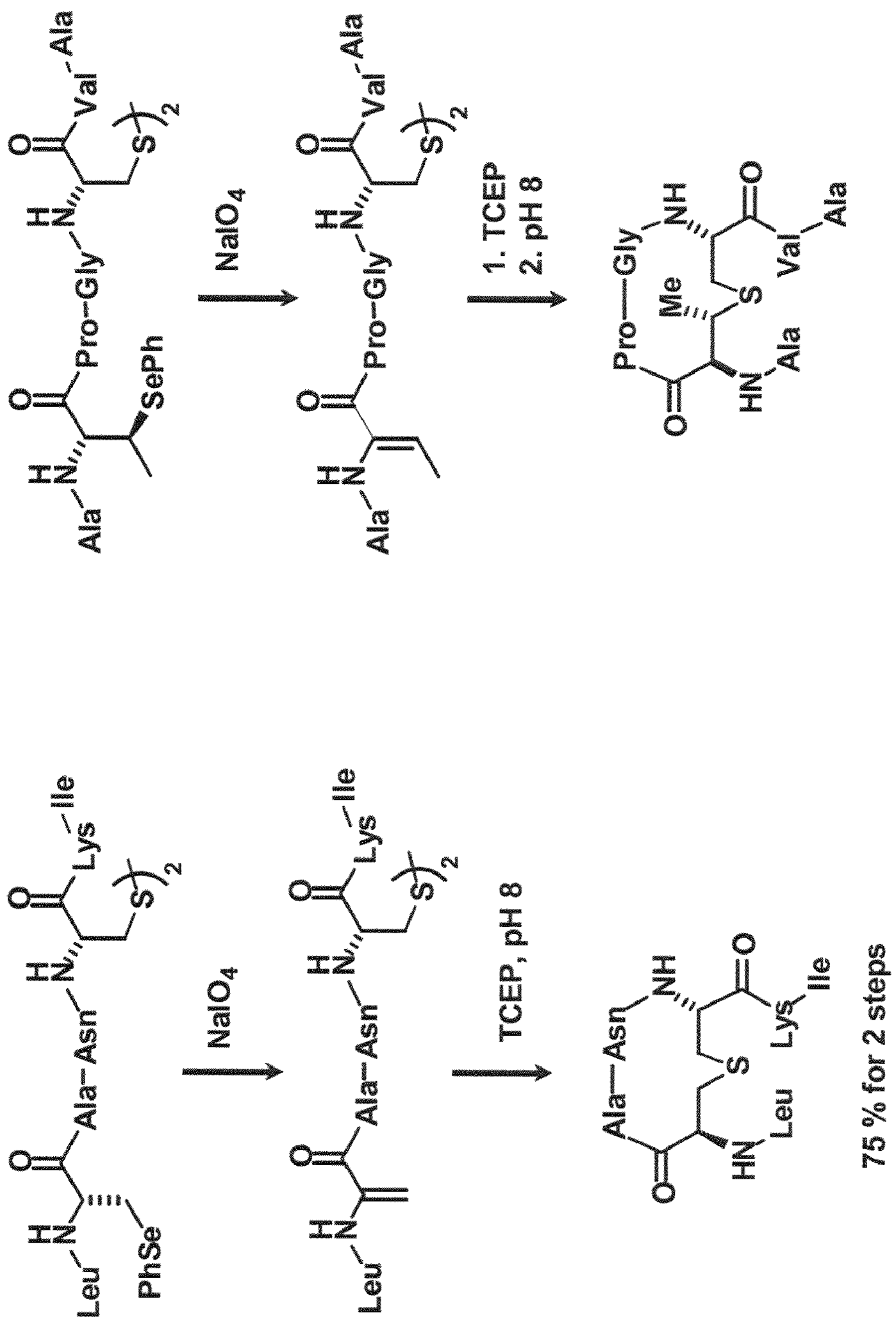
FIG. 63 illustrates examples of biomimetic lanthionine synthesis.
Figure 64:
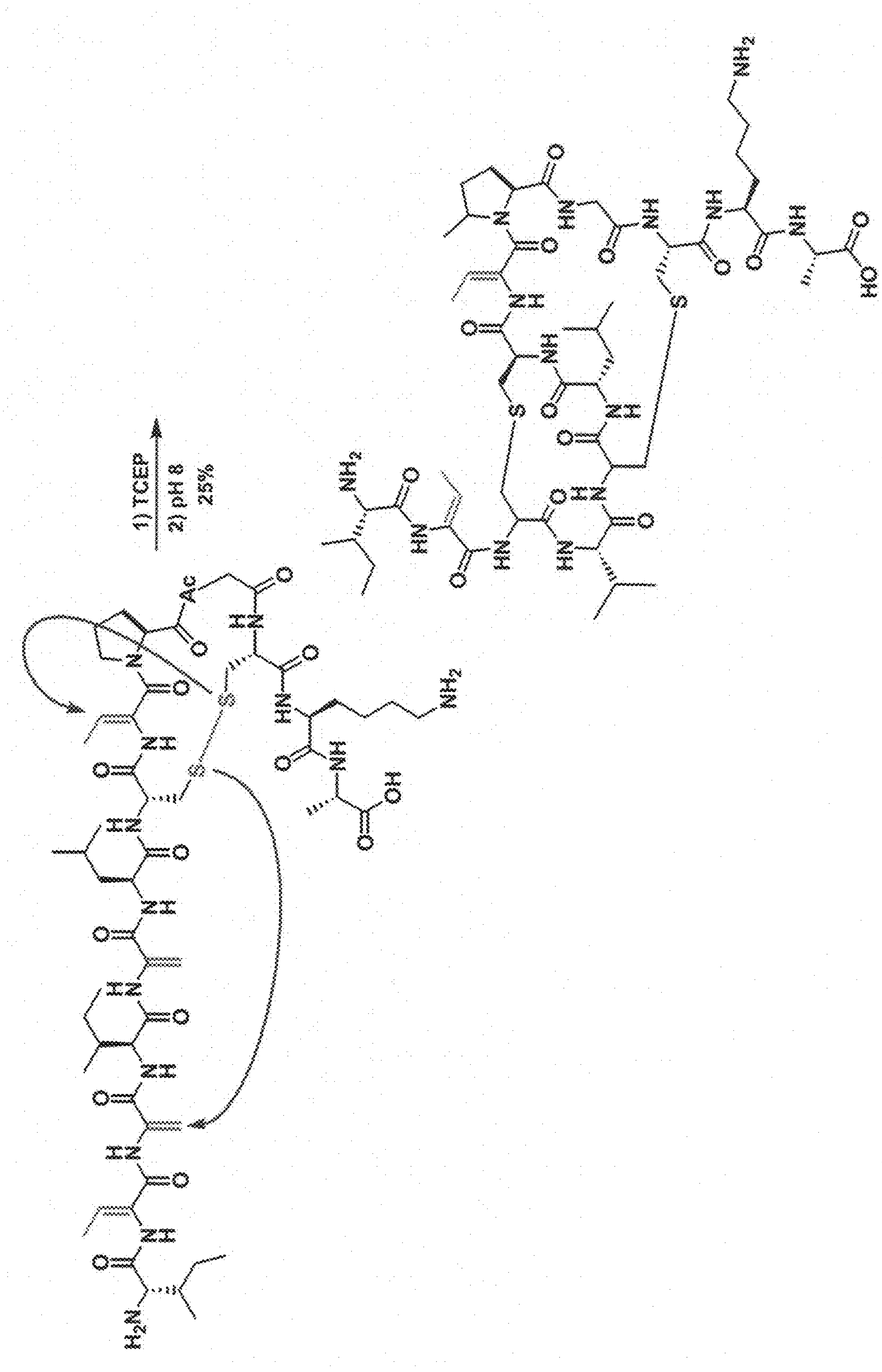
FIG. 64 illustrates an example of attempted biomimetic synthesis of Nisin A and B rings.
Figure 65:
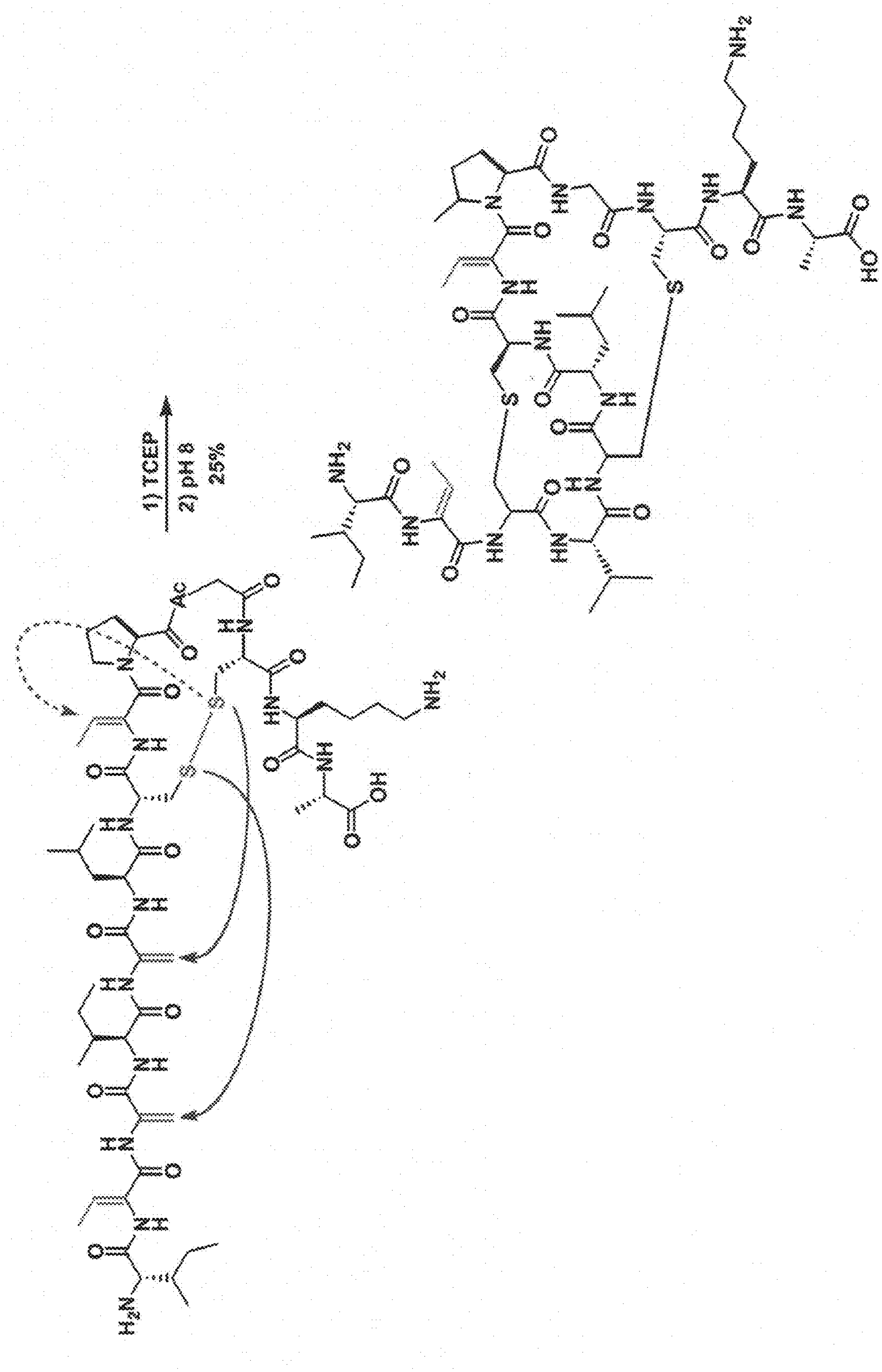
FIG. 65 illustrates an example of attempted biomimetic synthesis of Nisin A and B rings, indicating an alternative linkage.
Figure 66:
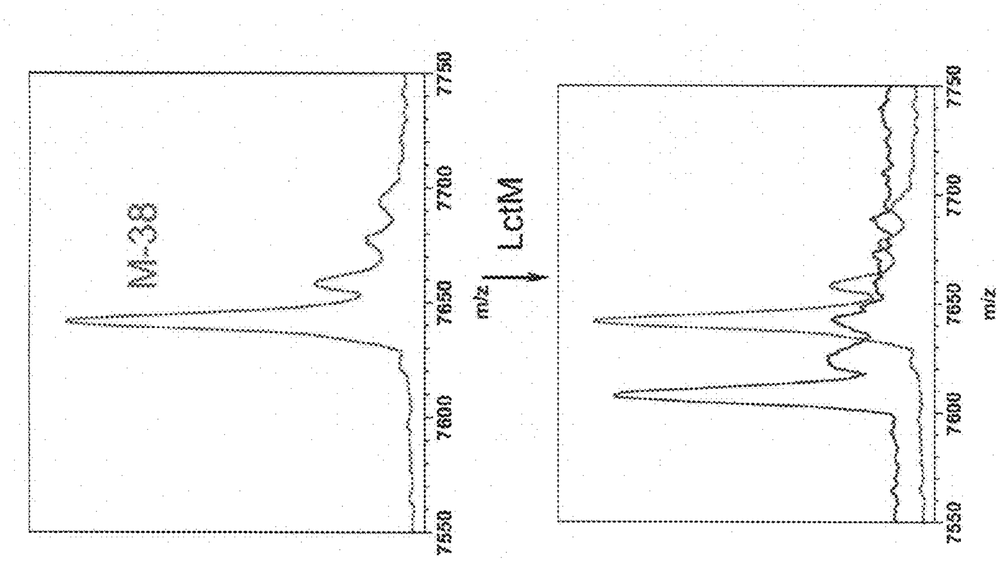
FIG. 66 illustrates mass spectrometry data for a lacticin analog, His-LctA-C49A (SEQ ID NO:13).
Figure 67:
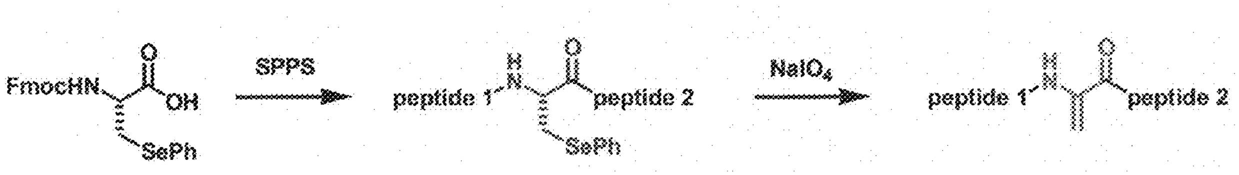
FIG. 67 illustrates examples of chemoselective oxidative elimination. See also SEQ ID NOs:123-134.
Figure 68:
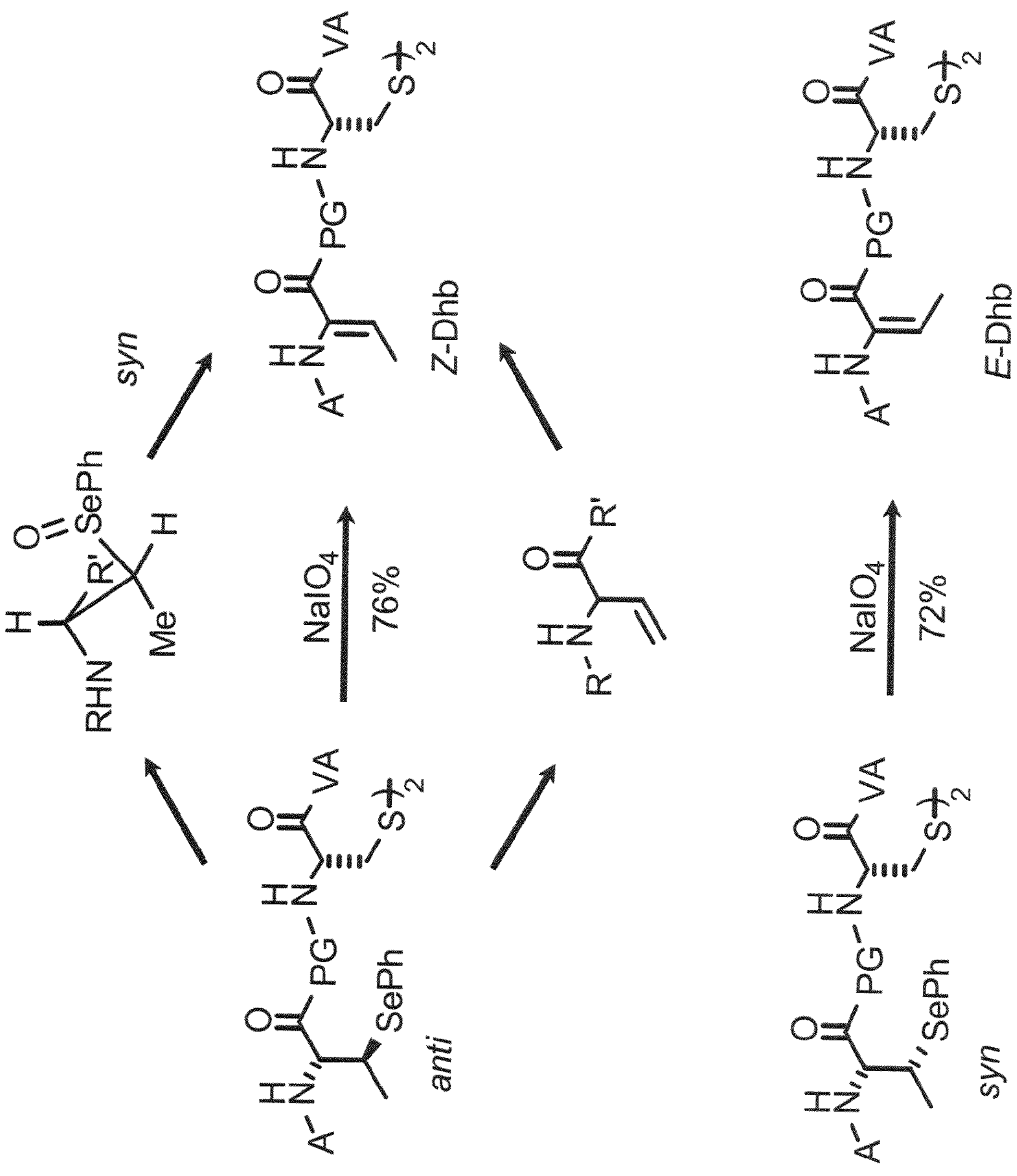
FIG. 68 illustrates preparation of Z- and E-dehydrobutyrines.
Figure 69:
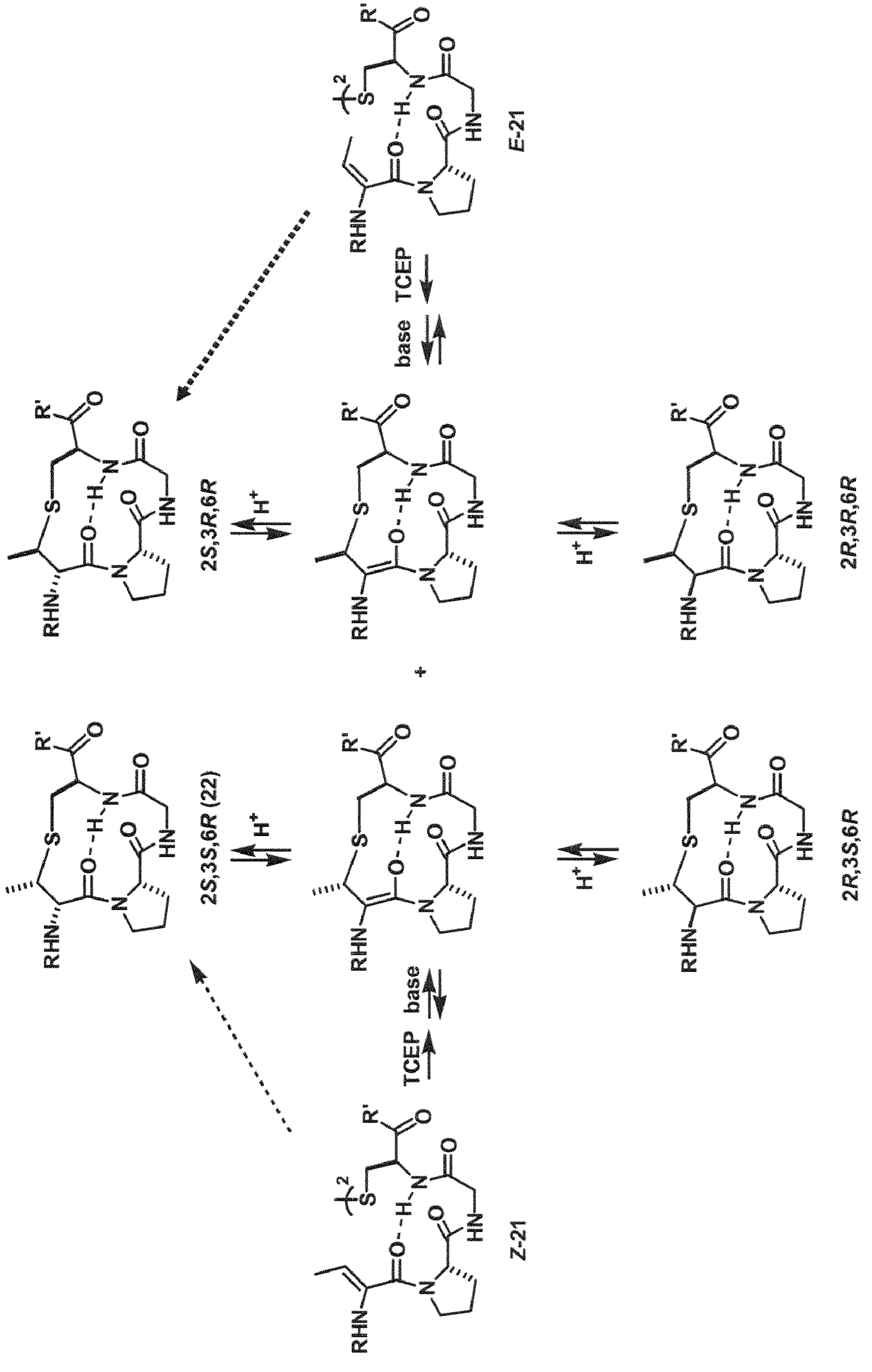
FIG. 69 illustrates examples of kinetic or thermodynamic control.

It is certified that error appears in the above-identified patent and that said Letters Patent is hereby corrected as shown below:

In the drawings, Sheet 42, Fig. 45:
Please delete the fourth line: "KGGSGVIHTISHECNMNSWQFVTCCS", and replace with
KGGSGVIHTISHECNMNSWQFVTCCS In the drawings, Sheet 42, Fig. 45:
Please delete the sixth line "AKGGSGVIHTISHECNMNSWQFVTCCS", and replace with
AKGGSGVIHTISHECNMNSWQFVTCCS Signed and Sealed this Thirtieth Day of November, 2010

David J. Kappos
*Director of the United States Patent and Trademark Office*